(12) United States Patent
Boojamra et al.

(10) Patent No.: US 7,300,924 B2
(45) Date of Patent: Nov. 27, 2007

(54) ANTI-INFECTIVE PHOSPHONATE ANALOGS

(75) Inventors: Constantine G. Boojamra, San Francisco, CA (US); Aesop Cho, Mountain View, CA (US); William J. Watkins, Sunnyvale, CA (US)

(73) Assignee: Gilead Sciences, Inc., Foster City, CA (US)

( * ) Notice: Subject to any disclaimer, the term of this patent is extended or adjusted under 35 U.S.C. 154(b) by 188 days.

(21) Appl. No.: 10/833,291

(22) Filed: Apr. 26, 2004

(65) Prior Publication Data

US 2005/0215525 A1    Sep. 29, 2005

Related U.S. Application Data

(60) Provisional application No. 60/514,043, filed on Oct. 24, 2003, provisional application No. 60/495,690, filed on Aug. 15, 2003, provisional application No. 60/495,689, filed on Aug. 15, 2003, provisional application No. 60/495,492, filed on Aug. 15, 2003, provisional application No. 60/495,487, filed on Aug. 15, 2003, provisional application No. 60/495,391, filed on Aug. 15, 2003, provisional application No. 60/495,390, filed on Aug. 15, 2003, provisional application No. 60/495,298, filed on Aug. 15, 2003, provisional application No. 60/465,728, filed on Apr. 25, 2003, provisional application No. 60/465,639, filed on Apr. 25, 2003, provisional application No. 60/465,601, filed on Apr. 25, 2003, provisional application No. 60/465,593, filed on Apr. 25, 2003, provisional application No. 60/465,546, filed on Apr. 25, 2003, provisional application No. 60/465,473, filed on Apr. 25, 2003, provisional application No. 60/465,472, filed on Apr. 25, 2003.

(51) Int. Cl.
*A61K 31/675* (2006.01)
*C07D 267/22* (2006.01)

(52) U.S. Cl. .......................... 514/80; 514/81; 540/458

(58) Field of Classification Search .................. 514/80, 514/81; 540/458
See application file for complete search history.

(56) References Cited

U.S. PATENT DOCUMENTS

| | | | |
|---|---|---|---|
| 4,271,155 A * | 6/1981 | Cricchio ....................... | 514/80 |
| 5,413,996 A | 5/1995 | Bodor | |
| 5,493,030 A | 2/1996 | Morgans et al. | |
| 5,585,397 A | 12/1996 | Tung et al. | |
| 5,633,279 A | 5/1997 | Morgans et al. | |
| 5,654,286 A | 8/1997 | Hostetler | |
| 5,670,497 A | 9/1997 | Bold et al. | |
| 5,747,498 A | 5/1998 | Schnur et al. | |
| 5,750,343 A | 5/1998 | Maag et al. | |
| 5,750,493 A | 5/1998 | Sommadossi et al. | |
| 5,811,422 A | 9/1998 | Lam et al. | |
| 5,874,577 A | 2/1999 | Chen et al. | |
| 5,914,332 A | 6/1999 | Chen et al. | |
| 6,072,053 A | 6/2000 | Vince et al. | |
| 6,174,888 B1 | 1/2001 | McQuire et al. | |
| 6,312,662 B1 | 11/2001 | Erion et al. | |
| 6,319,946 B1 | 11/2001 | Hale et al. | |
| 6,395,763 B1 | 5/2002 | Stamos et al. | |
| 6,608,027 B1 | 8/2003 | Tsantrizos et al. | |
| 6,767,900 B2 | 7/2004 | Ubasawa et al. | |
| 2001/0031773 A1 | 10/2001 | Camden | |
| 2002/0119443 A1 | 8/2002 | Becker et al. | |
| 2003/0109498 A1 | 6/2003 | Yuasa et al. | |
| 2004/0121316 A1 | 6/2004 | Birkus et al. | |

FOREIGN PATENT DOCUMENTS

| | | |
|---|---|---|
| EP | 0 267 050 | 5/1988 |
| EP | 0 441 192 | 1/1991 |
| EP | 0 465 297 | 1/1992 |
| EP | 0 531 597 | 3/1993 |
| EP | 0 632 048 | 1/1995 |
| EP | 0 786 455 | 7/1997 |
| EP | 0 852 233 | 7/1998 |
| EP | 0 919 562 | 6/1999 |
| EP | 1 295 879 | 3/2003 |
| WO | WO 88/06158 | 8/1988 |
| WO | WO91/19721 | 12/1991 |
| WO | WO 92/00988 | 1/1992 |
| WO | WO 92/18520 | 10/1992 |
| WO | WO 93/12123 | 6/1993 |
| WO | WO 93/24510 | 12/1993 |
| WO | WO 96/14314 | 5/1996 |
| WO | WO 96/40156 | 12/1996 |
| WO | WO 97/01558 | 1/1997 |
| WO | WO 98/04569 | 2/1998 |
| WO | WO 98/11906 | 3/1998 |

(Continued)

OTHER PUBLICATIONS

Cricchio, 1981, CAS:95:43192.*

(Continued)

*Primary Examiner*—Joseph K. McKane
*Assistant Examiner*—Rei-tsang Shiao
(74) *Attorney, Agent, or Firm*—Viksnins Harris & Padys PLLP

(57) ABSTRACT

The invention is related to phosphorus substituted anti-infective compounds, compositions containing such compounds, and therapeutic methods that include the administration of such compounds, as well as to processes and intermediates useful for preparing such compounds.

91 Claims, No Drawings

FOREIGN PATENT DOCUMENTS

| WO | WO 98/15563 | 4/1998 |
|---|---|---|
| WO | WO 99/33815 | 7/1999 |
| WO | WO 99/62921 | 12/1999 |
| WO | WO 00/04033 | 1/2000 |
| WO | WO 00/52015 A2 | 9/2000 |
| WO | WO 00/52015 A3 | 2/2001 |
| WO | WO 01/13957 | 3/2001 |
| WO | WO 01/17982 | 3/2001 |
| WO | WO 01/19320 | 3/2001 |
| WO | WO 01/39724 A2 | 6/2001 |
| WO | WO 01/46204 | 6/2001 |
| WO | WO 01/64693 | 9/2001 |
| WO | WO 01/39724 A3 | 10/2001 |
| WO | WO 01/96329 | 12/2001 |
| WO | WO 01/96354 | 12/2001 |
| WO | WO 02/03997 | 1/2002 |
| WO | WO 02/06292 | 1/2002 |
| WO | WO 02/08241 | 1/2002 |
| WO | WO 02/14344 | 2/2002 |
| WO | WO 02/48165 A2 | 6/2002 |
| WO | WO 02/057425 | 7/2002 |
| WO | WO 02/100415 | 12/2002 |
| WO | WO 02/103008 A2 | 12/2002 |
| WO | WO 03/028737 | 4/2003 |
| WO | WO 02/48165 A3 | 5/2003 |
| WO | WO 03/050129 | 6/2003 |
| WO | WO 03/059255 | 7/2003 |
| WO | WO 03/064383 | 8/2003 |
| WO | WO 03/066005 | 8/2003 |
| WO | WO 03/080078 | 10/2003 |
| WO | WO 02/103008 A3 | 11/2003 |
| WO | WO 03/090690 | 11/2003 |
| WO | WO 2004/096234 | 11/2004 |
| WO | WO 2004/096818 A2 | 11/2004 |
| WO | WO 2005/011709 | 2/2005 |
| WO | WO 2005/011709 A1 | 2/2005 |
| WO | WO 2004/096818 A3 | 4/2005 |

OTHER PUBLICATIONS

Allen, Lee F. et al., CI-1040 (PDI84352), a Targeted Signal Transduction Inhibitor of MEK (MAPKK), *Seminars in Oncology*, Oct. 2003, pp. 105-116, vol. 30, No. 5, Elsevier Inc.

Bantia, Shanta et al., Purine nucleoside phosphorylase inhibitor BCX-1777 (Immucillin-H)—a novel potent and orally active immunosuppressive agent, *International Immunopharmacology*, 2001, pp. 1199-1210, Elsevier Science B.V.

Beauchamp, Lilia M., et al., Guanine, Pyrazolo[3,4-d]pyrimidine, and Triazolo[4,5-d]pyrimidine(8-Azaguanine) Phosphonate Acyclic Derivatives as Inhibitors of Purine Nucleoside Phosphorylase, *Journal of Medicinal Chemistry*, 1996, pp. 949-956, American Chemical Society.

Bohani D. W. et al., A-420983: a potent, orally active inhibitor of Ick with efficacy in a model of transplant rejection, *Bioorganic & Medicinal Chemistry Letters*, 2004, vol. 14.

Bzowska, Agnieszka et al., Purine nucleoside phosphorylases: properties, functions, and clinical aspects, *Pharmacology & Therapeutics*, 2000, pp. 349-425, vol. 88, Elsevier Science Inc.

Chapman, H. et al., Practical Synthesis, Separation, and Stereochemical Assignment of the PMPA-Pro-Drug GS-7340, *Nucleosides, Nucleotides & Nucleic Acids*, 2001, pp. 621-628, vol. 20, Nos. 4-7, Marcel Dekker, Inc.

Clark, Jeremy L. et al., Mycophenolic Acid Analogues as Potential Agents Against West Nile Virus Infection.

Conklyn, Maryrose et al., The JAK3 inhibitor CP-690550 selectively reduces NK and CD8+ cell numbers in cynomolgus monkey blood following chronic oral dosing, *Journal of Leukocyte Biology*, Dec. 2004, pp. 1-8, vol. 76, The Society for Leukocyte Biology.

De Clereq, E., Highlights in the Development of New Antiviral Agents, *Mini Reviews in Medicinal Chemistry*, 2002, 163-175, vol. 2, No. 2., Bentharn Science Publishers, Ltd.

Evans, Gary B., Exploring Structure—Activity Relationships of Transition State Analogues of Human Purine Nucleoside Phosphorylase, *J. Med. Chem.*, 2003, 3412-3423, vol. 46, No. 15, American Chemical Society.

Gumina, Giuseppe et al., Advances in antiviral agents for hepatitis B virus, *Antiviral Chemistry & Chemotherapy*, 2001, 93-112, vol. 12, Suppl. 1, International Medical Press.

Gobec, S. et al., Phosphonate inhibitors of antiget 85C, a crucial enzyme involved in the biosynthesis of the mycobacterium tuberculosis cell wall, *Bioorganic and Medicinal Chemistry Letters*, 2004, vol. 14.

Hegedus, Louis S. et al., Synthesis of 4'-Methyl and 4'-cyano Carbocyclic 2',3'-Didehydro Nucleoside Analogues via 1,4-Addition to Substituted Cyclopentenones, *J. Org. Chem.*, 2004, 8492, 8495, vol. 69, No. 24, American Chemical Society.

Herczegh P., et al., Osteoadsorptive bisphosphonate derivatives of fluoroquinolone antibacterials, *J. Med. Chem.*, 2002, vol. 45.

Hirabayashi, Hideki et al., Bone-Specific Drug Delivery Systems, *Clinical Pharacokinetics*, 2003, 1319-1330, vol. 42, No. 15.

Holy A. et al., Synthesis, *Cllect. Czech. Chem. Commun.*, 1989, vol. 54, pp. 2190-2210.

Jain, Jugnu et al., Characterization of Pharmacological Efficacy of VX-148, a New, Potent Immunosuppresive Inosine 5'-Monophosphate Dehydrogenase Inhibitor, *Journal of Pharmacology and Experimental Therapeutics*, 2002, 1272-1277, vol. 302, No. 3, The American Society for Pharmacology and Experimental Therapeutics.

Karpenko, Inna L. et al., Synthesis and Antiherpetic Activity of Acyclovir Phosphonates, *Nucleosides, Nucleotides & Nucleic Acids*, 2003, 319-328, vol. 22, No. 3, Marcel Dekker, Inc.

Kato, Keisuke et al., Stereoselective synthesis of 4'-α-alkyclcarbovir derivatives based on an asymmetric synthesis of chemo-enzymatic procedure, *Chemical & Pharmaceutical Bulletin*, 1999, 1256-1264, vol. 49, No. 9, Pharmaceutical Society of Japan.

Kato, Keisuke et al., Enantio- and diastereoselective synthesis of 4'-α-substituted carbocyclic nucleosides, *Tetrahedron: Asymmetry*, 1998, 911-914, vol. 9, Elsevier Science Ltd.

Kilpatrick, J. Michael, Intravenous and oral pharmacokinetic study of BCX-1777, a novel purine nucleoside phosphorylase transition-state inhibitor, In vivo effects on blood 2'-deoxyguanosine in primates, *International Immunopharmacology*, 2003, 541-548, vol. 3, Elsevier Science B.V.

Kim, Choung UN et al., Regiospecific and Highly Stereoselective Electrophilic Addition to Furanoid Glycals: Synthesis of Phosphonate Nucleotide Analogues with Potent Activity against HIV, *J. Org. Chem.*, 1991, 2642-2647, vol. 56, No. 8, American Chemical Society.

Kinsky, Stephen C. et al., Inhibition of cell proliferation by putative metabolites and non-degradable analogs of methotrexate-.gama.-dimyristoylphosphatidylethanolamine, *Biochimica et Biphysica Acta*, 19878, 211-218, vol. 917, No. 2., Elsevier Science Publishers B. V.

Kinsky, Stephen C. et al., Effect of liposomes sentitized with methotrexate-y-dimyristoylphosphatidylethanolamine on cells that are resistant to methotrexate, *Biochimica et Biophysica Acta*, 1986, 129-135, vol. 885, Elsevier Science Publishers B.V.

Kinsky, Stephen C. et al., Circumvention of the methotrexate transport system by methotrexate-phosphatidylethanolamine derivatives effect of fatty acid chain length, *Biochimica et Biophysica Acta*, 1987, 96-103, vol. 921, Elsevier Science Publishers B.V.

Ko, Ok Hyun et al., Efficient synthesis of novel carbocyclic nucleosides via sequential Claisen rearrangement and ring-closing methathesis, *Tetrahedron Letters*, 2002, 6399-6402, vol. 43, Elsevier Science Ltd.

Reed, Leff et al., Antidiabetic PPARy Ligands: An update on Compounds in development, *Curr. Med. Chem.—Imun., Endoc. & Metab. Agents*, 2002, 33-47, vol. 2, No. 1, Bentham Science Publishers Ltd.

Lewandowicz, Andrzej et al., Achieving the Ultimate Physiological Goal in Transition State Analogue Inhibitors for Purine Nucleoside Phosphorylase, *The Journal of Biological Chemistry*, 2003, 31465-31468, vol. 278, No. 34, The American Society for Biochemistry and Molecular Biology, Inc.

Pankiewicz, Krzysztof W., Novel Mycophenolic Adenine Bis(phosphonate) Analogues As Potential Differentiation Agents against Human Leukemia, *J. Med. Chem.*, 2002 703-712, vol. 45, No. 3, American Chemical Society.

Ono-Nita, Suzane Kioko et al., Novel Nucleoside Analogue MCC-478 (LY582563) Is Effective against Wild-Type or Lamivudine-Resistant Hepatitis B Virus, *Antimicrobial Agents and Chemotherapy*, 2002, 2602-2605, vol. 46, No. 8, American Society for Microbiology.

Parang, Keykavous et al., Novel Approaches for Designing 5'-O-Ester Prodrugs of 3'-Azido-2',3'-dideoxythymidine (AZT), *Current Medicinal Chemistry*, 2000, 995-1039, vol. 7, No. 10, Bentham Science Publishers Ltd.

Prashad, Mahavir et al., An Efficient and Large-Scale Enantioselective Synthesis of PNP405: A Purine Nucleoside Phosphorylase Inhibitor, *J. Org. Chem.*, 2002, 6612-6617, vol. 67, No. 19, American Chemical Society.

Ray, Adrian S. et al., Role of Purine Nucleoside Phosphorylase in Interactions between 2', 3'-Dideoxyinosine and Allopurinal, Ganciclovir, or Tenofovir, Antimicrobial Agents and Chemotherapy, 2004, 1089-1095, vol. 48, No. 4, American Society for Microbiology.

Roberts, Stanley M., Development of the route to the new anti-AIDS drug abacavir: A highlight of academic/industry laison, *IDrugs*, 1998, 896-899, vol. 1, No. 8, Current Drugs Ltd.

Rosowsky, Andre et al., Methotrexate Analogues—27, *Biochemical Pharmacology*, 1986, 3327-3333, vol. 35, No. 19, Pergamon Journals Ltd.

Rosowsky, Andre et al., Methotrexate Analogues, 32, Chain Extension, α-Carboxyl Replacement by Sulfonate and Phosphonate: Effect on Enzyme Binding and Cell-Growth Inhibition, *J. Med. Chem.*, 1988, 1326-1331, vol. 31, No. 7, American Chemical Society.

Schultz, C., Prodrugs of biologically active phosphate esters, *Bioorganic & Medicinal Chemistry*, 2003, 885-898, vol. 11, Elsevier Science Ltd., GB.

Sekiya, Kouichi et al., 2-Amino-6-arylthio-9-[2-(phosphonomethoxy) ethyl] purine Bis(2,2,2-trifluoroethyl) Esters as Novel HBV-Specific Antiviral Reagents, Journal of Medicinal Chemistry, 2002, 3138-3142, vol. 45, No. 14, American Chemical Society.

Shi, Wuxian et al., *Plasmodium falciparum* Purine Nucleoside Phosphorylase, The Journal of Biological Chemistry, 2004, 18103-18106, vol. 279, No. 18, The American Society of Biochemistry and Molecular Biology, Inc.

Sintchak, Michael D. et al., The structure of inosine 5'-monophosphate dehydrogenase and the design of novel inhibitors, Immunopharmachology, 2000, 163-184, vol. 47, Elsevier.

Srinivas, Ranga V. et al., Metabolism and In Vitro Antiretroviral Activities of Bis(Pivaloyloxymethyl) Prodrugs of Acyclic Nucleoside Phosphonates, Antimicrobial Agents and Chemotherapy, 1993, 2247-2250, vol. 37, No. 10, American Society for Microbiology.

Sturtz, Georges et al., Su rune nouvelle approche de pharmacomodulation du methotrexate: synthese d'analogues gem-diphosphoniques d'amethopterine et de la N-10 deaza amethopterine, Medicinal Chemistry, C. R. Acad. Sci. Paris, 1990, vol. 10, No. 2, 739-742, Academie des Sciences.

Sturtz, Georges et al., Analogues phosphonoglutamiques d'amethopterine (methotrexate), Eur. J. Med. Chem—Chim. Ther., 1984, 267-273, vol. 19, No. 3.

Sturtz, G. et al., Synthesis of gem-bisphosphonic methotrexate conjugates and their biological response towards Walker's osteosarcoma, *Eur. J. Med. Chem.*, 1993, 899-903, vol. 28, Elsevier.

Sturtz, G. et al., A study of the delivery-targeting concept applied to antineoplasic drugs active on human osteosarcoma, I. Synthesis and biological activity in nude mice carrying human osteosarcoma xenografts of gem-bisphophonic methotrexate analogues, Eur J. Med. Chem., 1992, 825-833, vol. 27, No. 8, Elsevier.

Waegell W. et al. A420983, a novel, small molecule inhibitor of LCK prevents allograft rejection, Transplantation Proceedings, 2002, 1411-1417, vol. 34.

Wroblewski, Andrezej et al., Synthesis of (1R,2S)- and (1S,2S)-3-(4-carbamoyl-1,2,3-triazol-1-yl)-1,2-dihydroxypropylphosphonates, Tetrahedron: Asymmetry, 2004, 1457-1464, vol. 15, Elsevier.

Abdel-Meguid, Sherin S. et al., Inhibition of Human Immunodeficiency Virus-1 Protease by a $C_2$-Symmetric Phosphinate. Synthesis and Crystallographic Analysis, *Biochemistry*, 1993, 1543-1572, vol. 32, No. 31.

De Clercq, Erik, New Developments in Anti-HIV Chemotherapy, *Current Medicinal Chemistry*, 2001, 1543-1572, vol. 8, No. 13, Bentham Science Publishers Ltd.

Dvorakova, Hana et al., Synthesis of 2'-Aminomethyl Derivatives of N-(2-(Phosphonomethoxy)ethyl) Nucleotide Analogues as Potential Antiviral Agents, *J. Med. Chem.*, 1996, 3263-3268. vol. 38, No. 17.

Menendez-Arias, Luis et al. Targeting HIV: antiretroviral therapy and development of drug resistance, *TRENDS in Pharmacological Sciences*, 2002, 381-388, vol. 23, No. 8, Elsevier Science Ltd.

Vielhaber, Bernd, Bericht vorn 3rd International Workshop on Salvage Therapy for HIV-Infection, Deutsche Aids-Hilfe e.V. FaxReport zu HIV und AIDS, 2000, 12-14.

Hostetler, CAS:127:185859 (1997).

Morgans et al., CAS:124:86709 (1995).

Sturtz et al., CAS:101:143560 (1984).

* cited by examiner

ANTI-INFECTIVE PHOSPHONATE ANALOGS

PRIORITY OF INVENTION

This application claims the benefit of priority under 35 U.S.C. § 119(e) to U.S. Provisional Patent Application Ser. Nos. 60/465,728, 60/465,601, 60/465,639, 60/465,593, 60/465,546, 60/465,472, and 60/465,473, all filed Apr. 25, 2003; to U.S. Provisional Patent Application Ser. Nos. 60/495,689, 60/495,298, 60/495,492, 60/495,391, 60/495,690, 60/495,487, and 60/495,390, all filed Aug. 15, 2003; and to U.S. Provisional Patent Application Ser. No. 60/514,043, filed Oct. 24, 2003. The entirety of all Provisional Applications listed above are incorporated herein by reference.

FIELD OF THE INVENTION

The invention relates generally to phosphonate containing compounds with anti-infective activity.

BACKGROUND OF THE INVENTION

Improving the delivery of drugs and other agents to target cells and tissues has been the focus of considerable research for many years. Though many attempts have been made to develop effective methods for importing biologically active molecules into cells, both in vivo and in vitro, none has proved to be entirely satisfactory. Optimizing the association of the inhibitory drug with its intracellular target, while minimizing intercellular redistribution of the drug, e.g., to neighboring cells, is often difficult or inefficient.

Most agents currently administered to a patient parenterally are not targeted, resulting in systemic delivery of the agent to cells and tissues of the body where it is unnecessary, and often undesirable. This may result in adverse drug side effects, and often limits the dose of a drug (e.g., glucocorticoids and other anti-inflammatory drugs) that can be administered. By comparison, although oral administration of drugs is generally recognized as a convenient and economical method of administration, oral administration can result in either (a) uptake of the drug through the cellular and tissue barriers, e.g., blood/brain, epithelial, cell membrane, resulting in undesirable systemic distribution, or (b) temporary residence of the drug within the gastrointestinal tract. Accordingly, a major goal has been to develop methods for specifically targeting agents to cells and tissues. Benefits of such treatment includes avoiding the general physiological effects of inappropriate delivery of such agents to other cells and tissues, such as uninfected cells.

Intracellular pathogens are the etiologic agents of a number of human disease states, e.g., infections caused by *Mycoplasma pneumoniae* and *Chlamydia trachomatis*, coronary-artery disease associated with *Chlamydia pneumoniae* infection, tuberculosis, acquired immune deficiency syndrome (AIDS) and pneumonia, often associated with *Mycobacterium avium-intracellulare* complex (MAC).

Numerous compounds have been shown to be effective as anti-infective compounds. For example, Cefixime (U.S. Pat. No. 5,252,731) is an orally active third generation cephalosporin with in vitro antibacterial activity against most important lower respiratory pathogens. Cefixime is active against *Haemophilus influenzae*, *Moraxella catarrhalis* and penicillin-susceptible *Streptococcus pneumoniae* but not *Staphylococcus aureus*. Cefixime is an effective treatment for mild to moderate lower respiratory tract infections (*Drugs*, 1995, 49(6), 1007). It is also one of the best choices for uncomplicated gonococcal infections (*Clin Infect Dis.*, 1995, 20 Suppl 1, S47). As with certain other drugs of its class, gastrointestinal disturbances are the most frequently reported adverse events in patients taking cefixime, and cases of pseudomembranous colitis have been reported (*Drugs*, 1995, 49(6), 1007).

Erythromycin has enjoyed over 40 years of use as an agent primarily for the treatment of infections caused by gram-positive bacteria. Its semi-synthetic derivatives clarithromycin and azithromycin have seen use for empiric treatment of respiratory tract infections caused by both gram-positive organisms and some gram-negative organisms such as *Haemophilus influenzae* and *Moraxella catarrhalis* (see The Sanford Guide to Antimicrobial Therapy," 2002, $32^{nd}$ Edition, David N. Gilbert, MD, Robert C. Moellering, Jr. MD, Merle A. Sande, MD, Eds., Antimicrobial Therapy, Inc., Hyde Park, Vt., also EP 0041355, U.S. Pat. Nos. 4,328,334 and 4,331,803). The antibiotics of this family are also particularly useful at treating so-called "atypical" organisms such as *Chlamydia pneumoniae*, *Chlamydia trachomatis*, and *Mycoplasma pneumoniae*, among others.

*Chlamydia pneumonia* has recently been cited as a potential contributor to heart/coronary artery disease and there have been reports that antibiotics that clear infection by chlamydia may have value in treating or preventing heart or coronary artery disease (see U.S. Pat. No. 6,281,199 and references cited therein). Since *Chlamydia pneumonia* is an intracellular pathogen, a semi-synthetic erythromycin antibiotic designed to accumulate in the intracellular space may be superior to older erythromycins at treatment of infection by intracellular bacteria. The same may be a useful agent for the treatment and prevention of heart and coronary artery disease.

*Mycobacterium tuberculosis*, the causative agent of tuberculosis, is an intracellular organism. Drugs used in the treatment of tuberculosis accumulate inside infected cells at sufficient concentration in order to successfully eradicate the infection. Ethambutol is currently employed in the combination therapy of active tuberculosis infection, as well as in a number of other indications including treatment of mycobacterial illnesses, including pulmonary and extra-pulmonary tuberculosis (see "The Sanford Guide to Antimicrobial Therapy," 2002, $32^{nd}$ Edition, David N. Gilbert, MD, Robert C. Moellering, Jr. MD, Merle A. Sande, MD, Eds., Antimicrobial Therapy, Inc., Hyde Park, Vt.). As with other antimycobacterial drugs, there are significant toxicities associated with ethambutol use (see "Martindale—The Complete Drug Reference—Monographs", 2002-3003, The Pharmaceutical Press). An ethambutol derivative designed to concentrate in the intracellular space, which is the site of infection, may be of particular importance since such a derivative may be effective at treating or preventing mycobacterial illness at a lower dose than that which is currently used for ethambutol itself. Furthermore, such a derivative that concentrates within the cell may have pharmacodynamic properties that allow it to overcome strains that have developed resistance to standard-dose ethambutol treatment protocols.

Drugs such as isoniazid (INH) accumulate inside infected cells at sufficient concentration in order to effectively treat infections caused by *Mycobacterium tuberculosis*. INH is currently an agent of choice for the mono-therapy prophylaxis of tuberculosis and an agent of choice used in combination for the treatment of active tuberculosis infection (see "The Sanford Guide to Antimicrobial Therapy," 2002, 32nd Edition, David N. Gilbert, MD, Robert C. Moellering, Jr. MD, Merle A. Sande, MD, Eds. Antimicrobial Therapy, Inc. Hyde Park, Vt.). The hepatotoxicity of INH is known to increase with the age of the patient. In particular, patients over 35 years of age are thought to be at significant risk of liver damage associated with INH use (see "Martindale—The Complete Drug Reference—Monographs", 2002-2003, The Pharmaceutical Press).

Pyrazinamid (PZA, U.S. Pat. No. 2,149,279) is currently employed in the combination therapy of active tuberculosis infection (see "The Sanford Guide to Antimicrobial Therapy," 2002, $32^{nd}$ Edition, David N. Gilbert, MD, Robert C. Moellering, Jr. MD, Merle A. Sande, MD, Eds., Antimicrobial Therapy, Inc., Hyde Park, Vt.). As with other anti-mycobacterial drugs there are significant toxicities associated with PZA use (see "Martindale—The Complete Drug Reference—Monographs", 2002-2003, The Pharmaceutical Press).

Rifabutin (RBT, EP 0,552,018 and U.S. Pat. No. 4,086, 225) is currently employed in the combination therapy of active tuberculosis infection and has proven of particular value since 30% of strains resistant to rifampicin (an older semi-synthetic antibiotic also of the rifamycin family) remain sensitive to rifabutin (see "The Sanford Guide to Antimicrobial Therapy," 2002, 32nd Edition, David N. Gilbert, MD, Robert C. Moellering, Jr. MD, Merle A. Sande, MD, Eds., Antimicrobial Therapy, Inc., Hyde Park, Vt.). Rifabutin is also used in the treatment and/or prevention of other mycobacterial illness such as the *Mycobacterium avium-intracellulare* complex (MAC) associated with AIDS. Additionally, RBT was investigated in the potential chemotherapy of AIDS since it has been shown to be a reverse transcriptase inhibitor (see *Pharm. Pharmacol. Lett.* 1993, 3, 1) and to inhibit the growth of HIV in vitro (see *Antimicrob. Agents Chemother.* 1988, 32, 684). However, clinical efficacy against AIDS or HIV has not been demonstrated.

As with other anti-mycobacterial drugs there are side effects associated with RBT use (see any recent issue of "The Physicians Desk Reference"). An RBT derivative designed to concentrate in the intracellular space, which is the site of infection, may be of particular importance since such a derivative may be effective at treating or preventing mycobacterial illness at a lower dose than that which is currently used for RBT itself and is associated with toxicity. Furthermore, such a derivative that concentrates within the cell may have pharmacodynamic properties that allow it to overcome strains that have developed resistance to standard-dose RBT treatment protocols. Additionally, an RBT analog that is designed to accumulate within the cells of the immune system may have value in the treatment of HIV infection and AIDS, while RBT itself and older rifamycins so far have not shown promise in the antiviral chemotherapy of HIV.

Rifampicin (RIF, U.S. Pat. No. 3,342,810) is currently employed in the combination therapy of active tuberculosis infection (see "The Sanford Guide to Antimicrobial Therapy," 2002, $32^{nd}$ Edition, David N. Gilbert, MD, Robert C. Moellering, Jr. MD, Merle A. Sande, MD, Eds., Antimicrobial Therapy, Inc., Hyde Park, Vt.). RIF also has value in the treatment and prevention of other mycobacterial and bacterial illness. Other rifamycins such as rifabutin have been shown to be reverse transcriptase inhibitors (*Pharm. Pharmacol. Lett.* 1993, 3, 1) and to have activity against the human immunodeficiency virus in vitro (*Antimicrob. Agents Chemother.* 1988, 32, 684). For this reason, rifampicin derivatives also may have value in the treatment of HIV.

Fluoroquinolones are a broad-spectrum class of synthetic antibacterial agents and have the rare quality of being among the only common classes of broad-spectrum antibacterial drug, members of which have shown therapeutically significant antimicrobial activity against *Mycobacterium tuberculosis*. Ciprofloxacin (see U.S. Pat. No. 4,670,444), levofloxacin, and sparfloxacin, while not approved by the FDA for use in the treatment of tuberculosis, have been added to combination regimens for anti-tuberculosis therapy (see The Sanford Guide to Antimicrobial Therapy," 2002, $32^{nd}$ Edition, David N. Gilbert, MD, Robert C. Moellering, Jr. MD, Merle A. Sande, MD, Eds., Antimicrobial Therapy, Inc., Hyde Park, Vt.).

Thus, there is a need for therapeutic anti-infective agents with improved pharmacological properties, e.g., drugs having improved anti-infective activity and pharmacokinetic properties, including improved oral bioavailability, greater potency and extended effective half-life in vivo.

New anti-infective compounds should have fewer side effects, less complicated dosing schedules, and be orally active. In particular, there is a need for a less onerous dosage regimen, such as one pill, once per day.

Assay methods capable of determining the presence, absence or amounts of infection inhibition are of practical utility in the search for anti-infectives as well as for diagnosing the presence of conditions associated infection.

SUMMARY OF THE INVENTION

Intracellular targeting may be achieved by methods and compositions that allow accumulation or retention of biologically active agents inside cells. The present invention provides novel anti-infective analogs. Such novel analogs possess all the utilities of the anti-infectives and optionally provide cellular accumulation as set forth below. In addition, the present invention provides compositions and methods for inhibition of infection or therapeutic activity against infection.

The present invention relates generally to the accumulation or retention of therapeutic compounds inside cells. The invention is more particularly related to attaining high concentrations of phosphonate-containing molecules in target cells. Such effective targeting may be applicable to a variety of therapeutic formulations and procedures.

Compositions of the invention include anti-infective compounds having at least one phosphonate group. Accordingly, in one embodiment the invention provides a conjugate comprising an anti-infective compound linked to one or more phosphonate groups; or a pharmaceutically acceptable salt or solvate thereof.

In another embodiment the invention provides a compound of the invention, or a pharmaceutically acceptable salt or solvate thereof, that is a compound of any one of formulae 500-509:

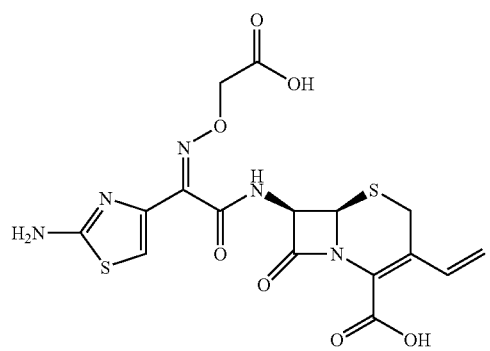
500
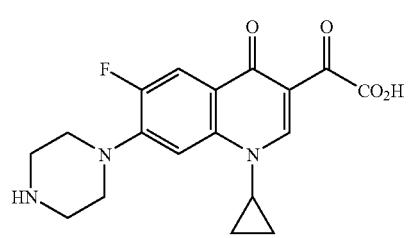
501
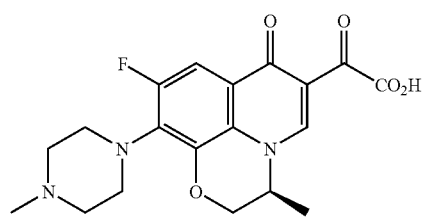
502
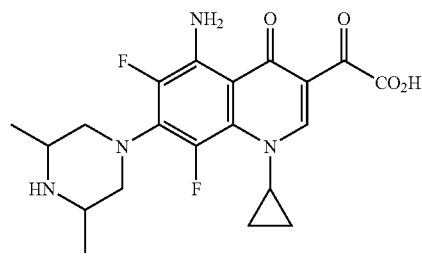
503
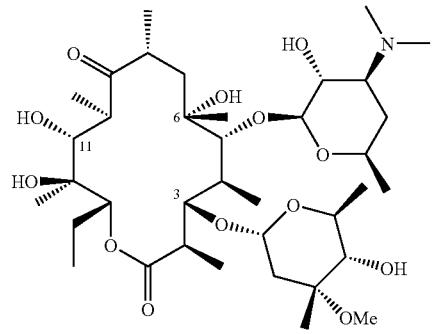
504
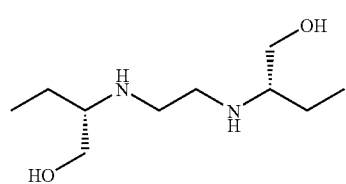
505
-continued
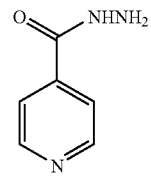
506
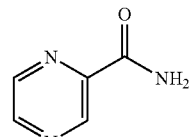
507
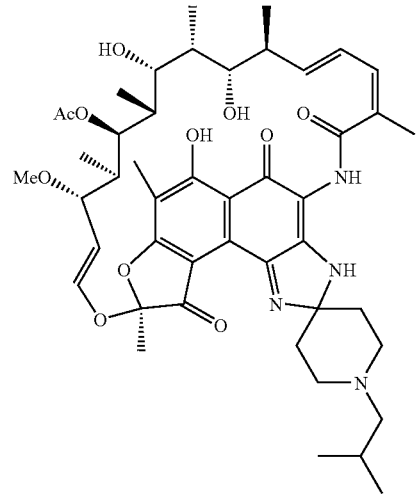
508
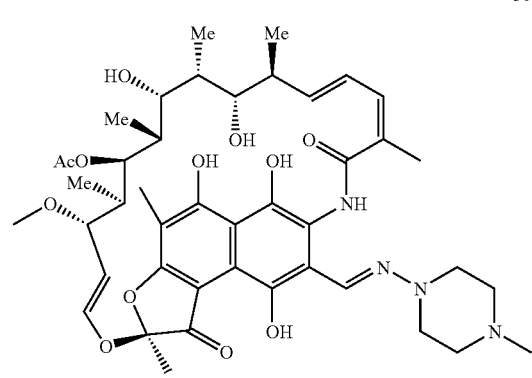
509
that is substituted with one or more groups $A^0$, wherein:
wherein:
$A^0$ is $A^1$, $A^2$ or $W^3$ with the proviso that the conjugate includes at least one $A^1$;
$A^1$ is:
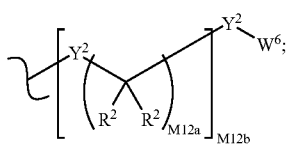

-continued $A^2$ is:

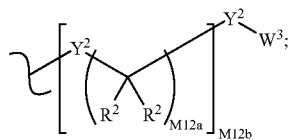

$A^3$ is:

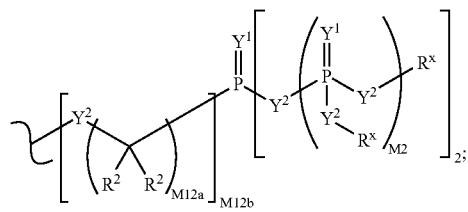

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $—S(O)_{M2}—$, or $—S(O)_{M2}—S(O)_{M2}—$; and when $Y^2$ joins two phosphorous atoms $Y^2$ can also be $C(R^2)(R^2)$;

$R^x$ is independently H, $R^1$, $R^2$, $W^3$, a protecting group, or the formula:

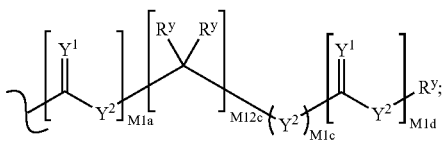

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or —$NO_2$;

$R^{3b}$ is $Y^1$;

$R^{3c}$ is $—R^x$, $—N(R^x)(R^x)$, $—SR^x$, $—S(O)R^x$, $—S(O)_2R^x$, $—S(O)(OR^x)$, $—S(O)_2(OR^x)$, $—OC(Y^1)R^x$, $—OC(Y^1)OR^x$, $—OC(Y^1)(N(R^x)(R^x))$, $—SC(Y^1)R^x$, $—SC(Y^1)OR^x$, $—SC(Y^1)(N(R^x)(R^x))$, $—N(R^x)C(Y^1)R^x$, $—N(R^x)C(Y^1)OR^x$, or $—N(R^x)C(Y^1)(N(R^x)(R^x))$;

$R^{3d}$ is $—C(Y^1)R^x$, $—C(Y^1)OR^x$ or $—C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, $—C(Y^1)R^5$, $—C(Y^1)W^5$, $—SO_{M2}R^5$, or $—SO_{M2}W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In another embodiment the invention provides a compound of the invention which is a compound of the formula:

[DRUG]-(A$^0$)$_{nn}$ or a pharmaceutically acceptable salt or solvate thereof wherein, DRUG is a compound of any one of formulae 500-509:

nn is 1, 2, or 3;

$A^0$ is $A^1$, $A^2$ or $W^3$ with the proviso that the conjugate includes at least one $A^1$;

$A^1$ is:

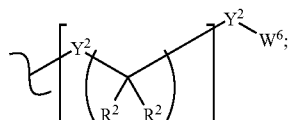

$A^2$ is:

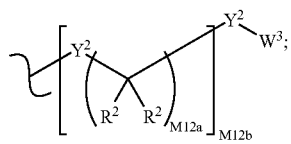

$A^3$ is:

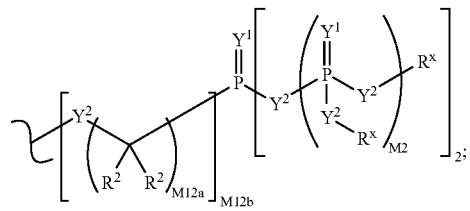

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $—S(O)_{M2}—$, or $—S(O)_{M2}—S(O)_{M2}—$; and when $Y^2$ joins two phosphorous atoms $Y^2$ can also be $C(R^2)(R^2)$;

$R^x$ is independently H, $R^1$, $R^2$, $W^3$, a protecting group, or the formula:

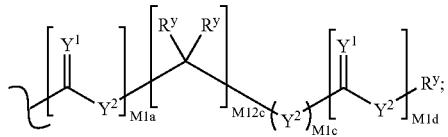

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

R³ is R³ᵃ, R³ᵇ, R³ᶜ or R³ᵈ, provided that when R³ is bound to a heteroatom, then R³ is R³ᶜ or R³ᵈ;

R³ᵃ is F, Cl, Br, I, —CN, N₃ or —NO₂;

R³ᵇ is Y¹;

R³ᶜ is —Rˣ, —N(Rˣ)(Rˣ), —SRˣ, —S(O)Rˣ, —S(O)₂Rˣ, —S(O)(ORˣ), —S(O)₂(ORˣ), —OC(Y¹)Rˣ, —OC(Y¹)ORˣ, —OC(Y¹)(N(Rˣ)(Rˣ)), —SC(Y¹)Rˣ, —SC(Y¹)ORˣ, —SC(Y¹)(N(Rˣ)(Rˣ)), —N(Rˣ)C(Y¹)Rˣ, —N(Rˣ)C(Y¹)ORˣ, or —N(Rˣ)C(Y¹)(N(Rˣ)(Rˣ));

R³ᵈ is —C(Y¹)Rˣ, —C(Y¹)ORˣ or —C(Y¹)(N(Rˣ)(Rˣ));

R⁴ is an alkyl of 1 to 18 carbon atoms, alkenyl of 2 to 18 carbon atoms, or alkynyl of 2 to 18 carbon atoms;

R⁵ is R⁴ wherein each R⁴ is substituted with 0 to 3 R³ groups;

W³ is W⁴ or W⁵;

W⁴ is R⁵, —C(Y¹)R⁵, —C(Y¹)W⁵, —SO_{M2}R⁵, or —SO_{M2}W⁵;

W⁵ is carbocycle or heterocycle wherein W⁵ is independently substituted with 0 to 3 R² groups;

W⁶ is W³ independently substituted with 1, 2, or 3 A³ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In another embodiment the invention provides a compound of the invention which is a compound of any one of formulae 1-14:

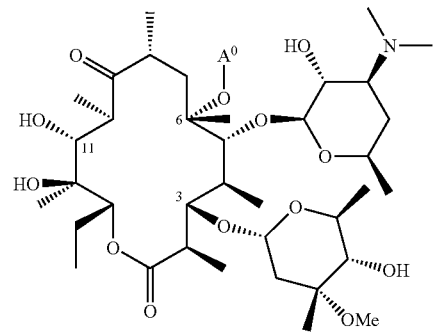

1

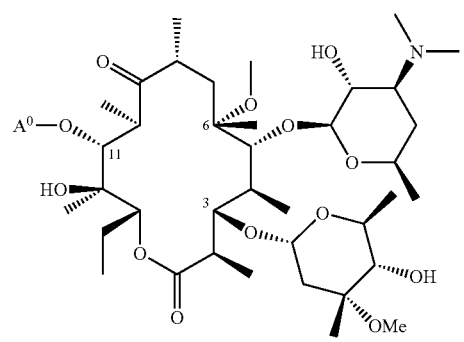

2

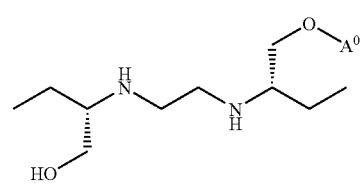

3

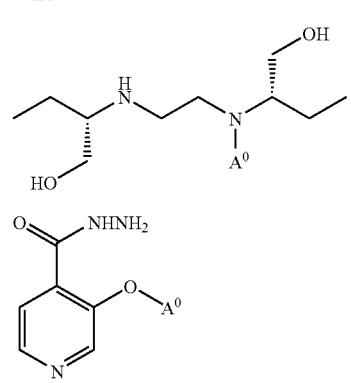

4

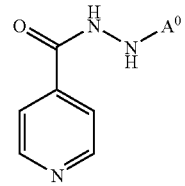

5

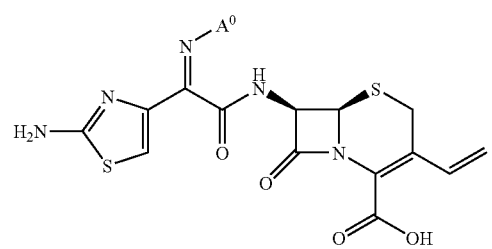

6

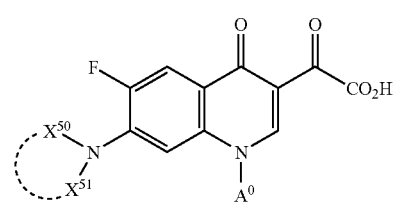

7

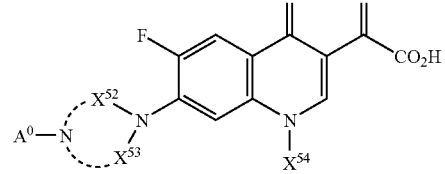

8

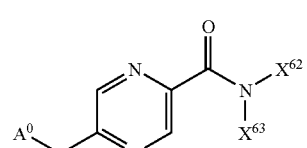

9

10

-continued

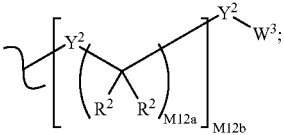

11

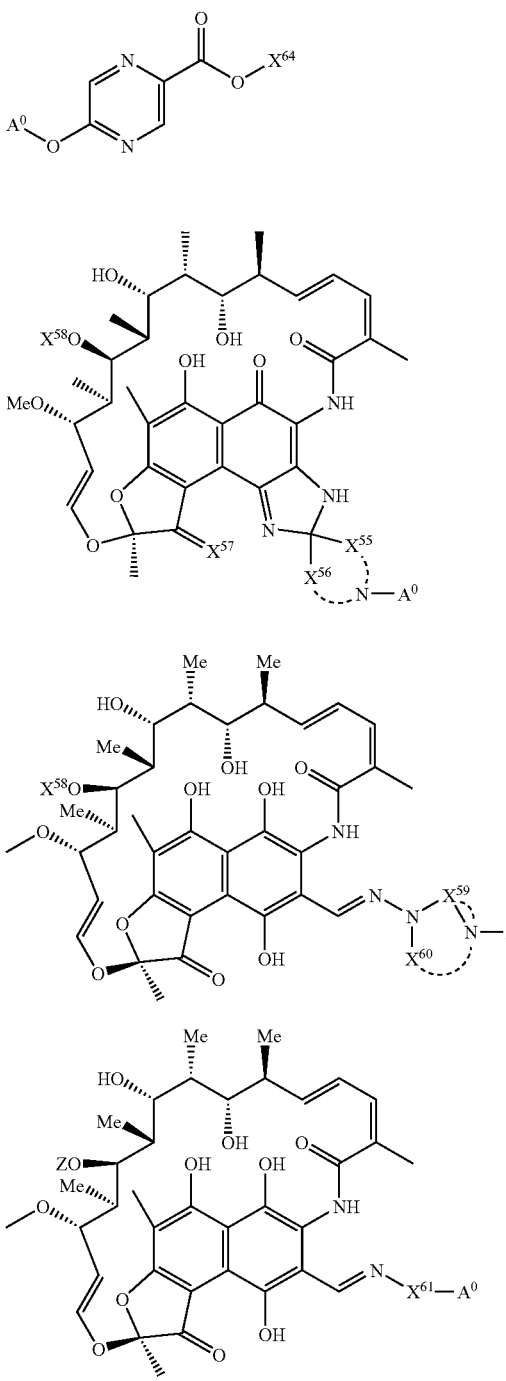

wherein:
$A^0$ is $A^1$, $A^2$ or $W^3$ with the proviso that one $A^0$ is $A^1$;
$A^1$ is:

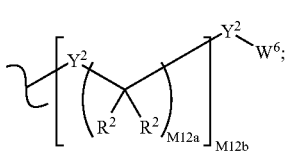

$A^2$ is:

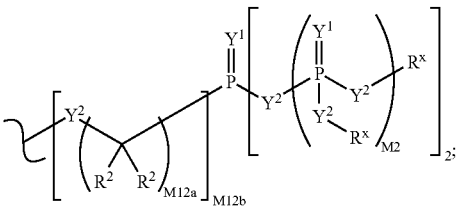

$A^3$ is:

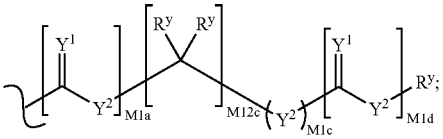

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$; and when $Y^2$ joins two phosphorous atoms $Y^2$ can also be $C(R^2)(R^2)$;

$R^x$ is independently H, $R^1$, $R^2$, $W^3$, a protecting group, or the formula:

[formula]

wherein:
$R^y$ is independently H, $W^3$, $R^2$ or a protecting group;
$R^1$ is independently H or alkyl of 1 to 18 carbon atoms;
$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;
$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;
$R^{3a}$ is F, Cl, Br, I, $-CN$, $N_3$ or $-NO_2$;
$R^{3b}$ is $Y^1$;
$R^{3c}$ is $-R^x$, $-N(R^x)(R^x)$, $-SR^x$, $-S(O)R^x$, $-S(O)_2R^x$, $-S(O)(OR^x)$, $-S(O)_2(OR^x)$, $-OC(Y^1)R^x$, $-OC(Y^1)OR^x$, $-OC(Y^1)(N(R^x)(R^x))$, $-SC(Y^1)R^x$, $-SC(Y^1)OR^x$, $-SC(Y^1)(N(R^x)(R^x))$, $-N(R^x)C(Y^1)R^x$, $N(R^x)C(Y^1)OR^x$, or $-N(R^x)C(Y^1)(N(R^x)(R^x))$;
$R^{3d}$ is $-C(Y^1)R^x$, $-C(Y^1)OR^x$ or $-C(Y^1)(N(R^x)(R^x))$;
$R^4$ is an alkyl of 1 to 18 carbon atoms, alkenyl of 2 to 18 carbon atoms, or alkynyl of 2 to 18 carbon atoms;
$R^5$ is $R^4$ wherein each $R^4$ is substituted with 0 to 3 $R^3$ groups;
$W^3$ is $W^4$ or $W^5$;
$W^4$ is $R^5$, $-C(Y^1)R^5$, $-C(Y^1)W^5$, $-SO_{M2}R^5$, or $-SO_{M2}W^5$;
$W^5$ is carbocycle or heterocycle wherein $W^5$ is independently substituted with 0 to 3 $R^2$ groups;
$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1;

M12c is 0, 1, 2, 3, 4, 5, 6, 7, 8, 9, 10, 11 or 12;

$X^{50}$ and $X^{51}$ are alkyl groups which may or may not be linked to each other to form a ring as shown by the dotted curve, which alkyl groups may optionally be substituted intra-chain or in a pendant manner with one or more (e.g. 1, 2, 3, or 4) heteroatoms such as nitrogen, oxygen, or halogen; or the identity of the group obtained with a particular $X^{50}$ and $X^{51}$ combination is equal to one that is known from the fluoroquinolone art to produce potent antibacterial activity art;

$X^{52}$ and $X^{53}$ are to be alkyl groups which may or may not be connected covalently to form a ring (e.g. a 5, 6, 7, or 8 membered ring); if they do form a ring they are substituted with at least one heteroatom such as nitrogen, either within the chain (intra-chain) or in a pendant manner, which can serve as a handle for the linkage to the phosphonate moiety; if $X^{52}$ and $X^{53}$ do not form a ring, either or both may be substituted with heteroatoms such as N, O or halogen, wherein one of those heteroatoms, preferably nitrogen, can be used as a linkage element to the phosphonate group;

$X^{54}$ is any alkyl, aryl or aralkyl group, which may be optionally substituted (e.g. in any way as has been shown to produce potent antibacterial activity in any of the fluoroquinolone antibacterial art);

$X^{56}$ and $X^{55}$ are alkyl groups which may be linked to each other to form a ring as shown by the dotted curve, which ring is substituted either in a pendant manner or within the ring itself with a heteroatom, which forms a site onto which $A^0$ is attached; or if $X^{56}$ and $X^{55}$ are not linked together, at least one of $X^{56}$ and $X^{55}$ is a heteroatom-substituted alkyl group and the other is an alkyl group or a heteroatom-substituted alkyl group, wherein one of $X^{56}$ and $X^{55}$ is linked to $A^0$;

$X^{57}$ is oxo (=O), thioxo (=S), or hydroxy (—OH), provided when $X^{57}$ is hydroxy, the second valence on the ring is occupied by H);

$X^{58}$ is H, formyl, or acetyl;

$X^{59}$ and $X^{60}$ are alkyl groups which may be linked to each other to form a ring as shown by the dotted curve, which ring is substituted either in a pendant manner or within the ring itself with a heteroatom, which forms a site onto which $A^0$ can be attached; or if $X^{59}$ and $X^{60}$ are not linked together, at least one of $X^{59}$ and $X^{60}$ is a heteroatom-substituted alkyl group and the other is an alkyl group or a heteroatom-substituted alkyl group, wherein one of $X^{59}$ and $X^{60}$ is linked to $A^0$;

$X^{61}$ is O or NH; and $X^{62}$, $X^{63}$, and $X^{64}$ are each independently H, alkyl, aryl, or arylalkyl.

The invention also provides a pharmaceutical composition comprising an effective amount of a compound of the invention, or a pharmaceutically acceptable salt thereof, in combination with a pharmaceutically acceptable diluent or carrier.

This invention also provides a method of increasing cellular accumulation and retention of an anti-infective agent, thus improving their therapeutic or diagnostic value, comprising linking the anti-infective agent to one or more (e.g. 1, 2, 3, or 4) phosphonates.

The invention also provides a method of inhibiting infection, comprising administering to a mammal afflicted with an infection, an amount of a compound of the invention, effective to inhibit infection.

The invention also provides a compound of the invention for use in medical therapy (preferably for use in inhibiting infection), as well as the use of a compound of the invention for the manufacture of a medicament useful for the treatment of infection.

The invention also provides processes and novel intermediates disclosed herein which are useful for preparing compounds of the invention. Some of the compounds of the invention are useful to prepare other compounds of the invention.

In another aspect of the invention, infection is inhibited by a method comprising the step of treating a sample suspected of containing an infection with a compound or composition of the invention.

In other aspects, novel methods for syntheses of the compounds of this invention are provided.

DETAILED DESCRIPTION OF EXEMPLARY CLAIMS

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

DEFINITIONS

Unless stated otherwise, the following terms and phrases as used herein are intended to have the following meanings:

When tradenames are used herein, applicants intend to independently include the tradename product and the active pharmaceutical ingredient(s) of the tradename product.

"Bioavailability" is the degree to which the pharmaceutically active agent becomes available to the target tissue after the agent's introduction into the body. Enhancement of the bioavailability of a pharmaceutically active agent can provide a more efficient and effective treatment for patients because, for a given dose, more of the pharmaceutically active agent will be available at the targeted tissue sites.

The terms "phosphonate" and "phosphonate group" include functional groups or moieties within a molecule that comprises a phosphorous that is 1) single-bonded to a carbon, 2) double-bonded to a heteroatom, 3) single-bonded to a heteroatom, and 4) single-bonded to another heteroatom, wherein each heteroatom can be the same or different. The terms "phosphonate" and "phosphonate group" also include functional groups or moieties that comprise a phosphorous in the same oxidation state as the phosphorous described above, as well as functional groups or moieties that comprise a prodrug moiety that can separate from a compound so that the compound retains a phosphorous having the characteriatics described above. For example, the terms "phosphonate" and "phosphonate group" include phosphonic acid, phosphonic monoester, phosphonic diester, phosphonamidate, and phosphonthioate functional groups. In one specific embodiment of the invention, the terms "phosphonate" and "phosphonate group" include functional groups or moieties within a molecule that comprises a phosphorous that is 1) single-bonded to a carbon, 2) double-bonded to an oxygen, 3) single-bonded to an oxygen, and 4) single-bonded to another oxygen, as well as functional groups or moieties that comprise a prodrug moiety that can separate from a compound so that the compound retains a phosphorous having such characteristics. In another specific embodiment of the invention, the terms "phosphonate" and "phosphonate group" include functional groups or moieties within a molecule that comprises a phosphorous that is 1) single-bonded to a carbon, 2) double-bonded to an oxygen, 3) single-bonded to an oxygen or nitrogen, and 4) single-bonded to another oxygen or nitrogen, as well as functional groups or moieties that comprise a prodrug moiety that can separate from a compound so that the compound retains a phosphorous having such characteristics.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2OC(=O)R^9$ and acyloxymethyl carbonates —$CH_2OC(=O)OR^9$ where $R^9$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968, 788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2OC(=O)C(CH_3)_3$. An exemplary acyloxymethyl carbonate prodrug moiety is pivaloyloxymethylcarbonate (POC)—$CH_2OC(=O)OC(CH_3)_3$.

The phosphonate group may be a phosphonate prodrug moiety. The prodrug moiety may be sensitive to hydrolysis, such as, but not limited to a pivaloyloxymethyl carbonate (POC) or POM group. Alternatively, the prodrug moiety may be sensitive to enzymatic potentiated cleavage, such as a lactate ester or a phosphonamidate-ester group.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho-or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate the phosphoric acid and the quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958). Cyclic phosphonate esters have also been described as prodrugs of phosphorus-containing compounds (Erion et al., U.S. Pat. No. 6,312,662).

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Any reference to any of the compounds of the invention also includes a reference to a physiologically acceptable salt thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of an hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

"Alkyl" is $C_1$-$C_{18}$ hydrocarbon containing normal, secondary, tertiary or cyclic carbon atoms. Examples are methyl (Me, —$CH_3$), ethyl(Et, —$CH_2CH_3$), 1-propyl(n-Pr, n-propyl, —$CH_2CH_2CH_3$), 2-propyl(i-Pr, i-propyl, —$CH(CH_3)_2$), 1-butyl(n-Bu, n-butyl, —$CH_2CH_2CH_2CH_3$), 2-methyl-1-propyl(i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl(n-pentyl, —$CH_2CH_2CH_2CH_2CH_3$), 2-pentyl (—$CH(CH_3)$ $CH_2CH_2CH_3$), 3-pentyl(—$CH(CH_2CH_3)_2$), 2-methyl-2-butyl(—$C(CH_3)_2CH_2CH_3$), 3-methyl-2-butyl(—$CH(CH_3)CH$ $(CH_3)_2$), 3-methyl-1-butyl(—$CH_2CH_2CH(CH_3)_2$), 2-methyl-1-butyl(—$CH_2CH(CH_3)CH_2CH_3$), 1-hexyl(— $CH_2CH_2CH_2CH_2CH_2CH_3$), 2-hexyl(—$CH(CH_3)$ $CH_2CH_2CH_2CH_3$), 3-hexyl(—$CH(CH_2CH_3)$ $(CH_2CH_2CH_3)$), 2-methyl-2-pentyl(—$C(CH_3)_2$ $CH_2CH_2CH_3$), 3-methyl-2-pentyl(—$CH(CH_3)CH(CH_3)$ $CH_2CH_3$), 4-methyl-2-pentyl(—$CH(CH_3)CH_2CH(CH_3)_2$), 3-methyl-3-pentyl(—$C(CH_3)(CH_2CH_3)_2$), 2-methyl-3-pentyl(—$CH(CH_2CH_3)CH(CH_3)_2$), 2,3-dimethyl-2-butyl(—$C$ $(CH_3)_2CH(CH_3)_2$), 3,3-dimethyl-2-butyl(—$CH(CH_3)C$ $(CH_3)_3$.

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to, ethylene or vinyl (—$CH=CH_2$), allyl(—$CH_2CH=CH_2$), cyclopentenyl(— $C_5H_7$), and 5-hexenyl(—$CH_2$ $CH_2CH_2CH_2CH=CH_2$).

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to, acetylenic (—C≡CH) and propargyl(—$CH_2$C≡CH), "Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—$CH_2$—) 1,2-ethyl(—$CH_2CH_2$—), 1,3-propyl(— $CH_2CH_2CH_2$—), 1,4-butyl(—$CH_2CH_2CH_2CH_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl(—$CH_2$C≡C—), and 4-pentynyl (—$CH_2CH_2CH_2$C≡CH—).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

"Substituted alkyl", "substituted aryl", and "substituted arylalkyl" mean alkyl, aryl, and arylalkyl respectively, in which one or more hydrogen atoms are each independently replaced with a non-hydrogen substituent. Typical substituents include, but are not limited to, —X, —R, —$O^-$, —OR, —SR, —$S^-$, —$NR_2$, —$NR_3$, =NR, —$CX_3$, —CN, —OCN, —SCN, —N=C=O, —NCS, —NO, —$NO_2$, =$N_2$, —$N_3$, NC(=O)R, —C(=O)R, —C(=O)NRR —S(=O)$_2$$O^-$, —S(=O)$_2$OH, —S(=O)$_2$R, —OS(=O)$_2$OR, —S(=O)$_2$ NR, —S(=O)R, —OP(=O)$O_2$RR, —P(=O)$O_2$RR, —P(=O)($O^-$)$_2$, —P(=O)(OH)$_2$, —C(=O)R, —C(=O)X, —C(S)R, —C(O)OR, —C(O)$O^-$, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, protecting group or prodrug moiety. Alkylene, alkenylene, and alkynylene groups may also be similarly substituted.

"Heterocycle" as used herein includes by way of example and not limitation these heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S).

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

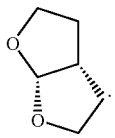

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

"Linker" or "link" refers to a chemical moiety comprising a covalent bond or a chain or group of atoms that covalently attaches a phosphonate group to a drug. Linkers include portions of substituents $A^1$ and $A^3$, which include moieties such as: repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protection. For example, protecting groups for —OH groups (whether hydroxyl, carboxylic acid, phosphonic acid, or other functions) are claims of "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

The phosphonate moieties of the compounds of the invention may or may not be prodrug moieties, i.e. they may or may be susceptible to hydrolytic or enzymatic cleavage or modification. Certain phosphonate moieties are stable under most or nearly all metabolic conditions. For example, a dialkylphosphonate, where the alkyl groups are two or more carbons, may have appreciable stability in vivo due to a slow rate of hydrolysis.

Within the context of phosphonate prodrug moieties, a large number of structurally-diverse prodrugs have been described for phosphonic acids (Freeman and Ross in *Progress in Medicinal Chemistry* 34: 112-147 (1997) and are included within the scope of the present invention. An exemplary phosphonate ester-forming group is the phenyl carbocycle in substructure $A_3$ having the formula:

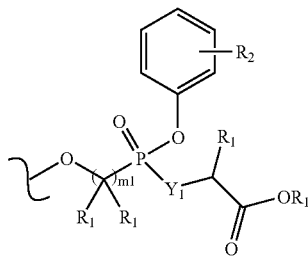

wherein $R_1$ may be H or $C_1$-$C_{12}$ alkyl; m1 is 1, 2, 3, 4, 5, 6, 7 or 8, and the phenyl carbocycle is substituted with 0 to 3 $R_2$ groups. Where $Y_1$ is O, a lactate ester is formed, and where $Y_1$ is $N(R_2)$, $N(OR_2)$ or $N(N(R_2)_2)$, a phosphonamidate ester results.

In its ester-forming role, a protecting group typically is bound to any acidic group such as, by way of example and not limitation, a —$CO_2H$ or —$C(S)OH$ group, thereby resulting in —$CO_2R^x$ where $R^x$ is defined herein. Also, $R^x$ for example includes the enumerated ester groups of WO 95/07920.

Examples of protecting groups include:

$C_3$-$C_{12}$ heterocycle (described above) or aryl. These aromatic groups optionally are polycyclic or monocyclic. Examples include phenyl, spiryl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl, $C_3$-$C_{12}$ heterocycle or aryl substituted with halo, $R^1$, $R^1$—O—$C_1$-$C_{12}$ alkylene, $C_1$-$C_{12}$ alkoxy, CN, $NO_2$, OH, carboxy, carboxyester, thiol, thioester, $C_1$-$C_{12}$ haloalkyl(1-6 halogen atoms), $C_2$-$C_{12}$ alkenyl or $C_2$-$C_{12}$ alkynyl. Such groups include 2-, 3- and 4-alkoxyphenyl ($C_1$-$C_{12}$ alkyl), 2-, 3- and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl), 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3- and 4-haloalkylphenyl (1 to 5 halogen atoms, $C_1$-$C_{12}$ alkyl including 4-trifluoromethylphenyl), 2-, 3- and 4-cyanophenyl, 2-, 3- and 4-nitrophenyl, 2-, 3- and 4-haloalkylbenzyl (1 to 5 halogen atoms, $C_1$-$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, alkylsalicylphenyl($C_1$-$C_4$ alkyl, including 2-, 3- and 4-ethylsalicylphenyl), 2-,3- and 4-acetylphenyl, 1,8-dihydroxynaphthyl(—$C_{10}H_6$—OH) and aryloxy ethyl [$C_6$-$C_9$ aryl (including phenoxy ethyl)], 2,2'-dihydroxybiphenyl, 2-, 3- and 4-N,N-dialkylaminophenol, —$C_6H_4CH_2$—$N(CH_3)_2$, trimethoxybenzyl, triethoxybenzyl, 2-alkyl pyridinyl($C_{1-4}$ alkyl);

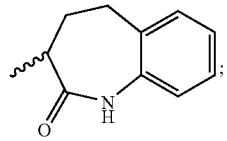

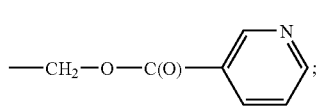

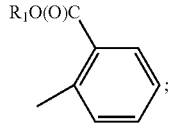

$C_4$-$C_8$ ester of 2-carboxyphenyl; and $C_1$-$C_4$ alkylene-$C_3$-$C_6$ aryl (including benzyl, —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl) substituted in the aryl moiety by 3 to 5 halogen atoms or 1 to 2 atoms or groups selected from halogen, $C_1$-$C_{12}$ alkoxy (including methoxy and ethoxy), cyano, nitro, OH, $C_1$-$C_{12}$ haloalkyl (1 to 6 halogen atoms; including —$CH_2CCl_3$), $C_1$-$C_{12}$ alkyl (including methyl and ethyl), $C_2$-$C_{12}$ alkenyl or $C_2$-$C_{12}$ alkynyl; alkoxy ethyl [C$_1$-C$_6$ alkyl including —CH$_2$—CH$_2$—O—CH$_3$ (methoxy ethyl)]; alkyl substituted by any of the groups set forth above for aryl, in particular OH or by 1 to 3 halo atoms (including —CH$_3$, —CH(CH$_3$)$_2$, —C(CH$_3$)$_3$, —CH$_2$CH$_3$, —(CH$_2$)$_2$CH$_3$, —(CH$_2$)$_3$CH$_3$, —(CH$_2$)$_4$CH$_3$, —(CH$_2$)$_5$CH$_3$, —CH$_2$CH$_2$F, —CH$_2$CH$_2$Cl, —CH$_2$CF$_3$, and —CH$_2$CCl$_3$);

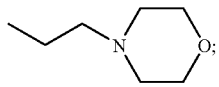

—N-2-propylmorpholino, 2,3-dihydro-6-hydroxyindene, sesamol, catechol monoester, —CH$_2$—C(O)—N(R$^1$)$_2$, —CH$_2$—S(O)(R$^1$), —CH$_2$—S(O)$_2$(R$^1$), —CH$_2$—CH(OC(O)CH$_2$R$^1$)—CH$_2$(OC(O)CH$_2$R$^1$), cholesteryl, enolpyruvate (HOOC—C(=CH$_2$)—), glycerol;

a 5 or 6 carbon monosaccharide, disaccharide or oligosaccharide (3 to 9 monosaccharide residues);

triglycerides such as α-D-β-diglycerides (wherein the fatty acids composing glyceride lipids generally are naturally occurring saturated or unsaturated C$_{6-26}$, C$_{6-18}$ or C$_{6-10}$ fatty acids such as linoleic, lauric, myristic, palmitic, stearic, oleic, palmitoleic, linolenic and the like fatty acids) linked to acyl of the parental compounds herein through a glyceryl oxygen of the triglyceride;

phospholipids linked to the carboxyl group through the phosphate of the phospholipid;

phthalidyl (shown in FIG. 1 of Clayton et al., *Antimicrob. Agents Chemo.* (1974) 5(6):670-671;

cyclic carbonates such as (5-R$_d$-2-oxo-1,3-dioxolen-4-yl) methyl esters (Sakamoto et al., *Chem. Pharm. Bull.* (1984) 32(6)2241-2248) where R$_d$ is R$_1$, R$_4$ or aryl; and

The hydroxyl groups of the compounds of this invention optionally are substituted with one of groups III, IV or V disclosed in WO 94/21604, or with isopropyl.

Table A lists examples of protecting group ester moieties that for example can be bonded via oxygen to —C(O)O— and —P(O)(O—)$_2$ groups. Several amidates also are shown, which are bound directly to —C(O)— or —P(O)$_2$. Esters of structures 1-5,8-10 and 16, 17, 19-22 are synthesized by reacting the compound herein having a free hydroxyl with the corresponding halide (chloride or acyl chloride and the like) and N,N-dicyclohexyl-N-morpholine carboxamidine (or another base such as DBU, triethylamine, CsCO$_3$, N,N-dimethylaniline and the like) in DMF (or other solvent such as acetonitrile or N-methylpyrrolidone). When the compound to be protected is a phosphonate, the esters of structures 5-7, 11, 12, 21, and 23-26 are synthesized by reaction of the alcohol or alkoxide salt (or the corresponding amines in the case of compounds such as 13, 14 and 15) with the monochlorophosphonate or dichlorophosphonate (or another activated phosphonate).

TABLE A

| 1. | —CH$_2$—C(O)—N(R$_1$)$_2$* |
|---|---|
| 2. | —CH$_2$—S(O)(R$_1$) |

TABLE A-continued

| 3. | —CH$_2$—S(O)$_2$(R$_1$) |
|---|---|
| 4. | —CH$_2$—O—C(O)—CH$_2$—C$_6$H$_5$ |
| 5. | 3-cholesteryl |
| 6. | 3-pyridyl |
| 7. | N-ethylmorpholino |
| 8. | —CH$_2$—O—C(O)—C$_6$H$_5$ |
| 9. | —CH$_2$—O—C(O)—CH$_2$CH$_3$ |
| 10. | —CH$_2$—O—C(O)—C(CH$_3$)$_3$ |
| 11. | —CH$_2$—CCl$_3$ |
| 12. | —C$_6$H$_5$ |
| 13. | —NH—CH$_2$—C(O)O—CH$_2$CH$_3$ |
| 14. | —N(CH$_3$)—CH$_2$—C(O)O—CH$_2$CH$_3$ |
| 15. | —NHR$_1$ |
| 16. | —CH$_2$—O—C(O)—C$_{10}$H$_{15}$ |
| 17. | —CH$_2$—O—C(O)—CH(CH$_3$)$_2$ |
| 18. | —CH$_2$—C#H(OC(O)CH$_2$R$_1$)—CH$_2$—(OC(O)CH$_2$R$_1$)* |
| 19. |  |
| 20. | 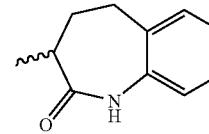 |
| 21. | 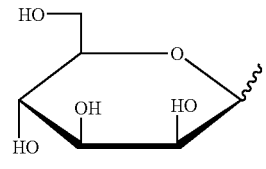 |
| 22. | 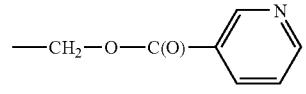 |
| 23. | 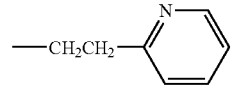 |
| 24. | 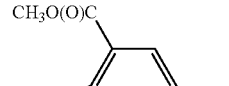 |
| 25. | 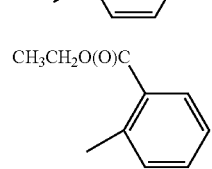 |
| 26. | 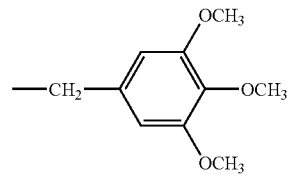 |

\# - chiral center is (R), (S) or racemate.

Other esters that are suitable for use herein are described in EP 632048.

Protecting groups also includes "double ester" forming profunctionalities such as —CH$_2$OC(O)OCH$_3$,

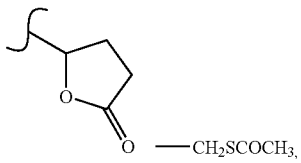

—CH$_2$OCON(CH$_3$)$_2$, or alkyl- or aryl-acyloxyalkyl groups of the structure —CH(R$^1$ or W$^5$)O((CO)R$^{37}$) or —CH(R$^1$ or W$^5$)((CO)OR$^{38}$) (linked to oxygen of the acidic group) wherein R$^{37}$ and R$^{38}$ are alkyl, aryl, or alkylaryl groups (see U.S. Pat. No. 4,968,788). Frequently R$^{37}$ and R$^{38}$ are bulky groups such as branched alkyl, ortho-substituted aryl, meta-substituted aryl, or combinations thereof, including normal, secondary, iso- and tertiary alkyls of 1-6 carbon atoms. An example is the pivaloyloxymethyl group. These are of particular use with prodrugs for oral administration. Examples of such useful protecting groups are alkylacyloxymethyl esters and their derivatives, including —CH(CH$_2$CH$_2$OCH$_3$)OC(O)C(CH$_3$)$_3$,

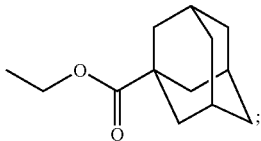

—CH$_2$OC(O)C$_{10}$H$_{15}$, —CH$_2$OC(O)C(CH$_3$)$_3$, —CH(CH$_2$OCH$_3$)OC(O)C(CH$_3$)$_3$, —CH(CH(CH$_3$)$_2$)OC(O)C(CH$_3$)$_3$, —CH$_2$OC(O)CH$_2$CH(CH$_3$)$_2$, —CH$_2$OC(O)C$_6$H$_{11}$, —CH$_2$OC(O)C$_6$H$_5$, —CH$_2$OC(O)C$_{10}$H$_{15}$, —CH$_2$OC(O)CH$_2$CH$_3$, —CH$_2$OC(O)CH(CH$_3$)$_2$, —CH$_2$OC(O)C(CH$_3$)$_3$ and —CH$_2$OC(O)CH$_2$C$_6$H$_5$.

In some claims the protected acidic group is an ester of the acidic group and is the residue of a hydroxyl-containing functionality. In other claims, an amino compound is used to protect the acid functionality. The residues of suitable hydroxyl or amino-containing functionalities are set forth above or are found in WO 95/07920. Of particular interest are the residues of amino acids, amino acid esters, polypeptides, or aryl alcohols. Typical amino acid, polypeptide and carboxyl-esterified amino acid residues are described on pages 11-18 and related text of WO 95/07920 as groups L1 or L2. WO 95/07920 expressly teaches the amidates of phosphonic acids, but it will be understood that such amidates are formed with any of the acid groups set forth herein and the amino acid residues set forth in WO 95/07920.

Typical esters for protecting acidic functionalities are also described in WO 95/07920, again understanding that the same esters can be formed with the acidic groups herein as with the phosphonate of the '920 publication. Typical ester groups are defined at least on WO 95/07920 pages 89-93 (under R$^{31}$ or R$^{35}$), the table on page 105, and pages 21-23 (as R). Of particular interest are esters of unsubstituted aryl such as phenyl or arylalkyl such benzyl, or hydroxy-, halo-, alkoxy-, carboxy- and/or alkylestercarboxy-substituted aryl or alkylaryl, especially phenyl, ortho-ethoxyphenyl, or C$_1$-C$_4$ alkylestercarboxyphenyl (salicylate C$_1$-C$_{12}$ alkylesters).

The protected acidic groups, particularly when using the esters or amides of WO 95/07920, are useful as prodrugs for oral administration. However, it is not essential that the acidic group be protected in order for the compounds of this invention to be effectively administered by the oral route. When the compounds of the invention having protected groups, in particular amino acid amidates or substituted and unsubstituted aryl esters are administered systemically or orally they are capable of hydrolytic cleavage in vivo to yield the free acid.

One or more of the acidic hydroxyls are protected. If more than one acidic hydroxyl is protected then the same or a different protecting group is employed, e.g., the esters may be different or the same, or a mixed amidate and ester may be used.

Typical hydroxy protecting groups described in Greene (pages 14-118) include substituted methyl and alkyl ethers, substituted benzyl ethers, silyl ethers, esters including sulfonic acid esters, and carbonates. For example:

Ethers (methyl, t-butyl, allyl);

Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydropthiopyranyl, 1-Methoxycyclohexyl, 4-Methoxytetrahydropyranyl, 4-Methoxytetrahydrothiopyranyl, 4-Methoxytetrahydropthiopyranyl S,S-Dioxido, 1-[(2-Chloro-4-methyl)phenyl]-4-methoxypiperidin-4-yl, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl));

Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl) ethyl, p-Chlorophenyl, p-Methoxyphenyl, 2,4-Dinitrophenyl, Benzyl);

Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, α-Naphthyldiphenylmethyl, p-methoxyphenyldiphenylmethyl, Di(p-methoxyphenyl) phenylmethyl, Tri(p-methoxyphenyl)methyl, 4-(4'-Bromophenacyloxy)phenyldiphenylmethyl, 4,4',4"-Tris(4,5-dichlorophthalimidophenyl)methyl, 4,4',4"-Tris (levulinoyloxyphenyl)methyl, 4,4',4"-Tris (benzoyloxyphenyl)methyl, 3-(Imidazol-1-ylmethyl)bis (4',4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido);

Silyl Ethers (Trimethylsilyl, Triethylsilyl, Triisopropylsilyl, Dimethylisopropylsilyl, Diethylisopropylsilyl, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl);

Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate));

Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate);

Groups With Assisted Cleavage (2-Iodobenzoate, 4-Azidobutyrate, 4-Nitro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3 tetramethylbutyl)phenoxyacetate, 2,4-Bis(1,1-dimethylpropyl)phenoxyacetate, Chlorodiphenylacetate, Isobutyrate, Monosuccinate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

Typical 1,2-diol protecting groups (thus, generally where two OH groups are taken together with the protecting functionality) are described in Greene at pages 118-142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table B, still more typically, epoxides, acetonides, cyclic ketals and aryl acetals.

TABLE B

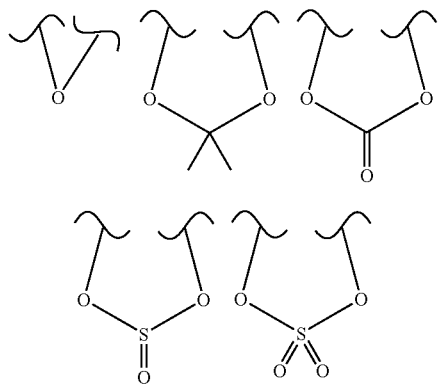

TABLE B-continued

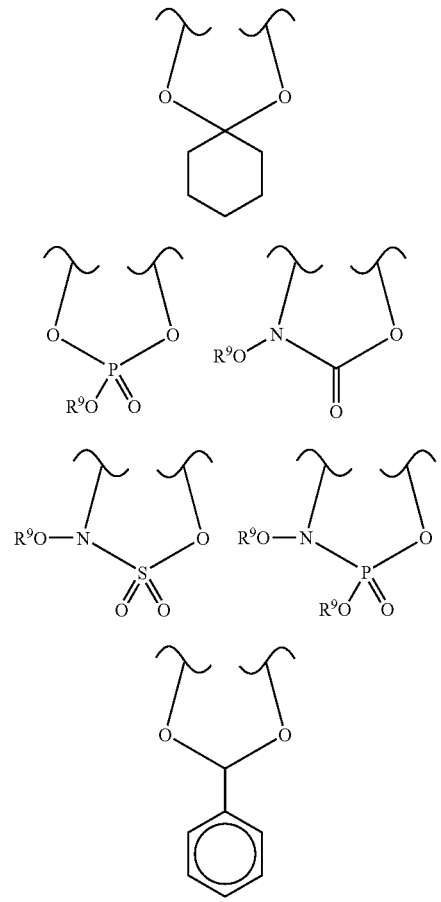

wherein $R^9$ is $C_1$–$C_6$ alkyl.

Amino Protecting Groups

Another set of protecting groups include any of the typical amino protecting groups described by Greene at pages 315-385. They include:

Carbamates: (methyl and ethyl, 9-fluorenylmethyl, 9(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, 4-methoxyphenacyl);

Substituted Ethyl: (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl);

Groups With Assisted Cleavage: (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl);

Groups Capable of Photolytic Cleavage: (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl);

Miscellaneous Carbamates: (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-Iodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl);

Amides: (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl);

Amides With Assisted Cleavage: (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one);

Cyclic Imide Derivatives: (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3-5-triazacyclohexan-2-one, 1-substituted 3,5-dinitro-4-pyridonyl);

N-Alkyl and N-Aryl Amines: (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide);

Imine Derivatives: (N-1,1-dimethylthiomethylene, N-benzylidene, N-p-methoxybenylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenylmethylene, N-cyclohexylidene);

Enamine Derivatives: (N-(5,5-dimethyl-3-oxo-1-cyclohexenyl));

N-Metal Derivatives (N-borane derivatives, N-diphenylborinic acid derivatives, N-[phenyl(pentacarbonylchromium- or -tungsten)]carbenyl, N-copper or N-zinc chelate);

N—N Derivatives: (N-nitro, N-nitroso, N-oxide);

N—P Derivatives: (N-diphenylphosphinyl, N-dimethylthiophosphinyl, N-diphenylthiophosphinyl, N-dialkyl phosphoryl, N-dibenzyl phosphoryl, N-diphenyl phosphoryl);

N—Si Derivatives, N—S Derivatives, and N-Sulfenyl Derivatives: (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl).

More typically, protected amino groups include carbamates and amides, still more typically, —NHC(O)$R^1$ or —N=CR$^1$N(R$^1$)$_2$. Another protecting group, also useful as a prodrug for amino or —NH(R$^5$), is:

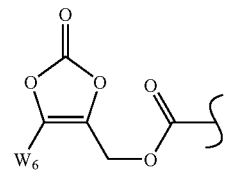

See, for example, Alexander, J. et al. (1996) *J. Med. Chem.* 39:480-486.

Amino Acid and Polypeptide Protecting Group and Conjugates

An amino acid or polypeptide protecting group of a compound of the invention has the structure $R^{15}$NHCH($R^{16}$)C(O)—, where $R^{15}$ is H, an amino acid or polypeptide residue, or $R^5$, and $R^{16}$ is defined below.

$R^{16}$ is lower alkyl or lower alkyl($C_1$-$C_6$) substituted with amino, carboxyl, amide, carboxyl ester, hydroxyl, $C_6$-$C_7$ aryl, guanidinyl, imidazolyl, indolyl, sulfhydryl, sulfoxide, and/or alkylphosphate. $R^{10}$ also is taken together with the amino acid α N to form a proline residue ($R^{10}$ =—CH$_2$)$_3$—). However, $R^{10}$ is generally the side group of a naturally-occurring amino acid such as H, —CH$_3$, —CH(CH$_3$)$_2$, —CH$_2$—CH(CH$_3$)$_2$, —CHCH$_3$—CH$_2$—CH$_3$, —CH$_2$—C$_6$H$_5$, —CH$_2$CH$_2$—S—CH$_3$, —CH$_2$OH, —CH(OH)—CH$_3$, —CH$_2$—SH, —CH$_2$—C$_6$H$_4$OH, —CH$_2$—CO—NH$_2$, —CH$_2$—CH$_2$—CO—NH$_2$, —CH$_2$—COOH, —CH$_2$—CH$_2$—COOH, —(CH$_2$)$_4$—NH$_2$ and —(CH$_2$)$_3$—NH—C(NH$_2$)—NH$_2$. $R_{10}$ also includes 1-guanidinoprop-3-yl, benzyl, 4-hydroxybenzyl, imidazol-4-yl, indol-3-yl, methoxyphenyl and ethoxyphenyl.

Another set of protecting groups include the residue of an amino-containing compound, in particular an amino acid, a polypeptide, a protecting group, —NHSO$_2$R, NHC(O)R, —N(R)$_2$, NH$_2$ or —NH(R)(H), whereby for example a carboxylic acid is reacted, i.e. coupled, with the amine to form an amide, as in C(O)NR$_2$. A phosphonic acid may be reacted with the amine to form a phosphonamidate, as in —P(O)(OR)(NR$_2$).

In general, amino acids have the structure $R^{17}$C(O)CH($R^{16}$)NH—, where $R^{17}$ is —OH, —OR, an amino acid or a polypeptide residue. Amino acids are low molecular weight compounds, on the order of less than about 1000 MW and which contain at least one amino or imino group and at least one carboxyl group. Generally the amino acids will be found in nature, i.e., can be detected in biological material such as bacteria or other microbes, plants, animals or man. Suitable amino acids typically are alpha amino acids, i.e. compounds characterized by one amino or imino nitrogen atom separated from the carbon atom of one carboxyl group by a single substituted or unsubstituted alpha carbon atom. Of particular interest are hydrophobic residues such as mono-or di-alkyl or aryl amino acids, cycloalkylamino acids and the like. These residues contribute to cell permeability by increasing the partition coefficient of the parental drug. Typically, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Additionally, unnatural amino acids, for example, valanine, phenylglycine and homoarginine are also included. Commonly encountered amino acids that are not gene-encoded may also be used in the present invention. All of the amino acids used in the present invention may be either the D- or L-optical isomer. In addition, other peptidomimetics are also useful in the present invention. For a general review, see Spatola, A. F., in *Chemistry and Biochemistry of Amino Acids, Peptides and Proteins*, B. Weinstein, eds., Marcel Dekker, New York, p. 267 (1983).

When protecting groups are single amino acid residues or polypeptides they optionally are substituted at $R^3$ of substituents $A^1$, $A^2$ or $A^3$ in a compound the invention. These conjugates are produced by forming an amide bond between a carboxyl group of the amino acid (or C-terminal amino acid of a polypeptide for example). Similarly, conjugates are formed between $R^3$ and an amino group of an amino acid or polypeptide. Generally, only one of any site in the parental molecule is amidated with an amino acid as described herein, although it is within the scope of this invention to introduce amino acids at more than one permitted site. Usually, a carboxyl group of $R^3$ is amidated with an amino acid. In general, the α-amino or α-carboxyl group of the amino acid or the terminal amino or carboxyl group of a polypeptide are bonded to the parental functionalities, i.e., carboxyl or amino groups in the amino acid side chains generally are not used to form the amide bonds with the parental compound (although these groups may need to be protected during synthesis of the conjugates as described further below).

With respect to the carboxyl-containing side chains of amino acids or polypeptides it will be understood that the carboxyl group optionally will be blocked, e.g., by $R^1$, esterified with $R^5$ or amidated. Similarly, the amino side chains $R^{16}$ optionally will be blocked with $R^1$ or substituted with $R^5$.

Such ester or amide bonds with side chain amino or carboxyl groups, like the esters or amides with the parental molecule, optionally are hydrolyzable in vivo or in vitro under acidic (pH <3) or basic (pH >10) conditions. Alternatively, they are substantially stable in the gastrointestinal tract of humans but are hydrolyzed enzymatically in blood or in intracellular environments. The esters or amino acid or polypeptide amidates also are useful as intermediates for the preparation of the parental molecule containing free amino or carboxyl groups. The free acid or base of the parental compound, for example, is readily formed from the esters or amino acid or polypeptide conjugates of this invention by conventional hydrolysis procedures.

When an amino acid residue contains one or more chiral centers, any of the D, L, meso, threo or erythro (as appropriate) racemates, scalemates or mixtures thereof may be used. In general, if the intermediates are to be hydrolyzed non-enzymatically (as would be the case where the amides are used as chemical intermediates for the free acids or free amines), D isomers are useful. On the other hand, L isomers are more versatile since they can be susceptible to both non-enzymatic and enzymatic hydrolysis, and are more efficiently transported by amino acid or dipeptidyl transport systems in the gastrointestinal tract.

Examples of suitable amino acids whose residues are represented by $R^x$ or $R^y$ include the following:

Glycine;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β, γ-dihydroxyglutamic acid, β-phenylglutamic acid, γ-methyleneglutamic acid, 3-aminoadipic acid, 2-aminopimelic acid, 2-aminosuberic acid and 2-aminosebacic acid;

Amino acid amides such as glutamine and asparagine;

Polyamino- or polybasic-monocarboxylic acids such as arginine, lysine, β-aminoalanine, γ-aminobutyrine, ornithine, citruline, homoarginine, homocitrulline, hydroxylysine, allohydroxylsine and diaminobutyric acid;

Other basic amino acid residues such as histidine;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid;

Imino acids such as proline, hydroxyproline, allohydroxyproline, γ-methylproline, pipecolic acid, 5-hydroxypipecolic acid, and azetidine-2-carboxylic acid;

A mono- or di-alkyl (typically $C_1$-$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid, isoleucine, alloisoleucine, tert-leucine, β-methyltryptophan and α-amino-β-ethyl-β-phenylpropionic acid;

β-phenylserinyl;

Aliphatic α-amino-β-hydroxy acids such as serine, β-hydroxyleucine, β-hydroxynorleucine, β-hydroxynorvaline, and α-amino-β-hydroxystearic acid;

α-Amino, α-, γ-, δ- or ε-hydroxy acids such as homoserine, δ-hydroxynorvaline, γ-hydroxynorvaline and ε-hydroxynorleucine residues; canavine and canaline; γ-hydroxyornithine;

2-hexosaminic acids such as D-glucosaminic acid or D-galactosaminic acid;

α-Amino-β-thiols such as penicillamine, β-thiolnorvaline or β-thiolbutyrine;

Other sulfur containing amino acid residues including cysteine; homocystine, β-phenylmethionine, methionine, S-allyl-L-cysteine sulfoxide, 2-thiolhistidine, cystathionine, and thiol ethers of cysteine or homocysteine;

Phenylalanine, tryptophan and ring-substituted α-amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4, 6-trimethyl-, 2-ethoxy-5-nitro-, 2-hydroxy-5-nitro- and p-nitro-phenylalanine); furyl-, thienyl-, pyridyl-, pyrimidinyl-, purinyl- or naphthyl-alanines; and tryptophan analogues and derivatives including kynurenine, 3-hydroxykynurenine, 2-hydroxytryptophan and 4-carboxytryptophan;

α-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acids including serine, threonine, allothreonine, phosphoserine and phosphothreonine.

Polypeptides are polymers of amino acids in which a carboxyl group of one amino acid monomer is bonded to an amino or imino group of the next amino acid monomer by an amide bond. Polypeptides include dipeptides, low molecular weight polypeptides (about 1500-5000 MW) and proteins. Proteins optionally contain 3, 5, 10, 50, 75, 100 or more residues, and suitably are substantially sequence-homologous with human, animal, plant or microbial proteins. They include enzymes (e.g., hydrogen peroxidase) as well as immunogens such as KLH, or antibodies or proteins of any type against which one wishes to raise an immune response. The nature and identity of the polypeptide may vary widely.

The polypeptide amidates are useful as immunogens in raising antibodies against either the polypeptide (if it is not immunogenic in the animal to which it is administered) or against the epitopes on the remainder of the compound of this invention.

Antibodies capable of binding to the parental non-peptidyl compound are used to separate the parental compound from mixtures, for example in diagnosis or manufacturing of the parental compound. The conjugates of parental compound and polypeptide generally are more immunogenic than the polypeptides in closely homologous animals, and therefore make the polypeptide more immunogenic for facilitating raising antibodies against it. Accordingly, the polypeptide or protein may not need to be immunogenic in an animal typically used to raise antibodies, e.g., rabbit, mouse, horse, or rat, but the final product conjugate should be immunogenic in at least one of such animals. The polypeptide optionally contains a peptidolytic enzyme cleavage site at the peptide bond between the first and second residues adjacent to the acidic heteroatom. Such cleavage sites are flanked by enzymatic recognition structures, e.g., a particular sequence of residues recognized by a peptidolytic enzyme.

Peptidolytic enzymes for cleaving the polypeptide conjugates of this invention are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide (having a given pair of residues and a free carboxyl terminus) is covalently bonded through its α-amino group to the phosphorus or carbon atoms of the compounds herein. In claims where $W_1$ is phosphonate it is expected that this peptide will be cleaved by the appropriate peptidolytic enzyme, leaving the carboxyl of the proximal amino acid residue to autocatalytically cleave the phosphonoamidate bond.

Suitable dipeptidyl groups (designated by their single letter code) are AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, F, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Tripeptide residues are also useful as protecting groups. When a phosphonate is to be protected, the sequence —$X^4$-pro-$X^5$— (where $X^4$ is any amino acid residue and $X^5$ is an amino acid residue, a carboxyl ester of proline, or hydrogen) will be cleaved by luminal carboxypeptidase to yield $X^4$ with a free carboxyl, which in turn is expected to autocatalytically cleave the phosphonoamidate bond. The carboxy group of $X^5$ optionally is esterified with benzyl.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J. P. F., (1992) *Pharm Res.* 9:969-978). Transport competent peptides can thus be used to enhance bioavailability of the amidate compounds. Di- or tripeptides having one or more amino acids in the D configuration are also compatible with peptide transport and can be utilized in the amidate compounds of this invention. Amino acids in the D configuration can be used to reduce the susceptibility of a di- or tripeptide to hydrolysis by proteases common to the brush border such as aminopeptidase N. In addition, di- or tripeptides alternatively are selected on the basis of their relative resistance to hydrolysis by proteases found in the lumen of the intestine. For example, tripeptides or polypeptides lacking asp and/or glu are poor substrates for aminopeptidase A, di- or tripeptides lacking amino acid residues on the N-terminal side of hydrophobic amino acids (leu, tyr, phe, val, trp) are poor substrates for endopeptidase, and peptides lacking a pro residue at the penultimate position at a free carboxyl terminus are poor substrates for carboxypeptidase P. Similar considerations can also be applied to the selection of peptides that are either relatively resistant or relatively susceptible to hydrolysis by cytosolic, renal, hepatic, serum or other peptidases. Such poorly cleaved polypeptide amidates are immunogens or are useful for bonding to proteins in order to prepare immunogens.

Specific Embodiments of the Invention

Specific values described for radicals, substituents, and ranges, as well as specific embodiments of the invention described herein, are for illustration only; they do not exclude other defined values or other values within defined ranges.

In one specific embodiment of the invention, the conjugate is a compound that is substituted with one or more phosphonate groups either directly or indirectly through a linker; and that is optionally substituted with one or more groups $A^0$; or a pharmaceutically acceptable salt thereof, wherein:

$A^0$ is $A^1$, $A^2$ or $W^3$;

$A^1$ is:

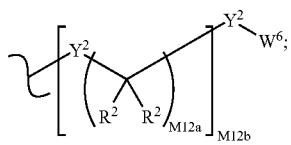

$A^2$ is:

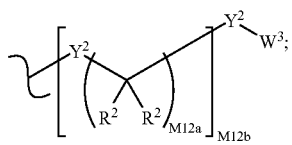

$A^3$ is:

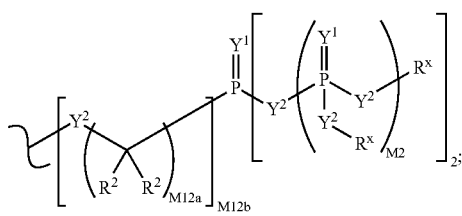

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$;

$R^x$ is independently H, $R^1$, $W^3$, a protecting group, or the formula:

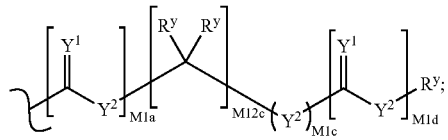

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, $-CN$, $N_3$ or $-NO_2$;

$R^{3b}$ is $Y^1$;

$R^{3c}$ is $-R^x$, $N(R^x)(R^x)$, $-SR^x$, $-S(O)R^x$, $-S(O)_2R^x$, $-S(O)(OR^x)$, $-S(O)_2(OR^x)$, $-OC(Y^1)R^x$, $-OC(Y^1)OR^x$, $-OC(Y^1)(N(R^x)(R^x))$, $-SC(Y^1)R^x$, $-SC(Y^1)OR^x$, $-SC(Y^1)(N(R^x)(R^x))$, $-N(R^x)C(Y^1)R^x$, $-N(R^x)C(Y^1)OR^x$, or $-N(R^x)C(Y^1)(N(R^x)(R^x))$;

$R^{3d}$ is $-C(Y^1)R^x$, $-C(Y^1)OR^x$ or $-C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, $-C(Y^1)R^5$, $-C(Y^1)W^5$, $-SO_2R^5$, or $-SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In another specific embodiment of the invention $A^1$ is of the formula:

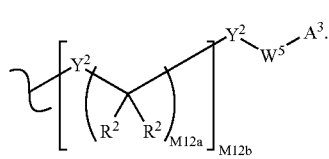

In another specific embodiment of the invention $A^1$ is of the formula:

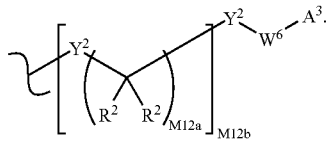

In another specific embodiment of the invention $A^1$ is of the formula:

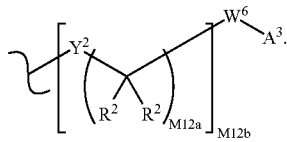

In another specific embodiment of the invention $A^1$ is of the formula:

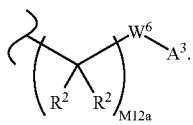

In another specific embodiment of the invention $A^1$ is of the formula:

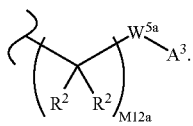

and $W^{5a}$ is a carbocycle or a heterocycle where $W^{5a}$ is independently substituted with 0 or 1 $R^2$ groups. A specific velue for M12a is 1.

In another specific embodiment of the invention $A^1$ is of the formula:

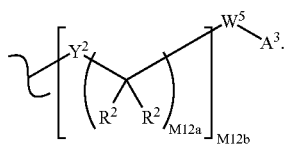

In another specific embodiment of the invention $A^1$ is of the formula:

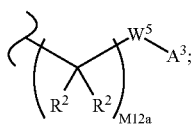

In another specific embodiment of the invention $A^1$ is of the formula:

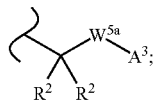

wherein $W^{5a}$ is a carbocycle independently substituted with 0 or 1 $R^2$ groups;

In another specific embodiment of the invention $A^1$ is of the formula:

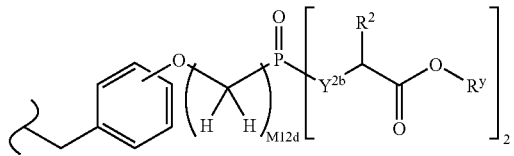

wherein $Y^{2b}$ is O or $N(R^2)$; and M12d is 1, 2, 3, 4, 5, 6, 7 or 8.

In another specific embodiment of the invention $A^1$ is of the formula:

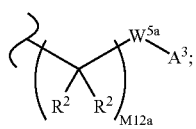

wherein $W^{5a}$ is a carbocycle independently substituted with 0 or 1 $R^2$ groups;

In another specific embodiment of the invention $A^1$ is of the formula:

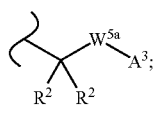

wherein $W^{5a}$ is a carbocycle or heterocycle where $W^{5a}$ is independently substituted with 0 or 1 $R^2$ groups.

In another specific embodiment of the invention $A^1$ is of the formula:

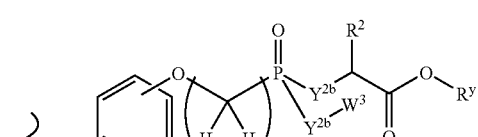

wherein $Y^{2b}$ is O or $N(R^2)$; and M12d is 1, 2, 3, 4, 5, 6, 7 or 8.

In a specific embodiment of the invention $A^2$ is of the formula:

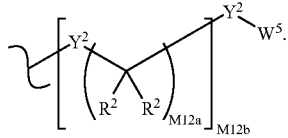

In another specific embodiment of the invention $A^2$ is of the formula:

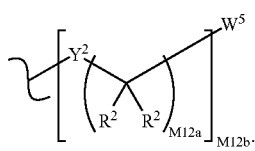

In another specific embodiment of the invention M12b is 1.

In another specific embodiment of the invention e M12b is 0, $Y^2$ is a bond and $W^5$ is a carbocycle or heterocycle where $W^5$ is optionally and independently substituted with 1, 2, or 3 $R^2$ groups.

In another specific embodiment of the invention $A^2$ is of the formula:

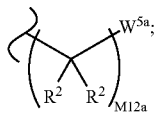

wherein $W^{5a}$ is a carbocycle or heterocycle where $W^{5a}$ is optionally and independently substituted with 1, 2, or 3 $R^2$ groups.

In another specific embodiment of the invention M12a is 1.

In another specific embodiment of the invention $A^2$ is selected from phenyl, substituted phenyl, benzyl, substituted benzyl, pyridyl and substituted pyridyl.

In another specific embodiment of the invention $A^2$ is of the formula:

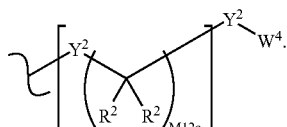

In another specific embodiment of the invention $A^2$ is of the formula:

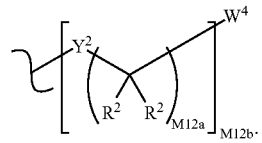

In another specific embodiment of the invention M12b is 1.

In a specific embodiment of the invention $A^3$ is of the formula:

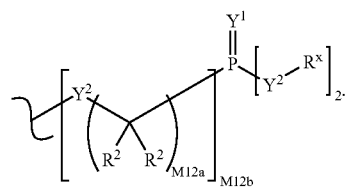

In another specific embodiment of the invention $A^3$ is of the formula:

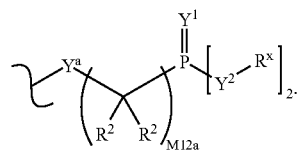

In another specific embodiment of the invention $A^3$ is of the formula:

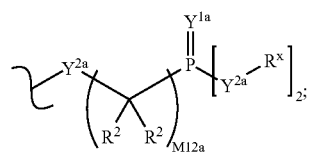

wherein $Y^{1a}$ is O or S; and $Y^{2a}$ is O, N($R^x$) or S.

In another specific embodiment of the invention $A^3$ is of the formula:

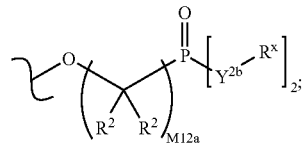

wherein $Y^{2b}$ is O or N($R^x$).

In another specific embodiment of the invention $A^3$ is of the formula:

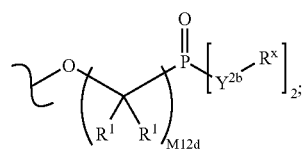

wherein $Y^{2b}$ is O or N($R^x$); and M12d is 1, 2, 3, 4, 5, 6, 7 or 8.

In another specific embodiment of the invention $A^3$ is of the formula:

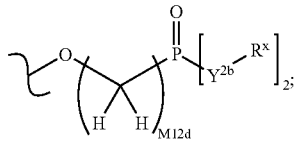

wherein $Y^{2b}$ is O or $N(R^x)$; and M12d is 1, 2, 3, 4, 5, 6, 7 or 8.

In another specific embodiment of the invention M12d is 1.

In another specific embodiment of the invention $A^3$ is of the formula:

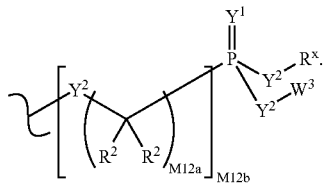

In another specific embodiment of the invention $A^3$ is of the formula:

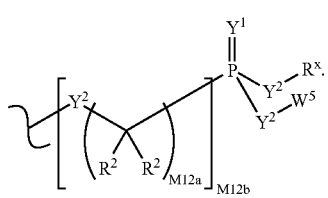

In another specific embodiment of the invention $W^5$ is a carbocycle.

In another specific embodiment of the invention $A^3$ is of the formula:

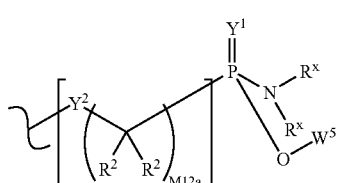

In another specific embodiment of the invention $W^5$ is phenyl.

In another specific embodiment of the invention $A^3$ is of the formula:

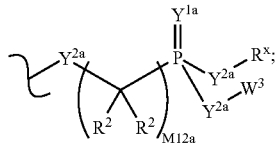

wherein $Y^{1a}$ is O or S; and $Y^{2a}$ is O, $N(R^x)$ or S.

In another specific embodiment of the invention $A^3$ is of the formula:

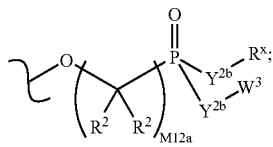

wherein $Y^{2b}$ is O or $N(R^x)$.

In another specific embodiment of the invention $A^3$ is of the formula:

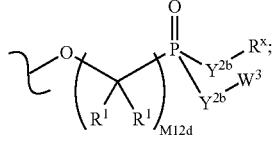

wherein $Y^{2b}$ is O or $N(R^x)$; and M12d is 1, 2, 3, 4, 5, 6, 7 or 8.

In another specific embodiment of the invention $R^1$ is H.

In another specific embodiment of the invention $A^3$ is of the formula:

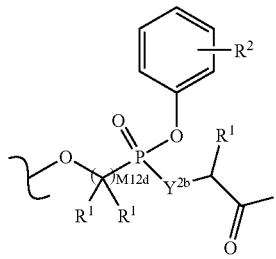

wherein the phenyl carbocycle is substituted with 0, 1, 2, or 3 $R^2$ groups.

In another specific embodiment of the invention $A^3$ is of the formula:

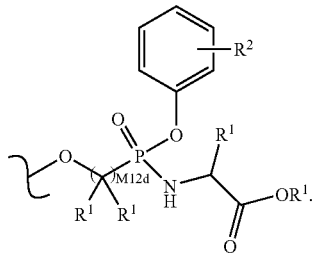

In another specific embodiment of the invention $A^3$ is of the formula:

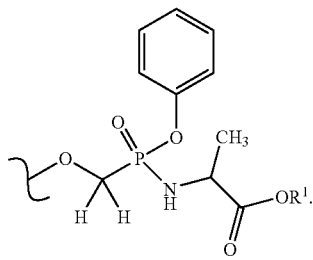

In another specific embodiment of the invention $A^3$ is of the formula:

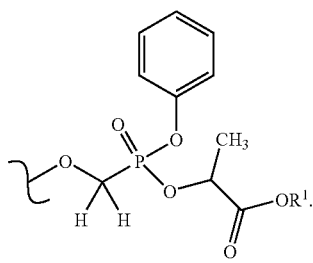

In another specific embodiment of the invention $A^3$ is of the formula:

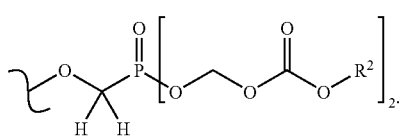

In another specific embodiment of the invention $A^3$ is of the formula:

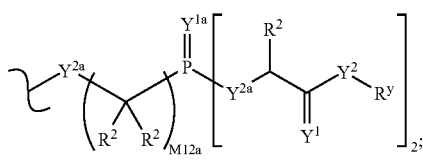

wherein $Y^{1a}$ is O or S; and $Y^{2a}$ is O, $N(R^2)$ or S.

In another specific embodiment of the invention $A^3$ is of the formula:

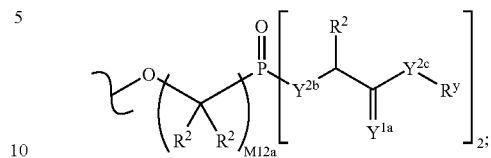

wherein $Y^{1a}$ is O or S; $Y^{2b}$ is O or $N(R^2)$; and $Y^{2c}$ is O, $N(R^y)$ or S.

In another specific embodiment of the invention $A^3$ is of the formula:

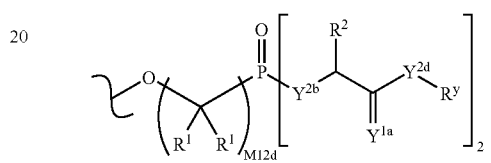

wheren $Y^{1a}$ is O or S; $Y^{2b}$ is O or $N(R^2)$; $Y^{2t}$ is O or $N(R^y)$; and M12d is 1, 2, 3, 4, 5, 6, 7 or 8.

In another specific embodiment of the invention $A^3$ is of the formula:

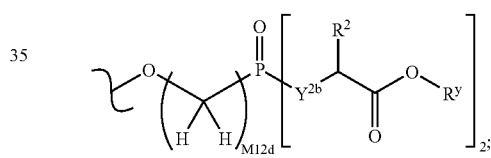

wherein $Y^{2b}$ is or $N(R^2)$; and M12d is 1, 2, 3, 4, 5, 6, 7 or 8.

In another specific embodiment of the invention $A^3$ is of the formula:

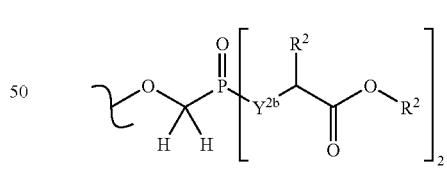

wherein $Y^{2b}$ is O or $N(R^2)$.

In another specific embodiment of the invention $A^3$ is of the formula:

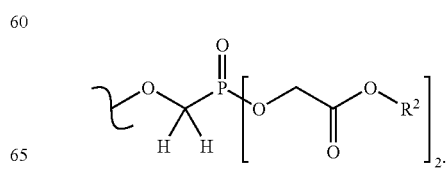

In another specific embodiment of the invention A³ is of the formula:

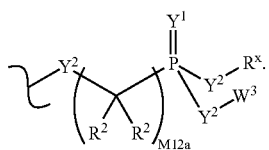

In another specific embodiment of the invention A³ is of the formula:

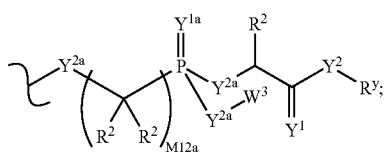

wherein Y¹ᵃ is O or S; and Y²ᵃ O, N(R²) or S.

In another specific embodiment of the invention A³ is of the formula:

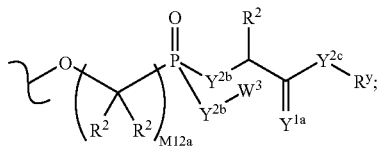

wherein Y¹ᵃ is O or S; Y²ᵇ is O or N(R²); and Y²ᶜ is O, N(Rʸ) or S.

In another specific embodiment of the invention A³ is of the formula:

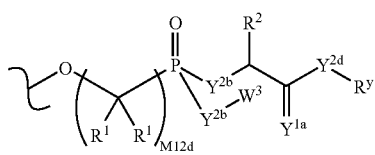

wherein Y¹ᵃ is O or S; Y²ᵇ is O or N(R²); Y²ᵈ is O or N(Rʸ); and M12d is 1, 2, 3, 4, 5, 6, 7 or 8.

In another specific embodiment of the invention A³ is of the formula:

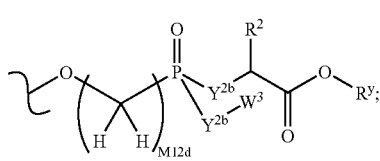

wherein Y²ᵇ is O or N(R²); and M12d is 1, 2, 3, 4, 5, 6, 7 or 8.

In another specific embodiment of the invention A³ is of the formula:

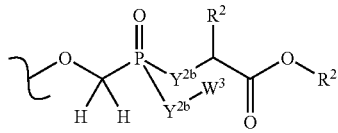

wherein Y²ᵇ is O or N(R²).

In another specific embodiment of the invention A³ is of the formula:

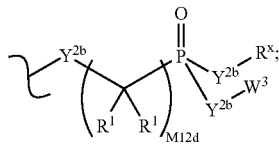

wherein: Y²ᵇ is O or N(Rˣ); and M12d is 1, 2, 3, 4, 5, 6, 7 or 8.

In another specific embodiment of the invention A³ is of the formula:

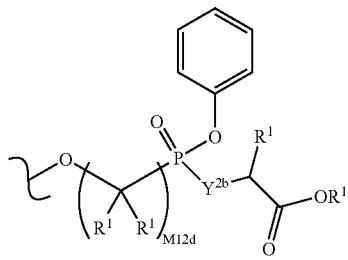

wherein the phenyl carbocycle is substituted with 0, 1, 2, or 3 R² groups.

In another specific embodiment of the invention A³ is of the formula:

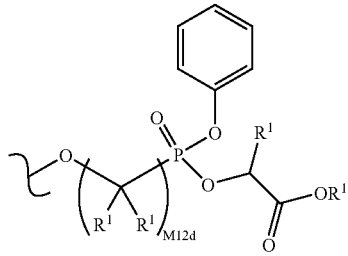

wherein the phenyl carbocycle is substituted with 0, 1, 2, or 3 R² groups.

In another specific embodiment of the invention A³ is of the formula:

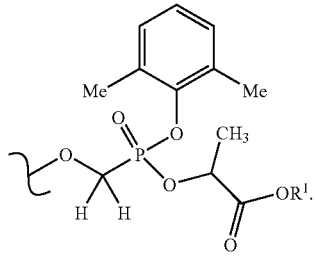

In a specific embodiment of the invention $A^0$ is of the formula:

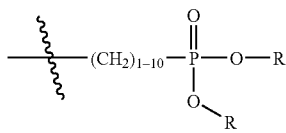

wherein each R is independently $(C_1-C_6)$alkyl.

In a specific embodiment of the invention $R^x$ is independently H, $R^1$, $W^3$, a protecting group, or the formula:

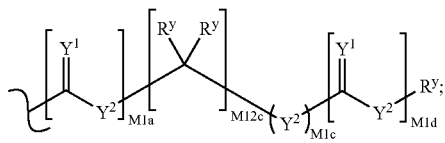

wherein:

$R^y$ is independently H, $W^3$, $R^2$ or a protecting group;

$R^1$ is independently H or alkyl of 1 to 18 carbon atoms; and $R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups.

In a specific embodiment of the invention $R^x$ is of the formula:

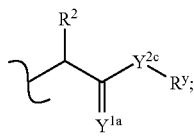

wherein $Y^{1a}$ is O or S; and $Y^{2c}$ is O, $N(R^y)$ or S.

In a specific embodiment of the invention $R^x$ is of the formula:

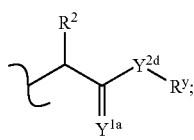

wherein $Y^{1a}$ is O or S; and $Y^{2d}$ is O or $N(R^y)$.

In a specific embodiment of the invention $R^x$ is of the formula:

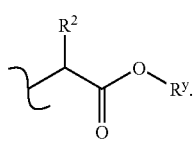

In a specific embodiment of the invention $R^y$ is hydrogen or alkyl of 1 to 10 carbons.

In a specific embodiment of the invention $R^x$ is of the formula:

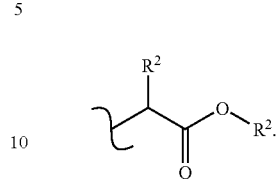

In a specific embodiment of the invention $R^x$ is of the formula:

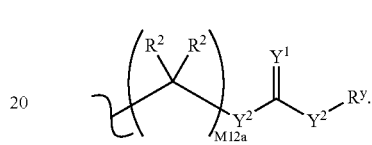

In a specific embodiment of the invention $R^x$ is of the formula:

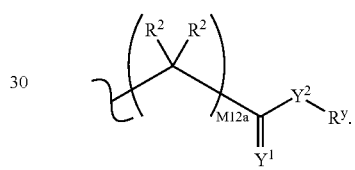

In a specific embodiment of the invention $Y^1$ is O or S

In a specific embodiment of the invention $Y^2$ is O, $N(R^y)$ or S.

In one specific embodiment of the invention $R^x$ is a group of the formula:

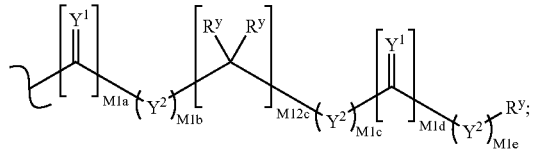

wherein:

m1a, m1b, m1c, m1d and m1e are independently 0 or 1;

m12c is 0, 1, 2, 3, 4, 5, 6, 7, 8, 9, 10, 11 or 12;

$R^y$ is H, $W^3$, $R^2$ or a protecting group;

provided that:

if m1a, m12c, and m1d are 0, then m1b, m1c and m1e are 0;

if m1a and m12c are 0 and m1d is not 0, then m1b and m1c are 0;

if m1a and m1d are 0 and m12c is not 0, then m1b and at least one of m1c and m1e are 0;

if m1a is 0 and m12c and m1d are not 0, then m1b is 0;

if m12c and m1d are 0 and m1a is not 0, then at least two of m1b, m1c and m1e are 0;

if m12c is 0 and m1a and m1d are not 0, then at least one of m1b and m1c are 0; and if m1d is 0 and m1a and m12c are not 0, then at least one of m1c and m1e are 0.

In another specific embodiment, the invention provides a compound of the formula:

[DRUG]-(A$^0$)$_{nn}$ or a pharmaceutically acceptable salt thereof wherein,
DRUG is a compound of any one of formulae 500-509
nn is 1, 2, or 3;
A$^0$ is A$^1$, A$^2$ or W$^3$ with the proviso that the compound includes at least one A$^1$;
A$^1$ is:

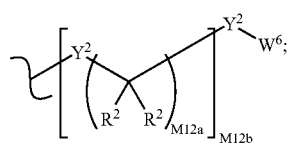

A$^2$ is:

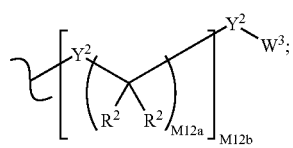

A$^3$ is:

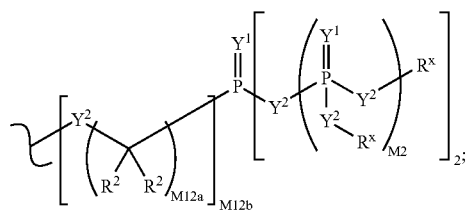

Y$^1$ is independently O, S, N(R$^x$), N(O)(R$^x$), N(OR$^x$), N(O)(OR$^x$), or N(N(R$^x$)(R$^x$));
Y$^2$ is independently a bond, O, N(R$^x$), N(O)(R$^x$), N(OR$^x$), N(O)(OR$^x$), N(N(R$^x$)(R$^x$)), —S(O)$_{M2}$—, or —S(O)$_{M2}$—S(O)$_{M2}$—;
R$^x$ is independently H, R$^1$, W$^3$, a protecting group, or the formula:

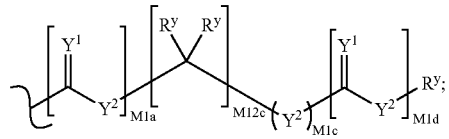

wherein:
R$^y$ is independently H, W$^3$, R$^2$ or a protecting group;
R$^1$ is independently H or alkyl of 1 to 18 carbon atoms;
R$^2$ is independently H, R$^1$, R$^3$ or R$^4$ wherein each R$^4$ is independently substituted with 0 to 3 R$^3$ groups or taken together at a carbon atom, two R$^2$ groups form a ring of 3 to 8 carbons and the ring may be substituted with 0 to 3 R$^3$ groups;

R$^3$ is R$^{3a}$, R$^{3b}$, R$^{3c}$ or R$^{3d}$, provided that when R$^3$ is bound to a heteroatom, then R$^3$ is R$^{3c}$ or R$^{3d}$;
R$^{3a}$ is F, Cl, Br, I, —CN, N$_3$ or —NO$_2$;
R$^{3b}$ is Y$^1$;
R$^{3c}$ is —R$^x$, —N(R$^x$)(R$^x$), —SR$^x$, —S(O)R$^x$, —S(O)$_2$R$^x$, —S(O)(OR$^x$), —S(O)$_2$(OR$^x$), —OC(Y$^1$)R$^x$, —OC(Y$^1$)OR$^x$, —OC(Y$^1$)(N(R$^x$)(R$^x$)), —SC(Y$^1$)R$^x$, SC(Y$^1$)OR$^x$, —SC(Y$^1$)(N(R$^x$)(R$^x$)), —N(R$^x$)C(Y$^1$)R$^x$, —N(R$^x$)C(Y$^1$)OR$^x$, or —N(R$^x$)C(Y$^1$)(N(R$^x$)(R$^x$));
R$^{3d}$ is —C(Y$^1$)R$^x$, —C(Y$^1$)OR$^x$ or —C(Y$^1$)(N(R$^x$)(R$^x$));
R$^4$ is an alkyl of 1 to 18 carbon atoms, alkenyl of 2 to 18 carbon atoms, or alkynyl of 2 to 18 carbon atoms;
R$^5$ is R$^4$ wherein each R$^4$ is substituted with 0 to 3 R$^3$ groups;
R$^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 R$^3$ groups;
W$^3$ is W$^4$ or W$^5$;
W$^4$ is R$^5$, —C(Y$^1$)R$^5$, —C(Y$^1$)W$^5$, —SO$_2$R$^5$, or —SO$_2$W$^5$;
W$^5$ is carbocycle or heterocycle wherein W$^5$ is independently substituted with 0 to 3 R$^2$ groups;
W$^6$ is W$^3$ independently substituted with 1, 2, or 3 A$^3$ groups;
M2 is 0, 1 or 2;
M12a is 1, 2, 3, 4, 5, 6, 7, 8, 9, 10, 11 or 12;
M12b is 0, 1, 2, 3, 4, 5, 6, 7, 8, 9, 10, 11 or 12;
M1a, M1c, and M1d are independently 0 or 1; and
M12c is 0, 1, 2, 3, 4, 5, 6, 7, 8, 9, 10, 11 or 12.

In another specific embodiment, the invention provides a compound of the formula 1-14, or a pharmaceutically acceptable salt thereof wherein:
A$^0$ is A$^1$;
A$^1$ is:

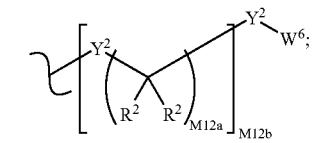

A$^3$ is:

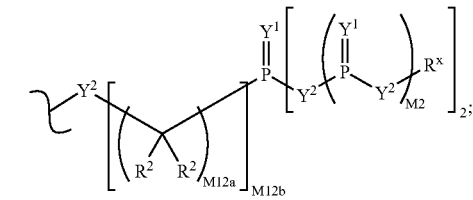

Y$^1$ is independently O, S, N(R$^x$), N(O)(R$^x$), N(OR$^x$), N(O)(OR$^x$), or N(N(R$^x$)(R$^x$));
Y$^2$ is independently a bond, O, N(R$^x$), N(O)(R$^x$), N(OR$^x$), N(O)(OR$^x$), N(N(R$^x$)(R$^x$)), —S(O)$_{M2}$—, or —S(O)$_{M2}$—S(O)$_{M2}$—;

$R^x$ is independently H, $W^3$, a protecting group, or the formula:

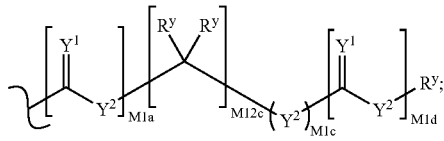

$R^y$ is independently H, $W^3$, $R^2$ or a protecting group;
$R^1$ is independently H or alkyl of 1 to 18 carbon atoms;
$R^2$ is independently H, $R^3$ or $R^4$ wherein each $R^4$ is independently substituted with 0 to 3 $R^3$ groups;
$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;
$R^{3a}$ is F, Cl, Br, I, —CN, $N_3$ or —$NO_2$;
$R^{3b}$ is $Y^1$;
$R^{3c}$ is —$R^x$, —$N(R^x)(R^x)$, —$SR^x$, —$S(O)R^x$, —$S(O)_2R^x$, —$S(O)(OR^x)$, —$S(O)_2(OR^x)$, —$OC(Y^1)R^x$, —$OC(Y^1)OR^x$, —$OC(Y^1)(N(R^x)(R^x))$, —$SC(Y^1)R^x$, —$SC(Y^1)OR^x$, —$SC(Y^1)(N(R^x)(R^x))$, —$N(R^x)C(Y^1)R^x$, —$N(R^x)C(Y^1)OR^x$, or —$N(R^x)C(Y^1)(N(R^x)(R^x))$;
$R^{3d}$ is —$C(Y^1)R^x$, —$C(Y^1)OR^x$ or —$C(Y^1)(N(R^x)(R^x))$;
$R^4$ is an alkyl of 1 to 18 carbon atoms, alkenyl of 2 to 18 carbon atoms, or alkynyl of 2 to 18 carbon atoms;
$R^5$ is $R^4$ wherein each $R^4$ is substituted with 0 to 3 $R^3$ groups;
$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;
$W^3$ is $W^4$ or $W^5$;
$W^4$ is $R^5$, —$C(Y^1)R^5$, —$C(Y^1)W^5$, —$SO_2W^5$, or —$SO_2W^5$;
$W^5$ is carbocycle or heterocycle wherein $W^5$ is independently substituted with 0 to 3 $R^2$ groups;
$W^6$ is $W^3$ independently substituted with 1, 2, or 3 $A^3$ groups;
M2 is 0, 1 or 2;
M12a is 1, 2, 3, 4, 5, 6, 7, 8, 9, 10, 11 or 12;
M12b is 0, 1, 2, 3, 4, 5, 6, 7, 8, 9, 10, 11 or 12;
M1a, M1c, and M1d are independently 0 or 1; and
M12c is 0, 1, 2, 3, 4, 5, 6, 7, 8, 9, 10, 11 or 12.

The present invention also provides a compound of any one of formulae 1-14 wherein:
$A^0$ is $A^1$;
$A^1$ is:

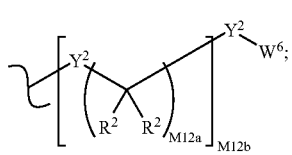

$A^3$ is:

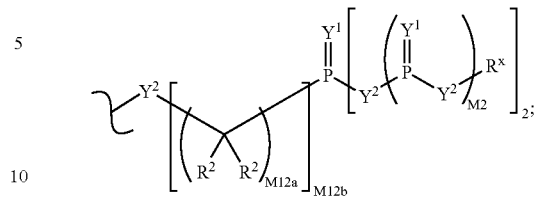

$Y^1$ is independently O, S, $N(R^x)$, $N(O)(R^x)$, $N(OR^x)$, $N(O)(OR^x)$, or $N(N(R^x)(R^x))$;
$Y^2$ is independently a bond, O, $N(R^x)$, $N(O)(R^x)$, $N(OR^x)$, $N(O)(OR^x)$, $N(N(R^x)(R^x))$, —$S(O)_{M2}$—, or —$S(O)_{M2}$—$S(O)_{M2}$—;
$R^x$ is independently H, $W^3$, a protecting group, or the formula:

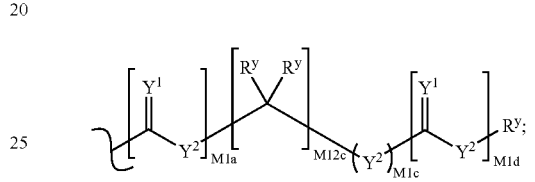

$R^y$ is independently H, $W^3$, $R^2$ or a protecting group;
$R^1$ is independently H or alkyl of 1 to 18 carbon atoms;
$R^2$ is independently H, $R^3$ or $R^4$ wherein each $R^4$ is independently substituted with 0 to 3 $R^3$ groups;
$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;
$R^{3a}$ is F, Cl, Br, I, —CN, $N_3$ or —$NO_2$;
$R^{3b}$ is $Y^1$;
$R^{3c}$ is $R^x$, —$N(R^x)(R^x)$, —$SR^x$, —$S(O)R^x$, —$S(O)_2R^x$, —$S(O)(OR^x)$, —$S(O)_2(OR^x)$, —$OC(Y^1)R^x$, —$OC(Y^1)OR^x$, —$OC(Y^1)(N(R^x)(R^x))$, —$SC(Y^1)R^x$, —$SC(Y^1)OR^x$, —$SC(Y^1)(N(R^x)(R^x))$, —$N(R^x)C(Y^1)R^x$, —$N(R^x)C(Y^1)OR^x$, or —$N(R^x)C(Y^1)(N(R^x)(R^x))$;
$R^{3d}$ is —$C(Y^1)R^x$, —$C(Y^1)OR^x$ or —$C(Y^1)(N(R^x)(R^x))$;
$R^4$ is an alkyl of 1 to 18 carbon atoms, alkenyl of 2 to 18 carbon atoms, or alkynyl of 2 to 18 carbon atoms;
$R^5$ is $R^4$ wherein each $R^4$ is substituted with 0 to 3 $R^3$ groups;
$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;
$W^3$ is $W^4$ or $W^5$;
$W^4$ is $R^5$, —$C(Y^1)R^5$, —$C(Y^1)W^5$, —$SO_2R^5$, or —$SO_2W^5$;
$W^5$ is carbocycle or heterocycle wherein $W^5$ is independently substituted with 0 to 3 $R^2$ groups;
$W^6$ is $W^3$ independently substituted with 1, 2, or 3 $A^3$ groups;
M2 is 0, 1 or 2;
M12a is 1, 2, 3, 4, 5, 6, 7, 8, 9, 10, 11 or 12;
M12b is 0, 1, 2, 3, 4, 5, 6, 7, 8, 9, 10, 11 or 12;
M1a, M1c, and M1d are independently 0 or 1; and
M12c is 0, 1, 2, 3, 4, 5, 6, 7, 8, 9, 10, 11 or 12.

$X^{50}$ and $X^{51}$ are alkyl groups which may or may not be linked to each other to form a ring as shown by the dotted curve, which alkyl groups may optionally be substituted intra-chain or in a pendant manner with one or more (e.g. 1, 2, 3, or 4) heteroatoms such as nitrogen, oxygen, or halogen; or the identity of the group obtained with a particular $X^{50}$ and $X^{51}$ combination is equal to one that is known from the fluoroquinolone art to produce potent antibacterial activity art;

$X^{52}$ and $X^{53}$ are to be alkyl groups which may or may not be connected covalently to form a ring (e.g. a 5, 6, 7, or 8 membered ring); if they do form a ring they are substituted with at least one heteroatom such as nitrogen, either within the chain (intra-chain) or in a pendant manner, which can serve as a handle for the linkage to the phosphonate moiety; if $X^{52}$ and $X^{53}$ do not form a ring, either or both may be substituted with heteroatoms such as N, O or halogen, wherein one of those heteroatoms, preferably nitrogen, can be used as a linkage element to the phosphonate group;

$X^{54}$ is any alkyl, aryl or aralkyl group, which may be optionally substituted (e.g. in any way as has been shown to produce potent antibacterial activity in any of the fluoroquinolone antibacterial art);

$X^{56}$ and $X^{55}$ are alkyl groups which may be linked to each other to form a ring as shown by the dotted curve, which ring is substituted either in a pendant manner or within the ring itself with a heteroatom, which forms a site onto which $A^0$ is attached; or if $X^{56}$ and $X^{55}$ are not linked together, at least one of $X^{56}$ and $X^{55}$ is a heteroatom-substituted alkyl group and the other is an alkyl group or a heteroatom-substituted alkyl group, wherein one of $X^{56}$ and $X^{55}$ is linked to $A^0$;

$X^{57}$ is oxo (=O), thioxo (=S), or hydroxy (—OH), provided when $X^{57}$ is hydroxy, the second valence on the ring is occupied by H);

$X^{58}$ is H, formyl, or acetyl;

$X^{59}$ and $X^{60}$ are alkyl groups which may be linked to each other to form a ring as shown by the dotted curve, which ring is substituted either in a pendant manner or within the ring itself with a heteroatom, which forms a site onto which $A^0$ can be attached; or if $X^{59}$ and $X^{60}$ are not linked together, at least one of $X^{59}$ and $X^{60}$ is a heteroatom-substituted alkyl group and the other is an alkyl group or a heteroatom-substituted alkyl group, wherein one of $X^{59}$ and $X^{60}$ is linked to $A^0$;

$X^{61}$ is O or NH; and $X^{62}$, $X^{63}$, and $X^{64}$ are each independently H, alkyl, aryl, or arylalkyl.

In another specific embodiment, the invention provides a compound of the formula:

$$[DRUG]\text{-}[L\text{-}P(=Y^1)\text{—}Y^2\text{—}R^x]_{nn}$$

or a pharmaceutically acceptable salt thereof wherein, DRUG is a compound of any one of 500-509;

$Y^1$ is independently O, S, N($R^x$), N(O)($R^x$), N(O$R^x$), N(O)(O$R^x$), or N(N($R^x$)($R^x$));

$Y^2$ is independently a bond, O, N($R^x$), N(O)($R^x$), N(O$R^x$), N(O)(O$R^x$), N(N($R^x$)($R^x$)), —S(O)$_{M2}$—, or —S(O)$_{M2}$—S(O)$_{M2}$—;

$R^x$ is independently H, $W^3$, a protecting group, or the formula:

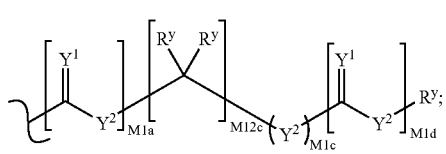

$R^y$ is independently H, $W^3$, $R^2$ or a protecting group;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or —NO$_2$;

$R^{3b}$ is $Y^1$;

$R^{3c}$ is —$R^x$, —N($R^x$)($R^x$), —S$R^x$, —S(O)$R^x$, —S(O)$_2R^x$, —S(O)(O$R^x$), —S(O)$_2$(O$R^x$), —OC($Y^1$)$R^x$, —OC($Y^1$)O$R^x$, —OC($Y^1$)(N($R^x$)($R^x$)), —SC($Y^1$)$R^x$, —SC($Y^1$)O$R^x$, —SC($Y^1$)(N($R^x$)($R^x$)), —N($R^x$)C($Y^1$)$R^x$, —N($R^x$)C($Y^1$)O$R^x$, or —N($R^x$)C($Y^1$)(N($R^x$)($R^x$));

$R^{3d}$ is —C($Y^1$)$R^x$, —C($Y^1$)O$R^x$ or —C($Y^1$)(N($R^x$)($R^x$));

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, —C($Y^1$)$R^5$, —C($Y^1$)$W^5$, —SO$_2R^5$, or —SO$_2W^5$;

$W^5$ is carbocycle or heterocycle wherein $W^5$ is independently substituted with 0 to 3 $R^2$ groups;

M2 is 1, 2, or 3;

M1a, M1c, and M1d are independently 0 or 1;

M12c is 0, 1, 2, 3, 4, 5, 6, 7, 8, 9, 10, 11 or 12;

nn is 1, 2, or 3; and

L is a linking group.

In another specific embodiment, the invention provides a compound of which is a compound of the formula:

$$[DRUG]\text{-}(A^0)_{nn}$$

or a pharmaceutically acceptable salt thereof wherein, DRUG is a compound of any one of formulae 500-509;

nn is 1, 2, or 3;

$A^0$ is $A^1$, $A^2$, or $W^3$ with the proviso that the compound includes at least one $A^1$;

$A^1$ is:

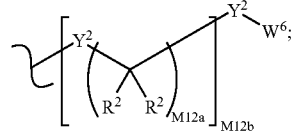

$A^2$ is:

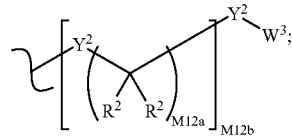

$A^2$ is:

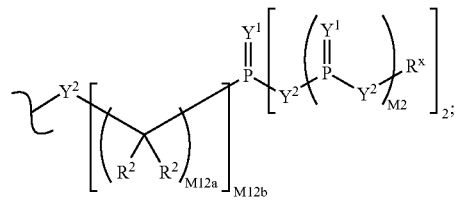

$Y^1$ is independently O, S, N($R^x$), N(O)($R^x$), N(O$R^x$), N(O)(O$R^x$), or N(N($R^x$)($R^x$));

Y² is independently a bond, O, N(R^x), N(O)(R^x), N(OR^x), N(O)(OR^x), N(N(R^x)(R^x)), —S(O)_{M2}—, or —S(O)_{M2}—S(O)_{M2}—;

R^x is independently H, W³, a protecting group, or the formula:

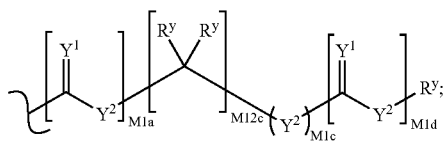

R^y is independently H, W³, R² or a protecting group;

R² is independently H, R³ or R⁴ wherein each R⁴ is independently substituted with 0 to 3 R³ groups;

R³ is R^{3a}, R^{3b}, R^{3c} or R^{3d}, provided that when R³ is bound to a heteroatom, then R³ is R^{3c} or R^{3d};

R^{3a} is F, Cl, Br, I, —CN, N₃ or —NO₂;

R^{3b} is Y¹;

R^{3c} is —R^x, —N(R^x)(R^x), —SR^x, —S(O)R^x, —S(O)₂R^x, —S(O)(OR^x), —S(O)₂(OR^x), —OC(Y¹)R^x, —OC(Y¹)OR^x, —OC(Y¹)(N(R^x)(R^x)), —SC(Y¹)R^x, —SC(Y¹)OR^x, —SC(Y¹)(N(R^x)(R^x)), —N(R^x)C(Y¹)R^x, —N(R^x)C(Y¹)OR^x, or —N(R^x)C(Y¹)(N(R^x)(R^x));

R^{3d} is —C(Y¹)R^x, —C(Y¹)OR^x or —C(Y)(N(R^x)(R^x));

R⁴ is an alkyl of 1 to 18 carbon atoms, alkenyl of 2 to 18 carbon atoms, or alkynyl of 2 to 18 carbon atoms;

R⁵ is R⁴ wherein each R⁴ is substituted with 0 to 3 R³ groups;

W³ is W⁴ or W⁵;

W⁴ is R⁵, —C(Y¹)R⁵, —C(Y¹)W⁵, —SO₂R⁵, or —SO₂W⁵;

W⁵ is carbocycle or heterocycle wherein W⁵ is independently substituted with 0 to 3 R² groups;

W⁶ is W³ independently substituted with 1, 2, or 3 A³ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In compounds of the invention W⁵ carbocycles and W⁵ heterocycles may be independently substituted with 0 to 3 R² groups. W⁵ may be a saturated, unsaturated or aromatic ring comprising a mono- or bicyclic carbocycle or heterocycle. W⁵ may have 3 to 10 ring atoms, e.g., 3 to 7 ring atoms. The W⁵ rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

A W⁵ heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). W⁵ heterocyclic monocycles may have 3 to 6 ring atoms (2 to 5 carbon atoms and 1 to 2 heteroatoms selected from N, O, and S); or 5 or 6 ring atoms (3 to 5 carbon atoms and 1 to 2 heteroatoms selected from N and S). W⁵ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The W⁵ heterocycle may be bonded to Y² through a carbon, nitrogen, sulfur or other atom by a stable covalent bond.

W⁵ heterocycles include for example, pyridyl, dihydropyridyl isomers, piperidine, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl. W⁵ also includes, but is not limited to, examples such as:

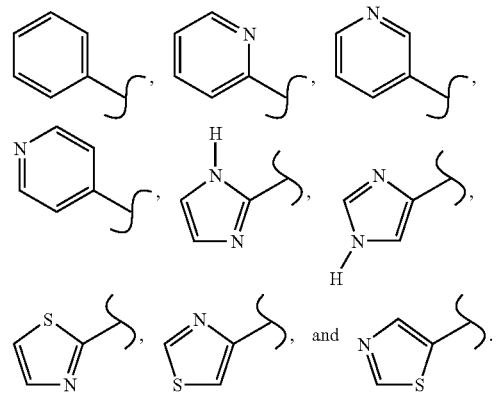

W⁵ carbocycles and heterocycles may be independently substituted with 0 to 3 R² groups, as defined above. For example, substituted W⁵ carbocycles include:

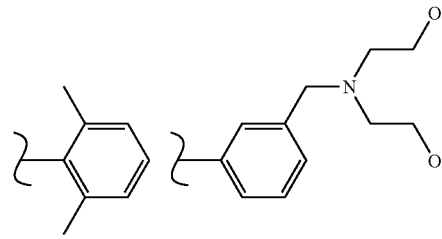

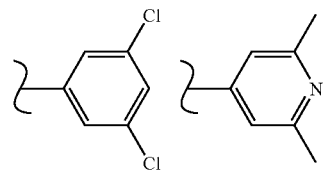

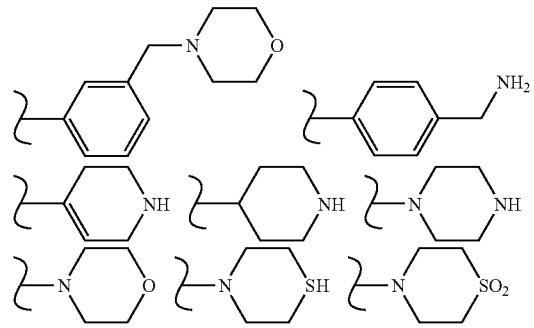

Examples of substituted phenyl carbocycles include:

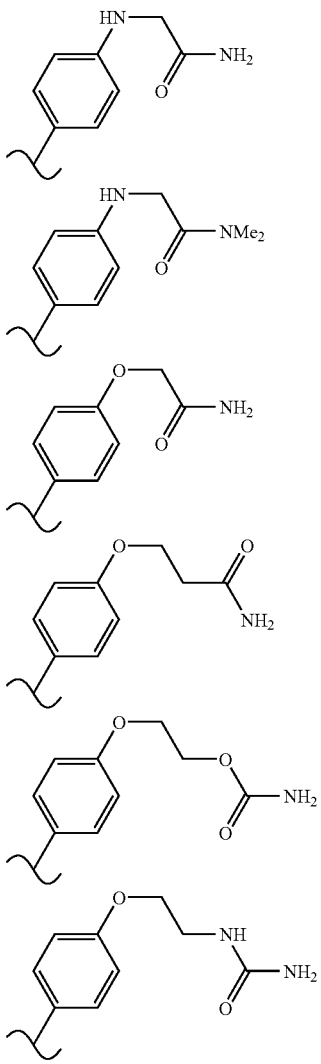

Linking Groups and Linkers

The invention provides conjugates that comprise an anti-infective compound that is linked to one or more phosphonate groups either directly (e.g. through a covalent bond) or through a linking group (i.e. a linker). The nature of the linker is not critical provided it does not interfere with the ability of the phosphonate containing compound to function as a therapeutic agent. The phosphonate or the linker can be linked to the compound (e.g., a compound of 500-509) at any synthetically feasible position on the compound by removing a hydrogen or any portion of the compound to provide an open valence for attachment of the phosphonate or the linker.

In one embodiment of the invention the linking group or linker (which can be designated "L") can include all or a portions of the group $A^0$, $A^1$, $A^2$, or $W^3$ described herein.

In another embodiment of the invention the linking group or linker has a molecular weight of from about 20 daltons to about 400 daltons.

In another embodiment of the invention the linking group or linker has a length of about 5 angstroms to about 300 angstroms.

In another embodiment of the invention the linking group or linker separates the anti-infective compound and the phosphorous of the phosphonate group by about 5 angstroms to about 200 angstroms, inclusive, in length.

In another embodiment of the invention the linking group or linker is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

In another embodiment of the invention the linking group or linker is of the formula W-A wherein A is $(C_1-C_{24})$alkyl, $(C_2-C_{24})$alkenyl, $(C_2-C_{24})$alkynyl, $(C_3-C_8)$cycloalkyl, $(C_6-C_{10})$aryl or a combination thereof, wherein W is —N(R)C(=O)—, —C(=O)N(R)—, —OC(=O)—, —C(=O)O—, —O—, —S—, —S(O)—, —S(O)$_2$—, —N(R)—, —C(=O)—, or a direct bond; wherein each R is independently H or $(C_1-C_6)$alkyl.

In another embodiment of the invention the linking group or linker is a divalent radical formed from a peptide.

In another embodiment of the invention the linking group or linker is a divalent radical formed from an amino acid.

In another embodiment of the invention the linking group or linker is a divalent radical formed from poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-lysine or poly-L-lysine-L-tyrosine.

In another embodiment of the invention the linking group or linker is of the formula W—$(CH_2)_n$ wherein, n is between about 1 and about 10; and W is —N(R)C(=O)—, —C(=O)N(R)—, —OC(=O)—, —C(=O)O—, —O—, —S—, —S(O)—, —S(O)$_2$—, —C(=O)—, —N(R)—, or a direct bond; wherein each R is independently H or $(C_1-C_6)$alkyl.

In another embodiment of the invention the linking group or linker is methylene, ethylene, or propylene.

In another embodiment of the invention the linking group or linker is attached to the phosphonate group through a carbon atom of the linker.

Intracellular Targeting

The phosphonate group of the compounds of the invention may cleave in vivo in stages after they have reached the desired site of action, i.e. inside a cell. One mechanism of action inside a cell may entail a first cleavage, e.g. by esterase, to provide a negatively-charged "locked-in" intermediate. Cleavage of a terminal ester grouping in a compound of the invention thus affords an unstable intermediate which releases a negatively charged "locked in" intermediate.

After passage inside a cell, intracellular enzymatic cleavage or modification of the phosphonate or prodrug compound may result in an intracellular accumulation of the cleaved or modified compound by a "trapping" mechanism. The cleaved or modified compound may then be "locked-in" the cell by a significant change in charge, polarity, or other physical property change which decreases the rate at which the cleaved or modified compound can exit the cell, relative to the rate at which it entered as the phosphonate prodrug. Other mechanisms by which a therapeutic effect are achieved may be operative as well. Enzymes which are capable of an enzymatic activation mechanism with the phosphonate prodrug compounds of the invention include, but are not limited to, amidases, esterases, microbial enzymes, phospholipases, cholinesterases, and phosphatases.

From the foregoing, it will be apparent that many different drugs can be derivatized in accord with the present invention. Numerous such drugs are specifically mentioned herein. However, it should be understood that the discussion of drug families and their specific members for derivatization according to this invention is not intended to be exhaustive, but merely illustrative.

Anti-Infective Compounds

The compounds of the invention include those with anti-infective activity. The compounds of the inventions bear one or more (e.g., 1, 2, 3, or 4) phosphonate groups, which may be a prodrug moiety.

The term "anti-infective compound" includes those compounds that inhibit infection. In particular, the compounds include Ethambutol, fluoroquinolones, rifabutin, rifampicin, erythomycin, isoniazid, pyrazinamid, and cefixime.

Typically, compounds of the invention have a molecular weight of from about 400 amu to about 10,000 amu; in a specific embodiment of the invention, compounds have a molecular weight of less than about 5000 amu; in another specific embodiment of the invention, compounds have a molecular weight of less than about 2500 amu; in another specific embodiment of the invention, compounds have a molecular weight of less than about 1000 amu; in another specific embodiment of the invention, compounds have a molecular weight of less than about 800 amu; in another specific embodiment of the invention, compounds have a molecular weight of less than about 600 amu; and in another specific embodiment of the invention, compounds have a molecular weight of less than about 600 amu and a molecular weight of greater than about 400 amu.

The compounds of the invention also typically have a logD (polarity) less than about 5. In one embodiment the invention provides compounds having a logD less than about 4; in another one embodiment the invention provides compounds having a logD less than about 3; in another one embodiment the invention provides compounds having a logD greater than about −5; in another one embodiment the invention provides compounds having a logD greater than about −3; and in another one embodiment the invention provides compounds having a logD greater than about 0 and less than about 3.

Selected substituents within the compounds of the invention are present to a recursive degree. In this context, "recursive substituent" means that a substituent may recite another instance of itself. Because of the recursive nature of such substituents, theoretically, a large number may be present in any given claim. For example, $R^x$ contains a $R^1$ substituent. $R^1$ can be $R^2$, which in turn can be $R^3$. If $R^3$ is selected to be $R^{3c}$, then a second instance of $R^x$ can be selected. One of ordinary skill in the art of medicinal chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

By way of example and not limitation, $W^3$, $R^y$ and $R^3$ are all recursive substituents in certain claims. Typically, each of these may independently occur 20, 19, 18, 17, 16, 15, 14, 13, 12, 11, 10, 9, 8, 7, 6, 5, 4, 3, 2, 1, or 0, times in a given claim. More typically, each of these may independently occur 12 or fewer times in a given claim. More typically yet, $W^3$ will occur 0 to 8 times, $R^y$ will occur 0 to 6 times and $R^3$ will occur 0 to 10 times in a given claim. Even more typically, $W^3$ will occur 0 to 6 times, $R^y$ will occur 0 to 4 times and $R^3$ will occur 0 to 8 times in a given claim.

Recursive substituents are an intended aspect of the invention. One of ordinary skill in the art of medicinal chemistry understands the versatility of such substituents. To the degree that recursive substituents are present in an claim of the invention, the total number will be determined as set forth above.

Whenever a compound described herein is substituted with more than one of the same designated group, e.g., "$R^1$" or "$R^{6a}$", then it will be understood that the groups may be the same or different, i.e., each group is independently selected. Wavy lines indicate the site of covalent bond attachments to the adjoining groups, moieties, or atoms.

The phosphonate group may be a phosphonate prodrug moiety. The prodrug moiety may be sensitive to hydrolysis, such as, but not limited to, a pivaloyloxymethyl carbonate (POC) or POM group. Alternatively, the prodrug moiety may be sensitive to enzymatic potentiated cleavage, such as a lactate ester or a phosphonamidate-ester group.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 50 wt. % free from biological materials; in another specific embodiment, the term means that the compound or conjugate of the invention is at least about 75 wt. % free from biological materials; in another specific embodiment, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

In one embodiment of the invention, the compound is not a purine nucleoside phosphorylase inhibitor; in one embodiment of the invention, the compound is not an anti-cancer agent; in one embodiment of the invention, the compound is not active against immune-mediated conditions; in one embodiment of the invention, the compound is not active against metabolic diseases; in one embodiment of the invention, the compound is not an antiviral agent; in one embodiment of the invention, the compound is not a nucleoside; in one embodiment of the invention, the compound is not a kinase inhibitor; in one embodiment of the invention, the compound is not an antimetabolite; in one embodiment of the invention, the compound is not an IMPDH inhibitor; and in one embodiment of the invention, the compound is not an anti-inflammatory.

Cellular Accumulation

In one embodiment, the invention is provides compounds capable of accumulating in human PBMC (peripheral blood mononuclear cells). PBMC refer to blood cells having round lymphocytes and monocytes. Physiologically, PBMC are critical components of the mechanism against infection. PBMC may be isolated from heparinized whole blood of normal healthy donors or buffy coats, by standard density gradient centrifugation and harvested from the interface, washed (e.g. phosphate-buffered saline) and stored in freezing medium. PBMC may be cultured in multi-well plates. At various times of culture, supernatant may be either removed for assessment, or cells may be harvested and analyzed (Smith R. etal (2003) *Blood* 102(7):2532-2540). The compounds of this claim may further comprise a phosphonate or phosphonate prodrug. More typically, the phosphonate or phosphonate prodrug can have the structure $A^3$ as described herein.

Typically, compounds of the invention demonstrate improved intracellular half-life of the compounds or intracellular metabolites of the compounds in human PBMC when compared to analogs of the compounds not having the phosphonate or phosphonate prodrug. Typically, the half-life is improved by at least about 50%, more typically at least in the range 50-100%, still more typically at least about 100%, more typically yet greater than about 100%.

In one embodiment of the invention the intracellular half-life of a metabolite of the compound in human PBMCs is improved when compared to an analog of the compound not having the phosphonate or phosphonate prodrug. In such claims, the metabolite may be generated intracellularly, e.g. generated within human PBMC. The metabolite may be a product of the cleavage of a phosphonate prodrug within human PBMCs. The phosphonate prodrug may be cleaved to form a metabolite having at least one negative charge at physiological pH. The phosphonate prodrug may be enzymatically cleaved within human PBMC to form a phosphonate having at least one active hydrogen atom of the form P—OH.

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. All though only one delocalized resonance structure may be depicted, all such forms are contemplated within the scope of the iinvention. For example, ene-amine tautomers can exist for purine, pyrimidine, imidazole, guanidine, amidine, and tetrazole systems and all their possible tautomeric forms are within the scope of the invention.

Salts and Hydrates

The compositions of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid. Monovalent salts are preferred if a water soluble salt is desired.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of Infection

Another aspect of the invention relates to methods of inhibiting infection comprising the step of treating a sample suspected of containing infection with a composition of the invention.

Compositions of the invention may act as anti-infectives, as intermediates for such inhibitors or have other utilities as described below. The inhibitors can bind to locations on the surface or in a cavity of a target. Compositions so binding may bind with varying degrees of reversibility. Those compounds binding substantially irreversibly are ideal candidates for use in this method of the invention. Once labeled, the substantially irreversibly binding compositions are useful as probes for the detection of infection. Accordingly, the invention relates to methods of detecting infection in a sample suspected of containing infection comprising the steps of: treating a sample suspected of containing infection with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino.

Within the context of the invention samples include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing infection. Samples can be contained in any medium including water and organic solvent/water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the anti-infective activity after application of the composition can be observed by any method including direct and indirect methods of detecting infection. Quantitative, qualitative, and semiquantitative methods of determining anti-infective activity are all contemplated. Typically one of the screening methods described above are applied, however, any other method such as observation of the physiological properties of a living organism are also applicable.

Many organisms can contain infections. The compounds of this invention are useful in the treatment or prophylaxis of infection in animals or in man.

However, in screening compounds capable of inhibiting infection it should be kept in mind that the results of enzyme assays may not correlate with cell culture assays. Thus, a cell based assay should be the primary screening tool.

Screens for Infection Inhibitors

Compositions of the invention are screened for inhibitory activity against infection by any of the conventional techniques for evaluating such activity. Within the context of the invention, typically compositions are first screened for inhibition of infection in vitro and compositions showing inhibitory activity are then screened for activity in vivo. Compositions having in vitro Ki (inhibitory constants) of less then about $5\times10^{-6}$ M, typically less than about $1\times10^{-7}$ M and preferably less than about $5\times10^{-8}$ M are preferred for in vivo use.

Useful in vitro screens have been described in detail and will not be elaborated here. However, the examples describe suitable in vitro assays.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

Effective dose of active ingredient depends at least on the nature of the condition being treated, toxicity, whether the compound is being used prophylactically (lower doses) or against an active infection, the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Active ingredients of the invention are also used in combination with other active ingredients. Such combinations are selected based on the condition to be treated, cross-reactivities of ingredients and pharmaco-properties of the combination. For example, when treating infection the compositions of the invention are combined with other anti-infective agents (such as those described herein).

It is also possible to combine any compound of the invention with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The phosphonate prodrugs of the invention typically will be stable in the digestive system but are substantially hydrolyzed to the parental drug in the digestive lumen, liver or other metabolic organ, or within cells in general.

Exemplary Methods of Making the Compounds of the Invention.

The invention also relates to methods of making the compositions of the invention. The compositions are prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., *Advanced Organic Chemistry, Third Edition*, (John Wiley & Sons, New York, 1985), *Comprehensive Organic Synthesis, Selectivity, Strategy & Efficiency in Modern Organic Chemistry. In 9 Volumes*, Barry M. Trost, Editor-in-Chief (Pergamon Press, New York, 1993 printing).

A number of exemplary methods for the preparation of the compositions of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

Schemes and Examples

General aspects of these exemplary methods are described below and in the Examples. Each of the products of the following processes is optionally separated, isolated, and/or purified prior to its use in subsequent processes.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the examples (hereafter "exemplary schemes") leads to various analogs of the specific exemplary materials produce. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (*Stereochemistry of Carbon Compounds*, (1962) by E. L. Eliel, McGraw Hill; Lochmuller, C. H., (1975) *J. Chromatogr.*, 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine(amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

Examples General Section

A number of exemplary methods for the preparation of compounds of the invention are provided herein, for example, in the Examples hereinbelow. These methods are intended to illustrate the nature of such preparations are not intended to limit the scope of applicable methods. Certain compounds of the invention can be used as intermediates for the preparation of other compounds of the invention. For example, the interconversion of various phosphonate compounds of the invention is illustrated below.

Interconversions of the Phosphonates R-LINK-P(O)(OR$^1$)$_2$, R-LINK-P(O)(OR$^1$)(OH) and R-LINK-P(O)(OH)$_2$.

The following schemes 32-38 described the preparation of phosphonate esters of the general structure R-link-P(O)(OR$^1$)$_2$, in which the groups R$^1$ may be the same or different. The R$^1$ groups attached to a phosphonate ester, or to precursors thereto, may be changed using established chemical transformations. The interconversion reactions of phosphonates are illustrated in Scheme S32. The group R in Scheme 32 represents the substructure, i.e. the drug "scaffold, to which the substituent link-P(O)(OR$^1$)$_2$ is attached, either in the compounds of the invention, or in precursors thereto. At the point in the synthetic route of conducting a phosphonate interconversion, certain functional groups in R may be protected. The methods employed for a given phosphonate transformation depend on the nature of the substituent R$^1$, and of the substrate to which the phosphonate group is attached. The preparation and hydrolysis of phosphonate esters is described in *Organic Phosphorus Compounds*, G. M. Kosolapoff, L. Maeir, eds, Wiley, 1976, p. 9ff.

In general, synthesis of phosphonate esters is achieved by coupling a nucleophile amine or alcohol with the corresponding activated phosphonate electrophilic precursor. For example, chlorophosphonate addition on to 5'-hydroxy of nucleoside is a well known method for preparation of nucleoside phosphate monoesters. The activated precursor can be prepared by several well known methods. Chlorophosphonates useful for synthesis of the prodrugs are prepared from the substituted-1,3-propanediol (Wissner, et al, (1992) *J. Med Chem.* 35:1650). Chlorophosphonates are made by oxidation of the corresponding chlorophospholanes (Anderson, et al, (1984) *J. Org. Chem.* 49:1304) which are obtained by reaction of the substituted diol with phosphorus trichloride. Alternatively, the chlorophosphonate agent is made by treating substituted-1,3-diols with phosphorusoxychloride (Patois, et al, (1990) *J. Chem. Soc. Perkin Trans. I,* 1577). Chlorophosphonate species may also be generated in situ from corresponding cyclic phosphites (Silverburg, et al., (1996) *Tetrahedron lett.,* 37:771-774), which in turn can be either made from chlorophospholane or phosphoramidate intermediate. Phosphorofluoridate intermediate prepared either from pyrophosphate or phosphoric acid may also act as precursor in preparation of cyclic prodrugs (Watanabe et al., (1988) *Tetrahedron lett.,* 29:5763-66).

Phosphonate prodrugs of the present invention may also be prepared from the free acid by Mitsunobu reactions (Mitsunobu, (1981) *Synthesis,* 1; Campbell, (1992) *J. Org. Chem.* 57:6331), and other acid coupling reagents including, but not limited to, carbodiimides (Alexander, et al, (1994) *Collect. Czech. Chem. Commun.* 59:1853; Casara et al, (1992) *Bioorg. Med. Chem. Lett.* 2:145; Ohashi et al, (1988) *Tetrahedron Lett.,* 29:1189), and benzotriazolyloxytris-(dimethylamino)phosphonium salts (Campagne et al (1993) *Tetrahedron Lett.* 34:6743).

Aryl halides undergo Ni$^{+2}$ catalyzed reaction with phosphite derivatives to give aryl phosphonate containing compounds (Balthazar, et al (1980) *J. Org. Chem.* 45:5425). Phosphonates may also be prepared from the chlorophosphonate in the presence of a palladium catalyst using aromatic triflates (Petrakis et al (1987) *J. Am. Chem. Soc.* 109:2831; Lu et al (1987) *Synthesis* 726). In another method, aryl phosphonate esters are prepared from aryl phosphates under anionic rearrangement conditions (Melvin (1981) *Tetrahedron Lett.* 22:3375; Casteel et al (1991) *Synthesis,* 691). N-Alkoxy aryl salts with alkali met al derivatives of cyclic alkyl phosphonate provide general synthesis for heteroaryl-2-phosphonate linkers (Redmore (1970) *J. Org. Chem.* 35:4114). These above mentioned methods can also be extended to compounds where the W$^5$ group is a heterocycle. Cyclic-1,3-propanyl prodrugs of phosphonates are also synthesized from phosphonic diacids and substituted propane-1,3-diols using a coupling reagent such as 1,3-dicyclohexylcarbodiimide (DCC) in presence of a base (e.g., pyridine). Other carbodiimide based coupling agents like 1,3-disopropylcarbodiimide or water soluble reagent, 1-(3-dimethylaminopropyl)-3-ethylcarbodiimide hydrochloride (EDCI) can also be utilized for the synthesis of cyclic phosphonate prodrugs.

The conversion of a phosphonate diester S32.1 into the corresponding phosphonate monoester S32.2 (Scheme 32, Reaction 1) is accomplished by a number of methods. For example, the ester S32.1 in which R$^1$ is an aralkyl group such as benzyl, is converted into the monoester compound S32.2 by reaction with a tertiary organic base such as diazabicyclooctane (DABCO) or quinuclidine, as described in *J. Org. Chem.* (1995) 60:2946. The reaction is performed in an inert hydrocarbon solvent such as toluene or xylene, at about 110° C. The conversion of the diester S32.1 in which R$^1$ is an aryl group such as phenyl, or an alkenyl group such as allyl, into the monoester S32.2 is effected by treatment of the ester S32.1 with a base such as aqueous sodium hydroxide in acetonitrile or lithium hydroxide in aqueous tetrahydrofuran. Phosphonate diesters S32.1 in which one of the groups R$^1$ is aralkyl, such as benzyl, and the other is alkyl, is converted into the monoesters S32.2 in which R$^1$ is alkyl by hydrogenation, for example using a palladium on carbon catalyst. Phosphonate diesters in which both of the groups R are alkenyl, such as allyl, is converted into the monoester S32.2 in which R$^1$ is alkenyl, by treatment with chlorotris (triphenylphosphine)rhodium (Wilkinson's catalyst) in aqueous ethanol at reflux, optionally in the presence of diazabicyclooctane, for example by using the procedure described in *J. Org. Chem.* (1973) 38:3224, for the cleavage of allyl carboxylates.

The conversion of a phosphonate diester S32.1 or a phosphonate monoester S32.2 into the corresponding phosphonic acid S32.3 (Scheme 32, Reactions 2 and 3) can be effected by reaction of the diester or the monoester with trimethylsilyl bromide, as described in *J. Chem. Soc., Chem. Comm.,* (1979) 739. The reaction is conducted in an inert solvent such as, for example, dichloromethane, optionally in the presence of a silylating agent such as bis(trimethylsilyl) trifluoroacetamide, at ambient temperature. A phosphonate monoester S32.2 in which R$^1$ is aralkyl such as benzyl, is converted into the corresponding phosphonic acid S32.3 by hydrogenation over a palladium catalyst, or by treatment with hydrogen chloride in an ethereal solvent such as dioxane. A phosphonate monoester S32.2 in which R$^1$ is alkenyl such as, for example, allyl, is converted into the phosphonic acid S32.3 by reaction with Wilkinson's catalyst in an aqueous organic solvent, for example in 15% aqueous acetonitrile, or in aqueous ethanol, for example using the procedure described in *Helv. Chim. Acta.* (1985) 68:618. Palladium catalyzed hydrogenolysis of phosphonate esters S32.1 in which R$^1$ is benzyl is described in *J. Org. Chem.* (1959) 24:434. Platinum-catalyzed hydrogenolysis of phosphonate esters S32.1 in which R$^1$ is phenyl is described in *J. Am. Chem. Soc.* (1956) 78:2336.

The conversion of a phosphonate monoester S32.2 into a phosphonate diester S32.1 (Scheme 32, Reaction 4) in which the newly introduced R$^1$ group is alkyl, aralkyl, haloalkyl such as chloroethyl, or aralkyl is effected by a number of reactions in which the substrate S32.2 is reacted with a hydroxy compound R$^1$OH, in the presence of a coupling agent. Typically, the second phosphonate ester group is different than the first introduced phosphonate ester group, i.e. R$^1$ is followed by the introduction of R$^2$ where each of R$^1$ and R$^2$ is alkyl, aralkyl, haloalkyl such as chloroethyl, or aralkyl (Scheme 32, Reaction 4a) whereby S32.2 is converted to S32.1a. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy) tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester S32.2 to the diester S32.1 is effected by the use of the Mitsunobu reaction, as described above (Scheme 7). The substrate is reacted with the hydroxy compound $R^1OH$, in the presence of diethyl azodicarboxylate and a triarylphosphine such as triphenyl phosphine. Alternatively, the phosphonate monoester S32.2 is transformed into the phosphonate diester S32.1, in which the introduced $R^1$ group is alkenyl or aralkyl, by reaction of the monoester with the halide $R^1Br$, in which $R^1$ is as alkenyl or aralkyl. The alkylation reaction is conducted in a polar organic solvent such as dimethylformamide or acetonitrile, in the presence of a base such as cesium carbonate. Alternatively, the phosphonate monoester is transformed into the phosphonate diester in a two step procedure. In the first step, the phosphonate monoester S32.2 is transformed into the chloro analog $RP(O)(OR^1)Cl$ by reaction with thionyl chloride or oxalyl chloride and the like, as described in *Organic Phosphorus Compounds*, G. M. Kosolapoff, L. Maeir, eds, Wiley, 1976, p. 17, and the thus-obtained product $RP(O)(OR^1)Cl$ is then reacted with the hydroxy compound $R^1OH$, in the presence of a base such as triethylamine, to afford the phosphonate diester S32.1.

A phosphonic acid R-link-P(O)(OH)$_2$ is transformed into a phosphonate monoester $RP(O)(OR^1)(OH)$ (Scheme 32, Reaction 5) by means of the methods described above of for the preparation of the phosphonate diester R-link-P(O)(OR$^1$)$_2$ S32.1, except that only one molar proportion of the component $R^1OH$ or $R^1Br$ is employed. Dialkyl phosphonates may be prepared according to the methods of: Quast et al (1974) *Synthesis* 490; Stowell et al (1990) *Tetrahedron Lett.* 3261; U.S. Pat. No. 5,663,159.

A phosphonic acid R-link-P(O)(OH)$_2$ S32.3 is transformed into a phosphonate diester R-link-P(O)(OR$^1$)$_2$ S32.1 (Scheme 32, Reaction 6) by a coupling reaction with the hydroxy compound $R^1OH$, in the presence of a coupling agent such as Aldrithiol-2 (Aldrich) and triphenylphosphine. The reaction is conducted in a basic solvent such as pyridine. Alternatively, phosphonic acids S32.3 are transformed into phosphonic esters S32.1 in which $R^1$ is aryl, by means of a coupling reaction employing, for example, dicyclohexylcarbodiimide in pyridine at ca 70° C. Alternatively, phosphonic acids S32.3 are transformed into phosphonic esters S32.1 in which $R^1$ is alkenyl, by means of an alkylation reaction. The phosphonic acid is reacted with the alkenyl bromide $R^1Br$ in a polar organic solvent such as acetonitrile solution at reflux temperature, the presence of a base such as cesium carbonate, to afford the phosphonic ester S32.1.

Scheme 32

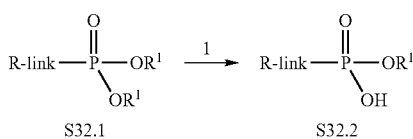

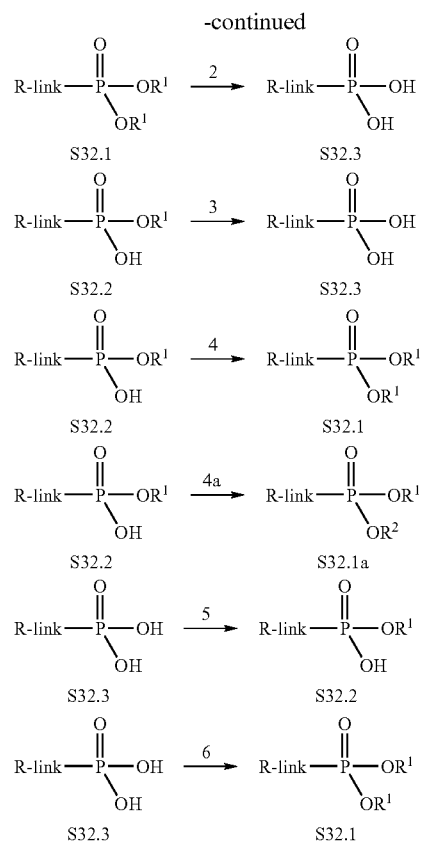

Preparation of Phosphonate Carbamates.

Phosphonate esters may contain a carbamate linkage. The preparation of carbamates is described in *Comprehensive Organic Functional Group Transformations*, A. R. Katritzky, ed., Pergamon, 1995, Vol. 6, p. 416ff, and in *Organic Functional Group Preparations*, by S. R. Sandler and W. Karo, Academic Press, 1986, p. 260ff. The carbamoyl group may be formed by reaction of a hydroxy group according to the methods known in the art, including the teachings of Ellis, US 2002/0103378 A$^1$ and Hajima, U.S. Pat. No. 6,018,049.

Scheme 33 illustrates various methods by which the carbamate linkage is synthesized. As shown in Scheme 33, in the general reaction generating carbamates, an alcohol S33.1, is converted into the activated derivative S33.2 in which Lv is a leaving group such as halo, imidazolyl, benztriazolyl and the like, as described herein. The activated derivative S33.2 is then reacted with an amine S33.3, to afford the carbamate product S33.4. Examples 1-7 in Scheme 33 depict methods by which the general reaction is effected. Examples 8-10 illustrate alternative methods for the preparation of carbamates.

Scheme 33, Example 1 illustrates the preparation of carbamates employing a chloroformyl derivative of the alcohol S33.5. In this procedure, the alcohol S33.5 is reacted with phosgene, in an inert solvent such as toluene, at about 0° C., as described in *Org. Syn. Coll. Vol.* 3, 167, 1965, or with an equivalent reagent such as trichloromethoxy chloroformate, as described in *Org. Syn. Coll. Vol.* 6, 715, 1988, to afford the chloroformate S33.6. The latter compound is then reacted with the amine component S33.3, in the presence of an organic or inorganic base, to afford the carbamate S33.7. For example, the chloroformyl compound S33.6 is reacted with the amine S33.3 in a water-miscible solvent such as tetrahydrofuran, in the presence of aqueous sodium hydroxide, as described in *Org. Syn. Coll. Vol.* 3, 167, 1965, to yield the carbamate S33.7. Alternatively, the reaction is performed in dichloromethane in the presence of an organic base such as diisopropylethylamine or dimethylaminopyridine.

Scheme 33, Example 2 depicts the reaction of the chloroformate compound S33.6 with imidazole to produce the imidazolide S33.8. The imidazolide product is then reacted with the amine S33.3 to yield the carbamate S33.7. The preparation of the imidazolide is performed in an aprotic solvent such as dichloromethane at 0°, and the preparation of the carbamate is conducted in a similar solvent at ambient temperature, optionally in the presence of a base such as dimethylaminopyridine, as described in *J. Med. Chem.*, 1989, 32, 357.

Scheme 33 Example 3, depicts the reaction of the chloroformate S33.6 with an activated hydroxyl compound R"OH, to yield the mixed carbonate ester S33.10. The reaction is conducted in an inert organic solvent such as ether or dichloromethane, in the presence of a base such as dicyclohexylamine or triethylamine. The hydroxyl component R"OH is selected from the group of compounds S33.19-S33.24 shown in Scheme 33, and similar compounds. For example, if the component R"OH is hydroxybenztriazole S33.19, N-hydroxysuccinimide S33.20, or pentachlorophenol, S33.21, the mixed carbonate S33.10 is obtained by the reaction of the chloroformate with the hydroxyl compound in an ethereal solvent in the presence of dicyclohexylamine, as described in *Can. J. Chem.*, 1982, 60, 976. A similar reaction in which the component R"OH is pentafluorophenol S33.22 or 2-hydroxypyridine S33.23 is performed in an ethereal solvent in the presence of triethylamine, as described in *Syn.*, 1986, 303, and *Chem. Ber.* 118, 468, 1985.

Scheme 33 Example 4 illustrates the preparation of carbamates in which an alkyloxycarbonylimidazole S33.8 is employed. In this procedure, an alcohol S33.5 is reacted with an equimolar amount of carbonyl diimidazole S33.11 to prepare the intermediate S33.8. The reaction is conducted in an aprotic organic solvent such as dichloromethane or tetrahydrofuran. The acyloxyimidazole S33.8 is then reacted with an equimolar amount of the amine R'NH$_2$ to afford the carbamate S33.7. The reaction is performed in an aprotic organic solvent such as dichloromethane, as described in *Tet. Lett.*, 42, 2001, 5227, to afford the carbamate S33.7.

Scheme 33, Example 5 illustrates the preparation of carbamates by means of an intermediate alkoxycarbonylbenztriazole S33.13. In this procedure, an alcohol ROH is reacted at ambient temperature with an equimolar amount of benztriazole carbonyl chloride S33.12, to afford the alkoxycarbonyl product S33.13. The reaction is performed in an organic solvent such as benzene or toluene, in the presence of a tertiary organic amine such as triethylamine, as described in *Synthesis.*, 1977, 704. The product is then reacted with the amine R'NH$_2$ to afford the carbamate S33.7. The reaction is conducted in toluene or ethanol, at from ambient temperature to about 80° C. as described in *Synthesis.*, 1977, 704.

Scheme 33, Example 6 illustrates the preparation of carbamates in which a carbonate (R"O)$_2$CO, S33.14, is reacted with an alcohol S33.5 to afford the intermediate alkyloxycarbonyl intermediate S33.15. The latter reagent is then reacted with the amine R'NH$_2$ to afford the carbamate S33.7. The procedure in which the reagent S33.15 is derived from hydroxybenztriazole S33.19 is described in *Synthesis,* 1993, 908; the procedure in which the reagent S33.15 is derived from N-hydroxysuccinimide S33.20 is described in *Tet. Lett.,* 1992, 2781; the procedure in which the reagent S33.15 is derived from 2-hydroxypyridine S33.23 is described in *Tet. Lett.,* 1991, 4251; the procedure in which the reagent S33.15 is derived from 4-nitrophenol S33.24 is described in *Synthesis.* 1993, 103. The reaction between equimolar amounts of the alcohol ROH and the carbonate S33.14 is conducted in an inert organic solvent at ambient temperature.

Scheme 33, Example 7 illustrates the preparation of carbamates from alkoxycarbonyl azides S33.16. In this procedure, an alkyl chloroformate S33.6 is reacted with an azide, for example sodium azide, to afford the alkoxycarbonyl azide S33.16. The latter compound is then reacted with an equimolar amount of the amine R'NH$_2$ to afford the carbamate S33.7. The reaction is conducted at ambient temperature in a polar aprotic solvent such as dimethylsulfoxide, for example as described in *Synthesis.,* 1982, 404.

Scheme 33, Example 8 illustrates the preparation of carbamates by means of the reaction between an alcohol ROH and the chloroformyl derivative of an amine S33.17. In this procedure, which is described in *Synthetic Organic Chemistry*, R. B. Wagner, H. D. Zook, Wiley, 1953, p. 647, the reactants are combined at ambient temperature in an aprotic solvent such as acetonitrile, in the presence of a base such as triethylamine, to afford the carbamate S33.7.

Scheme 33, Example 9 illustrates the preparation of carbamates by means of the reaction between an alcohol ROH and an isocyanate S33.18. In this procedure, which is described in *Synthetic Organic Chemistry*, R. B. Wagner, H. D. Zook, Wiley, 1953, p. 645, the reactants are combined at ambient temperature in an aprotic solvent such as ether or dichloromethane and the like, to afford the carbamate S33.7.

Scheme 33, Example 10 illustrates the preparation of carbamates by means of the reaction between an alcohol ROH and an amine R'NH$_2$. In this procedure, which is described in *Chem. Lett.* 1972, 373, the reactants are combined at ambient temperature in an aprotic organic solvent such as tetrahydrofuran, in the presence of a tertiary base such as triethylamine, and selenium. Carbon monoxide is passed through the solution and the reaction proceeds to afford the carbamate S33.7.

Scheme 33. Preparation of carbamates.

General reaction

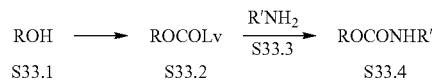

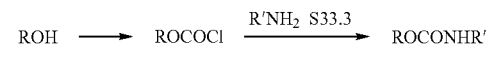

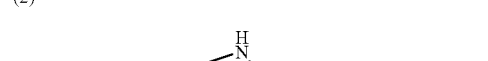

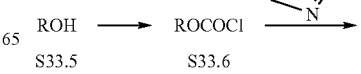

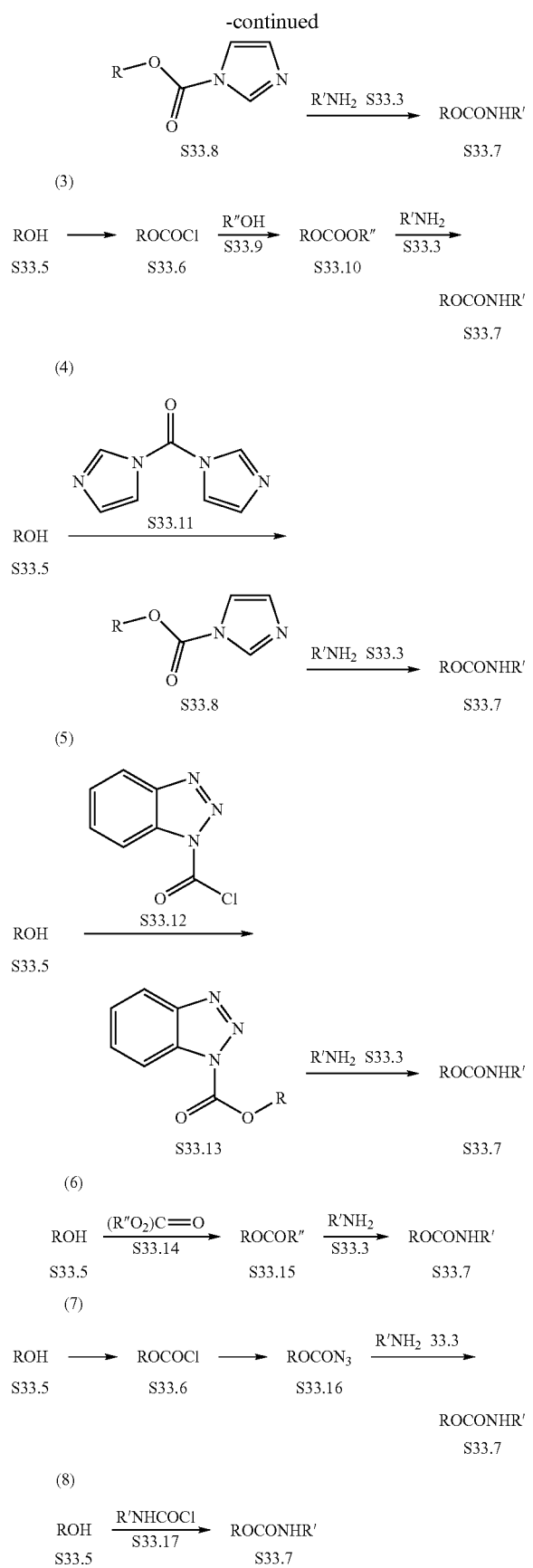
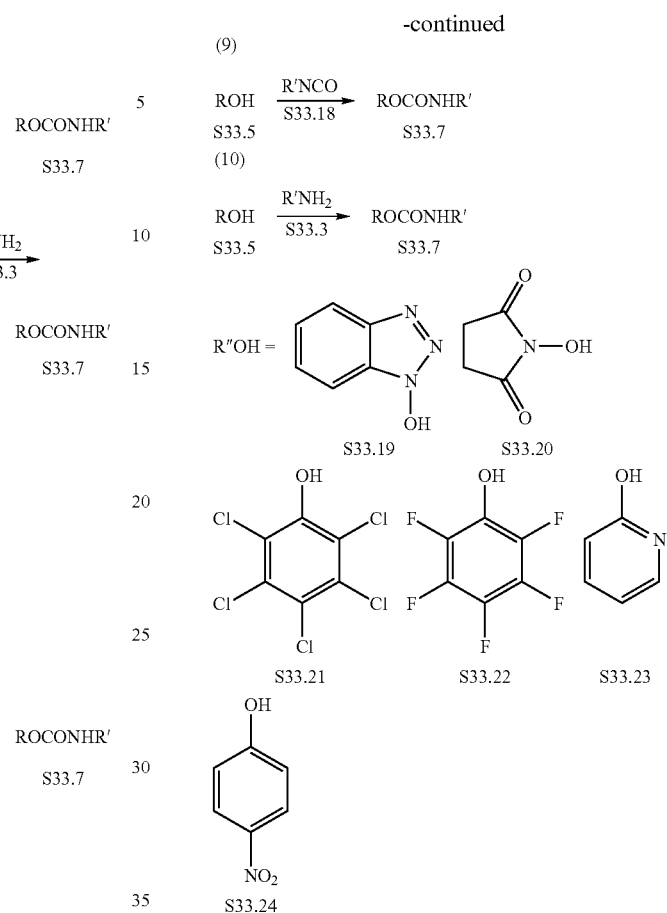

Preparation of Carboalkoxy-substituted Phosphonate Bisamidates, Monoamidates, Diesters and Monoesters.

A number of methods are available for the conversion of phosphonic acids into amidates and esters. In one group of methods, the phosphonic acid is either converted into an isolated activated intermediate such as a phosphoryl chloride, or the phosphonic acid is activated in situ for reaction with an amine or a hydroxy compound.

The conversion of phosphonic acids into phosphoryl chlorides is accomplished by reaction with thionyl chloride, for example as described in *J. Gen. Chem. USSR*, 1983, 53, 480, *Zh. Obschei Khim.*, 1958, 28, 1063, or *J. Org. Chem.*, 1994, 59, 6144, or by reaction with oxalyl chloride, as described in *J. Am. Chem. Soc.*, 1994, 116, 3251, or *J. Org. Chem.*, 1994, 59, 6144, or by reaction with phosphorus pentachloride, as described in *J. Org. Chem.*, 2001, 66, 329, or in *J. Med. Chem.*, 1995, 38, 1372. The resultant phosphoryl chlorides are then reacted with amines or hydroxy compounds in the presence of a base to afford the amidate or ester products.

Phosphonic acids are converted into activated imidazolyl derivatives by reaction with carbonyl diimidazole, as described in *J. Chem. Soc., Chem. Comm.* (1991) 312, or *Nucleosides & Nucleotides* (2000) 19:1885. Activated sulfonyloxy derivatives are obtained by the reaction of phosphonic acids with trichloromethylsulfonyl chloride or with triisopropylbenzenesulfonyl chloride, as described in *Tet. Lett.* (1996) 7857, or *Bioorg. Med. Chem. Lett.* (1998) 8:663. The activated sulfonyloxy derivatives are then reacted with amines or hydroxy compounds to afford amidates or esters.

Alternatively, the phosphonic acid and the amine or hydroxy reactant are combined in the presence of a diimide coupling agent. The preparation of phosphonic amidates and esters by means of coupling reactions in the presence of dicyclohexyl carbodiimide is described, for example, in *J. Chem. Soc., Chem. Comm.* (1991) 312 or *Coll. Czech. Chem. Comm.* (1987) 52:2792. The use of ethyl dimethylaminopropyl carbodiimide for activation and coupling of phosphonic acids is described in Tet. Lett., (2001) 42:8841, or *Nucleosides & Nucleotides* (2000) 19:1885.

A number of additional coupling reagents have been described for the preparation of amidates and esters from phosphonic acids. The agents include Aldrithiol-2, and PYBOP and BOP, as described in *J. Org. Chem.,* 1995, 60, 5214, and *J. Med. Chem.* (1997) 40:3842, mesitylene-2-sulfonyl-3-nitro-1,2,4-triazole (MSNT), as described in *J. Med. Chem.* (1996) 39:4958, diphenylphosphoryl azide, as described in *J. Org. Chem.* (1984) 49:1158, 1-(2,4,6-triisopropylbenzenesulfonyl-3-nitro-1,2,4-triazole (TPSNT) as described in *Bioorg. Med. Chem. Lett.* (1998) 8:1013, bromotris(dimethylamino)phosphonium hexafluorophosphate (BroP), as described in *Tet. Lett.,* (1996) 37:3997, 2-chloro-5,5-dimethyl-2-oxo-1,3,2-dioxaphosphinane, as described in *Nucleosides Nucleotides* 1995, 14, 871, and diphenyl chlorophosphate, as described in *J. Med. Chem.,* 1988, 31, 1305.

Phosphonic acids are converted into amidates and esters by means of the Mitsunobu reaction, in which the phosphonic acid and the amine or hydroxy reactant are combined in the presence of a triaryl phosphine and a dialkyl azodicarboxylate. The procedure is described in *Org. Lett.,* 2001, 3, 643, or *J. Med. Chem.,* 1997, 40, 3842.

Phosphonic esters are also obtained by the reaction between phosphonic acids and halo compounds, in the presence of a suitable base. The method is described, for example, in *Anal. Chem.,* 1987, 59, 1056, or *J. Chem. Soc. Perkin Trans.,* 1,1993, 19, 2303, or *J. Med. Chem.,* 1995, 38, 1372, or *Tet. Lett.,* 2002, 43, 1161.

Schemes 34-37 illustrate the conversion of phosphonate esters and phosphonic acids into carboalkoxy-substituted phosphonbisamidates (Scheme 34), phosphonamidates (Scheme 35), phosphonate monoesters (Scheme 36) and phosphonate diesters, (Scheme 37). Scheme 38 illustrates synthesis of gem-dialkyl amino phosphonate reagents.

Scheme 34 illustrates various methods for the conversion of phosphonate diesters S34.1 into phosphonbisamidates S34.5. The diester S34.1, prepared as described previously, is hydrolyzed, either to the monoester S34.2 or to the phosphonic acid S34.6. The methods employed for these transformations are described above. The monoester S34.2 is converted into the monoamidate S34.3 by reaction with an aminoester S34.9, in which the group $R^2$ is H or alkyl; the group $R^{4b}$ is a divalent alkylene moiety such as, for example, $CHCH_3$, $CHCH_2CH_3$, $CH(CH(CH_3)_2)$, $CH(CH_2Ph)$, and the like, or a side chain group present in natural or modified aminoacids; and the group $R^{1b}$ is $C_1$-$C_{12}$ alkyl, such as methyl, ethyl, propyl, isopropyl, or isobutyl; $C_6$-$C_{20}$ aryl, such as phenyl or substituted phenyl; or $C_6$-$C_{20}$ arylalkyl, such as benzyl or benzyhydryl. The reactants are combined in the presence of a coupling agent such as a carbodiimide, for example dicyclohexyl carbodiimide, as described in *J. Am. Chem. Soc.,* (1957) 79:3575, optionally in the presence of an activating agent such as hydroxybenztriazole, to yield the amidate product S34.3. The amidate-forming reaction is also effected in the presence of coupling agents such as BOP, as described in *J. Org. Chem.* (1995) 60:5214, Aldrithiol, PYBOP and similar coupling agents used for the preparation of amides and esters. Alternatively, the reactants S34.2 and S34.9 are transformed into the monoamidate S34.3 by means of a Mitsunobu reaction. The preparation of amidates by means of the Mitsunobu reaction is described in *J. Med. Chem.* (1995) 38:2742. Equimolar amounts of the reactants are combined in an inert solvent such as tetrahydrofuran in the presence of a triaryl phosphine and a dialkyl azodicarboxylate. The thus-obtained monoamidate ester S34.3 is then transformed into amidate phosphonic acid S34.4. The conditions used for the hydrolysis reaction depend on the nature of the $R^1$ group, as described previously. The phosphonic acid amidate S34.4 is then reacted with an aminoester S34.9, as described above, to yield the bisamidate product S34.5, in which the amino substituents are the same or different. Alternatively, the phosphonic acid S34.6 may be treated with two different amino ester reagents simulataneously, i.e. S34.9 where $R^2$, $R^{4b}$ or $R^{5b}$ are different. The resulting mixture of bisamidate products S34.5 may then be separable, e.g. by chromatography.

Scheme 34

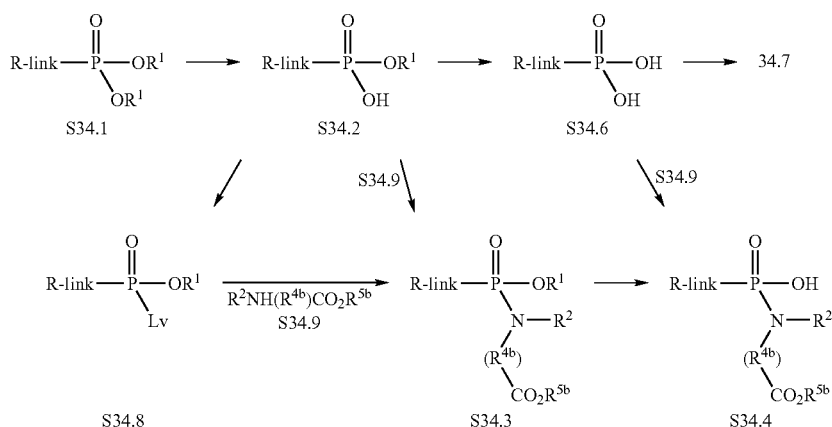

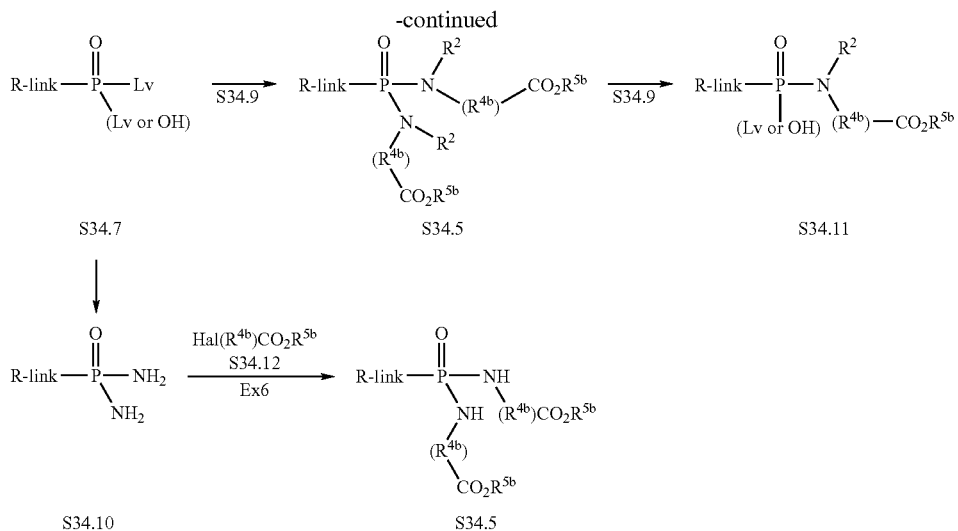

An example of this procedure is shown in Scheme 34, Example 1. In this procedure, a dibenzyl phosphonate S34.14 is reacted with diazabicyclooctane (DABCO) in toluene at reflux, as described in *J. Org. Chem.*, 1995, 60, 2946, to afford the monobenzyl phosphonate S34.15. The product is then reacted with equimolar amounts of ethyl alaninate S34.16 and dicyclohexyl carbodiimide in pyridine, to yield the amidate product S34.17. The benzyl group is then removed, for example by hydrogenolysis over a palladium catalyst, to give the monoacid product S34.18 which may be unstable according to J. Med. Chem. (1997) 40(23): 3842. This compound S34.18 is then reacted in a Mitsunobu reaction with ethyl leucinate S34.19, triphenyl phosphine and diethylazodicarboxylate, as described in *J. Med. Chem.*, 1995, 38, 2742, to produce the bisamidate product S34.20.

Using the above procedures, but employing in place of ethyl leucinate S34.19 or ethyl alaninate S34.16, different aminoesters S34.9, the corresponding products S34.5 are obtained.

Alternatively, the phosphonic acid S34.6 is converted into the bisamidate S34.5 by use of the coupling reactions described above. The reaction is performed in one step, in which case the nitrogen-related substituents present in the product S34.5 are the same, or in two steps, in which case the nitrogen-related substituents can be different.

An example of the method is shown in Scheme 34, Example 2. In this procedure, a phosphonic acid S34.6 is reacted in pyridine solution with excess ethyl phenylalaninate S34.21 and dicyclohexylcarbodiimide, for example as described in *J. Chem. Soc., Chem. Comm.*, 1991, 1063, to give the bisamidate product S34.22.

Using the above procedures, but employing in place of ethyl phenylalaninate, different aminoesters S34.9, the corresponding products S34.5 are obtained.

As a further alternative, the phosphonic acid S34.6 is converted into the mono or bis-activated derivative S34.7, in which Lv is a leaving group such as chloro, imidazolyl, triisopropylbenzenesulfonyloxy etc. The conversion of phosphonic acids into chlorides S34.7 (Lv=Cl) is effected by reaction with thionyl chloride or oxalyl chloride and the like, as described in *Organic Phosphorus Compounds*, G. M. Kosolapoff, L. Maeir, eds, Wiley, 1976, p. 17. The conversion of phosphonic acids into monoimidazolides S34.7 (Lv=imidazolyl) is described in *J. Med. Chem.*, 2002, 45, 1284 and in *J. Chem. Soc. Chem. Comm.*, 1991, 312. Alternatively, the phosphonic acid is activated by reaction with triisopropylbenzenesulfonyl chloride, as described in *Nucleosides and Nucleotides*, 2000, 10, 1885. The activated product is then reacted with the aminoester S34.9, in the presence of a base, to give the bisamidate S34.5. The reaction is performed in one step, in which case the nitrogen substituents present in the product S34.5 are the same, or in two steps, via the intermediate S34.11, in which case the nitrogen substituents can be different.

Examples of these methods are shown in Scheme 34, Examples 3 and 5. In the procedure illustrated in Scheme 34, Example 3, a phosphonic acid S34.6 is reacted with ten molar equivalents of thionyl chloride, as described in *Zh. Obschei Khim.*, 1958, 28, 1063, to give the dichloro compound S34.23. The product is then reacted at reflux temperature in a polar aprotic solvent such as acetonitrile, and in the presence of a base such as triethylamine, with butyl serinate S34.24 to afford the bisamidate product S34.25.

Using the above procedures, but employing, in place of butyl serinate S34.24, different aminoesters S34.9, the corresponding products S34.5 are obtained.

In the procedure illustrated in Scheme 34, Example 5, the phosphonic acid S34.6 is reacted, as described in *J. Chem. Soc. Chem. Comm.*, 1991, 312, with carbonyl diimidazole to give the imidazolide S34.S32. The product is then reacted in acetonitrile solution at ambient temperature, with one molar equivalent of ethyl alaninate S34.33 to yield the monodisplacement product S34.S34. The latter compound is then reacted with carbonyl diimidazole to produce the activated intermediate S34.35, and the product is then reacted, under the same conditions, with ethyl N-methylalaninate S34.33a to give the bisamidate product S34.36.

Using the above procedures, but employing, in place of ethyl alaninate S34.33 or ethyl N-methylalaninate S34.33a, different aminoesters S34.9, the corresponding products S34.5 are obtained.

The intermediate monoamidate S34.3 is also prepared from the monoester S34.2 by first converting the monoester into the activated derivative S34.8 in which Lv is a leaving group such as halo, imidazolyl etc, using the procedures described above. The product S34.8 is then reacted with an aminoester S34.9 in the presence of a base such as pyridine, to give an intermediate monoamidate product S34.3. The latter compound is then converted, by removal of the $R^1$ group and coupling of the product with the aminoester S34.9, as described above, into the bisamidate S34.5.

An example of this procedure, in which the phosphonic acid is activated by conversion to the chloro derivative S34.26, is shown in Scheme 34, Example 4. In this procedure, the phosphonic monobenzyl ester S34.15 is reacted, in dichloromethane, with thionyl chloride, as described in *Tet. Letters.,* 1994, 35, 4097, to afford the phosphoryl chloride S34.26. The product is then reacted in acetonitrile solution at ambient temperature with one molar equivalent of ethyl 3-amino-2-methylpropionate S34.27 to yield the monoamidate product S34.28. The latter compound is hydrogenated in ethylacetate over a 5% palladium on carbon catalyst to produce the monoacid product S34.29. The product is subjected to a Mitsunobu coupling procedure, with equimolar amounts of butyl alaninate S34.30, triphenyl phosphine, diethylazodicarboxylate and triethylamine in tetrahydrofuran, to give the bisamidate product S34.31.

Using the above procedures, but employing, in place of ethyl 3-amino-2-methylpropionate S34.27 or butyl alaninate S34.30, different aminoesters S34.9, the corresponding products S34.5 are obtained.

The activated phosphonic acid derivative S34.7 is also converted into the bisamidate S34.5 via the diamino compound S34.10. The conversion of activated phosphonic acid derivatives such as phosphoryl chlorides into the corresponding amino analogs S34.10, by reaction with ammonia, is described in *Organic Phosphorus Compounds*, G. M. Kosolapoff, L. Maeir, eds, Wiley, 1976. The bisamino compound S34.10 is then reacted at elevated temperature with a haloester S34.12 (Hal=halogen, i.e. F, Cl, Br, I), in a polar organic solvent such as dimethylformamide, in the presence of a base such as 4,4-dimethylaminopyridine (DMAP) or potassium carbonate, to yield the bisamidate S34.5. Alternatively, S34.6 may be treated with two different amino ester reagents simulataneously, i.e. S34.12 where $R^{4b}$ or $R^{5b}$ are different. The resulting mixture of bisamidate products S34.5 may then be separable, e.g. by chromatography.

An example of this procedure is shown in Scheme 34, Example 6. In this method, a dichlorophosphonate S34.23 is reacted with ammonia to afford the diamide S34.37. The reaction is performed in aqueous, aqueous alcoholic or alcoholic solution, at reflux temperature. The resulting diamino compound is then reacted with two molar equivalents of ethyl 2-bromo-3-methylbutyrate S34.38, in a polar organic solvent such as N-methylpyrrolidinone at ca. 150° C., in the presence of a base such as potassium carbonate, and optionally in the presence of a catalytic amount of potassium iodide, to afford the bisamidate product S34.39.

Using the above procedures, but employing, in place of ethyl 2-bromo-3-methylbutyrate S34.38, different haloesters S34.12 the corresponding products S34.5 are obtained.

The procedures shown in Scheme 34 are also applicable to the preparation of bisamidates in which the aminoester moiety incorporates different functional groups. Scheme 34, Example 7 illustrates the preparation of bisamidates derived from tyrosine. In this procedure, the monoimidazolide S34.32 is reacted with propyl tyrosinate S34.40, as described in Example 5, to yield the monoamidate S34.41. The product is reacted with carbonyl diimidazole to give the imidazolide S34.42, and this material is reacted with a further molar equivalent of propyl tyrosinate to produce the bisamidate product S34.43.

Using the above procedures, but employing, in place of propyl tyrosinate S34.40, different aminoesters S34.9, the corresponding products S34.5 are obtained. The aminoesters employed in the two stages of the above procedure can be the same or different, so that bisamidates with the same or different amino substituents are prepared.

Scheme 35 illustrates methods for the preparation of phosphonate monoamidates.

In one procedure, a phosphonate monoester S34.1 is converted, as described in Scheme 34, into the activated derivative S34.8. This compound is then reacted, as described above, with an aminoester S34.9, in the presence of a base, to afford the monoamidate product S35.1.

The procedure is illustrated in Scheme 35, Example 1. In this method, a monophenyl phosphonate S35.7 is reacted with, for example, thionyl chloride, as described in *J. Gen. Chem. USSR.,* 1983, 32, 367, to give the chloro product S35.8. The product is then reacted, as described in Scheme 34, with ethyl alaninateS3, to yield the amidate S35.10.

Using the above procedures, but employing, in place of ethyl alaninate S35.9, different aminoesters S34.9, the corresponding products S35.1 are obtained.

Alternatively, the phosphonate monoester S34.1 is coupled, as described in Scheme 34, with an aminoester S34.9 to produce the amidateS335.1. If necessary, the $R^1$ substituent is then altered, by initial cleavage to afford the phosphonic acid S35.2. The procedures for this transformation depend on the nature of the $R^1$ group, and are described above. The phosphonic acid is then transformed into the ester amidate product S35.3, by reaction with the hydroxy compound $R^3OH$, in which the group $R^3$ is aryl, heterocycle, alkyl, cycloalkyl, haloalkyl etc, using the same coupling procedures (carbodiimide, Aldrithiol-2, PYBOP, Mitsunobu reaction etc) described in Scheme 34 for the coupling of amines and phosphonic acids.

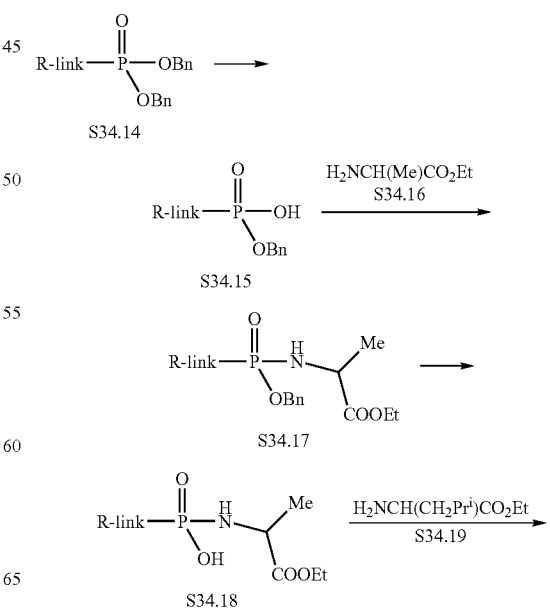

Scheme 34 Example 1

Scheme 34 Example 2
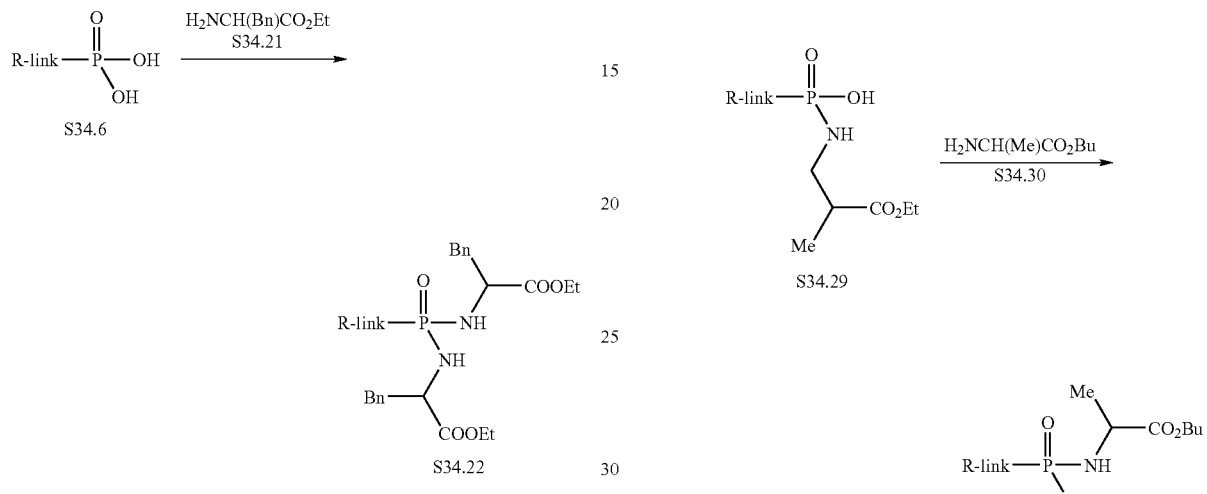
Scheme 34 Example 3
Scheme 34 Example 4
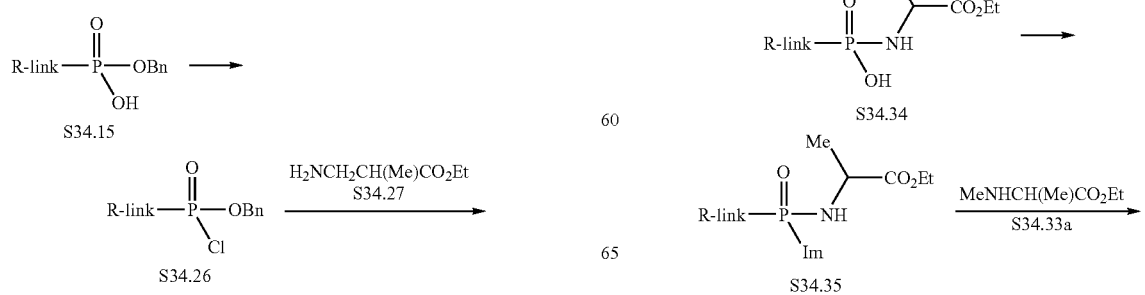
Scheme 35 Example 5

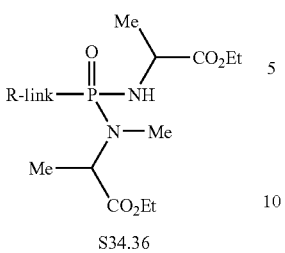

S34.36

Scheme 34 Example 6

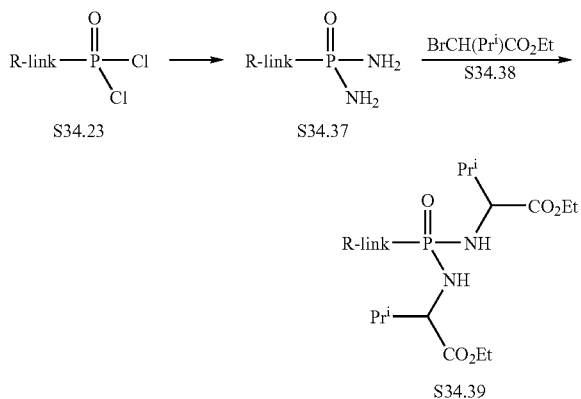

Scheme 34 Example 7

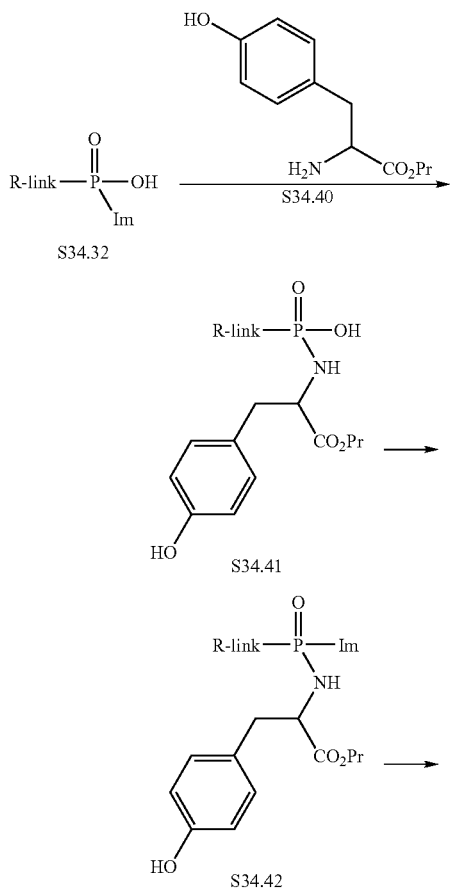

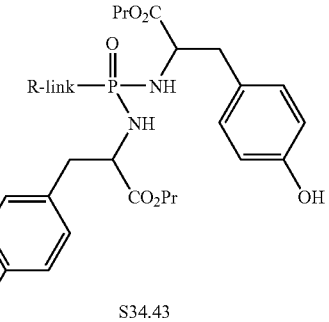

S34.43

Examples of this method are shown in Scheme 35, Examples and 2 and 3. In the sequence shown in Example 2, a monobenzyl phosphonate S35.11 is transformed by reaction with ethyl alaninate, using one of the methods described above, into the monoamidate S35.12. The benzyl group is then removed by catalytic hydrogenation in ethylacetate solution over a 5% palladium on carbon catalyst, to afford the phosphonic acid amidate S35.13. The product is then reacted in dichloromethane solution at ambient temperature with equimolar amounts of 1-(dimethylaminopropyl)-3-ethylcarbodiimide and trifluoroethanol S35.14, for example as described in *Tet. Lett.*, 2001, 42, 8841, to yield the amidate ester S35.15.

In the sequence shown in Scheme 35, Example 3, the monoamidate S35.13 is coupled, in tetrahydrofuran solution at ambient temperature, with equimolar amounts of dicyclohexyl carbodiimide and 4-hydroxy-N-methylpiperidine S35.16, to produce the amidate ester product S35.17.

Using the above procedures, but employing, in place of the ethyl alaninate product S35.12 different monoacids S35.2, and in place of trifluoroethanol S35.14 or 4-hydroxy-N-methylpiperidine S35.16, different hydroxy compounds $R^3OH$, the corresponding products S35.3 are obtained.

Alternatively, the activated phosphonate ester S34.8 is reacted with ammonia to yield the amidate S35.4. The product is then reacted, as described in Scheme 34, with a haloester S35.5, in the presence of a base, to produce the amidate product S35.6. If appropriate, the nature of the $R^1$ group is changed, using the procedures described above, to give the product S35.3. The method is illustrated in Scheme 35, Example 4. In this sequence, the monophenyl phosphoryl chloride S35.18 is reacted, as described in Scheme 34, with ammonia, to yield the amino product S35.19. This material is then reacted in N-methylpyrrolidinone solution at 170° with butyl 2-bromo-3-phenylpropionate S35.20 and potassium carbonate, to afford the amidate product S35.21.

Using these procedures, but employing, in place of butyl 2-bromo-3-phenylpropionate S35.20, different haloesters S35.5, the corresponding products S35.6 are obtained.

The monoamidate products S35.3 are also prepared from the doubly activated phosphonate derivatives S34.7. In this procedure, examples of which are described in *Synlett.*, 1998, 1, 73, the intermediate S34.7 is reacted with a limited amount of the aminoester S34.9 to give the mono-displacement product S34.11. The latter compound is then reacted with the hydroxy compound $R^3OH$ in a polar organic solvent such as dimethylformamide, in the presence of a base such as diisopropylethylamine, to yield the monoamidate ester S35.3.

The method is illustrated in Scheme 35, Example 5. In this method, the phosphoryl dichloride S35.22 is reacted in dichloromethane solution with one molar equivalent of ethyl N-methyl tyrosinate S35.23 and dimethylaminopyridine, to generate the monoamidate S35.24. The product is then reacted with phenol S35.25 in dimethylformamide containing potassium carbonate, to yield the ester amidate product S35.26.

Using these procedures, but employing, in place of ethyl N-methyl tyrosinate S35.23 or phenol S35.25, the aminoesters 34.9 and/or the hydroxy compounds R³OH, the corresponding products S35.3 are obtained.

Scheme 35

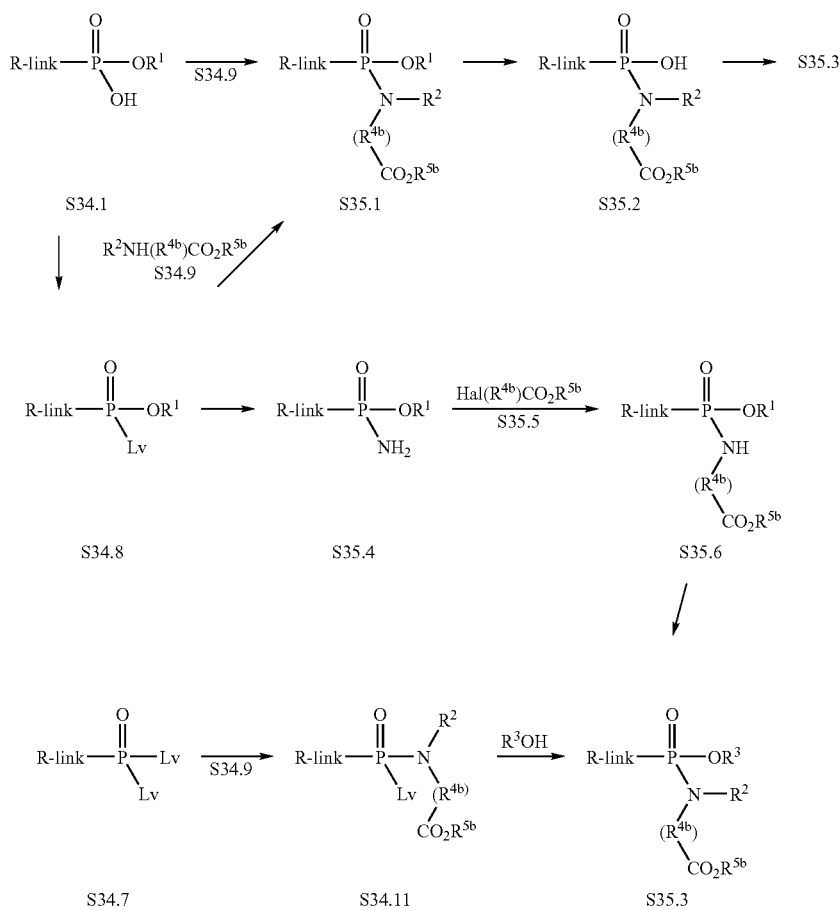

Scheme 35 Example 1

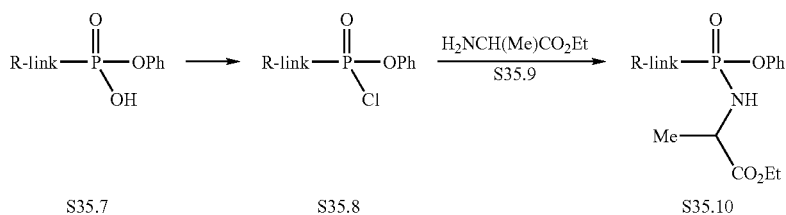

Scheme 35 Example 2

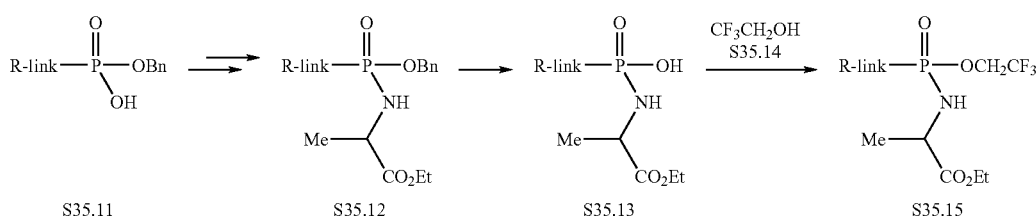

Scheme 35 Example 3

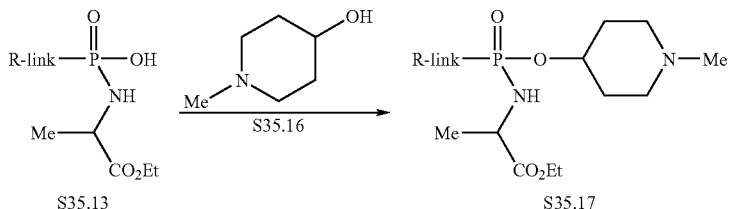

Scheme 35 Example 4

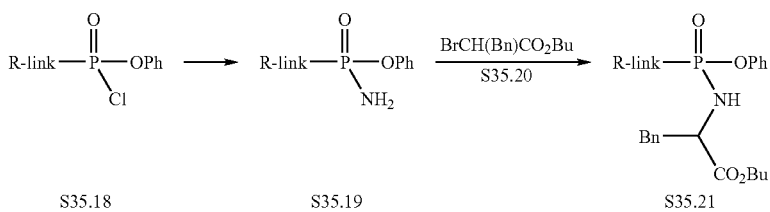

Scheme 35 Example 5

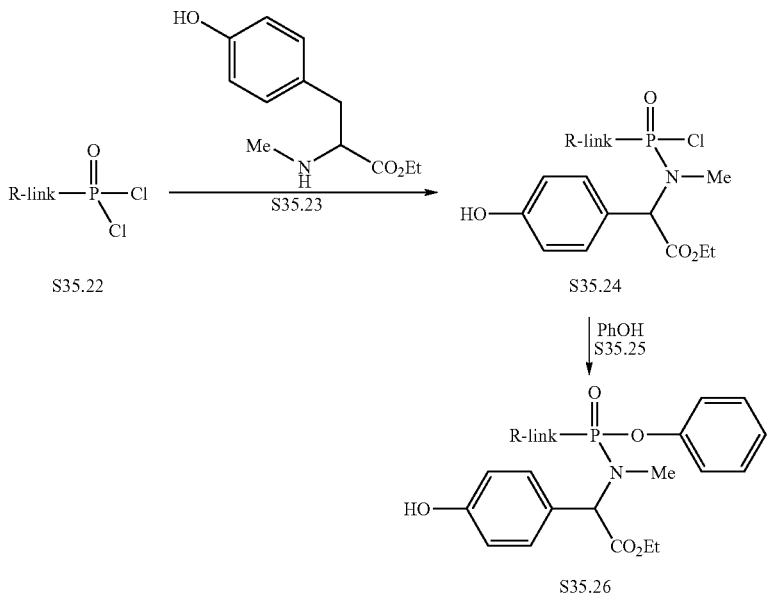

Scheme 36 illustrates methods for the preparation of carboalkoxy-substituted phosphonate diesters in which one of the ester groups incorporates a carboalkoxy substituent.

In one procedure, a phosphonate monoester S34.1, prepared as described above, is coupled, using one of the methods described above, with a hydroxyester S36.1, in which the groups $R^{4b}$ and $R^{5b}$ are as described in Scheme 34. For example, equimolar amounts of the reactants are coupled in the presence of a carbodiimide such as dicyclohexyl carbodiimide, as described in Aust. J. Chem., 1963, 609, optionally in the presence of dimethylaminopyridine, as described in Tet., 1999, 55, 12997. The reaction is conducted in an inert solvent at ambient temperature.

The procedure is illustrated in Scheme 36, Example 1. In this method, a monophenyl phosphonate S36.9 is coupled, in dichloromethane solution in the presence of dicyclohexyl carbodiimide, with ethyl 3-hydroxy-2-methylpropionate S36.10 to yield the phosphonate mixed diester S36.11.

Using this procedure, but employing, in place of ethyl 3-hydroxy-2-methylpropionate S36.10, different hydroxyesters S33.1, the corresponding products S33.2 are obtained.

The conversion of a phosphonate monoester S34.1 into a mixed diester S36.2 is also accomplished by means of a Mitsunobu coupling reaction with the hydroxyester S36.1, as described in Org. Lett., 2001, 643. In this method, the reactants 34.1 and S36.1 are combined in a polar solvent such as tetrahydrofuran, in the presence of a triarylphosphine and a dialkyl azodicarboxylate, to give the mixed diester S36.2. The $R^1$ substituent is varied by cleavage, using the methods described previously, to afford the monoacid product S36.3. The product is then coupled, for example using methods described above, with the hydroxy compound $R^3OH$, to give the diester product S36.4.

The procedure is illustrated in Scheme 36, Example 2. In this method, a monoallyl phosphonate S36.12 is coupled in tetrahydrofuran solution, in the presence of triphenylphosphine and diethylazodicarboxylate, with ethyl lactate S36.13 to give the mixed diester S36.14. The product is reacted with tris(triphenylphosphine) rhodium chloride (Wilkinson catalyst) in acetonitrile, as described previously, to remove the allyl group and produce the monoacid product S36.15. The latter compound is then coupled, in pyridine solution at ambient temperature, in the presence of dicyclohexyl carbodiimide, with one molar equivalent of 3-hydroxypyridine S36.16 to yield the mixed diester S36.17.

Using the above procedures, but employing, in place of the ethyl lactate S36.13 or 3-hydroxypyridine, a different hydroxyester S36.1 and/or a different hydroxy compound $R^3OH$, the corresponding products S36.4 are obtained.

The mixed diesters S36.2 are also obtained from the monoesters S34.1 via the intermediacy of the activated monoesters S36.5. In this procedure, the monoester S34.1 is converted into the activated compound S36.5 by reaction with, for example, phosphorus pentachloride, as described in *J. Org. Chem.*, 2001, 66, 329, or with thionyl chloride or oxalyl chloride (Lv=Cl), or with triisopropylbenzenesulfonyl chloride in pyridine, as described in *Nucleosides and Nucleotides*, 2000, 19, 1885, or with carbonyl diimidazole, as described in *J. Med. Chem.*, 2002, 45, 1284. The resultant activated monoester is then reacted with the hydroxyester S36.1, as described above, to yield the mixed diester S36.2.

The procedure is illustrated in Scheme 36, Example 3. In this sequence, a monophenyl phosphonate S36.9 is reacted, in acetonitrile solution at 70° C., with ten equivalents of thionyl chloride, so as to produce the phosphoryl chloride S36.19. The product is then reacted with ethyl 4-carbamoyl-2-hydroxybutyrate S36.20 in dichloromethane containing triethylamine, to give the mixed diester S36.21.

Using the above procedures, but employing, in place of ethyl 4-carbamoyl-2-hydroxybutyrate S36.20, different hydroxyesters S36.1, the corresponding products S36.2 are obtained.

The mixed phosphonate diesters are also obtained by an alternative route for incorporation of the $R^{30}$ group into intermediates S36.3 in which the hydroxyester moiety is already incorporated. In this procedure, the monoacid intermediate S36.3 is converted into the activated derivative S36.6 in which Lv is a leaving group such as chloro, imidazole, and the like, as previously described. The activated intermediate is then reacted with the hydroxy compound $R^3OH$, in the presence of a base, to yield the mixed diester product S36.4.

The method is illustrated in Scheme 36, Example 4. In this sequence, the phosphonate monoacid S36.22 is reacted with trichloromethanesulfonyl chloride in tetrahydrofuran containing collidine, as described in *J. Med. Chem.*, 1995, 38, 4648, to produce the trichloromethanesulfonyloxy product S36.23. This compound is reacted with 3-(morpholinomethyl)phenol S36.24 in dichloromethane containing triethylamine, to yield the mixed diester product S36.25.

Using the above procedures, but employing, in place of with 3-(morpholinomethyl)phenol S36.24, different alcohols $R^3OH$, the corresponding products S36.4 are obtained.

The phosphonate esters S36.4 are also obtained by means of alkylation reactions performed on the monoesters S34.1. The reaction between the monoacid S34.1 and the haloester S36.7 is performed in a polar solvent in the presence of a base such as diisopropylethylamine, as described in *Anal. Chem.*, 1987, 59, 1056, or triethylamine, as described in *J. Med. Chem.*, 1995, 38, 1372, or in a non-polar solvent such as benzene, in the presence of 18-crown-6, as described in *Syn. Comm.*, 1995, 25, 3565.

The method is illustrated in Scheme 36, Example 5. In this procedure, the monoacid S36.26 is reacted with ethyl 2-bromo-3-phenylpropionate S36.27 and diisopropylethylamine in dimethylformamide at 80° C. to afford the mixed diester product S36.28.

Using the above procedure, but employing, in place of ethyl 2-bromo-3-phenylpropionate S36.27, different haloesters S36.7, the corresponding products S36.4 are obtained.

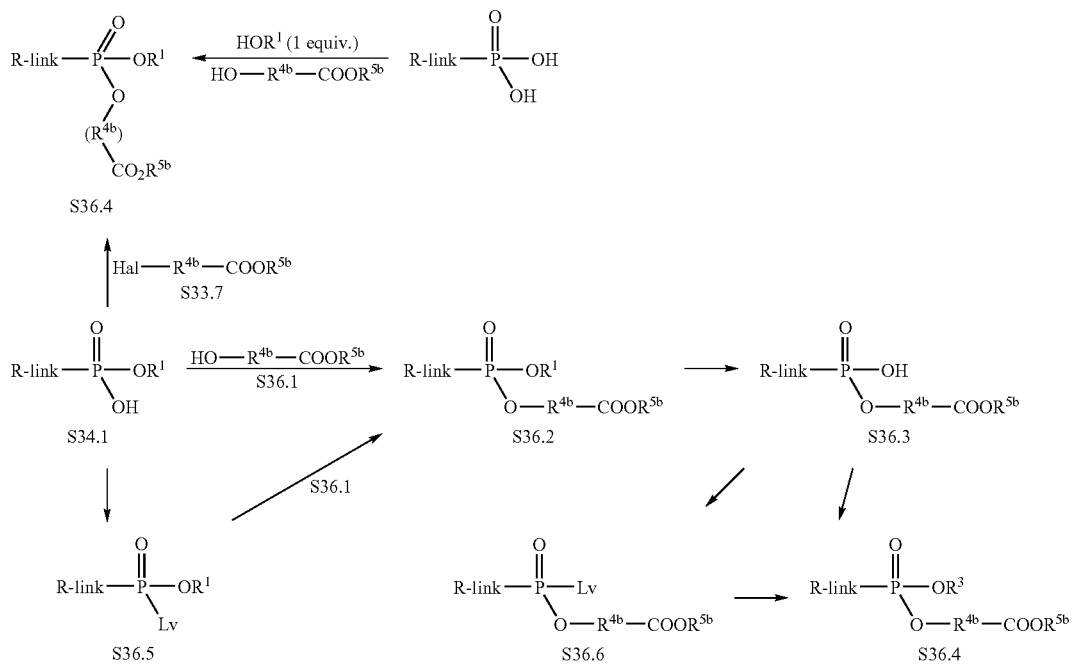

Scheme 36

-continued
Scheme 36 Example 1
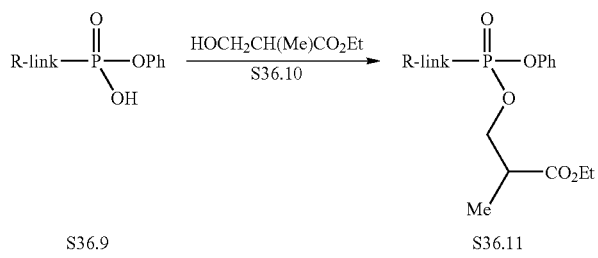
Scheme 36 Example 2
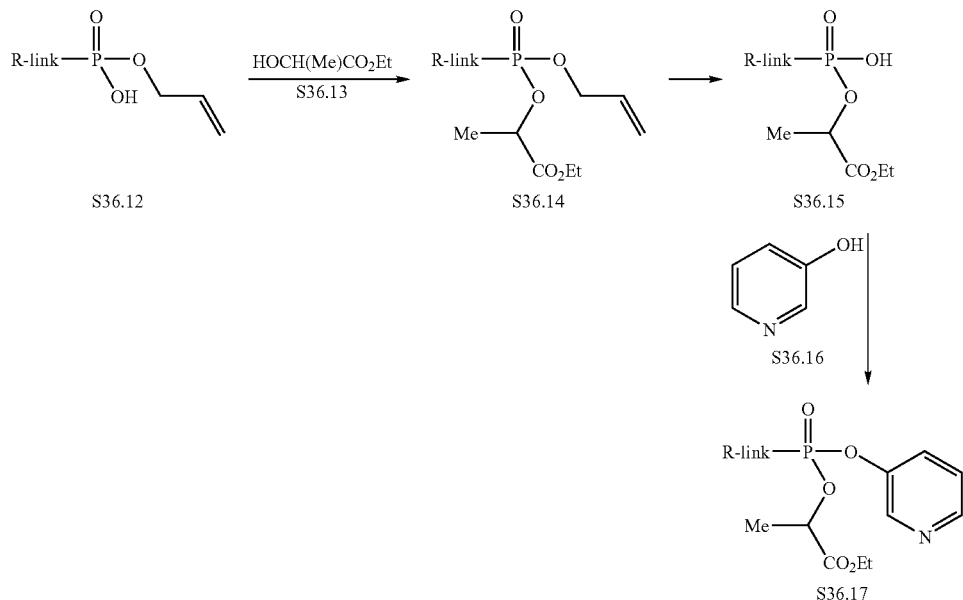
Scheme 36 Example 3
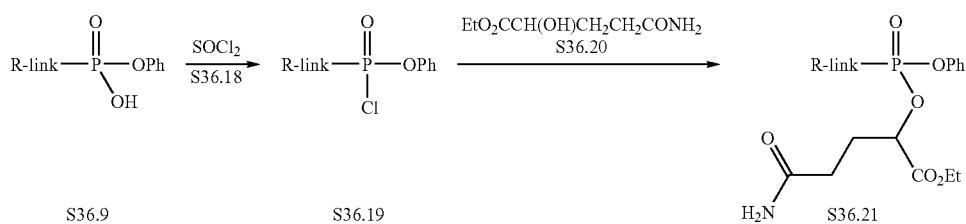
Scheme 36 Example 4
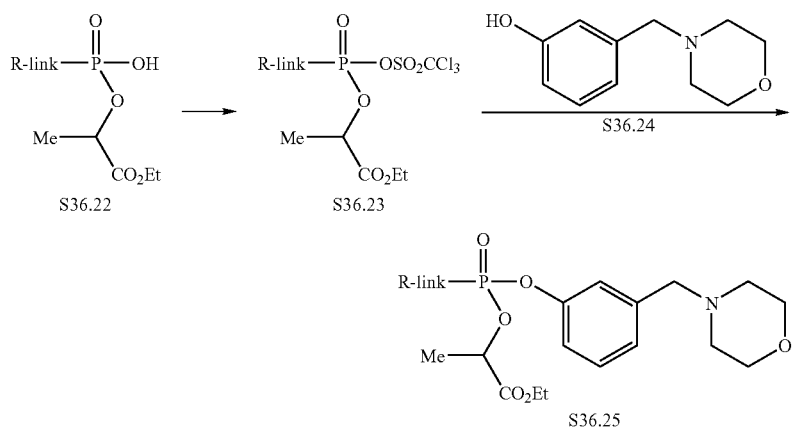

Scheme 36 Example 5

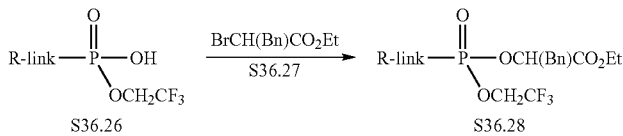

Scheme 37 illustrates methods for the preparation of phosphonate diesters in which both the ester substituents incorporate carboalkoxy groups.

The compounds are prepared directly or indirectly from the phosphonic acids S34.6. In one alternative, the phosphonic acid is coupled with the hydroxyester S37.2, using the conditions described previously in Schemes 34-36, such as coupling reactions using dicyclohexyl carbodiimide or similar reagents, or under the conditions of the Mitsunobu reaction, to afford the diester product S37.3 in which the ester substituents are identical.

This method is illustrated in Scheme 37, Example 1. In this procedure, the phosphonic acid S34.6 is reacted with three molar equivalents of butyl lactate S37.5 in the presence of Aldrithiol-2 and triphenyl phosphine in pyridine at ca. 70° C., to afford the diester S37.6.

Using the above procedure, but employing, in place of butyl lactate S37.5, different hydroxyesters S37.2, the corresponding products S37.3 are obtained.

Alternatively, the diesters S37.3 are obtained by alkylation of the phosphonic acid S34.6 with a haloester S37.1. The alkylation reaction is performed as described in Scheme 36 for the preparation of the esters S36.4.

This method is illustrated in Scheme 37, Example 2. In this procedure, the phosphonic acid S34.6 is reacted with excess ethyl 3-bromo-2-methylpropionate S37.7 and diisopropylethylamine in dimethylformamide at ca. 80° C., as described in *Anal. Chem.*, 1987, 59, 1056, to produce the diester S37.8.

Using the above procedure, but employing, in place of ethyl 3-bromo-2-methylpropionate S37.7, different haloesters S37.1, the corresponding products S37.3 are obtained.

The diesters S37.3 are also obtained by displacement reactions of activated derivatives S34.7 of the phosphonic acid with the hydroxyesters S37.2. The displacement reaction is performed in a polar solvent in the presence of a suitable base, as described in Scheme 36. The displacement reaction is performed in the presence of an excess of the hydroxyester, to afford the diester product S37.3 in which the ester substituents are identical, or sequentially with limited amounts of different hydroxyesters, to prepare diesters S37.3 in which the ester substituents are different.

The methods are illustrated in Scheme 37, Examples 3 and 4. As shown in Example 3, the phosphoryl dichloride S35.22 is reacted with three molar equivalents of ethyl 3-hydroxy-2-(hydroxymethyl)propionate S37.9 in tetrahydrofuran containing potassium carbonate, to obtain the diester product S37.10.

Using the above procedure, but employing, in place of ethyl 3-hydroxy-2-(hydroxymethyl)propionate S37.9, different hydroxyesters S37.2, the corresponding products S37.3 are obtained.

Scheme 37, Example 4 depicts the displacement reaction between equimolar amounts of the phosphoryl dichloride S35.22 and ethyl 2-methyl-3-hydroxypropionate S37.11, to yield the monoester product S37.12. The reaction is conducted in acetonitrile at 70° in the presence of diisopropylethylamine. The product S37.12 is then reacted, under the same conditions, with one molar equivalent of ethyl lactate S37.13, to give the diester product S37.14.

Using the above procedures, but employing, in place of ethyl 2-methyl-3-hydroxypropionate S37.11 and ethyl lactate S37.13, sequential reactions with different hydroxyesters S37.2, the corresponding products S37.3 are obtained.

Scheme 37

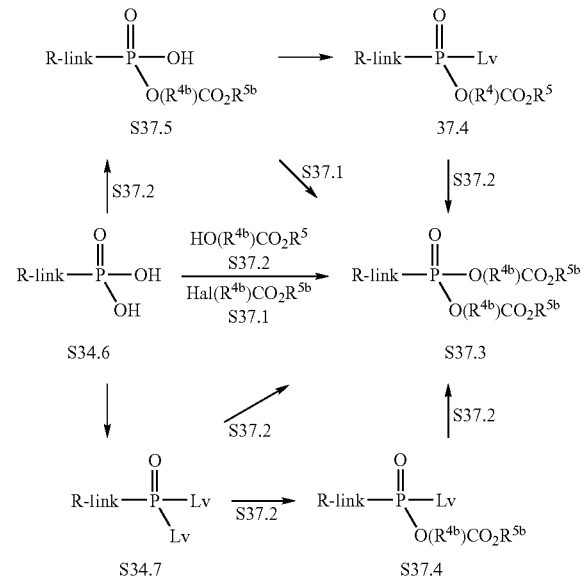

Scheme 37 Example 1

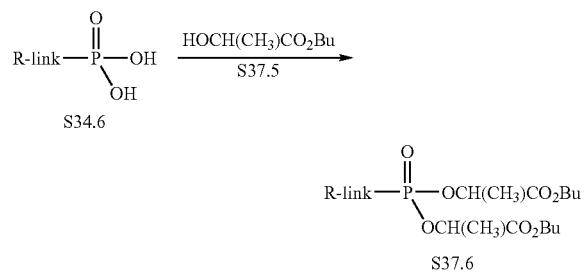

Scheme 37 Example 2

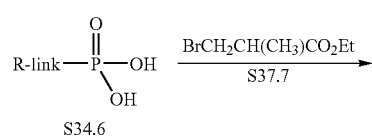

-continued

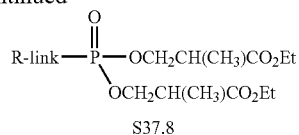
S37.8

Scheme 37 Example 3

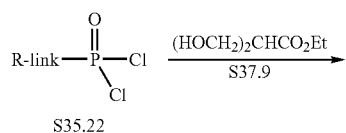

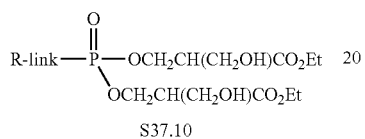
S37.10

Scheme 37 Example 4

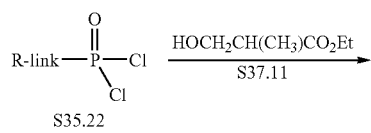

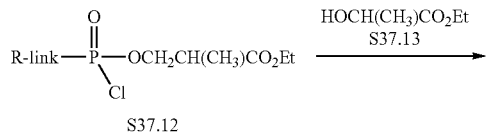
S37.12

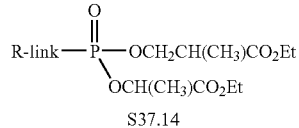
S37.14

-continued

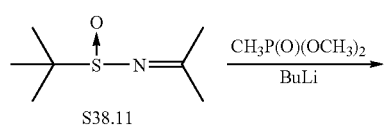
S38.11

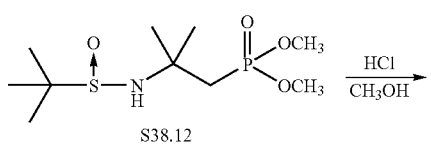
S38.12

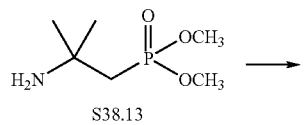
S38.13

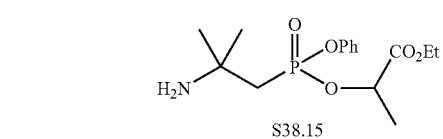
S38.14

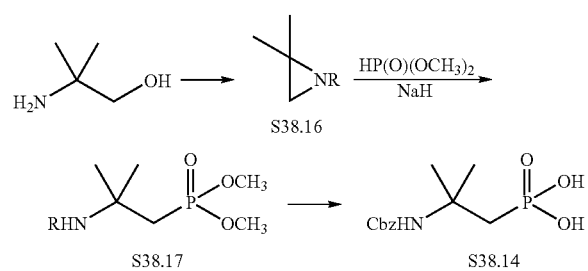
S38.15

Scheme 38b

[scheme showing conversion from H₂N—OH via S38.16 to S38.17 and then to S38.14]

R = Cbz, R'SO₂

The invention will now be illustrated by the following non-limiting Examples.

EXAMPLE 1

Preparation of Representative Compounds of Formula 1

Representative compounds of the invention can be made according to the general route outlined below.

[structure showing thiazole compound with 1. O-alkylation, 2. ester hydrolysis]

2,2-Dimethyl-2-aminoethylphosphonic acid intermediates can be prepared by the route in Scheme 5. Condensation of 2-methyl-2-propanesulfinamide with acetone give sulfinyl imine S38.11 (*J. Org. Chem.* 1999, 64, 12). Addition of dimethyl methylphosphonate lithium to S38.11 afford S38.12. Acidic methanolysis of S38.12 provide amine S38.13. Protection of amine with Cbz group and removal of methyl groups yield phosphonic acid S38.14, which can be converted to desired S38.15 (Scheme 38a) using methods reported earlier on. An alternative synthesis of compound S38.14 is also shown in Scheme 38b. Commercially available 2-amino-2-methyl-1-propanol is converted to aziridines S38.16 according to literature methods (*J. Org. Chem.* 1992, 57, 5813; *Syn. Lett.* 1997, 8, 893). Aziridine opening with phosphite give S38.17 (*Tetrahedron Lett.* 1980, 21, 1623). Reprotection) of S38.17 affords S38.14.

Scheme 38a

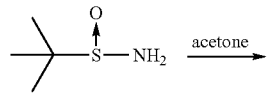

-continued

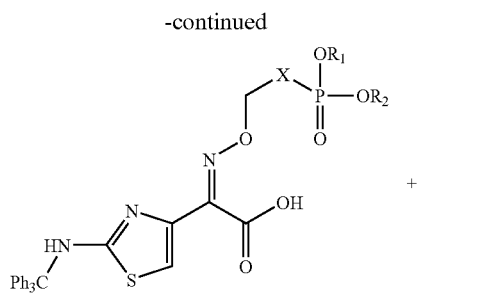

+

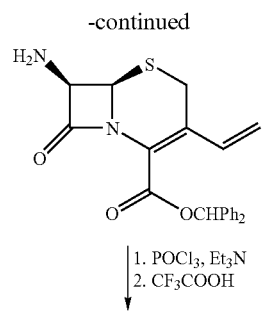

1. POCl₃, Et₃N
2. CF₃COOH

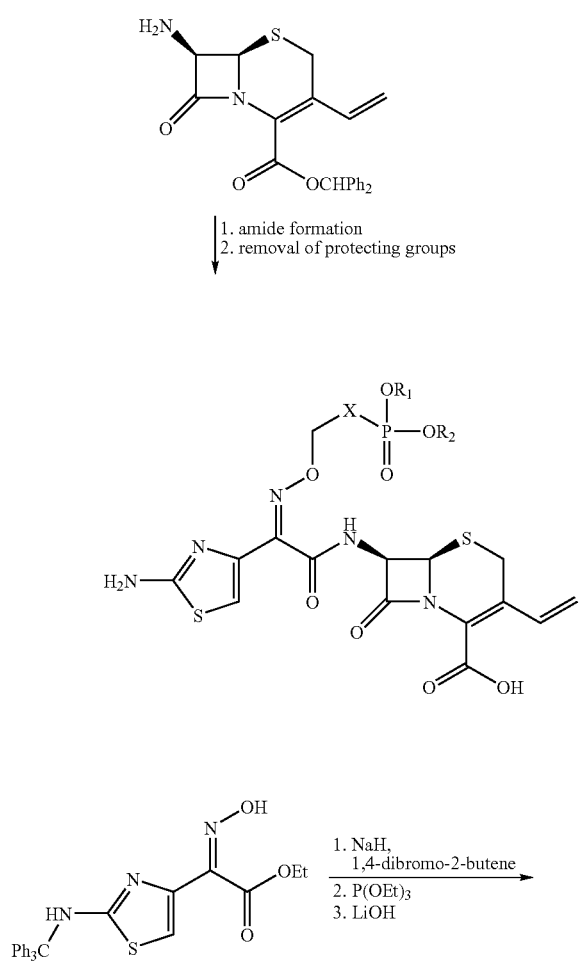

Hydroxyimino-[2-(tritylamino)-thiazol-4-yl]acetic acid ethyl ester (commercially available) can be treated in a solvent such as dimethylformamide (DMF) or tetrahydrofuran (THF) with a base such as sodium hydride. When bubbling ceases, 1,4-dibromo-2-butene is added in excess. After quenching the reaction with aqueous ammonium chloride and extracting the product with an organic solvent such as ethyl acetate, the mono-alkylated product is isolated by chromatography. The allylic bromide is then heated with triethylphosphite in a solvent such as toluene (or other Arbuzov reaction conditions; see Engel, R., "Synthesis of Carbon-phosphorus Bonds," CRC press, (1988)) to generate [4-(diethoxyphosphoryl)-but-2-enyloxyimino]-[2-(tritylamino)-thiazol-4-yl]-acetic acid ethyl ester.

The ester is hydolyzed to the acid, which is coupled with 7-amino-8-oxo-3-vinyl-5-thia-1-aza-bicyclo[4.2.0]oct-2-ene-2-carboxylic acid benzhydryl ester (obtained as described in *Tet. Lett.*, 35:9601 (1994)), following a procedure such as that reported in *J. Antibiotic.*, 53:1045 (2000). The coupled product is then treated with trifluoroacetic acid to afford the desired phosphonate-containing analog.

EXAMPLE 2

Preparation of Representative Compounds of Formulae 2-3

Representative compounds of the invention can be made according to the general route outlined below.

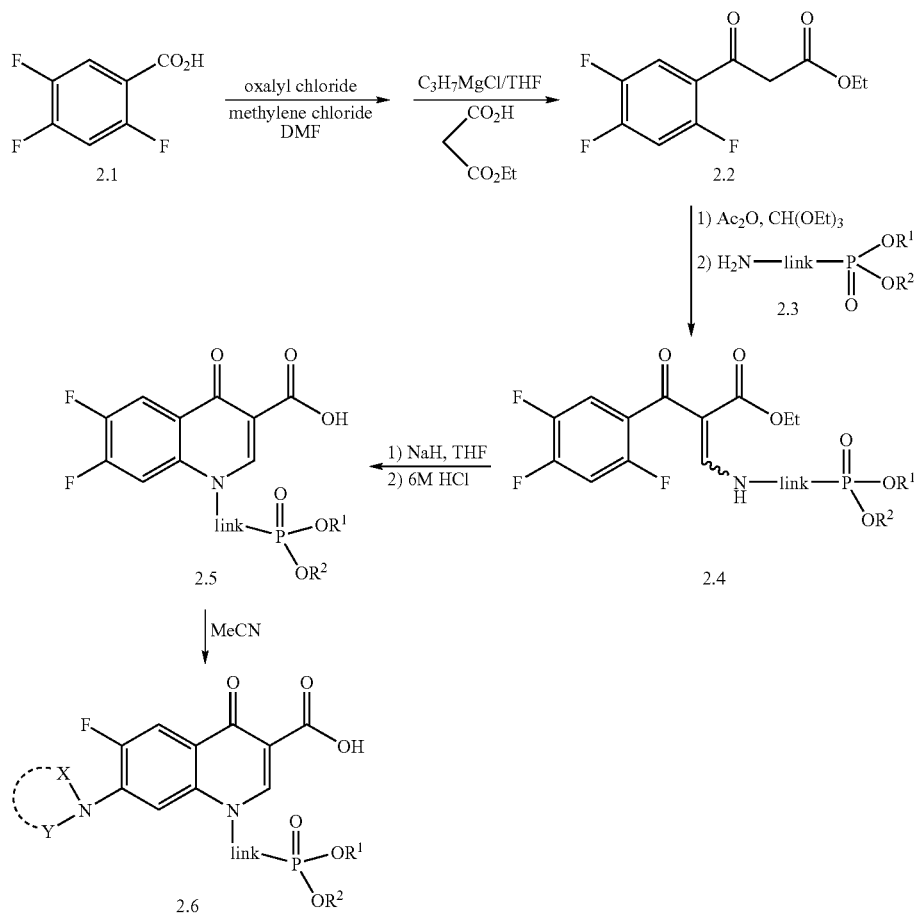
The synthesis of compounds of the invention proceeds through intermediates of type 2.6. Intermediates 2.6 are prepared according to methods reported in the literature.
For instance, a specific compound of the invention can be prepared as follows:
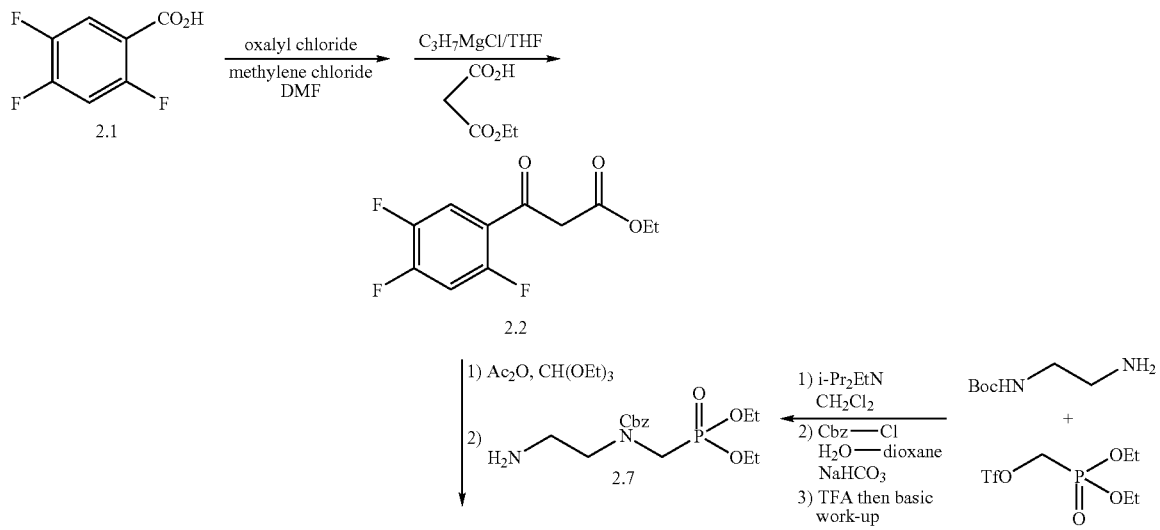

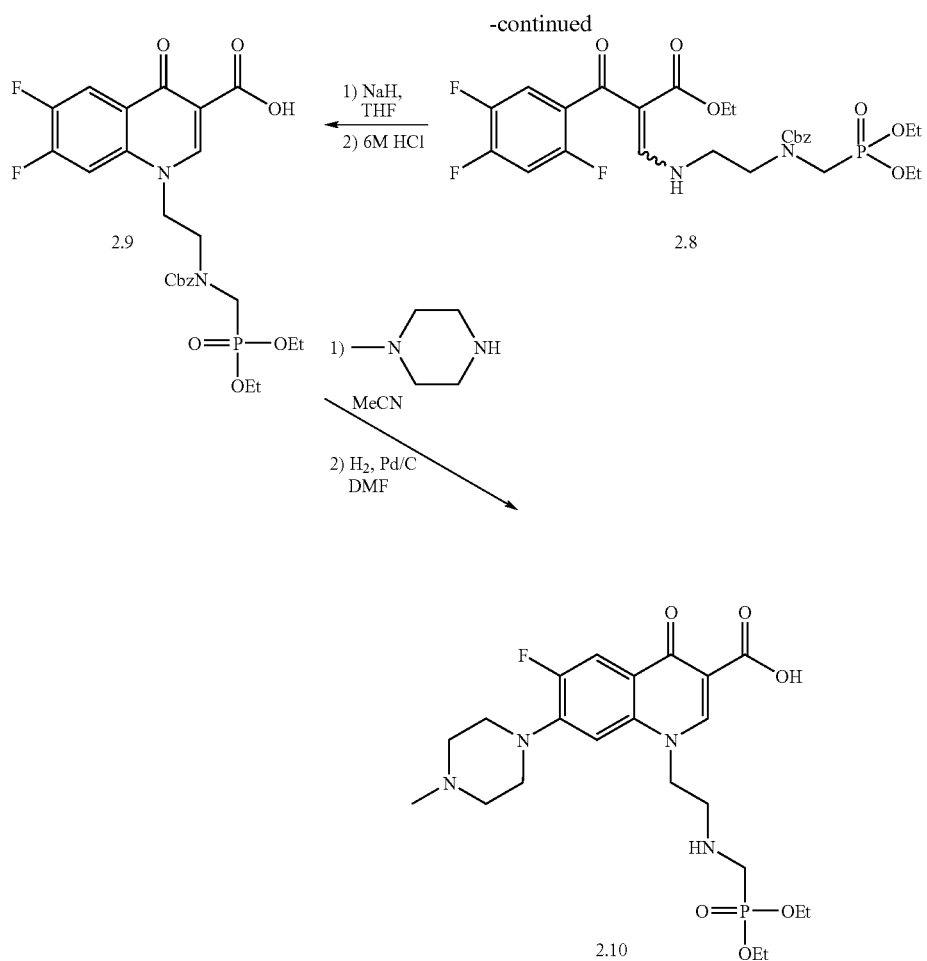

The scheme may be carried out where compound 2.3 of the above scheme has been replaced with 2.7, synthesized by reaction of excess N-Boc-ethylenediamine (available from a supplier such as Fluka) and diethyl phosphonomethyltriflate (prepared according to *Tetrahedron Lett.* 27:1477 (1986)) according to a procedure such as that reported in *J. Med. Chem.*, 43:489 (2000), followed by protection of the secondary amine with Cbz-Cl in dioxane-H$_2$O in the presence of NaHCO$_3$. Finally, the primary amine of 2.7 is liberated by deprotection with trifluoroacetic acid and a basic organic-aqueous work-up. Compound 2.9 of this scheme may then be reacted with an amine such as mono-methyl piperazine to provide quinolone intermediate 2.10 after Cbz group hydrogenolysis at 1 atmosphere of H$_2$ in the presence of 10% Pd/C.

The synthesis of compounds of the invention proceeds through intermediates of type 2.16, using a scheme similar to that shown above. In certain embodiments, as shown below, the linkage element is now introduced in a different area of the molecule through amine 2.17.

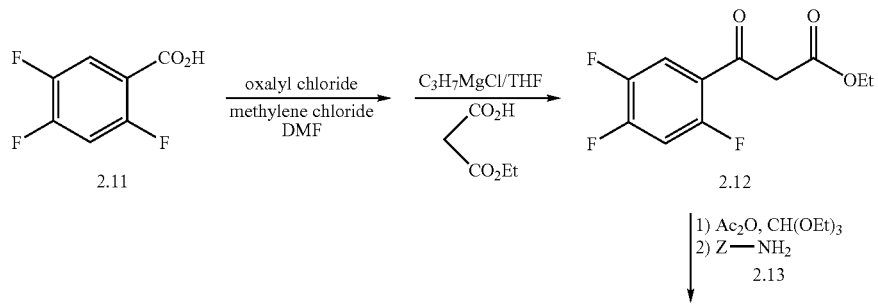

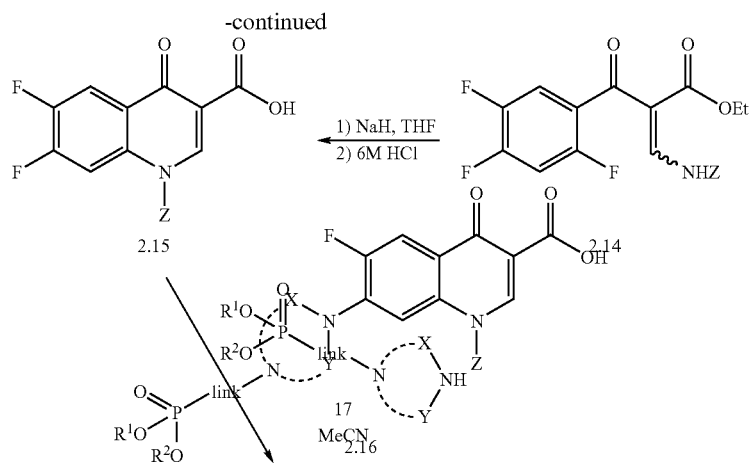

For instance, a specific compound of the invention can be prepared as shown below. The sequence shown above is executed using commercially available cyclopropyl amine in lieu of 2.13, and 2.20, prepared by reaction of excess piperazine with diethyl phosphonomethyltriflate (see citations hereinabove for reaction conditions, as well as preparation of diethyl phosphonomethyltriflate), in lieu of 2.17. Intermediate 2.21 may have its phosphonate ester converted to the desired prodrug.

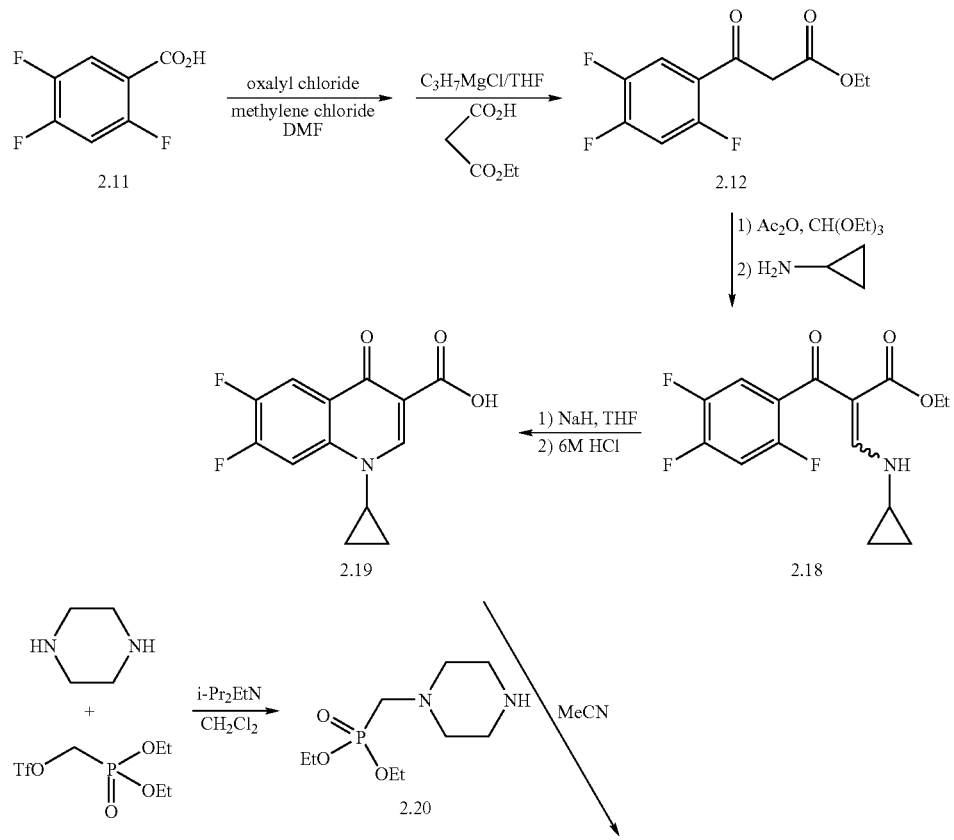

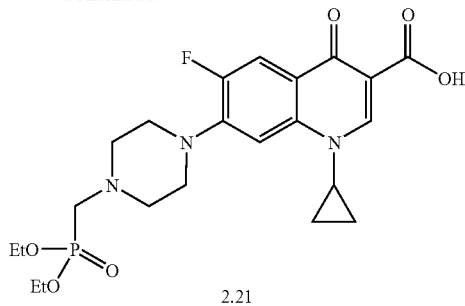

2.21

EXAMPLE 3

Preparation of Representative Compounds of Formulae 4-5

Representative compounds of the invention can be made according to the general route outlined below. Intermediate 3.1 is prepared as described in *J. Am. Chem. Soc.*, 77:3104 (1955). Its use proceeds as in U.S. Pat. No. 4,331,803 and EP 0041355. An alkylation is preformed selectively at the 11 position of 3.1 using a mixture of DMSO and THF with an alkylating agent of type 3.2 (where X=a leaving group such as, but not limited to bromide, iodide, chloride, methanesulfonate, trifluoromethanesulfonate, and p-toluenesulfonate) in the presence of NaH. It is known that when the hydroxy group at C-6 on the precursor to 3.1 is being methylated to give 3.1, one also can get over-methylation occurring selectively at the 11 position. Therefore, a second alkyl group other than methyl added to 3.1 is also expected to go to the 11 position. The functional groups of an active erythromycin are then replaced to give an intermediate of structural type 3.4. Phosphonate manipulations, as described below, may then be carried out.

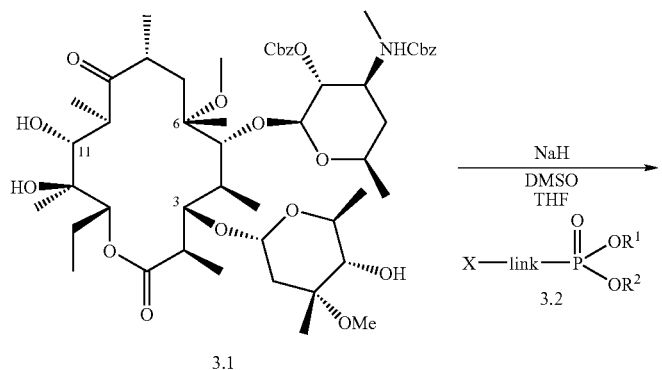

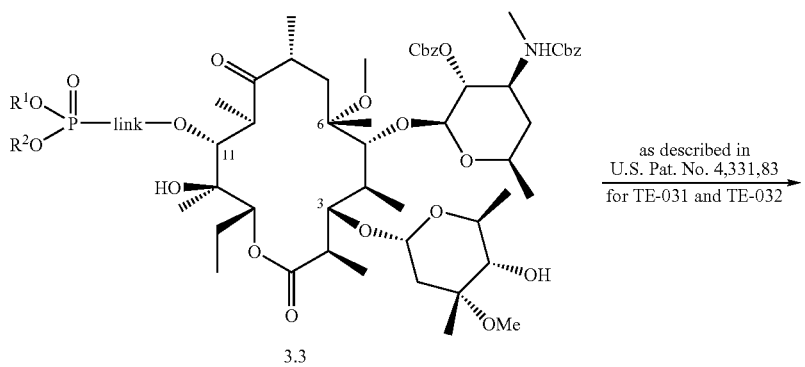

-continued
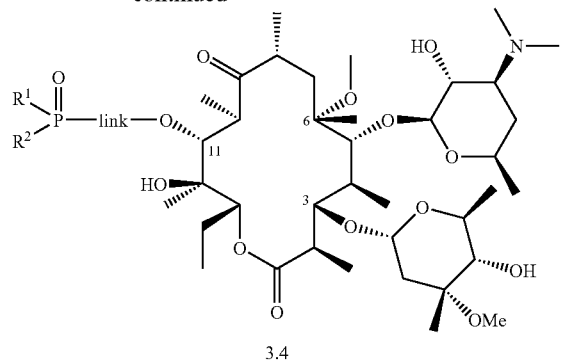
3.4
For instance, a specific compound of the invention can be prepared as follows:
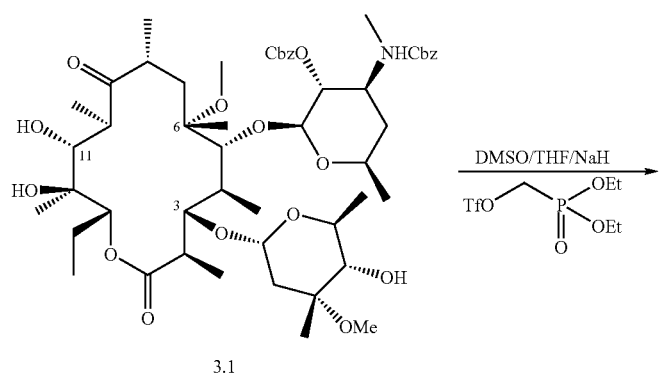
3.1
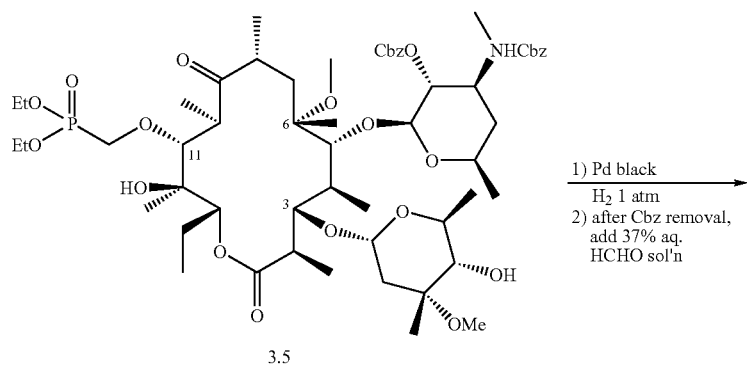
3.5
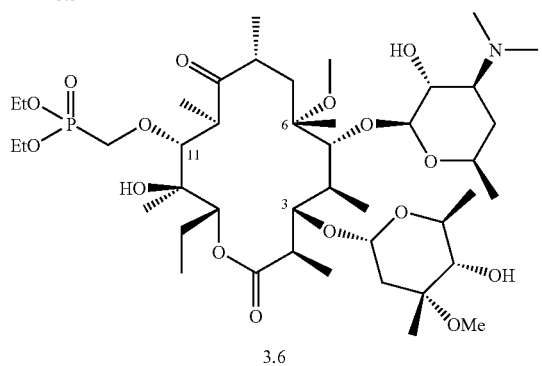
3.6

Compound 3.4 can be treated in DMSO/THF (1:2 v/v of anhydrous solvent) with NaH (1.2 molar equivalents), with rapid stirring under an $N_2$ atmosphere at $-10°$ C. When bubbling ceases, diethyl phosphonomethyltriflate (prepared according to *Tetrahedron Lett.*, 27:1477 (1986)) is added, yielding intermediate 3.5. This material is then deprotected and converted by methylation of the sugar nitrogen back into the active erythromycin species according to the method of U.S. Pat. No. 4,331,803.

Compound 3.5 is dissolved in a mixture of ethanol buffered with sodium acetate and acetic acid. The protecting groups are removed by hydrogenolysis at 1 atm $H_2$ after addition of Pd-black. When hydrogenolysis is complete, aqueous formaldehyde is added (37% solution) and reductive methylation under 1 atm of $H_2$ in the presence of the Pd black is effected providing intermediate 3.6, now with native erythromycin functional groups restored to its sugars. Compound 3.6 is then converted via the phosphonate manipulations described below into the final desired compound.

In addition, representative compounds of the invention can be made according to the general route outlined below.

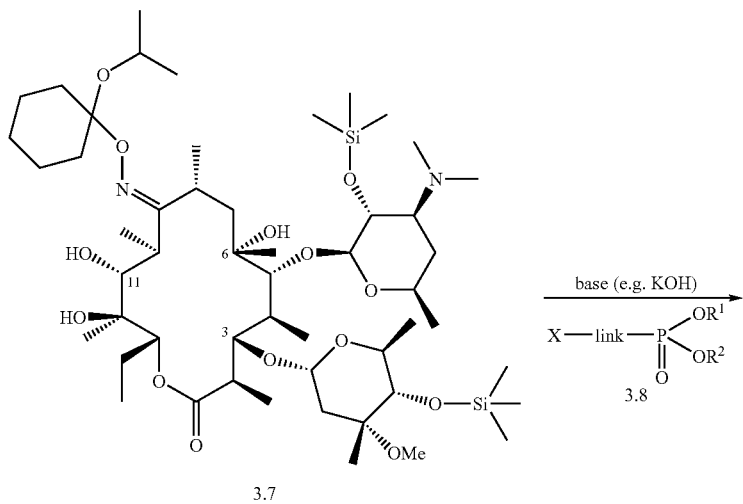

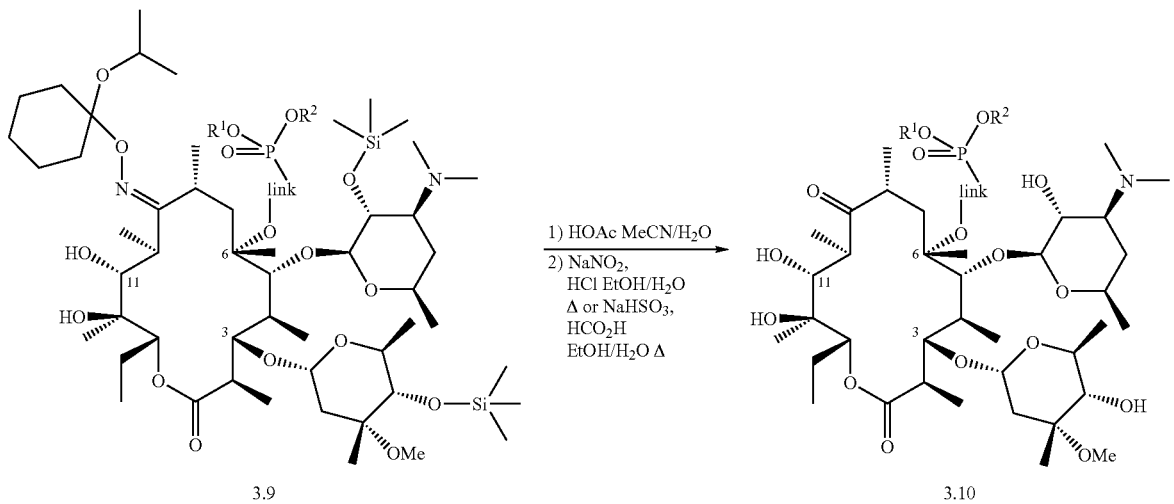

Intermediate 3.7 was prepared according to U.S. Pat. No. 4,990,602. It was used as described in *Bioorg. Med. Chem. Lett.*, 10:815 (2000). It is treated with an appropriate base such as KOH or KOtBu in a DMSO-THF mixture in the presence of an alkylating agent of type 3.8 at 0° C. The resultant intermediate 3.9 is then deprotected according to the same literature, by treatment first with HOAc in MeCN/$H_2O$, followed by deoximation with either $NaNO_2$ or $NaHSO_3$ in the presence of acid in an EtOH/$H_2O$ solvent system at 70 to 80° C.

A specific compound of the invention is prepared as follows:

EXAMPLE 4

Preparation of Representative Compounds of Formulae 6-7

Representative compounds of the invention can be made according to the general route outlined below. Ethambutol is available for purchase from commercial chemical suppliers such as Sigma.

Selective protection of the two amine functional groups in the presence of the two free hydroxyl groups may be accomplished with any number of amine protective groups

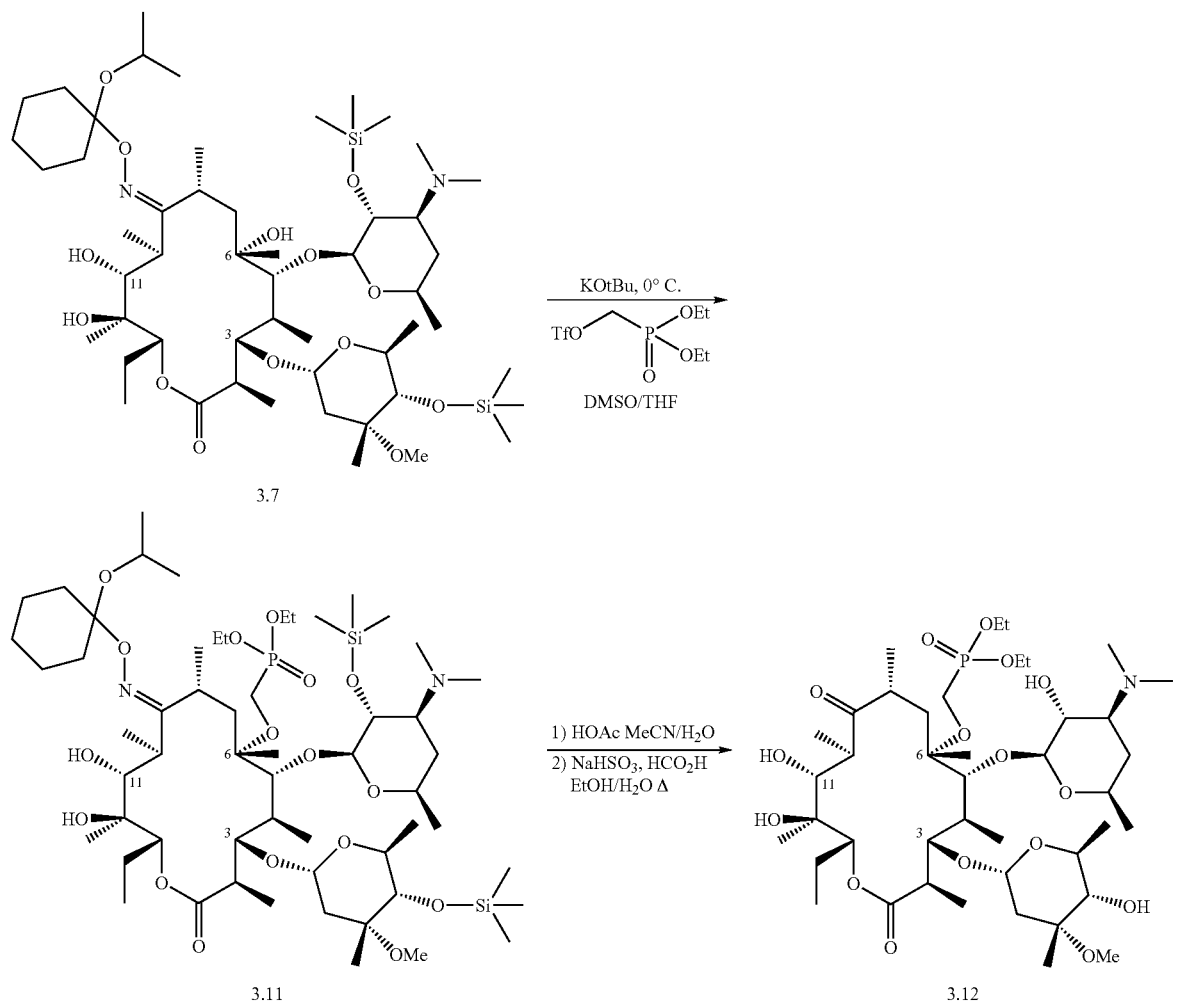

Compound 3.7 is alkylated in a DMSO/THF solution with diethyl phosphonomethyltriflate (prepared according to the reference cited above) in the presence of KOtBu at 0° C. The desired 3.11 is then treated with HOAc in MeCN/$H_2O$ followed by $NaHSO_3$ (4 molar equivalents) in the presence of $HCO_2H$ (2.5 equivalents) in EtOH/$H_2O$ solution at 80° C. The intermediate 3.12 is isolated by the appropriate chromatographic method and the phosphonate esters are converted into the desired final functionality as described herein.

under any number of conditions (as described in "Protective Groups in Organic Synthesis" Green and Wuts, $2^{nd}$ Ed., 1991, John Wiley & Sons, Inc., New York). To ensure that both amines are protected completely, at least two equivalents of the reagent(s) used to introduce the protecting group must be used.

The protected intermediates 4.1 (see below) are isolated by any number of purification/isolation methods well known to those skilled in the art. The protected derivatives 4.1 are then linked to the phosphonate linker element by treatment with a suitable base which may include, but is not limited to, a metal hydride, $Cs_2CO_3$, $Mg(OtBu)_2$ in an appropriate solvent for that particular base. The mixture is then treated with an alkylating agent of structural type 4.2, where X is a leaving group which may be, but is not limited to, bromide, chloride, iodide, tosylate, mesylate, or trifluoromethanesulfonate. This alkylating agent is used only in limiting amount so that only a single hydroxyl group is modified. This yields the desired intermediate 4.3, which is isolated by any one of the purification/isolation methods well known to those skilled in the art.

Depending on the identity of the final $R^1$ and $R^2$ groups of the final phosphonate product desired, it may or may not be practical to remove the protective groups on the nitrogen atoms at this point. If it is desirable to do so, this may be accomplished using the conditions described for the protective group in question in "Protective Groups in Organic Synthesis," supra, providing intermediates 4.4.

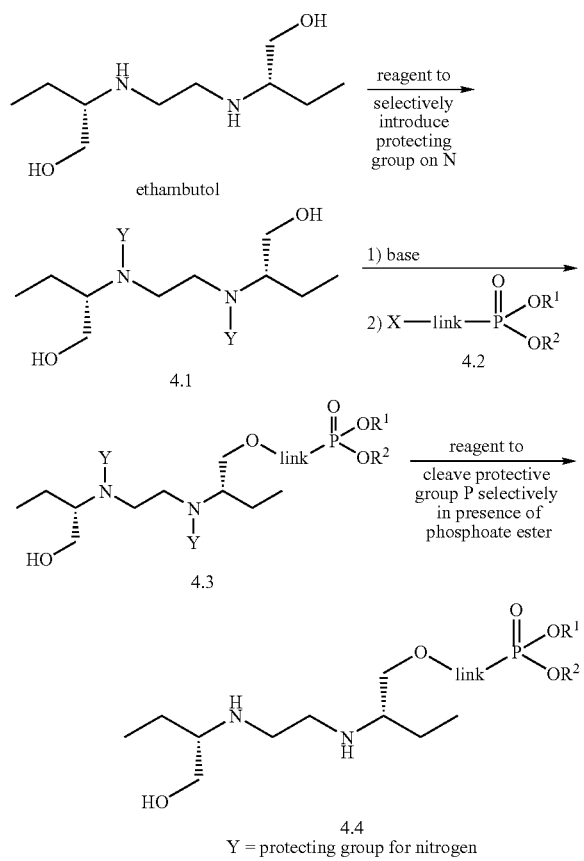

For instance, a specific compound of the invention can be prepared as follows:

Ethambutol can be treated with benzyl chloroformate in a mixture of aqueous $Na_2CO_3$ and 1,4-dioxane to provide compound 4.5. Compound 4.5 can then be treated with NaH in THF at 0° C. (for instance, see *Nucleosides & Nucleotides,* 11:1383 (1992)). After bubbling subsides, this will be treated with a limiting amount of diethyl phosphonomethyltriflate (prepared according to *Tetrahedron Lett.,* 27:1477 (1986)), yielding the monoalkylated derivative 4.6. The phosphonate esters of compound 4.6 may be transformed into the final desired functional groups at this time or alternatively, the Cbz group may be removed first. Removal of the Cbz group is accomplished by treatment with 1 atm of $H_2$ gas, supplied by a balloon reservoir while stirring the mixture rapidly over a fine suspension of 10 mol % of 10% Pd-content Pd/C, to yield deprotected derivative 4.7.

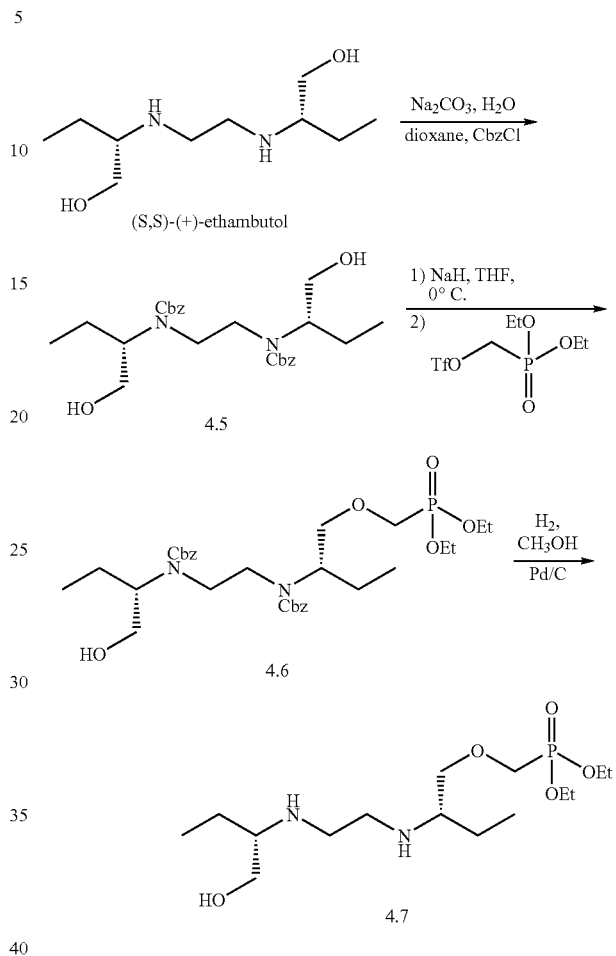

The synthesis of ethambutol phosphonate intermediates of the invention can be as follows.

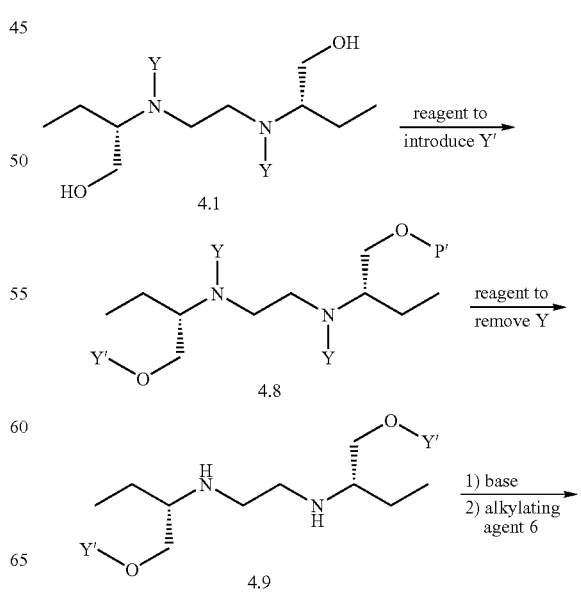

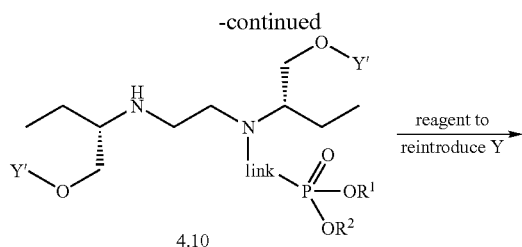

4.10

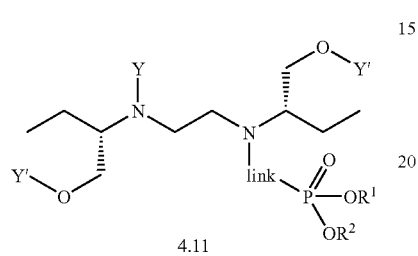

4.11

Y = nitrogen protecting group
Y' = oxygen protecting group orthogonol to Y

Compound 4.1 is treated with a reagent to introduce a protective group onto both hydroxyl groups, providing intermediate 4.8. This protecting group must be orthogonal to the protective group used to protect the nitrogen atoms. "Orthogonal" is defined as the condition wherein the reagents used to introduce or cleave one protective group will not react with or remove a second protective group present on the same molecule. With intermediate 4.8 in hand, the protective groups can be removed from the nitrogen according to the conditions listed in "Protective Groups in Organic Synthesis," supra, affording intermediate 4.9.

Compound 4.9 is then treated with a limiting amount of an alkylating agent of type 4.2, as defined above, providing intermediate 4.10. If necessary, 4.7 can be reprotected on the nitrogen to allow for further selective transformations of the phophonate ester groups. Depending on the identity of the final $R^1$ and $R^2$ groups of the final phosphonate product desired, it may or may not be practical to remove the protective groups on the oxygen atoms at this point. If it is desirable to do so, this may be accomplished using the conditions descibed for the protective group in question in "Protective Groups in Organic Synthesis," supra.

For instance, a specific compound of the invention can be prepared as follows.

Compound 4.5 can be treated with tert-butyldimethylsilyl chloride and imidazole in a suitable solvent such as methylene chloride or N,N-dimethylformamide to afford the bis-silylated derivative 4.12. The Cbz groups of 4.12 can then be hydrogenolyzed to afford the free diamine 4.13 that is then treated with a limiting amount of diethyl phosphonomethyltriflate in the presence of diisopropylethyl amine (in a procedure similar to that reported in J. Med. Chem., 43:488 (2000)) to afford monophosphonyl derivative 4.14. If necessary for purification purposes or for ease of manipulation of the phosphonate ester groups, the Cbz group can be reintroduced by treatment of 4.14 with benzyl chloroformate in aqueous $NaHCO_3$/dioxane to provide protected intermediate 4.15. This Cbz group can then be removed later after phosphonate manipulation is completed.

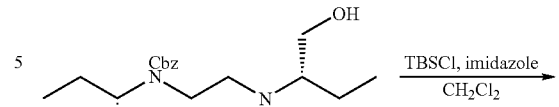

4.5

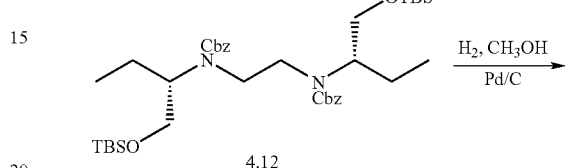

4.12

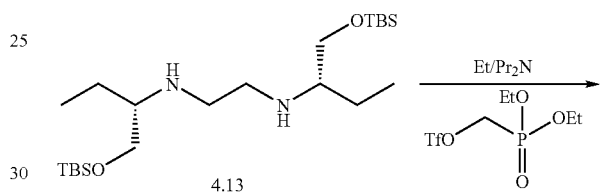

4.13

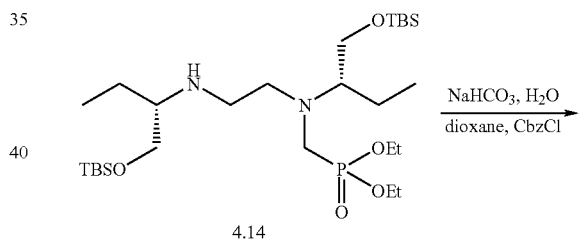

4.14

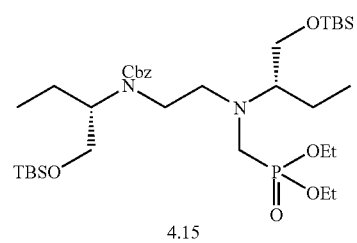

4.15

EXAMPLE 5

Preparation of Representative Compounds of Formulae 8-9

Representative compounds of the invention can be made according to the general route outlined below.

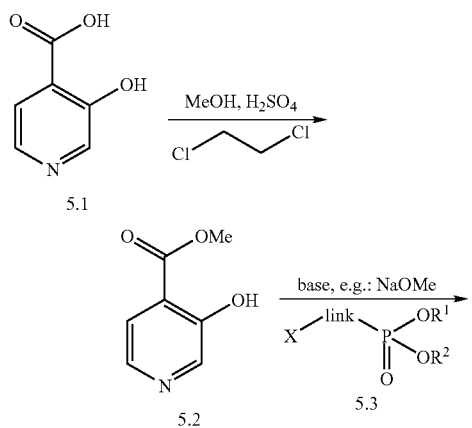

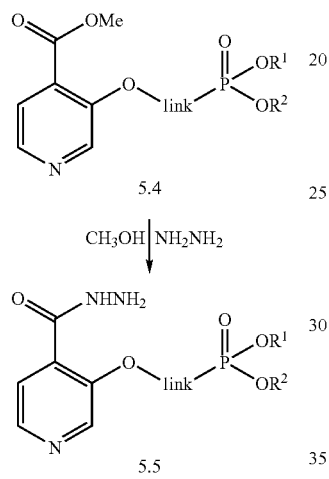

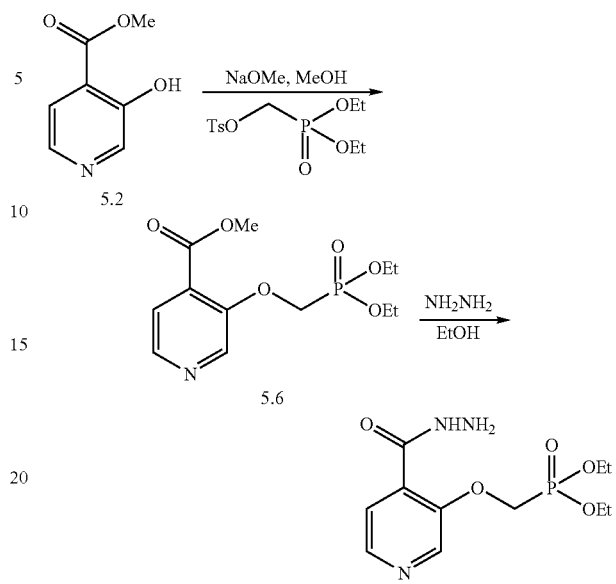

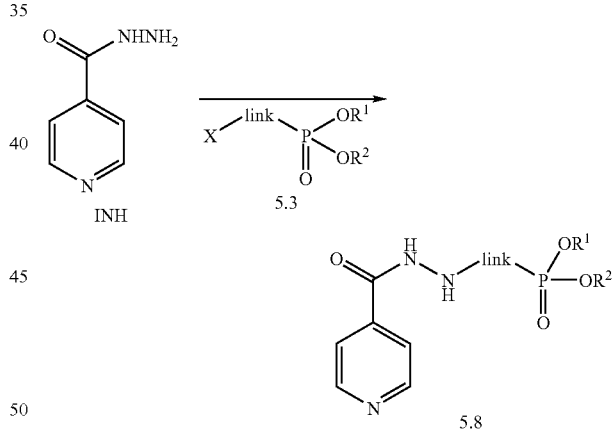

3-hydroxy-4-pyridinecarboxylic (5.1) acid may be purchased from a commercial supplier such as Tyger Chemical. This compound may then be converted into its methyl ester as shown above according to the procedure found in *Tetrahedron*, 3:49-56 (1968), to provide general intermediate 5.2. General intermediate 5.2 may then be converted into a phosphonate linked analog by reaction with an alkylating agent 5.3, where X is a leaving group that may include, but is not limited to, Br, Cl, I, tosylate, mesylate, and trifluoromethanesulfonate, and $R^1$ and $R^2$ may be, but are not limited to, alkyl groups such as methyl, ethyl, allyl, isopropyl or benzyl, in the presence of an appropriate base including, but not limited to, NaOMe, in an appropriate solvent including, but not limited to, methanol, using a procedure such as that reported by Zeng et al., *J. Am. Chem. Soc.*, 122:2635-2644 (2000). Treatment of the resultant intermediate with hydrazine in ethanol heated at reflux will convert the methyl ester to the acyl hydrazine. Such conditions are well known to those skilled in the art.

As an example, a specific compound of the invention may be prepared by treating compound 5.2 with one equivalent of NaOMe in MeOH, followed by dimethyl phosphonomethyltosylate (prepared by the analogous procedure reported for diethyl phosphonomethyltriflate in *Tetrahedron Letters*, 27:1477-1480 (1986)) to afford intermediate 5.6. This compound is then treated with hydrazine in ethanol heated at reflux to provide compound 5.7.

Representative compounds of the invention may be synthesized as follows:

Isoniazid may be purchased from Sigma and treated with the appropriate alkylating agent 5.3 as shown below to provide intermediates 5.8, according to conditions found in the literature (for example, *Indian J. Chem. Sect. B*, 32:760 (1993)).

As an example, a specific compound of the invention can be prepared as follows: Isoniazid is treated with diethyl phosphonomethyltriflate in refluxing benzene for 3 hours to provide derivative 5.9.

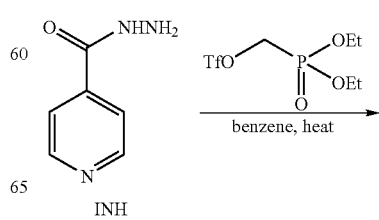

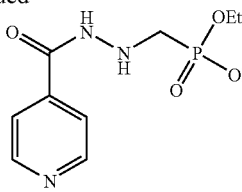

EXAMPLE 6

Preparation of Representative Compounds of Formulae 10-11

Representative compounds of the invention can be made according to the general route outlined below.

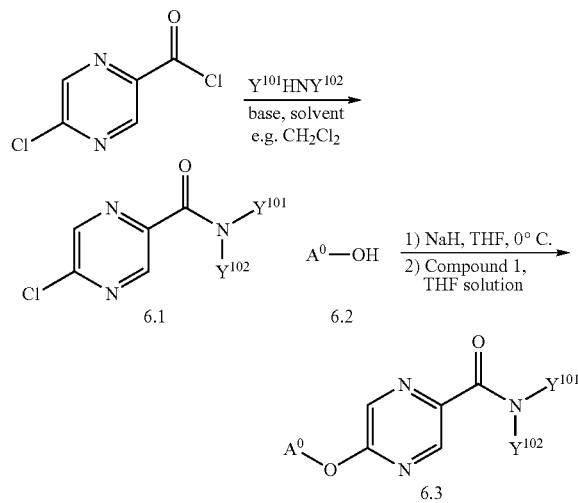

5-Chloropyrazinoyl chloride can be purchased from a supplier such as Lonza-DP. The acid chloride may be reacted with a primary or secondary amine in a suitable solvent that includes, but is not limited to, methylene chloride, in the presence of a base that includes but is not limited to, pyridine, triethylamine or diisopropylethylamine (see *J. Med. Chem.*, 38:3902 (1995)) providing intermediate 6.1. Compounds of type 6.2 are then treated with a base (such as, but not limited to, a metal hydride) in a suitable solvent (such as THF) in order to generate the alkoxide anion. The anion of 6.2 is then mixed with a solution of 6.1 in a suitable solvent (e.g. THF), the reaction of which provides intermediate 6.3 (see *Chem. Pharm. Bull.*, 38:201 (1990)).

For instance, a specific compound of the invention is prepared as shown below:

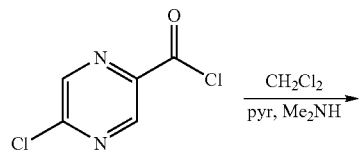

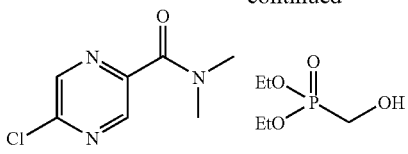

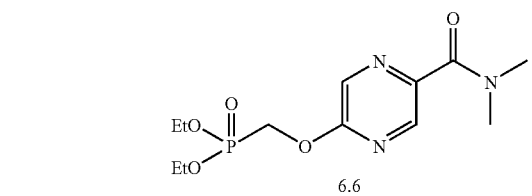

5-chloropyrazinoyl chloride is dissolved in methylene chloride and is treated with 2 molar equivalents of pyridine and one molar equivalent of dimethylamine. The mixture is stirred until all of the acid chloride is consumed. The product is isolated by silica gel chromatography providing intermediate 6.4. In anhydrous THF is dissolved diethyl phosphonomethanol (6.5, commercially available from suppliers such as Aldrich). The mixture is cooled to 0° C. and treated with 1 molar equivalent of sodium hydride. When bubbling has ceased, the mixture will be added to a THF solution of intermediate 6.4, providing pyrazinamide-phosphonate intermediate 6.6.

Synthesis of representative compounds of the invention is shown below.

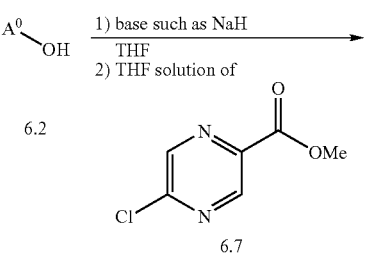

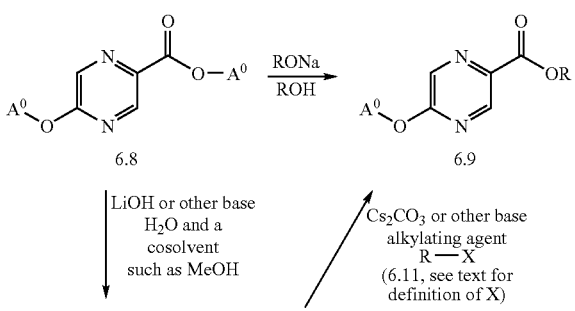

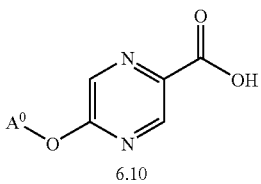

The anion of linker alcohol of type 6.2 is prepared by reaction with a base such as, but not limited to, a metal hydride. The anion (used in excess) is added to a solution of methyl 5-chloropyrazine-2-carboxylate (6.7, available from Lonza) in anhydrous THF solution at 0° C., the reaction of which produces an intermediate of structural type 6.8, which can be isolated by the appropriate purification/isolation method. The ester group at the carboxylic acid functionality is then selectively converted into the final desired functional group by stirring intermediate 6.8 in a solution of the desired alcohol and its alkoxide until transesterification is complete. Alternatively, the free carboxylic acid may be obtained by simple saponification under standard conditions such as those found in *J. Med. Chem.*, 36:3871 (1993).

If the carboxylic acid product 6.10 is desired, the synthesis is complete. If, however, additional esterification is desired, it may be accomplished by alkylation of the carboxylate with an alkylating agent corresponding to a group that provides the desired ester product. Alternatively, it may be appropriate to wait until all manipulation of the phosphonate ester groups is complete (infra) before installation of the final ester group. If this is the case, all phosphonate ester manipulations and conversions should be first executed followed by the transformations described herein above.

As an example of the synthesis of a specific compound of the invention, see below.

In anhydrous THF, a solution of the anion of diethyl phosphonomethanol (6.11) is generated by treatment with NaH in THF at 0° C. This is added to a THF solution of 6.7, which is available from Lonza, providing intermediate 6.12. If the free carboxylic acid product is desired, this may be obtained by treatment of 6.12 with LiOH in EtOH/H$_2$O. If the methyl ester 6.14 is desired, this may be obtained either by direct transesterification of 6.12 in MeOH/NaOMe, or by treatment of free acid 6.13 with MeI in THF over Cs$_2$CO$_3$. If the manipulation of the phosphonate ester will interfere with the final desired group at the carboxylate position, installation of the final ester, or saponification to the free acid can be delayed until the manipulations of the phosphonate moiety have been completed, infra.

EXAMPLE 7

Preparation of Representative Compounds of Formulae 12

Representative compounds of the invention can be made according to the general route outlined below.

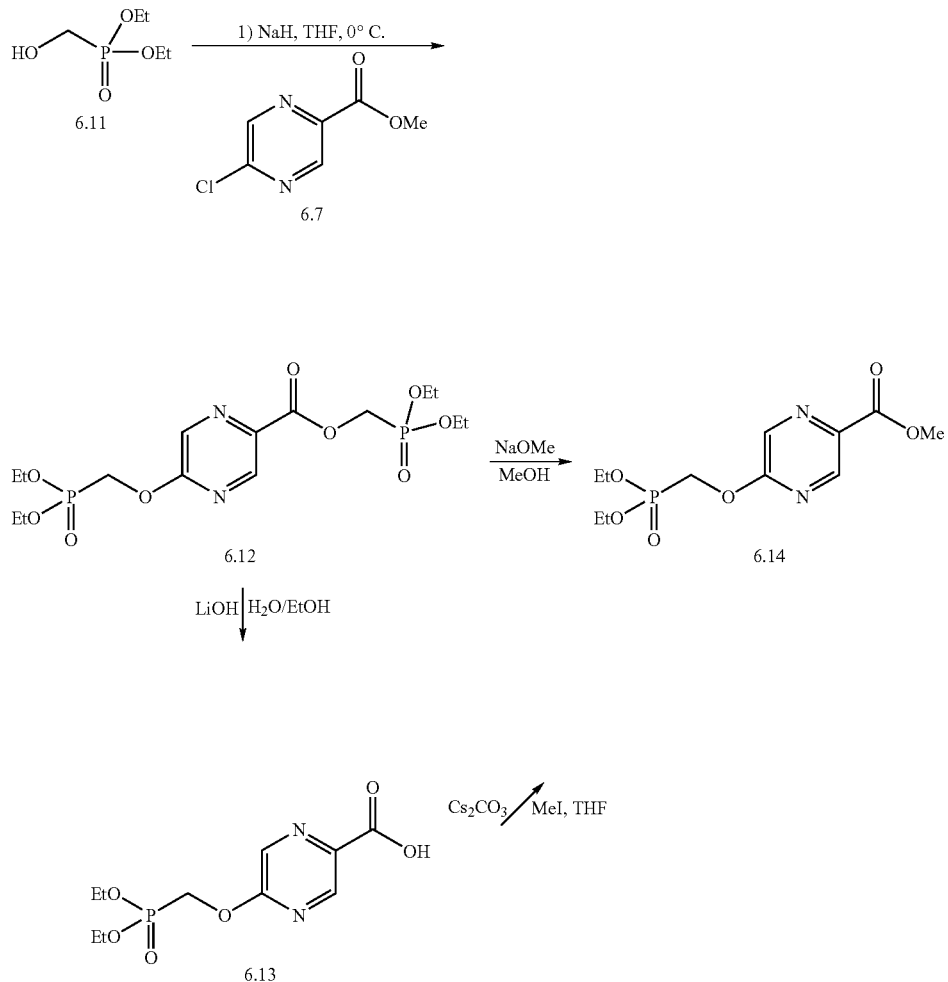

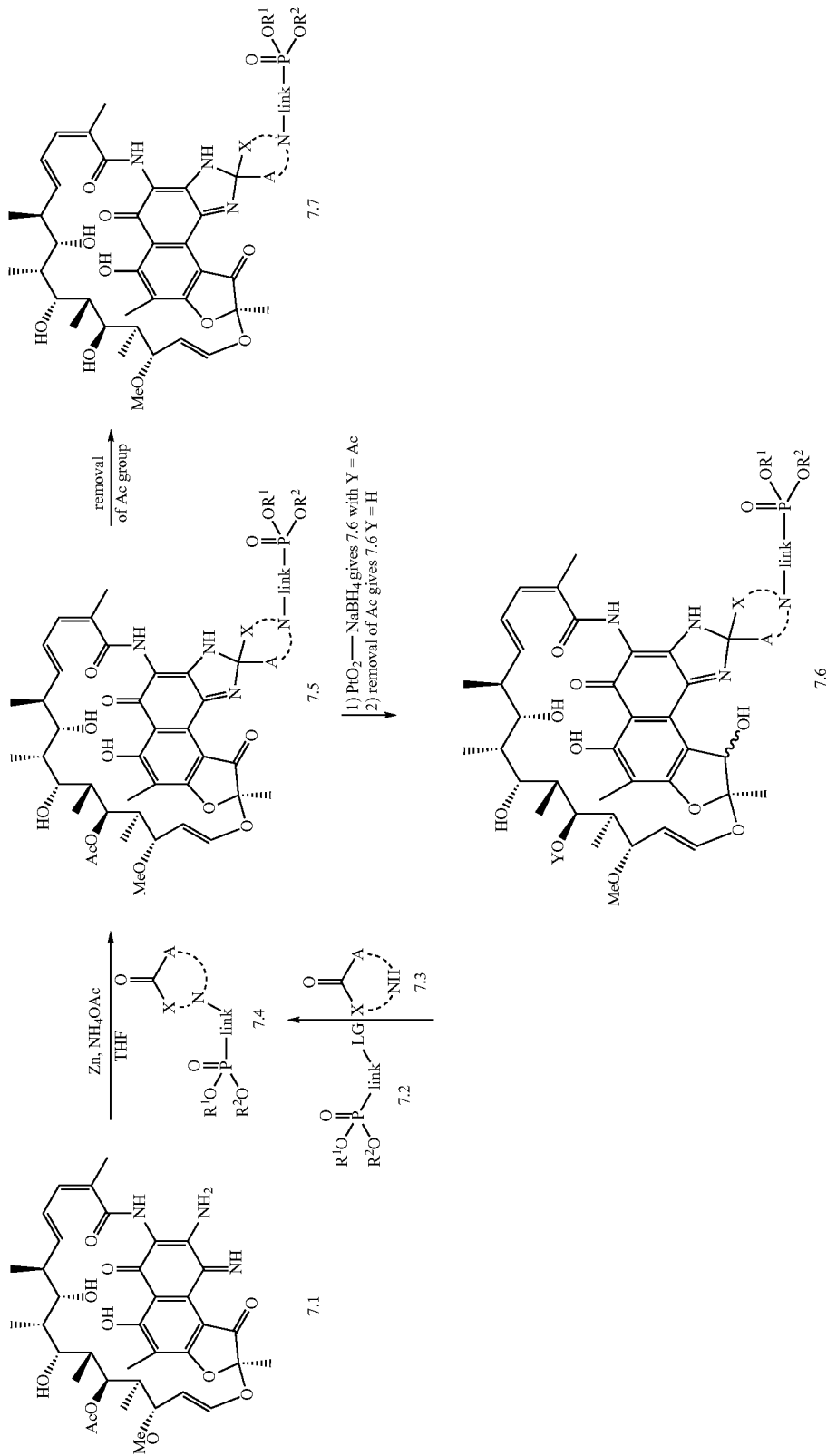

The synthesis of intermediates of type 7.5 begins with the reaction of alkylating agents such as 7.2 (LG=leaving group, such as methanesulfonate, p-toluenesulfonate, trifluoromethanesulfonate, bromo, iodo, chloro) and a ketone substituted on one side with alkyl group X and on the other side with alkyl group A, where A and X may form a ring or cyclic structure.

Either A or X is substituted within the chain or ring, or in a pendant manner, with a heteroatom, such as nitrogen, which serves as a handle for nucleophilic displacement of the leaving group of reagents of type 7.2. Reagents 7.2 and 7.3 provide ketones 7.4 under reaction conditions such as those reported in *J. Med. Chem.*, 43:488 (2000). Ketones 7.4 can be reacted with 3-amino-4-deoxo-4-imino-rifamycin S as in U.S. Pat. Nos. 4,219,478; 4,017,481 and 4,086,225 under the conditions described therein to provide compounds of the structural type 7.5.

Compounds 7.5 can then be transformed into reduced compounds of structural type 7.6 as described in *Magnetic Resonance in Chemistry*, 38:937 (2000). If the removal of the acetyl group of 7.6 or 7.5 is desired, it can be effected under standard conditions, such as those described in "Protective Groups in Organic Synthesis" (Green and Wuts, $2^{nd}$ Ed. Wiley Interscience) to provide a compound with a free hydroxyl group. Phosphonate manipulations can be carried out as described below at any point in the synthesis so as to prevent any undesired transformations on an of the other functional groups on the rifabutin core.

For instance a specific compound of the invention is as follows:

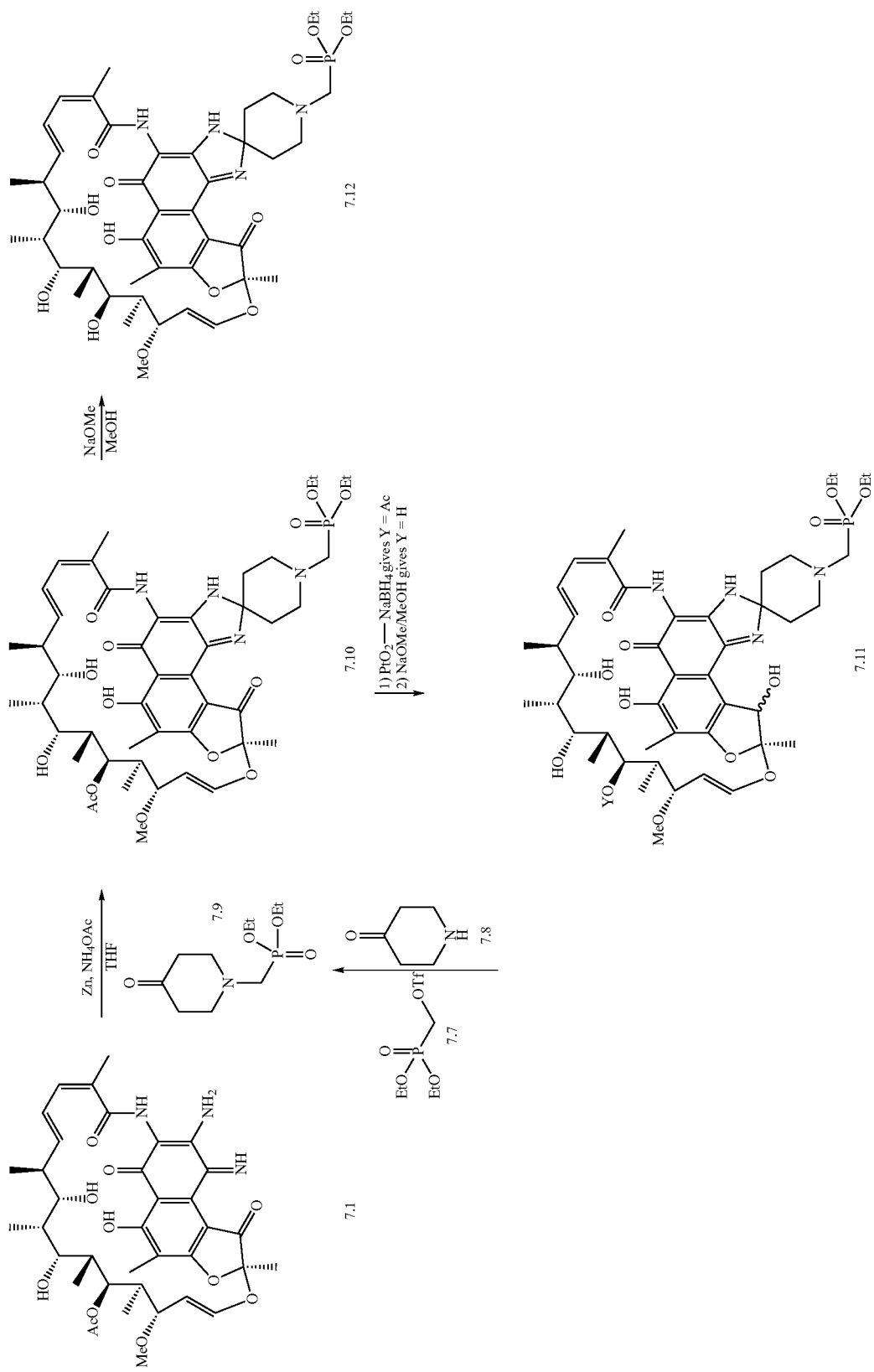

3-amino-4-deoxo-4-imino-rifamycin S (prepared and isolated as in U.S. Pat. Nos. 4,219,478; 4,017,481 and 4,086,225) can be treated with 4-piperidone derivative 7.9 in an appropriate solvent such as THF in the presence of Zn and ammonium acetate, as described, providing intermediate 7.10.

Ketone 7.9 itself is prepared by reaction of diethyl phosphonomethyltriflate (*Tetrahedron Lett.*, 27:1477 (1986)) with 4-piperidinone as in *J. Med. Chem.*, 43:488 (2000). Intermediate 7.10 can be converted to compound 7.11 (Y=Ac) by treatment with NaBH$_4$ in the presence of Pt$_2$O. The acetate can be removed by treatment of 7.11 (Y=Ac) with catalytic NaOMe in MeOH solution to give 7.11 (Y=H). Alternatively 7.10 can be converted to 7.12 by stirring in catalytic NaOMe in MeOH. Phosphonate manipulations may be carried out at any point during the synthesis as described, so as to minimize the impact on the rest of the functional groups in the molecule.

EXAMPLE 8

Preparation of Representative Compounds of Formulae 13-14

Representative compounds of the invention can be made according to the general route outlined below.

As shown above, 3-formyl-rifamycin SV (prepared according to the procedures in U.S. Pat. Nos. 3,342,810 and 3,150,046) can be reacted with a hydrazine of structural type 8.1, where X and Y are alkyl chains that may or may not be attached to each other so that they form a ring (as represented by a dotted semi-circle). These may be substituted with heteroatoms in a pendant manner, or within the chains themselves and at least one of those heteroatoms must be of sufficient valency to serve as a handle onto which to attach the linker to the phosphonate group.

The reaction of 8.1 and 3-formyl rifamycin SV provides rifamycin derivative 8.2. Treatment of 8.2 with an alkylating agent of type 8.3 (X=leaving group such as bromide, iodide, chloride, trifluoromethanesulfonate, methanesulfonate, p-toluenesulfonate), provides intermediates of type 8.4. Intermediates 8.4, or any of the phosphonate-containing intermediates, where it is chemically prudent to do so, may be converted into their phosphonate prodrugs as described below in the section on phosphonate interconversions.

For instance, preparation of a specific compound of the invention is illustrated below:

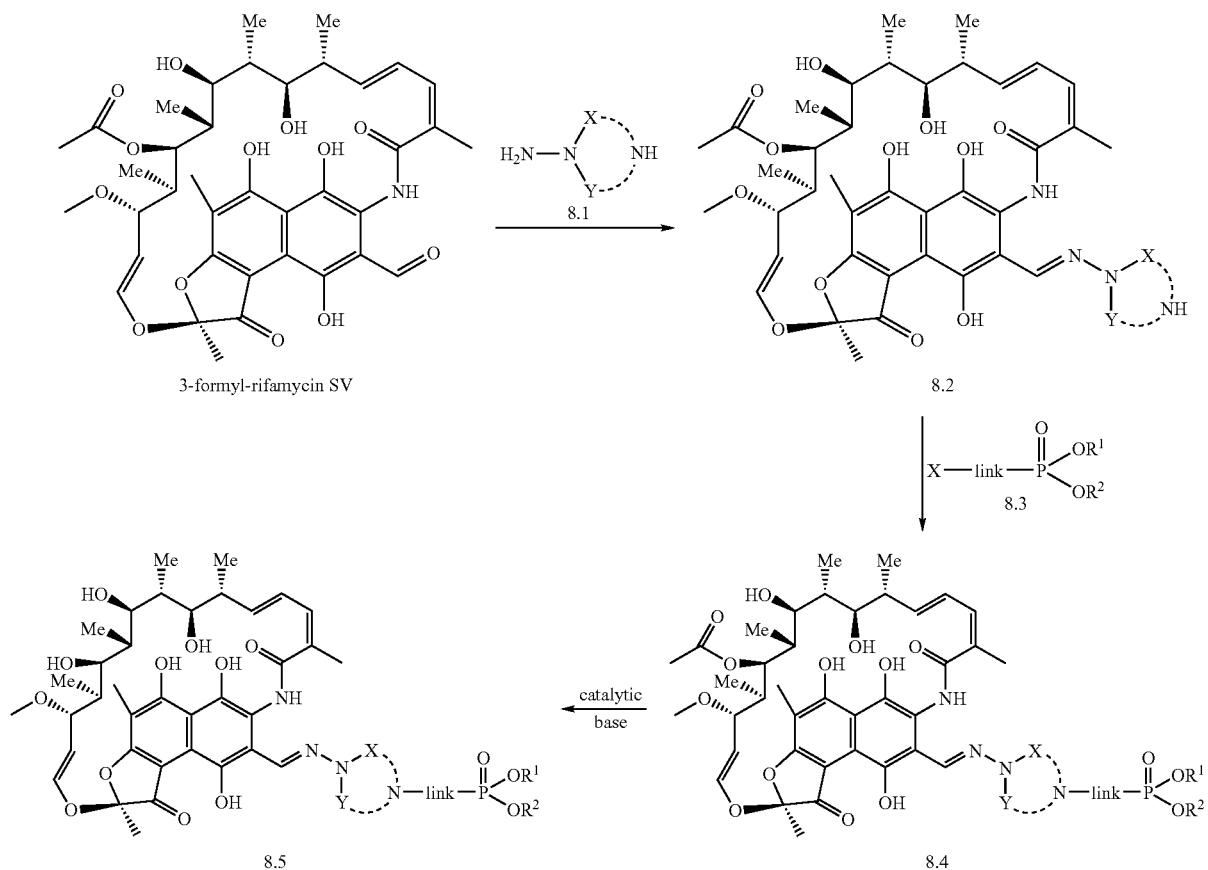

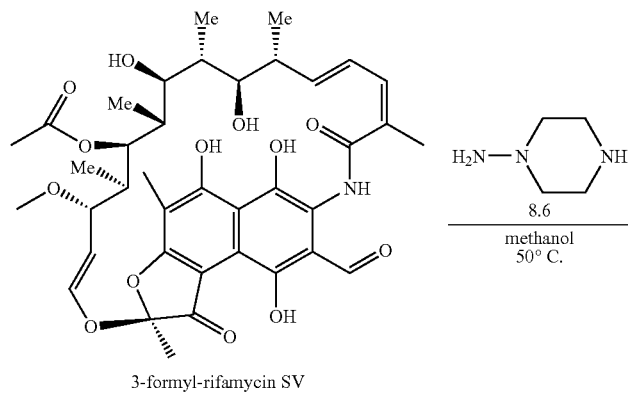

3-formyl-rifamycin SV

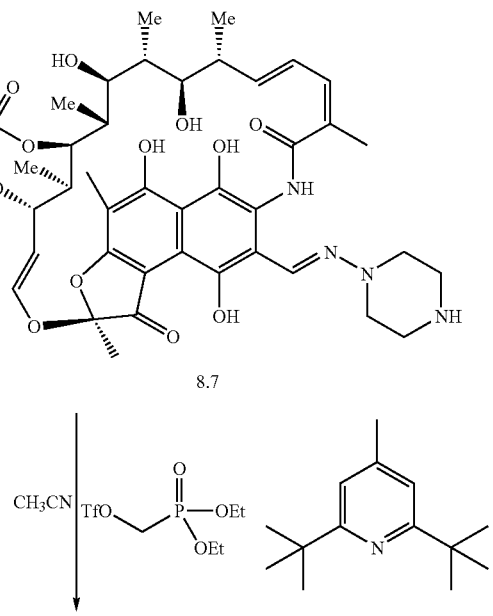

8.7

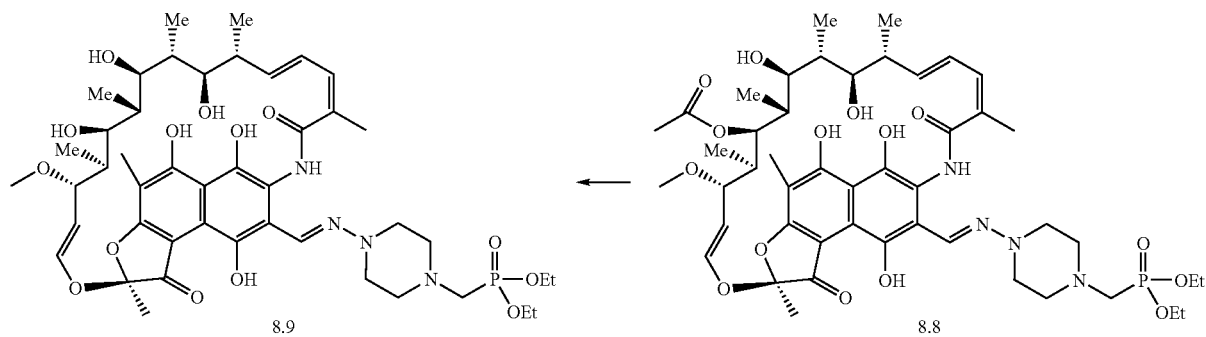

8.9    8.8

3-formyl-rifamycin SV is reacted with hydrazine 8.6 in a suitable solvent such as methanol at 50° C. to provide intermediate 8.7. Intermediate 8.7 is then reacted with diethyl phosphonomethyltriflate (prepared according to *Tetrahedron Lett.*, 27:1477 (1986)) in the presence of a base such as 2,6-di-tert-butyl-4-methylpyridine (in a procedure similar to that found in *J. Med. Chem.*, 43:488 (2000)) to provide 8.8. If desired, the acetate may be removed with catalytic NaOMe in MeOH to give intermediate 8.9. The phosphonate interconversions to the appropriate prodrugs may then be carried out on 8.8 or 8.9 as described below.

Hydrazine, used in excess, is treated with an alkylating agent of type 8.3 to get substituted hydrazines 8.10 (see below). Compounds 8.10 are then reacted in a suitable solvent such as methanol with 3-formyl-rifamycin SV to form intermediates of structural type 8.12. If oxime derivatives 8.12 are preferred, N-hydroxyphthalimide is treated with a base such as, but not limited to a $K_2CO_3$ in an appropriate solvent such as, but not limited to, DMSO, and an alkylating agent of type 8.3 (see *J. Org. Chem.*, 65:5639 (2000)). The hydroxylamines 8.11 are then liberated by treatment with hydrazine (see *J. Med. Chem.*, 15:470 1972)). The liberated hydroxylamine is then used in place of the hydrazine in reaction with 3-formyl-rifamycin SV to get compound 8.12 (A=O).

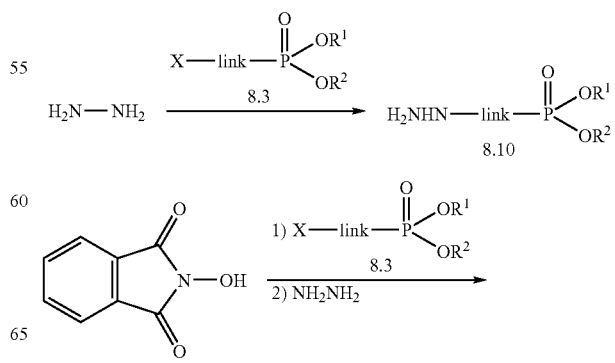

-continued

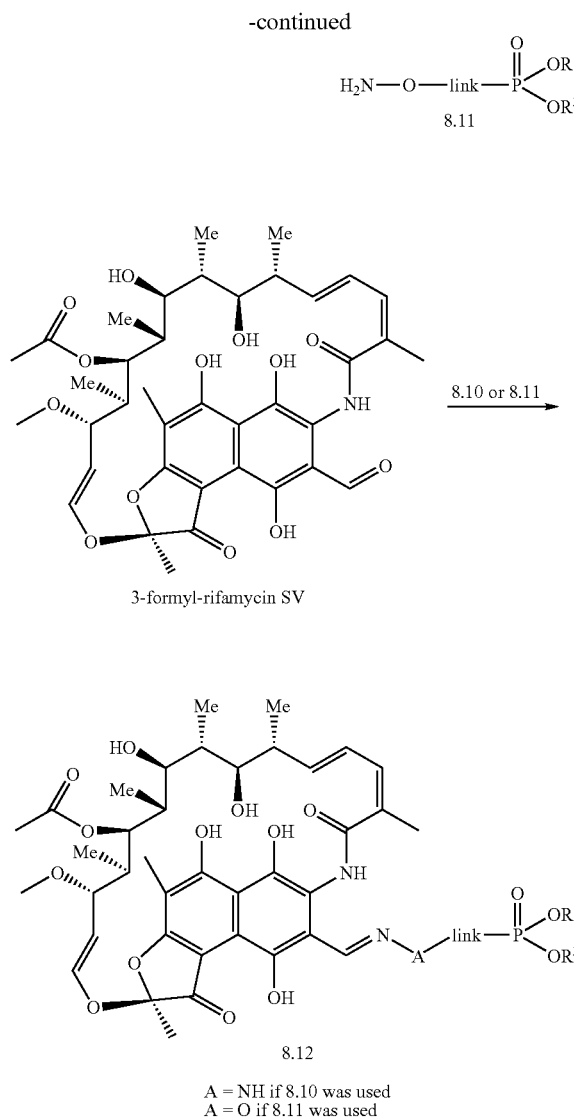

A = NH if 8.10 was used
A = O if 8.11 was used

For instance, synthesis of a specific compound of the invention is shown below:

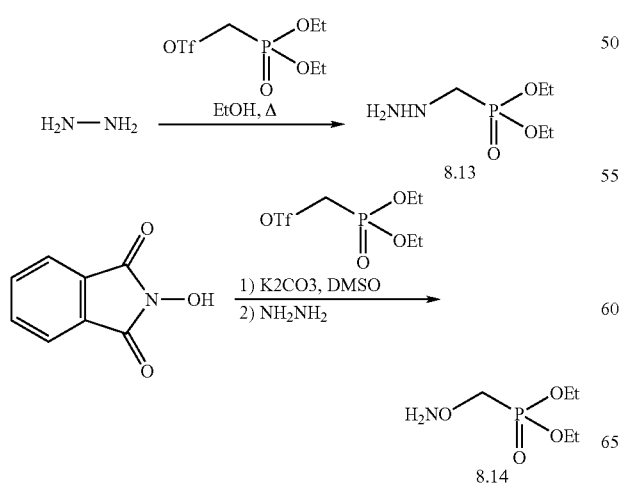

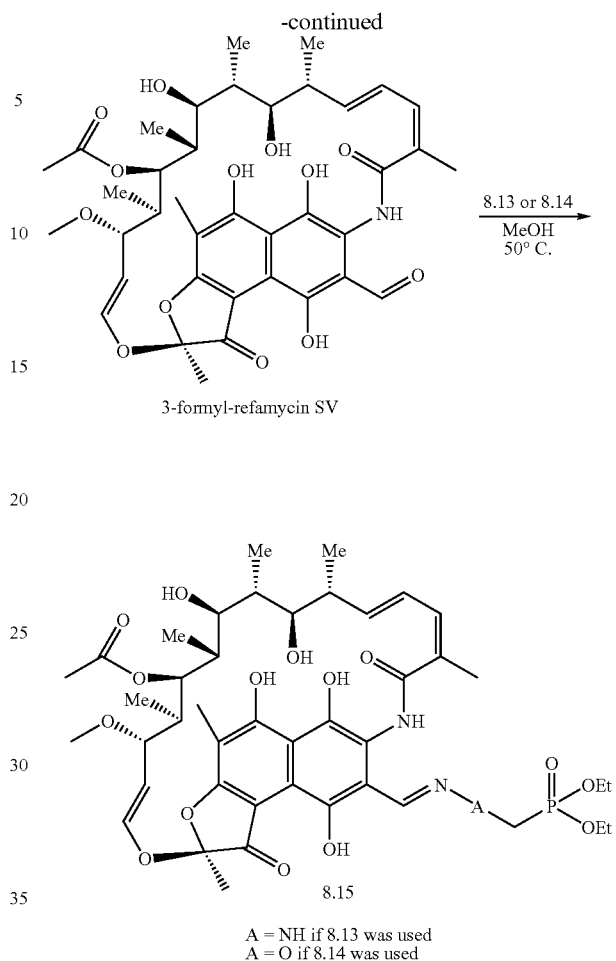

A = NH if 8.13 was used
A = O if 8.14 was used

Hydrazine (5 molar equivalents) is heated at reflux in ethanol with diethyl phosphonomethyltriflate, prepared as above, to provide substituted hydrazine 8.13. Separately, N-hydroxyphthalimide is treated with diethyl phosphonomethyltriflate in DMSO in the presence of $K_2CO_3$. The resultant product is then treated with hydrazine in refluxing ethanol to liberate hydroxylamine 8.14. Compounds 8.13 and 8.14 are each reacted in separate flasks in methanol with 3-formyl-rifamycin SV, with heating to 50° C. The products 8.15 are isolated by the appropriate chromatographic method. The acetate of each of these products may be removed by treatment with catalytic amounts of NaOMe in MeOH if desired. Conversion to the desired phosphonate prodrugs is then carried out as described.

EXAMPLE 9

By way of example and not limitation, embodiments of the invention are named below in tabular format (Table 100). These embodiments are of the general formula "MBF":

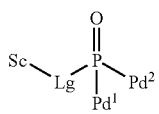

MBF

Each embodiment of MBF is depicted as a substituted nucleus (Sc). Sc is described in formula 1-14 herein, wherein $A^0$ is the point of covalent attachment of Sc to Lg, as well as in Tables 1.1 to 1.5 below. For those embodiments described in Table 100, Sc is a nucleus designated by a number and each substituent is designated in order by letter or number. Tables 1.1 to 1.5 are a schedule of nuclei used in forming the embodiments of Table 100. Each nucleus (Sc) is given a number designation from Tables 1.1 to 1.5, and this designation appears first in each embodiment name. Similarly, Tables 10.1 to 10.19 and 20.1 to 20.36 list the selected linking groups (Lg) and prodrug ($Pd^1$ and $Pd^2$) substituents, again by letter or number designation, respectively. Accordingly, a compound of the formula MBF includes compounds having Sc groups based on formula 1-14 herein as well as compounds according to Table 100 below. In all cases, compounds of the formula MBF have groups Lg, $Pd^1$ and $Pd^2$ setforth in the Tables below.

Accordingly, each named embodiment of Table 100 is depicted by a number designating the nucleus from Table 1.1-1.5, followed by a letter designating the linking group (Lg) from Table 10.1-10.19, and two numbers designating the two prodrug groups ($Pd^1$ and $Pd^2$) from Table 20.1-20.36. In graphical tabular form, each embodiment of Table 100 appears as a name having the syntax:

Sc.Lg.$Pd^1$.$Pd^2$

Each Sc group is shown having a tilda ("~"). The tilda is the point of covalent attachment of Sc to Lg. $Q^1$ and $Q^2$ of the linking groups (Lg), it should be understood, do not represent groups or atoms but are simply connectivity designations. $Q^1$ is the site of the covalent bond to the nucleus (Sc) and $Q^2$ is the site of the covalent bond to the phosphorous atom of formula MBF. Each prodrug group ($Pd^1$ and $Pd^2$) are covalently bonded to the phosphorous atom of MBF at the tilda symbol ("~"). Some embodiments of Tables 10.1-10.19 and 20.1-20.36 may be designated as a combination of letters and numbers (Table 10.1-10.19) or number and letter (Table 20.1-20.36). For example there are Table 10 entries for BJ1 and BJ2. In any event, entries of Table 10.1-10.19 always begin with a letter and those of Table 20.1-20.36 always begin with a number. When a nucleus (Sc) is shown enclosed within square brackets ("[ ]") and a covalent bond extends outside the brackets, the point of covalent attachment of Sc to Lg may be at any substitutable site on SC. Selection of the point of attachment is described herein. By way of example and not limitation, the point of attachment is selected from those depicted in the schemes and examples.

TABLE 1.1

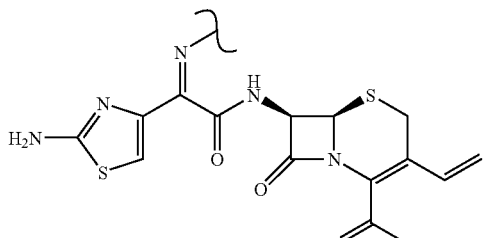

1

TABLE 1.1-continued

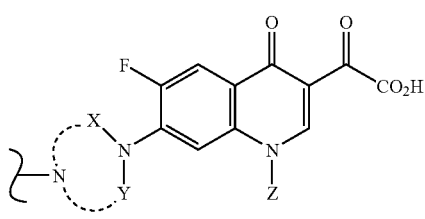

2

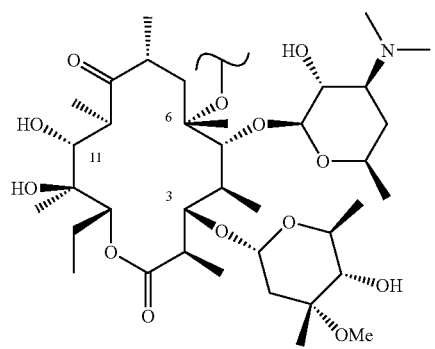

3

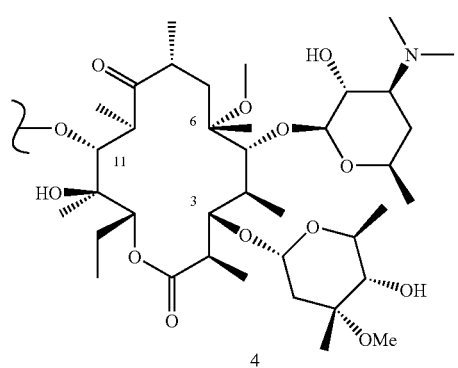

4

TABLE 1.2

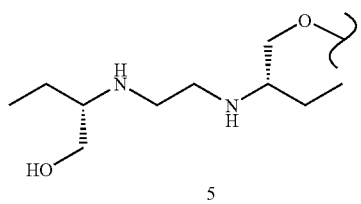

5

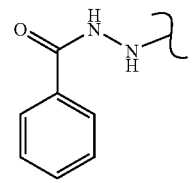

6

TABLE 1.3
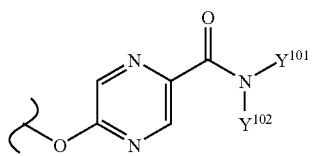
7
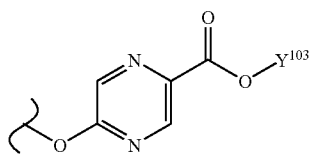
8
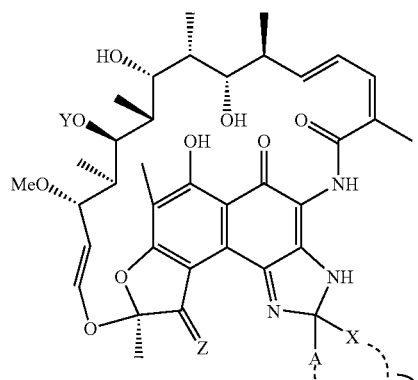
9
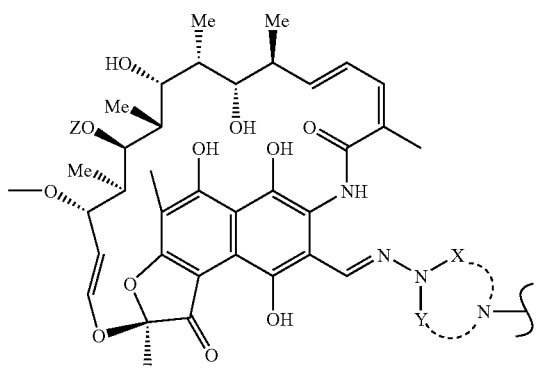
10
TABLE 1.4
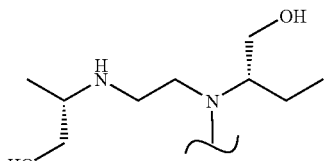
11
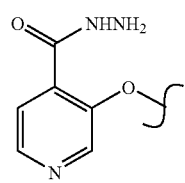
12
TABLE 1.5
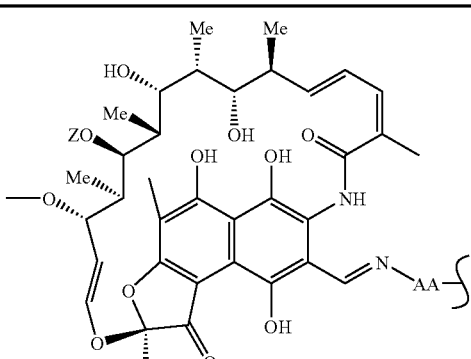
13
AA = Naturally Occurring Amino Acid Residue
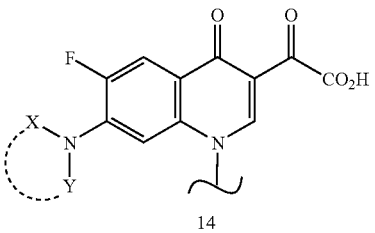
14
TABLE 10.1
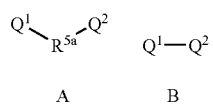
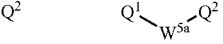
A    B    C    D TABLE 10.1-continued
| | |
|---|---|
| 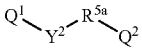 E | 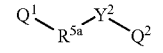 F |
| 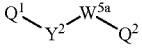 G | 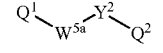 H |
| 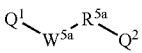 I | 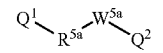 J |
| 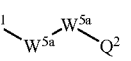 K | 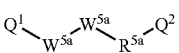 L |
| 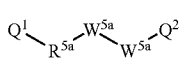 M | |
| 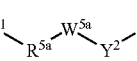 N | 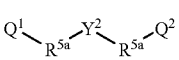 O |
TABLE 10.2
| | |
|---|---|
| 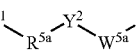 P | 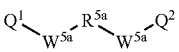 Q |
| 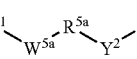 R | 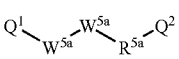 S |
| 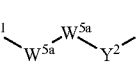 T | 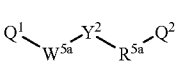 U |
| 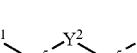 V | 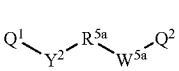 W |
| 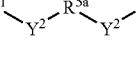 X | 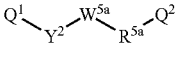 Y |
| 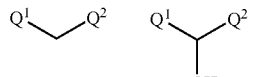 Z |  AA |
TABLE 10.3
| | |
|---|---|
| 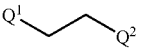 AB | 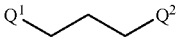 AC |
| 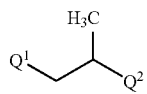 AD |  AE |
|  AF | 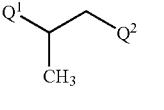 AG |
| 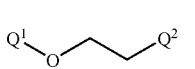 AH | 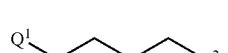 AI |
|  AJ |  AK |
| 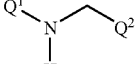 AL | 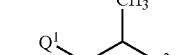 AM |
TABLE 10.4
| | |
|---|---|
|  AN |  AO |
|  AP |  AQ |
| 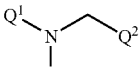 AR | AS |
| AT | AU |

TABLE 10.4-continued
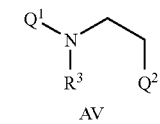
AV
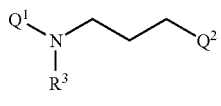
AW
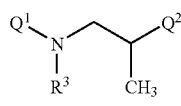
AX
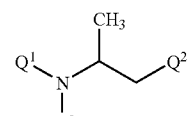
AY
TABLE 10.5
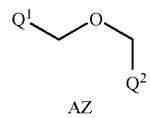
AZ
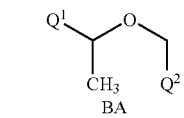
BA
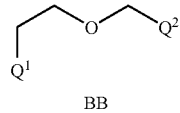
BB
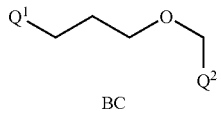
BC
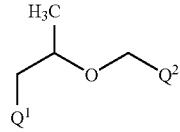
BD
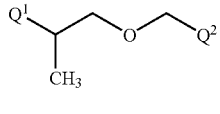
BE
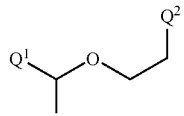
BG
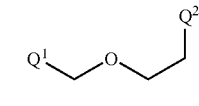
BF
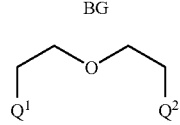
BI
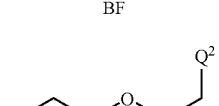
BH
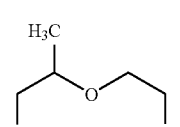
BJ2
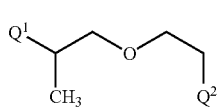
BJ1
TABLE 10.6
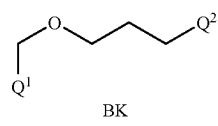
BK
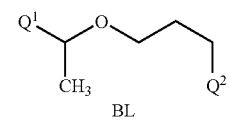
BL
TABLE 10.6-continued
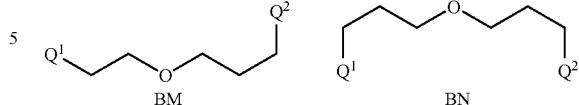
BM
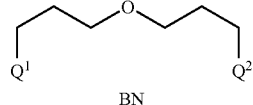
BN
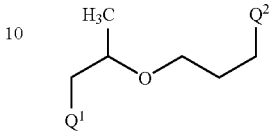
BO
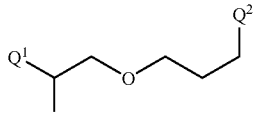
BP
TABLE 10.7
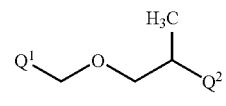
BQ
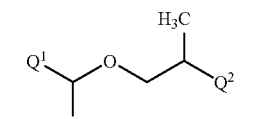
BR
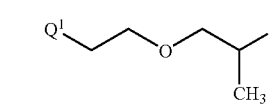
BS
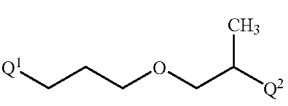
BT
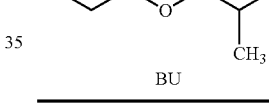
BU
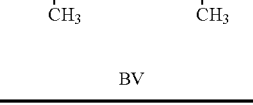
BV
TABLE 10.8
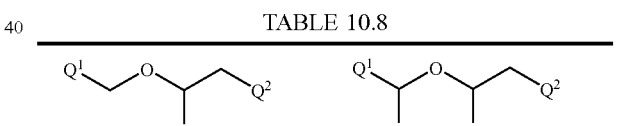
BW
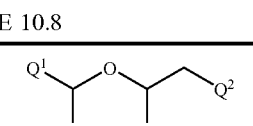
BX
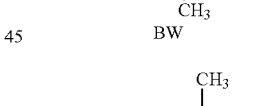
BY
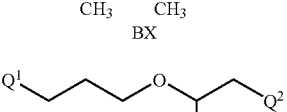
BZ
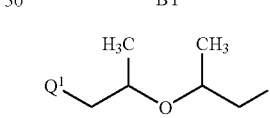
CA
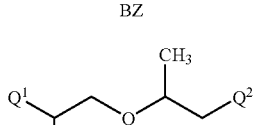
CB
TABLE 10.9
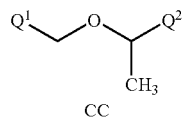
CC
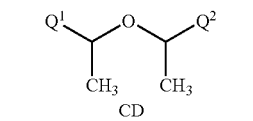
CD TABLE 10.9-continued
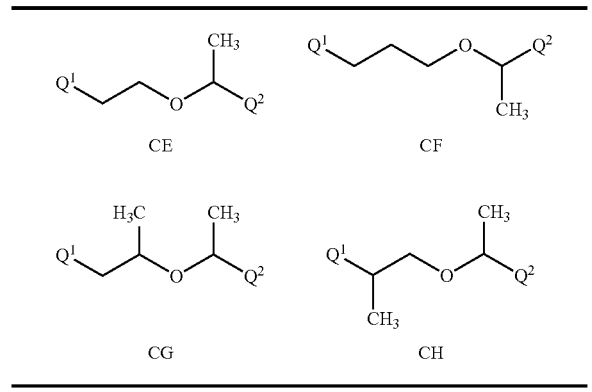
TABLE 10.10
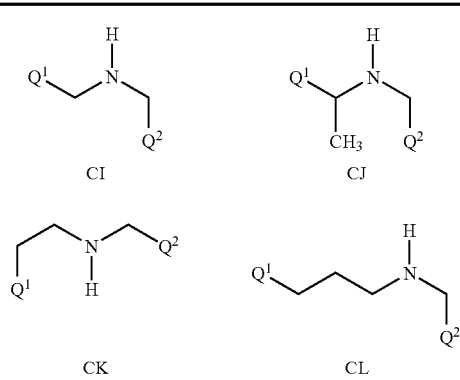
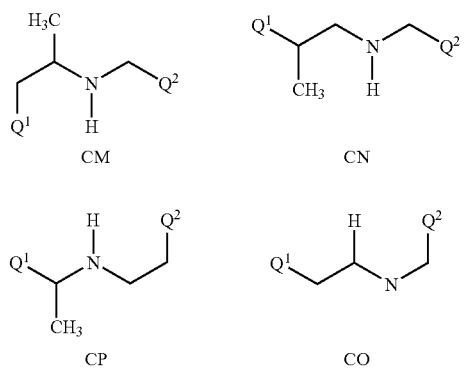
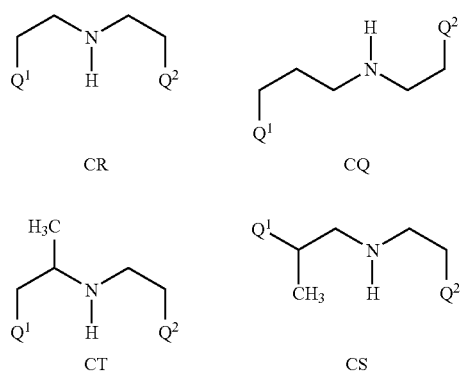
TABLE 10.11
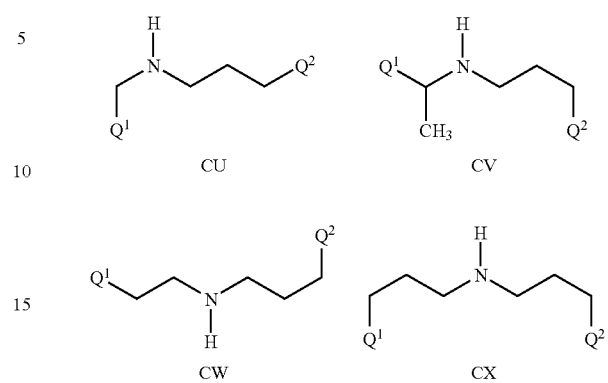
TABLE 10.12
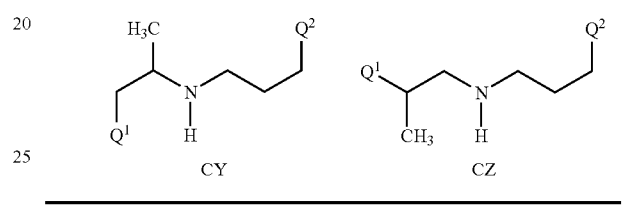
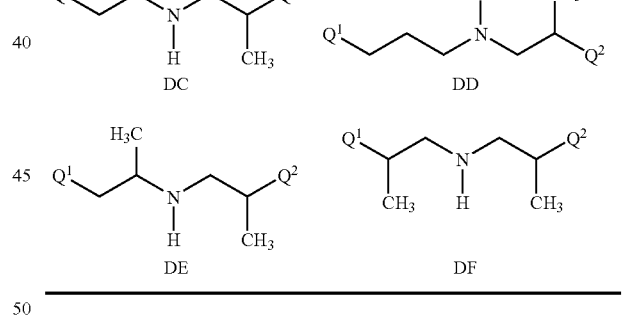
TABLE 10.13
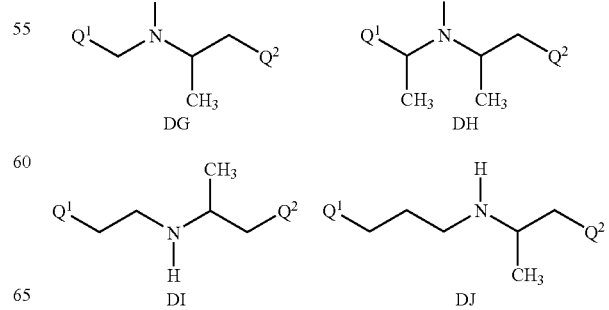

TABLE 10.13-continued
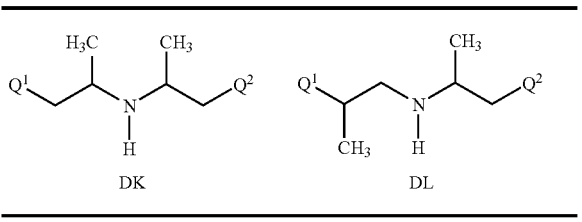
TABLE 10.14
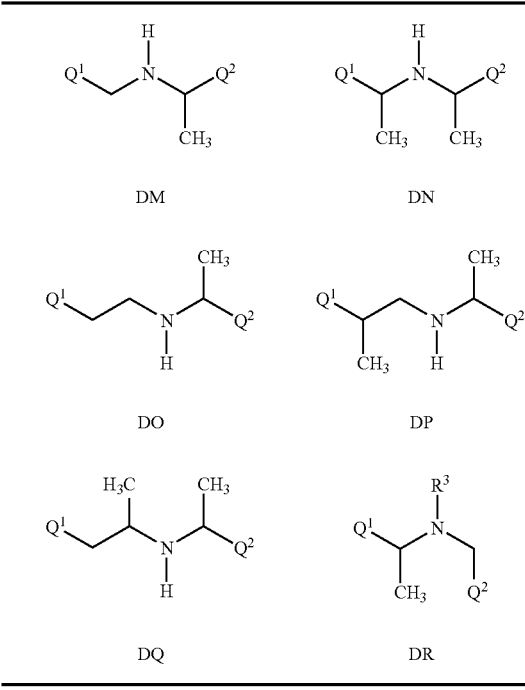
TABLE 10.15
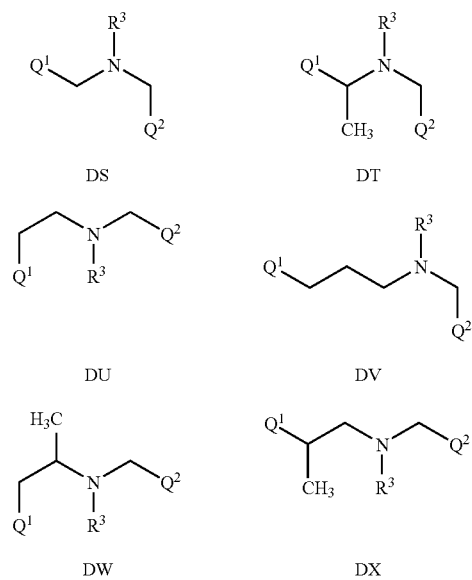
TABLE 10.15-continued
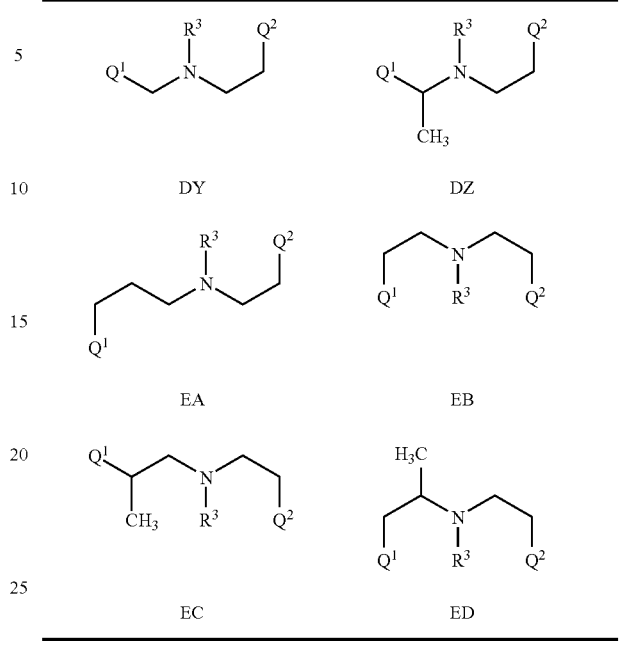
TABLE 10.16
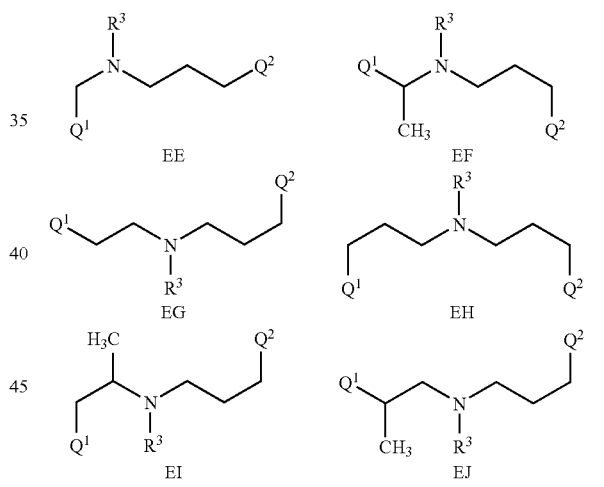
TABLE 10.17
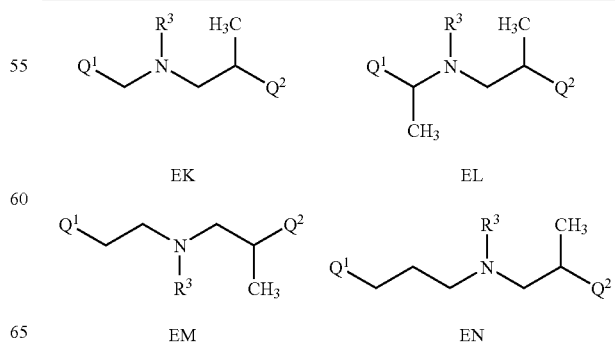

TABLE 10.17-continued

| EO | EP |

TABLE 10.18

| EQ | ER |
| ES | ET |
| EU | EV |

TABLE 10.19

| EW | EX |
| EY | EZ |
| FA | FB |

TABLE 20.1

| 1 | 2 |
| 3 | 4 |
| 5 | 6 |
| 7 | 8 |

TABLE 20.2

9

10

11

TABLE 20.3

| 12 | 13 |

TABLE 20.3-continued
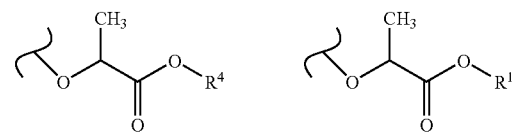
14 15
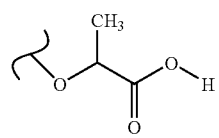 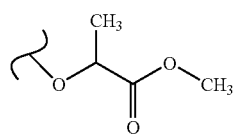
16 17
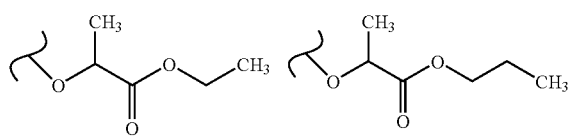
18 19
TABLE 20.4
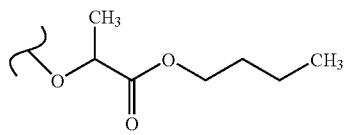
20
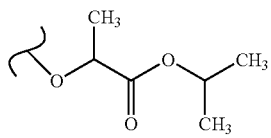
21
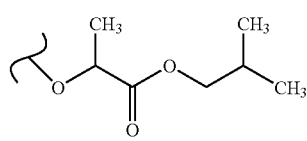
22
TABLE 20.5
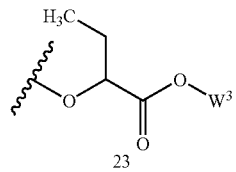 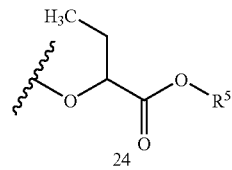
23 24
TABLE 20.5-continued
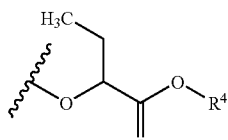 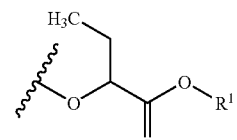
25 26
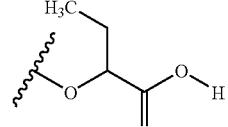 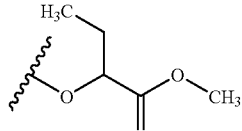
27 28
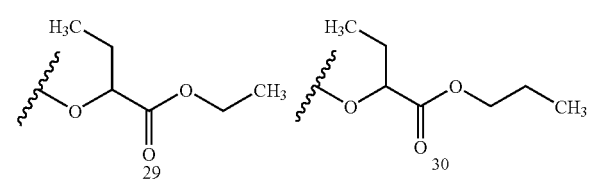
29 30
TABLE 20.6
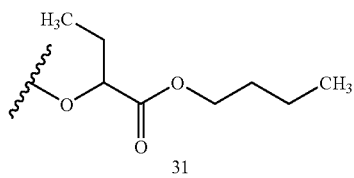
31
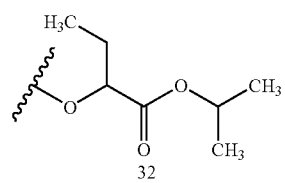
32
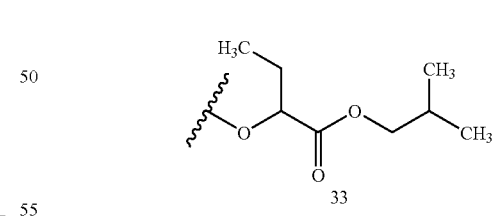
33
TABLE 20.7
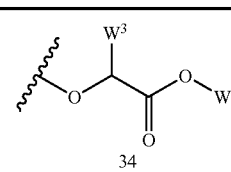 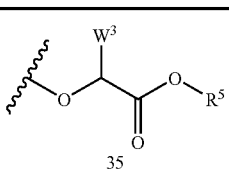
34 35

TABLE 20.7-continued
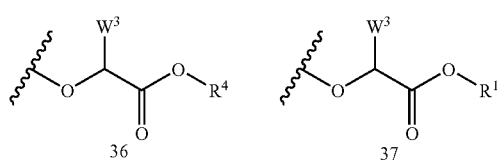
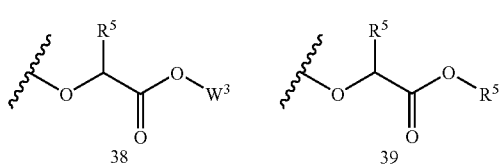
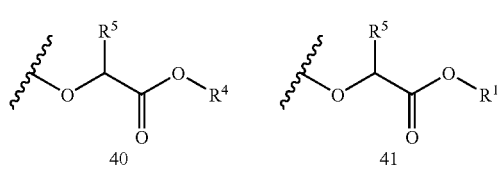
TABLE 20.8
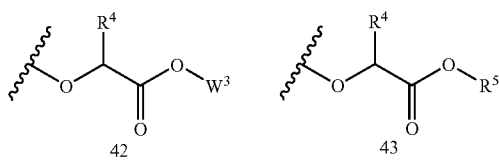
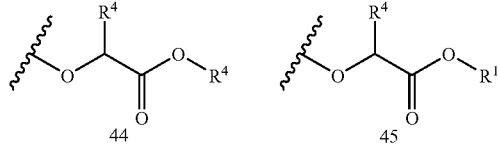
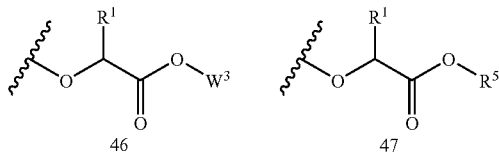
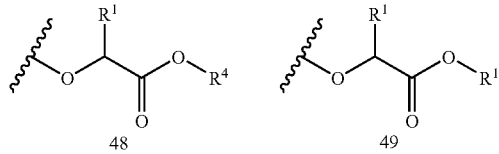
TABLE 20.9
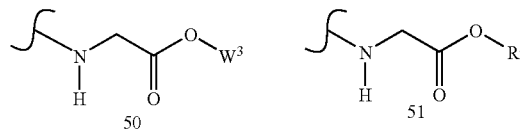
TABLE 20.9-continued
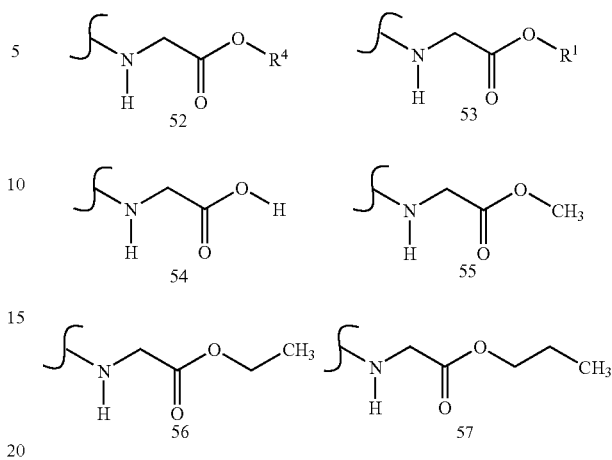
TABLE 20.10
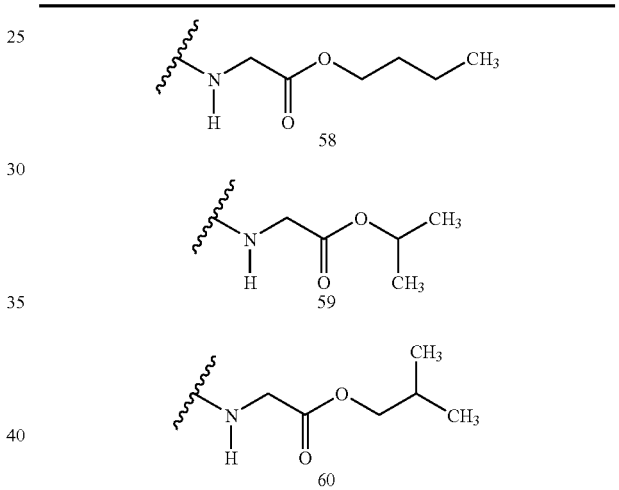
TABLE 20.11
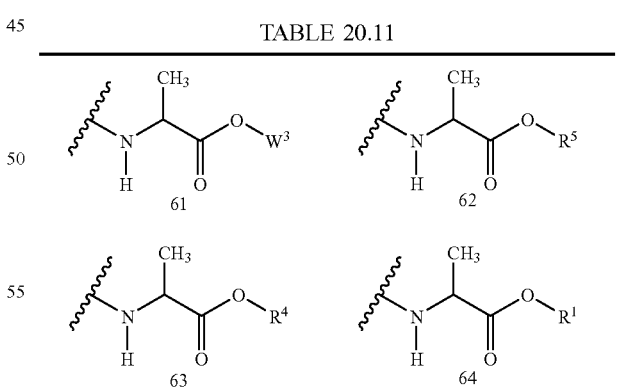

TABLE 20.11-continued
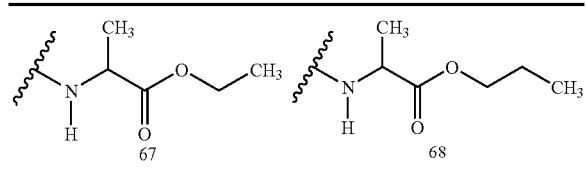
TABLE 20.12
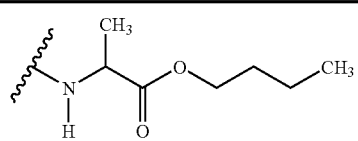
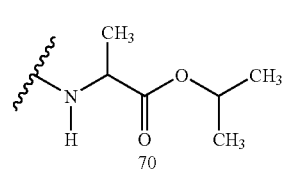
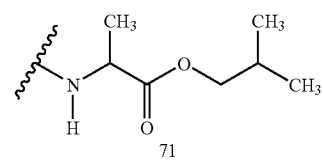
TABLE 20.13
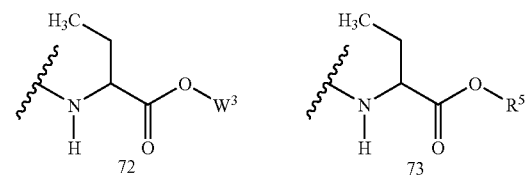
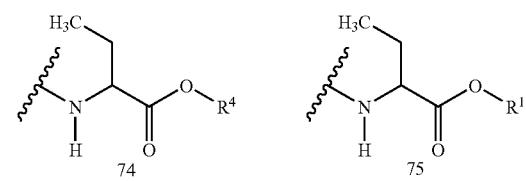
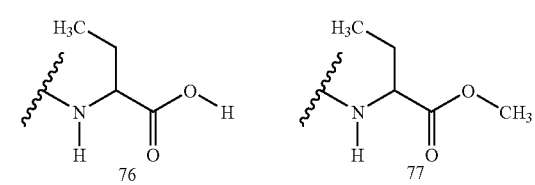
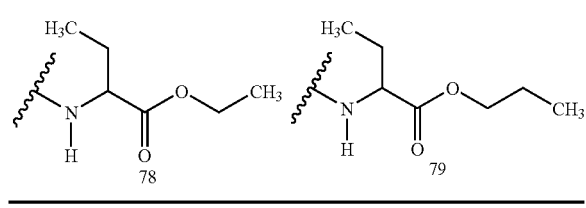
TABLE 20.14
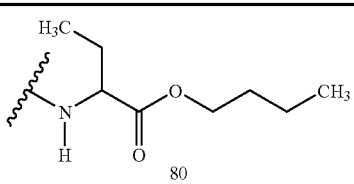
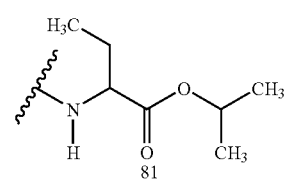
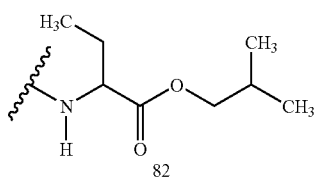
TABLE 20.15
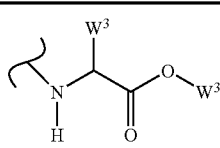 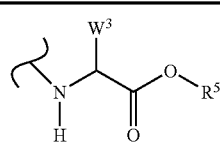
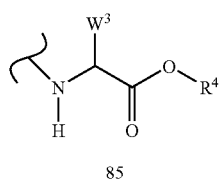 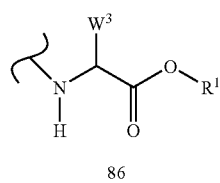
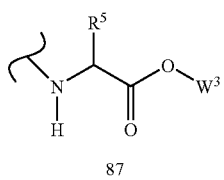 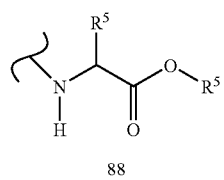
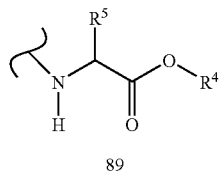 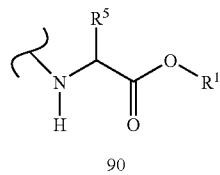
TABLE 20.16
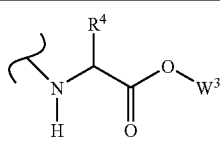 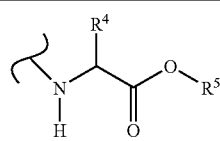

TABLE 20.16-continued 91, 92, 93, 94, 95, 96, 97, 98

TABLE 20.17

99, 100, 101, 102, 103, 104, 105, 106

TABLE 20.18

TABLE 20.18-continued 107, 108, 109

TABLE 20.19

110, 111, 112, 113, 114, 115, 116, 117

TABLE 20.20

118

TABLE 20.20-continued
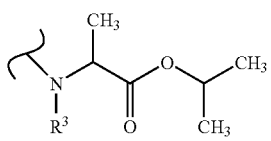
119
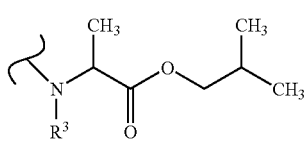
120
TABLE 20.21
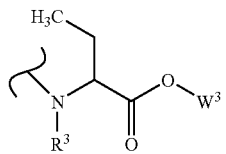   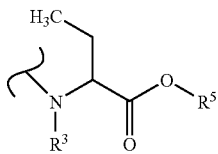
121   122
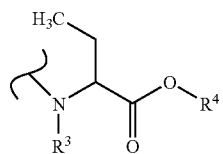   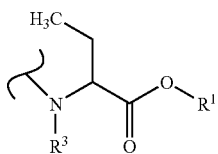
123   124
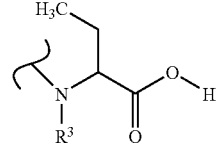   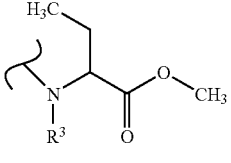
125   126
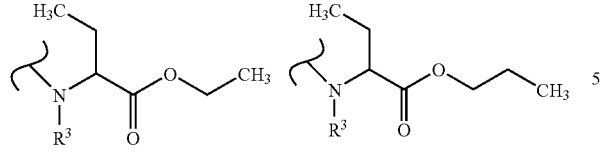
127   128
TABLE 20.22
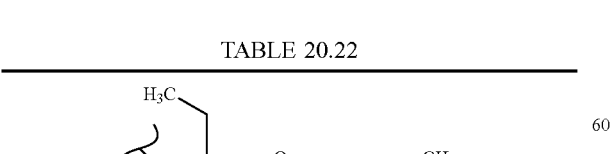
129
TABLE 20.22-continued
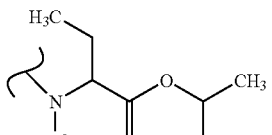
130
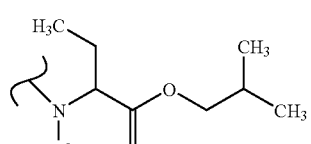
131
TABLE 20.23
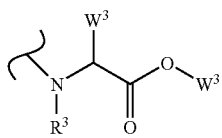
132
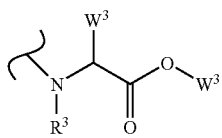
133
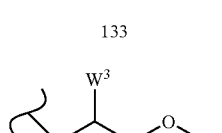
134
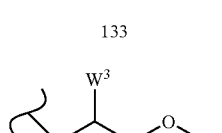
135
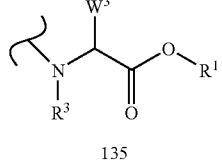
136
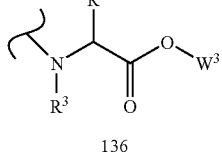
137

TABLE 20.23-continued
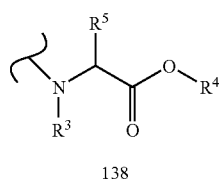
138
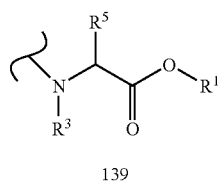
139
TABLE 20.24
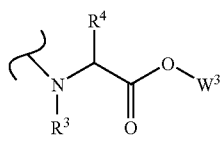
140
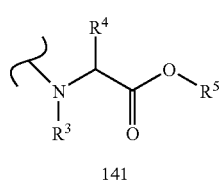
141
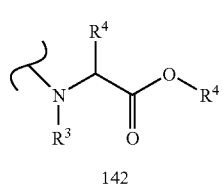
142
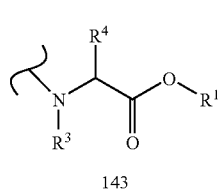
143
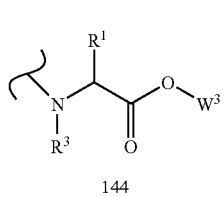
144
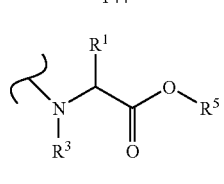
145
TABLE 20.24-continued
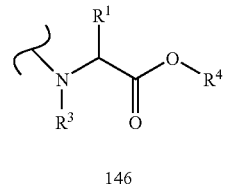
146
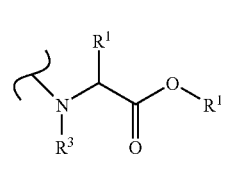
147
TABLE 20.25
|  148 |  149 | 150 |
| 151 | 152 | 153 |
| 154 | 155 | 156 |
| 157 | 158 | 159 |
TABLE 20.26
| 160 | 161 | 162 |
| 163 | 164 | 165 |
| 166 | 167 | 168 |
| 169 | 170 | 171 |
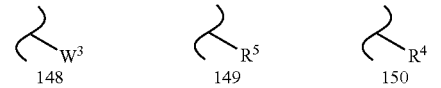
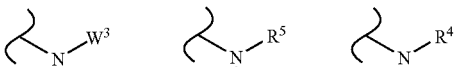
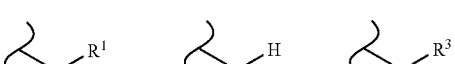
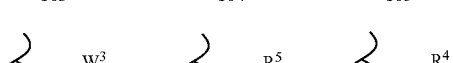
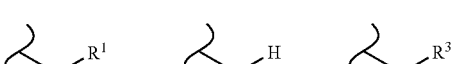

TABLE 20.27
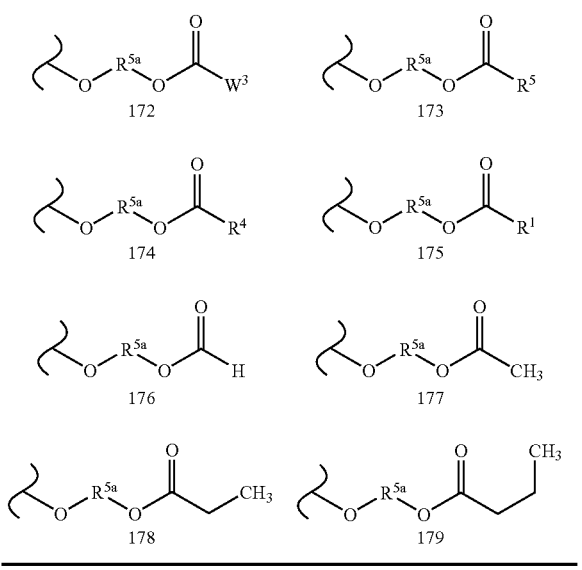
TABLE 20.28
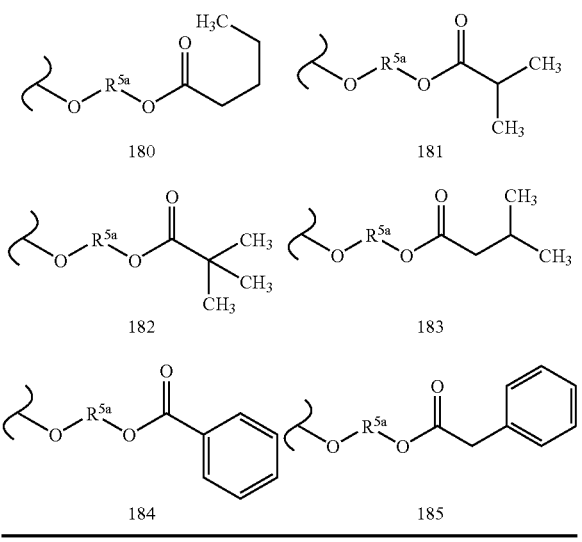
TABLE 20.29
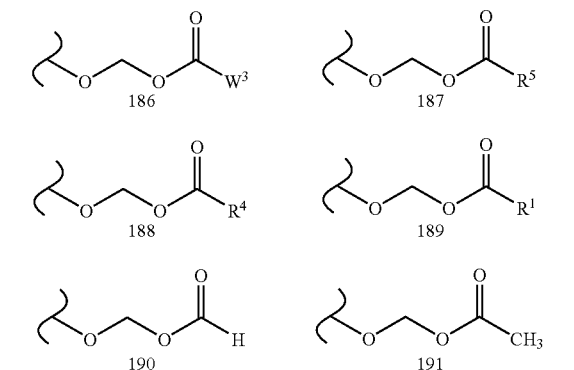
TABLE 20.29-continued
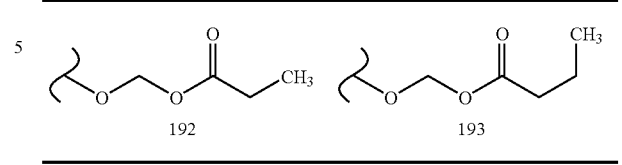
TABLE 20.30
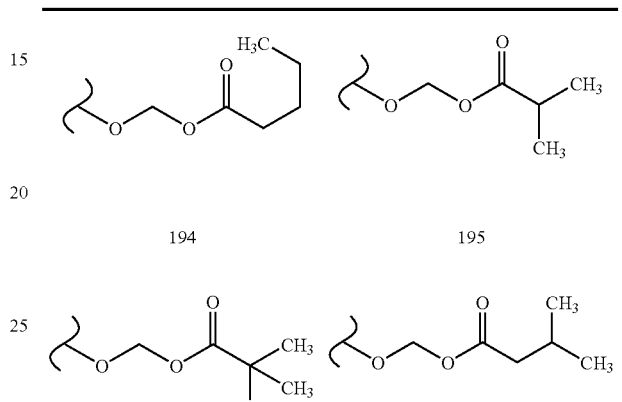
TABLE 20.31
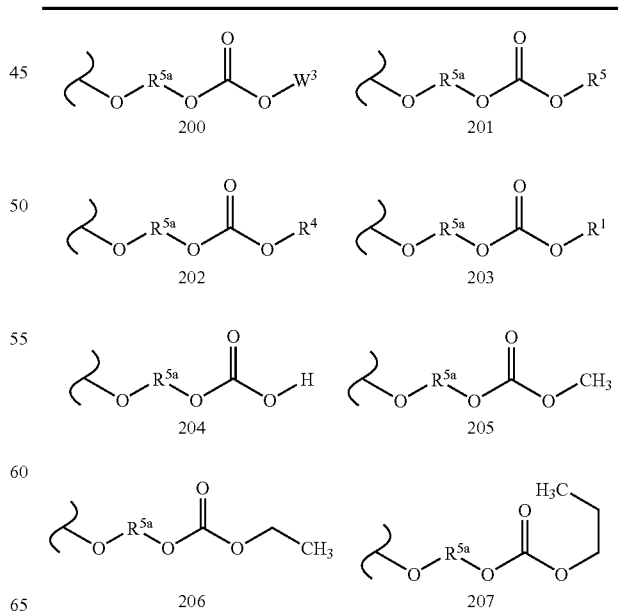

TABLE 20.32
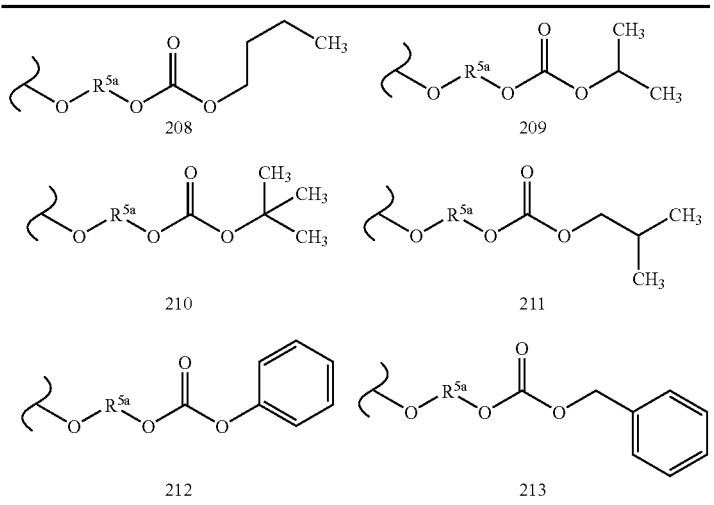
TABLE 20.33
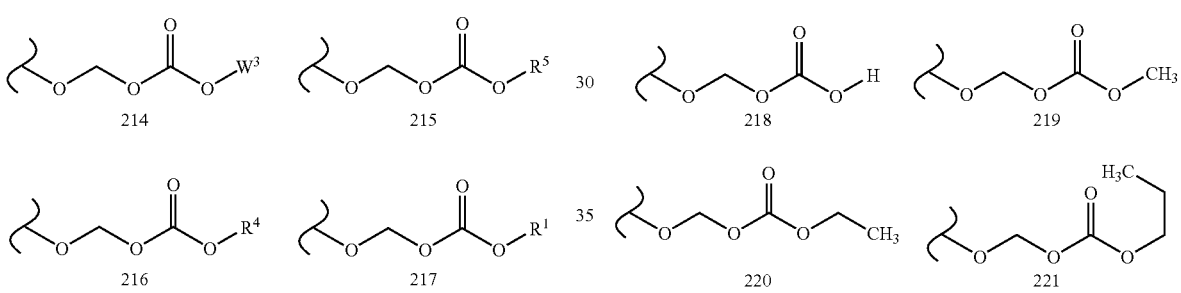
TABLE 20.34
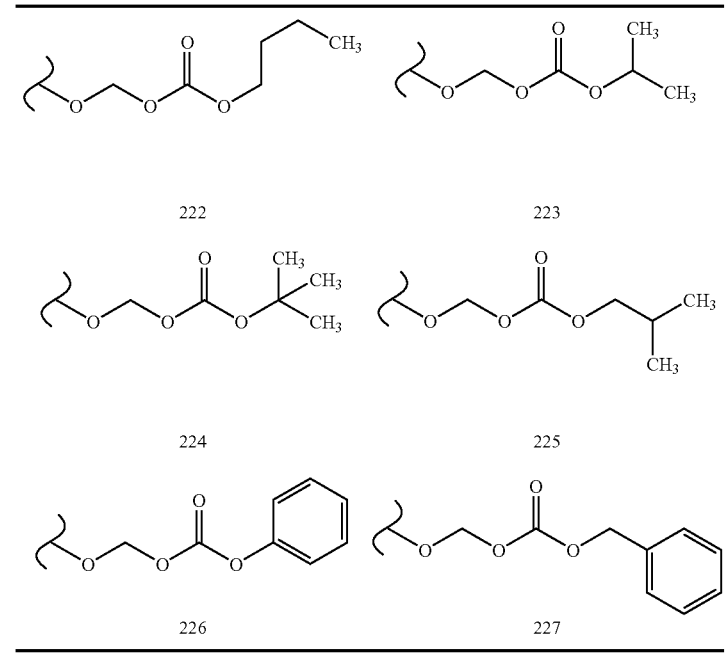

TABLE 20.35
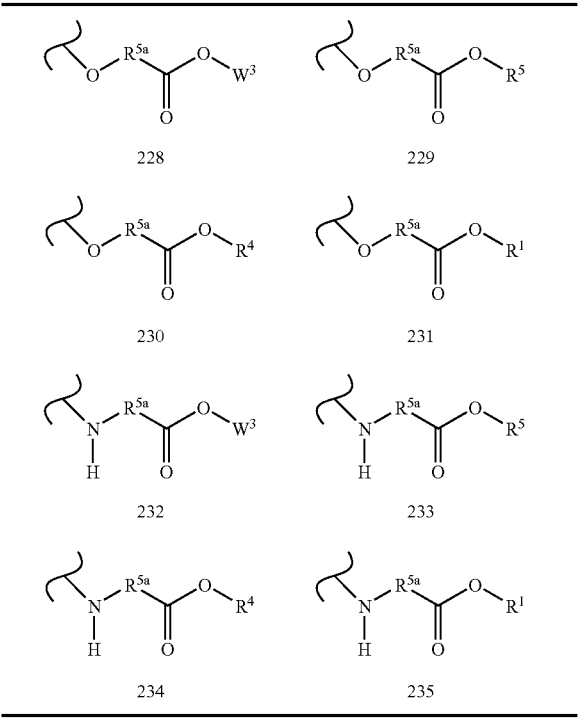
TABLE 20.36
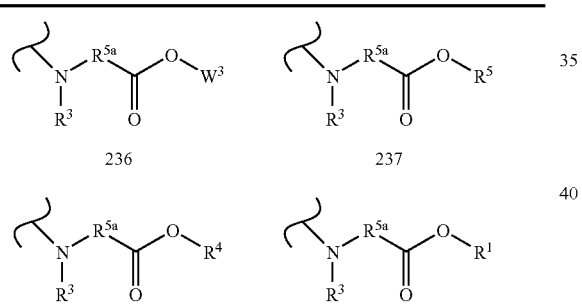
TABLE 20.36-continued
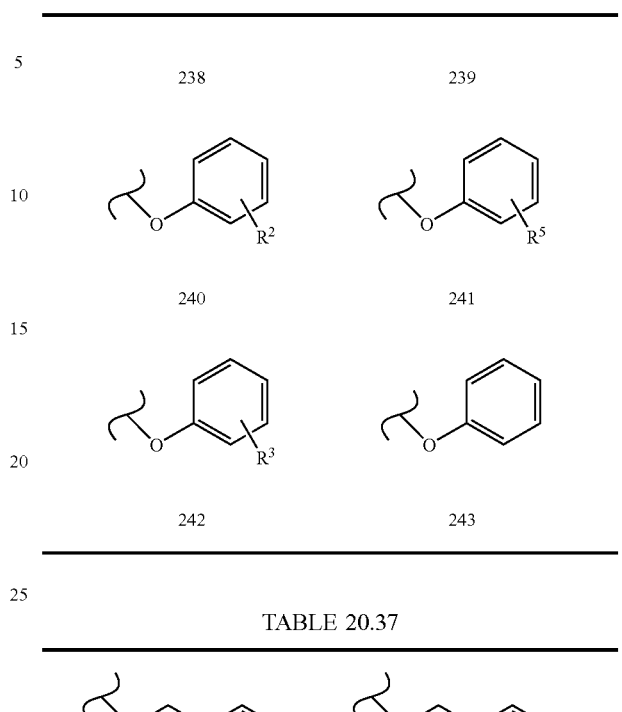
TABLE 20.37
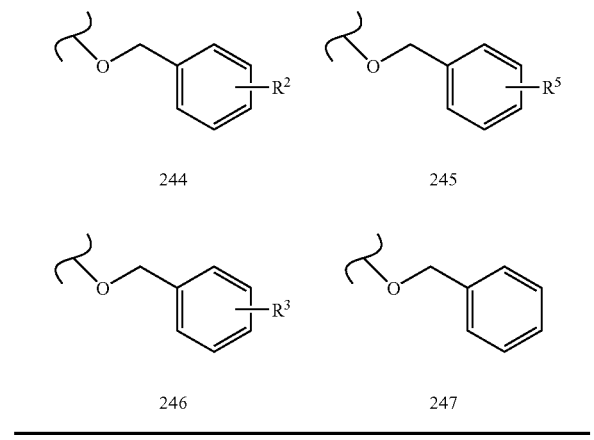
TABLE 100
Prodrugs of 1.B
1.B.228.228; 1.B.228.229; 1.B.228.230; 1.B.228.231; 1.B.228.236;
1.B.228.237; 1.B.228.238; 1.B.228.239; 1.B.228.154; 1.B.228.157; 1.B.228.166;
1.B.228.169; 1.B.228.172; 1.B.228.175; 1.B.228.240; 1.B.228.244; 1.B.229.228;
1.B.229.229; 1.B.229.230; 1.B.229.231; 1.B.229.236; 1.B.229.237; 1.B.229.238;
1.B.229.239; 1.B.229.154; 1.B.229.157; 1.B.229.166; 1.B.229.169; 1.B.229.172;
1.B.229.175; 1.B.229.240; 1.B.229.244; 1.B.230.228; 1.B.230.229; 1.B.230.230;
1.B.230.231; 1.B.230.236; 1.B.230.237; 1.B.230.238; 1.B.230.239; 1.B.230.154;
1.B.230.157; 1.B.230.166; 1.B.230.169; 1.B.230.172; 1.B.230.175; 1.B.230.240;
1.B.230.244; 1.B.231.228; 1.B.231.229; 1.B.231.230; 1.B.231.231; 1.B.231.236;
1.B.231.237; 1.B.231.238; 1.B.231.239; 1.B.231.154; 1.B.231.157; 1.B.231.166;
1.B.231.169; 1.B.231.172; 1.B.231.175; 1.B.231.240; 1.B.231.244; 1.B.236.228;
1.B.236.229; 1.B.236.230; 1.B.236.231; 1.B.236.236; 1.B.236.237; 1.B.236.238;
1.B.236.239; 1.B.236.154; 1.B.236.157; 1.B.236.166; 1.B.236.169; 1.B.236.172;
1.B.236.175; 1.B.236.240; 1.B.236.244; 1.B.237.228; 1.B.237.229; 1.B.237.230;
1.B.237.231; 1.B.237.236; 1.B.237.237; 1.B.237.238; 1.B.237.239; 1.B.237.154;
1.B.237.157; 1.B.237.166; 1.B.237.169; 1.B.237.172; 1.B.237.175; 1.B.237.240;
1.B.237.244; 1.B.238.228; 1.B.238.229; 1.B.238.230; 1.B.238.231; 1.B.238.236;
1.B.238.237; 1.B.238.238; 1.B.238.239; 1.B.238.154; 1.B.238.157; 1.B.238.166;
1.B.238.169; 1.B.238.172; 1.B.238.175; 1.B.238.240; 1.B.238.244; 1.B.239.228;
1.B.239.229; 1.B.239.230; 1.B.239.231; 1.B.239.236; 1.B.239.237; 1.B.239.238;

TABLE 100-continued

1.B.239.239; 1.B.239.154; 1.B.239.157; 1.B.239.166; 1.B.239.169; 1.B.239.172;
1.B.239.175; 1.B.239.240; 1.B.239.244; 1.B.154.228; 1.B.154.229; 1.B.154.230;
1.B.154.231; 1.B.154.236; 1.B.154.237; 1.B.154.238; 1.B.154.239; 1.B.154.154;
1.B.154.157; 1.B.154.166; 1.B.154.169; 1.B.154.172; 1.B.154.175; 1.B.154.240;
1.B.154.244; 1.B.157.228; 1.B.157.229; 1.B.157.230; 1.B.157.231; 1.B.157.236;
1.B.157.237; 1.B.157.238; 1.B.157.239; 1.B.157.154; 1.B.157.157; 1.B.157.166;
1.B.157.169; 1.B.157.172; 1.B.157.175; 1.B.157.240; 1.B.157.244; 1.B.166.228;
1.B.166.229; 1.B.166.230; 1.B.166.231; 1.B.166.236; 1.B.166.237; 1.B.166.238;
1.B.166.239; 1.B.166.154; 1.B.166.157; 1.B.166.166; 1.B.166.169; 1.B.166.172;
1.B.166.175; 1.B.166.240; 1.B.166.244; 1.B.169.228; 1.B.169.229; 1.B.169.230;
1.B.169.231; 1.B.169.236; 1.B.169.237; 1.B.169.238; 1.B.169.239; 1.B.169.154;
1.B.169.157; 1.B.169.166; 1.B.169.169; 1.B.169.172; 1.B.169.175; 1.B.169.240;
1.B.169.244; 1.B.172.228; 1.B.172.229; 1.B.172.230; 1.B.172.231; 1.B.172.236;
1.B.172.237; 1.B.172.238; 1.B.172.239; 1.B.172.154; 1.B.172.157; 1.B.172.166;
1.B.172.169; 1.B.172.172; 1.B.172.175; 1.B.172.240; 1.B.172.244; 1.B.175.228;
1.B.175.229; 1.B.175.230; 1.B.175.231; 1.B.175.236; 1.B.175.237; 1.B.175.238;
1.B.175.239; 1.B.175.154; 1.B.175.157; 1.B.175.166; 1.B.175.169; 1.B.175.172;
1.B.175.175; 1.B.175.240; 1.B.175.244; 1.B.240.228; 1.B.240.229; 1.B.240.230;
1.B.240.231; 1.B.240.236; 1.B.240.237; 1.B.240.238; 1.B.240.239; 1.B.240.154;
1.B.240.157; 1.B.240.166; 1.B.240.169; 1.B.240.172; 1.B.240.175; 1.B.240.240;
1.B.240.244; 1.B.244.228; 1.B.244.229; 1.B.244.230; 1.B.244.231; 1.B.244.236;
1.B.244.237; 1.B.244.238; 1.B.244.239; 1.B.244.154; 1.B.244.157; 1.B.244.166; 1.B.244.169;
1.B.244.172; 1.B.244.175; 1.B.244.240; 1.B.244.244;

Prodrugs of 1.D

1.D.228.228; 1.D.228.229; 1.D.228.230; 1.D.228.231; 1.D.228.236;
1.D.228.237; 1.D.228.238; 1.D.228.239; 1.D.228.154; 1.D.228.157;
1.D.228.166; 1.D.228.169; 1.D.228.172; 1.D.228.175; 1.D.228.240;
1.D.228.244; 1.D.229.228; 1.D.229.229; 1.D.229.230; 1.D.229.231;
1.D.229.236; 1.D.229.237; 1.D.229.238; 1.D.229.239; 1.D.229.154;
1.D.229.157; 1.D.229.166; 1.D.229.169; 1.D.229.172; 1.D.229.175;
1.D.229.240; 1.D.229.244; 1.D.230.228; 1.D.230.229; 1.D.230.230;
1.D.230.231; 1.D.230.236; 1.D.230.237; 1.D.230.238; 1.D.230.239;
1.D.230.154; 1.D.230.157; 1.D.230.166; 1.D.230.169; 1.D.230.172;
1.D.230.175; 1.D.230.240; 1.D.230.244; 1.D.231.228; 1.D.231.229;
1.D.231.230; 1.D.231.231; 1.D.231.236; 1.D.231.237; 1.D.231.238;
1.D.231.239; 1.D.231.154; 1.D.231.157; 1.D.231.166; 1.D.231.169;
1.D.231.172; 1.D.231.175; 1.D.231.240; 1.D.231.244; 1.D.236.228;
1.D.236.229; 1.D.236.230; 1.D.236.231; 1.D.236.236; 1.D.236.237;
1.D.236.238; 1.D.236.239; 1.D.236.154; 1.D.236.157; 1.D.236.166;
1.D.236.169; 1.D.236.172; 1.D.236.175; 1.D.236.240; 1.D.236.244;
1.D.237.228; 1.D.237.229; 1.D.237.230; 1.D.237.231; 1.D.237.236;
1.D.237.237; 1.D.237.238; 1.D.237.239; 1.D.237.154; 1.D.237.157;
1.D.237.166; 1.D.237.169; 1.D.237.172; 1.D.237.175; 1.D.237.240;
1.D.237.244; 1.D.238.228; 1.D.238.229; 1.D.238.230; 1.D.238.231;
1.D.238.236; 1.D.238.237; 1.D.238.238; 1.D.238.239; 1.D.238.154;
1.D.238.157; 1.D.238.166; 1.D.238.169; 1.D.238.172; 1.D.238.175;
1.D.238.240; 1.D.238.244; 1.D.239.228; 1.D.239.229; 1.D.239.230;
1.D.239.231; 1.D.239.236; 1.D.239.237; 1.D.239.238; 1.D.239.239;
1.D.239.154; 1.D.239.157; 1.D.239.166; 1.D.239.169; 1.D.239.172;
1.D.239.175; 1.D.239.240; 1.D.239.244; 1.D.154.228; 1.D.154.229;
1.D.154.230; 1.D.154.231; 1.D.154.236; 1.D.154.237; 1.D.154.238;
1.D.154.239; 1.D.154.154; 1.D.154.157; 1.D.154.166; 1.D.154.169;
1.D.154.172; 1.D.154.175; 1.D.154.240; 1.D.154.244; 1.D.157.228;
1.D.157.229; 1.D.157.230; 1.D.157.231; 1.D.157.236; 1.D.157.237;
1.D.157.238; 1.D.157.239; 1.D.157.154; 1.D.157.157; 1.D.157.166;
1.D.157.169; 1.D.157.172; 1.D.157.175; 1.D.157.240; 1.D.157.244;
1.D.166.228; 1.D.166.229; 1.D.166.230; 1.D.166.231; 1.D.166.236;
1.D.166.237; 1.D.166.238; 1.D.166.239; 1.D.166.154; 1.D.166.157;
1.D.166.166; 1.D.166.169; 1.D.166.172; 1.D.166.175; 1.D.166.240;
1.D.166.244; 1.D.169.228; 1.D.169.229; 1.D.169.230; 1.D.169.231;
1.D.169.236; 1.D.169.237; 1.D.169.238; 1.D.169.239; 1.D.169.154;
1.D.169.157; 1.D.169.166; 1.D.169.169; 1.D.169.172; 1.D.169.175;
1.D.169.240; 1.D.169.244; 1.D.172.228; 1.D.172.229; 1.D.172.230;
1.D.172.231; 1.D.172.236; 1.D.172.237; 1.D.172.238; 1.D.172.239;
1.D.172.154; 1.D.172.157; 1.D.172.166; 1.D.172.169; 1.D.172.172;
1.D.172.175; 1.D.172.240; 1.D.172.244; 1.D.175.228; 1.D.175.229;
1.D.175.230; 1.D.175.231; 1.D.175.236; 1.D.175.237; 1.D.175.238;
1.D.175.239; 1.D.175.154; 1.D.175.157; 1.D.175.166; 1.D.175.169;
1.D.175.172; 1.D.175.175; 1.D.175.240; 1.D.175.244; 1.D.240.228;
1.D.240.229; 1.D.240.230; 1.D.240.231; 1.D.240.236; 1.D.240.237;
1.D.240.238; 1.D.240.239; 1.D.240.154; 1.D.240.157; 1.D.240.166;
1.D.240.169; 1.D.240.172; 1.D.240.175; 1.D.240.240; 1.D.240.244;
1.D.244.228; 1.D.244.229; 1.D.244.230; 1.D.244.231; 1.D.244.236;
1.D.244.237; 1.D.244.238; 1.D.244.239; 1.D.244.154; 1.D.244.157;
1.D.244.166; 1.D.244.169; 1.D.244.172; 1.D.244.175; 1.D.244.240;
1.D.244.244;

TABLE 100-continued

Prodrugs of 1.E

1.E.228.228; 1.E.228.229; 1.E.228.230; 1.E.228.231; 1.E.228.236;
1.E.228.237; 1.E.228.238; 1.E.228.239; 1.E.228.154; 1.E.228.157; 1.E.228.166;
1.E.228.169; 1.E.228.172; 1.E.228.175; 1.E.228.240; 1.E.228.244; 1.E.229.228;
1.E.229.229; 1.E.229.230; 1.E.229.231; 1.E.229.236; 1.E.229.237; 1.E.229.238;
1.E.229.239; 1.E.229.154; 1.E.229.157; 1.E.229.166; 1.E.229.169; 1.E.229.172;
1.E.229.175; 1.E.229.240; 1.E.229.244; 1.E.230.228; 1.E.230.229; 1.E.230.230;
1.E.230.231; 1.E.230.236; 1.E.230.237; 1.E.230.238; 1.E.230.239; 1.E.230.154;
1.E.230.157; 1.E.230.166; 1.E.230.169; 1.E.230.172; 1.E.230.175; 1.E.230.240;
1.E.230.244; 1.E.231.228; 1.E.231.229; 1.E.231.230; 1.E.231.231; 1.E.231.236;
1.E.231.237; 1.E.231.238; 1.E.231.239; 1.E.231.154; 1.E.231.157; 1.E.231.166;
1.E.231.169; 1.E.231.172; 1.E.231.175; 1.E.231.240; 1.E.231.244; 1.E.236.228;
1.E.236.229; 1.E.236.230; 1.E.236.231; 1.E.236.236; 1.E.236.237; 1.E.236.238;
1.E.236.239; 1.E.236.154; 1.E.236.157; 1.E.236.166; 1.E.236.169; 1.E.236.172;
1.E.236.175; 1.E.236.240; 1.E.236.244; 1.E.237.228; 1.E.237.229; 1.E.237.230;
1.E.237.231; 1.E.237.236; 1.E.237.237; 1.E.237.238; 1.E.237.239; 1.E.237.154;
1.E.237.157; 1.E.237.166; 1.E.237.169; 1.E.237.172; 1.E.237.175; 1.E.237.240;
1.E.237.244; 1.E.238.228; 1.E.238.229; 1.E.238.230; 1.E.238.231; 1.E.238.236;
1.E.238.237; 1.E.238.238; 1.E.238.239; 1.E.238.154; 1.E.238.157; 1.E.238.166;
1.E.238.169; 1.E.238.172; 1.E.238.175; 1.E.238.240; 1.E.238.244; 1.E.239.228;
1.E.239.229; 1.E.239.230; 1.E.239.231; 1.E.239.236; 1.E.239.237; 1.E.239.238;
1.E.239.239; 1.E.239.154; 1.E.239.157; 1.E.239.166; 1.E.239.169; 1.E.239.172;
1.E.239.175; 1.E.239.240; 1.E.239.244; 1.E.154.228; 1.E.154.229; 1.E.154.230;
1.E.154.231; 1.E.154.236; 1.E.154.237; 1.E.154.238; 1.E.154.239; 1.E.154.154;
1.E.154.157; 1.E.154.166; 1.E.154.169; 1.E.154.172; 1.E.154.175; 1.E.154.240;
1.E.154.244; 1.E.157.228; 1.E.157.229; 1.E.157.230; 1.E.157.231; 1.E.157.236;
1.E.157.237; 1.E.157.238; 1.E.157.239; 1.E.157.154; 1.E.157.157; 1.E.157.166;
1.E.157.169; 1.E.157.172; 1.E.157.175; 1.E.157.240; 1.E.157.244; 1.E.166.228;
1.E.166.229; 1.E.166.230; 1.E.166.231; 1.E.166.236; 1.E.166.237; 1.E.166.238;
1.E.166.239; 1.E.166.154; 1.E.166.157; 1.E.166.166; 1.E.166.169; 1.E.166.172;
1.E.166.175; 1.E.166.240; 1.E.166.244; 1.E.169.228; 1.E.169.229; 1.E.169.230;
1.E.169.231; 1.E.169.236; 1.E.169.237; 1.E.169.238; 1.E.169.239; 1.E.169.154;
1.E.169.157; 1.E.169.166; 1.E.169.169; 1.E.169.172; 1.E.169.175; 1.E.169.240;
1.E.169.244; 1.E.172.228; 1.E.172.229; 1.E.172.230; 1.E.172.231; 1.E.172.236;
1.E.172.237; 1.E.172.238; 1.E.172.239; 1.E.172.154; 1.E.172.157; 1.E.172.166;
1.E.172.169; 1.E.172.172; 1.E.172.175; 1.E.172.240; 1.E.172.244; 1.E.175.228;
1.E.175.229; 1.E.175.230; 1.E.175.231; 1.E.175.236; 1.E.175.237; 1.E.175.238;
1.E.175.239; 1.E.175.154; 1.E.175.157; 1.E.175.166; 1.E.175.169; 1.E.175.172;
1.E.175.175; 1.E.175.240; 1.E.175.244; 1.E.240.228; 1.E.240.229; 1.E.240.230;
1.E.240.231; 1.E.240.236; 1.E.240.237; 1.E.240.238; 1.E.240.239; 1.E.240.154;
1.E.240.157; 1.E.240.166; 1.E.240.169; 1.E.240.172; 1.E.240.175; 1.E.240.240;
1.E.240.244; 1.E.244.228; 1.E.244.229; 1.E.244.230; 1.E.244.231; 1.E.244.236;
1.E.244.237; 1.E.244.238; 1.E.244.239; 1.E.244.154; 1.E.244.157; 1.E.244.166;
1.E.244.169; 1.E.244.172; 1.E.244.175; 1.E.244.240; 1.E.244.244;

Prodrugs of 1.G

1.G.228.228; 1.G.228.229; 1.G.228.230; 1.G.228.231; 1.G.228.236;
1.G.228.237; 1.G.228.238; 1.G.228.239; 1.G.228.154; 1.G.228.157;
1.G.228.166; 1.G.228.169; 1.G.228.172; 1.G.228.175; 1.G.228.240;
1.G.228.244; 1.G.229.228; 1.G.229.229; 1.G.229.230; 1.G.229.231;
1.G.229.236; 1.G.229.237; 1.G.229.238; 1.G.229.239; 1.G.229.154;
1.G.229.157; 1.G.229.166; 1.G.229.169; 1.G.229.172; 1.G.229.175;
1.G.229.240; 1.G.229.244; 1.G.230.228; 1.G.230.229; 1.G.230.230;
1.G.230.231; 1.G.230.236; 1.G.230.237; 1.G.230.238; 1.G.230.239;
1.G.230.154; 1.G.230.157; 1.G.230.166; 1.G.230.169; 1.G.230.172;
1.G.230.175; 1.G.230.240; 1.G.230.244; 1.G.231.228; 1.G.231.229;
1.G.231.230; 1.G.231.231; 1.G.231.236; 1.G.231.237; 1.G.231.238;
1.G.231.239; 1.G.231.154; 1.G.231.157; 1.G.231.166; 1.G.231.169;
1.G.231.172; 1.G.231.175; 1.G.231.240; 1.G.231.244; 1.G.236.228;
1.G.236.229; 1.G.236.230; 1.G.236.231; 1.G.236.236; 1.G.236.237;
1.G.236.238; 1.G.236.239; 1.G.236.154; 1.G.236.157; 1.G.236.166;
1.G.236.169; 1.G.236.172; 1.G.236.175; 1.G.236.240; 1.G.236.244;
1.G.237.228; 1.G.237.229; 1.G.237.230; 1.G.237.231; 1.G.237.236;
1.G.237.237; 1.G.237.238; 1.G.237.239; 1.G.237.154; 1.G.237.157;
1.G.237.166; 1.G.237.169; 1.G.237.172; 1.G.237.175; 1.G.237.240;
1.G.237.244; 1.G.238.228; 1.G.238.229; 1.G.238.230; 1.G.238.231;
1.G.238.236; 1.G.238.237; 1.G.238.238; 1.G.238.239; 1.G.238.154;
1.G.238.157; 1.G.238.166; 1.G.238.169; 1.G.238.172; 1.G.238.175;
1.G.238.240; 1.G.238.244; 1.G.239.228; 1.G.239.229; 1.G.239.230;
1.G.239.231; 1.G.239.236; 1.G.239.237; 1.G.239.238; 1.G.239.239;
1.G.239.154; 1.G.239.157; 1.G.239.166; 1.G.239.169; 1.G.239.172;
1.G.239.175; 1.G.239.240; 1.G.239.244; 1.G.154.228; 1.G.154.229;
1.G.154.230; 1.G.154.231; 1.G.154.236; 1.G.154.237; 1.G.154.238;
1.G.154.239; 1.G.154.154; 1.G.154.157; 1.G.154.166; 1.G.154.169;
1.G.154.172; 1.G.154.175; 1.G.154.240; 1.G.154.244; 1.G.157.228;
1.G.157.229; 1.G.157.230; 1.G.157.231; 1.G.157.236; 1.G.157.237;
1.G.157.238; 1.G.157.239; 1.G.157.154; 1.G.157.157; 1.G.157.166;
1.G.157.169; 1.G.157.172; 1.G.157.175; 1.G.157.240; 1.G.157.244;

TABLE 100-continued

1.G.166.228; 1.G.166.229; 1.G.166.230; 1.G.166.231; 1.G.166.236;
1.G.166.237; 1.G.166.238; 1.G.166.239; 1.G.166.154; 1.G.166.157;
1.G.166.166; 1.G.166.169; 1.G.166.172; 1.G.166.175; 1.G.166.240;
1.G.166.244; 1.G.169.228; 1.G.169.229; 1.G.169.230; 1.G.169.231;
1.G.169.236; 1.G.169.237; 1.G.169.238; 1.G.169.239; 1.G.169.154;
1.G.169.157; 1.G.169.166; 1.G.169.169; 1.G.169.172; 1.G.169.175;
1.G.169.240; 1.G.169.244; 1.G.172.228; 1.G.172.229; 1.G.172.230;
1.G.172.231; 1.G.172.236; 1.G.172.237; 1.G.172.238; 1.G.172.239;
1.G.172.154; 1.G.172.157; 1.G.172.166; 1.G.172.169; 1.G.172.172;
1.G.172.175; 1.G.172.240; 1.G.172.244; 1.G.175.228; 1.G.175.229;
1.G.175.230; 1.G.175.231; 1.G.175.236; 1.G.175.237; 1.G.175.238;
1.G.175.239; 1.G.175.154; 1.G.175.157; 1.G.175.166; 1.G.175.169;
1.G.175.172; 1.G.175.175; 1.G.175.240; 1.G.175.244; 1.G.240.228;
1.G.240.229; 1.G.240.230; 1.G.240.231; 1.G.240.236; 1.G.240.237;
1.G.240.238; 1.G.240.239; 1.G.240.154; 1.G.240.157; 1.G.240.166;
1.G.240.169; 1.G.240.172; 1.G.240.175; 1.G.240.240; 1.G.240.244;
1.G.244.228; 1.G.244.229; 1.G.244.230; 1.G.244.231; 1.G.244.236;
1.G.244.237; 1.G.244.238; 1.G.244.239; 1.G.244.154; 1.G.244.157;
1.G.244.166; 1.G.244.169; 1.G.244.172; 1.G.244.175; 1.G.244.240;
1.G.244.244;
Prodrugs of 1.I 1.I.228.228; 1.I.228.229; 1.I.228.230; 1.I.228.231; 1.I.228.236; 1.I.228.237;
1.I.228.238; 1.I.228.239; 1.I.228.154; 1.I.228.157; 1.I.228.166; 1.I.228.169;
1.I.228.172; 1.I.228.175; 1.I.228.240; 1.I.228.244; 1.I.229.228; 1.I.229.229;
1.I.229.230; 1.I.229.231; 1.I.229.236; 1.I.229.237; 1.I.229.238; 1.I.229.239;
1.I.229.154; 1.I.229.157; 1.I.229.166; 1.I.229.169; 1.I.229.172; 1.I.229.175;
1.I.229.240; 1.I.229.244; 1.I.230.228; 1.I.230.229; 1.I.230.230; 1.I.230.231;
1.I.230.236; 1.I.230.237; 1.I.230.238; 1.I.230.239; 1.I.230.154; 1.I.230.157;
1.I.230.166; 1.I.230.169; 1.I.230.172; 1.I.230.175; 1.I.230.240; 1.I.230.244;
1.I.231.228; 1.I.231.229; 1.I.231.230; 1.I.231.231; 1.I.231.236; 1.I.231.237;
1.I.231.238; 1.I.231.239; 1.I.231.154; 1.I.231.157; 1.I.231.166; 1.I.231.169;
1.I.231.172; 1.I.231.175; 1.I.231.240; 1.I.231.244; 1.I.236.228; 1.I.236.229;
1.I.236.230; 1.I.236.231; 1.I.236.236; 1.I.236.237; 1.I.236.238; 1.I.236.239;
1.I.236.154; 1.I.236.157; 1.I.236.166; 1.I.236.169; 1.I.236.172; 1.I.236.175;
1.I.236.240; 1.I.236.244; 1.I.237.228; 1.I.237.229; 1.I.237.230; 1.I.237.231;
1.I.237.236; 1.I.237.237; 1.I.237.238; 1.I.237.239; 1.I.237.154; 1.I.237.157;
1.I.237.166; 1.I.237.169; 1.I.237.172; 1.I.237.175; 1.I.237.240; 1.I.237.244;
1.I.238.228; 1.I.238.229; 1.I.238.230; 1.I.238.231; 1.I.238.236; 1.I.238.237;
1.I.238.238; 1.I.238.239; 1.I.238.154; 1.I.238.157; 1.I.238.166; 1.I.238.169;
1.I.238.172; 1.I.238.175; 1.I.238.240; 1.I.238.244; 1.I.239.228; 1.I.239.229;
1.I.239.230; 1.I.239.231; 1.I.239.236; 1.I.239.237; 1.I.239.238; 1.I.239.239;
1.I.239.154; 1.I.239.157; 1.I.239.166; 1.I.239.169; 1.I.239.172; 1.I.239.175;
1.I.239.240; 1.I.239.244; 1.I.154.228; 1.I.154.229; 1.I.154.230; 1.I.154.231;
1.I.154.236; 1.I.154.237; 1.I.154.238; 1.I.154.239; 1.I.154.154; 1.I.154.157;
1.I.154.166; 1.I.154.169; 1.I.154.172; 1.I.154.175; 1.I.154.240; 1.I.154.244;
1.I.157.228; 1.I.157.229; 1.I.157.230; 1.I.157.231; 1.I.157.236; 1.I.157.237;
1.I.157.238; 1.I.157.239; 1.I.157.154; 1.I.157.157; 1.I.157.166; 1.I.157.169;
1.I.157.172; 1.I.157.175; 1.I.157.240; 1.I.157.244; 1.I.166.228; 1.I.166.229;
1.I.166.230; 1.I.166.231; 1.I.166.236; 1.I.166.237; 1.I.166.238; 1.I.166.239;
1.I.166.154; 1.I.166.157; 1.I.166.166; 1.I.166.169; 1.I.166.172; 1.I.166.175;
1.I.166.240; 1.I.166.244; 1.I.169.228; 1.I.169.229; 1.I.169.230; 1.I.169.231;
1.I.169.236; 1.I.169.237; 1.I.169.238; 1.I.169.239; 1.I.169.154; 1.I.169.157;
1.I.169.166; 1.I.169.169; 1.I.169.172; 1.I.169.175; 1.I.169.240; 1.I.169.244;
1.I.172.228; 1.I.172.229; 1.I.172.230; 1.I.172.231; 1.I.172.236; 1.I.172.237;
1.I.172.238; 1.I.172.239; 1.I.172.154; 1.I.172.157; 1.I.172.166; 1.I.172.169;
1.I.172.172; 1.I.172.175; 1.I.172.240; 1.I.172.244; 1.I.175.228; 1.I.175.229;
1.I.175.230; 1.I.175.231; 1.I.175.236; 1.I.175.237; 1.I.175.238; 1.I.175.239;
1.I.175.154; 1.I.175.157; 1.I.175.166; 1.I.175.169; 1.I.175.172; 1.I.175.175;
1.I.175.240; 1.I.175.244; 1.I.240.228; 1.I.240.229; 1.I.240.230; 1.I.240.231;
1.I.240.236; 1.I.240.237; 1.I.240.238; 1.I.240.239; 1.I.240.154; 1.I.240.157;
1.I.240.166; 1.I.240.169; 1.I.240.172; 1.I.240.175; 1.I.240.240; 1.I.240.244;
1.I.244.228; 1.I.244.229; 1.I.244.230; 1.I.244.231; 1.I.244.236; 1.I.244.237;
1.I.244.238; 1.I.244.239; 1.I.244.154; 1.I.244.157; 1.I.244.166; 1.I.244.169;
1.I.244.172; 1.I.244.175; 1.I.244.240; 1.I.244.244;
Prodrugs of 1.J 1.J.228.228; 1.J.228.229; 1.J.228.230; 1.J.228.231; 1.J.228.236; 1.J.228.237;
1.J.228.238; 1.J.228.239; 1.J.228.154; 1.J.228.157; 1.J.228.166; 1.J.228.169;
1.J.228.172; 1.J.228.175; 1.J.228.240; 1.J.228.244; 1.J.229.228; 1.J.229.229;
1.J.229.230; 1.J.229.231; 1.J.229.236; 1.J.229.237; 1.J.229.238; 1.J.229.239;
1.J.229.154; 1.J.229.157; 1.J.229.166; 1.J.229.169; 1.J.229.172; 1.J.229.175;
1.J.229.240; 1.J.229.244; 1.J.230.228; 1.J.230.229; 1.J.230.230; 1.J.230.231;
1.J.230.236; 1.J.230.237; 1.J.230.238; 1.J.230.239; 1.J.230.154; 1.J.230.157;
1.J.230.166; 1.J.230.169; 1.J.230.172; 1.J.230.175; 1.J.230.240; 1.J.230.244;
1.J.231.228; 1.J.231.229; 1.J.231.230; 1.J.231.231; 1.J.231.236; 1.J.231.237;
1.J.231.238; 1.J.231.239; 1.J.231.154; 1.J.231.157; 1.J.231.166; 1.J.231.169;
1.J.231.172; 1.J.231.175; 1.J.231.240; 1.J.231.244; 1.J.236.228; 1.J.236.229;
1.J.236.230; 1.J.236.231; 1.J.236.236; 1.J.236.237; 1.J.236.238; 1.J.236.239;

TABLE 100-continued

1.J.236.154; 1.J.236.157; 1.J.236.166; 1.J.236.169; 1.J.236.172; 1.J.236.175;
1.J.236.240; 1.J.236.244; 1.J.237.228; 1.J.237.229; 1.J.237.230; 1.J.237.231;
1.J.237.236; 1.J.237.237; 1.J.237.238; 1.J.237.239; 1.J.237.154; 1.J.237.157;
1.J.237.166; 1.J.237.169; 1.J.237.172; 1.J.237.175; 1.J.237.240; 1.J.237.244;
1.J.238.228; 1.J.238.229; 1.J.238.230; 1.J.238.231; 1.J.238.236; 1.J.238.237;
1.J.238.238; 1.J.238.239; 1.J.238.154; 1.J.238.157; 1.J.238.166; 1.J.238.169;
1.J.238.172; 1.J.238.175; 1.J.238.240; 1.J.238.244; 1.J.239.228; 1.J.239.229;
1.J.239.230; 1.J.239.231; 1.J.239.236; 1.J.239.237; 1.J.239.238; 1.J.239.239;
1.J.239.154; 1.J.239.157; 1.J.239.166; 1.J.239.169; 1.J.239.172; 1.J.239.175;
1.J.239.240; 1.J.239.244; 1.J.154.228; 1.J.154.229; 1.J.154.230; 1.J.154.231;
1.J.154.236; 1.J.154.237; 1.J.154.238; 1.J.154.239; 1.J.154.154; 1.J.154.157;
1.J.154.166; 1.J.154.169; 1.J.154.172; 1.J.154.175; 1.J.154.240; 1.J.154.244;
1.J.157.228; 1.J.157.229; 1.J.157.230; 1.J.157.231; 1.J.157.236; 1.J.157.237;
1.J.157.238; 1.J.157.239; 1.J.157.154; 1.J.157.157; 1.J.157.166; 1.J.157.169;
1.J.157.172; 1.J.157.175; 1.J.157.240; 1.J.157.244; 1.J.166.228; 1.J.166.229;
1.J.166.230; 1.J.166.231; 1.J.166.236; 1.J.166.237; 1.J.166.238; 1.J.166.239;
1.J.166.154; 1.J.166.157; 1.J.166.166; 1.J.166.169; 1.J.166.172; 1.J.166.175;
1.J.166.240; 1.J.166.244; 1.J.169.228; 1.J.169.229; 1.J.169.230; 1.J.169.231;
1.J.169.236; 1.J.169.237; 1.J.169.238; 1.J.169.239; 1.J.169.154; 1.J.169.157;
1.J.169.166; 1.J.169.169; 1.J.169.172; 1.J.169.175; 1.J.169.240; 1.J.169.244;
1.J.172.228; 1.J.172.229; 1.J.172.230; 1.J.172.231; 1.J.172.236; 1.J.172.237;
1.J.172.238; 1.J.172.239; 1.J.172.154; 1.J.172.157; 1.J.172.166; 1.J.172.169;
1.J.172.172; 1.J.172.175; 1.J.172.240; 1.J.172.244; 1.J.175.228; 1.J.175.229;
1.J.175.230; 1.J.175.231; 1.J.175.236; 1.J.175.237; 1.J.175.238; 1.J.175.239;
1.J.175.154; 1.J.175.157; 1.J.175.166; 1.J.175.169; 1.J.175.172; 1.J.175.175;
1.J.175.240; 1.J.175.244; 1.J.240.228; 1.J.240.229; 1.J.240.230; 1.J.240.231;
1.J.240.236; 1.J.240.237; 1.J.240.238; 1.J.240.239; 1.J.240.154; 1.J.240.157;
1.J.240.166; 1.J.240.169; 1.J.240.172; 1.J.240.175; 1.J.240.240; 1.J.240.244;
1.J.244.228; 1.J.244.229; 1.J.244.230; 1.J.244.231; 1.J.244.236; 1.J.244.237;
1.J.244.238; 1.J.244.239; 1.J.244.154; 1.J.244.157; 1.J.244.166; 1.J.244.169;
1.J.244.172; 1.J.244.175; 1.J.244.240; 1.J.244.244;

Prodrugs of 1.L

1.L.228.228; 1.L.228.229; 1.L.228.230; 1.L.228.231; 1.L.228.236;
1.L.228.237; 1.L.228.238; 1.L.228.239; 1.L.228.154; 1.L.228.157; 1.L.228.166;
1.L.228.169; 1.L.228.172; 1.L.228.175; 1.L.228.240; 1.L.228.244; 1.L.229.228;
1.L.229.229; 1.L.229.230; 1.L.229.231; 1.L.229.236; 1.L.229.237; 1.L.229.238;
1.L.229.239; 1.L.229.154; 1.L.229.157; 1.L.229.166; 1.L.229.169; 1.L.229.172;
1.L.229.175; 1.L.229.240; 1.L.229.244; 1.L.230.228; 1.L.230.229; 1.L.230.230;
1.L.230.231; 1.L.230.236; 1.L.230.237; 1.L.230.238; 1.L.230.239; 1.L.230.154;
1.L.230.157; 1.L.230.166; 1.L.230.169; 1.L.230.172; 1.L.230.175; 1.L.230.240;
1.L.230.244; 1.L.231.228; 1.L.231.229; 1.L.231.230; 1.L.231.231; 1.L.231.236;
1.L.231.237; 1.L.231.238; 1.L.231.239; 1.L.231.154; 1.L.231.157; 1.L.231.166;
1.L.231.169; 1.L.231.172; 1.L.231.175; 1.L.231.240; 1.L.231.244; 1.L.236.228;
1.L.236.229; 1.L.236.230; 1.L.236.231; 1.L.236.236; 1.L.236.237; 1.L.236.238;
1.L.236.239; 1.L.236.154; 1.L.236.157; 1.L.236.166; 1.L.236.169; 1.L.236.172;
1.L.236.175; 1.L.236.240; 1.L.236.244; 1.L.237.228; 1.L.237.229; 1.L.237.230;
1.L.237.231; 1.L.237.236; 1.L.237.237; 1.L.237.238; 1.L.237.239; 1.L.237.154;
1.L.237.157; 1.L.237.166; 1.L.237.169; 1.L.237.172; 1.L.237.175; 1.L.237.240;
1.L.237.244; 1.L.238.228; 1.L.238.229; 1.L.238.230; 1.L.238.231; 1.L.238.236;
1.L.238.237; 1.L.238.238; 1.L.238.239; 1.L.238.154; 1.L.238.157; 1.L.238.166;
1.L.238.169; 1.L.238.172; 1.L.238.175; 1.L.238.240; 1.L.238.244; 1.L.239.228;
1.L.239.229; 1.L.239.230; 1.L.239.231; 1.L.239.236; 1.L.239.237; 1.L.239.238;
1.L.239.239; 1.L.239.154; 1.L.239.157; 1.L.239.166; 1.L.239.169; 1.L.239.172;
1.L.239.175; 1.L.239.240; 1.L.239.244; 1.L.154.228; 1.L.154.229; 1.L.154.230;
1.L.154.231; 1.L.154.236; 1.L.154.237; 1.L.154.238; 1.L.154.239; 1.L.154.154;
1.L.154.157; 1.L.154.166; 1.L.154.169; 1.L.154.172; 1.L.154.175; 1.L.154.240;
1.L.154.244; 1.L.157.228; 1.L.157.229; 1.L.157.230; 1.L.157.231; 1.L.157.236;
1.L.157.237; 1.L.157.238; 1.L.157.239; 1.L.157.154; 1.L.157.157; 1.L.157.166;
1.L.157.169; 1.L.157.172; 1.L.157.175; 1.L.157.240; 1.L.157.244; 1.L.166.228;
1.L.166.229; 1.L.166.230; 1.L.166.231; 1.L.166.236; 1.L.166.237; 1.L.166.238;
1.L.166.239; 1.L.166.154; 1.L.166.157; 1.L.166.166; 1.L.166.169; 1.L.166.172;
1.L.166.175; 1.L.166.240; 1.L.166.244; 1.L.169.228; 1.L.169.229; 1.L.169.230;
1.L.169.231; 1.L.169.236; 1.L.169.237; 1.L.169.238; 1.L.169.239; 1.L.169.154;
1.L.169.157; 1.L.169.166; 1.L.169.169; 1.L.169.172; 1.L.169.175; 1.L.169.240;
1.L.169.244; 1.L.172.228; 1.L.172.229; 1.L.172.230; 1.L.172.231; 1.L.172.236;
1.L.172.237; 1.L.172.238; 1.L.172.239; 1.L.172.154; 1.L.172.157; 1.L.172.166;
1.L.172.169; 1.L.172.172; 1.L.172.175; 1.L.172.240; 1.L.172.244; 1.L.175.228;
1.L.175.229; 1.L.175.230; 1.L.175.231; 1.L.175.236; 1.L.175.237; 1.L.175.238;
1.L.175.239; 1.L.175.154; 1.L.175.157; 1.L.175.166; 1.L.175.169; 1.L.175.172;
1.L.175.175; 1.L.175.240; 1.L.175.244; 1.L.240.228; 1.L.240.229; 1.L.240.230;
1.L.240.231; 1.L.240.236; 1.L.240.237; 1.L.240.238; 1.L.240.239; 1.L.240.154;
1.L.240.157; 1.L.240.166; 1.L.240.169; 1.L.240.172; 1.L.240.175; 1.L.240.240;
1.L.240.244; 1.L.244.228; 1.L.244.229; 1.L.244.230; 1.L.244.231; 1.L.244.236;
1.L.244.237; 1.L.244.238; 1.L.244.239; 1.L.244.154; 1.L.244.157; 1.L.244.166;
1.L.244.169; 1.L.244.172; 1.L.244.175; 1.L.244.240; 1.L.244.244;

TABLE 100-continued

Prodrugs of 1.O

1.O.228.228; 1.O.228.229; 1.O.228.230; 1.O.228.231; 1.O.228.236;
1.O.228.237; 1.O.228.238; 1.O.228.239; 1.O.228.154; 1.O.228.157;
1.O.228.166; 1.O.228.169; 1.O.228.172; 1.O.228.175; 1.O.228.240;
1.O.228.244; 1.O.229.228; 1.O.229.229; 1.O.229.230; 1.O.229.231;
1.O.229.236; 1.O.229.237; 1.O.229.238; 1.O.229.239; 1.O.229.154;
1.O.229.157; 1.O.229.166; 1.O.229.169; 1.O.229.172; 1.O.229.175;
1.O.229.240; 1.O.229.244; 1.O.230.228; 1.O.230.229; 1.O.230.230;
1.O.230.231; 1.O.230.236; 1.O.230.237; 1.O.230.238; 1.O.230.239;
1.O.230.154; 1.O.230.157; 1.O.230.166; 1.O.230.169; 1.O.230.172;
1.O.230.175; 1.O.230.240; 1.O.230.244; 1.O.231.228; 1.O.231.229;
1.O.231.230; 1.O.231.231; 1.O.231.236; 1.O.231.237; 1.O.231.238;
1.O.231.239; 1.O.231.154; 1.O.231.157; 1.O.231.166; 1.O.231.169;
1.O.231.172; 1.O.231.175; 1.O.231.240; 1.O.231.244; 1.O.236.228;
1.O.236.229; 1.O.236.230; 1.O.236.231; 1.O.236.236; 1.O.236.237;
1.O.236.238; 1.O.236.239; 1.O.236.154; 1.O.236.157; 1.O.236.166;
1.O.236.169; 1.O.236.172; 1.O.236.175; 1.O.236.240; 1.O.236.244;
1.O.237.228; 1.O.237.229; 1.O.237.230; 1.O.237.231; 1.O.237.236;
1.O.237.237; 1.O.237.238; 1.O.237.239; 1.O.237.154; 1.O.237.157;
1.O.237.166; 1.O.237.169; 1.O.237.172; 1.O.237.175; 1.O.237.240;
1.O.237.244; 1.O.238.228; 1.O.238.229; 1.O.238.230; 1.O.238.231;
1.O.238.236; 1.O.238.237; 1.O.238.238; 1.O.238.239; 1.O.238.154;
1.O.238.157; 1.O.238.166; 1.O.238.169; 1.O.238.172; 1.O.238.175;
1.O.238.240; 1.O.238.244; 1.O.239.228; 1.O.239.229; 1.O.239.230;
1.O.239.231; 1.O.239.236; 1.O.239.237; 1.O.239.238; 1.O.239.239;
1.O.239.154; 1.O.239.157; 1.O.239.166; 1.O.239.169; 1.O.239.172;
1.O.239.175; 1.O.239.240; 1.O.239.244; 1.O.154.228; 1.O.154.229;
1.O.154.230; 1.O.154.231; 1.O.154.236; 1.O.154.237; 1.O.154.238;
1.O.154.239; 1.O.154.154; 1.O.154.157; 1.O.154.166; 1.O.154.169;
1.O.154.172; 1.O.154.175; 1.O.154.240; 1.O.154.244; 1.O.157.228;
1.O.157.229; 1.O.157.230; 1.O.157.231; 1.O.157.236; 1.O.157.237;
1.O.157.238; 1.O.157.239; 1.O.157.154; 1.O.157.157; 1.O.157.166;
1.O.157.169; 1.O.157.172; 1.O.157.175; 1.O.157.240; 1.O.157.244;
1.O.166.228; 1.O.166.229; 1.O.166.230; 1.O.166.231; 1.O.166.236;
1.O.166.237; 1.O.166.238; 1.O.166.239; 1.O.166.154; 1.O.166.157;
1.O.166.166; 1.O.166.169; 1.O.166.172; 1.O.166.175; 1.O.166.240;
1.O.166.244; 1.O.169.228; 1.O.169.229; 1.O.169.230; 1.O.169.231;
1.O.169.236; 1.O.169.237; 1.O.169.238; 1.O.169.239; 1.O.169.154;
1.O.169.157; 1.O.169.166; 1.O.169.169; 1.O.169.172; 1.O.169.175;
1.O.169.240; 1.O.169.244; 1.O.172.228; 1.O.172.229; 1.O.172.230;
1.O.172.231; 1.O.172.236; 1.O.172.237; 1.O.172.238; 1.O.172.239;
1.O.172.154; 1.O.172.157; 1.O.172.166; 1.O.172.169; 1.O.172.172;
1.O.172.175; 1.O.172.240; 1.O.172.244; 1.O.175.228; 1.O.175.229;
1.O.175.230; 1.O.175.231; 1.O.175.236; 1.O.175.237; 1.O.175.238;
1.O.175.239; 1.O.175.154; 1.O.175.157; 1.O.175.166; 1.O.175.169;
1.O.175.172; 1.O.175.175; 1.O.175.240; 1.O.175.244; 1.O.240.228;
1.O.240.229; 1.O.240.230; 1.O.240.231; 1.O.240.236; 1.O.240.237;
1.O.240.238; 1.O.240.239; 1.O.240.154; 1.O.240.157; 1.O.240.166;
1.O.240.169; 1.O.240.172; 1.O.240.175; 1.O.240.240; 1.O.240.244;
1.O.244.228; 1.O.244.229; 1.O.244.230; 1.O.244.231; 1.O.244.236;
1.O.244.237; 1.O.244.238; 1.O.244.239; 1.O.244.154; 1.O.244.157;
1.O.244.166; 1.O.244.169; 1.O.244.172; 1.O.244.175; 1.O.244.240;
1.O.244.244;

Prodrugs of 1.P

1.P.228.228; 1.P.228.229; 1.P.228.230; 1.P.228.231; 1.P.228.236;
1.P.228.237; 1.P.228.238; 1.P.228.239; 1.P.228.154; 1.P.228.157; 1.P.228.166;
1.P.228.169; 1.P.228.172; 1.P.228.175; 1.P.228.240; 1.P.228.244; 1.P.229.228;
1.P.229.229; 1.P.229.230; 1.P.229.231; 1.P.229.236; 1.P.229.237; 1.P.229.238;
1.P.229.239; 1.P.229.154; 1.P.229.157; 1.P.229.166; 1.P.229.169; 1.P.229.172;
1.P.229.175; 1.P.229.240; 1.P.229.244; 1.P.230.228; 1.P.230.229; 1.P.230.230;
1.P.230.231; 1.P.230.236; 1.P.230.237; 1.P.230.238; 1.P.230.239; 1.P.230.154;
1.P.230.157; 1.P.230.166; 1.P.230.169; 1.P.230.172; 1.P.230.175; 1.P.230.240;
1.P.230.244; 1.P.231.228; 1.P.231.229; 1.P.231.230; 1.P.231.231; 1.P.231.236;
1.P.231.237; 1.P.231.238; 1.P.231.239; 1.P.231.154; 1.P.231.157; 1.P.231.166;
1.P.231.169; 1.P.231.172; 1.P.231.175; 1.P.231.240; 1.P.231.244; 1.P.236.228;
1.P.236.229; 1.P.236.230; 1.P.236.231; 1.P.236.236; 1.P.236.237; 1.P.236.238;
1.P.236.239; 1.P.236.154; 1.P.236.157; 1.P.236.166; 1.P.236.169; 1.P.236.172;
1.P.236.175; 1.P.236.240; 1.P.236.244; 1.P.237.228; 1.P.237.229; 1.P.237.230;
1.P.237.231; 1.P.237.236; 1.P.237.237; 1.P.237.238; 1.P.237.239; 1.P.237.154;
1.P.237.157; 1.P.237.166; 1.P.237.169; 1.P.237.172; 1.P.237.175; 1.P.237.240;
1.P.237.244; 1.P.238.228; 1.P.238.229; 1.P.238.230; 1.P.238.231; 1.P.238.236;
1.P.238.237; 1.P.238.238; 1.P.238.239; 1.P.238.154; 1.P.238.157; 1.P.238.166;
1.P.238.169; 1.P.238.172; 1.P.238.175; 1.P.238.240; 1.P.238.244; 1.P.239.228;
1.P.239.229; 1.P.239.230; 1.P.239.231; 1.P.239.236; 1.P.239.237; 1.P.239.238;
1.P.239.239; 1.P.239.154; 1.P.239.157; 1.P.239.166; 1.P.239.169; 1.P.239.172;
1.P.239.175; 1.P.239.240; 1.P.239.244; 1.P.154.228; 1.P.154.229; 1.P.154.230;
1.P.154.231; 1.P.154.236; 1.P.154.237; 1.P.154.238; 1.P.154.239; 1.P.154.154;

TABLE 100-continued

1.P.154.157; 1.P.154.166; 1.P.154.169; 1.P.154.172; 1.P.154.175; 1.P.154.240;
1.P.154.244; 1.P.157.228; 1.P.157.229; 1.P.157.230; 1.P.157.231; 1.P.157.236;
1.P.157.237; 1.P.157.238; 1.P.157.239; 1.P.157.154; 1.P.157.157; 1.P.157.166;
1.P.157.169; 1.P.157.172; 1.P.157.175; 1.P.157.240; 1.P.157.244; 1.P.166.228;
1.P.166.229; 1.P.166.230; 1.P.166.231; 1.P.166.236; 1.P.166.237; 1.P.166.238;
1.P.166.239; 1.P.166.154; 1.P.166.157; 1.P.166.166; 1.P.166.169; 1.P.166.172;
1.P.166.175; 1.P.166.240; 1.P.166.244; 1.P.169.228; 1.P.169.229; 1.P.169.230;
1.P.169.231; 1.P.169.236; 1.P.169.237; 1.P.169.238; 1.P.169.239; 1.P.169.154;
1.P.169.157; 1.P.169.166; 1.P.169.169; 1.P.169.172; 1.P.169.175; 1.P.169.240;
1.P.169.244; 1.P.172.228; 1.P.172.229; 1.P.172.230; 1.P.172.231; 1.P.172.236;
1.P.172.237; 1.P.172.238; 1.P.172.239; 1.P.172.154; 1.P.172.157; 1.P.172.166;
1.P.172.169; 1.P.172.172; 1.P.172.175; 1.P.172.240; 1.P.172.244; 1.P.175.228;
1.P.175.229; 1.P.175.230; 1.P.175.231; 1.P.175.236; 1.P.175.237; 1.P.175.238;
1.P.175.239; 1.P.175.154; 1.P.175.157; 1.P.175.166; 1.P.175.169; 1.P.175.172;
1.P.175.175; 1.P.175.240; 1.P.175.244; 1.P.240.228; 1.P.240.229; 1.P.240.230;
1.P.240.231; 1.P.240.236; 1.P.240.237; 1.P.240.238; 1.P.240.239; 1.P.240.154;
1.P.240.157; 1.P.240.166; 1.P.240.169; 1.P.240.172; 1.P.240.175; 1.P.240.240;
1.P.240.244; 1.P.244.228; 1.P.244.229; 1.P.244.230; 1.P.244.231; 1.P.244.236;
1.P.244.237; 1.P.244.238; 1.P.244.239; 1.P.244.154; 1.P.244.157; 1.P.244.166;
1.P.244.169; 1.P.244.172; 1.P.244.175; 1.P.244.240; 1.P.244.244;
Prodrugs of 1.U 1.U.228.228; 1.U.228.229; 1.U.228.230; 1.U.228.231; 1.U.228.236;
1.U.228.237; 1.U.228.238; 1.U.228.239; 1.U.228.154; 1.U.228.157;
1.U.228.166; 1.U.228.169; 1.U.228.172; 1.U.228.175; 1.U.228.240;
1.U.228.244; 1.U.229.228; 1.U.229.229; 1.U.229.230; 1.U.229.231;
1.U.229.236; 1.U.229.237; 1.U.229.238; 1.U.229.239; 1.U.229.154;
1.U.229.157; 1.U.229.166; 1.U.229.169; 1.U.229.172; 1.U.229.175;
1.U.229.240; 1.U.229.244; 1.U.230.228; 1.U.230.229; 1.U.230.230;
1.U.230.231; 1.U.230.236; 1.U.230.237; 1.U.230.238; 1.U.230.239;
1.U.230.154; 1.U.230.157; 1.U.230.166; 1.U.230.169; 1.U.230.172;
1.U.230.175; 1.U.230.240; 1.U.230.244; 1.U.231.228; 1.U.231.229;
1.U.231.230; 1.U.231.231; 1.U.231.236; 1.U.231.237; 1.U.231.238;
1.U.231.239; 1.U.231.154; 1.U.231.157; 1.U.231.166; 1.U.231.169;
1.U.231.172; 1.U.231.175; 1.U.231.240; 1.U.231.244; 1.U.236.228;
1.U.236.229; 1.U.236.230; 1.U.236.231; 1.U.236.236; 1.U.236.237;
1.U.236.238; 1.U.236.239; 1.U.236.154; 1.U.236.157; 1.U.236.166;
1.U.236.169; 1.U.236.172; 1.U.236.175; 1.U.236.240; 1.U.236.244;
1.U.237.228; 1.U.237.229; 1.U.237.230; 1.U.237.231; 1.U.237.236;
1.U.237.237; 1.U.237.238; 1.U.237.239; 1.U.237.154; 1.U.237.157;
1.U.237.166; 1.U.237.169; 1.U.237.172; 1.U.237.175; 1.U.237.240;
1.U.237.244; 1.U.238.228; 1.U.238.229; 1.U.238.230; 1.U.238.231;
1.U.238.236; 1.U.238.237; 1.U.238.238; 1.U.238.239; 1.U.238.154;
1.U.238.157; 1.U.238.166; 1.U.238.169; 1.U.238.172; 1.U.238.175;
1.U.238.240; 1.U.238.244; 1.U.239.228; 1.U.239.229; 1.U.239.230;
1.U.239.231; 1.U.239.236; 1.U.239.237; 1.U.239.238; 1.U.239.239;
1.U.239.154; 1.U.239.157; 1.U.239.166; 1.U.239.169; 1.U.239.172;
1.U.239.175; 1.U.239.240; 1.U.239.244; 1.U.154.228; 1.U.154.229;
1.U.154.230; 1.U.154.231; 1.U.154.236; 1.U.154.237; 1.U.154.238;
1.U.154.239; 1.U.154.154; 1.U.154.157; 1.U.154.166; 1.U.154.169;
1.U.154.172; 1.U.154.175; 1.U.154.240; 1.U.154.244; 1.U.157.228;
1.U.157.229; 1.U.157.230; 1.U.157.231; 1.U.157.236; 1.U.157.237;
1.U.157.238; 1.U.157.239; 1.U.157.154; 1.U.157.157; 1.U.157.166;
1.U.157.169; 1.U.157.172; 1.U.157.175; 1.U.157.240; 1.U.157.244;
1.U.166.228; 1.U.166.229; 1.U.166.230; 1.U.166.231; 1.U.166.236;
1.U.166.237; 1.U.166.238; 1.U.166.239; 1.U.166.154; 1.U.166.157;
1.U.166.166; 1.U.166.169; 1.U.166.172; 1.U.166.175; 1.U.166.240;
1.U.166.244; 1.U.169.228; 1.U.169.229; 1.U.169.230; 1.U.169.231;
1.U.169.236; 1.U.169.237; 1.U.169.238; 1.U.169.239; 1.U.169.154;
1.U.169.157; 1.U.169.166; 1.U.169.169; 1.U.169.172; 1.U.169.175;
1.U.169.240; 1.U.169.244; 1.U.172.228; 1.U.172.229; 1.U.172.230;
1.U.172.231; 1.U.172.236; 1.U.172.237; 1.U.172.238; 1.U.172.239;
1.U.172.154; 1.U.172.157; 1.U.172.166; 1.U.172.169; 1.U.172.172;
1.U.172.175; 1.U.172.240; 1.U.172.244; 1.U.175.228; 1.U.175.229;
1.U.175.230; 1.U.175.231; 1.U.175.236; 1.U.175.237; 1.U.175.238;
1.U.175.239; 1.U.175.154; 1.U.175.157; 1.U.175.166; 1.U.175.169;
1.U.175.172; 1.U.175.175; 1.U.175.240; 1.U.175.244; 1.U.240.228;
1.U.240.229; 1.U.240.230; 1.U.240.231; 1.U.240.236; 1.U.240.237;
1.U.240.238; 1.U.240.239; 1.U.240.154; 1.U.240.157; 1.U.240.166;
1.U.240.169; 1.U.240.172; 1.U.240.175; 1.U.240.240; 1.U.240.244;
1.U.244.228; 1.U.244.229; 1.U.244.230; 1.U.244.231; 1.U.244.236;
1.U.244.237; 1.U.244.238; 1.U.244.239; 1.U.244.154; 1.U.244.157;
1.U.244.166; 1.U.244.169; 1.U.244.172; 1.U.244.175; 1.U.244.240; 1.U.244.244;
Prodrugs of 1.W 1.W.228.228; 1.W.228.229; 1.W.228.230; 1.W.228.231; 1.W.228.236;
1.W.228.237; 1.W.228.238; 1.W.228.239; 1.W.228.154; 1.W.228.157;
1.W.228.166; 1.W.228.169; 1.W.228.172; 1.W.228.175; 1.W.228.240;
1.W.228.244; 1.W.229.228; 1.W.229.229; 1.W.229.230; 1.W.229.231;

TABLE 100-continued

1.W.229.236; 1.W.229.237; 1.W.229.238; 1.W.229.239; 1.W.229.154;
1.W.229.157; 1.W.229.166; 1.W.229.169; 1.W.229.172; 1.W.229.175;
1.W.229.240; 1.W.229.244; 1.W.230.228; 1.W.230.229; 1.W.230.230;
1.W.230.231; 1.W.230.236; 1.W.230.237; 1.W.230.238; 1.W.230.239;
1.W.230.154; 1.W.230.157; 1.W.230.166; 1.W.230.169; 1.W.230.172;
1.W.230.175; 1.W.230.240; 1.W.230.244; 1.W.231.228; 1.W.231.229;
1.W.231.230; 1.W.231.231; 1.W.231.236; 1.W.231.237; 1.W.231.238;
1.W.231.239; 1.W.231.154; 1.W.231.157; 1.W.231.166; 1.W.231.169;
1.W.231.172; 1.W.231.175; 1.W.231.240; 1.W.231.244; 1.W.236.228;
1.W.236.229; 1.W.236.230; 1.W.236.231; 1.W.236.236; 1.W.236.237;
1.W.236.238; 1.W.236.239; 1.W.236.154; 1.W.236.157; 1.W.236.166;
1.W.236.169; 1.W.236.172; 1.W.236.175; 1.W.236.240; 1.W.236.244;
1.W.237.228; 1.W.237.229; 1.W.237.230; 1.W.237.231; 1.W.237.236;
1.W.237.237; 1.W.237.238; 1.W.237.239; 1.W.237.154; 1.W.237.157;
1.W.237.166; 1.W.237.169; 1.W.237.172; 1.W.237.175; 1.W.237.240;
1.W.237.244; 1.W.238.228; 1.W.238.229; 1.W.238.230; 1.W.238.231;
1.W.238.236; 1.W.238.237; 1.W.238.238; 1.W.238.239; 1.W.238.154;
1.W.238.157; 1.W.238.166; 1.W.238.169; 1.W.238.172; 1.W.238.175;
1.W.238.240; 1.W.238.244; 1.W.239.228; 1.W.239.229; 1.W.239.230;
1.W.239.231; 1.W.239.236; 1.W.239.237; 1.W.239.238; 1.W.239.239;
1.W.239.154; 1.W.239.157; 1.W.239.166; 1.W.239.169; 1.W.239.172;
1.W.239.175; 1.W.239.240; 1.W.239.244; 1.W.154.228; 1.W.154.229;
1.W.154.230; 1.W.154.231; 1.W.154.236; 1.W.154.237; 1.W.154.238;
1.W.154.239; 1.W.154.154; 1.W.154.157; 1.W.154.166; 1.W.154.169;
1.W.154.172; 1.W.154.175; 1.W.154.240; 1.W.154.244; 1.W.157.228;
1.W.157.229; 1.W.157.230; 1.W.157.231; 1.W.157.236; 1.W.157.237;
1.W.157.238; 1.W.157.239; 1.W.157.154; 1.W.157.157; 1.W.157.166;
1.W.157.169; 1.W.157.172; 1.W.157.175; 1.W.157.240; 1.W.157.244;
1.W.166.228; 1.W.166.229; 1.W.166.230; 1.W.166.231; 1.W.166.236;
1.W.166.237; 1.W.166.238; 1.W.166.239; 1.W.166.154; 1.W.166.157;
1.W.166.166; 1.W.166.169; 1.W.166.172; 1.W.166.175; 1.W.166.240;
1.W.166.244; 1.W.169.228; 1.W.169.229; 1.W.169.230; 1.W.169.231;
1.W.169.236; 1.W.169.237; 1.W.169.238; 1.W.169.239; 1.W.169.154;
1.W.169.157; 1.W.169.166; 1.W.169.169; 1.W.169.172; 1.W.169.175;
1.W.169.240; 1.W.169.244; 1.W.172.228; 1.W.172.229; 1.W.172.230;
1.W.172.231; 1.W.172.236; 1.W.172.237; 1.W.172.238; 1.W.172.239;
1.W.172.154; 1.W.172.157; 1.W.172.166; 1.W.172.169; 1.W.172.172;
1.W.172.175; 1.W.172.240; 1.W.172.244; 1.W.175.228; 1.W.175.229;
1.W.175.230; 1.W.175.231; 1.W.175.236; 1.W.175.237; 1.W.175.238;
1.W.175.239; 1.W.175.154; 1.W.175.157; 1.W.175.166; 1.W.175.169;
1.W.175.172; 1.W.175.175; 1.W.175.240; 1.W.175.244; 1.W.240.228;
1.W.240.229; 1.W.240.230; 1.W.240.231; 1.W.240.236; 1.W.240.237;
1.W.240.238; 1.W.240.239; 1.W.240.154; 1.W.240.157; 1.W.240.166;
1.W.240.169; 1.W.240.172; 1.W.240.175; 1.W.240.240; 1.W.240.244;
1.W.244.228; 1.W.244.229; 1.W.244.230; 1.W.244.231; 1.W.244.236;
1.W.244.237; 1.W.244.238; 1.W.244.239; 1.W.244.154; 1.W.244.157;
1.W.244.166; 1.W.244.169; 1.W.244.172; 1.W.244.175; 1.W.244.240;
1.W.244.244;

Prodrugs of 1.Y

1.Y.228.228; 1.Y.228.229; 1.Y.228.230; 1.Y.228.231; 1.Y.228.236;
1.Y.228.237; 1.Y.228.238; 1.Y.228.239; 1.Y.228.154; 1.Y.228.157; 1.Y.228.166;
1.Y.228.169; 1.Y.228.172; 1.Y.228.175; 1.Y.228.240; 1.Y.228.244; 1.Y.229.228;
1.Y.229.229; 1.Y.229.230; 1.Y.229.231; 1.Y.229.236; 1.Y.229.237; 1.Y.229.238;
1.Y.229.239; 1.Y.229.154; 1.Y.229.157; 1.Y.229.166; 1.Y.229.169; 1.Y.229.172;
1.Y.229.175; 1.Y.229.240; 1.Y.229.244; 1.Y.230.228; 1.Y.230.229; 1.Y.230.230;
1.Y.230.231; 1.Y.230.236; 1.Y.230.237; 1.Y.230.238; 1.Y.230.239; 1.Y.230.154;
1.Y.230.157; 1.Y.230.166; 1.Y.230.169; 1.Y.230.172; 1.Y.230.175; 1.Y.230.240;
1.Y.230.244; 1.Y.231.228; 1.Y.231.229; 1.Y.231.230; 1.Y.231.231; 1.Y.231.236;
1.Y.231.237; 1.Y.231.238; 1.Y.231.239; 1.Y.231.154; 1.Y.231.157; 1.Y.231.166;
1.Y.231.169; 1.Y.231.172; 1.Y.231.175; 1.Y.231.240; 1.Y.231.244; 1.Y.236.228;
1.Y.236.229; 1.Y.236.230; 1.Y.236.231; 1.Y.236.236; 1.Y.236.237; 1.Y.236.238;
1.Y.236.239; 1.Y.236.154; 1.Y.236.157; 1.Y.236.166; 1.Y.236.169; 1.Y.236.172;
1.Y.236.175; 1.Y.236.240; 1.Y.236.244; 1.Y.237.228; 1.Y.237.229; 1.Y.237.230;
1.Y.237.231; 1.Y.237.236; 1.Y.237.237; 1.Y.237.238; 1.Y.237.239; 1.Y.237.154;
1.Y.237.157; 1.Y.237.166; 1.Y.237.169; 1.Y.237.172; 1.Y.237.175; 1.Y.237.240;
1.Y.237.244; 1.Y.238.228; 1.Y.238.229; 1.Y.238.230; 1.Y.238.231; 1.Y.238.236;
1.Y.238.237; 1.Y.238.238; 1.Y.238.239; 1.Y.238.154; 1.Y.238.157; 1.Y.238.166;
1.Y.238.169; 1.Y.238.172; 1.Y.238.175; 1.Y.238.240; 1.Y.238.244; 1.Y.239.228;
1.Y.239.229; 1.Y.239.230; 1.Y.239.231; 1.Y.239.236; 1.Y.239.237; 1.Y.239.238;
1.Y.239.239; 1.Y.239.154; 1.Y.239.157; 1.Y.239.166; 1.Y.239.169; 1.Y.239.172;
1.Y.239.175; 1.Y.239.240; 1.Y.239.244; 1.Y.154.228; 1.Y.154.229; 1.Y.154.230;
1.Y.154.231; 1.Y.154.236; 1.Y.154.237; 1.Y.154.238; 1.Y.154.239; 1.Y.154.154;
1.Y.154.157; 1.Y.154.166; 1.Y.154.169; 1.Y.154.172; 1.Y.154.175; 1.Y.154.240;
1.Y.154.244; 1.Y.157.228; 1.Y.157.229; 1.Y.157.230; 1.Y.157.231; 1.Y.157.236;
1.Y.157.237; 1.Y.157.238; 1.Y.157.239; 1.Y.157.154; 1.Y.157.157; 1.Y.157.166;
1.Y.157.169; 1.Y.157.172; 1.Y.157.175; 1.Y.157.240; 1.Y.157.244; 1.Y.166.228;
1.Y.166.229; 1.Y.166.230; 1.Y.166.231; 1.Y.166.236; 1.Y.166.237; 1.Y.166.238;
1.Y.166.239; 1.Y.166.154; 1.Y.166.157; 1.Y.166.166; 1.Y.166.169; 1.Y.166.172;

TABLE 100-continued

1.Y.166.175; 1.Y.166.240; 1.Y.166.244; 1.Y.169.228; 1.Y.169.229; 1.Y.169.230;
1.Y.169.231; 1.Y.169.236; 1.Y.169.237; 1.Y.169.238; 1.Y.169.239; 1.Y.169.154;
1.Y.169.157; 1.Y.169.166; 1.Y.169.169; 1.Y.169.172; 1.Y.169.175; 1.Y.169.240;
1.Y.169.244; 1.Y.172.228; 1.Y.172.229; 1.Y.172.230; 1.Y.172.231; 1.Y.172.236;
1.Y.172.237; 1.Y.172.238; 1.Y.172.239; 1.Y.172.154; 1.Y.172.157; 1.Y.172.166;
1.Y.172.169; 1.Y.172.172; 1.Y.172.175; 1.Y.172.240; 1.Y.172.244; 1.Y.175.228;
1.Y.175.229; 1.Y.175.230; 1.Y.175.231; 1.Y.175.236; 1.Y.175.237; 1.Y.175.238;
1.Y.175.239; 1.Y.175.154; 1.Y.175.157; 1.Y.175.166; 1.Y.175.169; 1.Y.175.172;
1.Y.175.175; 1.Y.175.240; 1.Y.175.244; 1.Y.240.228; 1.Y.240.229; 1.Y.240.230;
1.Y.240.231; 1.Y.240.236; 1.Y.240.237; 1.Y.240.238; 1.Y.240.239; 1.Y.240.154;
1.Y.240.157; 1.Y.240.166; 1.Y.240.169; 1.Y.240.172; 1.Y.240.175; 1.Y.240.240;
1.Y.240.244; 1.Y.244.228; 1.Y.244.229; 1.Y.244.230; 1.Y.244.231; 1.Y.244.236;
1.Y.244.237; 1.Y.244.238; 1.Y.244.239; 1.Y.244.154; 1.Y.244.157; 1.Y.244.166;
1.Y.244.169; 1.Y.244.172; 1.Y.244.175; 1.Y.244.154; 1.Y.244.240; 1.Y.244.244;
Prodrugs of 2.B 2.B.228.228; 2.B.228.229; 2.B.228.230; 2.B.228.231; 2.B.228.236;
2.B.228.237; 2.B.228.238; 2.B.228.239; 2.B.228.154; 2.B.228.157; 2.B.228.166;
2.B.228.169; 2.B.228.172; 2.B.228.175; 2.B.228.240; 2.B.228.244; 2.B.229.228;
2.B.229.229; 2.B.229.230; 2.B.229.231; 2.B.229.236; 2.B.229.237; 2.B.229.238;
2.B.229.239; 2.B.229.154; 2.B.229.157; 2.B.229.166; 2.B.229.169; 2.B.229.172;
2.B.229.175; 2.B.229.240; 2.B.229.244; 2.B.230.228; 2.B.230.229; 2.B.230.230;
2.B.230.231; 2.B.230.236; 2.B.230.237; 2.B.230.238; 2.B.230.239; 2.B.230.154;
2.B.230.157; 2.B.230.166; 2.B.230.169; 2.B.230.172; 2.B.230.175; 2.B.230.240;
2.B.230.244; 2.B.231.228; 2.B.231.229; 2.B.231.230; 2.B.231.231; 2.B.231.236;
2.B.231.237; 2.B.231.238; 2.B.231.239; 2.B.231.154; 2.B.231.157; 2.B.231.166;
2.B.231.169; 2.B.231.172; 2.B.231.175; 2.B.231.240; 2.B.231.244; 2.B.236.228;
2.B.236.229; 2.B.236.230; 2.B.236.231; 2.B.236.236; 2.B.236.237; 2.B.236.238;
2.B.236.239; 2.B.236.154; 2.B.236.157; 2.B.236.166; 2.B.236.169; 2.B.236.172;
2.B.236.175; 2.B.236.240; 2.B.236.244; 2.B.237.228; 2.B.237.229; 2.B.237.230;
2.B.237.231; 2.B.237.236; 2.B.237.237; 2.B.237.238; 2.B.237.239; 2.B.237.154;
2.B.237.157; 2.B.237.166; 2.B.237.169; 2.B.237.172; 2.B.237.175; 2.B.237.240;
2.B.237.244; 2.B.238.228; 2.B.238.229; 2.B.238.230; 2.B.238.231; 2.B.238.236;
2.B.238.237; 2.B.238.238; 2.B.238.239; 2.B.238.154; 2.B.238.157; 2.B.238.166;
2.B.238.169; 2.B.238.172; 2.B.238.175; 2.B.238.240; 2.B.238.244; 2.B.239.228;
2.B.239.229; 2.B.239.230; 2.B.239.231; 2.B.239.236; 2.B.239.237; 2.B.239.238;
2.B.239.239; 2.B.239.154; 2.B.239.157; 2.B.239.166; 2.B.239.169; 2.B.239.172;
2.B.239.175; 2.B.239.240; 2.B.239.244; 2.B.154.228; 2.B.154.229; 2.B.154.230;
2.B.154.231; 2.B.154.236; 2.B.154.237; 2.B.154.238; 2.B.154.239; 2.B.154.154;
2.B.154.157; 2.B.154.166; 2.B.154.169; 2.B.154.172; 2.B.154.175; 2.B.154.240;
2.B.154.244; 2.B.157.228; 2.B.157.229; 2.B.157.230; 2.B.157.231; 2.B.157.236;
2.B.157.237; 2.B.157.238; 2.B.157.239; 2.B.157.154; 2.B.157.157; 2.B.157.166;
2.B.157.169; 2.B.157.172; 2.B.157.175; 2.B.157.240; 2.B.157.244; 2.B.166.228;
2.B.166.229; 2.B.166.230; 2.B.166.231; 2.B.166.236; 2.B.166.237; 2.B.166.238;
2.B.166.239; 2.B.166.154; 2.B.166.157; 2.B.166.166; 2.B.166.169; 2.B.166.172;
2.B.166.175; 2.B.166.240; 2.B.166.244; 2.B.169.228; 2.B.169.229; 2.B.169.230;
2.B.169.231; 2.B.169.236; 2.B.169.237; 2.B.169.238; 2.B.169.239; 2.B.169.154;
2.B.169.157; 2.B.169.166; 2.B.169.169; 2.B.169.172; 2.B.169.175; 2.B.169.240;
2.B.169.244; 2.B.172.228; 2.B.172.229; 2.B.172.230; 2.B.172.231; 2.B.172.236;
2.B.172.237; 2.B.172.238; 2.B.172.239; 2.B.172.154; 2.B.172.157; 2.B.172.166;
2.B.172.169; 2.B.172.172; 2.B.172.175; 2.B.172.240; 2.B.172.244; 2.B.175.228;
2.B.175.229; 2.B.175.230; 2.B.175.231; 2.B.175.236; 2.B.175.237; 2.B.175.238;
2.B.175.239; 2.B.175.154; 2.B.175.157; 2.B.175.166; 2.B.175.169; 2.B.175.172;
2.B.175.175; 2.B.175.240; 2.B.175.244; 2.B.240.228; 2.B.240.229; 2.B.240.230;
2.B.240.231; 2.B.240.236; 2.B.240.237; 2.B.240.238; 2.B.240.239; 2.B.240.154;
2.B.240.157; 2.B.240.166; 2.B.240.169; 2.B.240.172; 2.B.240.175; 2.B.240.240;
2.B.240.244; 2.B.244.228; 2.B.244.229; 2.B.244.230; 2.B.244.231; 2.B.244.236;
2.B.244.237; 2.B.244.238; 2.B.244.239; 2.B.244.154; 2.B.244.157; 2.B.244.166; 2.B.244.169;
2.B.244.172; 2.B.244.175; 2.B.244.240; 2.B.244.244;
Prodrugs of 2.D 2.D.228.228; 2.D.228.229; 2.D.228.230; 2.D.228.231; 2.D.228.236;
2.D.228.237; 2.D.228.238; 2.D.228.239; 2.D.228.154; 2.D.228.157;
2.D.228.166; 2.D.228.169; 2.D.228.172; 2.D.228.175; 2.D.228.240;
2.D.228.244; 2.D.229.228; 2.D.229.229; 2.D.229.230; 2.D.229.231;
2.D.229.236; 2.D.229.237; 2.D.229.238; 2.D.229.239; 2.D.229.154;
2.D.229.157; 2.D.229.166; 2.D.229.169; 2.D.229.172; 2.D.229.175;
2.D.229.240; 2.D.229.244; 2.D.230.228; 2.D.230.229; 2.D.230.230;
2.D.230.231; 2.D.230.236; 2.D.230.237; 2.D.230.238; 2.D.230.239;
2.D.230.154; 2.D.230.157; 2.D.230.166; 2.D.230.169; 2.D.230.172;
2.D.230.175; 2.D.230.240; 2.D.230.244; 2.D.231.228; 2.D.231.229;
2.D.231.230; 2.D.231.231; 2.D.231.236; 2.D.231.237; 2.D.231.238;
2.D.231.239; 2.D.231.154; 2.D.231.157; 2.D.231.166; 2.D.231.169;
2.D.231.172; 2.D.231.175; 2.D.231.240; 2.D.231.244; 2.D.236.228;
2.D.236.229; 2.D.236.230; 2.D.236.231; 2.D.236.236; 2.D.236.237;
2.D.236.238; 2.D.236.239; 2.D.236.154; 2.D.236.157; 2.D.236.166;
2.D.236.169; 2.D.236.172; 2.D.236.175; 2.D.236.240; 2.D.236.244;
2.D.237.228; 2.D.237.229; 2.D.237.230; 2.D.237.231; 2.D.237.236;
2.D.237.237; 2.D.237.238; 2.D.237.239; 2.D.237.154; 2.D.237.157;

TABLE 100-continued

2.D.237.166; 2.D.237.169; 2.D.237.172; 2.D.237.175; 2.D.237.240;
2.D.237.244; 2.D.238.228; 2.D.238.229; 2.D.238.230; 2.D.238.231;
2.D.238.236; 2.D.238.237; 2.D.238.238; 2.D.238.239; 2.D.238.154;
2.D.238.157; 2.D.238.166; 2.D.238.169; 2.D.238.172; 2.D.238.175;
2.D.238.240; 2.D.238.244; 2.D.239.228; 2.D.239.229; 2.D.239.230;
2.D.239.231; 2.D.239.236; 2.D.239.237; 2.D.239.238; 2.D.239.239;
2.D.239.154; 2.D.239.157; 2.D.239.166; 2.D.239.169; 2.D.239.172;
2.D.239.175; 2.D.239.240; 2.D.239.244; 2.D.154.228; 2.D.154.229;
2.D.154.230; 2.D.154.231; 2.D.154.236; 2.D.154.237; 2.D.154.238;
2.D.154.239; 2.D.154.154; 2.D.154.157; 2.D.154.166; 2.D.154.169;
2.D.154.172; 2.D.154.175; 2.D.154.240; 2.D.154.244; 2.D.157.228;
2.D.157.229; 2.D.157.230; 2.D.157.231; 2.D.157.236; 2.D.157.237;
2.D.157.238; 2.D.157.239; 2.D.157.154; 2.D.157.157; 2.D.157.166;
2.D.157.169; 2.D.157.172; 2.D.157.175; 2.D.157.240; 2.D.157.244;
2.D.166.228; 2.D.166.229; 2.D.166.230; 2.D.166.231; 2.D.166.236;
2.D.166.237; 2.D.166.238; 2.D.166.239; 2.D.166.154; 2.D.166.157;
2.D.166.166; 2.D.166.169; 2.D.166.172; 2.D.166.175; 2.D.166.240;
2.D.166.244; 2.D.169.228; 2.D.169.229; 2.D.169.230; 2.D.169.231;
2.D.169.236; 2.D.169.237; 2.D.169.238; 2.D.169.239; 2.D.169.154;
2.D.169.157; 2.D.169.166; 2.D.169.169; 2.D.169.172; 2.D.169.175;
2.D.169.240; 2.D.169.244; 2.D.172.228; 2.D.172.229; 2.D.172.230;
2.D.172.231; 2.D.172.236; 2.D.172.237; 2.D.172.238; 2.D.172.239;
2.D.172.154; 2.D.172.157; 2.D.172.166; 2.D.172.169; 2.D.172.172;
2.D.172.175; 2.D.172.240; 2.D.172.244; 2.D.175.228; 2.D.175.229;
2.D.175.230; 2.D.175.231; 2.D.175.236; 2.D.175.237; 2.D.175.238;
2.D.175.239; 2.D.175.154; 2.D.175.157; 2.D.175.166; 2.D.175.169;
2.D.175.172; 2.D.175.175; 2.D.175.240; 2.D.175.244; 2.D.240.228;
2.D.240.229; 2.D.240.230; 2.D.240.231; 2.D.240.236; 2.D.240.237;
2.D.240.238; 2.D.240.239; 2.D.240.154; 2.D.240.157; 2.D.240.166;
2.D.240.169; 2.D.240.172; 2.D.240.175; 2.D.240.240; 2.D.240.244;
2.D.244.228; 2.D.244.229; 2.D.244.230; 2.D.244.231; 2.D.244.236;
2.D.244.237; 2.D.244.238; 2.D.244.239; 2.D.244.154; 2.D.244.157;
2.D.244.166; 2.D.244.169; 2.D.244.172; 2.D.244.175; 2.D.244.240;
2.D.244.244;
Prodrugs of 2.E 2.E.228.228; 2.E.228.229; 2.E.228.230; 2.E.228.231; 2.E.228.236;
2.E.228.237; 2.E.228.238; 2.E.228.239; 2.E.228.154; 2.E.228.157; 2.E.228.166;
2.E.228.169; 2.E.228.172; 2.E.228.175; 2.E.228.240; 2.E.228.244; 2.E.229.228;
2.E.229.229; 2.E.229.230; 2.E.229.231; 2.E.229.236; 2.E.229.237; 2.E.229.238;
2.E.229.239; 2.E.229.154; 2.E.229.157; 2.E.229.166; 2.E.229.169; 2.E.229.172;
2.E.229.175; 2.E.229.240; 2.E.229.244; 2.E.230.228; 2.E.230.229; 2.E.230.230;
2.E.230.231; 2.E.230.236; 2.E.230.237; 2.E.230.238; 2.E.230.239; 2.E.230.154;
2.E.230.157; 2.E.230.166; 2.E.230.169; 2.E.230.172; 2.E.230.175; 2.E.230.240;
2.E.230.244; 2.E.231.228; 2.E.231.229; 2.E.231.230; 2.E.231.231; 2.E.231.236;
2.E.231.237; 2.E.231.238; 2.E.231.239; 2.E.231.154; 2.E.231.157; 2.E.231.166;
2.E.231.169; 2.E.231.172; 2.E.231.175; 2.E.231.240; 2.E.231.244; 2.E.236.228;
2.E.236.229; 2.E.236.230; 2.E.236.231; 2.E.236.236; 2.E.236.237; 2.E.236.238;
2.E.236.239; 2.E.236.154; 2.E.236.157; 2.E.236.166; 2.E.236.169; 2.E.236.172;
2.E.236.175; 2.E.236.240; 2.E.236.244; 2.E.237.228; 2.E.237.229; 2.E.237.230;
2.E.237.231; 2.E.237.236; 2.E.237.237; 2.E.237.238; 2.E.237.239; 2.E.237.154;
2.E.237.157; 2.E.237.166; 2.E.237.169; 2.E.237.172; 2.E.237.175; 2.E.237.240;
2.E.237.244; 2.E.238.228; 2.E.238.229; 2.E.238.230; 2.E.238.231; 2.E.238.236;
2.E.238.237; 2.E.238.238; 2.E.238.239; 2.E.238.154; 2.E.238.157; 2.E.238.166;
2.E.238.169; 2.E.238.172; 2.E.238.175; 2.E.238.240; 2.E.238.244; 2.E.239.228;
2.E.239.229; 2.E.239.230; 2.E.239.231; 2.E.239.236; 2.E.239.237; 2.E.239.238;
2.E.239.239; 2.E.239.154; 2.E.239.157; 2.E.239.166; 2.E.239.169; 2.E.239.172;
2.E.239.175; 2.E.239.240; 2.E.239.244; 2.E.154.228; 2.E.154.229; 2.E.154.230;
2.E.154.231; 2.E.154.236; 2.E.154.237; 2.E.154.238; 2.E.154.239; 2.E.154.154;
2.E.154.157; 2.E.154.166; 2.E.154.169; 2.E.154.172; 2.E.154.175; 2.E.154.240;
2.E.154.244; 2.E.157.228; 2.E.157.229; 2.E.157.230; 2.E.157.231; 2.E.157.236;
2.E.157.237; 2.E.157.238; 2.E.157.239; 2.E.157.154; 2.E.157.157; 2.E.157.166;
2.E.157.169; 2.E.157.172; 2.E.157.175; 2.E.157.240; 2.E.157.244; 2.E.166.228;
2.E.166.229; 2.E.166.230; 2.E.166.231; 2.E.166.236; 2.E.166.237; 2.E.166.238;
2.E.166.239; 2.E.166.154; 2.E.166.157; 2.E.166.166; 2.E.166.169; 2.E.166.172;
2.E.166.175; 2.E.166.240; 2.E.166.244; 2.E.169.228; 2.E.169.229; 2.E.169.230;
2.E.169.231; 2.E.169.236; 2.E.169.237; 2.E.169.238; 2.E.169.239; 2.E.169.154;
2.E.169.157; 2.E.169.166; 2.E.169.169; 2.E.169.172; 2.E.169.175; 2.E.169.240;
2.E.169.244; 2.E.172.228; 2.E.172.229; 2.E.172.230; 2.E.172.231; 2.E.172.236;
2.E.172.237; 2.E.172.238; 2.E.172.239; 2.E.172.154; 2.E.172.157; 2.E.172.166;
2.E.172.169; 2.E.172.172; 2.E.172.175; 2.E.172.240; 2.E.172.244; 2.E.175.228;
2.E.175.229; 2.E.175.230; 2.E.175.231; 2.E.175.236; 2.E.175.237; 2.E.175.238;
2.E.175.239; 2.E.175.154; 2.E.175.157; 2.E.175.166; 2.E.175.169; 2.E.175.172;
2.E.175.175; 2.E.175.240; 2.E.175.244; 2.E.240.228; 2.E.240.229; 2.E.240.230;
2.E.240.231; 2.E.240.236; 2.E.240.237; 2.E.240.238; 2.E.240.239; 2.E.240.154;
2.E.240.157; 2.E.240.166; 2.E.240.169; 2.E.240.172; 2.E.240.175; 2.E.240.240;
2.E.240.244; 2.E.244.228; 2.E.244.229; 2.E.244.230; 2.E.244.231; 2.E.244.236;
2.E.244.237; 2.E.244.238; 2.E.244.239; 2.E.244.154; 2.E.244.157; 2.E.244.166;
2.E.244.169; 2.E.244.172; 2.E.244.175; 2.E.244.240; 2.E.244.244;

TABLE 100-continued

Prodrugs of 2.G

2.G.228.228; 2.G.228.229; 2.G.228.230; 2.G.228.231; 2.G.228.236;
2.G.228.237; 2.G.228.238; 2.G.228.239; 2.G.228.154; 2.G.228.157;
2.G.228.166; 2.G.228.169; 2.G.228.172; 2.G.228.175; 2.G.228.240;
2.G.228.244; 2.G.229.228; 2.G.229.229; 2.G.229.230; 2.G.229.231;
2.G.229.236; 2.G.229.237; 2.G.229.238; 2.G.229.239; 2.G.229.154;
2.G.229.157; 2.G.229.166; 2.G.229.169; 2.G.229.172; 2.G.229.175;
2.G.229.240; 2.G.229.244; 2.G.230.228; 2.G.230.229; 2.G.230.230;
2.G.230.231; 2.G.230.236; 2.G.230.237; 2.G.230.238; 2.G.230.239;
2.G.230.154; 2.G.230.157; 2.G.230.166; 2.G.230.169; 2.G.230.172;
2.G.230.175; 2.G.230.240; 2.G.230.244; 2.G.231.228; 2.G.231.229;
2.G.231.230; 2.G.231.231; 2.G.231.236; 2.G.231.237; 2.G.231.238;
2.G.231.239; 2.G.231.154; 2.G.231.157; 2.G.231.166; 2.G.231.169;
2.G.231.172; 2.G.231.175; 2.G.231.240; 2.G.231.244; 2.G.236.228;
2.G.236.229; 2.G.236.230; 2.G.236.231; 2.G.236.236; 2.G.236.237;
2.G.236.238; 2.G.236.239; 2.G.236.154; 2.G.236.157; 2.G.236.166;
2.G.236.169; 2.G.236.172; 2.G.236.175; 2.G.236.240; 2.G.236.244;
2.G.237.228; 2.G.237.229; 2.G.237.230; 2.G.237.231; 2.G.237.236;
2.G.237.237; 2.G.237.238; 2.G.237.239; 2.G.237.154; 2.G.237.157;
2.G.237.166; 2.G.237.169; 2.G.237.172; 2.G.237.175; 2.G.237.240;
2.G.237.244; 2.G.238.228; 2.G.238.229; 2.G.238.230; 2.G.238.231;
2.G.238.236; 2.G.238.237; 2.G.238.238; 2.G.238.239; 2.G.238.154;
2.G.238.157; 2.G.238.166; 2.G.238.169; 2.G.238.172; 2.G.238.175;
2.G.238.240; 2.G.238.244; 2.G.239.228; 2.G.239.229; 2.G.239.230;
2.G.239.231; 2.G.239.236; 2.G.239.237; 2.G.239.238; 2.G.239.239;
2.G.239.154; 2.G.239.157; 2.G.239.166; 2.G.239.169; 2.G.239.172;
2.G.239.175; 2.G.239.240; 2.G.239.244; 2.G.154.228; 2.G.154.229;
2.G.154.230; 2.G.154.231; 2.G.154.236; 2.G.154.237; 2.G.154.238;
2.G.154.239; 2.G.154.154; 2.G.154.157; 2.G.154.166; 2.G.154.169;
2.G.154.172; 2.G.154.175; 2.G.154.240; 2.G.154.244; 2.G.157.228;
2.G.157.229; 2.G.157.230; 2.G.157.231; 2.G.157.236; 2.G.157.237;
2.G.157.238; 2.G.157.239; 2.G.157.154; 2.G.157.157; 2.G.157.166;
2.G.157.169; 2.G.157.172; 2.G.157.175; 2.G.157.240; 2.G.157.244;
2.G.166.228; 2.G.166.229; 2.G.166.230; 2.G.166.231; 2.G.166.236;
2.G.166.237; 2.G.166.238; 2.G.166.239; 2.G.166.154; 2.G.166.157;
2.G.166.166; 2.G.166.169; 2.G.166.172; 2.G.166.175; 2.G.166.240;
2.G.166.244; 2.G.169.228; 2.G.169.229; 2.G.169.230; 2.G.169.231;
2.G.169.236; 2.G.169.237; 2.G.169.238; 2.G.169.239; 2.G.169.154;
2.G.169.157; 2.G.169.166; 2.G.169.169; 2.G.169.172; 2.G.169.175;
2.G.169.240; 2.G.169.244; 2.G.172.228; 2.G.172.229; 2.G.172.230;
2.G.172.231; 2.G.172.236; 2.G.172.237; 2.G.172.238; 2.G.172.239;
2.G.172.154; 2.G.172.157; 2.G.172.166; 2.G.172.169; 2.G.172.172;
2.G.172.175; 2.G.172.240; 2.G.172.244; 2.G.175.228; 2.G.175.229;
2.G.175.230; 2.G.175.231; 2.G.175.236; 2.G.175.237; 2.G.175.238;
2.G.175.239; 2.G.175.154; 2.G.175.157; 2.G.175.166; 2.G.175.169;
2.G.175.172; 2.G.175.175; 2.G.175.240; 2.G.175.244; 2.G.240.228;
2.G.240.229; 2.G.240.230; 2.G.240.231; 2.G.240.236; 2.G.240.237;
2.G.240.238; 2.G.240.239; 2.G.240.154; 2.G.240.157; 2.G.240.166;
2.G.240.169; 2.G.240.172; 2.G.240.175; 2.G.240.240; 2.G.240.244;
2.G.244.228; 2.G.244.229; 2.G.244.230; 2.G.244.231; 2.G.244.236;
2.G.244.237; 2.G.244.238; 2.G.244.239; 2.G.244.154; 2.G.244.157;
2.G.244.166; 2.G.244.169; 2.G.244.172; 2.G.244.175; 2.G.244.240;
2.G.244.244;

Prodrugs of 2.I

2.I.228.228; 2.I.228.229; 2.I.228.230; 2.I.228.231; 2.I.228.236; 2.I.228.237;
2.I.228.238; 2.I.228.239; 2.I.228.154; 2.I.228.157; 2.I.228.166; 2.I.228.169;
2.I.228.172; 2.I.228.175; 2.I.228.240; 2.I.228.244; 2.I.229.228; 2.I.229.229;
2.I.229.230; 2.I.229.231; 2.I.229.236; 2.I.229.237; 2.I.229.238; 2.I.229.239;
2.I.229.154; 2.I.229.157; 2.I.229.166; 2.I.229.169; 2.I.229.172; 2.I.229.175;
2.I.229.240; 2.I.229.244; 2.I.230.228; 2.I.230.229; 2.I.230.230; 2.I.230.231;
2.I.230.236; 2.I.230.237; 2.I.230.238; 2.I.230.239; 2.I.230.154; 2.I.230.157;
2.I.230.166; 2.I.230.169; 2.I.230.172; 2.I.230.175; 2.I.230.240; 2.I.230.244;
2.I.231.228; 2.I.231.229; 2.I.231.230; 2.I.231.231; 2.I.231.236; 2.I.231.237;
2.I.231.238; 2.I.231.239; 2.I.231.154; 2.I.231.157; 2.I.231.166; 2.I.231.169;
2.I.231.172; 2.I.231.175; 2.I.231.240; 2.I.231.244; 2.I.236.228; 2.I.236.229;
2.I.236.230; 2.I.236.231; 2.I.236.236; 2.I.236.237; 2.I.236.238; 2.I.236.239;
2.I.236.154; 2.I.236.157; 2.I.236.166; 2.I.236.169; 2.I.236.172; 2.I.236.175;
2.I.236.240; 2.I.236.244; 2.I.237.228; 2.I.237.229; 2.I.237.230; 2.I.237.231;
2.I.237.236; 2.I.237.237; 2.I.237.238; 2.I.237.239; 2.I.237.154; 2.I.237.157;
2.I.237.166; 2.I.237.169; 2.I.237.172; 2.I.237.175; 2.I.237.240; 2.I.237.244;
2.I.238.228; 2.I.238.229; 2.I.238.230; 2.I.238.231; 2.I.238.236; 2.I.238.237;
2.I.238.238; 2.I.238.239; 2.I.238.154; 2.I.238.157; 2.I.238.166; 2.I.238.169;
2.I.238.172; 2.I.238.175; 2.I.238.240; 2.I.238.244; 2.I.239.228; 2.I.239.229;
2.I.239.230; 2.I.239.231; 2.I.239.236; 2.I.239.237; 2.I.239.238; 2.I.239.239;
2.I.239.154; 2.I.239.157; 2.I.239.166; 2.I.239.169; 2.I.239.172; 2.I.239.175;
2.I.239.240; 2.I.239.244; 2.I.154.228; 2.I.154.229; 2.I.154.230; 2.I.154.231;
2.I.154.236; 2.I.154.237; 2.I.154.238; 2.I.154.239; 2.I.154.154; 2.I.154.157;

TABLE 100-continued

2.I.154.166; 2.I.154.169; 2.I.154.172; 2.I.154.175; 2.I.154.240; 2.I.154.244;
2.I.157.228; 2.I.157.229; 2.I.157.230; 2.I.157.231; 2.I.157.236; 2.I.157.237;
2.I.157.238; 2.I.157.239; 2.I.157.154; 2.I.157.157; 2.I.157.166; 2.I.157.169;
2.I.157.172; 2.I.157.175; 2.I.157.240; 2.I.157.244; 2.I.166.228; 2.I.166.229;
2.I.166.230; 2.I.166.231; 2.I.166.236; 2.I.166.237; 2.I.166.238; 2.I.166.239;
2.I.166.154; 2.I.166.157; 2.I.166.166; 2.I.166.169; 2.I.166.172; 2.I.166.175;
2.I.166.240; 2.I.166.244; 2.I.169.228; 2.I.169.229; 2.I.169.230; 2.I.169.231;
2.I.169.236; 2.I.169.237; 2.I.169.238; 2.I.169.239; 2.I.169.154; 2.I.169.157;
2.I.169.166; 2.I.169.169; 2.I.169.172; 2.I.169.175; 2.I.169.240; 2.I.169.244;
2.I.172.228; 2.I.172.229; 2.I.172.230; 2.I.172.231; 2.I.172.236; 2.I.172.237;
2.I.172.238; 2.I.172.239; 2.I.172.154; 2.I.172.157; 2.I.172.166; 2.I.172.169;
2.I.172.172; 2.I.172.175; 2.I.172.240; 2.I.172.244; 2.I.175.228; 2.I.175.229;
2.I.175.230; 2.I.175.231; 2.I.175.236; 2.I.175.237; 2.I.175.238; 2.I.175.239;
2.I.175.154; 2.I.175.157; 2.I.175.166; 2.I.175.169; 2.I.175.172; 2.I.175.175;
2.I.175.240; 2.I.175.244; 2.I.240.228; 2.I.240.229; 2.I.240.230; 2.I.240.231;
2.I.240.236; 2.I.240.237; 2.I.240.238; 2.I.240.239; 2.I.240.154; 2.I.240.157;
2.I.240.166; 2.I.240.169; 2.I.240.172; 2.I.240.175; 2.I.240.240; 2.I.240.244;
2.I.244.228; 2.I.244.229; 2.I.244.230; 2.I.244.231; 2.I.244.236; 2.I.244.237;
2.I.244.238; 2.I.244.239; 2.I.244.154; 2.I.244.157; 2.I.244.166; 2.I.244.169;
2.I.244.172; 2.I.244.175; 2.I.244.240; 2.I.244.244;
Prodrugs of 2.J 2.J.228.228; 2.J.228.229; 2.J.228.230; 2.J.228.231; 2.J.228.236; 2.J.228.237;
2.J.228.238; 2.J.228.239; 2.J.228.154; 2.J.228.157; 2.J.228.166; 2.J.228.169;
2.J.228.172; 2.J.228.175; 2.J.228.240; 2.J.228.244; 2.J.229.228; 2.J.229.229;
2.J.229.230; 2.J.229.231; 2.J.229.236; 2.J.229.237; 2.J.229.238; 2.J.229.239;
2.J.229.154; 2.J.229.157; 2.J.229.166; 2.J.229.169; 2.J.229.172; 2.J.229.175;
2.J.229.240; 2.J.229.244; 2.J.230.228; 2.J.230.229; 2.J.230.230; 2.J.230.231;
2.J.230.236; 2.J.230.237; 2.J.230.238; 2.J.230.239; 2.J.230.154; 2.J.230.157;
2.J.230.166; 2.J.230.169; 2.J.230.172; 2.J.230.175; 2.J.230.240; 2.J.230.244;
2.J.231.228; 2.J.231.229; 2.J.231.230; 2.J.231.231; 2.J.231.236; 2.J.231.237;
2.J.231.238; 2.J.231.239; 2.J.231.154; 2.J.231.157; 2.J.231.166; 2.J.231.169;
2.J.231.172; 2.J.231.175; 2.J.231.240; 2.J.231.244; 2.J.236.228; 2.J.236.229;
2.J.236.230; 2.J.236.231; 2.J.236.236; 2.J.236.237; 2.J.236.238; 2.J.236.239;
2.J.236.154; 2.J.236.157; 2.J.236.166; 2.J.236.169; 2.J.236.172; 2.J.236.175;
2.J.236.240; 2.J.236.244; 2.J.237.228; 2.J.237.229; 2.J.237.230; 2.J.237.231;
2.J.237.236; 2.J.237.237; 2.J.237.238; 2.J.237.239; 2.J.237.154; 2.J.237.157;
2.J.237.166; 2.J.237.169; 2.J.237.172; 2.J.237.175; 2.J.237.240; 2.J.237.244;
2.J.238.228; 2.J.238.229; 2.J.238.230; 2.J.238.231; 2.J.238.236; 2.J.238.237;
2.J.238.238; 2.J.238.239; 2.J.238.154; 2.J.238.157; 2.J.238.166; 2.J.238.169;
2.J.238.172; 2.J.238.175; 2.J.238.240; 2.J.238.244; 2.J.239.228; 2.J.239.229;
2.J.239.230; 2.J.239.231; 2.J.239.236; 2.J.239.237; 2.J.239.238; 2.J.239.239;
2.J.239.154; 2.J.239.157; 2.J.239.166; 2.J.239.169; 2.J.239.172; 2.J.239.175;
2.J.239.240; 2.J.239.244; 2.J.154.228; 2.J.154.229; 2.J.154.230; 2.J.154.231;
2.J.154.236; 2.J.154.237; 2.J.154.238; 2.J.154.239; 2.J.154.154; 2.J.154.157;
2.J.154.166; 2.J.154.169; 2.J.154.172; 2.J.154.175; 2.J.154.240; 2.J.154.244;
2.J.157.228; 2.J.157.229; 2.J.157.230; 2.J.157.231; 2.J.157.236; 2.J.157.237;
2.J.157.238; 2.J.157.239; 2.J.157.154; 2.J.157.157; 2.J.157.166; 2.J.157.169;
2.J.157.172; 2.J.157.175; 2.J.157.240; 2.J.157.244; 2.J.166.228; 2.J.166.229;
2.J.166.230; 2.J.166.231; 2.J.166.236; 2.J.166.237; 2.J.166.238; 2.J.166.239;
2.J.166.154; 2.J.166.157; 2.J.166.166; 2.J.166.169; 2.J.166.172; 2.J.166.175;
2.J.166.240; 2.J.166.244; 2.J.169.228; 2.J.169.229; 2.J.169.230; 2.J.169.231;
2.J.169.236; 2.J.169.237; 2.J.169.238; 2.J.169.239; 2.J.169.154; 2.J.169.157;
2.J.169.166; 2.J.169.169; 2.J.169.172; 2.J.169.175; 2.J.169.240; 2.J.169.244;
2.J.172.228; 2.J.172.229; 2.J.172.230; 2.J.172.231; 2.J.172.236; 2.J.172.237;
2.J.172.238; 2.J.172.239; 2.J.172.154; 2.J.172.157; 2.J.172.166; 2.J.172.169;
2.J.172.172; 2.J.172.175; 2.J.172.240; 2.J.172.244; 2.J.175.228; 2.J.175.229;
2.J.175.230; 2.J.175.231; 2.J.175.236; 2.J.175.237; 2.J.175.238; 2.J.175.239;
2.J.175.154; 2.J.175.157; 2.J.175.166; 2.J.175.169; 2.J.175.172; 2.J.175.175;
2.J.175.240; 2.J.175.244; 2.J.240.228; 2.J.240.229; 2.J.240.230; 2.J.240.231;
2.J.240.236; 2.J.240.237; 2.J.240.238; 2.J.240.239; 2.J.240.154; 2.J.240.157;
2.J.240.166; 2.J.240.169; 2.J.240.172; 2.J.240.175; 2.J.240.240; 2.J.240.244;
2.J.244.228; 2.J.244.229; 2.J.244.230; 2.J.244.231; 2.J.244.236; 2.J.244.237;
2.J.244.238; 2.J.244.239; 2.J.244.154; 2.J.244.157; 2.J.244.166; 2.J.244.169;
2.J.244.172; 2.J.244.175; 2.J.244.240; 2.J.244.244;
Prodrugs of 2.L 2.L.228.228; 2.L.228.229; 2.L.228.230; 2.L.228.231; 2.L.228.236;
2.L.228.237; 2.L.228.238; 2.L.228.239; 2.L.228.154; 2.L.228.157; 2.L.228.166;
2.L.228.169; 2.L.228.172; 2.L.228.175; 2.L.228.240; 2.L.228.244; 2.L.229.228;
2.L.229.229; 2.L.229.230; 2.L.229.231; 2.L.229.236; 2.L.229.237; 2.L.229.238;
2.L.229.239; 2.L.229.154; 2.L.229.157; 2.L.229.166; 2.L.229.169; 2.L.229.172;
2.L.229.175; 2.L.229.240; 2.L.229.244; 2.L.230.228; 2.L.230.229; 2.L.230.230;
2.L.230.231; 2.L.230.236; 2.L.230.237; 2.L.230.238; 2.L.230.239; 2.L.230.154;
2.L.230.157; 2.L.230.166; 2.L.230.169; 2.L.230.172; 2.L.230.175; 2.L.230.240;
2.L.230.244; 2.L.231.228; 2.L.231.229; 2.L.231.230; 2.L.231.231; 2.L.231.236;
2.L.231.237; 2.L.231.238; 2.L.231.239; 2.L.231.154; 2.L.231.157; 2.L.231.166;
2.L.231.169; 2.L.231.172; 2.L.231.175; 2.L.231.240; 2.L.231.244; 2.L.236.228;
2.L.236.229; 2.L.236.230; 2.L.236.231; 2.L.236.236; 2.L.236.237; 2.L.236.238;

TABLE 100-continued

2.L.236.239; 2.L.236.154; 2.L.236.157; 2.L.236.166; 2.L.236.169; 2.L.236.172; 2.L.236.175; 2.L.236.240; 2.L.236.244; 2.L.237.228; 2.L.237.229; 2.L.237.230; 2.L.237.231; 2.L.237.236; 2.L.237.237; 2.L.237.238; 2.L.237.239; 2.L.237.154; 2.L.237.157; 2.L.237.166; 2.L.237.169; 2.L.237.172; 2.L.237.175; 2.L.237.240; 2.L.237.244; 2.L.238.228; 2.L.238.229; 2.L.238.230; 2.L.238.231; 2.L.238.236; 2.L.238.237; 2.L.238.238; 2.L.238.239; 2.L.238.154; 2.L.238.157; 2.L.238.166; 2.L.238.169; 2.L.238.172; 2.L.238.175; 2.L.238.240; 2.L.238.244; 2.L.239.228; 2.L.239.229; 2.L.239.230; 2.L.239.231; 2.L.239.236; 2.L.239.237; 2.L.239.238; 2.L.239.239; 2.L.239.154; 2.L.239.157; 2.L.239.166; 2.L.239.169; 2.L.239.172; 2.L.239.175; 2.L.239.240; 2.L.239.244; 2.L.154.228; 2.L.154.229; 2.L.154.230; 2.L.154.231; 2.L.154.236; 2.L.154.237; 2.L.154.238; 2.L.154.239; 2.L.154.154; 2.L.154.157; 2.L.154.166; 2.L.154.169; 2.L.154.172; 2.L.154.175; 2.L.154.240; 2.L.154.244; 2.L.157.228; 2.L.157.229; 2.L.157.230; 2.L.157.231; 2.L.157.236; 2.L.157.237; 2.L.157.238; 2.L.157.239; 2.L.157.154; 2.L.157.157; 2.L.157.166; 2.L.157.169; 2.L.157.172; 2.L.157.175; 2.L.157.240; 2.L.157.244; 2.L.166.228; 2.L.166.229; 2.L.166.230; 2.L.166.231; 2.L.166.236; 2.L.166.237; 2.L.166.238; 2.L.166.239; 2.L.166.154; 2.L.166.157; 2.L.166.166; 2.L.166.169; 2.L.166.172; 2.L.166.175; 2.L.166.240; 2.L.166.244; 2.L.169.228; 2.L.169.229; 2.L.169.230; 2.L.169.231; 2.L.169.236; 2.L.169.237; 2.L.169.238; 2.L.169.239; 2.L.169.154; 2.L.169.157; 2.L.169.166; 2.L.169.169; 2.L.169.172; 2.L.169.175; 2.L.169.240; 2.L.169.244; 2.L.172.228; 2.L.172.229; 2.L.172.230; 2.L.172.231; 2.L.172.236; 2.L.172.237; 2.L.172.238; 2.L.172.239; 2.L.172.154; 2.L.172.157; 2.L.172.166; 2.L.172.169; 2.L.172.172; 2.L.172.175; 2.L.172.240; 2.L.172.244; 2.L.175.228; 2.L.175.229; 2.L.175.230; 2.L.175.231; 2.L.175.236; 2.L.175.237; 2.L.175.238; 2.L.175.239; 2.L.175.154; 2.L.175.157; 2.L.175.166; 2.L.175.169; 2.L.175.172; 2.L.175.175; 2.L.175.240; 2.L.175.244; 2.L.240.228; 2.L.240.229; 2.L.240.230; 2.L.240.231; 2.L.240.236; 2.L.240.237; 2.L.240.238; 2.L.240.239; 2.L.240.154; 2.L.240.157; 2.L.240.166; 2.L.240.169; 2.L.240.172; 2.L.240.175; 2.L.240.240; 2.L.240.244; 2.L.244.228; 2.L.244.229; 2.L.244.230; 2.L.244.231; 2.L.244.236; 2.L.244.237; 2.L.244.238; 2.L.244.239; 2.L.244.154; 2.L.244.157; 2.L.244.166; 2.L.244.169; 2.L.244.172; 2.L.244.175; 2.L.244.240; 2.L.244.244;

Prodrugs of 2.O

2.O.228.228; 2.O.228.229; 2.O.228.230; 2.O.228.231; 2.O.228.236; 2.O.228.237; 2.O.228.238; 2.O.228.239; 2.O.228.154; 2.O.228.157; 2.O.228.166; 2.O.228.169; 2.O.228.172; 2.O.228.175; 2.O.228.240; 2.O.228.244; 2.O.229.228; 2.O.229.229; 2.O.229.230; 2.O.229.231; 2.O.229.236; 2.O.229.237; 2.O.229.238; 2.O.229.239; 2.O.229.154; 2.O.229.157; 2.O.229.166; 2.O.229.169; 2.O.229.172; 2.O.229.175; 2.O.229.240; 2.O.229.244; 2.O.230.228; 2.O.230.229; 2.O.230.230; 2.O.230.231; 2.O.230.236; 2.O.230.237; 2.O.230.238; 2.O.230.239; 2.O.230.154; 2.O.230.157; 2.O.230.166; 2.O.230.169; 2.O.230.172; 2.O.230.175; 2.O.230.240; 2.O.230.244; 2.O.231.228; 2.O.231.229; 2.O.231.230; 2.O.231.231; 2.O.231.236; 2.O.231.237; 2.O.231.238; 2.O.231.239; 2.O.231.154; 2.O.231.157; 2.O.231.166; 2.O.231.169; 2.O.231.172; 2.O.231.175; 2.O.231.240; 2.O.231.244; 2.O.236.228; 2.O.236.229; 2.O.236.230; 2.O.236.231; 2.O.236.236; 2.O.236.237; 2.O.236.238; 2.O.236.239; 2.O.236.154; 2.O.236.157; 2.O.236.166; 2.O.236.169; 2.O.236.172; 2.O.236.175; 2.O.236.240; 2.O.236.244; 2.O.237.228; 2.O.237.229; 2.O.237.230; 2.O.237.231; 2.O.237.236; 2.O.237.237; 2.O.237.238; 2.O.237.239; 2.O.237.154; 2.O.237.157; 2.O.237.166; 2.O.237.169; 2.O.237.172; 2.O.237.175; 2.O.237.240; 2.O.237.244; 2.O.238.228; 2.O.238.229; 2.O.238.230; 2.O.238.231; 2.O.238.236; 2.O.238.237; 2.O.238.238; 2.O.238.239; 2.O.238.154; 2.O.238.157; 2.O.238.166; 2.O.238.169; 2.O.238.172; 2.O.238.175; 2.O.238.240; 2.O.238.244; 2.O.239.228; 2.O.239.229; 2.O.239.230; 2.O.239.231; 2.O.239.236; 2.O.239.237; 2.O.239.238; 2.O.239.239; 2.O.239.154; 2.O.239.157; 2.O.239.166; 2.O.239.169; 2.O.239.172; 2.O.239.175; 2.O.239.240; 2.O.239.244; 2.O.154.228; 2.O.154.229; 2.O.154.230; 2.O.154.231; 2.O.154.236; 2.O.154.237; 2.O.154.238; 2.O.154.239; 2.O.154.154; 2.O.154.157; 2.O.154.166; 2.O.154.169; 2.O.154.172; 2.O.154.175; 2.O.154.240; 2.O.154.244; 2.O.157.228; 2.O.157.229; 2.O.157.230; 2.O.157.231; 2.O.157.236; 2.O.157.237; 2.O.157.238; 2.O.157.239; 2.O.157.154; 2.O.157.157; 2.O.157.166; 2.O.157.169; 2.O.157.172; 2.O.157.175; 2.O.157.240; 2.O.157.244; 2.O.166.228; 2.O.166.229; 2.O.166.230; 2.O.166.231; 2.O.166.236; 2.O.166.237; 2.O.166.238; 2.O.166.239; 2.O.166.154; 2.O.166.157; 2.O.166.166; 2.O.166.169; 2.O.166.172; 2.O.166.175; 2.O.166.240; 2.O.166.244; 2.O.169.228; 2.O.169.229; 2.O.169.230; 2.O.169.231; 2.O.169.236; 2.O.169.237; 2.O.169.238; 2.O.169.239; 2.O.169.154; 2.O.169.157; 2.O.169.166; 2.O.169.169; 2.O.169.172; 2.O.169.175; 2.O.169.240; 2.O.169.244; 2.O.172.228; 2.O.172.229; 2.O.172.230; 2.O.172.231; 2.O.172.236; 2.O.172.237; 2.O.172.238; 2.O.172.239; 2.O.172.154; 2.O.172.157; 2.O.172.166; 2.O.172.169; 2.O.172.172; 2.O.172.175; 2.O.172.240; 2.O.172.244; 2.O.175.228; 2.O.175.229; 2.O.175.230; 2.O.175.231; 2.O.175.236; 2.O.175.237; 2.O.175.238; 2.O.175.239; 2.O.175.154; 2.O.175.157; 2.O.175.166; 2.O.175.169; 2.O.175.172; 2.O.175.175; 2.O.175.240; 2.O.175.244; 2.O.240.228; 2.O.240.229; 2.O.240.230; 2.O.240.231; 2.O.240.236; 2.O.240.237;

TABLE 100-continued

2.O.240.238; 2.O.240.239; 2.O.240.154; 2.O.240.157; 2.O.240.166;
2.O.240.169; 2.O.240.172; 2.O.240.175; 2.O.240.240; 2.O.240.244;
2.O.244.228; 2.O.244.229; 2.O.244.230; 2.O.244.231; 2.O.244.236;
2.O.244.237; 2.O.244.238; 2.O.244.239; 2.O.244.154; 2.O.244.157;
2.O.244.166; 2.O.244.169; 2.O.244.172; 2.O.244.175; 2.O.244.240;
2.O.244.244;

Prodrugs of 2.P

2.P.228.228; 2.P.228.229; 2.P.228.230; 2.P.228.231; 2.P.228.236;
2.P.228.237; 2.P.228.238; 2.P.228.239; 2.P.228.154; 2.P.228.157; 2.P.228.166;
2.P.228.169; 2.P.228.172; 2.P.228.175; 2.P.228.240; 2.P.228.244; 2.P.229.228;
2.P.229.229; 2.P.229.230; 2.P.229.231; 2.P.229.236; 2.P.229.237; 2.P.229.238;
2.P.229.239; 2.P.229.154; 2.P.229.157; 2.P.229.166; 2.P.229.169; 2.P.229.172;
2.P.229.175; 2.P.229.240; 2.P.229.244; 2.P.230.228; 2.P.230.229; 2.P.230.230;
2.P.230.231; 2.P.230.236; 2.P.230.237; 2.P.230.238; 2.P.230.239; 2.P.230.154;
2.P.230.157; 2.P.230.166; 2.P.230.169; 2.P.230.172; 2.P.230.175; 2.P.230.240;
2.P.230.244; 2.P.231.228; 2.P.231.229; 2.P.231.230; 2.P.231.231; 2.P.231.236;
2.P.231.237; 2.P.231.238; 2.P.231.239; 2.P.231.154; 2.P.231.157; 2.P.231.166;
2.P.231.169; 2.P.231.172; 2.P.231.175; 2.P.231.240; 2.P.231.244; 2.P.236.228;
2.P.236.229; 2.P.236.230; 2.P.236.231; 2.P.236.236; 2.P.236.237; 2.P.236.238;
2.P.236.239; 2.P.236.154; 2.P.236.157; 2.P.236.166; 2.P.236.169; 2.P.236.172;
2.P.236.175; 2.P.236.240; 2.P.236.244; 2.P.237.228; 2.P.237.229; 2.P.237.230;
2.P.237.231; 2.P.237.236; 2.P.237.237; 2.P.237.238; 2.P.237.239; 2.P.237.154;
2.P.237.157; 2.P.237.166; 2.P.237.169; 2.P.237.172; 2.P.237.175; 2.P.237.240;
2.P.237.244; 2.P.238.228; 2.P.238.229; 2.P.238.230; 2.P.238.231; 2.P.238.236;
2.P.238.237; 2.P.238.238; 2.P.238.239; 2.P.238.154; 2.P.238.157; 2.P.238.166;
2.P.238.169; 2.P.238.172; 2.P.238.175; 2.P.238.240; 2.P.238.244; 2.P.239.228;
2.P.239.229; 2.P.239.230; 2.P.239.231; 2.P.239.236; 2.P.239.237; 2.P.239.238;
2.P.239.239; 2.P.239.154; 2.P.239.157; 2.P.239.166; 2.P.239.169; 2.P.239.172;
2.P.239.175; 2.P.239.240; 2.P.239.244; 2.P.154.228; 2.P.154.229; 2.P.154.230;
2.P.154.231; 2.P.154.236; 2.P.154.237; 2.P.154.238; 2.P.154.239; 2.P.154.154;
2.P.154.157; 2.P.154.166; 2.P.154.169; 2.P.154.172; 2.P.154.175; 2.P.154.240;
2.P.154.244; 2.P.157.228; 2.P.157.229; 2.P.157.230; 2.P.157.231; 2.P.157.236;
2.P.157.237; 2.P.157.238; 2.P.157.239; 2.P.157.154; 2.P.157.157; 2.P.157.166;
2.P.157.169; 2.P.157.172; 2.P.157.175; 2.P.157.240; 2.P.157.244; 2.P.166.228;
2.P.166.229; 2.P.166.230; 2.P.166.231; 2.P.166.236; 2.P.166.237; 2.P.166.238;
2.P.166.239; 2.P.166.154; 2.P.166.157; 2.P.166.166; 2.P.166.169; 2.P.166.172;
2.P.166.175; 2.P.166.240; 2.P.166.244; 2.P.169.228; 2.P.169.229; 2.P.169.230;
2.P.169.231; 2.P.169.236; 2.P.169.237; 2.P.169.238; 2.P.169.239; 2.P.169.154;
2.P.169.157; 2.P.169.166; 2.P.169.169; 2.P.169.172; 2.P.169.175; 2.P.169.240;
2.P.169.244; 2.P.172.228; 2.P.172.229; 2.P.172.230; 2.P.172.231; 2.P.172.236;
2.P.172.237; 2.P.172.238; 2.P.172.239; 2.P.172.154; 2.P.172.157; 2.P.172.166;
2.P.172.169; 2.P.172.172; 2.P.172.175; 2.P.172.240; 2.P.172.244; 2.P.175.228;
2.P.175.229; 2.P.175.230; 2.P.175.231; 2.P.175.236; 2.P.175.237; 2.P.175.238;
2.P.175.239; 2.P.175.154; 2.P.175.157; 2.P.175.166; 2.P.175.169; 2.P.175.172;
2.P.175.175; 2.P.175.240; 2.P.175.244; 2.P.240.228; 2.P.240.229; 2.P.240.230;
2.P.240.231; 2.P.240.236; 2.P.240.237; 2.P.240.238; 2.P.240.239; 2.P.240.154;
2.P.240.157; 2.P.240.166; 2.P.240.169; 2.P.240.172; 2.P.240.175; 2.P.240.240;
2.P.240.244; 2.P.244.228; 2.P.244.229; 2.P.244.230; 2.P.244.231; 2.P.244.236;
2.P.244.237; 2.P.244.238; 2.P.244.239; 2.P.244.154; 2.P.244.157; 2.P.244.166;
2.P.244.169; 2.P.244.172; 2.P.244.175; 2.P.244.240; 2.P.244.244;

Prodrugs of 2.U

2.U.228.228; 2.U.228.229; 2.U.228.230; 2.U.228.231; 2.U.228.236;
2.U.228.237; 2.U.228.238; 2.U.228.239; 2.U.228.154; 2.U.228.157;
2.U.228.166; 2.U.228.169; 2.U.228.172; 2.U.228.175; 2.U.228.240;
2.U.228.244; 2.U.229.228; 2.U.229.229; 2.U.229.230; 2.U.229.231;
2.U.229.236; 2.U.229.237; 2.U.229.238; 2.U.229.239; 2.U.229.154;
2.U.229.157; 2.U.229.166; 2.U.229.169; 2.U.229.172; 2.U.229.175;
2.U.229.240; 2.U.229.244; 2.U.230.228; 2.U.230.229; 2.U.230.230;
2.U.230.231; 2.U.230.236; 2.U.230.237; 2.U.230.238; 2.U.230.239;
2.U.230.154; 2.U.230.157; 2.U.230.166; 2.U.230.169; 2.U.230.172;
2.U.230.175; 2.U.230.240; 2.U.230.244; 2.U.231.228; 2.U.231.229;
2.U.231.230; 2.U.231.231; 2.U.231.236; 2.U.231.237; 2.U.231.238;
2.U.231.239; 2.U.231.154; 2.U.231.157; 2.U.231.166; 2.U.231.169;
2.U.231.172; 2.U.231.175; 2.U.231.240; 2.U.231.244; 2.U.236.228;
2.U.236.229; 2.U.236.230; 2.U.236.231; 2.U.236.236; 2.U.236.237;
2.U.236.238; 2.U.236.239; 2.U.236.154; 2.U.236.157; 2.U.236.166;
2.U.236.169; 2.U.236.172; 2.U.236.175; 2.U.236.240; 2.U.236.244;
2.U.237.228; 2.U.237.229; 2.U.237.230; 2.U.237.231; 2.U.237.236;
2.U.237.237; 2.U.237.238; 2.U.237.239; 2.U.237.154; 2.U.237.157;
2.U.237.166; 2.U.237.169; 2.U.237.172; 2.U.237.175; 2.U.237.240;
2.U.237.244; 2.U.238.228; 2.U.238.229; 2.U.238.230; 2.U.238.231;
2.U.238.236; 2.U.238.237; 2.U.238.238; 2.U.238.239; 2.U.238.154;
2.U.238.157; 2.U.238.166; 2.U.238.169; 2.U.238.172; 2.U.238.175;
2.U.238.240; 2.U.238.244; 2.U.239.228; 2.U.239.229; 2.U.239.230;
2.U.239.231; 2.U.239.236; 2.U.239.237; 2.U.239.238; 2.U.239.239;
2.U.239.154; 2.U.239.157; 2.U.239.166; 2.U.239.169; 2.U.239.172;
2.U.239.175; 2.U.239.240; 2.U.239.244; 2.U.154.228; 2.U.154.229;

TABLE 100-continued

2.U.154.230; 2.U.154.231; 2.U.154.236; 2.U.154.237; 2.U.154.238;
2.U.154.239; 2.U.154.154; 2.U.154.157; 2.U.154.166; 2.U.154.169;
2.U.154.172; 2.U.154.175; 2.U.154.240; 2.U.154.244; 2.U.157.228;
2.U.157.229; 2.U.157.230; 2.U.157.231; 2.U.157.236; 2.U.157.237;
2.U.157.238; 2.U.157.239; 2.U.157.154; 2.U.157.157; 2.U.157.166;
2.U.157.169; 2.U.157.172; 2.U.157.175; 2.U.157.240; 2.U.157.244;
2.U.166.228; 2.U.166.229; 2.U.166.230; 2.U.166.231; 2.U.166.236;
2.U.166.237; 2.U.166.238; 2.U.166.239; 2.U.166.154; 2.U.166.157;
2.U.166.166; 2.U.166.169; 2.U.166.172; 2.U.166.175; 2.U.166.240;
2.U.166.244; 2.U.169.228; 2.U.169.229; 2.U.169.230; 2.U.169.231;
2.U.169.236; 2.U.169.237; 2.U.169.238; 2.U.169.239; 2.U.169.154;
2.U.169.157; 2.U.169.166; 2.U.169.169; 2.U.169.172; 2.U.169.175;
2.U.169.240; 2.U.169.244; 2.U.172.228; 2.U.172.229; 2.U.172.230;
2.U.172.231; 2.U.172.236; 2.U.172.237; 2.U.172.238; 2.U.172.239;
2.U.172.154; 2.U.172.157; 2.U.172.166; 2.U.172.169; 2.U.172.172;
2.U.172.175; 2.U.172.240; 2.U.172.244; 2.U.175.228; 2.U.175.229;
2.U.175.230; 2.U.175.231; 2.U.175.236; 2.U.175.237; 2.U.175.238;
2.U.175.239; 2.U.175.154; 2.U.175.157; 2.U.175.166; 2.U.175.169;
2.U.175.172; 2.U.175.175; 2.U.175.240; 2.U.175.244; 2.U.240.228;
2.U.240.229; 2.U.240.230; 2.U.240.231; 2.U.240.236; 2.U.240.237;
2.U.240.238; 2.U.240.239; 2.U.240.154; 2.U.240.157; 2.U.240.166;
2.U.240.169; 2.U.240.172; 2.U.240.175; 2.U.240.240; 2.U.240.244;
2.U.244.228; 2.U.244.229; 2.U.244.230; 2.U.244.231; 2.U.244.236;
2.U.244.237; 2.U.244.238; 2.U.244.239; 2.U.244.154; 2.U.244.157;
2.U.244.166; 2.U.244.169; 2.U.244.172; 2.U.244.175; 2.U.244.240;
2.U.244.244;
Prodrugs of 2.W 2.W.228.228; 2.W.228.229; 2.W.228.230; 2.W.228.231; 2.W.228.236;
2.W.228.237; 2.W.228.238; 2.W.228.239; 2.W.228.154; 2.W.228.157;
2.W.228.166; 2.W.228.169; 2.W.228.172; 2.W.228.175; 2.W.228.240;
2.W.228.244; 2.W.229.228; 2.W.229.229; 2.W.229.230; 2.W.229.231;
2.W.229.236; 2.W.229.237; 2.W.229.238; 2.W.229.239; 2.W.229.154;
2.W.229.157; 2.W.229.166; 2.W.229.169; 2.W.229.172; 2.W.229.175;
2.W.229.240; 2.W.229.244; 2.W.230.228; 2.W.230.229; 2.W.230.230;
2.W.230.231; 2.W.230.236; 2.W.230.237; 2.W.230.238; 2.W.230.239;
2.W.230.154; 2.W.230.157; 2.W.230.166; 2.W.230.169; 2.W.230.172;
2.W.230.175; 2.W.230.240; 2.W.230.244; 2.W.231.228; 2.W.231.229;
2.W.231.230; 2.W.231.231; 2.W.231.236; 2.W.231.237; 2.W.231.238;
2.W.231.239; 2.W.231.154; 2.W.231.157; 2.W.231.166; 2.W.231.169;
2.W.231.172; 2.W.231.175; 2.W.231.240; 2.W.231.244; 2.W.236.228;
2.W.236.229; 2.W.236.230; 2.W.236.231; 2.W.236.236; 2.W.236.237;
2.W.236.238; 2.W.236.239; 2.W.236.154; 2.W.236.157; 2.W.236.166;
2.W.236.169; 2.W.236.172; 2.W.236.175; 2.W.236.240; 2.W.236.244;
2.W.237.228; 2.W.237.229; 2.W.237.230; 2.W.237.231; 2.W.237.236;
2.W.237.237; 2.W.237.238; 2.W.237.239; 2.W.237.154; 2.W.237.157;
2.W.237.166; 2.W.237.169; 2.W.237.172; 2.W.237.175; 2.W.237.240;
2.W.237.244; 2.W.238.228; 2.W.238.229; 2.W.238.230; 2.W.238.231;
2.W.238.236; 2.W.238.237; 2.W.238.238; 2.W.238.239; 2.W.238.154;
2.W.238.157; 2.W.238.166; 2.W.238.169; 2.W.238.172; 2.W.238.175;
2.W.238.240; 2.W.238.244; 2.W.239.228; 2.W.239.229; 2.W.239.230;
2.W.239.231; 2.W.239.236; 2.W.239.237; 2.W.239.238; 2.W.239.239;
2.W.239.154; 2.W.239.157; 2.W.239.166; 2.W.239.169; 2.W.239.172;
2.W.239.175; 2.W.239.240; 2.W.239.244; 2.W.154.228; 2.W.154.229;
2.W.154.230; 2.W.154.231; 2.W.154.236; 2.W.154.237; 2.W.154.238;
2.W.154.239; 2.W.154.154; 2.W.154.157; 2.W.154.166; 2.W.154.169;
2.W.154.172; 2.W.154.175; 2.W.154.240; 2.W.154.244; 2.W.157.228;
2.W.157.229; 2.W.157.230; 2.W.157.231; 2.W.157.236; 2.W.157.237;
2.W.157.238; 2.W.157.239; 2.W.157.154; 2.W.157.157; 2.W.157.166;
2.W.157.169; 2.W.157.172; 2.W.157.175; 2.W.157.240; 2.W.157.244;
2.W.166.228; 2.W.166.229; 2.W.166.230; 2.W.166.231; 2.W.166.236;
2.W.166.237; 2.W.166.238; 2.W.166.239; 2.W.166.154; 2.W.166.157;
2.W.166.166; 2.W.166.169; 2.W.166.172; 2.W.166.175; 2.W.166.240;
2.W.166.244; 2.W.169.228; 2.W.169.229; 2.W.169.230; 2.W.169.231;
2.W.169.236; 2.W.169.237; 2.W.169.238; 2.W.169.239; 2.W.169.154;
2.W.169.157; 2.W.169.166; 2.W.169.169; 2.W.169.172; 2.W.169.175;
2.W.169.240; 2.W.169.244; 2.W.172.228; 2.W.172.229; 2.W.172.230;
2.W.172.231; 2.W.172.236; 2.W.172.237; 2.W.172.238; 2.W.172.239;
2.W.172.154; 2.W.172.157; 2.W.172.166; 2.W.172.169; 2.W.172.172;
2.W.172.175; 2.W.172.240; 2.W.172.244; 2.W.175.228; 2.W.175.229;
2.W.175.230; 2.W.175.231; 2.W.175.236; 2.W.175.237; 2.W.175.238;
2.W.175.239; 2.W.175.154; 2.W.175.157; 2.W.175.166; 2.W.175.169;
2.W.175.172; 2.W.175.175; 2.W.175.240; 2.W.175.244; 2.W.240.228;
2.W.240.229; 2.W.240.230; 2.W.240.231; 2.W.240.236; 2.W.240.237;
2.W.240.238; 2.W.240.239; 2.W.240.154; 2.W.240.157; 2.W.240.166;
2.W.240.169; 2.W.240.172; 2.W.240.175; 2.W.240.240; 2.W.240.244;
2.W.244.228; 2.W.244.229; 2.W.244.230; 2.W.244.231; 2.W.244.236;
2.W.244.237; 2.W.244.238; 2.W.244.239; 2.W.244.154; 2.W.244.157;

TABLE 100-continued

2.W.244.166; 2.W.244.169; 2.W.244.172; 2.W.244.175; 2.W.244.240;
2.W.244.244;
Prodrugs of 2.Y 2.Y.228.228; 2.Y.228.229; 2.Y.228.230; 2.Y.228.231; 2.Y.228.236;
2.Y.228.237; 2.Y.228.238; 2.Y.228.239; 2.Y.228.154; 2.Y.228.157; 2.Y.228.166;
2.Y.228.169; 2.Y.228.172; 2.Y.228.175; 2.Y.228.240; 2.Y.228.244; 2.Y.229.228;
2.Y.229.229; 2.Y.229.230; 2.Y.229.231; 2.Y.229.236; 2.Y.229.237; 2.Y.229.238;
2.Y.229.239; 2.Y.229.154; 2.Y.229.157; 2.Y.229.166; 2.Y.229.169; 2.Y.229.172;
2.Y.229.175; 2.Y.229.240; 2.Y.229.244; 2.Y.230.228; 2.Y.230.229; 2.Y.230.230;
2.Y.230.231; 2.Y.230.236; 2.Y.230.237; 2.Y.230.238; 2.Y.230.239; 2.Y.230.154;
2.Y.230.157; 2.Y.230.166; 2.Y.230.169; 2.Y.230.172; 2.Y.230.175; 2.Y.230.240;
2.Y.230.244; 2.Y.231.228; 2.Y.231.229; 2.Y.231.230; 2.Y.231.231; 2.Y.231.236;
2.Y.231.237; 2.Y.231.238; 2.Y.231.239; 2.Y.231.154; 2.Y.231.157; 2.Y.231.166;
2.Y.231.169; 2.Y.231.172; 2.Y.231.175; 2.Y.231.240; 2.Y.231.244; 2.Y.236.228;
2.Y.236.229; 2.Y.236.230; 2.Y.236.231; 2.Y.236.236; 2.Y.236.237; 2.Y.236.238;
2.Y.236.239; 2.Y.236.154; 2.Y.236.157; 2.Y.236.166; 2.Y.236.169; 2.Y.236.172;
2.Y.236.175; 2.Y.236.240; 2.Y.236.244; 2.Y.237.228; 2.Y.237.229; 2.Y.237.230;
2.Y.237.231; 2.Y.237.236; 2.Y.237.237; 2.Y.237.238; 2.Y.237.239; 2.Y.237.154;
2.Y.237.157; 2.Y.237.166; 2.Y.237.169; 2.Y.237.172; 2.Y.237.175; 2.Y.237.240;
2.Y.237.244; 2.Y.238.228; 2.Y.238.229; 2.Y.238.230; 2.Y.238.231; 2.Y.238.236;
2.Y.238.237; 2.Y.238.238; 2.Y.238.239; 2.Y.238.154; 2.Y.238.157; 2.Y.238.166;
2.Y.238.169; 2.Y.238.172; 2.Y.238.175; 2.Y.238.240; 2.Y.238.244; 2.Y.239.228;
2.Y.239.229; 2.Y.239.230; 2.Y.239.231; 2.Y.239.236; 2.Y.239.237; 2.Y.239.238;
2.Y.239.239; 2.Y.239.154; 2.Y.239.157; 2.Y.239.166; 2.Y.239.169; 2.Y.239.172;
2.Y.239.175; 2.Y.239.240; 2.Y.239.244; 2.Y.154.228; 2.Y.154.229; 2.Y.154.230;
2.Y.154.231; 2.Y.154.236; 2.Y.154.237; 2.Y.154.238; 2.Y.154.239; 2.Y.154.154;
2.Y.154.157; 2.Y.154.166; 2.Y.154.169; 2.Y.154.172; 2.Y.154.175; 2.Y.154.240;
2.Y.154.244; 2.Y.157.228; 2.Y.157.229; 2.Y.157.230; 2.Y.157.231; 2.Y.157.236;
2.Y.157.237; 2.Y.157.238; 2.Y.157.239; 2.Y.157.154; 2.Y.157.157; 2.Y.157.166;
2.Y.157.169; 2.Y.157.172; 2.Y.157.175; 2.Y.157.240; 2.Y.157.244; 2.Y.166.228;
2.Y.166.229; 2.Y.166.230; 2.Y.166.231; 2.Y.166.236; 2.Y.166.237; 2.Y.166.238;
2.Y.166.239; 2.Y.166.154; 2.Y.166.157; 2.Y.166.166; 2.Y.166.169; 2.Y.166.172;
2.Y.166.175; 2.Y.166.240; 2.Y.166.244; 2.Y.169.228; 2.Y.169.229; 2.Y.169.230;
2.Y.169.231; 2.Y.169.236; 2.Y.169.237; 2.Y.169.238; 2.Y.169.239; 2.Y.169.154;
2.Y.169.157; 2.Y.169.166; 2.Y.169.169; 2.Y.169.172; 2.Y.169.175; 2.Y.169.240;
2.Y.169.244; 2.Y.172.228; 2.Y.172.229; 2.Y.172.230; 2.Y.172.231; 2.Y.172.236;
2.Y.172.237; 2.Y.172.238; 2.Y.172.239; 2.Y.172.154; 2.Y.172.157; 2.Y.172.166;
2.Y.172.169; 2.Y.172.172; 2.Y.172.175; 2.Y.172.240; 2.Y.172.244; 2.Y.175.228;
2.Y.175.229; 2.Y.175.230; 2.Y.175.231; 2.Y.175.236; 2.Y.175.237; 2.Y.175.238;
2.Y.175.239; 2.Y.175.154; 2.Y.175.157; 2.Y.175.166; 2.Y.175.169; 2.Y.175.172;
2.Y.175.175; 2.Y.175.240; 2.Y.175.244; 2.Y.240.228; 2.Y.240.229; 2.Y.240.230;
2.Y.240.231; 2.Y.240.236; 2.Y.240.237; 2.Y.240.238; 2.Y.240.239; 2.Y.240.154;
2.Y.240.157; 2.Y.240.166; 2.Y.240.169; 2.Y.240.172; 2.Y.240.175; 2.Y.240.240;
2.Y.240.244; 2.Y.244.228; 2.Y.244.229; 2.Y.244.230; 2.Y.244.231; 2.Y.244.236;
2.Y.244.237; 2.Y.244.238; 2.Y.244.239; 2.Y.244.154; 2.Y.244.157; 2.Y.244.166;
2.Y.244.169; 2.Y.244.172; 2.Y.244.175; 2.Y.244.240; 2.Y.244.244;
Prodrugs of 3.B 3.B.228.228; 3.B.228.229; 3.B.228.230; 3.B.228.231; 3.B.228.236;
3.B.228.237; 3.B.228.238; 3.B.228.239; 3.B.228.154; 3.B.228.157; 3.B.228.166;
3.B.228.169; 3.B.228.172; 3.B.228.175; 3.B.228.240; 3.B.228.244; 3.B.229.228;
3.B.229.229; 3.B.229.230; 3.B.229.231; 3.B.229.236; 3.B.229.237; 3.B.229.238;
3.B.229.239; 3.B.229.154; 3.B.229.157; 3.B.229.166; 3.B.229.169; 3.B.229.172;
3.B.229.175; 3.B.229.240; 3.B.229.244; 3.B.230.228; 3.B.230.229; 3.B.230.230;
3.B.230.231; 3.B.230.236; 3.B.230.237; 3.B.230.238; 3.B.230.239; 3.B.230.154;
3.B.230.157; 3.B.230.166; 3.B.230.169; 3.B.230.172; 3.B.230.175; 3.B.230.240;
3.B.230.244; 3.B.231.228; 3.B.231.229; 3.B.231.230; 3.B.231.231; 3.B.231.236;
3.B.231.237; 3.B.231.238; 3.B.231.239; 3.B.231.154; 3.B.231.157; 3.B.231.166;
3.B.231.169; 3.B.231.172; 3.B.231.175; 3.B.231.240; 3.B.231.244; 3.B.236.228;
3.B.236.229; 3.B.236.230; 3.B.236.231; 3.B.236.236; 3.B.236.237; 3.B.236.238;
3.B.236.239; 3.B.236.154; 3.B.236.157; 3.B.236.166; 3.B.236.169; 3.B.236.172;
3.B.236.175; 3.B.236.240; 3.B.236.244; 3.B.237.228; 3.B.237.229; 3.B.237.230;
3.B.237.231; 3.B.237.236; 3.B.237.237; 3.B.237.238; 3.B.237.239; 3.B.237.154;
3.B.237.157; 3.B.237.166; 3.B.237.169; 3.B.237.172; 3.B.237.175; 3.B.237.240;
3.B.237.244; 3.B.238.228; 3.B.238.229; 3.B.238.230; 3.B.238.231; 3.B.238.236;
3.B.238.237; 3.B.238.238; 3.B.238.239; 3.B.238.154; 3.B.238.157; 3.B.238.166;
3.B.238.169; 3.B.238.172; 3.B.238.175; 3.B.238.240; 3.B.238.244; 3.B.239.228;
3.B.239.229; 3.B.239.230; 3.B.239.231; 3.B.239.236; 3.B.239.237; 3.B.239.238;
3.B.239.239; 3.B.239.154; 3.B.239.157; 3.B.239.166; 3.B.239.169; 3.B.239.172;
3.B.239.175; 3.B.239.240; 3.B.239.244; 3.B.154.228; 3.B.154.229; 3.B.154.230;
3.B.154.231; 3.B.154.236; 3.B.154.237; 3.B.154.238; 3.B.154.239; 3.B.154.154;
3.B.154.157; 3.B.154.166; 3.B.154.169; 3.B.154.172; 3.B.154.175; 3.B.154.240;
3.B.154.244; 3.B.157.228; 3.B.157.229; 3.B.157.230; 3.B.157.231; 3.B.157.236;
3.B.157.237; 3.B.157.238; 3.B.157.239; 3.B.157.154; 3.B.157.157; 3.B.157.166;
3.B.157.169; 3.B.157.172; 3.B.157.175; 3.B.157.240; 3.B.157.244; 3.B.166.228;
3.B.166.229; 3.B.166.230; 3.B.166.231; 3.B.166.236; 3.B.166.237; 3.B.166.238;
3.B.166.239; 3.B.166.154; 3.B.166.157; 3.B.166.166; 3.B.166.169; 3.B.166.172;
3.B.166.175; 3.B.166.240; 3.B.166.244; 3.B.169.228; 3.B.169.229; 3.B.169.230;

TABLE 100-continued

3.B.169.231; 3.B.169.236; 3.B.169.237; 3.B.169.238; 3.B.169.239; 3.B.169.154;
3.B.169.157; 3.B.169.166; 3.B.169.169; 3.B.169.172; 3.B.169.175; 3.B.169.240;
3.B.169.244; 3.B.172.228; 3.B.172.229; 3.B.172.230; 3.B.172.231; 3.B.172.236;
3.B.172.237; 3.B.172.238; 3.B.172.239; 3.B.172.154; 3.B.172.157; 3.B.172.166;
3.B.172.169; 3.B.172.172; 3.B.172.175; 3.B.172.240; 3.B.172.244; 3.B.175.228;
3.B.175.229; 3.B.175.230; 3.B.175.231; 3.B.175.236; 3.B.175.237; 3.B.175.238;
3.B.175.239; 3.B.175.154; 3.B.175.157; 3.B.175.166; 3.B.175.169; 3.B.175.172;
3.B.175.175; 3.B.175.240; 3.B.175.244; 3.B.240.228; 3.B.240.229; 3.B.240.230;
3.B.240.231; 3.B.240.236; 3.B.240.237; 3.B.240.238; 3.B.240.239; 3.B.240.154;
3.B.240.157; 3.B.240.166; 3.B.240.169; 3.B.240.172; 3.B.240.175; 3.B.240.240;
3.B.240.244; 3.B.244.228; 3.B.244.229; 3.B.244.230; 3.B.244.231; 3.B.244.236;
3.B.244.237; 3.B.244.238; 3.B.244.239; 3.B.244.154; 3.B.244.157; 3.B.244.166; 3.B.244.169;
3.B.244.172; 3.B.244.175; 3.B.244.240; 3.B.244.244;

Prodrugs of 3.D

3.D.228.228; 3.D.228.229; 3.D.228.230; 3.D.228.231; 3.D.228.236;
3.D.228.237; 3.D.228.238; 3.D.228.239; 3.D.228.154; 3.D.228.157;
3.D.228.166; 3.D.228.169; 3.D.228.172; 3.D.228.175; 3.D.228.240;
3.D.228.244; 3.D.229.228; 3.D.229.229; 3.D.229.230; 3.D.229.231;
3.D.229.236; 3.D.229.237; 3.D.229.238; 3.D.229.239; 3.D.229.154;
3.D.229.157; 3.D.229.166; 3.D.229.169; 3.D.229.172; 3.D.229.175;
3.D.229.240; 3.D.229.244; 3.D.230.228; 3.D.230.229; 3.D.230.230;
3.D.230.231; 3.D.230.236; 3.D.230.237; 3.D.230.238; 3.D.230.239;
3.D.230.154; 3.D.230.157; 3.D.230.166; 3.D.230.169; 3.D.230.172;
3.D.230.175; 3.D.230.240; 3.D.230.244; 3.D.231.228; 3.D.231.229;
3.D.231.230; 3.D.231.231; 3.D.231.236; 3.D.231.237; 3.D.231.238;
3.D.231.239; 3.D.231.154; 3.D.231.157; 3.D.231.166; 3.D.231.169;
3.D.231.172; 3.D.231.175; 3.D.231.240; 3.D.231.244; 3.D.236.228;
3.D.236.229; 3.D.236.230; 3.D.236.231; 3.D.236.236; 3.D.236.237;
3.D.236.238; 3.D.236.239; 3.D.236.154; 3.D.236.157; 3.D.236.166;
3.D.236.169; 3.D.236.172; 3.D.236.175; 3.D.236.240; 3.D.236.244;
3.D.237.228; 3.D.237.229; 3.D.237.230; 3.D.237.231; 3.D.237.236;
3.D.237.237; 3.D.237.238; 3.D.237.239; 3.D.237.154; 3.D.237.157;
3.D.237.166; 3.D.237.169; 3.D.237.172; 3.D.237.175; 3.D.237.240;
3.D.237.244; 3.D.238.228; 3.D.238.229; 3.D.238.230; 3.D.238.231;
3.D.238.236; 3.D.238.237; 3.D.238.238; 3.D.238.239; 3.D.238.154;
3.D.238.157; 3.D.238.166; 3.D.238.169; 3.D.238.172; 3.D.238.175;
3.D.238.240; 3.D.238.244; 3.D.239.228; 3.D.239.229; 3.D.239.230;
3.D.239.231; 3.D.239.236; 3.D.239.237; 3.D.239.238; 3.D.239.239;
3.D.239.154; 3.D.239.157; 3.D.239.166; 3.D.239.169; 3.D.239.172;
3.D.239.175; 3.D.239.240; 3.D.239.244; 3.D.154.228; 3.D.154.229;
3.D.154.230; 3.D.154.231; 3.D.154.236; 3.D.154.237; 3.D.154.238;
3.D.154.239; 3.D.154.154; 3.D.154.157; 3.D.154.166; 3.D.154.169;
3.D.154.172; 3.D.154.175; 3.D.154.240; 3.D.154.244; 3.D.157.228;
3.D.157.229; 3.D.157.230; 3.D.157.231; 3.D.157.236; 3.D.157.237;
3.D.157.238; 3.D.157.239; 3.D.157.154; 3.D.157.157; 3.D.157.166;
3.D.157.169; 3.D.157.172; 3.D.157.175; 3.D.157.240; 3.D.157.244;
3.D.166.228; 3.D.166.229; 3.D.166.230; 3.D.166.231; 3.D.166.236;
3.D.166.237; 3.D.166.238; 3.D.166.239; 3.D.166.154; 3.D.166.157;
3.D.166.166; 3.D.166.169; 3.D.166.172; 3.D.166.175; 3.D.166.240;
3.D.166.244; 3.D.169.228; 3.D.169.229; 3.D.169.230; 3.D.169.231;
3.D.169.236; 3.D.169.237; 3.D.169.238; 3.D.169.239; 3.D.169.154;
3.D.169.157; 3.D.169.166; 3.D.169.169; 3.D.169.172; 3.D.169.175;
3.D.169.240; 3.D.169.244; 3.D.172.228; 3.D.172.229; 3.D.172.230;
3.D.172.231; 3.D.172.236; 3.D.172.237; 3.D.172.238; 3.D.172.239;
3.D.172.154; 3.D.172.157; 3.D.172.166; 3.D.172.169; 3.D.172.172;
3.D.172.175; 3.D.172.240; 3.D.172.244; 3.D.175.228; 3.D.175.229;
3.D.175.230; 3.D.175.231; 3.D.175.236; 3.D.175.237; 3.D.175.238;
3.D.175.239; 3.D.175.154; 3.D.175.157; 3.D.175.166; 3.D.175.169;
3.D.175.172; 3.D.175.175; 3.D.175.240; 3.D.175.244; 3.D.240.228;
3.D.240.229; 3.D.240.230; 3.D.240.231; 3.D.240.236; 3.D.240.237;
3.D.240.238; 3.D.240.239; 3.D.240.154; 3.D.240.157; 3.D.240.166;
3.D.240.169; 3.D.240.172; 3.D.240.175; 3.D.240.240; 3.D.240.244;
3.D.244.228; 3.D.244.229; 3.D.244.230; 3.D.244.231; 3.D.244.236;
3.D.244.237; 3.D.244.238; 3.D.244.239; 3.D.244.154; 3.D.244.157;
3.D.244.166; 3.D.244.169; 3.D.244.172; 3.D.244.175; 3.D.244.240;
3.D.244.244;

Prodrugs of 3.E

3.E.228.228; 3.E.228.229; 3.E.228.230; 3.E.228.231; 3.E.228.236;
3.E.228.237; 3.E.228.238; 3.E.228.239; 3.E.228.154; 3.E.228.157; 3.E.228.166;
3.E.228.169; 3.E.228.172; 3.E.228.175; 3.E.228.240; 3.E.228.244; 3.E.229.228;
3.E.229.229; 3.E.229.230; 3.E.229.231; 3.E.229.236; 3.E.229.237; 3.E.229.238;
3.E.229.239; 3.E.229.154; 3.E.229.157; 3.E.229.166; 3.E.229.169; 3.E.229.172;
3.E.229.175; 3.E.229.240; 3.E.229.244; 3.E.230.228; 3.E.230.229; 3.E.230.230;
3.E.230.231; 3.E.230.236; 3.E.230.237; 3.E.230.238; 3.E.230.239; 3.E.230.154;
3.E.230.157; 3.E.230.166; 3.E.230.169; 3.E.230.172; 3.E.230.175; 3.E.230.240;
3.E.230.244; 3.E.231.228; 3.E.231.229; 3.E.231.230; 3.E.231.231; 3.E.231.236;
3.E.231.237; 3.E.231.238; 3.E.231.239; 3.E.231.154; 3.E.231.157; 3.E.231.166;

TABLE 100-continued

3.E.231.169; 3.E.231.172; 3.E.231.175; 3.E.231.240; 3.E.231.244; 3.E.236.228;
3.E.236.229; 3.E.236.230; 3.E.236.231; 3.E.236.236; 3.E.236.237; 3.E.236.238;
3.E.236.239; 3.E.236.154; 3.E.236.157; 3.E.236.166; 3.E.236.169; 3.E.236.172;
3.E.236.175; 3.E.236.240; 3.E.236.244; 3.E.237.228; 3.E.237.229; 3.E.237.230;
3.E.237.231; 3.E.237.236; 3.E.237.237; 3.E.237.238; 3.E.237.239; 3.E.237.154;
3.E.237.157; 3.E.237.166; 3.E.237.169; 3.E.237.172; 3.E.237.175; 3.E.237.240;
3.E.237.244; 3.E.238.228; 3.E.238.229; 3.E.238.230; 3.E.238.231; 3.E.238.236;
3.E.238.237; 3.E.238.238; 3.E.238.239; 3.E.238.154; 3.E.238.157; 3.E.238.166;
3.E.238.169; 3.E.238.172; 3.E.238.175; 3.E.238.240; 3.E.238.244; 3.E.239.228;
3.E.239.229; 3.E.239.230; 3.E.239.231; 3.E.239.236; 3.E.239.237; 3.E.239.238;
3.E.239.239; 3.E.239.154; 3.E.239.157; 3.E.239.166; 3.E.239.169; 3.E.239.172;
3.E.239.175; 3.E.239.240; 3.E.239.244; 3.E.154.228; 3.E.154.229; 3.E.154.230;
3.E.154.231; 3.E.154.236; 3.E.154.237; 3.E.154.238; 3.E.154.239; 3.E.154.154;
3.E.154.157; 3.E.154.166; 3.E.154.169; 3.E.154.172; 3.E.154.175; 3.E.154.240;
3.E.154.244; 3.E.157.228; 3.E.157.229; 3.E.157.230; 3.E.157.231; 3.E.157.236;
3.E.157.237; 3.E.157.238; 3.E.157.239; 3.E.157.154; 3.E.157.157; 3.E.157.166;
3.E.157.169; 3.E.157.172; 3.E.157.175; 3.E.157.240; 3.E.157.244; 3.E.166.228;
3.E.166.229; 3.E.166.230; 3.E.166.231; 3.E.166.236; 3.E.166.237; 3.E.166.238;
3.E.166.239; 3.E.166.154; 3.E.166.157; 3.E.166.166; 3.E.166.169; 3.E.166.172;
3.E.166.175; 3.E.166.240; 3.E.166.244; 3.E.169.228; 3.E.169.229; 3.E.169.230;
3.E.169.231; 3.E.169.236; 3.E.169.237; 3.E.169.238; 3.E.169.239; 3.E.169.154;
3.E.169.157; 3.E.169.166; 3.E.169.169; 3.E.169.172; 3.E.169.175; 3.E.169.240;
3.E.169.244; 3.E.172.228; 3.E.172.229; 3.E.172.230; 3.E.172.231; 3.E.172.236;
3.E.172.237; 3.E.172.238; 3.E.172.239; 3.E.172.154; 3.E.172.157; 3.E.172.166;
3.E.172.169; 3.E.172.172; 3.E.172.175; 3.E.172.240; 3.E.172.244; 3.E.175.228;
3.E.175.229; 3.E.175.230; 3.E.175.231; 3.E.175.236; 3.E.175.237; 3.E.175.238;
3.E.175.239; 3.E.175.154; 3.E.175.157; 3.E.175.166; 3.E.175.169; 3.E.175.172;
3.E.175.175; 3.E.175.240; 3.E.175.244; 3.E.240.228; 3.E.240.229; 3.E.240.230;
3.E.240.231; 3.E.240.236; 3.E.240.237; 3.E.240.238; 3.E.240.239; 3.E.240.154;
3.E.240.157; 3.E.240.166; 3.E.240.169; 3.E.240.172; 3.E.240.175; 3.E.240.240;
3.E.240.244; 3.E.244.228; 3.E.244.229; 3.E.244.230; 3.E.244.231; 3.E.244.236;
3.E.244.237; 3.E.244.238; 3.E.244.239; 3.E.244.154; 3.E.244.157; 3.E.244.166;
3.E.244.169; 3.E.244.172; 3.E.244.175; 3.E.244.240; 3.E.244.244;

Prodrugs of 3.G

3.G.228.228; 3.G.228.229; 3.G.228.230; 3.G.228.231; 3.G.228.236;
3.G.228.237; 3.G.228.238; 3.G.228.239; 3.G.228.154; 3.G.228.157;
3.G.228.166; 3.G.228.169; 3.G.228.172; 3.G.228.175; 3.G.228.240;
3.G.228.244; 3.G.229.228; 3.G.229.229; 3.G.229.230; 3.G.229.231;
3.G.229.236; 3.G.229.237; 3.G.229.238; 3.G.229.239; 3.G.229.154;
3.G.229.157; 3.G.229.166; 3.G.229.169; 3.G.229.172; 3.G.229.175;
3.G.229.240; 3.G.229.244; 3.G.230.228; 3.G.230.229; 3.G.230.230;
3.G.230.231; 3.G.230.236; 3.G.230.237; 3.G.230.238; 3.G.230.239;
3.G.230.154; 3.G.230.157; 3.G.230.166; 3.G.230.169; 3.G.230.172;
3.G.230.175; 3.G.230.240; 3.G.230.244; 3.G.231.228; 3.G.231.229;
3.G.231.230; 3.G.231.231; 3.G.231.236; 3.G.231.237; 3.G.231.238;
3.G.231.239; 3.G.231.154; 3.G.231.157; 3.G.231.166; 3.G.231.169;
3.G.231.172; 3.G.231.175; 3.G.231.240; 3.G.231.244; 3.G.236.228;
3.G.236.229; 3.G.236.230; 3.G.236.231; 3.G.236.236; 3.G.236.237;
3.G.236.238; 3.G.236.239; 3.G.236.154; 3.G.236.157; 3.G.236.166;
3.G.236.169; 3.G.236.172; 3.G.236.175; 3.G.236.240; 3.G.236.244;
3.G.237.228; 3.G.237.229; 3.G.237.230; 3.G.237.231; 3.G.237.236;
3.G.237.237; 3.G.237.238; 3.G.237.239; 3.G.237.154; 3.G.237.157;
3.G.237.166; 3.G.237.169; 3.G.237.172; 3.G.237.175; 3.G.237.240;
3.G.237.244; 3.G.238.228; 3.G.238.229; 3.G.238.230; 3.G.238.231;
3.G.238.236; 3.G.238.237; 3.G.238.238; 3.G.238.239; 3.G.238.154;
3.G.238.157; 3.G.238.166; 3.G.238.169; 3.G.238.172; 3.G.238.175;
3.G.238.240; 3.G.238.244; 3.G.239.228; 3.G.239.229; 3.G.239.230;
3.G.239.231; 3.G.239.236; 3.G.239.237; 3.G.239.238; 3.G.239.239;
3.G.239.154; 3.G.239.157; 3.G.239.166; 3.G.239.169; 3.G.239.172;
3.G.239.175; 3.G.239.240; 3.G.239.244; 3.G.154.228; 3.G.154.229;
3.G.154.230; 3.G.154.231; 3.G.154.236; 3.G.154.237; 3.G.154.238;
3.G.154.239; 3.G.154.154; 3.G.154.157; 3.G.154.166; 3.G.154.169;
3.G.154.172; 3.G.154.175; 3.G.154.240; 3.G.154.244; 3.G.157.228;
3.G.157.229; 3.G.157.230; 3.G.157.231; 3.G.157.236; 3.G.157.237;
3.G.157.238; 3.G.157.239; 3.G.157.154; 3.G.157.157; 3.G.157.166;
3.G.157.169; 3.G.157.172; 3.G.157.175; 3.G.157.240; 3.G.157.244;
3.G.166.228; 3.G.166.229; 3.G.166.230; 3.G.166.231; 3.G.166.236;
3.G.166.237; 3.G.166.238; 3.G.166.239; 3.G.166.154; 3.G.166.157;
3.G.166.166; 3.G.166.169; 3.G.166.172; 3.G.166.175; 3.G.166.240;
3.G.166.244; 3.G.169.228; 3.G.169.229; 3.G.169.230; 3.G.169.231;
3.G.169.236; 3.G.169.237; 3.G.169.238; 3.G.169.239; 3.G.169.154;
3.G.169.157; 3.G.169.166; 3.G.169.169; 3.G.169.172; 3.G.169.175;
3.G.169.240; 3.G.169.244; 3.G.172.228; 3.G.172.229; 3.G.172.230;
3.G.172.231; 3.G.172.236; 3.G.172.237; 3.G.172.238; 3.G.172.239;
3.G.172.154; 3.G.172.157; 3.G.172.166; 3.G.172.169; 3.G.172.172;
3.G.172.175; 3.G.172.240; 3.G.172.244; 3.G.175.228; 3.G.175.229;
3.G.175.230; 3.G.175.231; 3.G.175.236; 3.G.175.237; 3.G.175.238;
3.G.175.239; 3.G.175.154; 3.G.175.157; 3.G.175.166; 3.G.175.169;

TABLE 100-continued

3.G.175.172; 3.G.175.175; 3.G.175.240; 3.G.175.244; 3.G.240.228;
3.G.240.229; 3.G.240.230; 3.G.240.231; 3.G.240.236; 3.G.240.237;
3.G.240.238; 3.G.240.239; 3.G.240.154; 3.G.240.157; 3.G.240.166;
3.G.240.169; 3.G.240.172; 3.G.240.175; 3.G.240.240; 3.G.240.244;
3.G.244.228; 3.G.244.229; 3.G.244.230; 3.G.244.231; 3.G.244.236;
3.G.244.237; 3.G.244.238; 3.G.244.239; 3.G.244.154; 3.G.244.157;
3.G.244.166; 3.G.244.169; 3.G.244.172; 3.G.244.175; 3.G.244.240;
3.G.244.244;

Prodrugs of 3.I

3.I.228.228; 3.I.228.229; 3.I.228.230; 3.I.228.231; 3.I.228.236; 3.I.228.237;
3.I.228.238; 3.I.228.239; 3.I.228.154; 3.I.228.157; 3.I.228.166; 3.I.228.169;
3.I.228.172; 3.I.228.175; 3.I.228.240; 3.I.228.244; 3.I.229.228; 3.I.229.229;
3.I.229.230; 3.I.229.231; 3.I.229.236; 3.I.229.237; 3.I.229.238; 3.I.229.239;
3.I.229.154; 3.I.229.157; 3.I.229.166; 3.I.229.169; 3.I.229.172; 3.I.229.175;
3.I.229.240; 3.I.229.244; 3.I.230.228; 3.I.230.229; 3.I.230.230; 3.I.230.231;
3.I.230.236; 3.I.230.237; 3.I.230.238; 3.I.230.239; 3.I.230.154; 3.I.230.157;
3.I.230.166; 3.I.230.169; 3.I.230.172; 3.I.230.175; 3.I.230.240; 3.I.230.244;
3.I.231.228; 3.I.231.229; 3.I.231.230; 3.I.231.231; 3.I.231.236; 3.I.231.237;
3.I.231.238; 3.I.231.239; 3.I.231.154; 3.I.231.157; 3.I.231.166; 3.I.231.169;
3.I.231.172; 3.I.231.175; 3.I.231.240; 3.I.231.244; 3.I.236.228; 3.I.236.229;
3.I.236.230; 3.I.236.231; 3.I.236.236; 3.I.236.237; 3.I.236.238; 3.I.236.239;
3.I.236.154; 3.I.236.157; 3.I.236.166; 3.I.236.169; 3.I.236.172; 3.I.236.175;
3.I.236.240; 3.I.236.244; 3.I.237.228; 3.I.237.229; 3.I.237.230; 3.I.237.231;
3.I.237.236; 3.I.237.237; 3.I.237.238; 3.I.237.239; 3.I.237.154; 3.I.237.157;
3.I.237.166; 3.I.237.169; 3.I.237.172; 3.I.237.175; 3.I.237.240; 3.I.237.244;
3.I.238.228; 3.I.238.229; 3.I.238.230; 3.I.238.231; 3.I.238.236; 3.I.238.237;
3.I.238.238; 3.I.238.239; 3.I.238.154; 3.I.238.157; 3.I.238.166; 3.I.238.169;
3.I.238.172; 3.I.238.175; 3.I.238.240; 3.I.238.244; 3.I.239.228; 3.I.239.229;
3.I.239.230; 3.I.239.231; 3.I.239.236; 3.I.239.237; 3.I.239.238; 3.I.239.239;
3.I.239.154; 3.I.239.157; 3.I.239.166; 3.I.239.169; 3.I.239.172; 3.I.239.175;
3.I.239.240; 3.I.239.244; 3.I.154.228; 3.I.154.229; 3.I.154.230; 3.I.154.231;
3.I.154.236; 3.I.154.237; 3.I.154.238; 3.I.154.239; 3.I.154.154; 3.I.154.157;
3.I.154.166; 3.I.154.169; 3.I.154.172; 3.I.154.175; 3.I.154.240; 3.I.154.244;
3.I.157.228; 3.I.157.229; 3.I.157.230; 3.I.157.231; 3.I.157.236; 3.I.157.237;
3.I.157.238; 3.I.157.239; 3.I.157.154; 3.I.157.157; 3.I.157.166; 3.I.157.169;
3.I.157.172; 3.I.157.175; 3.I.157.240; 3.I.157.244; 3.I.166.228; 3.I.166.229;
3.I.166.230; 3.I.166.231; 3.I.166.236; 3.I.166.237; 3.I.166.238; 3.I.166.239;
3.I.166.154; 3.I.166.157; 3.I.166.166; 3.I.166.169; 3.I.166.172; 3.I.166.175;
3.I.166.240; 3.I.166.244; 3.I.169.228; 3.I.169.229; 3.I.169.230; 3.I.169.231;
3.I.169.236; 3.I.169.237; 3.I.169.238; 3.I.169.239; 3.I.169.154; 3.I.169.157;
3.I.169.166; 3.I.169.169; 3.I.169.172; 3.I.169.175; 3.I.169.240; 3.I.169.244;
3.I.172.228; 3.I.172.229; 3.I.172.230; 3.I.172.231; 3.I.172.236; 3.I.172.237;
3.I.172.238; 3.I.172.239; 3.I.172.154; 3.I.172.157; 3.I.172.166; 3.I.172.169;
3.I.172.172; 3.I.172.175; 3.I.172.240; 3.I.172.244; 3.I.175.228; 3.I.175.229;
3.I.175.230; 3.I.175.231; 3.I.175.236; 3.I.175.237; 3.I.175.238; 3.I.175.239;
3.I.175.154; 3.I.175.157; 3.I.175.166; 3.I.175.169; 3.I.175.172; 3.I.175.175;
3.I.175.240; 3.I.175.244; 3.I.240.228; 3.I.240.229; 3.I.240.230; 3.I.240.231;
3.I.240.236; 3.I.240.237; 3.I.240.238; 3.I.240.239; 3.I.240.154; 3.I.240.157;
3.I.240.166; 3.I.240.169; 3.I.240.172; 3.I.240.175; 3.I.240.240; 3.I.240.244;
3.I.244.228; 3.I.244.229; 3.I.244.230; 3.I.244.231; 3.I.244.236; 3.I.244.237;
3.I.244.238; 3.I.244.239; 3.I.244.154; 3.I.244.157; 3.I.244.166; 3.I.244.169;
3.I.244.172; 3.I.244.175; 3.I.244.240; 3.I.244.244;

Prodrugs of 3.J

3.J.228.228; 3.J.228.229; 3.J.228.230; 3.J.228.231; 3.J.228.236; 3.J.228.237;
3.J.228.238; 3.J.228.239; 3.J.228.154; 3.J.228.157; 3.J.228.166; 3.J.228.169;
3.J.228.172; 3.J.228.175; 3.J.228.240; 3.J.228.244; 3.J.229.228; 3.J.229.229;
3.J.229.230; 3.J.229.231; 3.J.229.236; 3.J.229.237; 3.J.229.238; 3.J.229.239;
3.J.229.154; 3.J.229.157; 3.J.229.166; 3.J.229.169; 3.J.229.172; 3.J.229.175;
3.J.229.240; 3.J.229.244; 3.J.230.228; 3.J.230.229; 3.J.230.230; 3.J.230.231;
3.J.230.236; 3.J.230.237; 3.J.230.238; 3.J.230.239; 3.J.230.154; 3.J.230.157;
3.J.230.166; 3.J.230.169; 3.J.230.172; 3.J.230.175; 3.J.230.240; 3.J.230.244;
3.J.231.228; 3.J.231.229; 3.J.231.230; 3.J.231.231; 3.J.231.236; 3.J.231.237;
3.J.231.238; 3.J.231.239; 3.J.231.154; 3.J.231.157; 3.J.231.166; 3.J.231.169;
3.J.231.172; 3.J.231.175; 3.J.231.240; 3.J.231.244; 3.J.236.228; 3.J.236.229;
3.J.236.230; 3.J.236.231; 3.J.236.236; 3.J.236.237; 3.J.236.238; 3.J.236.239;
3.J.236.154; 3.J.236.157; 3.J.236.166; 3.J.236.169; 3.J.236.172; 3.J.236.175;
3.J.236.240; 3.J.236.244; 3.J.237.228; 3.J.237.229; 3.J.237.230; 3.J.237.231;
3.J.237.236; 3.J.237.237; 3.J.237.238; 3.J.237.239; 3.J.237.154; 3.J.237.157;
3.J.237.166; 3.J.237.169; 3.J.237.172; 3.J.237.175; 3.J.237.240; 3.J.237.244;
3.J.238.228; 3.J.238.229; 3.J.238.230; 3.J.238.231; 3.J.238.236; 3.J.238.237;
3.J.238.238; 3.J.238.239; 3.J.238.154; 3.J.238.157; 3.J.238.166; 3.J.238.169;
3.J.238.172; 3.J.238.175; 3.J.238.240; 3.J.238.244; 3.J.239.228; 3.J.239.229;
3.J.239.230; 3.J.239.231; 3.J.239.236; 3.J.239.237; 3.J.239.238; 3.J.239.239;
3.J.239.154; 3.J.239.157; 3.J.239.166; 3.J.239.169; 3.J.239.172; 3.J.239.175;
3.J.239.240; 3.J.239.244; 3.J.154.228; 3.J.154.229; 3.J.154.230; 3.J.154.231;
3.J.154.236; 3.J.154.237; 3.J.154.238; 3.J.154.239; 3.J.154.154; 3.J.154.157;
3.J.154.166; 3.J.154.169; 3.J.154.172; 3.J.154.175; 3.J.154.240; 3.J.154.244;

TABLE 100-continued

3.J.157.228; 3.J.157.229; 3.J.157.230; 3.J.157.231; 3.J.157.236; 3.J.157.237;
3.J.157.238; 3.J.157.239; 3.J.157.154; 3.J.157.157; 3.J.157.166; 3.J.157.169;
3.J.157.172; 3.J.157.175; 3.J.157.240; 3.J.157.244; 3.J.166.228; 3.J.166.229;
3.J.166.230; 3.J.166.231; 3.J.166.236; 3.J.166.237; 3.J.166.238; 3.J.166.239;
3.J.166.154; 3.J.166.157; 3.J.166.166; 3.J.166.169; 3.J.166.172; 3.J.166.175;
3.J.166.240; 3.J.166.244; 3.J.169.228; 3.J.169.229; 3.J.169.230; 3.J.169.231;
3.J.169.236; 3.J.169.237; 3.J.169.238; 3.J.169.239; 3.J.169.154; 3.J.169.157;
3.J.169.166; 3.J.169.169; 3.J.169.172; 3.J.169.175; 3.J.169.240; 3.J.169.244;
3.J.172.228; 3.J.172.229; 3.J.172.230; 3.J.172.231; 3.J.172.236; 3.J.172.237;
3.J.172.238; 3.J.172.239; 3.J.172.154; 3.J.172.157; 3.J.172.166; 3.J.172.169;
3.J.172.172; 3.J.172.175; 3.J.172.240; 3.J.172.244; 3.J.175.228; 3.J.175.229;
3.J.175.230; 3.J.175.231; 3.J.175.236; 3.J.175.237; 3.J.175.238; 3.J.175.239;
3.J.175.154; 3.J.175.157; 3.J.175.166; 3.J.175.169; 3.J.175.172; 3.J.175.175;
3.J.175.240; 3.J.175.244; 3.J.240.228; 3.J.240.229; 3.J.240.230; 3.J.240.231;
3.J.240.236; 3.J.240.237; 3.J.240.238; 3.J.240.239; 3.J.240.154; 3.J.240.157;
3.J.240.166; 3.J.240.169; 3.J.240.172; 3.J.240.175; 3.J.240.240; 3.J.240.244;
3.J.244.228; 3.J.244.229; 3.J.244.230; 3.J.244.231; 3.J.244.236; 3.J.244.237;
3.J.244.238; 3.J.244.239; 3.J.244.154; 3.J.244.157; 3.J.244.166; 3.J.244.169;
3.J.244.172; 3.J.244.175; 3.J.244.240; 3.J.244.244;
Prodrugs of 3.L 3.L.228.228; 3.L.228.229; 3.L.228.230; 3.L.228.231; 3.L.228.236;
3.L.228.237; 3.L.228.238; 3.L.228.239; 3.L.228.154; 3.L.228.157; 3.L.228.166;
3.L.228.169; 3.L.228.172; 3.L.228.175; 3.L.228.240; 3.L.228.244; 3.L.229.228;
3.L.229.229; 3.L.229.230; 3.L.229.231; 3.L.229.236; 3.L.229.237; 3.L.229.238;
3.L.229.239; 3.L.229.154; 3.L.229.157; 3.L.229.166; 3.L.229.169; 3.L.229.172;
3.L.229.175; 3.L.229.240; 3.L.229.244; 3.L.230.228; 3.L.230.229; 3.L.230.230;
3.L.230.231; 3.L.230.236; 3.L.230.237; 3.L.230.238; 3.L.230.239; 3.L.230.154;
3.L.230.157; 3.L.230.166; 3.L.230.169; 3.L.230.172; 3.L.230.175; 3.L.230.240;
3.L.230.244; 3.L.231.228; 3.L.231.229; 3.L.231.230; 3.L.231.231; 3.L.231.236;
3.L.231.237; 3.L.231.238; 3.L.231.239; 3.L.231.154; 3.L.231.157; 3.L.231.166;
3.L.231.169; 3.L.231.172; 3.L.231.175; 3.L.231.240; 3.L.231.244; 3.L.236.228;
3.L.236.229; 3.L.236.230; 3.L.236.231; 3.L.236.236; 3.L.236.237; 3.L.236.238;
3.L.236.239; 3.L.236.154; 3.L.236.157; 3.L.236.166; 3.L.236.169; 3.L.236.172;
3.L.236.175; 3.L.236.240; 3.L.236.244; 3.L.237.228; 3.L.237.229; 3.L.237.230;
3.L.237.231; 3.L.237.236; 3.L.237.237; 3.L.237.238; 3.L.237.239; 3.L.237.154;
3.L.237.157; 3.L.237.166; 3.L.237.169; 3.L.237.172; 3.L.237.175; 3.L.237.240;
3.L.237.244; 3.L.238.228; 3.L.238.229; 3.L.238.230; 3.L.238.231; 3.L.238.236;
3.L.238.237; 3.L.238.238; 3.L.238.239; 3.L.238.154; 3.L.238.157; 3.L.238.166;
3.L.238.169; 3.L.238.172; 3.L.238.175; 3.L.238.240; 3.L.238.244; 3.L.239.228;
3.L.239.229; 3.L.239.230; 3.L.239.231; 3.L.239.236; 3.L.239.237; 3.L.239.238;
3.L.239.239; 3.L.239.154; 3.L.239.157; 3.L.239.166; 3.L.239.169; 3.L.239.172;
3.L.239.175; 3.L.239.240; 3.L.239.244; 3.L.154.228; 3.L.154.229; 3.L.154.230;
3.L.154.231; 3.L.154.236; 3.L.154.237; 3.L.154.238; 3.L.154.239; 3.L.154.154;
3.L.154.157; 3.L.154.166; 3.L.154.169; 3.L.154.172; 3.L.154.175; 3.L.154.240;
3.L.154.244; 3.L.157.228; 3.L.157.229; 3.L.157.230; 3.L.157.231; 3.L.157.236;
3.L.157.237; 3.L.157.238; 3.L.157.239; 3.L.157.154; 3.L.157.157; 3.L.157.166;
3.L.157.169; 3.L.157.172; 3.L.157.175; 3.L.157.240; 3.L.157.244; 3.L.166.228;
3.L.166.229; 3.L.166.230; 3.L.166.231; 3.L.166.236; 3.L.166.237; 3.L.166.238;
3.L.166.239; 3.L.166.154; 3.L.166.157; 3.L.166.166; 3.L.166.169; 3.L.166.172;
3.L.166.175; 3.L.166.240; 3.L.166.244; 3.L.169.228; 3.L.169.229; 3.L.169.230;
3.L.169.231; 3.L.169.236; 3.L.169.237; 3.L.169.238; 3.L.169.239; 3.L.169.154;
3.L.169.157; 3.L.169.166; 3.L.169.169; 3.L.169.172; 3.L.169.175; 3.L.169.240;
3.L.169.244; 3.L.172.228; 3.L.172.229; 3.L.172.230; 3.L.172.231; 3.L.172.236;
3.L.172.237; 3.L.172.238; 3.L.172.239; 3.L.172.154; 3.L.172.157; 3.L.172.166;
3.L.172.169; 3.L.172.172; 3.L.172.175; 3.L.172.240; 3.L.172.244; 3.L.175.228;
3.L.175.229; 3.L.175.230; 3.L.175.231; 3.L.175.236; 3.L.175.237; 3.L.175.238;
3.L.175.239; 3.L.175.154; 3.L.175.157; 3.L.175.166; 3.L.175.169; 3.L.175.172;
3.L.175.175; 3.L.175.240; 3.L.175.244; 3.L.240.228; 3.L.240.229; 3.L.240.230;
3.L.240.231; 3.L.240.236; 3.L.240.237; 3.L.240.238; 3.L.240.239; 3.L.240.154;
3.L.240.157; 3.L.240.166; 3.L.240.169; 3.L.240.172; 3.L.240.175; 3.L.240.240;
3.L.240.244; 3.L.244.228; 3.L.244.229; 3.L.244.230; 3.L.244.231; 3.L.244.236;
3.L.244.237; 3.L.244.238; 3.L.244.239; 3.L.244.154; 3.L.244.157; 3.L.244.166;
3.L.244.169; 3.L.244.172; 3.L.244.175; 3.L.244.240; 3.L.244.244;
Prodrugs of 3.O 3.O.228.228; 3.O.228.229; 3.O.228.230; 3.O.228.231; 3.O.228.236;
3.O.228.237; 3.O.228.238; 3.O.228.239; 3.O.228.154; 3.O.228.157;
3.O.228.166; 3.O.228.169; 3.O.228.172; 3.O.228.175; 3.O.228.240;
3.O.228.244; 3.O.229.228; 3.O.229.229; 3.O.229.230; 3.O.229.231;
3.O.229.236; 3.O.229.237; 3.O.229.238; 3.O.229.239; 3.O.229.154;
3.O.229.157; 3.O.229.166; 3.O.229.169; 3.O.229.172; 3.O.229.175;
3.O.229.240; 3.O.229.244; 3.O.230.228; 3.O.230.229; 3.O.230.230;
3.O.230.231; 3.O.230.236; 3.O.230.237; 3.O.230.238; 3.O.230.239;
3.O.230.154; 3.O.230.157; 3.O.230.166; 3.O.230.169; 3.O.230.172;
3.O.230.175; 3.O.230.240; 3.O.230.244; 3.O.231.228; 3.O.231.229;
3.O.231.230; 3.O.231.231; 3.O.231.236; 3.O.231.237; 3.O.231.238;
3.O.231.239; 3.O.231.154; 3.O.231.157; 3.O.231.166; 3.O.231.169;
3.O.231.172; 3.O.231.175; 3.O.231.240; 3.O.231.244; 3.O.236.228;

TABLE 100-continued

3.O.236.229; 3.O.236.230; 3.O.236.231; 3.O.236.236; 3.O.236.237;
3.O.236.238; 3.O.236.239; 3.O.236.154; 3.O.236.157; 3.O.236.166;
3.O.236.169; 3.O.236.172; 3.O.236.175; 3.O.236.240; 3.O.236.244;
3.O.237.228; 3.O.237.229; 3.O.237.230; 3.O.237.231; 3.O.237.236;
3.O.237.237; 3.O.237.238; 3.O.237.239; 3.O.237.154; 3.O.237.157;
3.O.237.166; 3.O.237.169; 3.O.237.172; 3.O.237.175; 3.O.237.240;
3.O.237.244; 3.O.238.228; 3.O.238.229; 3.O.238.230; 3.O.238.231;
3.O.238.236; 3.O.238.237; 3.O.238.238; 3.O.238.239; 3.O.238.154;
3.O.238.157; 3.O.238.166; 3.O.238.169; 3.O.238.172; 3.O.238.175;
3.O.238.240; 3.O.238.244; 3.O.239.228; 3.O.239.229; 3.O.239.230;
3.O.239.231; 3.O.239.236; 3.O.239.237; 3.O.239.238; 3.O.239.239;
3.O.239.154; 3.O.239.157; 3.O.239.166; 3.O.239.169; 3.O.239.172;
3.O.239.175; 3.O.239.240; 3.O.239.244; 3.O.154.228; 3.O.154.229;
3.O.154.230; 3.O.154.231; 3.O.154.236; 3.O.154.237; 3.O.154.238;
3.O.154.239; 3.O.154.154; 3.O.154.157; 3.O.154.166; 3.O.154.169;
3.O.154.172; 3.O.154.175; 3.O.154.240; 3.O.154.244; 3.O.157.228;
3.O.157.229; 3.O.157.230; 3.O.157.231; 3.O.157.236; 3.O.157.237;
3.O.157.238; 3.O.157.239; 3.O.157.154; 3.O.157.157; 3.O.157.166;
3.O.157.169; 3.O.157.172; 3.O.157.175; 3.O.157.240; 3.O.157.244;
3.O.166.228; 3.O.166.229; 3.O.166.230; 3.O.166.231; 3.O.166.236;
3.O.166.237; 3.O.166.238; 3.O.166.239; 3.O.166.154; 3.O.166.157;
3.O.166.166; 3.O.166.169; 3.O.166.172; 3.O.166.175; 3.O.166.240;
3.O.166.244; 3.O.169.228; 3.O.169.229; 3.O.169.230; 3.O.169.231;
3.O.169.236; 3.O.169.237; 3.O.169.238; 3.O.169.239; 3.O.169.154;
3.O.169.157; 3.O.169.166; 3.O.169.169; 3.O.169.172; 3.O.169.175;
3.O.169.240; 3.O.169.244; 3.O.172.228; 3.O.172.229; 3.O.172.230;
3.O.172.231; 3.O.172.236; 3.O.172.237; 3.O.172.238; 3.O.172.239;
3.O.172.154; 3.O.172.157; 3.O.172.166; 3.O.172.169; 3.O.172.172;
3.O.172.175; 3.O.172.240; 3.O.172.244; 3.O.175.228; 3.O.175.229;
3.O.175.230; 3.O.175.231; 3.O.175.236; 3.O.175.237; 3.O.175.238;
3.O.175.239; 3.O.175.154; 3.O.175.157; 3.O.175.166; 3.O.175.169;
3.O.175.172; 3.O.175.175; 3.O.175.240; 3.O.175.244; 3.O.240.228;
3.O.240.229; 3.O.240.230; 3.O.240.231; 3.O.240.236; 3.O.240.237;
3.O.240.238; 3.O.240.239; 3.O.240.154; 3.O.240.157; 3.O.240.166;
3.O.240.169; 3.O.240.172; 3.O.240.175; 3.O.240.240; 3.O.240.244;
3.O.244.228; 3.O.244.229; 3.O.244.230; 3.O.244.231; 3.O.244.236;
3.O.244.237; 3.O.244.238; 3.O.244.239; 3.O.244.154; 3.O.244.157;
3.O.244.166; 3.O.244.169; 3.O.244.172; 3.O.244.175; 3.O.244.240;
3.O.244.244;
Prodrugs of 3.P 3.P.228.228; 3.P.228.229; 3.P.228.230; 3.P.228.231; 3.P.228.236;
3.P.228.237; 3.P.228.238; 3.P.228.239; 3.P.228.154; 3.P.228.157; 3.P.228.166;
3.P.228.169; 3.P.228.172; 3.P.228.175; 3.P.228.240; 3.P.228.244; 3.P.229.228;
3.P.229.229; 3.P.229.230; 3.P.229.231; 3.P.229.236; 3.P.229.237; 3.P.229.238;
3.P.229.239; 3.P.229.154; 3.P.229.157; 3.P.229.166; 3.P.229.169; 3.P.229.172;
3.P.229.175; 3.P.229.240; 3.P.229.244; 3.P.230.228; 3.P.230.229; 3.P.230.230;
3.P.230.231; 3.P.230.236; 3.P.230.237; 3.P.230.238; 3.P.230.239; 3.P.230.154;
3.P.230.157; 3.P.230.166; 3.P.230.169; 3.P.230.172; 3.P.230.175; 3.P.230.240;
3.P.230.244; 3.P.231.228; 3.P.231.229; 3.P.231.230; 3.P.231.231; 3.P.231.236;
3.P.231.237; 3.P.231.238; 3.P.231.239; 3.P.231.154; 3.P.231.157; 3.P.231.166;
3.P.231.169; 3.P.231.172; 3.P.231.175; 3.P.231.240; 3.P.231.244; 3.P.236.228;
3.P.236.229; 3.P.236.230; 3.P.236.231; 3.P.236.236; 3.P.236.237; 3.P.236.238;
3.P.236.239; 3.P.236.154; 3.P.236.157; 3.P.236.166; 3.P.236.169; 3.P.236.172;
3.P.236.175; 3.P.236.240; 3.P.236.244; 3.P.237.228; 3.P.237.229; 3.P.237.230;
3.P.237.231; 3.P.237.236; 3.P.237.237; 3.P.237.238; 3.P.237.239; 3.P.237.154;
3.P.237.157; 3.P.237.166; 3.P.237.169; 3.P.237.172; 3.P.237.175; 3.P.237.240;
3.P.237.244; 3.P.238.228; 3.P.238.229; 3.P.238.230; 3.P.238.231; 3.P.238.236;
3.P.238.237; 3.P.238.238; 3.P.238.239; 3.P.238.154; 3.P.238.157; 3.P.238.166;
3.P.238.169; 3.P.238.172; 3.P.238.175; 3.P.238.240; 3.P.238.244; 3.P.239.228;
3.P.239.229; 3.P.239.230; 3.P.239.231; 3.P.239.236; 3.P.239.237; 3.P.239.238;
3.P.239.239; 3.P.239.154; 3.P.239.157; 3.P.239.166; 3.P.239.169; 3.P.239.172;
3.P.239.175; 3.P.239.240; 3.P.239.244; 3.P.154.228; 3.P.154.229; 3.P.154.230;
3.P.154.231; 3.P.154.236; 3.P.154.237; 3.P.154.238; 3.P.154.239; 3.P.154.154;
3.P.154.157; 3.P.154.166; 3.P.154.169; 3.P.154.172; 3.P.154.175; 3.P.154.240;
3.P.154.244; 3.P.157.228; 3.P.157.229; 3.P.157.230; 3.P.157.231; 3.P.157.236;
3.P.157.237; 3.P.157.238; 3.P.157.239; 3.P.157.154; 3.P.157.157; 3.P.157.166;
3.P.157.169; 3.P.157.172; 3.P.157.175; 3.P.157.240; 3.P.157.244; 3.P.166.228;
3.P.166.229; 3.P.166.230; 3.P.166.231; 3.P.166.236; 3.P.166.237; 3.P.166.238;
3.P.166.239; 3.P.166.154; 3.P.166.157; 3.P.166.166; 3.P.166.169; 3.P.166.172;
3.P.166.175; 3.P.166.240; 3.P.166.244; 3.P.169.228; 3.P.169.229; 3.P.169.230;
3.P.169.231; 3.P.169.236; 3.P.169.237; 3.P.169.238; 3.P.169.239; 3.P.169.154;
3.P.169.157; 3.P.169.166; 3.P.169.169; 3.P.169.172; 3.P.169.175; 3.P.169.240;
3.P.169.244; 3.P.172.228; 3.P.172.229; 3.P.172.230; 3.P.172.231; 3.P.172.236;
3.P.172.237; 3.P.172.238; 3.P.172.239; 3.P.172.154; 3.P.172.157; 3.P.172.166;
3.P.172.169; 3.P.172.172; 3.P.172.175; 3.P.172.240; 3.P.172.244; 3.P.175.228;
3.P.175.229; 3.P.175.230; 3.P.175.231; 3.P.175.236; 3.P.175.237; 3.P.175.238;
3.P.175.239; 3.P.175.154; 3.P.175.157; 3.P.175.166; 3.P.175.169; 3.P.175.172;
3.P.175.175; 3.P.175.240; 3.P.175.244; 3.P.240.228; 3.P.240.229; 3.P.240.230;

TABLE 100-continued

3.P.240.231; 3.P.240.236; 3.P.240.237; 3.P.240.238; 3.P.240.239; 3.P.240.154;
3.P.240.157; 3.P.240.166; 3.P.240.169; 3.P.240.172; 3.P.240.175; 3.P.240.240;
3.P.240.244; 3.P.244.228; 3.P.244.229; 3.P.244.230; 3.P.244.231; 3.P.244.236;
3.P.244.237; 3.P.244.238; 3.P.244.239; 3.P.244.154; 3.P.244.157; 3.P.244.166; 3.P.244.169;
3.P.244.172; 3.P.244.175; 3.P.244.240; 3.P.244.244;

Prodrugs of 3.U

3.U.228.228; 3.U.228.229; 3.U.228.230; 3.U.228.231; 3.U.228.236;
3.U.228.237; 3.U.228.238; 3.U.228.239; 3.U.228.154; 3.U.228.157;
3.U.228.166; 3.U.228.169; 3.U.228.172; 3.U.228.175; 3.U.228.240;
3.U.228.244; 3.U.229.228; 3.U.229.229; 3.U.229.230; 3.U.229.231;
3.U.229.236; 3.U.229.237; 3.U.229.238; 3.U.229.239; 3.U.229.154;
3.U.229.157; 3.U.229.166; 3.U.229.169; 3.U.229.172; 3.U.229.175;
3.U.229.240; 3.U.229.244; 3.U.230.228; 3.U.230.229; 3.U.230.230;
3.U.230.231; 3.U.230.236; 3.U.230.237; 3.U.230.238; 3.U.230.239;
3.U.230.154; 3.U.230.157; 3.U.230.166; 3.U.230.169; 3.U.230.172;
3.U.230.175; 3.U.230.240; 3.U.230.244; 3.U.231.228; 3.U.231.229;
3.U.231.230; 3.U.231.231; 3.U.231.236; 3.U.231.237; 3.U.231.238;
3.U.231.239; 3.U.231.154; 3.U.231.157; 3.U.231.166; 3.U.231.169;
3.U.231.172; 3.U.231.175; 3.U.231.240; 3.U.231.244; 3.U.236.228;
3.U.236.229; 3.U.236.230; 3.U.236.231; 3.U.236.236; 3.U.236.237;
3.U.236.238; 3.U.236.239; 3.U.236.154; 3.U.236.157; 3.U.236.166;
3.U.236.169; 3.U.236.172; 3.U.236.175; 3.U.236.240; 3.U.236.244;
3.U.237.228; 3.U.237.229; 3.U.237.230; 3.U.237.231; 3.U.237.236;
3.U.237.237; 3.U.237.238; 3.U.237.239; 3.U.237.154; 3.U.237.157;
3.U.237.166; 3.U.237.169; 3.U.237.172; 3.U.237.175; 3.U.237.240;
3.U.237.244; 3.U.238.228; 3.U.238.229; 3.U.238.230; 3.U.238.231;
3.U.238.236; 3.U.238.237; 3.U.238.238; 3.U.238.239; 3.U.238.154;
3.U.238.157; 3.U.238.166; 3.U.238.169; 3.U.238.172; 3.U.238.175;
3.U.238.240; 3.U.238.244; 3.U.239.228; 3.U.239.229; 3.U.239.230;
3.U.239.231; 3.U.239.236; 3.U.239.237; 3.U.239.238; 3.U.239.239;
3.U.239.154; 3.U.239.157; 3.U.239.166; 3.U.239.169; 3.U.239.172;
3.U.239.175; 3.U.239.240; 3.U.239.244; 3.U.154.228; 3.U.154.229;
3.U.154.230; 3.U.154.231; 3.U.154.236; 3.U.154.237; 3.U.154.238;
3.U.154.239; 3.U.154.154; 3.U.154.157; 3.U.154.166; 3.U.154.169;
3.U.154.172; 3.U.154.175; 3.U.154.240; 3.U.154.244; 3.U.157.228;
3.U.157.229; 3.U.157.230; 3.U.157.231; 3.U.157.236; 3.U.157.237;
3.U.157.238; 3.U.157.239; 3.U.157.154; 3.U.157.157; 3.U.157.166;
3.U.157.169; 3.U.157.172; 3.U.157.175; 3.U.157.240; 3.U.157.244;
3.U.166.228; 3.U.166.229; 3.U.166.230; 3.U.166.231; 3.U.166.236;
3.U.166.237; 3.U.166.238; 3.U.166.239; 3.U.166.154; 3.U.166.157;
3.U.166.166; 3.U.166.169; 3.U.166.172; 3.U.166.175; 3.U.166.240;
3.U.166.244; 3.U.169.228; 3.U.169.229; 3.U.169.230; 3.U.169.231;
3.U.169.236; 3.U.169.237; 3.U.169.238; 3.U.169.239; 3.U.169.154;
3.U.169.157; 3.U.169.166; 3.U.169.169; 3.U.169.172; 3.U.169.175;
3.U.169.240; 3.U.169.244; 3.U.172.228; 3.U.172.229; 3.U.172.230;
3.U.172.231; 3.U.172.236; 3.U.172.237; 3.U.172.238; 3.U.172.239;
3.U.172.154; 3.U.172.157; 3.U.172.166; 3.U.172.169; 3.U.172.172;
3.U.172.175; 3.U.172.240; 3.U.172.244; 3.U.175.228; 3.U.175.229;
3.U.175.230; 3.U.175.231; 3.U.175.236; 3.U.175.237; 3.U.175.238;
3.U.175.239; 3.U.175.154; 3.U.175.157; 3.U.175.166; 3.U.175.169;
3.U.175.172; 3.U.175.175; 3.U.175.240; 3.U.175.244; 3.U.240.228;
3.U.240.229; 3.U.240.230; 3.U.240.231; 3.U.240.236; 3.U.240.237;
3.U.240.238; 3.U.240.239; 3.U.240.154; 3.U.240.157; 3.U.240.166;
3.U.240.169; 3.U.240.172; 3.U.240.175; 3.U.240.240; 3.U.240.244;
3.U.244.228; 3.U.244.229; 3.U.244.230; 3.U.244.231; 3.U.244.236;
3.U.244.237; 3.U.244.238; 3.U.244.239; 3.U.244.154; 3.U.244.157;
3.U.244.166; 3.U.244.169; 3.U.244.172; 3.U.244.175; 3.U.244.240;
3.U.244.244;

Prodrugs of 3.W

3.W.228.228; 3.W.228.229; 3.W.228.230; 3.W.228.231; 3.W.228.236;
3.W.228.237; 3.W.228.238; 3.W.228.239; 3.W.228.154; 3.W.228.157;
3.W.228.166; 3.W.228.169; 3.W.228.172; 3.W.228.175; 3.W.228.240;
3.W.228.244; 3.W.229.228; 3.W.229.229; 3.W.229.230; 3.W.229.231;
3.W.229.236; 3.W.229.237; 3.W.229.238; 3.W.229.239; 3.W.229.154;
3.W.229.157; 3.W.229.166; 3.W.229.169; 3.W.229.172; 3.W.229.175;
3.W.229.240; 3.W.229.244; 3.W.230.228; 3.W.230.229; 3.W.230.230;
3.W.230.231; 3.W.230.236; 3.W.230.237; 3.W.230.238; 3.W.230.239;
3.W.230.154; 3.W.230.157; 3.W.230.166; 3.W.230.169; 3.W.230.172;
3.W.230.175; 3.W.230.240; 3.W.230.244; 3.W.231.228; 3.W.231.229;
3.W.231.230; 3.W.231.231; 3.W.231.236; 3.W.231.237; 3.W.231.238;
3.W.231.239; 3.W.231.154; 3.W.231.157; 3.W.231.166; 3.W.231.169;
3.W.231.172; 3.W.231.175; 3.W.231.240; 3.W.231.244; 3.W.236.228;
3.W.236.229; 3.W.236.230; 3.W.236.231; 3.W.236.236; 3.W.236.237;
3.W.236.238; 3.W.236.239; 3.W.236.154; 3.W.236.157; 3.W.236.166;
3.W.236.169; 3.W.236.172; 3.W.236.175; 3.W.236.240; 3.W.236.244;
3.W.237.228; 3.W.237.229; 3.W.237.230; 3.W.237.231; 3.W.237.236;
3.W.237.237; 3.W.237.238; 3.W.237.239; 3.W.237.154; 3.W.237.157;

TABLE 100-continued

3.W.237.166; 3.W.237.169; 3.W.237.172; 3.W.237.175; 3.W.237.240;
3.W.237.244; 3.W.238.228; 3.W.238.229; 3.W.238.230; 3.W.238.231;
3.W.238.236; 3.W.238.237; 3.W.238.238; 3.W.238.239; 3.W.238.154;
3.W.238.157; 3.W.238.166; 3.W.238.169; 3.W.238.172; 3.W.238.175;
3.W.238.240; 3.W.238.244; 3.W.239.228; 3.W.239.229; 3.W.239.230;
3.W.239.231; 3.W.239.236; 3.W.239.237; 3.W.239.238; 3.W.239.239;
3.W.239.154; 3.W.239.157; 3.W.239.166; 3.W.239.169; 3.W.239.172;
3.W.239.175; 3.W.239.240; 3.W.239.244; 3.W.154.228; 3.W.154.229;
3.W.154.230; 3.W.154.231; 3.W.154.236; 3.W.154.237; 3.W.154.238;
3.W.154.239; 3.W.154.154; 3.W.154.157; 3.W.154.166; 3.W.154.169;
3.W.154.172; 3.W.154.175; 3.W.154.240; 3.W.154.244; 3.W.157.228;
3.W.157.229; 3.W.157.230; 3.W.157.231; 3.W.157.236; 3.W.157.237;
3.W.157.238; 3.W.157.239; 3.W.157.154; 3.W.157.157; 3.W.157.166;
3.W.157.169; 3.W.157.172; 3.W.157.175; 3.W.157.240; 3.W.157.244;
3.W.166.228; 3.W.166.229; 3.W.166.230; 3.W.166.231; 3.W.166.236;
3.W.166.237; 3.W.166.238; 3.W.166.239; 3.W.166.154; 3.W.166.157;
3.W.166.166; 3.W.166.169; 3.W.166.172; 3.W.166.175; 3.W.166.240;
3.W.166.244; 3.W.169.228; 3.W.169.229; 3.W.169.230; 3.W.169.231;
3.W.169.236; 3.W.169.237; 3.W.169.238; 3.W.169.239; 3.W.169.154;
3.W.169.157; 3.W.169.166; 3.W.169.169; 3.W.169.172; 3.W.169.175;
3.W.169.240; 3.W.169.244; 3.W.172.228; 3.W.172.229; 3.W.172.230;
3.W.172.231; 3.W.172.236; 3.W.172.237; 3.W.172.238; 3.W.172.239;
3.W.172.154; 3.W.172.157; 3.W.172.166; 3.W.172.169; 3.W.172.172;
3.W.172.175; 3.W.172.240; 3.W.172.244; 3.W.175.228; 3.W.175.229;
3.W.175.230; 3.W.175.231; 3.W.175.236; 3.W.175.237; 3.W.175.238;
3.W.175.239; 3.W.175.154; 3.W.175.157; 3.W.175.166; 3.W.175.169;
3.W.175.172; 3.W.175.175; 3.W.175.240; 3.W.175.244; 3.W.240.228;
3.W.240.229; 3.W.240.230; 3.W.240.231; 3.W.240.236; 3.W.240.237;
3.W.240.238; 3.W.240.239; 3.W.240.154; 3.W.240.157; 3.W.240.166;
3.W.240.169; 3.W.240.172; 3.W.240.175; 3.W.240.240; 3.W.240.244;
3.W.244.228; 3.W.244.229; 3.W.244.230; 3.W.244.231; 3.W.244.236;
3.W.244.237; 3.W.244.238; 3.W.244.239; 3.W.244.154; 3.W.244.157;
3.W.244.166; 3.W.244.169; 3.W.244.172; 3.W.244.175; 3.W.244.240;
3.W.244.244;

Prodrugs of 3.Y

3.Y.228.228; 3.Y.228.229; 3.Y.228.230; 3.Y.228.231; 3.Y.228.236;
3.Y.228.237; 3.Y.228.238; 3.Y.228.239; 3.Y.228.154; 3.Y.228.157; 3.Y.228.166;
3.Y.228.169; 3.Y.228.172; 3.Y.228.175; 3.Y.228.240; 3.Y.228.244; 3.Y.229.228;
3.Y.229.229; 3.Y.229.230; 3.Y.229.231; 3.Y.229.236; 3.Y.229.237; 3.Y.229.238;
3.Y.229.239; 3.Y.229.154; 3.Y.229.157; 3.Y.229.166; 3.Y.229.169; 3.Y.229.172;
3.Y.229.175; 3.Y.229.240; 3.Y.229.244; 3.Y.230.228; 3.Y.230.229; 3.Y.230.230;
3.Y.230.231; 3.Y.230.236; 3.Y.230.237; 3.Y.230.238; 3.Y.230.239; 3.Y.230.154;
3.Y.230.157; 3.Y.230.166; 3.Y.230.169; 3.Y.230.172; 3.Y.230.175; 3.Y.230.240;
3.Y.230.244; 3.Y.231.228; 3.Y.231.229; 3.Y.231.230; 3.Y.231.231; 3.Y.231.236;
3.Y.231.237; 3.Y.231.238; 3.Y.231.239; 3.Y.231.154; 3.Y.231.157; 3.Y.231.166;
3.Y.231.169; 3.Y.231.172; 3.Y.231.175; 3.Y.231.240; 3.Y.231.244; 3.Y.236.228;
3.Y.236.229; 3.Y.236.230; 3.Y.236.231; 3.Y.236.236; 3.Y.236.237; 3.Y.236.238;
3.Y.236.239; 3.Y.236.154; 3.Y.236.157; 3.Y.236.166; 3.Y.236.169; 3.Y.236.172;
3.Y.236.175; 3.Y.236.240; 3.Y.236.244; 3.Y.237.228; 3.Y.237.229; 3.Y.237.230;
3.Y.237.231; 3.Y.237.236; 3.Y.237.237; 3.Y.237.238; 3.Y.237.239; 3.Y.237.154;
3.Y.237.157; 3.Y.237.166; 3.Y.237.169; 3.Y.237.172; 3.Y.237.175; 3.Y.237.240;
3.Y.237.244; 3.Y.238.228; 3.Y.238.229; 3.Y.238.230; 3.Y.238.231; 3.Y.238.236;
3.Y.238.237; 3.Y.238.238; 3.Y.238.239; 3.Y.238.154; 3.Y.238.157; 3.Y.238.166;
3.Y.238.169; 3.Y.238.172; 3.Y.238.175; 3.Y.238.240; 3.Y.238.244; 3.Y.239.228;
3.Y.239.229; 3.Y.239.230; 3.Y.239.231; 3.Y.239.236; 3.Y.239.237; 3.Y.239.238;
3.Y.239.239; 3.Y.239.154; 3.Y.239.157; 3.Y.239.166; 3.Y.239.169; 3.Y.239.172;
3.Y.239.175; 3.Y.239.240; 3.Y.239.244; 3.Y.154.228; 3.Y.154.229; 3.Y.154.230;
3.Y.154.231; 3.Y.154.236; 3.Y.154.237; 3.Y.154.238; 3.Y.154.239; 3.Y.154.154;
3.Y.154.157; 3.Y.154.166; 3.Y.154.169; 3.Y.154.172; 3.Y.154.175; 3.Y.154.240;
3.Y.154.244; 3.Y.157.228; 3.Y.157.229; 3.Y.157.230; 3.Y.157.231; 3.Y.157.236;
3.Y.157.237; 3.Y.157.238; 3.Y.157.239; 3.Y.157.154; 3.Y.157.157; 3.Y.157.166;
3.Y.157.169; 3.Y.157.172; 3.Y.157.175; 3.Y.157.240; 3.Y.157.244; 3.Y.166.228;
3.Y.166.229; 3.Y.166.230; 3.Y.166.231; 3.Y.166.236; 3.Y.166.237; 3.Y.166.238;
3.Y.166.239; 3.Y.166.154; 3.Y.166.157; 3.Y.166.166; 3.Y.166.169; 3.Y.166.172;
3.Y.166.175; 3.Y.166.240; 3.Y.166.244; 3.Y.169.228; 3.Y.169.229; 3.Y.169.230;
3.Y.169.231; 3.Y.169.236; 3.Y.169.237; 3.Y.169.238; 3.Y.169.239; 3.Y.169.154;
3.Y.169.157; 3.Y.169.166; 3.Y.169.169; 3.Y.169.172; 3.Y.169.175; 3.Y.169.240;
3.Y.169.244; 3.Y.172.228; 3.Y.172.229; 3.Y.172.230; 3.Y.172.231; 3.Y.172.236;
3.Y.172.237; 3.Y.172.238; 3.Y.172.239; 3.Y.172.154; 3.Y.172.157; 3.Y.172.166;
3.Y.172.169; 3.Y.172.172; 3.Y.172.175; 3.Y.172.240; 3.Y.172.244; 3.Y.175.228;
3.Y.175.229; 3.Y.175.230; 3.Y.175.231; 3.Y.175.236; 3.Y.175.237; 3.Y.175.238;
3.Y.175.239; 3.Y.175.154; 3.Y.175.157; 3.Y.175.166; 3.Y.175.169; 3.Y.175.172;
3.Y.175.175; 3.Y.175.240; 3.Y.175.244; 3.Y.240.228; 3.Y.240.229; 3.Y.240.230;
3.Y.240.231; 3.Y.240.236; 3.Y.240.237; 3.Y.240.238; 3.Y.240.239; 3.Y.240.154;
3.Y.240.157; 3.Y.240.166; 3.Y.240.169; 3.Y.240.172; 3.Y.240.175; 3.Y.240.240;
3.Y.240.244; 3.Y.244.228; 3.Y.244.229; 3.Y.244.230; 3.Y.244.231; 3.Y.244.236;
3.Y.244.237; 3.Y.244.238; 3.Y.244.239; 3.Y.244.154; 3.Y.244.157; 3.Y.244.166;
3.Y.244.169; 3.Y.244.172; 3.Y.244.175; 3.Y.244.240; 3.Y.244.244;

TABLE 100-continued

Prodrugs of 4.B

4.B.228.228; 4.B.228.229; 4.B.228.230; 4.B.228.231; 4.B.228.236;
4.B.228.237; 4.B.228.238; 4.B.228.239; 4.B.228.154; 4.B.228.157; 4.B.228.166;
4.B.228.169; 4.B.228.172; 4.B.228.175; 4.B.228.240; 4.B.228.244; 4.B.229.228;
4.B.229.229; 4.B.229.230; 4.B.229.231; 4.B.229.236; 4.B.229.237; 4.B.229.238;
4.B.229.239; 4.B.229.154; 4.B.229.157; 4.B.229.166; 4.B.229.169; 4.B.229.172;
4.B.229.175; 4.B.229.240; 4.B.229.244; 4.B.230.228; 4.B.230.229; 4.B.230.230;
4.B.230.231; 4.B.230.236; 4.B.230.237; 4.B.230.238; 4.B.230.239; 4.B.230.154;
4.B.230.157; 4.B.230.166; 4.B.230.169; 4.B.230.172; 4.B.230.175; 4.B.230.240;
4.B.230.244; 4.B.231.228; 4.B.231.229; 4.B.231.230; 4.B.231.231; 4.B.231.236;
4.B.231.237; 4.B.231.238; 4.B.231.239; 4.B.231.154; 4.B.231.157; 4.B.231.166;
4.B.231.169; 4.B.231.172; 4.B.231.175; 4.B.231.240; 4.B.231.244; 4.B.236.228;
4.B.236.229; 4.B.236.230; 4.B.236.231; 4.B.236.236; 4.B.236.237; 4.B.236.238;
4.B.236.239; 4.B.236.154; 4.B.236.157; 4.B.236.166; 4.B.236.169; 4.B.236.172;
4.B.236.175; 4.B.236.240; 4.B.236.244; 4.B.237.228; 4.B.237.229; 4.B.237.230;
4.B.237.231; 4.B.237.236; 4.B.237.237; 4.B.237.238; 4.B.237.239; 4.B.237.154;
4.B.237.157; 4.B.237.166; 4.B.237.169; 4.B.237.172; 4.B.237.175; 4.B.237.240;
4.B.237.244; 4.B.238.228; 4.B.238.229; 4.B.238.230; 4.B.238.231; 4.B.238.236;
4.B.238.237; 4.B.238.238; 4.B.238.239; 4.B.238.154; 4.B.238.157; 4.B.238.166;
4.B.238.169; 4.B.238.172; 4.B.238.175; 4.B.238.240; 4.B.238.244; 4.B.239.228;
4.B.239.229; 4.B.239.230; 4.B.239.231; 4.B.239.236; 4.B.239.237; 4.B.239.238;
4.B.239.239; 4.B.239.154; 4.B.239.157; 4.B.239.166; 4.B.239.169; 4.B.239.172;
4.B.239.175; 4.B.239.240; 4.B.239.244; 4.B.154.228; 4.B.154.229; 4.B.154.230;
4.B.154.231; 4.B.154.236; 4.B.154.237; 4.B.154.238; 4.B.154.239; 4.B.154.154;
4.B.154.157; 4.B.154.166; 4.B.154.169; 4.B.154.172; 4.B.154.175; 4.B.154.240;
4.B.154.244; 4.B.157.228; 4.B.157.229; 4.B.157.230; 4.B.157.231; 4.B.157.236;
4.B.157.237; 4.B.157.238; 4.B.157.239; 4.B.157.154; 4.B.157.157; 4.B.157.166;
4.B.157.169; 4.B.157.172; 4.B.157.175; 4.B.157.240; 4.B.157.244; 4.B.166.228;
4.B.166.229; 4.B.166.230; 4.B.166.231; 4.B.166.236; 4.B.166.237; 4.B.166.238;
4.B.166.239; 4.B.166.154; 4.B.166.157; 4.B.166.166; 4.B.166.169; 4.B.166.172;
4.B.166.175; 4.B.166.240; 4.B.166.244; 4.B.169.228; 4.B.169.229; 4.B.169.230;
4.B.169.231; 4.B.169.236; 4.B.169.237; 4.B.169.238; 4.B.169.239; 4.B.169.154;
4.B.169.157; 4.B.169.166; 4.B.169.169; 4.B.169.172; 4.B.169.175; 4.B.169.240;
4.B.169.244; 4.B.172.228; 4.B.172.229; 4.B.172.230; 4.B.172.231; 4.B.172.236;
4.B.172.237; 4.B.172.238; 4.B.172.239; 4.B.172.154; 4.B.172.157; 4.B.172.166;
4.B.172.169; 4.B.172.172; 4.B.172.175; 4.B.172.240; 4.B.172.244; 4.B.175.228;
4.B.175.229; 4.B.175.230; 4.B.175.231; 4.B.175.236; 4.B.175.237; 4.B.175.238;
4.B.175.239; 4.B.175.154; 4.B.175.157; 4.B.175.166; 4.B.175.169; 4.B.175.172;
4.B.175.175; 4.B.175.240; 4.B.175.244; 4.B.240.228; 4.B.240.229; 4.B.240.230;
4.B.240.231; 4.B.240.236; 4.B.240.237; 4.B.240.238; 4.B.240.239; 4.B.240.154;
4.B.240.157; 4.B.240.166; 4.B.240.169; 4.B.240.172; 4.B.240.175; 4.B.240.240;
4.B.240.244; 4.B.244.228; 4.B.244.229; 4.B.244.230; 4.B.244.231; 4.B.244.236;
4.B.244.237; 4.B.244.238; 4.B.244.239; 4.B.244.154; 4.B.244.157; 4.B.244.166; 4.B.244.169;
4.B.244.172; 4.B.244.175; 4.B.244.240; 4.B.244.244;

Prodrugs of 4.D

4.D.228.228; 4.D.228.229; 4.D.228.230; 4.D.228.231; 4.D.228.236;
4.D.228.237; 4.D.228.238; 4.D.228.239; 4.D.228.154; 4.D.228.157;
4.D.228.166; 4.D.228.169; 4.D.228.172; 4.D.228.175; 4.D.228.240;
4.D.228.244; 4.D.229.228; 4.D.229.229; 4.D.229.230; 4.D.229.231;
4.D.229.236; 4.D.229.237; 4.D.229.238; 4.D.229.239; 4.D.229.154;
4.D.229.157; 4.D.229.166; 4.D.229.169; 4.D.229.172; 4.D.229.175;
4.D.229.240; 4.D.229.244; 4.D.230.228; 4.D.230.229; 4.D.230.230;
4.D.230.231; 4.D.230.236; 4.D.230.237; 4.D.230.238; 4.D.230.239;
4.D.230.154; 4.D.230.157; 4.D.230.166; 4.D.230.169; 4.D.230.172;
4.D.230.175; 4.D.230.240; 4.D.230.244; 4.D.231.228; 4.D.231.229;
4.D.231.230; 4.D.231.231; 4.D.231.236; 4.D.231.237; 4.D.231.238;
4.D.231.239; 4.D.231.154; 4.D.231.157; 4.D.231.166; 4.D.231.169;
4.D.231.172; 4.D.231.175; 4.D.231.240; 4.D.231.244; 4.D.236.228;
4.D.236.229; 4.D.236.230; 4.D.236.231; 4.D.236.236; 4.D.236.237;
4.D.236.238; 4.D.236.239; 4.D.236.154; 4.D.236.157; 4.D.236.166;
4.D.236.169; 4.D.236.172; 4.D.236.175; 4.D.236.240; 4.D.236.244;
4.D.237.228; 4.D.237.229; 4.D.237.230; 4.D.237.231; 4.D.237.236;
4.D.237.237; 4.D.237.238; 4.D.237.239; 4.D.237.154; 4.D.237.157;
4.D.237.166; 4.D.237.169; 4.D.237.172; 4.D.237.175; 4.D.237.240;
4.D.237.244; 4.D.238.228; 4.D.238.229; 4.D.238.230; 4.D.238.231;
4.D.238.236; 4.D.238.237; 4.D.238.238; 4.D.238.239; 4.D.238.154;
4.D.238.157; 4.D.238.166; 4.D.238.169; 4.D.238.172; 4.D.238.175;
4.D.238.240; 4.D.238.244; 4.D.239.228; 4.D.239.229; 4.D.239.230;
4.D.239.231; 4.D.239.236; 4.D.239.237; 4.D.239.238; 4.D.239.239;
4.D.239.154; 4.D.239.157; 4.D.239.166; 4.D.239.169; 4.D.239.172;
4.D.239.175; 4.D.239.240; 4.D.239.244; 4.D.154.228; 4.D.154.229;
4.D.154.230; 4.D.154.231; 4.D.154.236; 4.D.154.237; 4.D.154.238;
4.D.154.239; 4.D.154.154; 4.D.154.157; 4.D.154.166; 4.D.154.169;
4.D.154.172; 4.D.154.175; 4.D.154.240; 4.D.154.244; 4.D.157.228;
4.D.157.229; 4.D.157.230; 4.D.157.231; 4.D.157.236; 4.D.157.237;
4.D.157.238; 4.D.157.239; 4.D.157.154; 4.D.157.157; 4.D.157.166;
4.D.157.169; 4.D.157.172; 4.D.157.175; 4.D.157.240; 4.D.157.244;

TABLE 100-continued

4.D.166.228; 4.D.166.229; 4.D.166.230; 4.D.166.231; 4.D.166.236;
4.D.166.237; 4.D.166.238; 4.D.166.239; 4.D.166.154; 4.D.166.157;
4.D.166.166; 4.D.166.169; 4.D.166.172; 4.D.166.175; 4.D.166.240;
4.D.166.244; 4.D.169.228; 4.D.169.229; 4.D.169.230; 4.D.169.231;
4.D.169.236; 4.D.169.237; 4.D.169.238; 4.D.169.239; 4.D.169.154;
4.D.169.157; 4.D.169.166; 4.D.169.169; 4.D.169.172; 4.D.169.175;
4.D.169.240; 4.D.169.244; 4.D.172.228; 4.D.172.229; 4.D.172.230;
4.D.172.231; 4.D.172.236; 4.D.172.237; 4.D.172.238; 4.D.172.239;
4.D.172.154; 4.D.172.157; 4.D.172.166; 4.D.172.169; 4.D.172.172;
4.D.172.175; 4.D.172.240; 4.D.172.244; 4.D.175.228; 4.D.175.229;
4.D.175.230; 4.D.175.231; 4.D.175.236; 4.D.175.237; 4.D.175.238;
4.D.175.239; 4.D.175.154; 4.D.175.157; 4.D.175.166; 4.D.175.169;
4.D.175.172; 4.D.175.175; 4.D.175.240; 4.D.175.244; 4.D.240.228;
4.D.240.229; 4.D.240.230; 4.D.240.231; 4.D.240.236; 4.D.240.237;
4.D.240.238; 4.D.240.239; 4.D.240.154; 4.D.240.157; 4.D.240.166;
4.D.240.169; 4.D.240.172; 4.D.240.175; 4.D.240.240; 4.D.240.244;
4.D.244.228; 4.D.244.229; 4.D.244.230; 4.D.244.231; 4.D.244.236;
4.D.244.237; 4.D.244.238; 4.D.244.239; 4.D.244.154; 4.D.244.157;
4.D.244.166; 4.D.244.169; 4.D.244.172; 4.D.244.175; 4.D.244.240;
4.D.244.244;
Prodrugs of 4.E 4.E.228.228; 4.E.228.229; 4.E.228.230; 4.E.228.231; 4.E.228.236;
4.E.228.237; 4.E.228.238; 4.E.228.239; 4.E.228.154; 4.E.228.157; 4.E.228.166;
4.E.228.169; 4.E.228.172; 4.E.228.175; 4.E.228.240; 4.E.228.244; 4.E.229.228;
4.E.229.229; 4.E.229.230; 4.E.229.231; 4.E.229.236; 4.E.229.237; 4.E.229.238;
4.E.229.239; 4.E.229.154; 4.E.229.157; 4.E.229.166; 4.E.229.169; 4.E.229.172;
4.E.229.175; 4.E.229.240; 4.E.229.244; 4.E.230.228; 4.E.230.229; 4.E.230.230;
4.E.230.231; 4.E.230.236; 4.E.230.237; 4.E.230.238; 4.E.230.239; 4.E.230.154;
4.E.230.157; 4.E.230.166; 4.E.230.169; 4.E.230.172; 4.E.230.175; 4.E.230.240;
4.E.230.244; 4.E.231.228; 4.E.231.229; 4.E.231.230; 4.E.231.231; 4.E.231.236;
4.E.231.237; 4.E.231.238; 4.E.231.239; 4.E.231.154; 4.E.231.157; 4.E.231.166;
4.E.231.169; 4.E.231.172; 4.E.231.175; 4.E.231.240; 4.E.231.244; 4.E.236.228;
4.E.236.229; 4.E.236.230; 4.E.236.231; 4.E.236.236; 4.E.236.237; 4.E.236.238;
4.E.236.239; 4.E.236.154; 4.E.236.157; 4.E.236.166; 4.E.236.169; 4.E.236.172;
4.E.236.175; 4.E.236.240; 4.E.236.244; 4.E.237.228; 4.E.237.229; 4.E.237.230;
4.E.237.231; 4.E.237.236; 4.E.237.237; 4.E.237.238; 4.E.237.239; 4.E.237.154;
4.E.237.157; 4.E.237.166; 4.E.237.169; 4.E.237.172; 4.E.237.175; 4.E.237.240;
4.E.237.244; 4.E.238.228; 4.E.238.229; 4.E.238.230; 4.E.238.231; 4.E.238.236;
4.E.238.237; 4.E.238.238; 4.E.238.239; 4.E.238.154; 4.E.238.157; 4.E.238.166;
4.E.238.169; 4.E.238.172; 4.E.238.175; 4.E.238.240; 4.E.238.244; 4.E.239.228;
4.E.239.229; 4.E.239.230; 4.E.239.231; 4.E.239.236; 4.E.239.237; 4.E.239.238;
4.E.239.239; 4.E.239.154; 4.E.239.157; 4.E.239.166; 4.E.239.169; 4.E.239.172;
4.E.239.175; 4.E.239.240; 4.E.239.244; 4.E.154.228; 4.E.154.229; 4.E.154.230;
4.E.154.231; 4.E.154.236; 4.E.154.237; 4.E.154.238; 4.E.154.239; 4.E.154.154;
4.E.154.157; 4.E.154.166; 4.E.154.169; 4.E.154.172; 4.E.154.175; 4.E.154.240;
4.E.154.244; 4.E.157.228; 4.E.157.229; 4.E.157.230; 4.E.157.231; 4.E.157.236;
4.E.157.237; 4.E.157.238; 4.E.157.239; 4.E.157.154; 4.E.157.157; 4.E.157.166;
4.E.157.169; 4.E.157.172; 4.E.157.175; 4.E.157.240; 4.E.157.244; 4.E.166.228;
4.E.166.229; 4.E.166.230; 4.E.166.231; 4.E.166.236; 4.E.166.237; 4.E.166.238;
4.E.166.239; 4.E.166.154; 4.E.166.157; 4.E.166.166; 4.E.166.169; 4.E.166.172;
4.E.166.175; 4.E.166.240; 4.E.166.244; 4.E.169.228; 4.E.169.229; 4.E.169.230;
4.E.169.231; 4.E.169.236; 4.E.169.237; 4.E.169.238; 4.E.169.239; 4.E.169.154;
4.E.169.157; 4.E.169.166; 4.E.169.169; 4.E.169.172; 4.E.169.175; 4.E.169.240;
4.E.169.244; 4.E.172.228; 4.E.172.229; 4.E.172.230; 4.E.172.231; 4.E.172.236;
4.E.172.237; 4.E.172.238; 4.E.172.239; 4.E.172.154; 4.E.172.157; 4.E.172.166;
4.E.172.169; 4.E.172.172; 4.E.172.175; 4.E.172.240; 4.E.172.244; 4.E.175.228;
4.E.175.229; 4.E.175.230; 4.E.175.231; 4.E.175.236; 4.E.175.237; 4.E.175.238;
4.E.175.239; 4.E.175.154; 4.E.175.157; 4.E.175.166; 4.E.175.169; 4.E.175.172;
4.E.175.175; 4.E.175.240; 4.E.175.244; 4.E.240.228; 4.E.240.229; 4.E.240.230;
4.E.240.231; 4.E.240.236; 4.E.240.237; 4.E.240.238; 4.E.240.239; 4.E.240.154;
4.E.240.157; 4.E.240.166; 4.E.240.169; 4.E.240.172; 4.E.240.175; 4.E.240.240;
4.E.240.244; 4.E.244.228; 4.E.244.229; 4.E.244.230; 4.E.244.231; 4.E.244.236;
4.E.244.237; 4.E.244.238; 4.E.244.239; 4.E.244.154; 4.E.244.157; 4.E.244.166;
4.E.244.169; 4.E.244.172; 4.E.244.175; 4.E.244.240; 4.E.244.244;
Prodrugs of 4.G 4.G.228.228; 4.G.228.229; 4.G.228.230; 4.G.228.231; 4.G.228.236;
4.G.228.237; 4.G.228.238; 4.G.228.239; 4.G.228.154; 4.G.228.157;
4.G.228.166; 4.G.228.169; 4.G.228.172; 4.G.228.175; 4.G.228.240;
4.G.228.244; 4.G.229.228; 4.G.229.229; 4.G.229.230; 4.G.229.231;
4.G.229.236; 4.G.229.237; 4.G.229.238; 4.G.229.239; 4.G.229.154;
4.G.229.157; 4.G.229.166; 4.G.229.169; 4.G.229.172; 4.G.229.175;
4.G.229.240; 4.G.229.244; 4.G.230.228; 4.G.230.229; 4.G.230.230;
4.G.230.231; 4.G.230.236; 4.G.230.237; 4.G.230.238; 4.G.230.239;
4.G.230.154; 4.G.230.157; 4.G.230.166; 4.G.230.169; 4.G.230.172;
4.G.230.175; 4.G.230.240; 4.G.230.244; 4.G.231.228; 4.G.231.229;
4.G.231.230; 4.G.231.231; 4.G.231.236; 4.G.231.237; 4.G.231.238;
4.G.231.239; 4.G.231.154; 4.G.231.157; 4.G.231.166; 4.G.231.169;

TABLE 100-continued

4.G.231.172; 4.G.231.175; 4.G.231.240; 4.G.231.244; 4.G.236.228;
4.G.236.229; 4.G.236.230; 4.G.236.231; 4.G.236.236; 4.G.236.237;
4.G.236.238; 4.G.236.239; 4.G.236.154; 4.G.236.157; 4.G.236.166;
4.G.236.169; 4.G.236.172; 4.G.236.175; 4.G.236.240; 4.G.236.244;
4.G.237.228; 4.G.237.229; 4.G.237.230; 4.G.237.231; 4.G.237.236;
4.G.237.237; 4.G.237.238; 4.G.237.239; 4.G.237.154; 4.G.237.157;
4.G.237.166; 4.G.237.169; 4.G.237.172; 4.G.237.175; 4.G.237.240;
4.G.237.244; 4.G.238.228; 4.G.238.229; 4.G.238.230; 4.G.238.231;
4.G.238.236; 4.G.238.237; 4.G.238.238; 4.G.238.239; 4.G.238.154;
4.G.238.157; 4.G.238.166; 4.G.238.169; 4.G.238.172; 4.G.238.175;
4.G.238.240; 4.G.238.244; 4.G.239.228; 4.G.239.229; 4.G.239.230;
4.G.239.231; 4.G.239.236; 4.G.239.237; 4.G.239.238; 4.G.239.239;
4.G.239.154; 4.G.239.157; 4.G.239.166; 4.G.239.169; 4.G.239.172;
4.G.239.175; 4.G.239.240; 4.G.239.244; 4.G.154.228; 4.G.154.229;
4.G.154.230; 4.G.154.231; 4.G.154.236; 4.G.154.237; 4.G.154.238;
4.G.154.239; 4.G.154.154; 4.G.154.157; 4.G.154.166; 4.G.154.169;
4.G.154.172; 4.G.154.175; 4.G.154.240; 4.G.154.244; 4.G.157.228;
4.G.157.229; 4.G.157.230; 4.G.157.231; 4.G.157.236; 4.G.157.237;
4.G.157.238; 4.G.157.239; 4.G.157.154; 4.G.157.157; 4.G.157.166;
4.G.157.169; 4.G.157.172; 4.G.157.175; 4.G.157.240; 4.G.157.244;
4.G.166.228; 4.G.166.229; 4.G.166.230; 4.G.166.231; 4.G.166.236;
4.G.166.237; 4.G.166.238; 4.G.166.239; 4.G.166.154; 4.G.166.157;
4.G.166.166; 4.G.166.169; 4.G.166.172; 4.G.166.175; 4.G.166.240;
4.G.166.244; 4.G.169.228; 4.G.169.229; 4.G.169.230; 4.G.169.231;
4.G.169.236; 4.G.169.237; 4.G.169.238; 4.G.169.239; 4.G.169.154;
4.G.169.157; 4.G.169.166; 4.G.169.169; 4.G.169.172; 4.G.169.175;
4.G.169.240; 4.G.169.244; 4.G.172.228; 4.G.172.229; 4.G.172.230;
4.G.172.231; 4.G.172.236; 4.G.172.237; 4.G.172.238; 4.G.172.239;
4.G.172.154; 4.G.172.157; 4.G.172.166; 4.G.172.169; 4.G.172.172;
4.G.172.175; 4.G.172.240; 4.G.172.244; 4.G.175.228; 4.G.175.229;
4.G.175.230; 4.G.175.231; 4.G.175.236; 4.G.175.237; 4.G.175.238;
4.G.175.239; 4.G.175.154; 4.G.175.157; 4.G.175.166; 4.G.175.169;
4.G.175.172; 4.G.175.175; 4.G.175.240; 4.G.175.244; 4.G.240.228;
4.G.240.229; 4.G.240.230; 4.G.240.231; 4.G.240.236; 4.G.240.237;
4.G.240.238; 4.G.240.239; 4.G.240.154; 4.G.240.157; 4.G.240.166;
4.G.240.169; 4.G.240.172; 4.G.240.175; 4.G.240.240; 4.G.240.244;
4.G.244.228; 4.G.244.229; 4.G.244.230; 4.G.244.231; 4.G.244.236;
4.G.244.237; 4.G.244.238; 4.G.244.239; 4.G.244.154; 4.G.244.157;
4.G.244.166; 4.G.244.169; 4.G.244.172; 4.G.244.175; 4.G.244.240;
4.G.244.244;

Prodrugs of 4.I

4.I.228.228; 4.I.228.229; 4.I.228.230; 4.I.228.231; 4.I.228.236; 4.I.228.237;
4.I.228.238; 4.I.228.239; 4.I.228.154; 4.I.228.157; 4.I.228.166; 4.I.228.169;
4.I.228.172; 4.I.228.175; 4.I.228.240; 4.I.228.244; 4.I.229.228; 4.I.229.229;
4.I.229.230; 4.I.229.231; 4.I.229.236; 4.I.229.237; 4.I.229.238; 4.I.229.239;
4.I.229.154; 4.I.229.157; 4.I.229.166; 4.I.229.169; 4.I.229.172; 4.I.229.175;
4.I.229.240; 4.I.229.244; 4.I.230.228; 4.I.230.229; 4.I.230.230; 4.I.230.231;
4.I.230.236; 4.I.230.237; 4.I.230.238; 4.I.230.239; 4.I.230.154; 4.I.230.157;
4.I.230.166; 4.I.230.169; 4.I.230.172; 4.I.230.175; 4.I.230.240; 4.I.230.244;
4.I.231.228; 4.I.231.229; 4.I.231.230; 4.I.231.231; 4.I.231.236; 4.I.231.237;
4.I.231.238; 4.I.231.239; 4.I.231.154; 4.I.231.157; 4.I.231.166; 4.I.231.169;
4.I.231.172; 4.I.231.175; 4.I.231.240; 4.I.231.244; 4.I.236.228; 4.I.236.229;
4.I.236.230; 4.I.236.231; 4.I.236.236; 4.I.236.237; 4.I.236.238; 4.I.236.239;
4.I.236.154; 4.I.236.157; 4.I.236.166; 4.I.236.169; 4.I.236.172; 4.I.236.175;
4.I.236.240; 4.I.236.244; 4.I.237.228; 4.I.237.229; 4.I.237.230; 4.I.237.231;
4.I.237.236; 4.I.237.237; 4.I.237.238; 4.I.237.239; 4.I.237.154; 4.I.237.157;
4.I.237.166; 4.I.237.169; 4.I.237.172; 4.I.237.175; 4.I.237.240; 4.I.237.244;
4.I.238.228; 4.I.238.229; 4.I.238.230; 4.I.238.231; 4.I.238.236; 4.I.238.237;
4.I.238.238; 4.I.238.239; 4.I.238.154; 4.I.238.157; 4.I.238.166; 4.I.238.169;
4.I.238.172; 4.I.238.175; 4.I.238.240; 4.I.238.244; 4.I.239.228; 4.I.239.229;
4.I.239.230; 4.I.239.231; 4.I.239.236; 4.I.239.237; 4.I.239.238; 4.I.239.239;
4.I.239.154; 4.I.239.157; 4.I.239.166; 4.I.239.169; 4.I.239.172; 4.I.239.175;
4.I.239.240; 4.I.239.244; 4.I.154.228; 4.I.154.229; 4.I.154.230; 4.I.154.231;
4.I.154.236; 4.I.154.237; 4.I.154.238; 4.I.154.239; 4.I.154.154; 4.I.154.157;
4.I.154.166; 4.I.154.169; 4.I.154.172; 4.I.154.175; 4.I.154.240; 4.I.154.244;
4.I.157.228; 4.I.157.229; 4.I.157.230; 4.I.157.231; 4.I.157.236; 4.I.157.237;
4.I.157.238; 4.I.157.239; 4.I.157.154; 4.I.157.157; 4.I.157.166; 4.I.157.169;
4.I.157.172; 4.I.157.175; 4.I.157.240; 4.I.157.244; 4.I.166.228; 4.I.166.229;
4.I.166.230; 4.I.166.231; 4.I.166.236; 4.I.166.237; 4.I.166.238; 4.I.166.239;
4.I.166.154; 4.I.166.157; 4.I.166.166; 4.I.166.169; 4.I.166.172; 4.I.166.175;
4.I.166.240; 4.I.166.244; 4.I.169.228; 4.I.169.229; 4.I.169.230; 4.I.169.231;
4.I.169.236; 4.I.169.237; 4.I.169.238; 4.I.169.239; 4.I.169.154; 4.I.169.157;
4.I.169.166; 4.I.169.169; 4.I.169.172; 4.I.169.175; 4.I.169.240; 4.I.169.244;
4.I.172.228; 4.I.172.229; 4.I.172.230; 4.I.172.231; 4.I.172.236; 4.I.172.237;
4.I.172.238; 4.I.172.239; 4.I.172.154; 4.I.172.157; 4.I.172.166; 4.I.172.169;
4.I.172.172; 4.I.172.175; 4.I.172.240; 4.I.172.244; 4.I.175.228; 4.I.175.229;
4.I.175.230; 4.I.175.231; 4.I.175.236; 4.I.175.237; 4.I.175.238; 4.I.175.239;
4.I.175.154; 4.I.175.157; 4.I.175.166; 4.I.175.169; 4.I.175.172; 4.I.175.175;

TABLE 100-continued

4.I.175.240; 4.I.175.244; 4.I.240.228; 4.I.240.229; 4.I.240.230; 4.I.240.231;
4.I.240.236; 4.I.240.237; 4.I.240.238; 4.I.240.239; 4.I.240.154; 4.I.240.157;
4.I.240.166; 4.I.240.169; 4.I.240.172; 4.I.240.175; 4.I.240.240; 4.I.240.244;
4.I.244.228; 4.I.244.229; 4.I.244.230; 4.I.244.231; 4.I.244.236; 4.I.244.237;
4.I.244.238; 4.I.244.239; 4.I.244.154; 4.I.244.157; 4.I.244.166; 4.I.244.169;
4.I.244.172; 4.I.244.175; 4.I.244.240; 4.I.244.244;

Prodrugs of 4.J

4.J.228.228; 4.J.228.229; 4.J.228.230; 4.J.228.231; 4.J.228.236; 4.J.228.237;
4.J.228.238; 4.J.228.239; 4.J.228.154; 4.J.228.157; 4.J.228.166; 4.J.228.169;
4.J.228.172; 4.J.228.175; 4.J.228.240; 4.J.228.244; 4.J.229.228; 4.J.229.229;
4.J.229.230; 4.J.229.231; 4.J.229.236; 4.J.229.237; 4.J.229.238; 4.J.229.239;
4.J.229.154; 4.J.229.157; 4.J.229.166; 4.J.229.169; 4.J.229.172; 4.J.229.175;
4.J.229.240; 4.J.229.244; 4.J.230.228; 4.J.230.229; 4.J.230.230; 4.J.230.231;
4.J.230.236; 4.J.230.237; 4.J.230.238; 4.J.230.239; 4.J.230.154; 4.J.230.157;
4.J.230.166; 4.J.230.169; 4.J.230.172; 4.J.230.175; 4.J.230.240; 4.J.230.244;
4.J.231.228; 4.J.231.229; 4.J.231.230; 4.J.231.231; 4.J.231.236; 4.J.231.237;
4.J.231.238; 4.J.231.239; 4.J.231.154; 4.J.231.157; 4.J.231.166; 4.J.231.169;
4.J.231.172; 4.J.231.175; 4.J.231.240; 4.J.231.244; 4.J.236.228; 4.J.236.229;
4.J.236.230; 4.J.236.231; 4.J.236.236; 4.J.236.237; 4.J.236.238; 4.J.236.239;
4.J.236.154; 4.J.236.157; 4.J.236.166; 4.J.236.169; 4.J.236.172; 4.J.236.175;
4.J.236.240; 4.J.236.244; 4.J.237.228; 4.J.237.229; 4.J.237.230; 4.J.237.231;
4.J.237.236; 4.J.237.237; 4.J.237.238; 4.J.237.239; 4.J.237.154; 4.J.237.157;
4.J.237.166; 4.J.237.169; 4.J.237.172; 4.J.237.175; 4.J.237.240; 4.J.237.244;
4.J.238.228; 4.J.238.229; 4.J.238.230; 4.J.238.231; 4.J.238.236; 4.J.238.237;
4.J.238.238; 4.J.238.239; 4.J.238.154; 4.J.238.157; 4.J.238.166; 4.J.238.169;
4.J.238.172; 4.J.238.175; 4.J.238.240; 4.J.238.244; 4.J.239.228; 4.J.239.229;
4.J.239.230; 4.J.239.231; 4.J.239.236; 4.J.239.237; 4.J.239.238; 4.J.239.239;
4.J.239.154; 4.J.239.157; 4.J.239.166; 4.J.239.169; 4.J.239.172; 4.J.239.175;
4.J.239.240; 4.J.239.244; 4.J.154.228; 4.J.154.229; 4.J.154.230; 4.J.154.231;
4.J.154.236; 4.J.154.237; 4.J.154.238; 4.J.154.239; 4.J.154.154; 4.J.154.157;
4.J.154.166; 4.J.154.169; 4.J.154.172; 4.J.154.175; 4.J.154.240; 4.J.154.244;
4.J.157.228; 4.J.157.229; 4.J.157.230; 4.J.157.231; 4.J.157.236; 4.J.157.237;
4.J.157.238; 4.J.157.239; 4.J.157.154; 4.J.157.157; 4.J.157.166; 4.J.157.169;
4.J.157.172; 4.J.157.175; 4.J.157.240; 4.J.157.244; 4.J.166.228; 4.J.166.229;
4.J.166.230; 4.J.166.231; 4.J.166.236; 4.J.166.237; 4.J.166.238; 4.J.166.239;
4.J.166.154; 4.J.166.157; 4.J.166.166; 4.J.166.169; 4.J.166.172; 4.J.166.175;
4.J.166.240; 4.J.166.244; 4.J.169.228; 4.J.169.229; 4.J.169.230; 4.J.169.231;
4.J.169.236; 4.J.169.237; 4.J.169.238; 4.J.169.239; 4.J.169.154; 4.J.169.157;
4.J.169.166; 4.J.169.169; 4.J.169.172; 4.J.169.175; 4.J.169.240; 4.J.169.244;
4.J.172.228; 4.J.172.229; 4.J.172.230; 4.J.172.231; 4.J.172.236; 4.J.172.237;
4.J.172.238; 4.J.172.239; 4.J.172.154; 4.J.172.157; 4.J.172.166; 4.J.172.169;
4.J.172.172; 4.J.172.175; 4.J.172.240; 4.J.172.244; 4.J.175.228; 4.J.175.229;
4.J.175.230; 4.J.175.231; 4.J.175.236; 4.J.175.237; 4.J.175.238; 4.J.175.239;
4.J.175.154; 4.J.175.157; 4.J.175.166; 4.J.175.169; 4.J.175.172; 4.J.175.175;
4.J.175.240; 4.J.175.244; 4.J.240.228; 4.J.240.229; 4.J.240.230; 4.J.240.231;
4.J.240.236; 4.J.240.237; 4.J.240.238; 4.J.240.239; 4.J.240.154; 4.J.240.157;
4.J.240.166; 4.J.240.169; 4.J.240.172; 4.J.240.175; 4.J.240.240; 4.J.240.244;
4.J.244.228; 4.J.244.229; 4.J.244.230; 4.J.244.231; 4.J.244.236; 4.J.244.237;
4.J.244.238; 4.J.244.239; 4.J.244.154; 4.J.244.157; 4.J.244.166; 4.J.244.169;
4.J.244.172; 4.J.244.175; 4.J.244.240; 4.J.244.244;

Prodrugs of 4.L

4.L.228.228; 4.L.228.229; 4.L.228.230; 4.L.228.231; 4.L.228.236;
4.L.228.237; 4.L.228.238; 4.L.228.239; 4.L.228.154; 4.L.228.157; 4.L.228.166;
4.L.228.169; 4.L.228.172; 4.L.228.175; 4.L.228.240; 4.L.228.244; 4.L.229.228;
4.L.229.229; 4.L.229.230; 4.L.229.231; 4.L.229.236; 4.L.229.237; 4.L.229.238;
4.L.229.239; 4.L.229.154; 4.L.229.157; 4.L.229.166; 4.L.229.169; 4.L.229.172;
4.L.229.175; 4.L.229.240; 4.L.229.244; 4.L.230.228; 4.L.230.229; 4.L.230.230;
4.L.230.231; 4.L.230.236; 4.L.230.237; 4.L.230.238; 4.L.230.239; 4.L.230.154;
4.L.230.157; 4.L.230.166; 4.L.230.169; 4.L.230.172; 4.L.230.175; 4.L.230.240;
4.L.230.244; 4.L.231.228; 4.L.231.229; 4.L.231.230; 4.L.231.231; 4.L.231.236;
4.L.231.237; 4.L.231.238; 4.L.231.239; 4.L.231.154; 4.L.231.157; 4.L.231.166;
4.L.231.169; 4.L.231.172; 4.L.231.175; 4.L.231.240; 4.L.231.244; 4.L.236.228;
4.L.236.229; 4.L.236.230; 4.L.236.231; 4.L.236.236; 4.L.236.237; 4.L.236.238;
4.L.236.239; 4.L.236.154; 4.L.236.157; 4.L.236.166; 4.L.236.169; 4.L.236.172;
4.L.236.175; 4.L.236.240; 4.L.236.244; 4.L.237.228; 4.L.237.229; 4.L.237.230;
4.L.237.231; 4.L.237.236; 4.L.237.237; 4.L.237.238; 4.L.237.239; 4.L.237.154;
4.L.237.157; 4.L.237.166; 4.L.237.169; 4.L.237.172; 4.L.237.175; 4.L.237.240;
4.L.237.244; 4.L.238.228; 4.L.238.229; 4.L.238.230; 4.L.238.231; 4.L.238.236;
4.L.238.237; 4.L.238.238; 4.L.238.239; 4.L.238.154; 4.L.238.157; 4.L.238.166;
4.L.238.169; 4.L.238.172; 4.L.238.175; 4.L.238.240; 4.L.238.244; 4.L.239.228;
4.L.239.229; 4.L.239.230; 4.L.239.231; 4.L.239.236; 4.L.239.237; 4.L.239.238;
4.L.239.239; 4.L.239.154; 4.L.239.157; 4.L.239.166; 4.L.239.169; 4.L.239.172;
4.L.239.175; 4.L.239.240; 4.L.239.244; 4.L.154.228; 4.L.154.229; 4.L.154.230;
4.L.154.231; 4.L.154.236; 4.L.154.237; 4.L.154.238; 4.L.154.239; 4.L.154.154;
4.L.154.157; 4.L.154.166; 4.L.154.169; 4.L.154.172; 4.L.154.175; 4.L.154.240;
4.L.154.244; 4.L.157.228; 4.L.157.229; 4.L.157.230; 4.L.157.231; 4.L.157.236;
4.L.157.237; 4.L.157.238; 4.L.157.239; 4.L.157.154; 4.L.157.157; 4.L.157.166;

TABLE 100-continued

4.L.157.169; 4.L.157.172; 4.L.157.175; 4.L.157.240; 4.L.157.244; 4.L.166.228;
4.L.166.229; 4.L.166.230; 4.L.166.231; 4.L.166.236; 4.L.166.237; 4.L.166.238;
4.L.166.239; 4.L.166.154; 4.L.166.157; 4.L.166.166; 4.L.166.169; 4.L.166.172;
4.L.166.175; 4.L.166.240; 4.L.166.244; 4.L.169.228; 4.L.169.229; 4.L.169.230;
4.L.169.231; 4.L.169.236; 4.L.169.237; 4.L.169.238; 4.L.169.239; 4.L.169.154;
4.L.169.157; 4.L.169.166; 4.L.169.169; 4.L.169.172; 4.L.169.175; 4.L.169.240;
4.L.169.244; 4.L.172.228; 4.L.172.229; 4.L.172.230; 4.L.172.231; 4.L.172.236;
4.L.172.237; 4.L.172.238; 4.L.172.239; 4.L.172.154; 4.L.172.157; 4.L.172.166;
4.L.172.169; 4.L.172.172; 4.L.172.175; 4.L.172.240; 4.L.172.244; 4.L.175.228;
4.L.175.229; 4.L.175.230; 4.L.175.231; 4.L.175.236; 4.L.175.237; 4.L.175.238;
4.L.175.239; 4.L.175.154; 4.L.175.157; 4.L.175.166; 4.L.175.169; 4.L.175.172;
4.L.175.175; 4.L.175.240; 4.L.175.244; 4.L.240.228; 4.L.240.229; 4.L.240.230;
4.L.240.231; 4.L.240.236; 4.L.240.237; 4.L.240.238; 4.L.240.239; 4.L.240.154;
4.L.240.157; 4.L.240.166; 4.L.240.169; 4.L.240.172; 4.L.240.175; 4.L.240.240;
4.L.240.244; 4.L.244.228; 4.L.244.229; 4.L.244.230; 4.L.244.231; 4.L.244.236;
4.L.244.237; 4.L.244.238; 4.L.244.239; 4.L.244.154; 4.L.244.157; 4.L.244.166;
4.L.244.169; 4.L.244.172; 4.L.244.175; 4.L.244.240; 4.L.244.244;

Prodrugs of 4.O

4.O.228.228; 4.O.228.229; 4.O.228.230; 4.O.228.231; 4.O.228.236;
4.O.228.237; 4.O.228.238; 4.O.228.239; 4.O.228.154; 4.O.228.157;
4.O.228.166; 4.O.228.169; 4.O.228.172; 4.O.228.175; 4.O.228.240;
4.O.228.244; 4.O.229.228; 4.O.229.229; 4.O.229.230; 4.O.229.231;
4.O.229.236; 4.O.229.237; 4.O.229.238; 4.O.229.239; 4.O.229.154;
4.O.229.157; 4.O.229.166; 4.O.229.169; 4.O.229.172; 4.O.229.175;
4.O.229.240; 4.O.229.244; 4.O.230.228; 4.O.230.229; 4.O.230.230;
4.O.230.231; 4.O.230.236; 4.O.230.237; 4.O.230.238; 4.O.230.239;
4.O.230.154; 4.O.230.157; 4.O.230.166; 4.O.230.169; 4.O.230.172;
4.O.230.175; 4.O.230.240; 4.O.230.244; 4.O.231.228; 4.O.231.229;
4.O.231.230; 4.O.231.231; 4.O.231.236; 4.O.231.237; 4.O.231.238;
4.O.231.239; 4.O.231.154; 4.O.231.157; 4.O.231.166; 4.O.231.169;
4.O.231.172; 4.O.231.175; 4.O.231.240; 4.O.231.244; 4.O.236.228;
4.O.236.229; 4.O.236.230; 4.O.236.231; 4.O.236.236; 4.O.236.237;
4.O.236.238; 4.O.236.239; 4.O.236.154; 4.O.236.157; 4.O.236.166;
4.O.236.169; 4.O.236.172; 4.O.236.175; 4.O.236.240; 4.O.236.244;
4.O.237.228; 4.O.237.229; 4.O.237.230; 4.O.237.231; 4.O.237.236;
4.O.237.237; 4.O.237.238; 4.O.237.239; 4.O.237.154; 4.O.237.157;
4.O.237.166; 4.O.237.169; 4.O.237.172; 4.O.237.175; 4.O.237.240;
4.O.237.244; 4.O.238.228; 4.O.238.229; 4.O.238.230; 4.O.238.231;
4.O.238.236; 4.O.238.237; 4.O.238.238; 4.O.238.239; 4.O.238.154;
4.O.238.157; 4.O.238.166; 4.O.238.169; 4.O.238.172; 4.O.238.175;
4.O.238.240; 4.O.238.244; 4.O.239.228; 4.O.239.229; 4.O.239.230;
4.O.239.231; 4.O.239.236; 4.O.239.237; 4.O.239.238; 4.O.239.239;
4.O.239.154; 4.O.239.157; 4.O.239.166; 4.O.239.169; 4.O.239.172;
4.O.239.175; 4.O.239.240; 4.O.239.244; 4.O.154.228; 4.O.154.229;
4.O.154.230; 4.O.154.231; 4.O.154.236; 4.O.154.237; 4.O.154.238;
4.O.154.239; 4.O.154.154; 4.O.154.157; 4.O.154.166; 4.O.154.169;
4.O.154.172; 4.O.154.175; 4.O.154.240; 4.O.154.244; 4.O.157.228;
4.O.157.229; 4.O.157.230; 4.O.157.231; 4.O.157.236; 4.O.157.237;
4.O.157.238; 4.O.157.239; 4.O.157.154; 4.O.157.157; 4.O.157.166;
4.O.157.169; 4.O.157.172; 4.O.157.175; 4.O.157.240; 4.O.157.244;
4.O.166.228; 4.O.166.229; 4.O.166.230; 4.O.166.231; 4.O.166.236;
4.O.166.237; 4.O.166.238; 4.O.166.239; 4.O.166.154; 4.O.166.157;
4.O.166.166; 4.O.166.169; 4.O.166.172; 4.O.166.175; 4.O.166.240;
4.O.166.244; 4.O.169.228; 4.O.169.229; 4.O.169.230; 4.O.169.231;
4.O.169.236; 4.O.169.237; 4.O.169.238; 4.O.169.239; 4.O.169.154;
4.O.169.157; 4.O.169.166; 4.O.169.169; 4.O.169.172; 4.O.169.175;
4.O.169.240; 4.O.169.244; 4.O.172.228; 4.O.172.229; 4.O.172.230;
4.O.172.231; 4.O.172.236; 4.O.172.237; 4.O.172.238; 4.O.172.239;
4.O.172.154; 4.O.172.157; 4.O.172.166; 4.O.172.169; 4.O.172.172;
4.O.172.175; 4.O.172.240; 4.O.172.244; 4.O.175.228; 4.O.175.229;
4.O.175.230; 4.O.175.231; 4.O.175.236; 4.O.175.237; 4.O.175.238;
4.O.175.239; 4.O.175.154; 4.O.175.157; 4.O.175.166; 4.O.175.169;
4.O.175.172; 4.O.175.175; 4.O.175.240; 4.O.175.244; 4.O.240.228;
4.O.240.229; 4.O.240.230; 4.O.240.231; 4.O.240.236; 4.O.240.237;
4.O.240.238; 4.O.240.239; 4.O.240.154; 4.O.240.157; 4.O.240.166;
4.O.240.169; 4.O.240.172; 4.O.240.175; 4.O.240.240; 4.O.240.244;
4.O.244.228; 4.O.244.229; 4.O.244.230; 4.O.244.231; 4.O.244.236;
4.O.244.237; 4.O.244.238; 4.O.244.239; 4.O.244.154; 4.O.244.157;
4.O.244.166; 4.O.244.169; 4.O.244.172; 4.O.244.175; 4.O.244.240;
4.O.244.244;

Prodrugs of 4.P

4.P.228.228; 4.P.228.229; 4.P.228.230; 4.P.228.231; 4.P.228.236;
4.P.228.237; 4.P.228.238; 4.P.228.239; 4.P.228.154; 4.P.228.157; 4.P.228.166;
4.P.228.169; 4.P.228.172; 4.P.228.175; 4.P.228.240; 4.P.228.244; 4.P.229.228;
4.P.229.229; 4.P.229.230; 4.P.229.231; 4.P.229.236; 4.P.229.237; 4.P.229.238;
4.P.229.239; 4.P.229.154; 4.P.229.157; 4.P.229.166; 4.P.229.169; 4.P.229.172;
4.P.229.175; 4.P.229.240; 4.P.229.244; 4.P.230.228; 4.P.230.229; 4.P.230.230;

TABLE 100-continued

4.P.230.231; 4.P.230.236; 4.P.230.237; 4.P.230.238; 4.P.230.239; 4.P.230.154;
4.P.230.157; 4.P.230.166; 4.P.230.169; 4.P.230.172; 4.P.230.175; 4.P.230.240;
4.P.230.244; 4.P.231.228; 4.P.231.229; 4.P.231.230; 4.P.231.231; 4.P.231.236;
4.P.231.237; 4.P.231.238; 4.P.231.239; 4.P.231.154; 4.P.231.157; 4.P.231.166;
4.P.231.169; 4.P.231.172; 4.P.231.175; 4.P.231.240; 4.P.231.244; 4.P.236.228;
4.P.236.229; 4.P.236.230; 4.P.236.231; 4.P.236.236; 4.P.236.237; 4.P.236.238;
4.P.236.239; 4.P.236.154; 4.P.236.157; 4.P.236.166; 4.P.236.169; 4.P.236.172;
4.P.236.175; 4.P.236.240; 4.P.236.244; 4.P.237.228; 4.P.237.229; 4.P.237.230;
4.P.237.231; 4.P.237.236; 4.P.237.237; 4.P.237.238; 4.P.237.239; 4.P.237.154;
4.P.237.157; 4.P.237.166; 4.P.237.169; 4.P.237.172; 4.P.237.175; 4.P.237.240;
4.P.237.244; 4.P.238.228; 4.P.238.229; 4.P.238.230; 4.P.238.231; 4.P.238.236;
4.P.238.237; 4.P.238.238; 4.P.238.239; 4.P.238.154; 4.P.238.157; 4.P.238.166;
4.P.238.169; 4.P.238.172; 4.P.238.175; 4.P.238.240; 4.P.238.244; 4.P.239.228;
4.P.239.229; 4.P.239.230; 4.P.239.231; 4.P.239.236; 4.P.239.237; 4.P.239.238;
4.P.239.239; 4.P.239.154; 4.P.239.157; 4.P.239.166; 4.P.239.169; 4.P.239.172;
4.P.239.175; 4.P.239.240; 4.P.239.244; 4.P.154.228; 4.P.154.229; 4.P.154.230;
4.P.154.231; 4.P.154.236; 4.P.154.237; 4.P.154.238; 4.P.154.239; 4.P.154.154;
4.P.154.157; 4.P.154.166; 4.P.154.169; 4.P.154.172; 4.P.154.175; 4.P.154.240;
4.P.154.244; 4.P.157.228; 4.P.157.229; 4.P.157.230; 4.P.157.231; 4.P.157.236;
4.P.157.237; 4.P.157.238; 4.P.157.239; 4.P.157.154; 4.P.157.157; 4.P.157.166;
4.P.157.169; 4.P.157.172; 4.P.157.175; 4.P.157.240; 4.P.157.244; 4.P.166.228;
4.P.166.229; 4.P.166.230; 4.P.166.231; 4.P.166.236; 4.P.166.237; 4.P.166.238;
4.P.166.239; 4.P.166.154; 4.P.166.157; 4.P.166.166; 4.P.166.169; 4.P.166.172;
4.P.166.175; 4.P.166.240; 4.P.166.244; 4.P.169.228; 4.P.169.229; 4.P.169.230;
4.P.169.231; 4.P.169.236; 4.P.169.237; 4.P.169.238; 4.P.169.239; 4.P.169.154;
4.P.169.157; 4.P.169.166; 4.P.169.169; 4.P.169.172; 4.P.169.175; 4.P.169.240;
4.P.169.244; 4.P.172.228; 4.P.172.229; 4.P.172.230; 4.P.172.231; 4.P.172.236;
4.P.172.237; 4.P.172.238; 4.P.172.239; 4.P.172.154; 4.P.172.157; 4.P.172.166;
4.P.172.169; 4.P.172.172; 4.P.172.175; 4.P.172.240; 4.P.172.244; 4.P.175.228;
4.P.175.229; 4.P.175.230; 4.P.175.231; 4.P.175.236; 4.P.175.237; 4.P.175.238;
4.P.175.239; 4.P.175.154; 4.P.175.157; 4.P.175.166; 4.P.175.169; 4.P.175.172;
4.P.175.175; 4.P.175.240; 4.P.175.244; 4.P.240.228; 4.P.240.229; 4.P.240.230;
4.P.240.231; 4.P.240.236; 4.P.240.237; 4.P.240.238; 4.P.240.239; 4.P.240.154;
4.P.240.157; 4.P.240.166; 4.P.240.169; 4.P.240.172; 4.P.240.175; 4.P.240.240;
4.P.240.244; 4.P.244.228; 4.P.244.229; 4.P.244.230; 4.P.244.231; 4.P.244.236;
4.P.244.237; 4.P.244.238; 4.P.244.239; 4.P.244.154; 4.P.244.157; 4.P.244.166;
4.P.244.169; 4.P.244.172; 4.P.244.175; 4.P.244.240; 4.P.244.244;
Prodrugs of 4.U 4.U.228.228; 4.U.228.229; 4.U.228.230; 4.U.228.231; 4.U.228.236;
4.U.228.237; 4.U.228.238; 4.U.228.239; 4.U.228.154; 4.U.228.157;
4.U.228.166; 4.U.228.169; 4.U.228.172; 4.U.228.175; 4.U.228.240;
4.U.228.244; 4.U.229.228; 4.U.229.229; 4.U.229.230; 4.U.229.231;
4.U.229.236; 4.U.229.237; 4.U.229.238; 4.U.229.239; 4.U.229.154;
4.U.229.157; 4.U.229.166; 4.U.229.169; 4.U.229.172; 4.U.229.175;
4.U.229.240; 4.U.229.244; 4.U.230.228; 4.U.230.229; 4.U.230.230;
4.U.230.231; 4.U.230.236; 4.U.230.237; 4.U.230.238; 4.U.230.239;
4.U.230.154; 4.U.230.157; 4.U.230.166; 4.U.230.169; 4.U.230.172;
4.U.230.175; 4.U.230.240; 4.U.230.244; 4.U.231.228; 4.U.231.229;
4.U.231.230; 4.U.231.231; 4.U.231.236; 4.U.231.237; 4.U.231.238;
4.U.231.239; 4.U.231.154; 4.U.231.157; 4.U.231.166; 4.U.231.169;
4.U.231.172; 4.U.231.175; 4.U.231.240; 4.U.231.244; 4.U.236.228;
4.U.236.229; 4.U.236.230; 4.U.236.231; 4.U.236.236; 4.U.236.237;
4.U.236.238; 4.U.236.239; 4.U.236.154; 4.U.236.157; 4.U.236.166;
4.U.236.169; 4.U.236.172; 4.U.236.175; 4.U.236.240; 4.U.236.244;
4.U.237.228; 4.U.237.229; 4.U.237.230; 4.U.237.231; 4.U.237.236;
4.U.237.237; 4.U.237.238; 4.U.237.239; 4.U.237.154; 4.U.237.157;
4.U.237.166; 4.U.237.169; 4.U.237.172; 4.U.237.175; 4.U.237.240;
4.U.237.244; 4.U.238.228; 4.U.238.229; 4.U.238.230; 4.U.238.231;
4.U.238.236; 4.U.238.237; 4.U.238.238; 4.U.238.239; 4.U.238.154;
4.U.238.157; 4.U.238.166; 4.U.238.169; 4.U.238.172; 4.U.238.175;
4.U.238.240; 4.U.238.244; 4.U.239.228; 4.U.239.229; 4.U.239.230;
4.U.239.231; 4.U.239.236; 4.U.239.237; 4.U.239.238; 4.U.239.239;
4.U.239.154; 4.U.239.157; 4.U.239.166; 4.U.239.169; 4.U.239.172;
4.U.239.175; 4.U.239.240; 4.U.239.244; 4.U.154.228; 4.U.154.229;
4.U.154.230; 4.U.154.231; 4.U.154.236; 4.U.154.237; 4.U.154.238;
4.U.154.239; 4.U.154.154; 4.U.154.157; 4.U.154.166; 4.U.154.169;
4.U.154.172; 4.U.154.175; 4.U.154.240; 4.U.154.244; 4.U.157.228;
4.U.157.229; 4.U.157.230; 4.U.157.231; 4.U.157.236; 4.U.157.237;
4.U.157.238; 4.U.157.239; 4.U.157.154; 4.U.157.157; 4.U.157.166;
4.U.157.169; 4.U.157.172; 4.U.157.175; 4.U.157.240; 4.U.157.244;
4.U.166.228; 4.U.166.229; 4.U.166.230; 4.U.166.231; 4.U.166.236;
4.U.166.237; 4.U.166.238; 4.U.166.239; 4.U.166.154; 4.U.166.157;
4.U.166.166; 4.U.166.169; 4.U.166.172; 4.U.166.175; 4.U.166.240;
4.U.166.244; 4.U.169.228; 4.U.169.229; 4.U.169.230; 4.U.169.231;
4.U.169.236; 4.U.169.237; 4.U.169.238; 4.U.169.239; 4.U.169.154;
4.U.169.157; 4.U.169.166; 4.U.169.169; 4.U.169.172; 4.U.169.175;
4.U.169.240; 4.U.169.244; 4.U.172.228; 4.U.172.229; 4.U.172.230;
4.U.172.231; 4.U.172.236; 4.U.172.237; 4.U.172.238; 4.U.172.239;

TABLE 100-continued

4.U.172.154; 4.U.172.157; 4.U.172.166; 4.U.172.169; 4.U.172.172;
4.U.172.175; 4.U.172.240; 4.U.172.244; 4.U.175.228; 4.U.175.229;
4.U.175.230; 4.U.175.231; 4.U.175.236; 4.U.175.237; 4.U.175.238;
4.U.175.239; 4.U.175.154; 4.U.175.157; 4.U.175.166; 4.U.175.169;
4.U.175.172; 4.U.175.175; 4.U.175.240; 4.U.175.244; 4.U.240.228;
4.U.240.229; 4.U.240.230; 4.U.240.231; 4.U.240.236; 4.U.240.237;
4.U.240.238; 4.U.240.239; 4.U.240.154; 4.U.240.157; 4.U.240.166;
4.U.240.169; 4.U.240.172; 4.U.240.175; 4.U.240.240; 4.U.240.244;
4.U.244.228; 4.U.244.229; 4.U.244.230; 4.U.244.231; 4.U.244.236;
4.U.244.237; 4.U.244.238; 4.U.244.239; 4.U.244.154; 4.U.244.157;
4.U.244.166; 4.U.244.169; 4.U.244.172; 4.U.244.175; 4.U.244.240;
4.U.244.244;
Prodrugs of 4.W 4.W.228.228; 4.W.228.229; 4.W.228.230; 4.W.228.231; 4.W.228.236;
4.W.228.237; 4.W.228.238; 4.W.228.239; 4.W.228.154; 4.W.228.157;
4.W.228.166; 4.W.228.169; 4.W.228.172; 4.W.228.175; 4.W.228.240;
4.W.228.244; 4.W.229.228; 4.W.229.229; 4.W.229.230; 4.W.229.231;
4.W.229.236; 4.W.229.237; 4.W.229.238; 4.W.229.239; 4.W.229.154;
4.W.229.157; 4.W.229.166; 4.W.229.169; 4.W.229.172; 4.W.229.175;
4.W.229.240; 4.W.229.244; 4.W.230.228; 4.W.230.229; 4.W.230.230;
4.W.230.231; 4.W.230.236; 4.W.230.237; 4.W.230.238; 4.W.230.239;
4.W.230.154; 4.W.230.157; 4.W.230.166; 4.W.230.169; 4.W.230.172;
4.W.230.175; 4.W.230.240; 4.W.230.244; 4.W.231.228; 4.W.231.229;
4.W.231.230; 4.W.231.231; 4.W.231.236; 4.W.231.237; 4.W.231.238;
4.W.231.239; 4.W.231.154; 4.W.231.157; 4.W.231.166; 4.W.231.169;
4.W.231.172; 4.W.231.175; 4.W.231.240; 4.W.231.244; 4.W.236.228;
4.W.236.229; 4.W.236.230; 4.W.236.231; 4.W.236.236; 4.W.236.237;
4.W.236.238; 4.W.236.239; 4.W.236.154; 4.W.236.157; 4.W.236.166;
4.W.236.169; 4.W.236.172; 4.W.236.175; 4.W.236.240; 4.W.236.244;
4.W.237.228; 4.W.237.229; 4.W.237.230; 4.W.237.231; 4.W.237.236;
4.W.237.237; 4.W.237.238; 4.W.237.239; 4.W.237.154; 4.W.237.157;
4.W.237.166; 4.W.237.169; 4.W.237.172; 4.W.237.175; 4.W.237.240;
4.W.237.244; 4.W.238.228; 4.W.238.229; 4.W.238.230; 4.W.238.231;
4.W.238.236; 4.W.238.237; 4.W.238.238; 4.W.238.239; 4.W.238.154;
4.W.238.157; 4.W.238.166; 4.W.238.169; 4.W.238.172; 4.W.238.175;
4.W.238.240; 4.W.238.244; 4.W.239.228; 4.W.239.229; 4.W.239.230;
4.W.239.231; 4.W.239.236; 4.W.239.237; 4.W.239.238; 4.W.239.239;
4.W.239.154; 4.W.239.157; 4.W.239.166; 4.W.239.169; 4.W.239.172;
4.W.239.175; 4.W.239.240; 4.W.239.244; 4.W.154.228; 4.W.154.229;
4.W.154.230; 4.W.154.231; 4.W.154.236; 4.W.154.237; 4.W.154.238;
4.W.154.239; 4.W.154.154; 4.W.154.157; 4.W.154.166; 4.W.154.169;
4.W.154.172; 4.W.154.175; 4.W.154.240; 4.W.154.244; 4.W.157.228;
4.W.157.229; 4.W.157.230; 4.W.157.231; 4.W.157.236; 4.W.157.237;
4.W.157.238; 4.W.157.239; 4.W.157.154; 4.W.157.157; 4.W.157.166;
4.W.157.169; 4.W.157.172; 4.W.157.175; 4.W.157.240; 4.W.157.244;
4.W.166.228; 4.W.166.229; 4.W.166.230; 4.W.166.231; 4.W.166.236;
4.W.166.237; 4.W.166.238; 4.W.166.239; 4.W.166.154; 4.W.166.157;
4.W.166.166; 4.W.166.169; 4.W.166.172; 4.W.166.175; 4.W.166.240;
4.W.166.244; 4.W.169.228; 4.W.169.229; 4.W.169.230; 4.W.169.231;
4.W.169.236; 4.W.169.237; 4.W.169.238; 4.W.169.239; 4.W.169.154;
4.W.169.157; 4.W.169.166; 4.W.169.169; 4.W.169.172; 4.W.169.175;
4.W.169.240; 4.W.169.244; 4.W.172.228; 4.W.172.229; 4.W.172.230;
4.W.172.231; 4.W.172.236; 4.W.172.237; 4.W.172.238; 4.W.172.239;
4.W.172.154; 4.W.172.157; 4.W.172.166; 4.W.172.169; 4.W.172.172;
4.W.172.175; 4.W.172.240; 4.W.172.244; 4.W.175.228; 4.W.175.229;
4.W.175.230; 4.W.175.231; 4.W.175.236; 4.W.175.237; 4.W.175.238;
4.W.175.239; 4.W.175.154; 4.W.175.157; 4.W.175.166; 4.W.175.169;
4.W.175.172; 4.W.175.175; 4.W.175.240; 4.W.175.244; 4.W.240.228;
4.W.240.229; 4.W.240.230; 4.W.240.231; 4.W.240.236; 4.W.240.237;
4.W.240.238; 4.W.240.239; 4.W.240.154; 4.W.240.157; 4.W.240.166;
4.W.240.169; 4.W.240.172; 4.W.240.175; 4.W.240.240; 4.W.240.244;
4.W.244.228; 4.W.244.229; 4.W.244.230; 4.W.244.231; 4.W.244.236;
4.W.244.237; 4.W.244.238; 4.W.244.239; 4.W.244.154; 4.W.244.157;
4.W.244.166; 4.W.244.169; 4.W.244.172; 4.W.244.175; 4.W.244.240; 4.W.244.244;
Prodrugs of 4.Y 4.Y.228.228; 4.Y.228.229; 4.Y.228.230; 4.Y.228.231; 4.Y.228.236;
4.Y.228.237; 4.Y.228.238; 4.Y.228.239; 4.Y.228.154; 4.Y.228.157; 4.Y.228.166;
4.Y.228.169; 4.Y.228.172; 4.Y.228.175; 4.Y.228.240; 4.Y.228.244; 4.Y.229.228;
4.Y.229.229; 4.Y.229.230; 4.Y.229.231; 4.Y.229.236; 4.Y.229.237; 4.Y.229.238;
4.Y.229.239; 4.Y.229.154; 4.Y.229.157; 4.Y.229.166; 4.Y.229.169; 4.Y.229.172;
4.Y.229.175; 4.Y.229.240; 4.Y.229.244; 4.Y.230.228; 4.Y.230.229; 4.Y.230.230;
4.Y.230.231; 4.Y.230.236; 4.Y.230.237; 4.Y.230.238; 4.Y.230.239; 4.Y.230.154;
4.Y.230.157; 4.Y.230.166; 4.Y.230.169; 4.Y.230.172; 4.Y.230.175; 4.Y.230.240;
4.Y.230.244; 4.Y.231.228; 4.Y.231.229; 4.Y.231.230; 4.Y.231.231; 4.Y.231.236;
4.Y.231.237; 4.Y.231.238; 4.Y.231.239; 4.Y.231.154; 4.Y.231.157; 4.Y.231.166;
4.Y.231.169; 4.Y.231.172; 4.Y.231.175; 4.Y.231.240; 4.Y.231.244; 4.Y.236.228;
4.Y.236.229; 4.Y.236.230; 4.Y.236.231; 4.Y.236.236; 4.Y.236.237; 4.Y.236.238;

TABLE 100-continued

4.Y.236.239; 4.Y.236.154; 4.Y.236.157; 4.Y.236.166; 4.Y.236.169; 4.Y.236.172;
4.Y.236.175; 4.Y.236.240; 4.Y.236.244; 4.Y.237.228; 4.Y.237.229; 4.Y.237.230;
4.Y.237.231; 4.Y.237.236; 4.Y.237.237; 4.Y.237.238; 4.Y.237.239; 4.Y.237.154;
4.Y.237.157; 4.Y.237.166; 4.Y.237.169; 4.Y.237.172; 4.Y.237.175; 4.Y.237.240;
4.Y.237.244; 4.Y.238.228; 4.Y.238.229; 4.Y.238.230; 4.Y.238.231; 4.Y.238.236;
4.Y.238.237; 4.Y.238.238; 4.Y.238.239; 4.Y.238.154; 4.Y.238.157; 4.Y.238.166;
4.Y.238.169; 4.Y.238.172; 4.Y.238.175; 4.Y.238.240; 4.Y.238.244; 4.Y.239.228;
4.Y.239.229; 4.Y.239.230; 4.Y.239.231; 4.Y.239.236; 4.Y.239.237; 4.Y.239.238;
4.Y.239.239; 4.Y.239.154; 4.Y.239.157; 4.Y.239.166; 4.Y.239.169; 4.Y.239.172;
4.Y.239.175; 4.Y.239.240; 4.Y.239.244; 4.Y.154.228; 4.Y.154.229; 4.Y.154.230;
4.Y.154.231; 4.Y.154.236; 4.Y.154.237; 4.Y.154.238; 4.Y.154.239; 4.Y.154.154;
4.Y.154.157; 4.Y.154.166; 4.Y.154.169; 4.Y.154.172; 4.Y.154.175; 4.Y.154.240;
4.Y.154.244; 4.Y.157.228; 4.Y.157.229; 4.Y.157.230; 4.Y.157.231; 4.Y.157.236;
4.Y.157.237; 4.Y.157.238; 4.Y.157.239; 4.Y.157.154; 4.Y.157.157; 4.Y.157.166;
4.Y.157.169; 4.Y.157.172; 4.Y.157.175; 4.Y.157.240; 4.Y.157.244; 4.Y.166.228;
4.Y.166.229; 4.Y.166.230; 4.Y.166.231; 4.Y.166.236; 4.Y.166.237; 4.Y.166.238;
4.Y.166.239; 4.Y.166.154; 4.Y.166.157; 4.Y.166.166; 4.Y.166.169; 4.Y.166.172;
4.Y.166.175; 4.Y.166.240; 4.Y.166.244; 4.Y.169.228; 4.Y.169.229; 4.Y.169.230;
4.Y.169.231; 4.Y.169.236; 4.Y.169.237; 4.Y.169.238; 4.Y.169.239; 4.Y.169.154;
4.Y.169.157; 4.Y.169.166; 4.Y.169.169; 4.Y.169.172; 4.Y.169.175; 4.Y.169.240;
4.Y.169.244; 4.Y.172.228; 4.Y.172.229; 4.Y.172.230; 4.Y.172.231; 4.Y.172.236;
4.Y.172.237; 4.Y.172.238; 4.Y.172.239; 4.Y.172.154; 4.Y.172.157; 4.Y.172.166;
4.Y.172.169; 4.Y.172.172; 4.Y.172.175; 4.Y.172.240; 4.Y.172.244; 4.Y.175.228;
4.Y.175.229; 4.Y.175.230; 4.Y.175.231; 4.Y.175.236; 4.Y.175.237; 4.Y.175.238;
4.Y.175.239; 4.Y.175.154; 4.Y.175.157; 4.Y.175.166; 4.Y.175.169; 4.Y.175.172;
4.Y.175.175; 4.Y.175.240; 4.Y.175.244; 4.Y.240.228; 4.Y.240.229; 4.Y.240.230;
4.Y.240.231; 4.Y.240.236; 4.Y.240.237; 4.Y.240.238; 4.Y.240.239; 4.Y.240.154;
4.Y.240.157; 4.Y.240.166; 4.Y.240.169; 4.Y.240.172; 4.Y.240.175; 4.Y.240.240;
4.Y.240.244; 4.Y.244.228; 4.Y.244.229; 4.Y.244.230; 4.Y.244.231; 4.Y.244.236;
4.Y.244.237; 4.Y.244.238; 4.Y.244.239; 4.Y.244.154; 4.Y.244.157; 4.Y.244.166; 4.Y.244.169;
4.Y.244.172; 4.Y.244.175; 4.Y.244.240; 4.Y.244.244;
Prodrugs of 5.B 5.B.228.228; 5.B.228.229; 5.B.228.230; 5.B.228.231; 5.B.228.236;
5.B.228.237; 5.B.228.238; 5.B.228.239; 5.B.228.154; 5.B.228.157; 5.B.228.166;
5.B.228.169; 5.B.228.172; 5.B.228.175; 5.B.228.240; 5.B.228.244; 5.B.229.228;
5.B.229.229; 5.B.229.230; 5.B.229.231; 5.B.229.236; 5.B.229.237; 5.B.229.238;
5.B.229.239; 5.B.229.154; 5.B.229.157; 5.B.229.166; 5.B.229.169; 5.B.229.172;
5.B.229.175; 5.B.229.240; 5.B.229.244; 5.B.230.228; 5.B.230.229; 5.B.230.230;
5.B.230.231; 5.B.230.236; 5.B.230.237; 5.B.230.238; 5.B.230.239; 5.B.230.154;
5.B.230.157; 5.B.230.166; 5.B.230.169; 5.B.230.172; 5.B.230.175; 5.B.230.240;
5.B.230.244; 5.B.231.228; 5.B.231.229; 5.B.231.230; 5.B.231.231; 5.B.231.236;
5.B.231.237; 5.B.231.238; 5.B.231.239; 5.B.231.154; 5.B.231.157; 5.B.231.166;
5.B.231.169; 5.B.231.172; 5.B.231.175; 5.B.231.240; 5.B.231.244; 5.B.236.228;
5.B.236.229; 5.B.236.230; 5.B.236.231; 5.B.236.236; 5.B.236.237; 5.B.236.238;
5.B.236.239; 5.B.236.154; 5.B.236.157; 5.B.236.166; 5.B.236.169; 5.B.236.172;
5.B.236.175; 5.B.236.240; 5.B.236.244; 5.B.237.228; 5.B.237.229; 5.B.237.230;
5.B.237.231; 5.B.237.236; 5.B.237.237; 5.B.237.238; 5.B.237.239; 5.B.237.154;
5.B.237.157; 5.B.237.166; 5.B.237.169; 5.B.237.172; 5.B.237.175; 5.B.237.240;
5.B.237.244; 5.B.238.228; 5.B.238.229; 5.B.238.230; 5.B.238.231; 5.B.238.236;
5.B.238.237; 5.B.238.238; 5.B.238.239; 5.B.238.154; 5.B.238.157; 5.B.238.166;
5.B.238.169; 5.B.238.172; 5.B.238.175; 5.B.238.240; 5.B.238.244; 5.B.239.228;
5.B.239.229; 5.B.239.230; 5.B.239.231; 5.B.239.236; 5.B.239.237; 5.B.239.238;
5.B.239.239; 5.B.239.154; 5.B.239.157; 5.B.239.166; 5.B.239.169; 5.B.239.172;
5.B.239.175; 5.B.239.240; 5.B.239.244; 5.B.154.228; 5.B.154.229; 5.B.154.230;
5.B.154.231; 5.B.154.236; 5.B.154.237; 5.B.154.238; 5.B.154.239; 5.B.154.154;
5.B.154.157; 5.B.154.166; 5.B.154.169; 5.B.154.172; 5.B.154.175; 5.B.154.240;
5.B.154.244; 5.B.157.228; 5.B.157.229; 5.B.157.230; 5.B.157.231; 5.B.157.236;
5.B.157.237; 5.B.157.238; 5.B.157.239; 5.B.157.154; 5.B.157.157; 5.B.157.166;
5.B.157.169; 5.B.157.172; 5.B.157.175; 5.B.157.240; 5.B.157.244; 5.B.166.228;
5.B.166.229; 5.B.166.230; 5.B.166.231; 5.B.166.236; 5.B.166.237; 5.B.166.238;
5.B.166.239; 5.B.166.154; 5.B.166.157; 5.B.166.166; 5.B.166.169; 5.B.166.172;
5.B.166.175; 5.B.166.240; 5.B.166.244; 5.B.169.228; 5.B.169.229; 5.B.169.230;
5.B.169.231; 5.B.169.236; 5.B.169.237; 5.B.169.238; 5.B.169.239; 5.B.169.154;
5.B.169.157; 5.B.169.166; 5.B.169.169; 5.B.169.172; 5.B.169.175; 5.B.169.240;
5.B.169.244; 5.B.172.228; 5.B.172.229; 5.B.172.230; 5.B.172.231; 5.B.172.236;
5.B.172.237; 5.B.172.238; 5.B.172.239; 5.B.172.154; 5.B.172.157; 5.B.172.166;
5.B.172.169; 5.B.172.172; 5.B.172.175; 5.B.172.240; 5.B.172.244; 5.B.175.228;
5.B.175.229; 5.B.175.230; 5.B.175.231; 5.B.175.236; 5.B.175.237; 5.B.175.238;
5.B.175.239; 5.B.175.154; 5.B.175.157; 5.B.175.166; 5.B.175.169; 5.B.175.172;
5.B.175.175; 5.B.175.240; 5.B.175.244; 5.B.240.228; 5.B.240.229; 5.B.240.230;
5.B.240.231; 5.B.240.236; 5.B.240.237; 5.B.240.238; 5.B.240.239; 5.B.240.154;
5.B.240.157; 5.B.240.166; 5.B.240.169; 5.B.240.172; 5.B.240.175; 5.B.240.240;
5.B.240.244; 5.B.244.228; 5.B.244.229; 5.B.244.230; 5.B.244.231; 5.B.244.236;
5.B.244.237; 5.B.244.238; 5.B.244.239; 5.B.244.154; 5.B.244.157; 5.B.244.166;
5.B.244.169; 5.B.244.172; 5.B.244.175; 5.B.244.240; 5.B.244.244;

TABLE 100-continued

Prodrugs of 5.D

5.D.228.228; 5.D.228.229; 5.D.228.230; 5.D.228.231; 5.D.228.236;
5.D.228.237; 5.D.228.238; 5.D.228.239; 5.D.228.154; 5.D.228.157;
5.D.228.166; 5.D.228.169; 5.D.228.172; 5.D.228.175; 5.D.228.240;
5.D.228.244; 5.D.229.228; 5.D.229.229; 5.D.229.230; 5.D.229.231;
5.D.229.236; 5.D.229.237; 5.D.229.238; 5.D.229.239; 5.D.229.154;
5.D.229.157; 5.D.229.166; 5.D.229.169; 5.D.229.172; 5.D.229.175;
5.D.229.240; 5.D.229.244; 5.D.230.228; 5.D.230.229; 5.D.230.230;
5.D.230.231; 5.D.230.236; 5.D.230.237; 5.D.230.238; 5.D.230.239;
5.D.230.154; 5.D.230.157; 5.D.230.166; 5.D.230.169; 5.D.230.172;
5.D.230.175; 5.D.230.240; 5.D.230.244; 5.D.231.228; 5.D.231.229;
5.D.231.230; 5.D.231.231; 5.D.231.236; 5.D.231.237; 5.D.231.238;
5.D.231.239; 5.D.231.154; 5.D.231.157; 5.D.231.166; 5.D.231.169;
5.D.231.172; 5.D.231.175; 5.D.231.240; 5.D.231.244; 5.D.236.228;
5.D.236.229; 5.D.236.230; 5.D.236.231; 5.D.236.236; 5.D.236.237;
5.D.236.238; 5.D.236.239; 5.D.236.154; 5.D.236.157; 5.D.236.166;
5.D.236.169; 5.D.236.172; 5.D.236.175; 5.D.236.240; 5.D.236.244;
5.D.237.228; 5.D.237.229; 5.D.237.230; 5.D.237.231; 5.D.237.236;
5.D.237.237; 5.D.237.238; 5.D.237.239; 5.D.237.154; 5.D.237.157;
5.D.237.166; 5.D.237.169; 5.D.237.172; 5.D.237.175; 5.D.237.240;
5.D.237.244; 5.D.238.228; 5.D.238.229; 5.D.238.230; 5.D.238.231;
5.D.238.236; 5.D.238.237; 5.D.238.238; 5.D.238.239; 5.D.238.154;
5.D.238.157; 5.D.238.166; 5.D.238.169; 5.D.238.172; 5.D.238.175;
5.D.238.240; 5.D.238.244; 5.D.239.228; 5.D.239.229; 5.D.239.230;
5.D.239.231; 5.D.239.236; 5.D.239.237; 5.D.239.238; 5.D.239.239;
5.D.239.154; 5.D.239.157; 5.D.239.166; 5.D.239.169; 5.D.239.172;
5.D.239.175; 5.D.239.240; 5.D.239.244; 5.D.154.228; 5.D.154.229;
5.D.154.230; 5.D.154.231; 5.D.154.236; 5.D.154.237; 5.D.154.238;
5.D.154.239; 5.D.154.154; 5.D.154.157; 5.D.154.166; 5.D.154.169;
5.D.154.172; 5.D.154.175; 5.D.154.240; 5.D.154.244; 5.D.157.228;
5.D.157.229; 5.D.157.230; 5.D.157.231; 5.D.157.236; 5.D.157.237;
5.D.157.238; 5.D.157.239; 5.D.157.154; 5.D.157.157; 5.D.157.166;
5.D.157.169; 5.D.157.172; 5.D.157.175; 5.D.157.240; 5.D.157.244;
5.D.166.228; 5.D.166.229; 5.D.166.230; 5.D.166.231; 5.D.166.236;
5.D.166.237; 5.D.166.238; 5.D.166.239; 5.D.166.154; 5.D.166.157;
5.D.166.166; 5.D.166.169; 5.D.166.172; 5.D.166.175; 5.D.166.240;
5.D.166.244; 5.D.169.228; 5.D.169.229; 5.D.169.230; 5.D.169.231;
5.D.169.236; 5.D.169.237; 5.D.169.238; 5.D.169.239; 5.D.169.154;
5.D.169.157; 5.D.169.166; 5.D.169.169; 5.D.169.172; 5.D.169.175;
5.D.169.240; 5.D.169.244; 5.D.172.228; 5.D.172.229; 5.D.172.230;
5.D.172.231; 5.D.172.236; 5.D.172.237; 5.D.172.238; 5.D.172.239;
5.D.172.154; 5.D.172.157; 5.D.172.166; 5.D.172.169; 5.D.172.172;
5.D.172.175; 5.D.172.240; 5.D.172.244; 5.D.175.228; 5.D.175.229;
5.D.175.230; 5.D.175.231; 5.D.175.236; 5.D.175.237; 5.D.175.238;
5.D.175.239; 5.D.175.154; 5.D.175.157; 5.D.175.166; 5.D.175.169;
5.D.175.172; 5.D.175.175; 5.D.175.240; 5.D.175.244; 5.D.240.228;
5.D.240.229; 5.D.240.230; 5.D.240.231; 5.D.240.236; 5.D.240.237;
5.D.240.238; 5.D.240.239; 5.D.240.154; 5.D.240.157; 5.D.240.166;
5.D.240.169; 5.D.240.172; 5.D.240.175; 5.D.240.240; 5.D.240.244;
5.D.244.228; 5.D.244.229; 5.D.244.230; 5.D.244.231; 5.D.244.236;
5.D.244.237; 5.D.244.238; 5.D.244.239; 5.D.244.154; 5.D.244.157;
5.D.244.166; 5.D.244.169; 5.D.244.172; 5.D.244.175; 5.D.244.240;
5.D.244.244;

Prodrugs of 5.E

5.E.228.228; 5.E.228.229; 5.E.228.230; 5.E.228.231; 5.E.228.236;
5.E.228.237; 5.E.228.238; 5.E.228.239; 5.E.228.154; 5.E.228.157; 5.E.228.166;
5.E.228.169; 5.E.228.172; 5.E.228.175; 5.E.228.240; 5.E.228.244; 5.E.229.228;
5.E.229.229; 5.E.229.230; 5.E.229.231; 5.E.229.236; 5.E.229.237; 5.E.229.238;
5.E.229.239; 5.E.229.154; 5.E.229.157; 5.E.229.166; 5.E.229.169; 5.E.229.172;
5.E.229.175; 5.E.229.240; 5.E.229.244; 5.E.230.228; 5.E.230.229; 5.E.230.230;
5.E.230.231; 5.E.230.236; 5.E.230.237; 5.E.230.238; 5.E.230.239; 5.E.230.154;
5.E.230.157; 5.E.230.166; 5.E.230.169; 5.E.230.172; 5.E.230.175; 5.E.230.240;
5.E.230.244; 5.E.231.228; 5.E.231.229; 5.E.231.230; 5.E.231.231; 5.E.231.236;
5.E.231.237; 5.E.231.238; 5.E.231.239; 5.E.231.154; 5.E.231.157; 5.E.231.166;
5.E.231.169; 5.E.231.172; 5.E.231.175; 5.E.231.240; 5.E.231.244; 5.E.236.228;
5.E.236.229; 5.E.236.230; 5.E.236.231; 5.E.236.236; 5.E.236.237; 5.E.236.238;
5.E.236.239; 5.E.236.154; 5.E.236.157; 5.E.236.166; 5.E.236.169; 5.E.236.172;
5.E.236.175; 5.E.236.240; 5.E.236.244; 5.E.237.228; 5.E.237.229; 5.E.237.230;
5.E.237.231; 5.E.237.236; 5.E.237.237; 5.E.237.238; 5.E.237.239; 5.E.237.154;
5.E.237.157; 5.E.237.166; 5.E.237.169; 5.E.237.172; 5.E.237.175; 5.E.237.240;
5.E.237.244; 5.E.238.228; 5.E.238.229; 5.E.238.230; 5.E.238.231; 5.E.238.236;
5.E.238.237; 5.E.238.238; 5.E.238.239; 5.E.238.154; 5.E.238.157; 5.E.238.166;
5.E.238.169; 5.E.238.172; 5.E.238.175; 5.E.238.240; 5.E.238.244; 5.E.239.228;
5.E.239.229; 5.E.239.230; 5.E.239.231; 5.E.239.236; 5.E.239.237; 5.E.239.238;
5.E.239.239; 5.E.239.154; 5.E.239.157; 5.E.239.166; 5.E.239.169; 5.E.239.172;
5.E.239.175; 5.E.239.240; 5.E.239.244; 5.E.154.228; 5.E.154.229; 5.E.154.230;
5.E.154.231; 5.E.154.236; 5.E.154.237; 5.E.154.238; 5.E.154.239; 5.E.154.154;

TABLE 100-continued

5.E.154.157; 5.E.154.166; 5.E.154.169; 5.E.154.172; 5.E.154.175; 5.E.154.240;
5.E.154.244; 5.E.157.228; 5.E.157.229; 5.E.157.230; 5.E.157.231; 5.E.157.236;
5.E.157.237; 5.E.157.238; 5.E.157.239; 5.E.157.154; 5.E.157.157; 5.E.157.166;
5.E.157.169; 5.E.157.172; 5.E.157.175; 5.E.157.240; 5.E.157.244; 5.E.166.228;
5.E.166.229; 5.E.166.230; 5.E.166.231; 5.E.166.236; 5.E.166.237; 5.E.166.238;
5.E.166.239; 5.E.166.154; 5.E.166.157; 5.E.166.166; 5.E.166.169; 5.E.166.172;
5.E.166.175; 5.E.166.240; 5.E.166.244; 5.E.169.228; 5.E.169.229; 5.E.169.230;
5.E.169.231; 5.E.169.236; 5.E.169.237; 5.E.169.238; 5.E.169.239; 5.E.169.154;
5.E.169.157; 5.E.169.166; 5.E.169.169; 5.E.169.172; 5.E.169.175; 5.E.169.240;
5.E.169.244; 5.E.172.228; 5.E.172.229; 5.E.172.230; 5.E.172.231; 5.E.172.236;
5.E.172.237; 5.E.172.238; 5.E.172.239; 5.E.172.154; 5.E.172.157; 5.E.172.166;
5.E.172.169; 5.E.172.172; 5.E.172.175; 5.E.172.240; 5.E.172.244; 5.E.175.228;
5.E.175.229; 5.E.175.230; 5.E.175.231; 5.E.175.236; 5.E.175.237; 5.E.175.238;
5.E.175.239; 5.E.175.154; 5.E.175.157; 5.E.175.166; 5.E.175.169; 5.E.175.172;
5.E.175.175; 5.E.175.240; 5.E.175.244; 5.E.240.228; 5.E.240.229; 5.E.240.230;
5.E.240.231; 5.E.240.236; 5.E.240.237; 5.E.240.238; 5.E.240.239; 5.E.240.154;
5.E.240.157; 5.E.240.166; 5.E.240.169; 5.E.240.172; 5.E.240.175; 5.E.240.240;
5.E.240.244; 5.E.244.228; 5.E.244.229; 5.E.244.230; 5.E.244.231; 5.E.244.236;
5.E.244.237; 5.E.244.238; 5.E.244.239; 5.E.244.154; 5.E.244.157; 5.E.244.166;
5.E.244.169; 5.E.244.172; 5.E.244.175; 5.E.244.240; 5.E.244.244;
Prodrugs of 5.G 5.G.228.228; 5.G.228.229; 5.G.228.230; 5.G.228.231; 5.G.228.236;
5.G.228.237; 5.G.228.238; 5.G.228.239; 5.G.228.154; 5.G.228.157;
5.G.228.166; 5.G.228.169; 5.G.228.172; 5.G.228.175; 5.G.228.240;
5.G.228.244; 5.G.229.228; 5.G.229.229; 5.G.229.230; 5.G.229.231;
5.G.229.236; 5.G.229.237; 5.G.229.238; 5.G.229.239; 5.G.229.154;
5.G.229.157; 5.G.229.166; 5.G.229.169; 5.G.229.172; 5.G.229.175;
5.G.229.240; 5.G.229.244; 5.G.230.228; 5.G.230.229; 5.G.230.230;
5.G.230.231; 5.G.230.236; 5.G.230.237; 5.G.230.238; 5.G.230.239;
5.G.230.154; 5.G.230.157; 5.G.230.166; 5.G.230.169; 5.G.230.172;
5.G.230.175; 5.G.230.240; 5.G.230.244; 5.G.231.228; 5.G.231.229;
5.G.231.230; 5.G.231.231; 5.G.231.236; 5.G.231.237; 5.G.231.238;
5.G.231.239; 5.G.231.154; 5.G.231.157; 5.G.231.166; 5.G.231.169;
5.G.231.172; 5.G.231.175; 5.G.231.240; 5.G.231.244; 5.G.236.228;
5.G.236.229; 5.G.236.230; 5.G.236.231; 5.G.236.236; 5.G.236.237;
5.G.236.238; 5.G.236.239; 5.G.236.154; 5.G.236.157; 5.G.236.166;
5.G.236.169; 5.G.236.172; 5.G.236.175; 5.G.236.240; 5.G.236.244;
5.G.237.228; 5.G.237.229; 5.G.237.230; 5.G.237.231; 5.G.237.236;
5.G.237.237; 5.G.237.238; 5.G.237.239; 5.G.237.154; 5.G.237.157;
5.G.237.166; 5.G.237.169; 5.G.237.172; 5.G.237.175; 5.G.237.240;
5.G.237.244; 5.G.238.228; 5.G.238.229; 5.G.238.230; 5.G.238.231;
5.G.238.236; 5.G.238.237; 5.G.238.238; 5.G.238.239; 5.G.238.154;
5.G.238.157; 5.G.238.166; 5.G.238.169; 5.G.238.172; 5.G.238.175;
5.G.238.240; 5.G.238.244; 5.G.239.228; 5.G.239.229; 5.G.239.230;
5.G.239.231; 5.G.239.236; 5.G.239.237; 5.G.239.238; 5.G.239.239;
5.G.239.154; 5.G.239.157; 5.G.239.166; 5.G.239.169; 5.G.239.172;
5.G.239.175; 5.G.239.240; 5.G.239.244; 5.G.154.228; 5.G.154.229;
5.G.154.230; 5.G.154.231; 5.G.154.236; 5.G.154.237; 5.G.154.238;
5.G.154.239; 5.G.154.154; 5.G.154.157; 5.G.154.166; 5.G.154.169;
5.G.154.172; 5.G.154.175; 5.G.154.240; 5.G.154.244; 5.G.157.228;
5.G.157.229; 5.G.157.230; 5.G.157.231; 5.G.157.236; 5.G.157.237;
5.G.157.238; 5.G.157.239; 5.G.157.154; 5.G.157.157; 5.G.157.166;
5.G.157.169; 5.G.157.172; 5.G.157.175; 5.G.157.240; 5.G.157.244;
5.G.166.228; 5.G.166.229; 5.G.166.230; 5.G.166.231; 5.G.166.236;
5.G.166.237; 5.G.166.238; 5.G.166.239; 5.G.166.154; 5.G.166.157;
5.G.166.166; 5.G.166.169; 5.G.166.172; 5.G.166.175; 5.G.166.240;
5.G.166.244; 5.G.169.228; 5.G.169.229; 5.G.169.230; 5.G.169.231;
5.G.169.236; 5.G.169.237; 5.G.169.238; 5.G.169.239; 5.G.169.154;
5.G.169.157; 5.G.169.166; 5.G.169.169; 5.G.169.172; 5.G.169.175;
5.G.169.240; 5.G.169.244; 5.G.172.228; 5.G.172.229; 5.G.172.230;
5.G.172.231; 5.G.172.236; 5.G.172.237; 5.G.172.238; 5.G.172.239;
5.G.172.154; 5.G.172.157; 5.G.172.166; 5.G.172.169; 5.G.172.172;
5.G.172.175; 5.G.172.240; 5.G.172.244; 5.G.175.228; 5.G.175.229;
5.G.175.230; 5.G.175.231; 5.G.175.236; 5.G.175.237; 5.G.175.238;
5.G.175.239; 5.G.175.154; 5.G.175.157; 5.G.175.166; 5.G.175.169;
5.G.175.172; 5.G.175.175; 5.G.175.240; 5.G.175.244; 5.G.240.228;
5.G.240.229; 5.G.240.230; 5.G.240.231; 5.G.240.236; 5.G.240.237;
5.G.240.238; 5.G.240.239; 5.G.240.154; 5.G.240.157; 5.G.240.166;
5.G.240.169; 5.G.240.172; 5.G.240.175; 5.G.240.240; 5.G.240.244;
5.G.244.228; 5.G.244.229; 5.G.244.230; 5.G.244.231; 5.G.244.236;
5.G.244.237; 5.G.244.238; 5.G.244.239; 5.G.244.154; 5.G.244.157;
5.G.244.166; 5.G.244.169; 5.G.244.172; 5.G.244.175; 5.G.244.240;
5.G.244.244;
Prodrugs of 5.I 5.I.228.228; 5.I.228.229; 5.I.228.230; 5.I.228.231; 5.I.228.236; 5.I.228.237;
5.I.228.238; 5.I.228.239; 5.I.228.154; 5.I.228.157; 5.I.228.166; 5.I.228.169;
5.I.228.172; 5.I.228.175; 5.I.228.240; 5.I.228.244; 5.I.229.228; 5.I.229.229;

TABLE 100-continued

5.I.229.230; 5.I.229.231; 5.I.229.236; 5.I.229.237; 5.I.229.238; 5.I.229.239;
5.I.229.154; 5.I.229.157; 5.I.229.166; 5.I.229.169; 5.I.229.172; 5.I.229.175;
5.I.229.240; 5.I.229.244; 5.I.230.228; 5.I.230.229; 5.I.230.230; 5.I.230.231;
5.I.230.236; 5.I.230.237; 5.I.230.238; 5.I.230.239; 5.I.230.154; 5.I.230.157;
5.I.230.166; 5.I.230.169; 5.I.230.172; 5.I.230.175; 5.I.230.240; 5.I.230.244;
5.I.231.228; 5.I.231.229; 5.I.231.230; 5.I.231.231; 5.I.231.236; 5.I.231.237;
5.I.231.238; 5.I.231.239; 5.I.231.154; 5.I.231.157; 5.I.231.166; 5.I.231.169;
5.I.231.172; 5.I.231.175; 5.I.231.240; 5.I.231.244; 5.I.236.228; 5.I.236.229;
5.I.236.230; 5.I.236.231; 5.I.236.236; 5.I.236.237; 5.I.236.238; 5.I.236.239;
5.I.236.154; 5.I.236.157; 5.I.236.166; 5.I.236.169; 5.I.236.172; 5.I.236.175;
5.I.236.240; 5.I.236.244; 5.I.237.228; 5.I.237.229; 5.I.237.230; 5.I.237.231;
5.I.237.236; 5.I.237.237; 5.I.237.238; 5.I.237.239; 5.I.237.154; 5.I.237.157;
5.I.237.166; 5.I.237.169; 5.I.237.172; 5.I.237.175; 5.I.237.240; 5.I.237.244;
5.I.238.228; 5.I.238.229; 5.I.238.230; 5.I.238.231; 5.I.238.236; 5.I.238.237;
5.I.238.238; 5.I.238.239; 5.I.238.154; 5.I.238.157; 5.I.238.166; 5.I.238.169;
5.I.238.172; 5.I.238.175; 5.I.238.240; 5.I.238.244; 5.I.239.228; 5.I.239.229;
5.I.239.230; 5.I.239.231; 5.I.239.236; 5.I.239.237; 5.I.239.238; 5.I.239.239;
5.I.239.154; 5.I.239.157; 5.I.239.166; 5.I.239.169; 5.I.239.172; 5.I.239.175;
5.I.239.240; 5.I.239.244; 5.I.154.228; 5.I.154.229; 5.I.154.230; 5.I.154.231;
5.I.154.236; 5.I.154.237; 5.I.154.238; 5.I.154.239; 5.I.154.154; 5.I.154.157;
5.I.154.166; 5.I.154.169; 5.I.154.172; 5.I.154.175; 5.I.154.240; 5.I.154.244;
5.I.157.228; 5.I.157.229; 5.I.157.230; 5.I.157.231; 5.I.157.236; 5.I.157.237;
5.I.157.238; 5.I.157.239; 5.I.157.154; 5.I.157.157; 5.I.157.166; 5.I.157.169;
5.I.157.172; 5.I.157.175; 5.I.157.240; 5.I.157.244; 5.I.166.228; 5.I.166.229;
5.I.166.230; 5.I.166.231; 5.I.166.236; 5.I.166.237; 5.I.166.238; 5.I.166.239;
5.I.166.154; 5.I.166.157; 5.I.166.166; 5.I.166.169; 5.I.166.172; 5.I.166.175;
5.I.166.240; 5.I.166.244; 5.I.169.228; 5.I.169.229; 5.I.169.230; 5.I.169.231;
5.I.169.236; 5.I.169.237; 5.I.169.238; 5.I.169.239; 5.I.169.154; 5.I.169.157;
5.I.169.166; 5.I.169.169; 5.I.169.172; 5.I.169.175; 5.I.169.240; 5.I.169.244;
5.I.172.228; 5.I.172.229; 5.I.172.230; 5.I.172.231; 5.I.172.236; 5.I.172.237;
5.I.172.238; 5.I.172.239; 5.I.172.154; 5.I.172.157; 5.I.172.166; 5.I.172.169;
5.I.172.172; 5.I.172.175; 5.I.172.240; 5.I.172.244; 5.I.175.228; 5.I.175.229;
5.I.175.230; 5.I.175.231; 5.I.175.236; 5.I.175.237; 5.I.175.238; 5.I.175.239;
5.I.175.154; 5.I.175.157; 5.I.175.166; 5.I.175.169; 5.I.175.172; 5.I.175.175;
5.I.175.240; 5.I.175.244; 5.I.240.228; 5.I.240.229; 5.I.240.230; 5.I.240.231;
5.I.240.236; 5.I.240.237; 5.I.240.238; 5.I.240.239; 5.I.240.154; 5.I.240.157;
5.I.240.166; 5.I.240.169; 5.I.240.172; 5.I.240.175; 5.I.240.240; 5.I.240.244;
5.I.244.228; 5.I.244.229; 5.I.244.230; 5.I.244.231; 5.I.244.236; 5.I.244.237;
5.I.244.238; 5.I.244.239; 5.I.244.154; 5.I.244.157; 5.I.244.166; 5.I.244.169;
5.I.244.172; 5.I.244.175; 5.I.244.240; 5.I.244.244;
Prodrugs of 5.J 5.J.228.228; 5.J.228.229; 5.J.228.230; 5.J.228.231; 5.J.228.236; 5.J.228.237;
5.J.228.238; 5.J.228.239; 5.J.228.154; 5.J.228.157; 5.J.228.166; 5.J.228.169;
5.J.228.172; 5.J.228.175; 5.J.228.240; 5.J.228.244; 5.J.229.228; 5.J.229.229;
5.J.229.230; 5.J.229.231; 5.J.229.236; 5.J.229.237; 5.J.229.238; 5.J.229.239;
5.J.229.154; 5.J.229.157; 5.J.229.166; 5.J.229.169; 5.J.229.172; 5.J.229.175;
5.J.229.240; 5.J.229.244; 5.J.230.228; 5.J.230.229; 5.J.230.230; 5.J.230.231;
5.J.230.236; 5.J.230.237; 5.J.230.238; 5.J.230.239; 5.J.230.154; 5.J.230.157;
5.J.230.166; 5.J.230.169; 5.J.230.172; 5.J.230.175; 5.J.230.240; 5.J.230.244;
5.J.231.228; 5.J.231.229; 5.J.231.230; 5.J.231.231; 5.J.231.236; 5.J.231.237;
5.J.231.238; 5.J.231.239; 5.J.231.154; 5.J.231.157; 5.J.231.166; 5.J.231.169;
5.J.231.172; 5.J.231.175; 5.J.231.240; 5.J.231.244; 5.J.236.228; 5.J.236.229;
5.J.236.230; 5.J.236.231; 5.J.236.236; 5.J.236.237; 5.J.236.238; 5.J.236.239;
5.J.236.154; 5.J.236.157; 5.J.236.166; 5.J.236.169; 5.J.236.172; 5.J.236.175;
5.J.236.240; 5.J.236.244; 5.J.237.228; 5.J.237.229; 5.J.237.230; 5.J.237.231;
5.J.237.236; 5.J.237.237; 5.J.237.238; 5.J.237.239; 5.J.237.154; 5.J.237.157;
5.J.237.166; 5.J.237.169; 5.J.237.172; 5.J.237.175; 5.J.237.240; 5.J.237.244;
5.J.238.228; 5.J.238.229; 5.J.238.230; 5.J.238.231; 5.J.238.236; 5.J.238.237;
5.J.238.238; 5.J.238.239; 5.J.238.154; 5.J.238.157; 5.J.238.166; 5.J.238.169;
5.J.238.172; 5.J.238.175; 5.J.238.240; 5.J.238.244; 5.J.239.228; 5.J.239.229;
5.J.239.230; 5.J.239.231; 5.J.239.236; 5.J.239.237; 5.J.239.238; 5.J.239.239;
5.J.239.154; 5.J.239.157; 5.J.239.166; 5.J.239.169; 5.J.239.172; 5.J.239.175;
5.J.239.240; 5.J.239.244; 5.J.154.228; 5.J.154.229; 5.J.154.230; 5.J.154.231;
5.J.154.236; 5.J.154.237; 5.J.154.238; 5.J.154.239; 5.J.154.154; 5.J.154.157;
5.J.154.166; 5.J.154.169; 5.J.154.172; 5.J.154.175; 5.J.154.240; 5.J.154.244;
5.J.157.228; 5.J.157.229; 5.J.157.230; 5.J.157.231; 5.J.157.236; 5.J.157.237;
5.J.157.238; 5.J.157.239; 5.J.157.154; 5.J.157.157; 5.J.157.166; 5.J.157.169;
5.J.157.172; 5.J.157.175; 5.J.157.240; 5.J.157.244; 5.J.166.228; 5.J.166.229;
5.J.166.230; 5.J.166.231; 5.J.166.236; 5.J.166.237; 5.J.166.238; 5.J.166.239;
5.J.166.154; 5.J.166.157; 5.J.166.166; 5.J.166.169; 5.J.166.172; 5.J.166.175;
5.J.166.240; 5.J.166.244; 5.J.169.228; 5.J.169.229; 5.J.169.230; 5.J.169.231;
5.J.169.236; 5.J.169.237; 5.J.169.238; 5.J.169.239; 5.J.169.154; 5.J.169.157;
5.J.169.166; 5.J.169.169; 5.J.169.172; 5.J.169.175; 5.J.169.240; 5.J.169.244;
5.J.172.228; 5.J.172.229; 5.J.172.230; 5.J.172.231; 5.J.172.236; 5.J.172.237;
5.J.172.238; 5.J.172.239; 5.J.172.154; 5.J.172.157; 5.J.172.166; 5.J.172.169;
5.J.172.172; 5.J.172.175; 5.J.172.240; 5.J.172.244; 5.J.175.228; 5.J.175.229;
5.J.175.230; 5.J.175.231; 5.J.175.236; 5.J.175.237; 5.J.175.238; 5.J.175.239;
5.J.175.154; 5.J.175.157; 5.J.175.166; 5.J.175.169; 5.J.175.172; 5.J.175.175;

TABLE 100-continued

5.J.175.240; 5.J.175.244; 5.J.240.228; 5.J.240.229; 5.J.240.230; 5.J.240.231;
5.J.240.236; 5.J.240.237; 5.J.240.238; 5.J.240.239; 5.J.240.154; 5.J.240.157;
5.J.240.166; 5.J.240.169; 5.J.240.172; 5.J.240.175; 5.J.240.240; 5.J.240.244;
5.J.244.228; 5.J.244.229; 5.J.244.230; 5.J.244.231; 5.J.244.236; 5.J.244.237;
5.J.244.238; 5.J.244.239; 5.J.244.154; 5.J.244.157; 5.J.244.166; 5.J.244.169;
5.J.244.172; 5.J.244.175; 5.J.244.240; 5.J.244.244;
Prodrugs of 5.L 5.L.228.228; 5.L.228.229; 5.L.228.230; 5.L.228.231; 5.L.228.236;
5.L.228.237; 5.L.228.238; 5.L.228.239; 5.L.228.154; 5.L.228.157; 5.L.228.166;
5.L.228.169; 5.L.228.172; 5.L.228.175; 5.L.228.240; 5.L.228.244; 5.L.229.228;
5.L.229.229; 5.L.229.230; 5.L.229.231; 5.L.229.236; 5.L.229.237; 5.L.229.238;
5.L.229.239; 5.L.229.154; 5.L.229.157; 5.L.229.166; 5.L.229.169; 5.L.229.172;
5.L.229.175; 5.L.229.240; 5.L.229.244; 5.L.230.228; 5.L.230.229; 5.L.230.230;
5.L.230.231; 5.L.230.236; 5.L.230.237; 5.L.230.238; 5.L.230.239; 5.L.230.154;
5.L.230.157; 5.L.230.166; 5.L.230.169; 5.L.230.172; 5.L.230.175; 5.L.230.240;
5.L.230.244; 5.L.231.228; 5.L.231.229; 5.L.231.230; 5.L.231.231; 5.L.231.236;
5.L.231.237; 5.L.231.238; 5.L.231.239; 5.L.231.154; 5.L.231.157; 5.L.231.166;
5.L.231.169; 5.L.231.172; 5.L.231.175; 5.L.231.240; 5.L.231.244; 5.L.236.228;
5.L.236.229; 5.L.236.230; 5.L.236.231; 5.L.236.236; 5.L.236.237; 5.L.236.238;
5.L.236.239; 5.L.236.154; 5.L.236.157; 5.L.236.166; 5.L.236.169; 5.L.236.172;
5.L.236.175; 5.L.236.240; 5.L.236.244; 5.L.237.228; 5.L.237.229; 5.L.237.230;
5.L.237.231; 5.L.237.236; 5.L.237.237; 5.L.237.238; 5.L.237.239; 5.L.237.154;
5.L.237.157; 5.L.237.166; 5.L.237.169; 5.L.237.172; 5.L.237.175; 5.L.237.240;
5.L.237.244; 5.L.238.228; 5.L.238.229; 5.L.238.230; 5.L.238.231; 5.L.238.236;
5.L.238.237; 5.L.238.238; 5.L.238.239; 5.L.238.154; 5.L.238.157; 5.L.238.166;
5.L.238.169; 5.L.238.172; 5.L.238.175; 5.L.238.240; 5.L.238.244; 5.L.239.228;
5.L.239.229; 5.L.239.230; 5.L.239.231; 5.L.239.236; 5.L.239.237; 5.L.239.238;
5.L.239.239; 5.L.239.154; 5.L.239.157; 5.L.239.166; 5.L.239.169; 5.L.239.172;
5.L.239.175; 5.L.239.240; 5.L.239.244; 5.L.154.228; 5.L.154.229; 5.L.154.230;
5.L.154.231; 5.L.154.236; 5.L.154.237; 5.L.154.238; 5.L.154.239; 5.L.154.154;
5.L.154.157; 5.L.154.166; 5.L.154.169; 5.L.154.172; 5.L.154.175; 5.L.154.240;
5.L.154.244; 5.L.157.228; 5.L.157.229; 5.L.157.230; 5.L.157.231; 5.L.157.236;
5.L.157.237; 5.L.157.238; 5.L.157.239; 5.L.157.154; 5.L.157.157; 5.L.157.166;
5.L.157.169; 5.L.157.172; 5.L.157.175; 5.L.157.240; 5.L.157.244; 5.L.166.228;
5.L.166.229; 5.L.166.230; 5.L.166.231; 5.L.166.236; 5.L.166.237; 5.L.166.238;
5.L.166.239; 5.L.166.154; 5.L.166.157; 5.L.166.166; 5.L.166.169; 5.L.166.172;
5.L.166.175; 5.L.166.240; 5.L.166.244; 5.L.169.228; 5.L.169.229; 5.L.169.230;
5.L.169.231; 5.L.169.236; 5.L.169.237; 5.L.169.238; 5.L.169.239; 5.L.169.154;
5.L.169.157; 5.L.169.166; 5.L.169.169; 5.L.169.172; 5.L.169.175; 5.L.169.240;
5.L.169.244; 5.L.172.228; 5.L.172.229; 5.L.172.230; 5.L.172.231; 5.L.172.236;
5.L.172.237; 5.L.172.238; 5.L.172.239; 5.L.172.154; 5.L.172.157; 5.L.172.166;
5.L.172.169; 5.L.172.172; 5.L.172.175; 5.L.172.240; 5.L.172.244; 5.L.175.228;
5.L.175.229; 5.L.175.230; 5.L.175.231; 5.L.175.236; 5.L.175.237; 5.L.175.238;
5.L.175.239; 5.L.175.154; 5.L.175.157; 5.L.175.166; 5.L.175.169; 5.L.175.172;
5.L.175.175; 5.L.175.240; 5.L.175.244; 5.L.240.228; 5.L.240.229; 5.L.240.230;
5.L.240.231; 5.L.240.236; 5.L.240.237; 5.L.240.238; 5.L.240.239; 5.L.240.154;
5.L.240.157; 5.L.240.166; 5.L.240.169; 5.L.240.172; 5.L.240.175; 5.L.240.240;
5.L.240.244; 5.L.244.228; 5.L.244.229; 5.L.244.230; 5.L.244.231; 5.L.244.236;
5.L.244.237; 5.L.244.238; 5.L.244.239; 5.L.244.154; 5.L.244.157; 5.L.244.166;
5.L.244.169; 5.L.244.172; 5.L.244.175; 5.L.244.240; 5.L.244.244;
Prodrugs of 5.O 5.O.228.228; 5.O.228.229; 5.O.228.230; 5.O.228.231; 5.O.228.236;
5.O.228.237; 5.O.228.238; 5.O.228.239; 5.O.228.154; 5.O.228.157;
5.O.228.166; 5.O.228.169; 5.O.228.172; 5.O.228.175; 5.O.228.240;
5.O.228.244; 5.O.229.228; 5.O.229.229; 5.O.229.230; 5.O.229.231;
5.O.229.236; 5.O.229.237; 5.O.229.238; 5.O.229.239; 5.O.229.154;
5.O.229.157; 5.O.229.166; 5.O.229.169; 5.O.229.172; 5.O.229.175;
5.O.229.240; 5.O.229.244; 5.O.230.228; 5.O.230.229; 5.O.230.230;
5.O.230.231; 5.O.230.236; 5.O.230.237; 5.O.230.238; 5.O.230.239;
5.O.230.154; 5.O.230.157; 5.O.230.166; 5.O.230.169; 5.O.230.172;
5.O.230.175; 5.O.230.240; 5.O.230.244; 5.O.231.228; 5.O.231.229;
5.O.231.230; 5.O.231.231; 5.O.231.236; 5.O.231.237; 5.O.231.238;
5.O.231.239; 5.O.231.154; 5.O.231.157; 5.O.231.166; 5.O.231.169;
5.O.231.172; 5.O.231.175; 5.O.231.240; 5.O.231.244; 5.O.236.228;
5.O.236.229; 5.O.236.230; 5.O.236.231; 5.O.236.236; 5.O.236.237;
5.O.236.238; 5.O.236.239; 5.O.236.154; 5.O.236.157; 5.O.236.166;
5.O.236.169; 5.O.236.172; 5.O.236.175; 5.O.236.240; 5.O.236.244;
5.O.237.228; 5.O.237.229; 5.O.237.230; 5.O.237.231; 5.O.237.236;
5.O.237.237; 5.O.237.238; 5.O.237.239; 5.O.237.154; 5.O.237.157;
5.O.237.166; 5.O.237.169; 5.O.237.172; 5.O.237.175; 5.O.237.240;
5.O.237.244; 5.O.238.228; 5.O.238.229; 5.O.238.230; 5.O.238.231;
5.O.238.236; 5.O.238.237; 5.O.238.238; 5.O.238.239; 5.O.238.154;
5.O.238.157; 5.O.238.166; 5.O.238.169; 5.O.238.172; 5.O.238.175;
5.O.238.240; 5.O.238.244; 5.O.239.228; 5.O.239.229; 5.O.239.230;
5.O.239.231; 5.O.239.236; 5.O.239.237; 5.O.239.238; 5.O.239.239;
5.O.239.154; 5.O.239.157; 5.O.239.166; 5.O.239.169; 5.O.239.172;
5.O.239.175; 5.O.239.240; 5.O.239.244; 5.O.154.228; 5.O.154.229;

TABLE 100-continued

5.O.154.230; 5.O.154.231; 5.O.154.236; 5.O.154.237; 5.O.154.238;
5.O.154.239; 5.O.154.154; 5.O.154.157; 5.O.154.166; 5.O.154.169;
5.O.154.172; 5.O.154.175; 5.O.154.240; 5.O.154.244; 5.O.157.228;
5.O.157.229; 5.O.157.230; 5.O.157.231; 5.O.157.236; 5.O.157.237;
5.O.157.238; 5.O.157.239; 5.O.157.154; 5.O.157.157; 5.O.157.166;
5.O.157.169; 5.O.157.172; 5.O.157.175; 5.O.157.240; 5.O.157.244;
5.O.166.228; 5.O.166.229; 5.O.166.230; 5.O.166.231; 5.O.166.236;
5.O.166.237; 5.O.166.238; 5.O.166.239; 5.O.166.154; 5.O.166.157;
5.O.166.166; 5.O.166.169; 5.O.166.172; 5.O.166.175; 5.O.166.240;
5.O.166.244; 5.O.169.228; 5.O.169.229; 5.O.169.230; 5.O.169.231;
5.O.169.236; 5.O.169.237; 5.O.169.238; 5.O.169.239; 5.O.169.154;
5.O.169.157; 5.O.169.166; 5.O.169.169; 5.O.169.172; 5.O.169.175;
5.O.169.240; 5.O.169.244; 5.O.172.228; 5.O.172.229; 5.O.172.230;
5.O.172.231; 5.O.172.236; 5.O.172.237; 5.O.172.238; 5.O.172.239;
5.O.172.154; 5.O.172.157; 5.O.172.166; 5.O.172.169; 5.O.172.172;
5.O.172.175; 5.O.172.240; 5.O.172.244; 5.O.175.228; 5.O.175.229;
5.O.175.230; 5.O.175.231; 5.O.175.236; 5.O.175.237; 5.O.175.238;
5.O.175.239; 5.O.175.154; 5.O.175.157; 5.O.175.166; 5.O.175.169;
5.O.175.172; 5.O.175.175; 5.O.175.240; 5.O.175.244; 5.O.240.228;
5.O.240.229; 5.O.240.230; 5.O.240.231; 5.O.240.236; 5.O.240.237;
5.O.240.238; 5.O.240.239; 5.O.240.154; 5.O.240.157; 5.O.240.166;
5.O.240.169; 5.O.240.172; 5.O.240.175; 5.O.240.240; 5.O.240.244;
5.O.244.228; 5.O.244.229; 5.O.244.230; 5.O.244.231; 5.O.244.236;
5.O.244.237; 5.O.244.238; 5.O.244.239; 5.O.244.154; 5.O.244.157;
5.O.244.166; 5.O.244.169; 5.O.244.172; 5.O.244.175; 5.O.244.240;
5.O.244.244;

Prodrugs of 5.P

5.P.228.228; 5.P.228.229; 5.P.228.230; 5.P.228.231; 5.P.228.236;
5.P.228.237; 5.P.228.238; 5.P.228.239; 5.P.228.154; 5.P.228.157; 5.P.228.166;
5.P.228.169; 5.P.228.172; 5.P.228.175; 5.P.228.240; 5.P.228.244; 5.P.229.228;
5.P.229.229; 5.P.229.230; 5.P.229.231; 5.P.229.236; 5.P.229.237; 5.P.229.238;
5.P.229.239; 5.P.229.154; 5.P.229.157; 5.P.229.166; 5.P.229.169; 5.P.229.172;
5.P.229.175; 5.P.229.240; 5.P.229.244; 5.P.230.228; 5.P.230.229; 5.P.230.230;
5.P.230.231; 5.P.230.236; 5.P.230.237; 5.P.230.238; 5.P.230.239; 5.P.230.154;
5.P.230.157; 5.P.230.166; 5.P.230.169; 5.P.230.172; 5.P.230.175; 5.P.230.240;
5.P.230.244; 5.P.231.228; 5.P.231.229; 5.P.231.230; 5.P.231.231; 5.P.231.236;
5.P.231.237; 5.P.231.238; 5.P.231.239; 5.P.231.154; 5.P.231.157; 5.P.231.166;
5.P.231.169; 5.P.231.172; 5.P.231.175; 5.P.231.240; 5.P.231.244; 5.P.236.228;
5.P.236.229; 5.P.236.230; 5.P.236.231; 5.P.236.236; 5.P.236.237; 5.P.236.238;
5.P.236.239; 5.P.236.154; 5.P.236.157; 5.P.236.166; 5.P.236.169; 5.P.236.172;
5.P.236.175; 5.P.236.240; 5.P.236.244; 5.P.237.228; 5.P.237.229; 5.P.237.230;
5.P.237.231; 5.P.237.236; 5.P.237.237; 5.P.237.238; 5.P.237.239; 5.P.237.154;
5.P.237.157; 5.P.237.166; 5.P.237.169; 5.P.237.172; 5.P.237.175; 5.P.237.240;
5.P.237.244; 5.P.238.228; 5.P.238.229; 5.P.238.230; 5.P.238.231; 5.P.238.236;
5.P.238.237; 5.P.238.238; 5.P.238.239; 5.P.238.154; 5.P.238.157; 5.P.238.166;
5.P.238.169; 5.P.238.172; 5.P.238.175; 5.P.238.240; 5.P.238.244; 5.P.239.228;
5.P.239.229; 5.P.239.230; 5.P.239.231; 5.P.239.236; 5.P.239.237; 5.P.239.238;
5.P.239.239; 5.P.239.154; 5.P.239.157; 5.P.239.166; 5.P.239.169; 5.P.239.172;
5.P.239.175; 5.P.239.240; 5.P.239.244; 5.P.154.228; 5.P.154.229; 5.P.154.230;
5.P.154.231; 5.P.154.236; 5.P.154.237; 5.P.154.238; 5.P.154.239; 5.P.154.154;
5.P.154.157; 5.P.154.166; 5.P.154.169; 5.P.154.172; 5.P.154.175; 5.P.154.240;
5.P.154.244; 5.P.157.228; 5.P.157.229; 5.P.157.230; 5.P.157.231; 5.P.157.236;
5.P.157.237; 5.P.157.238; 5.P.157.239; 5.P.157.154; 5.P.157.157; 5.P.157.166;
5.P.157.169; 5.P.157.172; 5.P.157.175; 5.P.157.240; 5.P.157.244; 5.P.166.228;
5.P.166.229; 5.P.166.230; 5.P.166.231; 5.P.166.236; 5.P.166.237; 5.P.166.238;
5.P.166.239; 5.P.166.154; 5.P.166.157; 5.P.166.166; 5.P.166.169; 5.P.166.172;
5.P.166.175; 5.P.166.240; 5.P.166.244; 5.P.169.228; 5.P.169.229; 5.P.169.230;
5.P.169.231; 5.P.169.236; 5.P.169.237; 5.P.169.238; 5.P.169.239; 5.P.169.154;
5.P.169.157; 5.P.169.166; 5.P.169.169; 5.P.169.172; 5.P.169.175; 5.P.169.240;
5.P.169.244; 5.P.172.228; 5.P.172.229; 5.P.172.230; 5.P.172.231; 5.P.172.236;
5.P.172.237; 5.P.172.238; 5.P.172.239; 5.P.172.154; 5.P.172.157; 5.P.172.166;
5.P.172.169; 5.P.172.172; 5.P.172.175; 5.P.172.240; 5.P.172.244; 5.P.175.228;
5.P.175.229; 5.P.175.230; 5.P.175.231; 5.P.175.236; 5.P.175.237; 5.P.175.238;
5.P.175.239; 5.P.175.154; 5.P.175.157; 5.P.175.166; 5.P.175.169; 5.P.175.172;
5.P.175.175; 5.P.175.240; 5.P.175.244; 5.P.240.228; 5.P.240.229; 5.P.240.230;
5.P.240.231; 5.P.240.236; 5.P.240.237; 5.P.240.238; 5.P.240.239; 5.P.240.154;
5.P.240.157; 5.P.240.166; 5.P.240.169; 5.P.240.172; 5.P.240.175; 5.P.240.240;
5.P.240.244; 5.P.244.228; 5.P.244.229; 5.P.244.230; 5.P.244.231; 5.P.244.236;
5.P.244.237; 5.P.244.238; 5.P.244.239; 5.P.244.154; 5.P.244.157; 5.P.244.166;
5.P.244.169; 5.P.244.172; 5.P.244.175; 5.P.244.240; 5.P.244.244;

Prodrugs of 5.U

5.U.228.228; 5.U.228.229; 5.U.228.230; 5.U.228.231; 5.U.228.236;
5.U.228.237; 5.U.228.238; 5.U.228.239; 5.U.228.154; 5.U.228.157;
5.U.228.166; 5.U.228.169; 5.U.228.172; 5.U.228.175; 5.U.228.240;
5.U.228.244; 5.U.229.228; 5.U.229.229; 5.U.229.230; 5.U.229.231;
5.U.229.236; 5.U.229.237; 5.U.229.238; 5.U.229.239; 5.U.229.154;
5.U.229.157; 5.U.229.166; 5.U.229.169; 5.U.229.172; 5.U.229.175;

TABLE 100-continued

5.U.229.240; 5.U.229.244; 5.U.230.228; 5.U.230.229; 5.U.230.230;
5.U.230.231; 5.U.230.236; 5.U.230.237; 5.U.230.238; 5.U.230.239;
5.U.230.154; 5.U.230.157; 5.U.230.166; 5.U.230.169; 5.U.230.172;
5.U.230.175; 5.U.230.240; 5.U.230.244; 5.U.231.228; 5.U.231.229;
5.U.231.230; 5.U.231.231; 5.U.231.236; 5.U.231.237; 5.U.231.238;
5.U.231.239; 5.U.231.154; 5.U.231.157; 5.U.231.166; 5.U.231.169;
5.U.231.172; 5.U.231.175; 5.U.231.240; 5.U.231.244; 5.U.236.228;
5.U.236.229; 5.U.236.230; 5.U.236.231; 5.U.236.236; 5.U.236.237;
5.U.236.238; 5.U.236.239; 5.U.236.154; 5.U.236.157; 5.U.236.166;
5.U.236.169; 5.U.236.172; 5.U.236.175; 5.U.236.240; 5.U.236.244;
5.U.237.228; 5.U.237.229; 5.U.237.230; 5.U.237.231; 5.U.237.236;
5.U.237.237; 5.U.237.238; 5.U.237.239; 5.U.237.154; 5.U.237.157;
5.U.237.166; 5.U.237.169; 5.U.237.172; 5.U.237.175; 5.U.237.240;
5.U.237.244; 5.U.238.228; 5.U.238.229; 5.U.238.230; 5.U.238.231;
5.U.238.236; 5.U.238.237; 5.U.238.238; 5.U.238.239; 5.U.238.154;
5.U.238.157; 5.U.238.166; 5.U.238.169; 5.U.238.172; 5.U.238.175;
5.U.238.240; 5.U.238.244; 5.U.239.228; 5.U.239.229; 5.U.239.230;
5.U.239.231; 5.U.239.236; 5.U.239.237; 5.U.239.238; 5.U.239.239;
5.U.239.154; 5.U.239.157; 5.U.239.166; 5.U.239.169; 5.U.239.172;
5.U.239.175; 5.U.239.240; 5.U.239.244; 5.U.154.228; 5.U.154.229;
5.U.154.230; 5.U.154.231; 5.U.154.236; 5.U.154.237; 5.U.154.238;
5.U.154.239; 5.U.154.154; 5.U.154.157; 5.U.154.166; 5.U.154.169;
5.U.154.172; 5.U.154.175; 5.U.154.240; 5.U.154.244; 5.U.157.228;
5.U.157.229; 5.U.157.230; 5.U.157.231; 5.U.157.236; 5.U.157.237;
5.U.157.238; 5.U.157.239; 5.U.157.154; 5.U.157.157; 5.U.157.166;
5.U.157.169; 5.U.157.172; 5.U.157.175; 5.U.157.240; 5.U.157.244;
5.U.166.228; 5.U.166.229; 5.U.166.230; 5.U.166.231; 5.U.166.236;
5.U.166.237; 5.U.166.238; 5.U.166.239; 5.U.166.154; 5.U.166.157;
5.U.166.166; 5.U.166.169; 5.U.166.172; 5.U.166.175; 5.U.166.240;
5.U.166.244; 5.U.169.228; 5.U.169.229; 5.U.169.230; 5.U.169.231;
5.U.169.236; 5.U.169.237; 5.U.169.238; 5.U.169.239; 5.U.169.154;
5.U.169.157; 5.U.169.166; 5.U.169.169; 5.U.169.172; 5.U.169.175;
5.U.169.240; 5.U.169.244; 5.U.172.228; 5.U.172.229; 5.U.172.230;
5.U.172.231; 5.U.172.236; 5.U.172.237; 5.U.172.238; 5.U.172.239;
5.U.172.154; 5.U.172.157; 5.U.172.166; 5.U.172.169; 5.U.172.172;
5.U.172.175; 5.U.172.240; 5.U.172.244; 5.U.175.228; 5.U.175.229;
5.U.175.230; 5.U.175.231; 5.U.175.236; 5.U.175.237; 5.U.175.238;
5.U.175.239; 5.U.175.154; 5.U.175.157; 5.U.175.166; 5.U.175.169;
5.U.175.172; 5.U.175.175; 5.U.175.240; 5.U.175.244; 5.U.240.228;
5.U.240.229; 5.U.240.230; 5.U.240.231; 5.U.240.236; 5.U.240.237;
5.U.240.238; 5.U.240.239; 5.U.240.154; 5.U.240.157; 5.U.240.166;
5.U.240.169; 5.U.240.172; 5.U.240.175; 5.U.240.240; 5.U.240.244;
5.U.244.228; 5.U.244.229; 5.U.244.230; 5.U.244.231; 5.U.244.236;
5.U.244.237; 5.U.244.238; 5.U.244.239; 5.U.244.154; 5.U.244.157;
5.U.244.166; 5.U.244.169; 5.U.244.172; 5.U.244.175; 5.U.244.240;
5.U.244.244;

Prodrugs of 5.W

5.W.228.228; 5.W.228.229; 5.W.228.230; 5.W.228.231; 5.W.228.236;
5.W.228.237; 5.W.228.238; 5.W.228.239; 5.W.228.154; 5.W.228.157;
5.W.228.166; 5.W.228.169; 5.W.228.172; 5.W.228.175; 5.W.228.240;
5.W.228.244; 5.W.229.228; 5.W.229.229; 5.W.229.230; 5.W.229.231;
5.W.229.236; 5.W.229.237; 5.W.229.238; 5.W.229.239; 5.W.229.154;
5.W.229.157; 5.W.229.166; 5.W.229.169; 5.W.229.172; 5.W.229.175;
5.W.229.240; 5.W.229.244; 5.W.230.228; 5.W.230.229; 5.W.230.230;
5.W.230.231; 5.W.230.236; 5.W.230.237; 5.W.230.238; 5.W.230.239;
5.W.230.154; 5.W.230.157; 5.W.230.166; 5.W.230.169; 5.W.230.172;
5.W.230.175; 5.W.230.240; 5.W.230.244; 5.W.231.228; 5.W.231.229;
5.W.231.230; 5.W.231.231; 5.W.231.236; 5.W.231.237; 5.W.231.238;
5.W.231.239; 5.W.231.154; 5.W.231.157; 5.W.231.166; 5.W.231.169;
5.W.231.172; 5.W.231.175; 5.W.231.240; 5.W.231.244; 5.W.236.228;
5.W.236.229; 5.W.236.230; 5.W.236.231; 5.W.236.236; 5.W.236.237;
5.W.236.238; 5.W.236.239; 5.W.236.154; 5.W.236.157; 5.W.236.166;
5.W.236.169; 5.W.236.172; 5.W.236.175; 5.W.236.240; 5.W.236.244;
5.W.237.228; 5.W.237.229; 5.W.237.230; 5.W.237.231; 5.W.237.236;
5.W.237.237; 5.W.237.238; 5.W.237.239; 5.W.237.154; 5.W.237.157;
5.W.237.166; 5.W.237.169; 5.W.237.172; 5.W.237.175; 5.W.237.240;
5.W.237.244; 5.W.238.228; 5.W.238.229; 5.W.238.230; 5.W.238.231;
5.W.238.236; 5.W.238.237; 5.W.238.238; 5.W.238.239; 5.W.238.154;
5.W.238.157; 5.W.238.166; 5.W.238.169; 5.W.238.172; 5.W.238.175;
5.W.238.240; 5.W.238.244; 5.W.239.228; 5.W.239.229; 5.W.239.230;
5.W.239.231; 5.W.239.236; 5.W.239.237; 5.W.239.238; 5.W.239.239;
5.W.239.154; 5.W.239.157; 5.W.239.166; 5.W.239.169; 5.W.239.172;
5.W.239.175; 5.W.239.240; 5.W.239.244; 5.W.154.228; 5.W.154.229;
5.W.154.230; 5.W.154.231; 5.W.154.236; 5.W.154.237; 5.W.154.238;
5.W.154.239; 5.W.154.154; 5.W.154.157; 5.W.154.166; 5.W.154.169;
5.W.154.172; 5.W.154.175; 5.W.154.240; 5.W.154.244; 5.W.157.228;
5.W.157.229; 5.W.157.230; 5.W.157.231; 5.W.157.236; 5.W.157.237;
5.W.157.238; 5.W.157.239; 5.W.157.154; 5.W.157.157; 5.W.157.166;

TABLE 100-continued

5.W.157.169; 5.W.157.172; 5.W.157.175; 5.W.157.240; 5.W.157.244;
5.W.166.228; 5.W.166.229; 5.W.166.230; 5.W.166.231; 5.W.166.236;
5.W.166.237; 5.W.166.238; 5.W.166.239; 5.W.166.154; 5.W.166.157;
5.W.166.166; 5.W.166.169; 5.W.166.172; 5.W.166.175; 5.W.166.240;
5.W.166.244; 5.W.169.228; 5.W.169.229; 5.W.169.230; 5.W.169.231;
5.W.169.236; 5.W.169.237; 5.W.169.238; 5.W.169.239; 5.W.169.154;
5.W.169.157; 5.W.169.166; 5.W.169.169; 5.W.169.172; 5.W.169.175;
5.W.169.240; 5.W.169.244; 5.W.172.228; 5.W.172.229; 5.W.172.230;
5.W.172.231; 5.W.172.236; 5.W.172.237; 5.W.172.238; 5.W.172.239;
5.W.172.154; 5.W.172.157; 5.W.172.166; 5.W.172.169; 5.W.172.172;
5.W.172.175; 5.W.172.240; 5.W.172.244; 5.W.175.228; 5.W.175.229;
5.W.175.230; 5.W.175.231; 5.W.175.236; 5.W.175.237; 5.W.175.238;
5.W.175.239; 5.W.175.154; 5.W.175.157; 5.W.175.166; 5.W.175.169;
5.W.175.172; 5.W.175.175; 5.W.175.240; 5.W.175.244; 5.W.240.228;
5.W.240.229; 5.W.240.230; 5.W.240.231; 5.W.240.236; 5.W.240.237;
5.W.240.238; 5.W.240.239; 5.W.240.154; 5.W.240.157; 5.W.240.166;
5.W.240.169; 5.W.240.172; 5.W.240.175; 5.W.240.240; 5.W.240.244;
5.W.244.228; 5.W.244.229; 5.W.244.230; 5.W.244.231; 5.W.244.236;
5.W.244.237; 5.W.244.238; 5.W.244.239; 5.W.244.154; 5.W.244.157;
5.W.244.166; 5.W.244.169; 5.W.244.172; 5.W.244.175; 5.W.244.240;
5.W.244.244;
Prodrugs of 5.Y 5.Y.228.228; 5.Y.228.229; 5.Y.228.230; 5.Y.228.231; 5.Y.228.236;
5.Y.228.237; 5.Y.228.238; 5.Y.228.239; 5.Y.228.154; 5.Y.228.157; 5.Y.228.166;
5.Y.228.169; 5.Y.228.172; 5.Y.228.175; 5.Y.228.240; 5.Y.228.244; 5.Y.229.228;
5.Y.229.229; 5.Y.229.230; 5.Y.229.231; 5.Y.229.236; 5.Y.229.237; 5.Y.229.238;
5.Y.229.239; 5.Y.229.154; 5.Y.229.157; 5.Y.229.166; 5.Y.229.169; 5.Y.229.172;
5.Y.229.175; 5.Y.229.240; 5.Y.229.244; 5.Y.230.228; 5.Y.230.229; 5.Y.230.230;
5.Y.230.231; 5.Y.230.236; 5.Y.230.237; 5.Y.230.238; 5.Y.230.239; 5.Y.230.154;
5.Y.230.157; 5.Y.230.166; 5.Y.230.169; 5.Y.230.172; 5.Y.230.175; 5.Y.230.240;
5.Y.230.244; 5.Y.231.228; 5.Y.231.229; 5.Y.231.230; 5.Y.231.231; 5.Y.231.236;
5.Y.231.237; 5.Y.231.238; 5.Y.231.239; 5.Y.231.154; 5.Y.231.157; 5.Y.231.166;
5.Y.231.169; 5.Y.231.172; 5.Y.231.175; 5.Y.231.240; 5.Y.231.244; 5.Y.236.228;
5.Y.236.229; 5.Y.236.230; 5.Y.236.231; 5.Y.236.236; 5.Y.236.237; 5.Y.236.238;
5.Y.236.239; 5.Y.236.154; 5.Y.236.157; 5.Y.236.166; 5.Y.236.169; 5.Y.236.172;
5.Y.236.175; 5.Y.236.240; 5.Y.236.244; 5.Y.237.228; 5.Y.237.229; 5.Y.237.230;
5.Y.237.231; 5.Y.237.236; 5.Y.237.237; 5.Y.237.238; 5.Y.237.239; 5.Y.237.154;
5.Y.237.157; 5.Y.237.166; 5.Y.237.169; 5.Y.237.172; 5.Y.237.175; 5.Y.237.240;
5.Y.237.244; 5.Y.238.228; 5.Y.238.229; 5.Y.238.230; 5.Y.238.231; 5.Y.238.236;
5.Y.238.237; 5.Y.238.238; 5.Y.238.239; 5.Y.238.154; 5.Y.238.157; 5.Y.238.166;
5.Y.238.169; 5.Y.238.172; 5.Y.238.175; 5.Y.238.240; 5.Y.238.244; 5.Y.239.228;
5.Y.239.229; 5.Y.239.230; 5.Y.239.231; 5.Y.239.236; 5.Y.239.237; 5.Y.239.238;
5.Y.239.239; 5.Y.239.154; 5.Y.239.157; 5.Y.239.166; 5.Y.239.169; 5.Y.239.172;
5.Y.239.175; 5.Y.239.240; 5.Y.239.244; 5.Y.154.228; 5.Y.154.229; 5.Y.154.230;
5.Y.154.231; 5.Y.154.236; 5.Y.154.237; 5.Y.154.238; 5.Y.154.239; 5.Y.154.154;
5.Y.154.157; 5.Y.154.166; 5.Y.154.169; 5.Y.154.172; 5.Y.154.175; 5.Y.154.240;
5.Y.154.244; 5.Y.157.228; 5.Y.157.229; 5.Y.157.230; 5.Y.157.231; 5.Y.157.236;
5.Y.157.237; 5.Y.157.238; 5.Y.157.239; 5.Y.157.154; 5.Y.157.157; 5.Y.157.166;
5.Y.157.169; 5.Y.157.172; 5.Y.157.175; 5.Y.157.240; 5.Y.157.244; 5.Y.166.228;
5.Y.166.229; 5.Y.166.230; 5.Y.166.231; 5.Y.166.236; 5.Y.166.237; 5.Y.166.238;
5.Y.166.239; 5.Y.166.154; 5.Y.166.157; 5.Y.166.166; 5.Y.166.169; 5.Y.166.172;
5.Y.166.175; 5.Y.166.240; 5.Y.166.244; 5.Y.169.228; 5.Y.169.229; 5.Y.169.230;
5.Y.169.231; 5.Y.169.236; 5.Y.169.237; 5.Y.169.238; 5.Y.169.239; 5.Y.169.154;
5.Y.169.157; 5.Y.169.166; 5.Y.169.169; 5.Y.169.172; 5.Y.169.175; 5.Y.169.240;
5.Y.169.244; 5.Y.172.228; 5.Y.172.229; 5.Y.172.230; 5.Y.172.231; 5.Y.172.236;
5.Y.172.237; 5.Y.172.238; 5.Y.172.239; 5.Y.172.154; 5.Y.172.157; 5.Y.172.166;
5.Y.172.169; 5.Y.172.172; 5.Y.172.175; 5.Y.172.240; 5.Y.172.244; 5.Y.175.228;
5.Y.175.229; 5.Y.175.230; 5.Y.175.231; 5.Y.175.236; 5.Y.175.237; 5.Y.175.238;
5.Y.175.239; 5.Y.175.154; 5.Y.175.157; 5.Y.175.166; 5.Y.175.169; 5.Y.175.172;
5.Y.175.175; 5.Y.175.240; 5.Y.175.244; 5.Y.240.228; 5.Y.240.229; 5.Y.240.230;
5.Y.240.231; 5.Y.240.236; 5.Y.240.237; 5.Y.240.238; 5.Y.240.239; 5.Y.240.154;
5.Y.240.157; 5.Y.240.166; 5.Y.240.169; 5.Y.240.172; 5.Y.240.175; 5.Y.240.240;
5.Y.240.244; 5.Y.244.228; 5.Y.244.229; 5.Y.244.230; 5.Y.244.231; 5.Y.244.236;
5.Y.244.237; 5.Y.244.238; 5.Y.244.239; 5.Y.244.154; 5.Y.244.157; 5.Y.244.166;
5.Y.244.169; 5.Y.244.172; 5.Y.244.175; 5.Y.244.240; 5.Y.244.244;
Prodrugs of 6.B 6.B.228.228; 6.B.228.229; 6.B.228.230; 6.B.228.231; 6.B.228.236;
6.B.228.237; 6.B.228.238; 6.B.228.239; 6.B.228.154; 6.B.228.157; 6.B.228.166;
6.B.228.169; 6.B.228.172; 6.B.228.175; 6.B.228.240; 6.B.228.244; 6.B.229.228;
6.B.229.229; 6.B.229.230; 6.B.229.231; 6.B.229.236; 6.B.229.237; 6.B.229.238;
6.B.229.239; 6.B.229.154; 6.B.229.157; 6.B.229.166; 6.B.229.169; 6.B.229.172;
6.B.229.175; 6.B.229.240; 6.B.229.244; 6.B.230.228; 6.B.230.229; 6.B.230.230;
6.B.230.231; 6.B.230.236; 6.B.230.237; 6.B.230.238; 6.B.230.239; 6.B.230.154;
6.B.230.157; 6.B.230.166; 6.B.230.169; 6.B.230.172; 6.B.230.175; 6.B.230.240;
6.B.230.244; 6.B.231.228; 6.B.231.229; 6.B.231.230; 6.B.231.231; 6.B.231.236;
6.B.231.237; 6.B.231.238; 6.B.231.239; 6.B.231.154; 6.B.231.157; 6.B.231.166;
6.B.231.169; 6.B.231.172; 6.B.231.175; 6.B.231.240; 6.B.231.244; 6.B.236.228;

TABLE 100-continued

6.B.236.229; 6.B.236.230; 6.B.236.231; 6.B.236.236; 6.B.236.237; 6.B.236.238; 6.B.236.239; 6.B.236.154; 6.B.236.157; 6.B.236.166; 6.B.236.169; 6.B.236.172; 6.B.236.175; 6.B.236.240; 6.B.236.244; 6.B.237.228; 6.B.237.229; 6.B.237.230; 6.B.237.231; 6.B.237.236; 6.B.237.237; 6.B.237.238; 6.B.237.239; 6.B.237.154; 6.B.237.157; 6.B.237.166; 6.B.237.169; 6.B.237.172; 6.B.237.175; 6.B.237.240; 6.B.237.244; 6.B.238.228; 6.B.238.229; 6.B.238.230; 6.B.238.231; 6.B.238.236; 6.B.238.237; 6.B.238.238; 6.B.238.239; 6.B.238.154; 6.B.238.157; 6.B.238.166; 6.B.238.169; 6.B.238.172; 6.B.238.175; 6.B.238.240; 6.B.238.244; 6.B.239.228; 6.B.239.229; 6.B.239.230; 6.B.239.231; 6.B.239.236; 6.B.239.237; 6.B.239.238; 6.B.239.239; 6.B.239.154; 6.B.239.157; 6.B.239.166; 6.B.239.169; 6.B.239.172; 6.B.239.175; 6.B.239.240; 6.B.239.244; 6.B.154.228; 6.B.154.229; 6.B.154.230; 6.B.154.231; 6.B.154.236; 6.B.154.237; 6.B.154.238; 6.B.154.239; 6.B.154.154; 6.B.154.157; 6.B.154.166; 6.B.154.169; 6.B.154.172; 6.B.154.175; 6.B.154.240; 6.B.154.244; 6.B.157.228; 6.B.157.229; 6.B.157.230; 6.B.157.231; 6.B.157.236; 6.B.157.237; 6.B.157.238; 6.B.157.239; 6.B.157.154; 6.B.157.157; 6.B.157.166; 6.B.157.169; 6.B.157.172; 6.B.157.175; 6.B.157.240; 6.B.157.244; 6.B.166.228; 6.B.166.229; 6.B.166.230; 6.B.166.231; 6.B.166.236; 6.B.166.237; 6.B.166.238; 6.B.166.239; 6.B.166.154; 6.B.166.157; 6.B.166.166; 6.B.166.169; 6.B.166.172; 6.B.166.175; 6.B.166.240; 6.B.166.244; 6.B.169.228; 6.B.169.229; 6.B.169.230; 6.B.169.231; 6.B.169.236; 6.B.169.237; 6.B.169.238; 6.B.169.239; 6.B.169.154; 6.B.169.157; 6.B.169.166; 6.B.169.169; 6.B.169.172; 6.B.169.175; 6.B.169.240; 6.B.169.244; 6.B.172.228; 6.B.172.229; 6.B.172.230; 6.B.172.231; 6.B.172.236; 6.B.172.237; 6.B.172.238; 6.B.172.239; 6.B.172.154; 6.B.172.157; 6.B.172.166; 6.B.172.169; 6.B.172.172; 6.B.172.175; 6.B.172.240; 6.B.172.244; 6.B.175.228; 6.B.175.229; 6.B.175.230; 6.B.175.231; 6.B.175.236; 6.B.175.237; 6.B.175.238; 6.B.175.239; 6.B.175.154; 6.B.175.157; 6.B.175.166; 6.B.175.169; 6.B.175.172; 6.B.175.175; 6.B.175.240; 6.B.175.244; 6.B.240.228; 6.B.240.229; 6.B.240.230; 6.B.240.231; 6.B.240.236; 6.B.240.237; 6.B.240.238; 6.B.240.239; 6.B.240.154; 6.B.240.157; 6.B.240.166; 6.B.240.169; 6.B.240.172; 6.B.240.175; 6.B.240.240; 6.B.240.244; 6.B.244.228; 6.B.244.229; 6.B.244.230; 6.B.244.231; 6.B.244.236; 6.B.244.237; 6.B.244.238; 6.B.244.239; 6.B.244.154; 6.B.244.157; 6.B.244.166; 6.B.244.169; 6.B.244.172; 6.B.244.175; 6.B.244.240; 6.B.244.244;

Prodrugs of 6.D

6.D.228.228; 6.D.228.229; 6.D.228.230; 6.D.228.231; 6.D.228.236; 6.D.228.237; 6.D.228.238; 6.D.228.239; 6.D.228.154; 6.D.228.157; 6.D.228.166; 6.D.228.169; 6.D.228.172; 6.D.228.175; 6.D.228.240; 6.D.228.244; 6.D.229.228; 6.D.229.229; 6.D.229.230; 6.D.229.231; 6.D.229.236; 6.D.229.237; 6.D.229.238; 6.D.229.239; 6.D.229.154; 6.D.229.157; 6.D.229.166; 6.D.229.169; 6.D.229.172; 6.D.229.175; 6.D.229.240; 6.D.229.244; 6.D.230.228; 6.D.230.229; 6.D.230.230; 6.D.230.231; 6.D.230.236; 6.D.230.237; 6.D.230.238; 6.D.230.239; 6.D.230.154; 6.D.230.157; 6.D.230.166; 6.D.230.169; 6.D.230.172; 6.D.230.175; 6.D.230.240; 6.D.230.244; 6.D.231.228; 6.D.231.229; 6.D.231.230; 6.D.231.231; 6.D.231.236; 6.D.231.237; 6.D.231.238; 6.D.231.239; 6.D.231.154; 6.D.231.157; 6.D.231.166; 6.D.231.169; 6.D.231.172; 6.D.231.175; 6.D.231.240; 6.D.231.244; 6.D.236.228; 6.D.236.229; 6.D.236.230; 6.D.236.231; 6.D.236.236; 6.D.236.237; 6.D.236.238; 6.D.236.239; 6.D.236.154; 6.D.236.157; 6.D.236.166; 6.D.236.169; 6.D.236.172; 6.D.236.175; 6.D.236.240; 6.D.236.244; 6.D.237.228; 6.D.237.229; 6.D.237.230; 6.D.237.231; 6.D.237.236; 6.D.237.237; 6.D.237.238; 6.D.237.239; 6.D.237.154; 6.D.237.157; 6.D.237.166; 6.D.237.169; 6.D.237.172; 6.D.237.175; 6.D.237.240; 6.D.237.244; 6.D.238.228; 6.D.238.229; 6.D.238.230; 6.D.238.231; 6.D.238.236; 6.D.238.237; 6.D.238.238; 6.D.238.239; 6.D.238.154; 6.D.238.157; 6.D.238.166; 6.D.238.169; 6.D.238.172; 6.D.238.175; 6.D.238.240; 6.D.238.244; 6.D.239.228; 6.D.239.229; 6.D.239.230; 6.D.239.231; 6.D.239.236; 6.D.239.237; 6.D.239.238; 6.D.239.239; 6.D.239.154; 6.D.239.157; 6.D.239.166; 6.D.239.169; 6.D.239.172; 6.D.239.175; 6.D.239.240; 6.D.239.244; 6.D.154.228; 6.D.154.229; 6.D.154.230; 6.D.154.231; 6.D.154.236; 6.D.154.237; 6.D.154.238; 6.D.154.239; 6.D.154.154; 6.D.154.157; 6.D.154.166; 6.D.154.169; 6.D.154.172; 6.D.154.175; 6.D.154.240; 6.D.154.244; 6.D.157.228; 6.D.157.229; 6.D.157.230; 6.D.157.231; 6.D.157.236; 6.D.157.237; 6.D.157.238; 6.D.157.239; 6.D.157.154; 6.D.157.157; 6.D.157.166; 6.D.157.169; 6.D.157.172; 6.D.157.175; 6.D.157.240; 6.D.157.244; 6.D.166.228; 6.D.166.229; 6.D.166.230; 6.D.166.231; 6.D.166.236; 6.D.166.237; 6.D.166.238; 6.D.166.239; 6.D.166.154; 6.D.166.157; 6.D.166.166; 6.D.166.169; 6.D.166.172; 6.D.166.175; 6.D.166.240; 6.D.166.244; 6.D.169.228; 6.D.169.229; 6.D.169.230; 6.D.169.231; 6.D.169.236; 6.D.169.237; 6.D.169.238; 6.D.169.239; 6.D.169.154; 6.D.169.157; 6.D.169.166; 6.D.169.169; 6.D.169.172; 6.D.169.175; 6.D.169.240; 6.D.169.244; 6.D.172.228; 6.D.172.229; 6.D.172.230; 6.D.172.231; 6.D.172.236; 6.D.172.237; 6.D.172.238; 6.D.172.239; 6.D.172.154; 6.D.172.157; 6.D.172.166; 6.D.172.169; 6.D.172.172; 6.D.172.175; 6.D.172.240; 6.D.172.244; 6.D.175.228; 6.D.175.229; 6.D.175.230; 6.D.175.231; 6.D.175.236; 6.D.175.237; 6.D.175.238; 6.D.175.239; 6.D.175.154; 6.D.175.157; 6.D.175.166; 6.D.175.169; 6.D.175.172; 6.D.175.175; 6.D.175.240; 6.D.175.244; 6.D.240.228;

TABLE 100-continued

6.D.240.229; 6.D.240.230; 6.D.240.231; 6.D.240.236; 6.D.240.237;
6.D.240.238; 6.D.240.239; 6.D.240.154; 6.D.240.157; 6.D.240.166;
6.D.240.169; 6.D.240.172; 6.D.240.175; 6.D.240.240; 6.D.240.244;
6.D.244.228; 6.D.244.229; 6.D.244.230; 6.D.244.231; 6.D.244.236;
6.D.244.237; 6.D.244.238; 6.D.244.239; 6.D.244.154; 6.D.244.157;
6.D.244.166; 6.D.244.169; 6.D.244.172; 6.D.244.175; 6.D.244.240;
6.D.244.244;
Prodrugs of 6.E 6.E.228.228; 6.E.228.229; 6.E.228.230; 6.E.228.231; 6.E.228.236;
6.E.228.237; 6.E.228.238; 6.E.228.239; 6.E.228.154; 6.E.228.157; 6.E.228.166;
6.E.228.169; 6.E.228.172; 6.E.228.175; 6.E.228.240; 6.E.228.244; 6.E.229.228;
6.E.229.229; 6.E.229.230; 6.E.229.231; 6.E.229.236; 6.E.229.237; 6.E.229.238;
6.E.229.239; 6.E.229.154; 6.E.229.157; 6.E.229.166; 6.E.229.169; 6.E.229.172;
6.E.229.175; 6.E.229.240; 6.E.229.244; 6.E.230.228; 6.E.230.229; 6.E.230.230;
6.E.230.231; 6.E.230.236; 6.E.230.237; 6.E.230.238; 6.E.230.239; 6.E.230.154;
6.E.230.157; 6.E.230.166; 6.E.230.169; 6.E.230.172; 6.E.230.175; 6.E.230.240;
6.E.230.244; 6.E.231.228; 6.E.231.229; 6.E.231.230; 6.E.231.231; 6.E.231.236;
6.E.231.237; 6.E.231.238; 6.E.231.239; 6.E.231.154; 6.E.231.157; 6.E.231.166;
6.E.231.169; 6.E.231.172; 6.E.231.175; 6.E.231.240; 6.E.231.244; 6.E.236.228;
6.E.236.229; 6.E.236.230; 6.E.236.231; 6.E.236.236; 6.E.236.237; 6.E.236.238;
6.E.236.239; 6.E.236.154; 6.E.236.157; 6.E.236.166; 6.E.236.169; 6.E.236.172;
6.E.236.175; 6.E.236.240; 6.E.236.244; 6.E.237.228; 6.E.237.229; 6.E.237.230;
6.E.237.231; 6.E.237.236; 6.E.237.237; 6.E.237.238; 6.E.237.239; 6.E.237.154;
6.E.237.157; 6.E.237.166; 6.E.237.169; 6.E.237.172; 6.E.237.175; 6.E.237.240;
6.E.237.244; 6.E.238.228; 6.E.238.229; 6.E.238.230; 6.E.238.231; 6.E.238.236;
6.E.238.237; 6.E.238.238; 6.E.238.239; 6.E.238.154; 6.E.238.157; 6.E.238.166;
6.E.238.169; 6.E.238.172; 6.E.238.175; 6.E.238.240; 6.E.238.244; 6.E.239.228;
6.E.239.229; 6.E.239.230; 6.E.239.231; 6.E.239.236; 6.E.239.237; 6.E.239.238;
6.E.239.239; 6.E.239.154; 6.E.239.157; 6.E.239.166; 6.E.239.169; 6.E.239.172;
6.E.239.175; 6.E.239.240; 6.E.239.244; 6.E.154.228; 6.E.154.229; 6.E.154.230;
6.E.154.231; 6.E.154.236; 6.E.154.237; 6.E.154.238; 6.E.154.239; 6.E.154.154;
6.E.154.157; 6.E.154.166; 6.E.154.169; 6.E.154.172; 6.E.154.175; 6.E.154.240;
6.E.154.244; 6.E.157.228; 6.E.157.229; 6.E.157.230; 6.E.157.231; 6.E.157.236;
6.E.157.237; 6.E.157.238; 6.E.157.239; 6.E.157.154; 6.E.157.157; 6.E.157.166;
6.E.157.169; 6.E.157.172; 6.E.157.175; 6.E.157.240; 6.E.157.244; 6.E.166.228;
6.E.166.229; 6.E.166.230; 6.E.166.231; 6.E.166.236; 6.E.166.237; 6.E.166.238;
6.E.166.239; 6.E.166.154; 6.E.166.157; 6.E.166.166; 6.E.166.169; 6.E.166.172;
6.E.166.175; 6.E.166.240; 6.E.166.244; 6.E.169.228; 6.E.169.229; 6.E.169.230;
6.E.169.231; 6.E.169.236; 6.E.169.237; 6.E.169.238; 6.E.169.239; 6.E.169.154;
6.E.169.157; 6.E.169.166; 6.E.169.169; 6.E.169.172; 6.E.169.175; 6.E.169.240;
6.E.169.244; 6.E.172.228; 6.E.172.229; 6.E.172.230; 6.E.172.231; 6.E.172.236;
6.E.172.237; 6.E.172.238; 6.E.172.239; 6.E.172.154; 6.E.172.157; 6.E.172.166;
6.E.172.169; 6.E.172.172; 6.E.172.175; 6.E.172.240; 6.E.172.244; 6.E.175.228;
6.E.175.229; 6.E.175.230; 6.E.175.231; 6.E.175.236; 6.E.175.237; 6.E.175.238;
6.E.175.239; 6.E.175.154; 6.E.175.157; 6.E.175.166; 6.E.175.169; 6.E.175.172;
6.E.175.175; 6.E.175.240; 6.E.175.244; 6.E.240.228; 6.E.240.229; 6.E.240.230;
6.E.240.231; 6.E.240.236; 6.E.240.237; 6.E.240.238; 6.E.240.239; 6.E.240.154;
6.E.240.157; 6.E.240.166; 6.E.240.169; 6.E.240.172; 6.E.240.175; 6.E.240.240;
6.E.240.244; 6.E.244.228; 6.E.244.229; 6.E.244.230; 6.E.244.231; 6.E.244.236;
6.E.244.237; 6.E.244.238; 6.E.244.239; 6.E.244.154; 6.E.244.157; 6.E.244.166;
6.E.244.169; 6.E.244.172; 6.E.244.175; 6.E.244.240; 6.E.244.244;
Prodrugs of 6.G 6.G.228.228; 6.G.228.229; 6.G.228.230; 6.G.228.231; 6.G.228.236;
6.G.228.237; 6.G.228.238; 6.G.228.239; 6.G.228.154; 6.G.228.157;
6.G.228.166; 6.G.228.169; 6.G.228.172; 6.G.228.175; 6.G.228.240;
6.G.228.244; 6.G.229.228; 6.G.229.229; 6.G.229.230; 6.G.229.231;
6.G.229.236; 6.G.229.237; 6.G.229.238; 6.G.229.239; 6.G.229.154;
6.G.229.157; 6.G.229.166; 6.G.229.169; 6.G.229.172; 6.G.229.175;
6.G.229.240; 6.G.229.244; 6.G.230.228; 6.G.230.229; 6.G.230.230;
6.G.230.231; 6.G.230.236; 6.G.230.237; 6.G.230.238; 6.G.230.239;
6.G.230.154; 6.G.230.157; 6.G.230.166; 6.G.230.169; 6.G.230.172;
6.G.230.175; 6.G.230.240; 6.G.230.244; 6.G.231.228; 6.G.231.229;
6.G.231.230; 6.G.231.231; 6.G.231.236; 6.G.231.237; 6.G.231.238;
6.G.231.239; 6.G.231.154; 6.G.231.157; 6.G.231.166; 6.G.231.169;
6.G.231.172; 6.G.231.175; 6.G.231.240; 6.G.231.244; 6.G.236.228;
6.G.236.229; 6.G.236.230; 6.G.236.231; 6.G.236.236; 6.G.236.237;
6.G.236.238; 6.G.236.239; 6.G.236.154; 6.G.236.157; 6.G.236.166;
6.G.236.169; 6.G.236.172; 6.G.236.175; 6.G.236.240; 6.G.236.244;
6.G.237.228; 6.G.237.229; 6.G.237.230; 6.G.237.231; 6.G.237.236;
6.G.237.237; 6.G.237.238; 6.G.237.239; 6.G.237.154; 6.G.237.157;
6.G.237.166; 6.G.237.169; 6.G.237.172; 6.G.237.175; 6.G.237.240;
6.G.237.244; 6.G.238.228; 6.G.238.229; 6.G.238.230; 6.G.238.231;
6.G.238.236; 6.G.238.237; 6.G.238.238; 6.G.238.239; 6.G.238.154;
6.G.238.157; 6.G.238.166; 6.G.238.169; 6.G.238.172; 6.G.238.175;
6.G.238.240; 6.G.238.244; 6.G.239.228; 6.G.239.229; 6.G.239.230;
6.G.239.231; 6.G.239.236; 6.G.239.237; 6.G.239.238; 6.G.239.239;
6.G.239.154; 6.G.239.157; 6.G.239.166; 6.G.239.169; 6.G.239.172;

TABLE 100-continued

6.G.239.175; 6.G.239.240; 6.G.239.244; 6.G.154.228; 6.G.154.229;
6.G.154.230; 6.G.154.231; 6.G.154.236; 6.G.154.237; 6.G.154.238;
6.G.154.239; 6.G.154.154; 6.G.154.157; 6.G.154.166; 6.G.154.169;
6.G.154.172; 6.G.154.175; 6.G.154.240; 6.G.154.244; 6.G.157.228;
6.G.157.229; 6.G.157.230; 6.G.157.231; 6.G.157.236; 6.G.157.237;
6.G.157.238; 6.G.157.239; 6.G.157.154; 6.G.157.157; 6.G.157.166;
6.G.157.169; 6.G.157.172; 6.G.157.175; 6.G.157.240; 6.G.157.244;
6.G.166.228; 6.G.166.229; 6.G.166.230; 6.G.166.231; 6.G.166.236;
6.G.166.237; 6.G.166.238; 6.G.166.239; 6.G.166.154; 6.G.166.157;
6.G.166.166; 6.G.166.169; 6.G.166.172; 6.G.166.175; 6.G.166.240;
6.G.166.244; 6.G.169.228; 6.G.169.229; 6.G.169.230; 6.G.169.231;
6.G.169.236; 6.G.169.237; 6.G.169.238; 6.G.169.239; 6.G.169.154;
6.G.169.157; 6.G.169.166; 6.G.169.169; 6.G.169.172; 6.G.169.175;
6.G.169.240; 6.G.169.244; 6.G.172.228; 6.G.172.229; 6.G.172.230;
6.G.172.231; 6.G.172.236; 6.G.172.237; 6.G.172.238; 6.G.172.239;
6.G.172.154; 6.G.172.157; 6.G.172.166; 6.G.172.169; 6.G.172.172;
6.G.172.175; 6.G.172.240; 6.G.172.244; 6.G.175.228; 6.G.175.229;
6.G.175.230; 6.G.175.231; 6.G.175.236; 6.G.175.237; 6.G.175.238;
6.G.175.239; 6.G.175.154; 6.G.175.157; 6.G.175.166; 6.G.175.169;
6.G.175.172; 6.G.175.175; 6.G.175.240; 6.G.175.244; 6.G.240.228;
6.G.240.229; 6.G.240.230; 6.G.240.231; 6.G.240.236; 6.G.240.237;
6.G.240.238; 6.G.240.239; 6.G.240.154; 6.G.240.157; 6.G.240.166;
6.G.240.169; 6.G.240.172; 6.G.240.175; 6.G.240.240; 6.G.240.244;
6.G.244.228; 6.G.244.229; 6.G.244.230; 6.G.244.231; 6.G.244.236;
6.G.244.237; 6.G.244.238; 6.G.244.239; 6.G.244.154; 6.G.244.157;
6.G.244.166; 6.G.244.169; 6.G.244.172; 6.G.244.175; 6.G.244.240;
6.G.244.244;

Prodrugs of 6.I

6.I.228.228; 6.I.228.229; 6.I.228.230; 6.I.228.231; 6.I.228.236; 6.I.228.237;
6.I.228.238; 6.I.228.239; 6.I.228.154; 6.I.228.157; 6.I.228.166; 6.I.228.169;
6.I.228.172; 6.I.228.175; 6.I.228.240; 6.I.228.244; 6.I.229.228; 6.I.229.229;
6.I.229.230; 6.I.229.231; 6.I.229.236; 6.I.229.237; 6.I.229.238; 6.I.229.239;
6.I.229.154; 6.I.229.157; 6.I.229.166; 6.I.229.169; 6.I.229.172; 6.I.229.175;
6.I.229.240; 6.I.229.244; 6.I.230.228; 6.I.230.229; 6.I.230.230; 6.I.230.231;
6.I.230.236; 6.I.230.237; 6.I.230.238; 6.I.230.239; 6.I.230.154; 6.I.230.157;
6.I.230.166; 6.I.230.169; 6.I.230.172; 6.I.230.175; 6.I.230.240; 6.I.230.244;
6.I.231.228; 6.I.231.229; 6.I.231.230; 6.I.231.231; 6.I.231.236; 6.I.231.237;
6.I.231.238; 6.I.231.239; 6.I.231.154; 6.I.231.157; 6.I.231.166; 6.I.231.169;
6.I.231.172; 6.I.231.175; 6.I.231.240; 6.I.231.244; 6.I.236.228; 6.I.236.229;
6.I.236.230; 6.I.236.231; 6.I.236.236; 6.I.236.237; 6.I.236.238; 6.I.236.239;
6.I.236.154; 6.I.236.157; 6.I.236.166; 6.I.236.169; 6.I.236.172; 6.I.236.175;
6.I.236.240; 6.I.236.244; 6.I.237.228; 6.I.237.229; 6.I.237.230; 6.I.237.231;
6.I.237.236; 6.I.237.237; 6.I.237.238; 6.I.237.239; 6.I.237.154; 6.I.237.157;
6.I.237.166; 6.I.237.169; 6.I.237.172; 6.I.237.175; 6.I.237.240; 6.I.237.244;
6.I.238.228; 6.I.238.229; 6.I.238.230; 6.I.238.231; 6.I.238.236; 6.I.238.237;
6.I.238.238; 6.I.238.239; 6.I.238.154; 6.I.238.157; 6.I.238.166; 6.I.238.169;
6.I.238.172; 6.I.238.175; 6.I.238.240; 6.I.238.244; 6.I.239.228; 6.I.239.229;
6.I.239.230; 6.I.239.231; 6.I.239.236; 6.I.239.237; 6.I.239.238; 6.I.239.239;
6.I.239.154; 6.I.239.157; 6.I.239.166; 6.I.239.169; 6.I.239.172; 6.I.239.175;
6.I.239.240; 6.I.239.244; 6.I.154.228; 6.I.154.229; 6.I.154.230; 6.I.154.231;
6.I.154.236; 6.I.154.237; 6.I.154.238; 6.I.154.239; 6.I.154.154; 6.I.154.157;
6.I.154.166; 6.I.154.169; 6.I.154.172; 6.I.154.175; 6.I.154.240; 6.I.154.244;
6.I.157.228; 6.I.157.229; 6.I.157.230; 6.I.157.231; 6.I.157.236; 6.I.157.237;
6.I.157.238; 6.I.157.239; 6.I.157.154; 6.I.157.157; 6.I.157.166; 6.I.157.169;
6.I.157.172; 6.I.157.175; 6.I.157.240; 6.I.157.244; 6.I.166.228; 6.I.166.229;
6.I.166.230; 6.I.166.231; 6.I.166.236; 6.I.166.237; 6.I.166.238; 6.I.166.239;
6.I.166.154; 6.I.166.157; 6.I.166.166; 6.I.166.169; 6.I.166.172; 6.I.166.175;
6.I.166.240; 6.I.166.244; 6.I.169.228; 6.I.169.229; 6.I.169.230; 6.I.169.231;
6.I.169.236; 6.I.169.237; 6.I.169.238; 6.I.169.239; 6.I.169.154; 6.I.169.157;
6.I.169.166; 6.I.169.169; 6.I.169.172; 6.I.169.175; 6.I.169.240; 6.I.169.244;
6.I.172.228; 6.I.172.229; 6.I.172.230; 6.I.172.231; 6.I.172.236; 6.I.172.237;
6.I.172.238; 6.I.172.239; 6.I.172.154; 6.I.172.157; 6.I.172.166; 6.I.172.169;
6.I.172.172; 6.I.172.175; 6.I.172.240; 6.I.172.244; 6.I.175.228; 6.I.175.229;
6.I.175.230; 6.I.175.231; 6.I.175.236; 6.I.175.237; 6.I.175.238; 6.I.175.239;
6.I.175.154; 6.I.175.157; 6.I.175.166; 6.I.175.169; 6.I.175.172; 6.I.175.175;
6.I.175.240; 6.I.175.244; 6.I.240.228; 6.I.240.229; 6.I.240.230; 6.I.240.231;
6.I.240.236; 6.I.240.237; 6.I.240.238; 6.I.240.239; 6.I.240.154; 6.I.240.157;
6.I.240.166; 6.I.240.169; 6.I.240.172; 6.I.240.175; 6.I.240.240; 6.I.240.244;
6.I.244.228; 6.I.244.229; 6.I.244.230; 6.I.244.231; 6.I.244.236; 6.I.244.237;
6.I.244.238; 6.I.244.239; 6.I.244.154; 6.I.244.157; 6.I.244.166; 6.I.244.169;
6.I.244.172; 6.I.244.175; 6.I.244.240; 6.I.244.244;

Prodrugs of 6.J

6.J.228.228; 6.J.228.229; 6.J.228.230; 6.J.228.231; 6.J.228.236; 6.J.228.237;
6.J.228.238; 6.J.228.239; 6.J.228.154; 6.J.228.157; 6.J.228.166; 6.J.228.169;
6.J.228.172; 6.J.228.175; 6.J.228.240; 6.J.228.244; 6.J.229.228; 6.J.229.229;
6.J.229.230; 6.J.229.231; 6.J.229.236; 6.J.229.237; 6.J.229.238; 6.J.229.239;
6.J.229.154; 6.J.229.157; 6.J.229.166; 6.J.229.169; 6.J.229.172; 6.J.229.175;

TABLE 100-continued

6.J.229.240; 6.J.229.244; 6.J.230.228; 6.J.230.229; 6.J.230.230; 6.J.230.231;
6.J.230.236; 6.J.230.237; 6.J.230.238; 6.J.230.239; 6.J.230.154; 6.J.230.157;
6.J.230.166; 6.J.230.169; 6.J.230.172; 6.J.230.175; 6.J.230.240; 6.J.230.244;
6.J.231.228; 6.J.231.229; 6.J.231.230; 6.J.231.231; 6.J.231.236; 6.J.231.237;
6.J.231.238; 6.J.231.239; 6.J.231.154; 6.J.231.157; 6.J.231.166; 6.J.231.169;
6.J.231.172; 6.J.231.175; 6.J.231.240; 6.J.231.244; 6.J.236.228; 6.J.236.229;
6.J.236.230; 6.J.236.231; 6.J.236.236; 6.J.236.237; 6.J.236.238; 6.J.236.239;
6.J.236.154; 6.J.236.157; 6.J.236.166; 6.J.236.169; 6.J.236.172; 6.J.236.175;
6.J.236.240; 6.J.236.244; 6.J.237.228; 6.J.237.229; 6.J.237.230; 6.J.237.231;
6.J.237.236; 6.J.237.237; 6.J.237.238; 6.J.237.239; 6.J.237.154; 6.J.237.157;
6.J.237.166; 6.J.237.169; 6.J.237.172; 6.J.237.175; 6.J.237.240; 6.J.237.244;
6.J.238.228; 6.J.238.229; 6.J.238.230; 6.J.238.231; 6.J.238.236; 6.J.238.237;
6.J.238.238; 6.J.238.239; 6.J.238.154; 6.J.238.157; 6.J.238.166; 6.J.238.169;
6.J.238.172; 6.J.238.175; 6.J.238.240; 6.J.238.244; 6.J.239.228; 6.J.239.229;
6.J.239.230; 6.J.239.231; 6.J.239.236; 6.J.239.237; 6.J.239.238; 6.J.239.239;
6.J.239.154; 6.J.239.157; 6.J.239.166; 6.J.239.169; 6.J.239.172; 6.J.239.175;
6.J.239.240; 6.J.239.244; 6.J.154.228; 6.J.154.229; 6.J.154.230; 6.J.154.231;
6.J.154.236; 6.J.154.237; 6.J.154.238; 6.J.154.239; 6.J.154.154; 6.J.154.157;
6.J.154.166; 6.J.154.169; 6.J.154.172; 6.J.154.175; 6.J.154.240; 6.J.154.244;
6.J.157.228; 6.J.157.229; 6.J.157.230; 6.J.157.231; 6.J.157.236; 6.J.157.237;
6.J.157.238; 6.J.157.239; 6.J.157.154; 6.J.157.157; 6.J.157.166; 6.J.157.169;
6.J.157.172; 6.J.157.175; 6.J.157.240; 6.J.157.244; 6.J.166.228; 6.J.166.229;
6.J.166.230; 6.J.166.231; 6.J.166.236; 6.J.166.237; 6.J.166.238; 6.J.166.239;
6.J.166.154; 6.J.166.157; 6.J.166.166; 6.J.166.169; 6.J.166.172; 6.J.166.175;
6.J.166.240; 6.J.166.244; 6.J.169.228; 6.J.169.229; 6.J.169.230; 6.J.169.231;
6.J.169.236; 6.J.169.237; 6.J.169.238; 6.J.169.239; 6.J.169.154; 6.J.169.157;
6.J.169.166; 6.J.169.169; 6.J.169.172; 6.J.169.175; 6.J.169.240; 6.J.169.244;
6.J.172.228; 6.J.172.229; 6.J.172.230; 6.J.172.231; 6.J.172.236; 6.J.172.237;
6.J.172.238; 6.J.172.239; 6.J.172.154; 6.J.172.157; 6.J.172.166; 6.J.172.169;
6.J.172.172; 6.J.172.175; 6.J.172.240; 6.J.172.244; 6.J.175.228; 6.J.175.229;
6.J.175.230; 6.J.175.231; 6.J.175.236; 6.J.175.237; 6.J.175.238; 6.J.175.239;
6.J.175.154; 6.J.175.157; 6.J.175.166; 6.J.175.169; 6.J.175.172; 6.J.175.175;
6.J.175.240; 6.J.175.244; 6.J.240.228; 6.J.240.229; 6.J.240.230; 6.J.240.231;
6.J.240.236; 6.J.240.237; 6.J.240.238; 6.J.240.239; 6.J.240.154; 6.J.240.157;
6.J.240.166; 6.J.240.169; 6.J.240.172; 6.J.240.175; 6.J.240.240; 6.J.240.244;
6.J.244.228; 6.J.244.229; 6.J.244.230; 6.J.244.231; 6.J.244.236; 6.J.244.237;
6.J.244.238; 6.J.244.239; 6.J.244.154; 6.J.244.157; 6.J.244.166; 6.J.244.169;
6.J.244.172; 6.J.244.175; 6.J.244.240; 6.J.244.244;

Prodrugs of 6.L

6.L.228.228; 6.L.228.229; 6.L.228.230; 6.L.228.231; 6.L.228.236;
6.L.228.237; 6.L.228.238; 6.L.228.239; 6.L.228.154; 6.L.228.157; 6.L.228.166;
6.L.228.169; 6.L.228.172; 6.L.228.175; 6.L.228.240; 6.L.228.244; 6.L.229.228;
6.L.229.229; 6.L.229.230; 6.L.229.231; 6.L.229.236; 6.L.229.237; 6.L.229.238;
6.L.229.239; 6.L.229.154; 6.L.229.157; 6.L.229.166; 6.L.229.169; 6.L.229.172;
6.L.229.175; 6.L.229.240; 6.L.229.244; 6.L.230.228; 6.L.230.229; 6.L.230.230;
6.L.230.231; 6.L.230.236; 6.L.230.237; 6.L.230.238; 6.L.230.239; 6.L.230.154;
6.L.230.157; 6.L.230.166; 6.L.230.169; 6.L.230.172; 6.L.230.175; 6.L.230.240;
6.L.230.244; 6.L.231.228; 6.L.231.229; 6.L.231.230; 6.L.231.231; 6.L.231.236;
6.L.231.237; 6.L.231.238; 6.L.231.239; 6.L.231.154; 6.L.231.157; 6.L.231.166;
6.L.231.169; 6.L.231.172; 6.L.231.175; 6.L.231.240; 6.L.231.244; 6.L.236.228;
6.L.236.229; 6.L.236.230; 6.L.236.231; 6.L.236.236; 6.L.236.237; 6.L.236.238;
6.L.236.239; 6.L.236.154; 6.L.236.157; 6.L.236.166; 6.L.236.169; 6.L.236.172;
6.L.236.175; 6.L.236.240; 6.L.236.244; 6.L.237.228; 6.L.237.229; 6.L.237.230;
6.L.237.231; 6.L.237.236; 6.L.237.237; 6.L.237.238; 6.L.237.239; 6.L.237.154;
6.L.237.157; 6.L.237.166; 6.L.237.169; 6.L.237.172; 6.L.237.175; 6.L.237.240;
6.L.237.244; 6.L.238.228; 6.L.238.229; 6.L.238.230; 6.L.238.231; 6.L.238.236;
6.L.238.237; 6.L.238.238; 6.L.238.239; 6.L.238.154; 6.L.238.157; 6.L.238.166;
6.L.238.169; 6.L.238.172; 6.L.238.175; 6.L.238.240; 6.L.238.244; 6.L.239.228;
6.L.239.229; 6.L.239.230; 6.L.239.231; 6.L.239.236; 6.L.239.237; 6.L.239.238;
6.L.239.239; 6.L.239.154; 6.L.239.157; 6.L.239.166; 6.L.239.169; 6.L.239.172;
6.L.239.175; 6.L.239.240; 6.L.239.244; 6.L.154.228; 6.L.154.229; 6.L.154.230;
6.L.154.231; 6.L.154.236; 6.L.154.237; 6.L.154.238; 6.L.154.239; 6.L.154.154;
6.L.154.157; 6.L.154.166; 6.L.154.169; 6.L.154.172; 6.L.154.175; 6.L.154.240;
6.L.154.244; 6.L.157.228; 6.L.157.229; 6.L.157.230; 6.L.157.231; 6.L.157.236;
6.L.157.237; 6.L.157.238; 6.L.157.239; 6.L.157.154; 6.L.157.157; 6.L.157.166;
6.L.157.169; 6.L.157.172; 6.L.157.175; 6.L.157.240; 6.L.157.244; 6.L.166.228;
6.L.166.229; 6.L.166.230; 6.L.166.231; 6.L.166.236; 6.L.166.237; 6.L.166.238;
6.L.166.239; 6.L.166.154; 6.L.166.157; 6.L.166.166; 6.L.166.169; 6.L.166.172;
6.L.166.175; 6.L.166.240; 6.L.166.244; 6.L.169.228; 6.L.169.229; 6.L.169.230;
6.L.169.231; 6.L.169.236; 6.L.169.237; 6.L.169.238; 6.L.169.239; 6.L.169.154;
6.L.169.157; 6.L.169.166; 6.L.169.169; 6.L.169.172; 6.L.169.175; 6.L.169.240;
6.L.169.244; 6.L.172.228; 6.L.172.229; 6.L.172.230; 6.L.172.231; 6.L.172.236;
6.L.172.237; 6.L.172.238; 6.L.172.239; 6.L.172.154; 6.L.172.157; 6.L.172.166;
6.L.172.169; 6.L.172.172; 6.L.172.175; 6.L.172.240; 6.L.172.244; 6.L.175.228;
6.L.175.229; 6.L.175.230; 6.L.175.231; 6.L.175.236; 6.L.175.237; 6.L.175.238;
6.L.175.239; 6.L.175.154; 6.L.175.157; 6.L.175.166; 6.L.175.169; 6.L.175.172;
6.L.175.175; 6.L.175.240; 6.L.175.244; 6.L.240.228; 6.L.240.229; 6.L.240.230;
6.L.240.231; 6.L.240.236; 6.L.240.237; 6.L.240.238; 6.L.240.239; 6.L.240.154;

TABLE 100-continued

6.L.240.157; 6.L.240.166; 6.L.240.169; 6.L.240.172; 6.L.240.175; 6.L.240.240;
6.L.240.244; 6.L.244.228; 6.L.244.229; 6.L.244.230; 6.L.244.231; 6.L.244.236;
6.L.244.237; 6.L.244.238; 6.L.244.239; 6.L.244.154; 6.L.244.157; 6.L.244.166;
6.L.244.169; 6.L.244.172; 6.L.244.175; 6.L.244.240; 6.L.244.244;
Prodrugs of 6.O 6.O.228.228; 6.O.228.229; 6.O.228.230; 6.O.228.231; 6.O.228.236;
6.O.228.237; 6.O.228.238; 6.O.228.239; 6.O.228.154; 6.O.228.157;
6.O.228.166; 6.O.228.169; 6.O.228.172; 6.O.228.175; 6.O.228.240;
6.O.228.244; 6.O.229.228; 6.O.229.229; 6.O.229.230; 6.O.229.231;
6.O.229.236; 6.O.229.237; 6.O.229.238; 6.O.229.239; 6.O.229.154;
6.O.229.157; 6.O.229.166; 6.O.229.169; 6.O.229.172; 6.O.229.175;
6.O.229.240; 6.O.229.244; 6.O.230.228; 6.O.230.229; 6.O.230.230;
6.O.230.231; 6.O.230.236; 6.O.230.237; 6.O.230.238; 6.O.230.239;
6.O.230.154; 6.O.230.157; 6.O.230.166; 6.O.230.169; 6.O.230.172;
6.O.230.175; 6.O.230.240; 6.O.230.244; 6.O.231.228; 6.O.231.229;
6.O.231.230; 6.O.231.231; 6.O.231.236; 6.O.231.237; 6.O.231.238;
6.O.231.239; 6.O.231.154; 6.O.231.157; 6.O.231.166; 6.O.231.169;
6.O.231.172; 6.O.231.175; 6.O.231.240; 6.O.231.244; 6.O.236.228;
6.O.236.229; 6.O.236.230; 6.O.236.231; 6.O.236.236; 6.O.236.237;
6.O.236.238; 6.O.236.239; 6.O.236.154; 6.O.236.157; 6.O.236.166;
6.O.236.169; 6.O.236.172; 6.O.236.175; 6.O.236.240; 6.O.236.244;
6.O.237.228; 6.O.237.229; 6.O.237.230; 6.O.237.231; 6.O.237.236;
6.O.237.237; 6.O.237.238; 6.O.237.239; 6.O.237.154; 6.O.237.157;
6.O.237.166; 6.O.237.169; 6.O.237.172; 6.O.237.175; 6.O.237.240;
6.O.237.244; 6.O.238.228; 6.O.238.229; 6.O.238.230; 6.O.238.231;
6.O.238.236; 6.O.238.237; 6.O.238.238; 6.O.238.239; 6.O.238.154;
6.O.238.157; 6.O.238.166; 6.O.238.169; 6.O.238.172; 6.O.238.175;
6.O.238.240; 6.O.238.244; 6.O.239.228; 6.O.239.229; 6.O.239.230;
6.O.239.231; 6.O.239.236; 6.O.239.237; 6.O.239.238; 6.O.239.239;
6.O.239.154; 6.O.239.157; 6.O.239.166; 6.O.239.169; 6.O.239.172;
6.O.239.175; 6.O.239.240; 6.O.239.244; 6.O.154.228; 6.O.154.229;
6.O.154.230; 6.O.154.231; 6.O.154.236; 6.O.154.237; 6.O.154.238;
6.O.154.239; 6.O.154.154; 6.O.154.157; 6.O.154.166; 6.O.154.169;
6.O.154.172; 6.O.154.175; 6.O.154.240; 6.O.154.244; 6.O.157.228;
6.O.157.229; 6.O.157.230; 6.O.157.231; 6.O.157.236; 6.O.157.237;
6.O.157.238; 6.O.157.239; 6.O.157.154; 6.O.157.157; 6.O.157.166;
6.O.157.169; 6.O.157.172; 6.O.157.175; 6.O.157.240; 6.O.157.244;
6.O.166.228; 6.O.166.229; 6.O.166.230; 6.O.166.231; 6.O.166.236;
6.O.166.237; 6.O.166.238; 6.O.166.239; 6.O.166.154; 6.O.166.157;
6.O.166.166; 6.O.166.169; 6.O.166.172; 6.O.166.175; 6.O.166.240;
6.O.166.244; 6.O.169.228; 6.O.169.229; 6.O.169.230; 6.O.169.231;
6.O.169.236; 6.O.169.237; 6.O.169.238; 6.O.169.239; 6.O.169.154;
6.O.169.157; 6.O.169.166; 6.O.169.169; 6.O.169.172; 6.O.169.175;
6.O.169.240; 6.O.169.244; 6.O.172.228; 6.O.172.229; 6.O.172.230;
6.O.172.231; 6.O.172.236; 6.O.172.237; 6.O.172.238; 6.O.172.239;
6.O.172.154; 6.O.172.157; 6.O.172.166; 6.O.172.169; 6.O.172.172;
6.O.172.175; 6.O.172.240; 6.O.172.244; 6.O.175.228; 6.O.175.229;
6.O.175.230; 6.O.175.231; 6.O.175.236; 6.O.175.237; 6.O.175.238;
6.O.175.239; 6.O.175.154; 6.O.175.157; 6.O.175.166; 6.O.175.169;
6.O.175.172; 6.O.175.175; 6.O.175.240; 6.O.175.244; 6.O.240.228;
6.O.240.229; 6.O.240.230; 6.O.240.231; 6.O.240.236; 6.O.240.237;
6.O.240.238; 6.O.240.239; 6.O.240.154; 6.O.240.157; 6.O.240.166;
6.O.240.169; 6.O.240.172; 6.O.240.175; 6.O.240.240; 6.O.240.244;
6.O.244.228; 6.O.244.229; 6.O.244.230; 6.O.244.231; 6.O.244.236;
6.O.244.237; 6.O.244.238; 6.O.244.239; 6.O.244.154; 6.O.244.157;
6.O.244.166; 6.O.244.169; 6.O.244.172; 6.O.244.175; 6.O.244.240;
6.O.244.244;
Prodrugs of 6.P 6.P.228.228; 6.P.228.229; 6.P.228.230; 6.P.228.231; 6.P.228.236;
6.P.228.237; 6.P.228.238; 6.P.228.239; 6.P.228.154; 6.P.228.157; 6.P.228.166;
6.P.228.169; 6.P.228.172; 6.P.228.175; 6.P.228.240; 6.P.228.244; 6.P.229.228;
6.P.229.229; 6.P.229.230; 6.P.229.231; 6.P.229.236; 6.P.229.237; 6.P.229.238;
6.P.229.239; 6.P.229.154; 6.P.229.157; 6.P.229.166; 6.P.229.169; 6.P.229.172;
6.P.229.175; 6.P.229.240; 6.P.229.244; 6.P.230.228; 6.P.230.229; 6.P.230.230;
6.P.230.231; 6.P.230.236; 6.P.230.237; 6.P.230.238; 6.P.230.239; 6.P.230.154;
6.P.230.157; 6.P.230.166; 6.P.230.169; 6.P.230.172; 6.P.230.175; 6.P.230.240;
6.P.230.244; 6.P.231.228; 6.P.231.229; 6.P.231.230; 6.P.231.231; 6.P.231.236;
6.P.231.237; 6.P.231.238; 6.P.231.239; 6.P.231.154; 6.P.231.157; 6.P.231.166;
6.P.231.169; 6.P.231.172; 6.P.231.175; 6.P.231.240; 6.P.231.244; 6.P.236.228;
6.P.236.229; 6.P.236.230; 6.P.236.231; 6.P.236.236; 6.P.236.237; 6.P.236.238;
6.P.236.239; 6.P.236.154; 6.P.236.157; 6.P.236.166; 6.P.236.169; 6.P.236.172;
6.P.236.175; 6.P.236.240; 6.P.236.244; 6.P.237.228; 6.P.237.229; 6.P.237.230;
6.P.237.231; 6.P.237.236; 6.P.237.237; 6.P.237.238; 6.P.237.239; 6.P.237.154;
6.P.237.157; 6.P.237.166; 6.P.237.169; 6.P.237.172; 6.P.237.175; 6.P.237.240;
6.P.237.244; 6.P.238.228; 6.P.238.229; 6.P.238.230; 6.P.238.231; 6.P.238.236;
6.P.238.237; 6.P.238.238; 6.P.238.239; 6.P.238.154; 6.P.238.157; 6.P.238.166;
6.P.238.169; 6.P.238.172; 6.P.238.175; 6.P.238.240; 6.P.238.244; 6.P.239.228;

TABLE 100-continued

6.P.239.229; 6.P.239.230; 6.P.239.231; 6.P.239.236; 6.P.239.237; 6.P.239.238;
6.P.239.239; 6.P.239.154; 6.P.239.157; 6.P.239.166; 6.P.239.169; 6.P.239.172;
6.P.239.175; 6.P.239.240; 6.P.239.244; 6.P.154.228; 6.P.154.229; 6.P.154.230;
6.P.154.231; 6.P.154.236; 6.P.154.237; 6.P.154.238; 6.P.154.239; 6.P.154.154;
6.P.154.157; 6.P.154.166; 6.P.154.169; 6.P.154.172; 6.P.154.175; 6.P.154.240;
6.P.154.244; 6.P.157.228; 6.P.157.229; 6.P.157.230; 6.P.157.231; 6.P.157.236;
6.P.157.237; 6.P.157.238; 6.P.157.239; 6.P.157.154; 6.P.157.157; 6.P.157.166;
6.P.157.169; 6.P.157.172; 6.P.157.175; 6.P.157.240; 6.P.157.244; 6.P.166.228;
6.P.166.229; 6.P.166.230; 6.P.166.231; 6.P.166.236; 6.P.166.237; 6.P.166.238;
6.P.166.239; 6.P.166.154; 6.P.166.157; 6.P.166.166; 6.P.166.169; 6.P.166.172;
6.P.166.175; 6.P.166.240; 6.P.166.244; 6.P.169.228; 6.P.169.229; 6.P.169.230;
6.P.169.231; 6.P.169.236; 6.P.169.237; 6.P.169.238; 6.P.169.239; 6.P.169.154;
6.P.169.157; 6.P.169.166; 6.P.169.169; 6.P.169.172; 6.P.169.175; 6.P.169.240;
6.P.169.244; 6.P.172.228; 6.P.172.229; 6.P.172.230; 6.P.172.231; 6.P.172.236;
6.P.172.237; 6.P.172.238; 6.P.172.239; 6.P.172.154; 6.P.172.157; 6.P.172.166;
6.P.172.169; 6.P.172.172; 6.P.172.175; 6.P.172.240; 6.P.172.244; 6.P.175.228;
6.P.175.229; 6.P.175.230; 6.P.175.231; 6.P.175.236; 6.P.175.237; 6.P.175.238;
6.P.175.239; 6.P.175.154; 6.P.175.157; 6.P.175.166; 6.P.175.169; 6.P.175.172;
6.P.175.175; 6.P.175.240; 6.P.175.244; 6.P.240.228; 6.P.240.229; 6.P.240.230;
6.P.240.231; 6.P.240.236; 6.P.240.237; 6.P.240.238; 6.P.240.239; 6.P.240.154;
6.P.240.157; 6.P.240.166; 6.P.240.169; 6.P.240.172; 6.P.240.175; 6.P.240.240;
6.P.240.244; 6.P.244.228; 6.P.244.229; 6.P.244.230; 6.P.244.231; 6.P.244.236;
6.P.244.237; 6.P.244.238; 6.P.244.239; 6.P.244.154; 6.P.244.157; 6.P.244.166;
6.P.244.169; 6.P.244.172; 6.P.244.175; 6.P.244.240; 6.P.244.244;
Prodrugs of 6.U 6.U.228.228; 6.U.228.229; 6.U.228.230; 6.U.228.231; 6.U.228.236;
6.U.228.237; 6.U.228.238; 6.U.228.239; 6.U.228.154; 6.U.228.157;
6.U.228.166; 6.U.228.169; 6.U.228.172; 6.U.228.175; 6.U.228.240;
6.U.228.244; 6.U.229.228; 6.U.229.229; 6.U.229.230; 6.U.229.231;
6.U.229.236; 6.U.229.237; 6.U.229.238; 6.U.229.239; 6.U.229.154;
6.U.229.157; 6.U.229.166; 6.U.229.169; 6.U.229.172; 6.U.229.175;
6.U.229.240; 6.U.229.244; 6.U.230.228; 6.U.230.229; 6.U.230.230;
6.U.230.231; 6.U.230.236; 6.U.230.237; 6.U.230.238; 6.U.230.239;
6.U.230.154; 6.U.230.157; 6.U.230.166; 6.U.230.169; 6.U.230.172;
6.U.230.175; 6.U.230.240; 6.U.230.244; 6.U.231.228; 6.U.231.229;
6.U.231.230; 6.U.231.231; 6.U.231.236; 6.U.231.237; 6.U.231.238;
6.U.231.239; 6.U.231.154; 6.U.231.157; 6.U.231.166; 6.U.231.169;
6.U.231.172; 6.U.231.175; 6.U.231.240; 6.U.231.244; 6.U.236.228;
6.U.236.229; 6.U.236.230; 6.U.236.231; 6.U.236.236; 6.U.236.237;
6.U.236.238; 6.U.236.239; 6.U.236.154; 6.U.236.157; 6.U.236.166;
6.U.236.169; 6.U.236.172; 6.U.236.175; 6.U.236.240; 6.U.236.244;
6.U.237.228; 6.U.237.229; 6.U.237.230; 6.U.237.231; 6.U.237.236;
6.U.237.237; 6.U.237.238; 6.U.237.239; 6.U.237.154; 6.U.237.157;
6.U.237.166; 6.U.237.169; 6.U.237.172; 6.U.237.175; 6.U.237.240;
6.U.237.244; 6.U.238.228; 6.U.238.229; 6.U.238.230; 6.U.238.231;
6.U.238.236; 6.U.238.237; 6.U.238.238; 6.U.238.239; 6.U.238.154;
6.U.238.157; 6.U.238.166; 6.U.238.169; 6.U.238.172; 6.U.238.175;
6.U.238.240; 6.U.238.244; 6.U.239.228; 6.U.239.229; 6.U.239.230;
6.U.239.231; 6.U.239.236; 6.U.239.237; 6.U.239.238; 6.U.239.239;
6.U.239.154; 6.U.239.157; 6.U.239.166; 6.U.239.169; 6.U.239.172;
6.U.239.175; 6.U.239.240; 6.U.239.244; 6.U.154.228; 6.U.154.229;
6.U.154.230; 6.U.154.231; 6.U.154.236; 6.U.154.237; 6.U.154.238;
6.U.154.239; 6.U.154.154; 6.U.154.157; 6.U.154.166; 6.U.154.169;
6.U.154.172; 6.U.154.175; 6.U.154.240; 6.U.154.244; 6.U.157.228;
6.U.157.229; 6.U.157.230; 6.U.157.231; 6.U.157.236; 6.U.157.237;
6.U.157.238; 6.U.157.239; 6.U.157.154; 6.U.157.157; 6.U.157.166;
6.U.157.169; 6.U.157.172; 6.U.157.175; 6.U.157.240; 6.U.157.244;
6.U.166.228; 6.U.166.229; 6.U.166.230; 6.U.166.231; 6.U.166.236;
6.U.166.237; 6.U.166.238; 6.U.166.239; 6.U.166.154; 6.U.166.157;
6.U.166.166; 6.U.166.169; 6.U.166.172; 6.U.166.175; 6.U.166.240;
6.U.166.244; 6.U.169.228; 6.U.169.229; 6.U.169.230; 6.U.169.231;
6.U.169.236; 6.U.169.237; 6.U.169.238; 6.U.169.239; 6.U.169.154;
6.U.169.157; 6.U.169.166; 6.U.169.169; 6.U.169.172; 6.U.169.175;
6.U.169.240; 6.U.169.244; 6.U.172.228; 6.U.172.229; 6.U.172.230;
6.U.172.231; 6.U.172.236; 6.U.172.237; 6.U.172.238; 6.U.172.239;
6.U.172.154; 6.U.172.157; 6.U.172.166; 6.U.172.169; 6.U.172.172;
6.U.172.175; 6.U.172.240; 6.U.172.244; 6.U.175.228; 6.U.175.229;
6.U.175.230; 6.U.175.231; 6.U.175.236; 6.U.175.237; 6.U.175.238;
6.U.175.239; 6.U.175.154; 6.U.175.157; 6.U.175.166; 6.U.175.169;
6.U.175.172; 6.U.175.175; 6.U.175.240; 6.U.175.244; 6.U.240.228;
6.U.240.229; 6.U.240.230; 6.U.240.231; 6.U.240.236; 6.U.240.237;
6.U.240.238; 6.U.240.239; 6.U.240.154; 6.U.240.157; 6.U.240.166;
6.U.240.169; 6.U.240.172; 6.U.240.175; 6.U.240.240; 6.U.240.244;
6.U.244.228; 6.U.244.229; 6.U.244.230; 6.U.244.231; 6.U.244.236;
6.U.244.237; 6.U.244.238; 6.U.244.239; 6.U.244.154; 6.U.244.157;
6.U.244.166; 6.U.244.169; 6.U.244.172; 6.U.244.175; 6.U.244.240;
6.U.244.244;

TABLE 100-continued

Prodrugs of 6.W

6.W.228.228; 6.W.228.229; 6.W.228.230; 6.W.228.231; 6.W.228.236;
6.W.228.237; 6.W.228.238; 6.W.228.239; 6.W.228.154; 6.W.228.157;
6.W.228.166; 6.W.228.169; 6.W.228.172; 6.W.228.175; 6.W.228.240;
6.W.228.244; 6.W.229.228; 6.W.229.229; 6.W.229.230; 6.W.229.231;
6.W.229.236; 6.W.229.237; 6.W.229.238; 6.W.229.239; 6.W.229.154;
6.W.229.157; 6.W.229.166; 6.W.229.169; 6.W.229.172; 6.W.229.175;
6.W.229.240; 6.W.229.244; 6.W.230.228; 6.W.230.229; 6.W.230.230;
6.W.230.231; 6.W.230.236; 6.W.230.237; 6.W.230.238; 6.W.230.239;
6.W.230.154; 6.W.230.157; 6.W.230.166; 6.W.230.169; 6.W.230.172;
6.W.230.175; 6.W.230.240; 6.W.230.244; 6.W.231.228; 6.W.231.229;
6.W.231.230; 6.W.231.231; 6.W.231.236; 6.W.231.237; 6.W.231.238;
6.W.231.239; 6.W.231.154; 6.W.231.157; 6.W.231.166; 6.W.231.169;
6.W.231.172; 6.W.231.175; 6.W.231.240; 6.W.231.244; 6.W.236.228;
6.W.236.229; 6.W.236.230; 6.W.236.231; 6.W.236.236; 6.W.236.237;
6.W.236.238; 6.W.236.239; 6.W.236.154; 6.W.236.157; 6.W.236.166;
6.W.236.169; 6.W.236.172; 6.W.236.175; 6.W.236.240; 6.W.236.244;
6.W.237.228; 6.W.237.229; 6.W.237.230; 6.W.237.231; 6.W.237.236;
6.W.237.237; 6.W.237.238; 6.W.237.239; 6.W.237.154; 6.W.237.157;
6.W.237.166; 6.W.237.169; 6.W.237.172; 6.W.237.175; 6.W.237.240;
6.W.237.244; 6.W.238.228; 6.W.238.229; 6.W.238.230; 6.W.238.231;
6.W.238.236; 6.W.238.237; 6.W.238.238; 6.W.238.239; 6.W.238.154;
6.W.238.157; 6.W.238.166; 6.W.238.169; 6.W.238.172; 6.W.238.175;
6.W.238.240; 6.W.238.244; 6.W.239.228; 6.W.239.229; 6.W.239.230;
6.W.239.231; 6.W.239.236; 6.W.239.237; 6.W.239.238; 6.W.239.239;
6.W.239.154; 6.W.239.157; 6.W.239.166; 6.W.239.169; 6.W.239.172;
6.W.239.175; 6.W.239.240; 6.W.239.244; 6.W.154.228; 6.W.154.229;
6.W.154.230; 6.W.154.231; 6.W.154.236; 6.W.154.237; 6.W.154.238;
6.W.154.239; 6.W.154.154; 6.W.154.157; 6.W.154.166; 6.W.154.169;
6.W.154.172; 6.W.154.175; 6.W.154.240; 6.W.154.244; 6.W.157.228;
6.W.157.229; 6.W.157.230; 6.W.157.231; 6.W.157.236; 6.W.157.237;
6.W.157.238; 6.W.157.239; 6.W.157.154; 6.W.157.157; 6.W.157.166;
6.W.157.169; 6.W.157.172; 6.W.157.175; 6.W.157.240; 6.W.157.244;
6.W.166.228; 6.W.166.229; 6.W.166.230; 6.W.166.231; 6.W.166.236;
6.W.166.237; 6.W.166.238; 6.W.166.239; 6.W.166.154; 6.W.166.157;
6.W.166.166; 6.W.166.169; 6.W.166.172; 6.W.166.175; 6.W.166.240;
6.W.166.244; 6.W.169.228; 6.W.169.229; 6.W.169.230; 6.W.169.231;
6.W.169.236; 6.W.169.237; 6.W.169.238; 6.W.169.239; 6.W.169.154;
6.W.169.157; 6.W.169.166; 6.W.169.169; 6.W.169.172; 6.W.169.175;
6.W.169.240; 6.W.169.244; 6.W.172.228; 6.W.172.229; 6.W.172.230;
6.W.172.231; 6.W.172.236; 6.W.172.237; 6.W.172.238; 6.W.172.239;
6.W.172.154; 6.W.172.157; 6.W.172.166; 6.W.172.169; 6.W.172.172;
6.W.172.175; 6.W.172.240; 6.W.172.244; 6.W.175.228; 6.W.175.229;
6.W.175.230; 6.W.175.231; 6.W.175.236; 6.W.175.237; 6.W.175.238;
6.W.175.239; 6.W.175.154; 6.W.175.157; 6.W.175.166; 6.W.175.169;
6.W.175.172; 6.W.175.175; 6.W.175.240; 6.W.175.244; 6.W.240.228;
6.W.240.229; 6.W.240.230; 6.W.240.231; 6.W.240.236; 6.W.240.237;
6.W.240.238; 6.W.240.239; 6.W.240.154; 6.W.240.157; 6.W.240.166;
6.W.240.169; 6.W.240.172; 6.W.240.175; 6.W.240.240; 6.W.240.244;
6.W.244.228; 6.W.244.229; 6.W.244.230; 6.W.244.231; 6.W.244.236;
6.W.244.237; 6.W.244.238; 6.W.244.239; 6.W.244.154; 6.W.244.157;
6.W.244.166; 6.W.244.169; 6.W.244.172; 6.W.244.175; 6.W.244.240;
6.W.244.244;

Prodrugs of 6.Y

6.Y.228.228; 6.Y.228.229; 6.Y.228.230; 6.Y.228.231; 6.Y.228.236;
6.Y.228.237; 6.Y.228.238; 6.Y.228.239; 6.Y.228.154; 6.Y.228.157;
6.Y.228.166; 6.Y.228.169; 6.Y.228.172; 6.Y.228.175; 6.Y.228.240;
6.Y.228.244; 6.Y.229.228; 6.Y.229.229; 6.Y.229.230; 6.Y.229.231;
6.Y.229.236; 6.Y.229.237; 6.Y.229.238; 6.Y.229.239; 6.Y.229.154;
6.Y.229.157; 6.Y.229.166; 6.Y.229.169; 6.Y.229.172; 6.Y.229.175;
6.Y.229.240; 6.Y.229.244; 6.Y.230.228; 6.Y.230.229; 6.Y.230.230;
6.Y.230.231; 6.Y.230.236; 6.Y.230.237; 6.Y.230.238; 6.Y.230.239;
6.Y.230.154; 6.Y.230.157; 6.Y.230.166; 6.Y.230.169; 6.Y.230.172;
6.Y.230.175; 6.Y.230.240; 6.Y.230.244; 6.Y.231.228; 6.Y.231.229;
6.Y.231.230; 6.Y.231.231; 6.Y.231.236; 6.Y.231.237; 6.Y.231.238;
6.Y.231.239; 6.Y.231.154; 6.Y.231.157; 6.Y.231.166; 6.Y.231.169;
6.Y.231.172; 6.Y.231.175; 6.Y.231.240; 6.Y.231.244; 6.Y.236.228;
6.Y.236.229; 6.Y.236.230; 6.Y.236.231; 6.Y.236.236; 6.Y.236.237;
6.Y.236.238; 6.Y.236.239; 6.Y.236.154; 6.Y.236.157; 6.Y.236.166;
6.Y.236.169; 6.Y.236.172; 6.Y.236.175; 6.Y.236.240; 6.Y.236.244;
6.Y.237.228; 6.Y.237.229; 6.Y.237.230; 6.Y.237.231; 6.Y.237.236;
6.Y.237.237; 6.Y.237.238; 6.Y.237.239; 6.Y.237.154; 6.Y.237.157;
6.Y.237.166; 6.Y.237.169; 6.Y.237.172; 6.Y.237.175; 6.Y.237.240;
6.Y.237.244; 6.Y.238.228; 6.Y.238.229; 6.Y.238.230; 6.Y.238.231;
6.Y.238.236; 6.Y.238.237; 6.Y.238.238; 6.Y.238.239; 6.Y.238.154;
6.Y.238.157; 6.Y.238.166; 6.Y.238.169; 6.Y.238.172; 6.Y.238.175;
6.Y.238.240; 6.Y.238.244; 6.Y.239.228; 6.Y.239.229; 6.Y.239.230;

TABLE 100-continued

6.Y.239.231; 6.Y.239.236; 6.Y.239.237; 6.Y.239.238; 6.Y.239.239;
6.Y.239.154; 6.Y.239.157; 6.Y.239.166; 6.Y.239.169; 6.Y.239.172;
6.Y.239.175; 6.Y.239.240; 6.Y.239.244; 6.Y.154.228; 6.Y.154.229;
6.Y.154.230; 6.Y.154.231; 6.Y.154.236; 6.Y.154.237; 6.Y.154.238;
6.Y.154.239; 6.Y.154.154; 6.Y.154.157; 6.Y.154.166; 6.Y.154.169;
6.Y.154.172; 6.Y.154.175; 6.Y.154.240; 6.Y.154.244; 6.Y.157.228;
6.Y.157.229; 6.Y.157.230; 6.Y.157.231; 6.Y.157.236; 6.Y.157.237;
6.Y.157.238; 6.Y.157.239; 6.Y.157.154; 6.Y.157.157; 6.Y.157.166;
6.Y.157.169; 6.Y.157.172; 6.Y.157.175; 6.Y.157.240; 6.Y.157.244;
6.Y.166.228; 6.Y.166.229; 6.Y.166.230; 6.Y.166.231; 6.Y.166.236;
6.Y.166.237; 6.Y.166.238; 6.Y.166.239; 6.Y.166.154; 6.Y.166.157;
6.Y.166.166; 6.Y.166.169; 6.Y.166.172; 6.Y.166.175; 6.Y.166.240;
6.Y.166.244; 6.Y.169.228; 6.Y.169.229; 6.Y.169.230; 6.Y.169.231;
6.Y.169.236; 6.Y.169.237; 6.Y.169.238; 6.Y.169.239; 6.Y.169.154;
6.Y.169.157; 6.Y.169.166; 6.Y.169.169; 6.Y.169.172; 6.Y.169.175;
6.Y.169.240; 6.Y.169.244; 6.Y.172.228; 6.Y.172.229; 6.Y.172.230;
6.Y.172.231; 6.Y.172.236; 6.Y.172.237; 6.Y.172.238; 6.Y.172.239;
6.Y.172.154; 6.Y.172.157; 6.Y.172.166; 6.Y.172.169; 6.Y.172.172;
6.Y.172.175; 6.Y.172.240; 6.Y.172.244; 6.Y.175.228; 6.Y.175.229;
6.Y.175.230; 6.Y.175.231; 6.Y.175.236; 6.Y.175.237; 6.Y.175.238;
6.Y.175.239; 6.Y.175.154; 6.Y.175.157; 6.Y.175.166; 6.Y.175.169;
6.Y.175.172; 6.Y.175.175; 6.Y.175.240; 6.Y.175.244; 6.Y.240.228;
6.Y.240.229; 6.Y.240.230; 6.Y.240.231; 6.Y.240.236; 6.Y.240.237;
6.Y.240.238; 6.Y.240.239; 6.Y.240.154; 6.Y.240.157; 6.Y.240.166;
6.Y.240.169; 6.Y.240.172; 6.Y.240.175; 6.Y.240.240; 6.Y.240.244;
6.Y.244.228; 6.Y.244.229; 6.Y.244.230; 6.Y.244.231; 6.Y.244.236;
6.Y.244.237; 6.Y.244.238; 6.Y.244.239; 6.Y.244.154; 6.Y.244.157;
6.Y.244.166; 6.Y.244.169; 6.Y.244.172; 6.Y.244.175; 6.Y.244.240;
6.Y.244.244;

Prodrugs of 7.AH

7.AH.4.157; 7.AH.4.158; 7.AH.4.196; 7.AH.4.223; 7.AH.4.240; 7.AH.4.244;
7.AH.4.243; 7.AH.4.247; 7.AH.5.157; 7.AH.5.158; 7.AH.5.196; 7.AH.5.223;
7.AH.5.240; 7.AH.5.244; 7.AH.5.243; 7.AH.5.247; 7.AH.7.157; 7.AH.7.158;
7.AH.7.196; 7.AH.7.223; 7.AH.7.240; 7.AH.7.244; 7.AH.7.243; 7.AH.7.247;
7.AH.15.157; 7.AH.15.158; 7.AH.15.196; 7.AH.15.223; 7.AH.15.240;
7.AH.15.244; 7.AH.15.243; 7.AH.15.247; 7.AH.16.157; 7.AH.16.158;
7.AH.16.196; 7.AH.16.223; 7.AH.16.240; 7.AH.16.244; 7.AH.16.243;
7.AH.16.247; 7.AH.18.157; 7.AH.18.158; 7.AH.18.196; 7.AH.18.223;
7.AH.18.240; 7.AH.18.244; 7.AH.18.243; 7.AH.18.247; 7.AH.26.157;
7.AH.26.158; 7.AH.26.196; 7.AH.26.223; 7.AH.26.240; 7.AH.26.244;
7.AH.26.243; 7.AH.26.247; 7.AH.27.157; 7.AH.27.158; 7.AH.27.196;
7.AH.27.223; 7.AH.27.240; 7.AH.27.244; 7.AH.27.243; 7.AH.27.247;
7.AH.29.157; 7.AH.29.158; 7.AH.29.196; 7.AH.29.223; 7.AH.29.240;
7.AH.29.244; 7.AH.29.243; 7.AH.29.247; 7.AH.54.157; 7.AH.54.158;
7.AH.54.196; 7.AH.54.223; 7.AH.54.240; 7.AH.54.244; 7.AH.54.243;
7.AH.54.247; 7.AH.55.157; 7.AH.55.158; 7.AH.55.196; 7.AH.55.223;
7.AH.55.240; 7.AH.55.244; 7.AH.55.243; 7.AH.55.247; 7.AH.56.157;
7.AH.56.158; 7.AH.56.196; 7.AH.56.223; 7.AH.56.240; 7.AH.56.244;
7.AH.56.243; 7.AH.56.247; 7.AH.157.157; 7.AH.157.158; 7.AH.157.196;
7.AH.157.223; 7.AH.157.240; 7.AH.157.244; 7.AH.157.243; 7.AH.157.247;
7.AH.196.157; 7.AH.196.158; 7.AH.196.196; 7.AH.196.223; 7.AH.196.240;
7.AH.196.244; 7.AH.196.243; 7.AH.196.247; 7.AH.223.157; 7.AH.223.158;
7.AH.223.196; 7.AH.223.223; 7.AH.223.240; 7.AH.223.244; 7.AH.223.243;
7.AH.223.247; 7.AH.240.157; 7.AH.240.158; 7.AH.240.196; 7.AH.240.223;
7.AH.240.240; 7.AH.240.244; 7.AH.240.243; 7.AH.240.247; 7.AH.244.157;
7.AH.244.158; 7.AH.244.196; 7.AH.244.223; 7.AH.244.240; 7.AH.244.244;
7.AH.244.243; 7.AH.244.247; 7.AH.247.157; 7.AH.247.158; 7.AH.247.196;
7.AH.247.223; 7.AH.247.240; 7.AH.247.244; 7.AH.247.243; 7.AH.247.247;

Prodrugs of 7.AJ

7.AJ.4.157; 7.AJ.4.158; 7.AJ.4.196; 7.AJ.4.223; 7.AJ.4.240; 7.AJ.4.244;
7.AJ.4.243; 7.AJ.4.247; 7.AJ.5.157; 7.AJ.5.158; 7.AJ.5.196; 7.AJ.5.223;
7.AJ.5.240; 7.AJ.5.244; 7.AJ.5.243; 7.AJ.5.247; 7.AJ.7.157; 7.AJ.7.158;
7.AJ.7.196; 7.AJ.7.223; 7.AJ.7.240; 7.AJ.7.244; 7.AJ.7.243; 7.AJ.7.247;
7.AJ.15.157; 7.AJ.15.158; 7.AJ.15.196; 7.AJ.15.223; 7.AJ.15.240; 7.AJ.15.244;
7.AJ.15.243; 7.AJ.15.247; 7.AJ.16.157; 7.AJ.16.158; 7.AJ.16.196; 7.AJ.16.223;
7.AJ.16.240; 7.AJ.16.244; 7.AJ.16.243; 7.AJ.16.247; 7.AJ.18.157; 7.AJ.18.158;
7.AJ.18.196; 7.AJ.18.223; 7.AJ.18.240; 7.AJ.18.244; 7.AJ.18.243; 7.AJ.18.247;
7.AJ.26.157; 7.AJ.26.158; 7.AJ.26.196; 7.AJ.26.223; 7.AJ.26.240; 7.AJ.26.244;
7.AJ.26.243; 7.AJ.26.247; 7.AJ.27.157; 7.AJ.27.158; 7.AJ.27.196; 7.AJ.27.223;
7.AJ.27.240; 7.AJ.27.244; 7.AJ.27.243; 7.AJ.27.247; 7.AJ.29.157; 7.AJ.29.158;
7.AJ.29.196; 7.AJ.29.223; 7.AJ.29.240; 7.AJ.29.244; 7.AJ.29.243; 7.AJ.29.247;
7.AJ.54.157; 7.AJ.54.158; 7.AJ.54.196; 7.AJ.54.223; 7.AJ.54.240; 7.AJ.54.244;
7.AJ.54.243; 7.AJ.54.247; 7.AJ.55.157; 7.AJ.55.158; 7.AJ.55.196; 7.AJ.55.223;
7.AJ.55.240; 7.AJ.55.244; 7.AJ.55.243; 7.AJ.55.247; 7.AJ.56.157; 7.AJ.56.158;
7.AJ.56.196; 7.AJ.56.223; 7.AJ.56.240; 7.AJ.56.244; 7.AJ.56.243; 7.AJ.56.247;
7.AJ.157.157; 7.AJ.157.158; 7.AJ.157.196; 7.AJ.157.223; 7.AJ.157.240;
7.AJ.157.244; 7.AJ.157.243; 7.AJ.157.247; 7.AJ.196.157; 7.AJ.196.158;

TABLE 100-continued

7.AJ.196.196; 7.AJ.196.223; 7.AJ.196.240; 7.AJ.196.244; 7.AJ.196.243;
7.AJ.196.247; 7.AJ.223.157; 7.AJ.223.158; 7.AJ.223.196; 7.AJ.223.223;
7.AJ.223.240; 7.AJ.223.244; 7.AJ.223.243; 7.AJ.223.247; 7.AJ.240.157;
7.AJ.240.158; 7.AJ.240.196; 7.AJ.240.223; 7.AJ.240.240; 7.AJ.240.244;
7.AJ.240.243; 7.AJ.240.247; 7.AJ.244.157; 7.AJ.244.158; 7.AJ.244.196;
7.AJ.244.223; 7.AJ.244.240; 7.AJ.244.244; 7.AJ.244.243; 7.AJ.244.247;
7.AJ.247.157; 7.AJ.247.158; 7.AJ.247.196; 7.AJ.247.223; 7.AJ.247.240;
7.AJ.247.244; 7.AJ.247.243; 7.AJ.247.247;
Prodrugs of 7.AN 7.AN.4.157; 7.AN.4.158; 7.AN.4.196; 7.AN.4.223; 7.AN.4.240; 7.AN.4.244;
7.AN.4.243; 7.AN.4.247; 7.AN.5.157; 7.AN.5.158; 7.AN.5.196; 7.AN.5.223;
7.AN.5.240; 7.AN.5.244; 7.AN.5.243; 7.AN.5.247; 7.AN.7.157; 7.AN.7.158;
7.AN.7.196; 7.AN.7.223; 7.AN.7.240; 7.AN.7.244; 7.AN.7.243; 7.AN.7.247;
7.AN.15.157; 7.AN.15.158; 7.AN.15.196; 7.AN.15.223; 7.AN.15.240;
7.AN.15.244; 7.AN.15.243; 7.AN.15.247; 7.AN.16.157; 7.AN.16.158;
7.AN.16.196; 7.AN.16.223; 7.AN.16.240; 7.AN.16.244; 7.AN.16.243;
7.AN.16.247; 7.AN.18.157; 7.AN.18.158; 7.AN.18.196; 7.AN.18.223;
7.AN.18.240; 7.AN.18.244; 7.AN.18.243; 7.AN.18.247; 7.AN.26.157;
7.AN.26.158; 7.AN.26.196; 7.AN.26.223; 7.AN.26.240; 7.AN.26.244;
7.AN.26.243; 7.AN.26.247; 7.AN.27.157; 7.AN.27.158; 7.AN.27.196;
7.AN.27.223; 7.AN.27.240; 7.AN.27.244; 7.AN.27.243; 7.AN.27.247;
7.AN.29.157; 7.AN.29.158; 7.AN.29.196; 7.AN.29.223; 7.AN.29.240;
7.AN.29.244; 7.AN.29.243; 7.AN.29.247; 7.AN.54.157; 7.AN.54.158;
7.AN.54.196; 7.AN.54.223; 7.AN.54.240; 7.AN.54.244; 7.AN.54.243;
7.AN.54.247; 7.AN.55.157; 7.AN.55.158; 7.AN.55.196; 7.AN.55.223;
7.AN.55.240; 7.AN.55.244; 7.AN.55.243; 7.AN.55.247; 7.AN.56.157;
7.AN.56.158; 7.AN.56.196; 7.AN.56.223; 7.AN.56.240; 7.AN.56.244;
7.AN.56.243; 7.AN.56.247; 7.AN.157.157; 7.AN.157.158; 7.AN.157.196;
7.AN.157.223; 7.AN.157.240; 7.AN.157.244; 7.AN.157.243; 7.AN.157.247;
7.AN.196.157; 7.AN.196.158; 7.AN.196.196; 7.AN.196.223; 7.AN.196.240;
7.AN.196.244; 7.AN.196.243; 7.AN.196.247; 7.AN.223.157; 7.AN.223.158;
7.AN.223.196; 7.AN.223.223; 7.AN.223.240; 7.AN.223.244; 7.AN.223.243;
7.AN.223.247; 7.AN.240.157; 7.AN.240.158; 7.AN.240.196; 7.AN.240.223;
7.AN.240.240; 7.AN.240.244; 7.AN.240.243; 7.AN.240.247; 7.AN.244.157;
7.AN.244.158; 7.AN.244.196; 7.AN.244.223; 7.AN.244.240; 7.AN.244.244;
7.AN.244.243; 7.AN.244.247; 7.AN.247.157; 7.AN.247.158; 7.AN.247.196;
7.AN.247.223; 7.AN.247.240; 7.AN.247.244; 7.AN.247.243; 7.AN.247.247;
Prodrugs of 7.AP 7.AP.4.157; 7.AP.4.158; 7.AP.4.196; 7.AP.4.223; 7.AP.4.240; 7.AP.4.244;
7.AP.4.243; 7.AP.4.247; 7.AP.5.157; 7.AP.5.158; 7.AP.5.196; 7.AP.5.223;
7.AP.5.240; 7.AP.5.244; 7.AP.5.243; 7.AP.5.247; 7.AP.7.157; 7.AP.7.158;
7.AP.7.196; 7.AP.7.223; 7.AP.7.240; 7.AP.7.244; 7.AP.7.243; 7.AP.7.247;
7.AP.15.157; 7.AP.15.158; 7.AP.15.196; 7.AP.15.223; 7.AP.15.240;
7.AP.15.244; 7.AP.15.243; 7.AP.15.247; 7.AP.16.157; 7.AP.16.158;
7.AP.16.196; 7.AP.16.223; 7.AP.16.240; 7.AP.16.244; 7.AP.16.243;
7.AP.16.247; 7.AP.18.157; 7.AP.18.158; 7.AP.18.196; 7.AP.18.223;
7.AP.18.240; 7.AP.18.244; 7.AP.18.243; 7.AP.18.247; 7.AP.26.157;
7.AP.26.158; 7.AP.26.196; 7.AP.26.223; 7.AP.26.240; 7.AP.26.244;
7.AP.26.243; 7.AP.26.247; 7.AP.27.157; 7.AP.27.158; 7.AP.27.196;
7.AP.27.223; 7.AP.27.240; 7.AP.27.244; 7.AP.27.243; 7.AP.27.247;
7.AP.29.157; 7.AP.29.158; 7.AP.29.196; 7.AP.29.223; 7.AP.29.240;
7.AP.29.244; 7.AP.29.243; 7.AP.29.247; 7.AP.54.157; 7.AP.54.158;
7.AP.54.196; 7.AP.54.223; 7.AP.54.240; 7.AP.54.244; 7.AP.54.243;
7.AP.54.247; 7.AP.55.157; 7.AP.55.158; 7.AP.55.196; 7.AP.55.223;
7.AP.55.240; 7.AP.55.244; 7.AP.55.243; 7.AP.55.247; 7.AP.56.157;
7.AP.56.158; 7.AP.56.196; 7.AP.56.223; 7.AP.56.240; 7.AP.56.244;
7.AP.56.243; 7.AP.56.247; 7.AP.157.157; 7.AP.157.158; 7.AP.157.196;
7.AP.157.223; 7.AP.157.240; 7.AP.157.244; 7.AP.157.243; 7.AP.157.247;
7.AP.196.157; 7.AP.196.158; 7.AP.196.196; 7.AP.196.223; 7.AP.196.240;
7.AP.196.244; 7.AP.196.243; 7.AP.196.247; 7.AP.223.157; 7.AP.223.158;
7.AP.223.196; 7.AP.223.223; 7.AP.223.240; 7.AP.223.244; 7.AP.223.243;
7.AP.223.247; 7.AP.240.157; 7.AP.240.158; 7.AP.240.196; 7.AP.240.223;
7.AP.240.240; 7.AP.240.244; 7.AP.240.243; 7.AP.240.247; 7.AP.244.157;
7.AP.244.158; 7.AP.244.196; 7.AP.244.223; 7.AP.244.240; 7.AP.244.244;
7.AP.244.243; 7.AP.244.247; 7.AP.247.157; 7.AP.247.158; 7.AP.247.196;
7.AP.247.223; 7.AP.247.240; 7.AP.247.244; 7.AP.247.243; 7.AP.247.247;
Prodrugs of 7.AZ 7.AZ.4.157; 7.AZ.4.158; 7.AZ.4.196; 7.AZ.4.223; 7.AZ.4.240; 7.AZ.4.244;
7.AZ.4.243; 7.AZ.4.247; 7.AZ.5.157; 7.AZ.5.158; 7.AZ.5.196; 7.AZ.5.223;
7.AZ.5.240; 7.AZ.5.244; 7.AZ.5.243; 7.AZ.5.247; 7.AZ.7.157; 7.AZ.7.158;
7.AZ.7.196; 7.AZ.7.223; 7.AZ.7.240; 7.AZ.7.244; 7.AZ.7.243; 7.AZ.7.247;
7.AZ.15.157; 7.AZ.15.158; 7.AZ.15.196; 7.AZ.15.223; 7.AZ.15.240;
7.AZ.15.244; 7.AZ.15.243; 7.AZ.15.247; 7.AZ.16.157; 7.AZ.16.158;
7.AZ.16.196; 7.AZ.16.223; 7.AZ.16.240; 7.AZ.16.244; 7.AZ.16.243;
7.AZ.16.247; 7.AZ.18.157; 7.AZ.18.158; 7.AZ.18.196; 7.AZ.18.223;
7.AZ.18.240; 7.AZ.18.244; 7.AZ.18.243; 7.AZ.18.247; 7.AZ.26.157;

TABLE 100-continued

7.AZ.26.158; 7.AZ.26.196; 7.AZ.26.223; 7.AZ.26.240; 7.AZ.26.244;
7.AZ.26.243; 7.AZ.26.247; 7.AZ.27.157; 7.AZ.27.158; 7.AZ.27.196;
7.AZ.27.223; 7.AZ.27.240; 7.AZ.27.244; 7.AZ.27.243; 7.AZ.27.247;
7.AZ.29.157; 7.AZ.29.158; 7.AZ.29.196; 7.AZ.29.223; 7.AZ.29.240;
7.AZ.29.244; 7.AZ.29.243; 7.AZ.29.247; 7.AZ.54.157; 7.AZ.54.158;
7.AZ.54.196; 7.AZ.54.223; 7.AZ.54.240; 7.AZ.54.244; 7.AZ.54.243;
7.AZ.54.247; 7.AZ.55.157; 7.AZ.55.158; 7.AZ.55.196; 7.AZ.55.223;
7.AZ.55.240; 7.AZ.55.244; 7.AZ.55.243; 7.AZ.55.247; 7.AZ.56.157;
7.AZ.56.158; 7.AZ.56.196; 7.AZ.56.223; 7.AZ.56.240; 7.AZ.56.244;
7.AZ.56.243; 7.AZ.56.247; 7.AZ.157.157; 7.AZ.157.158; 7.AZ.157.196;
7.AZ.157.223; 7.AZ.157.240; 7.AZ.157.244; 7.AZ.157.243; 7.AZ.157.247;
7.AZ.196.157; 7.AZ.196.158; 7.AZ.196.196; 7.AZ.196.223; 7.AZ.196.240;
7.AZ.196.244; 7.AZ.196.243; 7.AZ.196.247; 7.AZ.223.157; 7.AZ.223.158;
7.AZ.223.196; 7.AZ.223.223; 7.AZ.223.240; 7.AZ.223.244; 7.AZ.223.243;
7.AZ.223.247; 7.AZ.240.157; 7.AZ.240.158; 7.AZ.240.196; 7.AZ.240.223;
7.AZ.240.240; 7.AZ.240.244; 7.AZ.240.243; 7.AZ.240.247; 7.AZ.244.157;
7.AZ.244.158; 7.AZ.244.196; 7.AZ.244.223; 7.AZ.244.240; 7.AZ.244.244;
7.AZ.244.243; 7.AZ.244.247; 7.AZ.247.157; 7.AZ.247.158; 7.AZ.247.196;
7.AZ.247.223; 7.AZ.247.240; 7.AZ.247.244; 7.AZ.247.243; 7.AZ.247.247;
Prodrugs of 7.BF 7.BF.4.157; 7.BF.4.158; 7.BF.4.196; 7.BF.4.223; 7.BF.4.240; 7.BF.4.244;
7.BF.4.243; 7.BF.4.247; 7.BF.5.157; 7.BF.5.158; 7.BF.5.196; 7.BF.5.223;
7.BF.5.240; 7.BF.5.244; 7.BF.5.243; 7.BF.5.247; 7.BF.7.157; 7.BF.7.158;
7.BF.7.196; 7.BF.7.223; 7.BF.7.240; 7.BF.7.244; 7.BF.7.243; 7.BF.7.247;
7.BF.15.157; 7.BF.15.158; 7.BF.15.196; 7.BF.15.223; 7.BF.15.240;
7.BF.15.244; 7.BF.15.243; 7.BF.15.247; 7.BF.16.157; 7.BF.16.158;
7.BF.16.196; 7.BF.16.223; 7.BF.16.240; 7.BF.16.244; 7.BF.16.243;
7.BF.16.247; 7.BF.18.157; 7.BF.18.158; 7.BF.18.196; 7.BF.18.223;
7.BF.18.240; 7.BF.18.244; 7.BF.18.243; 7.BF.18.247; 7.BF.26.157;
7.BF.26.158; 7.BF.26.196; 7.BF.26.223; 7.BF.26.240; 7.BF.26.244;
7.BF.26.243; 7.BF.26.247; 7.BF.27.157; 7.BF.27.158; 7.BF.27.196;
7.BF.27.223; 7.BF.27.240; 7.BF.27.244; 7.BF.27.243; 7.BF.27.247;
7.BF.29.157; 7.BF.29.158; 7.BF.29.196; 7.BF.29.223; 7.BF.29.240;
7.BF.29.244; 7.BF.29.243; 7.BF.29.247; 7.BF.54.157; 7.BF.54.158;
7.BF.54.196; 7.BF.54.223; 7.BF.54.240; 7.BF.54.244; 7.BF.54.243;
7.BF.54.247; 7.BF.55.157; 7.BF.55.158; 7.BF.55.196; 7.BF.55.223;
7.BF.55.240; 7.BF.55.244; 7.BF.55.243; 7.BF.55.247; 7.BF.56.157;
7.BF.56.158; 7.BF.56.196; 7.BF.56.223; 7.BF.56.240; 7.BF.56.244;
7.BF.56.243; 7.BF.56.247; 7.BF.157.157; 7.BF.157.158; 7.BF.157.196;
7.BF.157.223; 7.BF.157.240; 7.BF.157.244; 7.BF.157.243; 7.BF.157.247;
7.BF.196.157; 7.BF.196.158; 7.BF.196.196; 7.BF.196.223; 7.BF.196.240;
7.BF.196.244; 7.BF.196.243; 7.BF.196.247; 7.BF.223.157; 7.BF.223.158;
7.BF.223.196; 7.BF.223.223; 7.BF.223.240; 7.BF.223.244; 7.BF.223.243;
7.BF.223.247; 7.BF.240.157; 7.BF.240.158; 7.BF.240.196; 7.BF.240.223;
7.BF.240.240; 7.BF.240.244; 7.BF.240.243; 7.BF.240.247; 7.BF.244.157;
7.BF.244.158; 7.BF.244.196; 7.BF.244.223; 7.BF.244.240; 7.BF.244.244;
7.BF.244.243; 7.BF.244.247; 7.BF.247.157; 7.BF.247.158; 7.BF.247.196;
7.BF.247.223; 7.BF.247.240; 7.BF.247.244; 7.BF.247.243; 7.BF.247.247;
Prodrugs of 7.CI 7.CI.4.157; 7.CI.4.158; 7.CI.4.196; 7.CI.4.223; 7.CI.4.240; 7.CI.4.244;
7.CI.4.243; 7.CI.4.247; 7.CI.5.157; 7.CI.5.158; 7.CI.5.196; 7.CI.5.223;
7.CI.5.240; 7.CI.5.244; 7.CI.5.243; 7.CI.5.247; 7.CI.7.157; 7.CI.7.158;
7.CI.7.196; 7.CI.7.223; 7.CI.7.240; 7.CI.7.244; 7.CI.7.243; 7.CI.7.247;
7.CI.15.157; 7.CI.15.158; 7.CI.15.196; 7.CI.15.223; 7.CI.15.240; 7.CI.15.244;
7.CI.15.243; 7.CI.15.247; 7.CI.16.157; 7.CI.16.158; 7.CI.16.196; 7.CI.16.223;
7.CI.16.240; 7.CI.16.244; 7.CI.16.243; 7.CI.16.247; 7.CI.18.157; 7.CI.18.158;
7.CI.18.196; 7.CI.18.223; 7.CI.18.240; 7.CI.18.244; 7.CI.18.243; 7.CI.18.247;
7.CI.26.157; 7.CI.26.158; 7.CI.26.196; 7.CI.26.223; 7.CI.26.240; 7.CI.26.244;
7.CI.26.243; 7.CI.26.247; 7.CI.27.157; 7.CI.27.158; 7.CI.27.196; 7.CI.27.223;
7.CI.27.240; 7.CI.27.244; 7.CI.27.243; 7.CI.27.247; 7.CI.29.157; 7.CI.29.158;
7.CI.29.196; 7.CI.29.223; 7.CI.29.240; 7.CI.29.244; 7.CI.29.243; 7.CI.29.247;
7.CI.54.157; 7.CI.54.158; 7.CI.54.196; 7.CI.54.223; 7.CI.54.240; 7.CI.54.244;
7.CI.54.243; 7.CI.54.247; 7.CI.55.157; 7.CI.55.158; 7.CI.55.196; 7.CI.55.223;
7.CI.55.240; 7.CI.55.244; 7.CI.55.243; 7.CI.55.247; 7.CI.56.157; 7.CI.56.158;
7.CI.56.196; 7.CI.56.223; 7.CI.56.240; 7.CI.56.244; 7.CI.56.243; 7.CI.56.247;
7.CI.157.157; 7.CI.157.158; 7.CI.157.196; 7.CI.157.223; 7.CI.157.240;
7.CI.157.244; 7.CI.157.243; 7.CI.157.247; 7.CI.196.157; 7.CI.196.158;
7.CI.196.196; 7.CI.196.223; 7.CI.196.240; 7.CI.196.244; 7.CI.196.243;
7.CI.196.247; 7.CI.223.157; 7.CI.223.158; 7.CI.223.196; 7.CI.223.223;
7.CI.223.240; 7.CI.223.244; 7.CI.223.243; 7.CI.223.247; 7.CI.240.157;
7.CI.240.158; 7.CI.240.196; 7.CI.240.223; 7.CI.240.240; 7.CI.240.244;
7.CI.240.243; 7.CI.240.247; 7.CI.244.157; 7.CI.244.158; 7.CI.244.196;
7.CI.244.223; 7.CI.244.240; 7.CI.244.244; 7.CI.244.243; 7.CI.244.247;
7.CI.247.157; 7.CI.247.158; 7.CI.247.196; 7.CI.247.223; 7.CI.247.240;
7.CI.247.244; 7.CI.247.243; 7.CI.247.247;

TABLE 100-continued

Prodrugs of 7.CO

7.CO.4.157; 7.CO.4.158; 7.CO.4.196; 7.CO.4.223; 7.CO.4.240; 7.CO.4.244;
7.CO.4.243; 7.CO.4.247; 7.CO.5.157; 7.CO.5.158; 7.CO.5.196; 7.CO.5.223;
7.CO.5.240; 7.CO.5.244; 7.CO.5.243; 7.CO.5.247; 7.CO.7.157; 7.CO.7.158;
7.CO.7.196; 7.CO.7.223; 7.CO.7.240; 7.CO.7.244; 7.CO.7.243; 7.CO.7.247;
7.CO.15.157; 7.CO.15.158; 7.CO.15.196; 7.CO.15.223; 7.CO.15.240;
7.CO.15.244; 7.CO.15.243; 7.CO.15.247; 7.CO.16.157; 7.CO.16.158;
7.CO.16.196; 7.CO.16.223; 7.CO.16.240; 7.CO.16.244; 7.CO.16.243;
7.CO.16.247; 7.CO.18.157; 7.CO.18.158; 7.CO.18.196; 7.CO.18.223;
7.CO.18.240; 7.CO.18.244; 7.CO.18.243; 7.CO.18.247; 7.CO.26.157;
7.CO.26.158; 7.CO.26.196; 7.CO.26.223; 7.CO.26.240; 7.CO.26.244;
7.CO.26.243; 7.CO.26.247; 7.CO.27.157; 7.CO.27.158; 7.CO.27.196;
7.CO.27.223; 7.CO.27.240; 7.CO.27.244; 7.CO.27.243; 7.CO.27.247;
7.CO.29.157; 7.CO.29.158; 7.CO.29.196; 7.CO.29.223; 7.CO.29.240;
7.CO.29.244; 7.CO.29.243; 7.CO.29.247; 7.CO.54.157; 7.CO.54.158;
7.CO.54.196; 7.CO.54.223; 7.CO.54.240; 7.CO.54.244; 7.CO.54.243;
7.CO.54.247; 7.CO.55.157; 7.CO.55.158; 7.CO.55.196; 7.CO.55.223;
7.CO.55.240; 7.CO.55.244; 7.CO.55.243; 7.CO.55.247; 7.CO.56.157;
7.CO.56.158; 7.CO.56.196; 7.CO.56.223; 7.CO.56.240; 7.CO.56.244;
7.CO.56.243; 7.CO.56.247; 7.CO.157.157; 7.CO.157.158; 7.CO.157.196;
7.CO.157.223; 7.CO.157.240; 7.CO.157.244; 7.CO.157.243; 7.CO.157.247;
7.CO.196.157; 7.CO.196.158; 7.CO.196.196; 7.CO.196.223; 7.CO.196.240;
7.CO.196.244; 7.CO.196.243; 7.CO.196.247; 7.CO.223.157; 7.CO.223.158;
7.CO.223.196; 7.CO.223.223; 7.CO.223.240; 7.CO.223.244; 7.CO.223.243;
7.CO.223.247; 7.CO.240.157; 7.CO.240.158; 7.CO.240.196; 7.CO.240.223;
7.CO.240.240; 7.CO.240.244; 7.CO.240.243; 7.CO.240.247; 7.CO.244.157;
7.CO.244.158; 7.CO.244.196; 7.CO.244.223; 7.CO.244.240; 7.CO.244.244;
7.CO.244.243; 7.CO.244.247; 7.CO.4.157; 7.CO.4.158; 7.CO.4.196;
7.CO.4.223; 7.CO.4.240; 7.CO.4.244; 7.CO.4.243; 7.CO.4.247;

Prodrugs of 8.AH

8.AH.4.157; 8.AH.4.158; 8.AH.4.196; 8.AH.4.223; 8.AH.4.240; 8.AH.4.244;
8.AH.4.243; 8.AH.4.247; 8.AH.5.157; 8.AH.5.158; 8.AH.5.196; 8.AH.5.223;
8.AH.5.240; 8.AH.5.244; 8.AH.5.243; 8.AH.5.247; 8.AH.7.157; 8.AH.7.158;
8.AH.7.196; 8.AH.7.223; 8.AH.7.240; 8.AH.7.244; 8.AH.7.243; 8.AH.7.247;
8.AH.15.157; 8.AH.15.158; 8.AH.15.196; 8.AH.15.223; 8.AH.15.240;
8.AH.15.244; 8.AH.15.243; 8.AH.15.247; 8.AH.16.157; 8.AH.16.158;
8.AH.16.196; 8.AH.16.223; 8.AH.16.240; 8.AH.16.244; 8.AH.16.243;
8.AH.16.247; 8.AH.18.157; 8.AH.18.158; 8.AH.18.196; 8.AH.18.223;
8.AH.18.240; 8.AH.18.244; 8.AH.18.243; 8.AH.18.247; 8.AH.26.157;
8.AH.26.158; 8.AH.26.196; 8.AH.26.223; 8.AH.26.240; 8.AH.26.244;
8.AH.26.243; 8.AH.26.247; 8.AH.27.157; 8.AH.27.158; 8.AH.27.196;
8.AH.27.223; 8.AH.27.240; 8.AH.27.244; 8.AH.27.243; 8.AH.27.247;
8.AH.29.157; 8.AH.29.158; 8.AH.29.196; 8.AH.29.223; 8.AH.29.240;
8.AH.29.244; 8.AH.29.243; 8.AH.29.247; 8.AH.54.157; 8.AH.54.158;
8.AH.54.196; 8.AH.54.223; 8.AH.54.240; 8.AH.54.244; 8.AH.54.243;
8.AH.54.247; 8.AH.55.157; 8.AH.55.158; 8.AH.55.196; 8.AH.55.223;
8.AH.55.240; 8.AH.55.244; 8.AH.55.243; 8.AH.55.247; 8.AH.56.157;
8.AH.56.158; 8.AH.56.196; 8.AH.56.223; 8.AH.56.240; 8.AH.56.244;
8.AH.56.243; 8.AH.56.247; 8.AH.157.157; 8.AH.157.158; 8.AH.157.196;
8.AH.157.223; 8.AH.157.240; 8.AH.157.244; 8.AH.157.243; 8.AH.157.247;
8.AH.196.157; 8.AH.196.158; 8.AH.196.196; 8.AH.196.223; 8.AH.196.240;
8.AH.196.244; 8.AH.196.243; 8.AH.196.247; 8.AH.223.157; 8.AH.223.158;
8.AH.223.196; 8.AH.223.223; 8.AH.223.240; 8.AH.223.244; 8.AH.223.243;
8.AH.223.247; 8.AH.240.157; 8.AH.240.158; 8.AH.240.196; 8.AH.240.223;
8.AH.240.240; 8.AH.240.244; 8.AH.240.243; 8.AH.240.247; 8.AH.244.157;
8.AH.244.158; 8.AH.244.196; 8.AH.244.223; 8.AH.244.240; 8.AH.244.244;
8.AH.244.243; 8.AH.244.247; 8.AH.247.157; 8.AH.247.158; 8.AH.247.196;
8.AH.247.223; 8.AH.247.240; 8.AH.247.244; 8.AH.247.243; 8.AH.247.247;

Prodrugs of 8.AJ

8.AJ.4.157; 8.AJ.4.158; 8.AJ.4.196; 8.AJ.4.223; 8.AJ.4.240; 8.AJ.4.244;
8.AJ.4.243; 8.AJ.4.247; 8.AJ.5.157; 8.AJ.5.158; 8.AJ.5.196; 8.AJ.5.223;
8.AJ.5.240; 8.AJ.5.244; 8.AJ.5.243; 8.AJ.5.247; 8.AJ.7.157; 8.AJ.7.158;
8.AJ.7.196; 8.AJ.7.223; 8.AJ.7.240; 8.AJ.7.244; 8.AJ.7.243; 8.AJ.7.247;
8.AJ.15.157; 8.AJ.15.158; 8.AJ.15.196; 8.AJ.15.223; 8.AJ.15.240; 8.AJ.15.244;
8.AJ.15.243; 8.AJ.15.247; 8.AJ.16.157; 8.AJ.16.158; 8.AJ.16.196; 8.AJ.16.223;
8.AJ.16.240; 8.AJ.16.244; 8.AJ.16.243; 8.AJ.16.247; 8.AJ.18.157; 8.AJ.18.158;
8.AJ.18.196; 8.AJ.18.223; 8.AJ.18.240; 8.AJ.18.244; 8.AJ.18.243; 8.AJ.18.247;
8.AJ.26.157; 8.AJ.26.158; 8.AJ.26.196; 8.AJ.26.223; 8.AJ.26.240; 8.AJ.26.244;
8.AJ.26.243; 8.AJ.26.247; 8.AJ.27.157; 8.AJ.27.158; 8.AJ.27.196; 8.AJ.27.223;
8.AJ.27.240; 8.AJ.27.244; 8.AJ.27.243; 8.AJ.27.247; 8.AJ.29.157; 8.AJ.29.158;
8.AJ.29.196; 8.AJ.29.223; 8.AJ.29.240; 8.AJ.29.244; 8.AJ.29.243; 8.AJ.29.247;
8.AJ.54.157; 8.AJ.54.158; 8.AJ.54.196; 8.AJ.54.223; 8.AJ.54.240; 8.AJ.54.244;
8.AJ.54.243; 8.AJ.54.247; 8.AJ.55.157; 8.AJ.55.158; 8.AJ.55.196; 8.AJ.55.223;
8.AJ.55.240; 8.AJ.55.244; 8.AJ.55.243; 8.AJ.55.247; 8.AJ.56.157; 8.AJ.56.158;
8.AJ.56.196; 8.AJ.56.223; 8.AJ.56.240; 8.AJ.56.244; 8.AJ.56.243; 8.AJ.56.247;
8.AJ.157.157; 8.AJ.157.158; 8.AJ.157.196; 8.AJ.157.223; 8.AJ.157.240;

TABLE 100-continued

8.AJ.157.244; 8.AJ.157.243; 8.AJ.157.247; 8.AJ.196.157; 8.AJ.196.158;
8.AJ.196.196; 8.AJ.196.223; 8.AJ.196.240; 8.AJ.196.244; 8.AJ.196.243;
8.AJ.196.247; 8.AJ.223.157; 8.AJ.223.158; 8.AJ.223.196; 8.AJ.223.223;
8.AJ.223.240; 8.AJ.223.244; 8.AJ.223.243; 8.AJ.223.247; 8.AJ.240.157;
8.AJ.240.158; 8.AJ.240.196; 8.AJ.240.223; 8.AJ.240.240; 8.AJ.240.244;
8.AJ.240.243; 8.AJ.240.247; 8.AJ.244.157; 8.AJ.244.158; 8.AJ.244.196;
8.AJ.244.223; 8.AJ.244.240; 8.AJ.244.244; 8.AJ.244.243; 8.AJ.244.247;
8.AJ.247.157; 8.AJ.247.158; 8.AJ.247.196; 8.AJ.247.223; 8.AJ.247.240;
8.AJ.247.244; 8.AJ.247.243; 8.AJ.247.247;
Prodrugs of 8.AN 8.AN.4.157; 8.AN.4.158; 8.AN.4.196; 8.AN.4.223; 8.AN.4.240; 8.AN.4.244;
8.AN.4.243; 8.AN.4.247; 8.AN.5.157; 8.AN.5.158; 8.AN.5.196; 8.AN.5.223;
8.AN.5.240; 8.AN.5.244; 8.AN.5.243; 8.AN.5.247; 8.AN.7.157; 8.AN.7.158;
8.AN.7.196; 8.AN.7.223; 8.AN.7.240; 8.AN.7.244; 8.AN.7.243; 8.AN.7.247;
8.AN.15.157; 8.AN.15.158; 8.AN.15.196; 8.AN.15.223; 8.AN.15.240;
8.AN.15.244; 8.AN.15.243; 8.AN.15.247; 8.AN.16.157; 8.AN.16.158;
8.AN.16.196; 8.AN.16.223; 8.AN.16.240; 8.AN.16.244; 8.AN.16.243;
8.AN.16.247; 8.AN.18.157; 8.AN.18.158; 8.AN.18.196; 8.AN.18.223;
8.AN.18.240; 8.AN.18.244; 8.AN.18.243; 8.AN.18.247; 8.AN.26.157;
8.AN.26.158; 8.AN.26.196; 8.AN.26.223; 8.AN.26.240; 8.AN.26.244;
8.AN.26.243; 8.AN.26.247; 8.AN.27.157; 8.AN.27.158; 8.AN.27.196;
8.AN.27.223; 8.AN.27.240; 8.AN.27.244; 8.AN.27.243; 8.AN.27.247;
8.AN.29.157; 8.AN.29.158; 8.AN.29.196; 8.AN.29.223; 8.AN.29.240;
8.AN.29.244; 8.AN.29.243; 8.AN.29.247; 8.AN.54.157; 8.AN.54.158;
8.AN.54.196; 8.AN.54.223; 8.AN.54.240; 8.AN.54.244; 8.AN.54.243;
8.AN.54.247; 8.AN.55.157; 8.AN.55.158; 8.AN.55.196; 8.AN.55.223;
8.AN.55.240; 8.AN.55.244; 8.AN.55.243; 8.AN.55.247; 8.AN.56.157;
8.AN.56.158; 8.AN.56.196; 8.AN.56.223; 8.AN.56.240; 8.AN.56.244;
8.AN.56.243; 8.AN.56.247; 8.AN.157.157; 8.AN.157.158; 8.AN.157.196;
8.AN.157.223; 8.AN.157.240; 8.AN.157.244; 8.AN.157.243; 8.AN.157.247;
8.AN.196.157; 8.AN.196.158; 8.AN.196.196; 8.AN.196.223; 8.AN.196.240;
8.AN.196.244; 8.AN.196.243; 8.AN.196.247; 8.AN.223.157; 8.AN.223.158;
8.AN.223.196; 8.AN.223.223; 8.AN.223.240; 8.AN.223.244; 8.AN.223.243;
8.AN.223.247; 8.AN.240.157; 8.AN.240.158; 8.AN.240.196; 8.AN.240.223;
8.AN.240.240; 8.AN.240.244; 8.AN.240.243; 8.AN.240.247; 8.AN.244.157;
8.AN.244.158; 8.AN.244.196; 8.AN.244.223; 8.AN.244.240; 8.AN.244.244;
8.AN.244.243; 8.AN.244.247; 8.AN.247.157; 8.AN.247.158; 8.AN.247.196;
8.AN.247.223; 8.AN.247.240; 8.AN.247.244; 8.AN.247.243; 8.AN.247.247;
Prodrugs of 8.AP 8.AP.4.157; 8.AP.4.158; 8.AP.4.196; 8.AP.4.223; 8.AP.4.240; 8.AP.4.244;
8.AP.4.243; 8.AP.4.247; 8.AP.5.157; 8.AP.5.158; 8.AP.5.196; 8.AP.5.223;
8.AP.5.240; 8.AP.5.244; 8.AP.5.243; 8.AP.5.247; 8.AP.7.157; 8.AP.7.158;
8.AP.7.196; 8.AP.7.223; 8.AP.7.240; 8.AP.7.244; 8.AP.7.243; 8.AP.7.247;
8.AP.15.157; 8.AP.15.158; 8.AP.15.196; 8.AP.15.223; 8.AP.15.240;
8.AP.15.244; 8.AP.15.243; 8.AP.15.247; 8.AP.16.157; 8.AP.16.158;
8.AP.16.196; 8.AP.16.223; 8.AP.16.240; 8.AP.16.244; 8.AP.16.243;
8.AP.16.247; 8.AP.18.157; 8.AP.18.158; 8.AP.18.196; 8.AP.18.223;
8.AP.18.240; 8.AP.18.244; 8.AP.18.243; 8.AP.18.247; 8.AP.26.157;
8.AP.26.158; 8.AP.26.196; 8.AP.26.223; 8.AP.26.240; 8.AP.26.244;
8.AP.26.243; 8.AP.26.247; 8.AP.27.157; 8.AP.27.158; 8.AP.27.196;
8.AP.27.223; 8.AP.27.240; 8.AP.27.244; 8.AP.27.243; 8.AP.27.247;
8.AP.29.157; 8.AP.29.158; 8.AP.29.196; 8.AP.29.223; 8.AP.29.240;
8.AP.29.244; 8.AP.29.243; 8.AP.29.247; 8.AP.54.157; 8.AP.54.158;
8.AP.54.196; 8.AP.54.223; 8.AP.54.240; 8.AP.54.244; 8.AP.54.243;
8.AP.54.247; 8.AP.55.157; 8.AP.55.158; 8.AP.55.196; 8.AP.55.223;
8.AP.55.240; 8.AP.55.244; 8.AP.55.243; 8.AP.55.247; 8.AP.56.157;
8.AP.56.158; 8.AP.56.196; 8.AP.56.223; 8.AP.56.240; 8.AP.56.244;
8.AP.56.243; 8.AP.56.247; 8.AP.157.157; 8.AP.157.158; 8.AP.157.196;
8.AP.157.223; 8.AP.157.240; 8.AP.157.244; 8.AP.157.243; 8.AP.157.247;
8.AP.196.157; 8.AP.196.158; 8.AP.196.196; 8.AP.196.223; 8.AP.196.240;
8.AP.196.244; 8.AP.196.243; 8.AP.196.247; 8.AP.223.157; 8.AP.223.158;
8.AP.223.196; 8.AP.223.223; 8.AP.223.240; 8.AP.223.244; 8.AP.223.243;
8.AP.223.247; 8.AP.240.157; 8.AP.240.158; 8.AP.240.196; 8.AP.240.223;
8.AP.240.240; 8.AP.240.244; 8.AP.240.243; 8.AP.240.247; 8.AP.244.157;
8.AP.244.158; 8.AP.244.196; 8.AP.244.223; 8.AP.244.240; 8.AP.244.244;
8.AP.244.243; 8.AP.244.247; 8.AP.247.157; 8.AP.247.158; 8.AP.247.196;
8.AP.247.223; 8.AP.247.240; 8.AP.247.244; 8.AP.247.243; 8.AP.247.247;
Prodrugs of 8.AZ 8.AZ.4.157; 8.AZ.4.158; 8.AZ.4.196; 8.AZ.4.223; 8.AZ.4.240; 8.AZ.4.244;
8.AZ.4.243; 8.AZ.4.247; 8.AZ.5.157; 8.AZ.5.158; 8.AZ.5.196; 8.AZ.5.223;
8.AZ.5.240; 8.AZ.5.244; 8.AZ.5.243; 8.AZ.5.247; 8.AZ.7.157; 8.AZ.7.158;
8.AZ.7.196; 8.AZ.7.223; 8.AZ.7.240; 8.AZ.7.244; 8.AZ.7.243; 8.AZ.7.247;
8.AZ.15.157; 8.AZ.15.158; 8.AZ.15.196; 8.AZ.15.223; 8.AZ.15.240;
8.AZ.15.244; 8.AZ.15.243; 8.AZ.15.247; 8.AZ.16.157; 8.AZ.16.158;
8.AZ.16.196; 8.AZ.16.223; 8.AZ.16.240; 8.AZ.16.244; 8.AZ.16.243;
8.AZ.16.247; 8.AZ.18.157; 8.AZ.18.158; 8.AZ.18.196; 8.AZ.18.223;

TABLE 100-continued

8.AZ.18.240; 8.AZ.18.244; 8.AZ.18.243; 8.AZ.18.247; 8.AZ.26.157;
8.AZ.26.158; 8.AZ.26.196; 8.AZ.26.223; 8.AZ.26.240; 8.AZ.26.244;
8.AZ.26.243; 8.AZ.26.247; 8.AZ.27.157; 8.AZ.27.158; 8.AZ.27.196;
8.AZ.27.223; 8.AZ.27.240; 8.AZ.27.244; 8.AZ.27.243; 8.AZ.27.247;
8.AZ.29.157; 8.AZ.29.158; 8.AZ.29.196; 8.AZ.29.223; 8.AZ.29.240;
8.AZ.29.244; 8.AZ.29.243; 8.AZ.29.247; 8.AZ.54.157; 8.AZ.54.158;
8.AZ.54.196; 8.AZ.54.223; 8.AZ.54.240; 8.AZ.54.244; 8.AZ.54.243;
8.AZ.54.247; 8.AZ.55.157; 8.AZ.55.158; 8.AZ.55.196; 8.AZ.55.223;
8.AZ.55.240; 8.AZ.55.244; 8.AZ.55.243; 8.AZ.55.247; 8.AZ.56.157;
8.AZ.56.158; 8.AZ.56.196; 8.AZ.56.223; 8.AZ.56.240; 8.AZ.56.244;
8.AZ.56.243; 8.AZ.56.247; 8.AZ.157.157; 8.AZ.157.158; 8.AZ.157.196;
8.AZ.157.223; 8.AZ.157.240; 8.AZ.157.244; 8.AZ.157.243; 8.AZ.157.247;
8.AZ.196.157; 8.AZ.196.158; 8.AZ.196.196; 8.AZ.196.223; 8.AZ.196.240;
8.AZ.196.244; 8.AZ.196.243; 8.AZ.196.247; 8.AZ.223.157; 8.AZ.223.158;
8.AZ.223.196; 8.AZ.223.223; 8.AZ.223.240; 8.AZ.223.244; 8.AZ.223.243;
8.AZ.223.247; 8.AZ.240.157; 8.AZ.240.158; 8.AZ.240.196; 8.AZ.240.223;
8.AZ.240.240; 8.AZ.240.244; 8.AZ.240.243; 8.AZ.240.247; 8.AZ.244.157;
8.AZ.244.158; 8.AZ.244.196; 8.AZ.244.223; 8.AZ.244.240; 8.AZ.244.244;
8.AZ.244.243; 8.AZ.244.247; 8.AZ.247.157; 8.AZ.247.158; 8.AZ.247.196;
8.AZ.247.223; 8.AZ.247.240; 8.AZ.247.244; 8.AZ.247.243; 8.AZ.247.247;
Prodrugs of 8.BF 8.BF.4.157; 8.BF.4.158; 8.BF.4.196; 8.BF.4.223; 8.BF.4.240; 8.BF.4.244;
8.BF.4.243; 8.BF.4.247; 8.BF.5.157; 8.BF.5.158; 8.BF.5.196; 8.BF.5.223;
8.BF.5.240; 8.BF.5.244; 8.BF.5.243; 8.BF.5.247; 8.BF.7.157; 8.BF.7.158;
8.BF.7.196; 8.BF.7.223; 8.BF.7.240; 8.BF.7.244; 8.BF.7.243; 8.BF.7.247;
8.BF.15.157; 8.BF.15.158; 8.BF.15.196; 8.BF.15.223; 8.BF.15.240;
8.BF.15.244; 8.BF.15.243; 8.BF.15.247; 8.BF.16.157; 8.BF.16.158;
8.BF.16.196; 8.BF.16.223; 8.BF.16.240; 8.BF.16.244; 8.BF.16.243;
8.BF.16.247; 8.BF.18.157; 8.BF.18.158; 8.BF.18.196; 8.BF.18.223;
8.BF.18.240; 8.BF.18.244; 8.BF.18.243; 8.BF.18.247; 8.BF.26.157;
8.BF.26.158; 8.BF.26.196; 8.BF.26.223; 8.BF.26.240; 8.BF.26.244;
8.BF.26.243; 8.BF.26.247; 8.BF.27.157; 8.BF.27.158; 8.BF.27.196;
8.BF.27.223; 8.BF.27.240; 8.BF.27.244; 8.BF.27.243; 8.BF.27.247;
8.BF.29.157; 8.BF.29.158; 8.BF.29.196; 8.BF.29.223; 8.BF.29.240;
8.BF.29.244; 8.BF.29.243; 8.BF.29.247; 8.BF.54.157; 8.BF.54.158;
8.BF.54.196; 8.BF.54.223; 8.BF.54.240; 8.BF.54.244; 8.BF.54.243;
8.BF.54.247; 8.BF.55.157; 8.BF.55.158; 8.BF.55.196; 8.BF.55.223;
8.BF.55.240; 8.BF.55.244; 8.BF.55.243; 8.BF.55.247; 8.BF.56.157;
8.BF.56.158; 8.BF.56.196; 8.BF.56.223; 8.BF.56.240; 8.BF.56.244;
8.BF.56.243; 8.BF.56.247; 8.BF.157.157; 8.BF.157.158; 8.BF.157.196;
8.BF.157.223; 8.BF.157.240; 8.BF.157.244; 8.BF.157.243; 8.BF.157.247;
8.BF.196.157; 8.BF.196.158; 8.BF.196.196; 8.BF.196.223; 8.BF.196.240;
8.BF.196.244; 8.BF.196.243; 8.BF.196.247; 8.BF.223.157; 8.BF.223.158;
8.BF.223.196; 8.BF.223.223; 8.BF.223.240; 8.BF.223.244; 8.BF.223.243;
8.BF.223.247; 8.BF.240.157; 8.BF.240.158; 8.BF.240.196; 8.BF.240.223;
8.BF.240.240; 8.BF.240.244; 8.BF.240.243; 8.BF.240.247; 8.BF.244.157;
8.BF.244.158; 8.BF.244.196; 8.BF.244.223; 8.BF.244.240; 8.BF.244.244;
8.BF.244.243; 8.BF.244.247; 8.BF.247.157; 8.BF.247.158; 8.BF.247.196;
8.BF.247.223; 8.BF.247.240; 8.BF.247.244; 8.BF.247.243; 8.BF.247.247;
Prodrugs of 8.CI 8.CI.4.157; 8.CI.4.158; 8.CI.4.196; 8.CI.4.223; 8.CI.4.240; 8.CI.4.244;
8.CI.4.243; 8.CI.4.247; 8.CI.5.157; 8.CI.5.158; 8.CI.5.196; 8.CI.5.223;
8.CI.5.240; 8.CI.5.244; 8.CI.5.243; 8.CI.5.247; 8.CI.7.157; 8.CI.7.158;
8.CI.7.196; 8.CI.7.223; 8.CI.7.240; 8.CI.7.244; 8.CI.7.243; 8.CI.7.247;
8.CI.15.157; 8.CI.15.158; 8.CI.15.196; 8.CI.15.223; 8.CI.15.240; 8.CI.15.244;
8.CI.15.243; 8.CI.15.247; 8.CI.16.157; 8.CI.16.158; 8.CI.16.196; 8.CI.16.223;
8.CI.16.240; 8.CI.16.244; 8.CI.16.243; 8.CI.16.247; 8.CI.18.157; 8.CI.18.158;
8.CI.18.196; 8.CI.18.223; 8.CI.18.240; 8.CI.18.244; 8.CI.18.243; 8.CI.18.247;
8.CI.26.157; 8.CI.26.158; 8.CI.26.196; 8.CI.26.223; 8.CI.26.240; 8.CI.26.244;
8.CI.26.243; 8.CI.26.247; 8.CI.27.157; 8.CI.27.158; 8.CI.27.196; 8.CI.27.223;
8.CI.27.240; 8.CI.27.244; 8.CI.27.243; 8.CI.27.247; 8.CI.29.157; 8.CI.29.158;
8.CI.29.196; 8.CI.29.223; 8.CI.29.240; 8.CI.29.244; 8.CI.29.243; 8.CI.29.247;
8.CI.54.157; 8.CI.54.158; 8.CI.54.196; 8.CI.54.223; 8.CI.54.240; 8.CI.54.244;
8.CI.54.243; 8.CI.54.247; 8.CI.55.157; 8.CI.55.158; 8.CI.55.196; 8.CI.55.223;
8.CI.55.240; 8.CI.55.244; 8.CI.55.243; 8.CI.55.247; 8.CI.56.157; 8.CI.56.158;
8.CI.56.196; 8.CI.56.223; 8.CI.56.240; 8.CI.56.244; 8.CI.56.243; 8.CI.56.247;
8.CI.157.157; 8.CI.157.158; 8.CI.157.196; 8.CI.157.223; 8.CI.157.240;
8.CI.157.244; 8.CI.157.243; 8.CI.157.247; 8.CI.196.157; 8.CI.196.158;
8.CI.196.196; 8.CI.196.223; 8.CI.196.240; 8.CI.196.244; 8.CI.196.243;
8.CI.196.247; 8.CI.223.157; 8.CI.223.158; 8.CI.223.196; 8.CI.223.223;
8.CI.223.240; 8.CI.223.244; 8.CI.223.243; 8.CI.223.247; 8.CI.240.157;
8.CI.240.158; 8.CI.240.196; 8.CI.240.223; 8.CI.240.240; 8.CI.240.244;
8.CI.240.243; 8.CI.240.247; 8.CI.244.157; 8.CI.244.158; 8.CI.244.196;
8.CI.244.223; 8.CI.244.240; 8.CI.244.244; 8.CI.244.243; 8.CI.244.247;
8.CI.247.157; 8.CI.247.158; 8.CI.247.196; 8.CI.247.223; 8.CI.247.240; 8.CI.247.244;
8.CI.247.243; 8.CI.247.247;

TABLE 100-continued

Prodrugs of 8.CO

8.CO.4.157; 8.CO.4.158; 8.CO.4.196; 8.CO.4.223; 8.CO.4.240; 8.CO.4.244;
8.CO.4.243; 8.CO.4.247; 8.CO.5.157; 8.CO.5.158; 8.CO.5.196; 8.CO.5.223;
8.CO.5.240; 8.CO.5.244; 8.CO.5.243; 8.CO.5.247; 8.CO.7.157; 8.CO.7.158;
8.CO.7.196; 8.CO.7.223; 8.CO.7.240; 8.CO.7.244; 8.CO.7.243; 8.CO.7.247;
8.CO.15.157; 8.CO.15.158; 8.CO.15.196; 8.CO.15.223; 8.CO.15.240;
8.CO.15.244; 8.CO.15.243; 8.CO.15.247; 8.CO.16.157; 8.CO.16.158;
8.CO.16.196; 8.CO.16.223; 8.CO.16.240; 8.CO.16.244; 8.CO.16.243;
8.CO.16.247; 8.CO.18.157; 8.CO.18.158; 8.CO.18.196; 8.CO.18.223;
8.CO.18.240; 8.CO.18.244; 8.CO.18.243; 8.CO.18.247; 8.CO.26.157;
8.CO.26.158; 8.CO.26.196; 8.CO.26.223; 8.CO.26.240; 8.CO.26.244;
8.CO.26.243; 8.CO.26.247; 8.CO.27.157; 8.CO.27.158; 8.CO.27.196;
8.CO.27.223; 8.CO.27.240; 8.CO.27.244; 8.CO.27.243; 8.CO.27.247;
8.CO.29.157; 8.CO.29.158; 8.CO.29.196; 8.CO.29.223; 8.CO.29.240;
8.CO.29.244; 8.CO.29.243; 8.CO.29.247; 8.CO.54.157; 8.CO.54.158;
8.CO.54.196; 8.CO.54.223; 8.CO.54.240; 8.CO.54.244; 8.CO.54.243;
8.CO.54.247; 8.CO.55.157; 8.CO.55.158; 8.CO.55.196; 8.CO.55.223;
8.CO.55.240; 8.CO.55.244; 8.CO.55.243; 8.CO.55.247; 8.CO.56.157;
8.CO.56.158; 8.CO.56.196; 8.CO.56.223; 8.CO.56.240; 8.CO.56.244;
8.CO.56.243; 8.CO.56.247; 8.CO.157.157; 8.CO.157.158; 8.CO.157.196;
8.CO.157.223; 8.CO.157.240; 8.CO.157.244; 8.CO.157.243; 8.CO.157.247;
8.CO.196.157; 8.CO.196.158; 8.CO.196.196; 8.CO.196.223; 8.CO.196.240;
8.CO.196.244; 8.CO.196.243; 8.CO.196.247; 8.CO.223.157; 8.CO.223.158;
8.CO.223.196; 8.CO.223.223; 8.CO.223.240; 8.CO.223.244; 8.CO.223.243;
8.CO.223.247; 8.CO.240.157; 8.CO.240.158; 8.CO.240.196; 8.CO.240.223;
8.CO.240.240; 8.CO.240.244; 8.CO.240.243; 8.CO.240.247; 8.CO.244.157;
8.CO.244.158; 8.CO.244.196; 8.CO.244.223; 8.CO.244.240; 8.CO.244.244;
8.CO.244.243; 8.CO.244.247; 8.CO.247.157; 8.CO.247.158; 8.CO.247.196;
8.CO.247.223; 8.CO.247.240; 8.CO.247.244; 8.CO.247.243; 8.CO.247.247;

Prodrugs of 9.AH

9.AH.4.157; 9.AH.4.158; 9.AH.4.196; 9.AH.4.223; 9.AH.4.240; 9.AH.4.244;
9.AH.4.243; 9.AH.4.247; 9.AH.5.157; 9.AH.5.158; 9.AH.5.196; 9.AH.5.223;
9.AH.5.240; 9.AH.5.244; 9.AH.5.243; 9.AH.5.247; 9.AH.7.157; 9.AH.7.158;
9.AH.7.196; 9.AH.7.223; 9.AH.7.240; 9.AH.7.244; 9.AH.7.243; 9.AH.7.247;
9.AH.15.157; 9.AH.15.158; 9.AH.15.196; 9.AH.15.223; 9.AH.15.240;
9.AH.15.244; 9.AH.15.243; 9.AH.15.247; 9.AH.16.157; 9.AH.16.158;
9.AH.16.196; 9.AH.16.223; 9.AH.16.240; 9.AH.16.244; 9.AH.16.243;
9.AH.16.247; 9.AH.18.157; 9.AH.18.158; 9.AH.18.196; 9.AH.18.223;
9.AH.18.240; 9.AH.18.244; 9.AH.18.243; 9.AH.18.247; 9.AH.26.157;
9.AH.26.158; 9.AH.26.196; 9.AH.26.223; 9.AH.26.240; 9.AH.26.244;
9.AH.26.243; 9.AH.26.247; 9.AH.27.157; 9.AH.27.158; 9.AH.27.196;
9.AH.27.223; 9.AH.27.240; 9.AH.27.244; 9.AH.27.243; 9.AH.27.247;
9.AH.29.157; 9.AH.29.158; 9.AH.29.196; 9.AH.29.223; 9.AH.29.240;
9.AH.29.244; 9.AH.29.243; 9.AH.29.247; 9.AH.54.157; 9.AH.54.158;
9.AH.54.196; 9.AH.54.223; 9.AH.54.240; 9.AH.54.244; 9.AH.54.243;
9.AH.54.247; 9.AH.55.157; 9.AH.55.158; 9.AH.55.196; 9.AH.55.223;
9.AH.55.240; 9.AH.55.244; 9.AH.55.243; 9.AH.55.247; 9.AH.56.157;
9.AH.56.158; 9.AH.56.196; 9.AH.56.223; 9.AH.56.240; 9.AH.56.244;
9.AH.56.243; 9.AH.56.247; 9.AH.157.157; 9.AH.157.158; 9.AH.157.196;
9.AH.157.223; 9.AH.157.240; 9.AH.157.244; 9.AH.157.243; 9.AH.157.247;
9.AH.196.157; 9.AH.196.158; 9.AH.196.196; 9.AH.196.223; 9.AH.196.240;
9.AH.196.244; 9.AH.196.243; 9.AH.196.247; 9.AH.223.157; 9.AH.223.158;
9.AH.223.196; 9.AH.223.223; 9.AH.223.240; 9.AH.223.244; 9.AH.223.243;
9.AH.223.247; 9.AH.240.157; 9.AH.240.158; 9.AH.240.196; 9.AH.240.223;
9.AH.240.240; 9.AH.240.244; 9.AH.240.243; 9.AH.240.247; 9.AH.244.157;
9.AH.244.158; 9.AH.244.196; 9.AH.244.223; 9.AH.244.240; 9.AH.244.244;
9.AH.244.243; 9.AH.244.247; 9.AH.247.157; 9.AH.247.158; 9.AH.247.196;
9.AH.247.223; 9.AH.247.240; 9.AH.247.244; 9.AH.247.243; 9.AH.247.247;

Prodrugs of 9.AJ

9.AJ.4.157; 9.AJ.4.158; 9.AJ.4.196; 9.AJ.4.223; 9.AJ.4.240; 9.AJ.4.244;
9.AJ.4.243; 9.AJ.4.247; 9.AJ.5.157; 9.AJ.5.158; 9.AJ.5.196; 9.AJ.5.223;
9.AJ.5.240; 9.AJ.5.244; 9.AJ.5.243; 9.AJ.5.247; 9.AJ.7.157; 9.AJ.7.158;
9.AJ.7.196; 9.AJ.7.223; 9.AJ.7.240; 9.AJ.7.244; 9.AJ.7.243; 9.AJ.7.247;
9.AJ.15.157; 9.AJ.15.158; 9.AJ.15.196; 9.AJ.15.223; 9.AJ.15.240; 9.AJ.15.244;
9.AJ.15.243; 9.AJ.15.247; 9.AJ.16.157; 9.AJ.16.158; 9.AJ.16.196; 9.AJ.16.223;
9.AJ.16.240; 9.AJ.16.244; 9.AJ.16.243; 9.AJ.16.247; 9.AJ.18.157; 9.AJ.18.158;
9.AJ.18.196; 9.AJ.18.223; 9.AJ.18.240; 9.AJ.18.244; 9.AJ.18.243; 9.AJ.18.247;
9.AJ.26.157; 9.AJ.26.158; 9.AJ.26.196; 9.AJ.26.223; 9.AJ.26.240; 9.AJ.26.244;
9.AJ.26.243; 9.AJ.26.247; 9.AJ.27.157; 9.AJ.27.158; 9.AJ.27.196; 9.AJ.27.223;
9.AJ.27.240; 9.AJ.27.244; 9.AJ.27.243; 9.AJ.27.247; 9.AJ.29.157; 9.AJ.29.158;
9.AJ.29.196; 9.AJ.29.223; 9.AJ.29.240; 9.AJ.29.244; 9.AJ.29.243; 9.AJ.29.247;
9.AJ.54.157; 9.AJ.54.158; 9.AJ.54.196; 9.AJ.54.223; 9.AJ.54.240; 9.AJ.54.244;
9.AJ.54.243; 9.AJ.54.247; 9.AJ.55.157; 9.AJ.55.158; 9.AJ.55.196; 9.AJ.55.223;
9.AJ.55.240; 9.AJ.55.244; 9.AJ.55.243; 9.AJ.55.247; 9.AJ.56.157; 9.AJ.56.158;
9.AJ.56.196; 9.AJ.56.223; 9.AJ.56.240; 9.AJ.56.244; 9.AJ.56.243; 9.AJ.56.247;
9.AJ.157.157; 9.AJ.157.158; 9.AJ.157.196; 9.AJ.157.223; 9.AJ.157.240;

TABLE 100-continued

9.AJ.157.244; 9.AJ.157.243; 9.AJ.157.247; 9.AJ.196.157; 9.AJ.196.158;
9.AJ.196.196; 9.AJ.196.223; 9.AJ.196.240; 9.AJ.196.244; 9.AJ.196.243;
9.AJ.196.247; 9.AJ.223.157; 9.AJ.223.158; 9.AJ.223.196; 9.AJ.223.223;
9.AJ.223.240; 9.AJ.223.244; 9.AJ.223.243; 9.AJ.223.247; 9.AJ.240.157;
9.AJ.240.158; 9.AJ.240.196; 9.AJ.240.223; 9.AJ.240.240; 9.AJ.240.244;
9.AJ.240.243; 9.AJ.240.247; 9.AJ.244.157; 9.AJ.244.158; 9.AJ.244.196;
9.AJ.244.223; 9.AJ.244.240; 9.AJ.244.244; 9.AJ.244.243; 9.AJ.244.247;
9.AJ.247.157; 9.AJ.247.158; 9.AJ.247.196; 9.AJ.247.223; 9.AJ.247.240;
9.AJ.247.244; 9.AJ.247.243; 9.AJ.247.247;
Prodrugs of 9.AN 9.AN.4.157; 9.AN.4.158; 9.AN.4.196; 9.AN.4.223; 9.AN.4.240; 9.AN.4.244;
9.AN.4.243; 9.AN.4.247; 9.AN.5.157; 9.AN.5.158; 9.AN.5.196; 9.AN.5.223;
9.AN.5.240; 9.AN.5.244; 9.AN.5.243; 9.AN.5.247; 9.AN.7.157; 9.AN.7.158;
9.AN.7.196; 9.AN.7.223; 9.AN.7.240; 9.AN.7.244; 9.AN.7.243; 9.AN.7.247;
9.AN.15.157; 9.AN.15.158; 9.AN.15.196; 9.AN.15.223; 9.AN.15.240;
9.AN.15.244; 9.AN.15.243; 9.AN.15.247; 9.AN.16.157; 9.AN.16.158;
9.AN.16.196; 9.AN.16.223; 9.AN.16.240; 9.AN.16.244; 9.AN.16.243;
9.AN.16.247; 9.AN.18.157; 9.AN.18.158; 9.AN.18.196; 9.AN.18.223;
9.AN.18.240; 9.AN.18.244; 9.AN.18.243; 9.AN.18.247; 9.AN.26.157;
9.AN.26.158; 9.AN.26.196; 9.AN.26.223; 9.AN.26.240; 9.AN.26.244;
9.AN.26.243; 9.AN.26.247; 9.AN.27.157; 9.AN.27.158; 9.AN.27.196;
9.AN.27.223; 9.AN.27.240; 9.AN.27.244; 9.AN.27.243; 9.AN.27.247;
9.AN.29.157; 9.AN.29.158; 9.AN.29.196; 9.AN.29.223; 9.AN.29.240;
9.AN.29.244; 9.AN.29.243; 9.AN.29.247; 9.AN.54.157; 9.AN.54.158;
9.AN.54.196; 9.AN.54.223; 9.AN.54.240; 9.AN.54.244; 9.AN.54.243;
9.AN.54.247; 9.AN.55.157; 9.AN.55.158; 9.AN.55.196; 9.AN.55.223;
9.AN.55.240; 9.AN.55.244; 9.AN.55.243; 9.AN.55.247; 9.AN.56.157;
9.AN.56.158; 9.AN.56.196; 9.AN.56.223; 9.AN.56.240; 9.AN.56.244;
9.AN.56.243; 9.AN.56.247; 9.AN.157.157; 9.AN.157.158; 9.AN.157.196;
9.AN.157.223; 9.AN.157.240; 9.AN.157.244; 9.AN.157.243; 9.AN.157.247;
9.AN.196.157; 9.AN.196.158; 9.AN.196.196; 9.AN.196.223; 9.AN.196.240;
9.AN.196.244; 9.AN.196.243; 9.AN.196.247; 9.AN.223.157; 9.AN.223.158;
9.AN.223.196; 9.AN.223.223; 9.AN.223.240; 9.AN.223.244; 9.AN.223.243;
9.AN.223.247; 9.AN.240.157; 9.AN.240.158; 9.AN.240.196; 9.AN.240.223;
9.AN.240.240; 9.AN.240.244; 9.AN.240.243; 9.AN.240.247; 9.AN.244.157;
9.AN.244.158; 9.AN.244.196; 9.AN.244.223; 9.AN.244.240; 9.AN.244.244;
9.AN.244.243; 9.AN.244.247; 9.AN.247.157; 9.AN.247.158; 9.AN.247.196;
9.AN.247.223; 9.AN.247.240; 9.AN.247.244; 9.AN.247.243; 9.AN.247.247;
Prodrugs of 9.AP 9.AP.4.157; 9.AP.4.158; 9.AP.4.196; 9.AP.4.223; 9.AP.4.240; 9.AP.4.244;
9.AP.4.243; 9.AP.4.247; 9.AP.5.157; 9.AP.5.158; 9.AP.5.196; 9.AP.5.223;
9.AP.5.240; 9.AP.5.244; 9.AP.5.243; 9.AP.5.247; 9.AP.7.157; 9.AP.7.158;
9.AP.7.196; 9.AP.7.223; 9.AP.7.240; 9.AP.7.244; 9.AP.7.243; 9.AP.7.247;
9.AP.15.157; 9.AP.15.158; 9.AP.15.196; 9.AP.15.223; 9.AP.15.240;
9.AP.15.244; 9.AP.15.243; 9.AP.15.247; 9.AP.16.157; 9.AP.16.158;
9.AP.16.196; 9.AP.16.223; 9.AP.16.240; 9.AP.16.244; 9.AP.16.243;
9.AP.16.247; 9.AP.18.157; 9.AP.18.158; 9.AP.18.196; 9.AP.18.223;
9.AP.18.240; 9.AP.18.244; 9.AP.18.243; 9.AP.18.247; 9.AP.26.157;
9.AP.26.158; 9.AP.26.196; 9.AP.26.223; 9.AP.26.240; 9.AP.26.244;
9.AP.26.243; 9.AP.26.247; 9.AP.27.157; 9.AP.27.158; 9.AP.27.196;
9.AP.27.223; 9.AP.27.240; 9.AP.27.244; 9.AP.27.243; 9.AP.27.247;
9.AP.29.157; 9.AP.29.158; 9.AP.29.196; 9.AP.29.223; 9.AP.29.240;
9.AP.29.244; 9.AP.29.243; 9.AP.29.247; 9.AP.54.157; 9.AP.54.158;
9.AP.54.196; 9.AP.54.223; 9.AP.54.240; 9.AP.54.244; 9.AP.54.243;
9.AP.54.247; 9.AP.55.157; 9.AP.55.158; 9.AP.55.196; 9.AP.55.223;
9.AP.55.240; 9.AP.55.244; 9.AP.55.243; 9.AP.55.247; 9.AP.56.157;
9.AP.56.158; 9.AP.56.196; 9.AP.56.223; 9.AP.56.240; 9.AP.56.244;
9.AP.56.243; 9.AP.56.247; 9.AP.157.157; 9.AP.157.158; 9.AP.157.196;
9.AP.157.223; 9.AP.157.240; 9.AP.157.244; 9.AP.157.243; 9.AP.157.247;
9.AP.196.157; 9.AP.196.158; 9.AP.196.196; 9.AP.196.223; 9.AP.196.240;
9.AP.196.244; 9.AP.196.243; 9.AP.196.247; 9.AP.223.157; 9.AP.223.158;
9.AP.223.196; 9.AP.223.223; 9.AP.223.240; 9.AP.223.244; 9.AP.223.243;
9.AP.223.247; 9.AP.240.157; 9.AP.240.158; 9.AP.240.196; 9.AP.240.223;
9.AP.240.240; 9.AP.240.244; 9.AP.240.243; 9.AP.240.247; 9.AP.244.157;
9.AP.244.158; 9.AP.244.196; 9.AP.244.223; 9.AP.244.240; 9.AP.244.244;
9.AP.244.243; 9.AP.244.247; 9.AP.247.157; 9.AP.247.158; 9.AP.247.196;
9.AP.247.223; 9.AP.247.240; 9.AP.247.244; 9.AP.247.243; 9.AP.247.247;
Prodrugs of 9.AZ 9.AZ.4.157; 9.AZ.4.158; 9.AZ.4.196; 9.AZ.4.223; 9.AZ.4.240; 9.AZ.4.244;
9.AZ.4.243; 9.AZ.4.247; 9.AZ.5.157; 9.AZ.5.158; 9.AZ.5.196; 9.AZ.5.223;
9.AZ.5.240; 9.AZ.5.244; 9.AZ.5.243; 9.AZ.5.247; 9.AZ.7.157; 9.AZ.7.158;
9.AZ.7.196; 9.AZ.7.223; 9.AZ.7.240; 9.AZ.7.244; 9.AZ.7.243; 9.AZ.7.247;
9.AZ.15.157; 9.AZ.15.158; 9.AZ.15.196; 9.AZ.15.223; 9.AZ.15.240;
9.AZ.15.244; 9.AZ.15.243; 9.AZ.15.247; 9.AZ.16.157; 9.AZ.16.158;
9.AZ.16.196; 9.AZ.16.223; 9.AZ.16.240; 9.AZ.16.244; 9.AZ.16.243;
9.AZ.16.247; 9.AZ.18.157; 9.AZ.18.158; 9.AZ.18.196; 9.AZ.18.223;

TABLE 100-continued

9.AZ.18.240; 9.AZ.18.244; 9.AZ.18.243; 9.AZ.18.247; 9.AZ.26.157;
9.AZ.26.158; 9.AZ.26.196; 9.AZ.26.223; 9.AZ.26.240; 9.AZ.26.244;
9.AZ.26.243; 9.AZ.26.247; 9.AZ.27.157; 9.AZ.27.158; 9.AZ.27.196;
9.AZ.27.223; 9.AZ.27.240; 9.AZ.27.244; 9.AZ.27.243; 9.AZ.27.247;
9.AZ.29.157; 9.AZ.29.158; 9.AZ.29.196; 9.AZ.29.223; 9.AZ.29.240;
9.AZ.29.244; 9.AZ.29.243; 9.AZ.29.247; 9.AZ.54.157; 9.AZ.54.158;
9.AZ.54.196; 9.AZ.54.223; 9.AZ.54.240; 9.AZ.54.244; 9.AZ.54.243;
9.AZ.54.247; 9.AZ.55.157; 9.AZ.55.158; 9.AZ.55.196; 9.AZ.55.223;
9.AZ.55.240; 9.AZ.55.244; 9.AZ.55.243; 9.AZ.55.247; 9.AZ.56.157;
9.AZ.56.158; 9.AZ.56.196; 9.AZ.56.223; 9.AZ.56.240; 9.AZ.56.244;
9.AZ.56.243; 9.AZ.56.247; 9.AZ.157.157; 9.AZ.157.158; 9.AZ.157.196;
9.AZ.157.223; 9.AZ.157.240; 9.AZ.157.244; 9.AZ.157.243; 9.AZ.157.247;
9.AZ.196.157; 9.AZ.196.158; 9.AZ.196.196; 9.AZ.196.223; 9.AZ.196.240;
9.AZ.196.244; 9.AZ.196.243; 9.AZ.196.247; 9.AZ.223.157; 9.AZ.223.158;
9.AZ.223.196; 9.AZ.223.223; 9.AZ.223.240; 9.AZ.223.244; 9.AZ.223.243;
9.AZ.223.247; 9.AZ.240.157; 9.AZ.240.158; 9.AZ.240.196; 9.AZ.240.223;
9.AZ.240.240; 9.AZ.240.244; 9.AZ.240.243; 9.AZ.240.247; 9.AZ.244.157;
9.AZ.244.158; 9.AZ.244.196; 9.AZ.244.223; 9.AZ.244.240; 9.AZ.244.244;
9.AZ.244.243; 9.AZ.244.247; 9.AZ.247.157; 9.AZ.247.158; 9.AZ.247.196;
9.AZ.247.223; 9.AZ.247.240; 9.AZ.247.244; 9.AZ.247.243; 9.AZ.247.247;
Prodrugs of 9.BF 9.BF.4.157; 9.BF.4.158; 9.BF.4.196; 9.BF.4.223; 9.BF.4.240; 9.BF.4.244;
9.BF.4.243; 9.BF.4.247; 9.BF.5.157; 9.BF.5.158; 9.BF.5.196; 9.BF.5.223;
9.BF.5.240; 9.BF.5.244; 9.BF.5.243; 9.BF.5.247; 9.BF.7.157; 9.BF.7.158;
9.BF.7.196; 9.BF.7.223; 9.BF.7.240; 9.BF.7.244; 9.BF.7.243; 9.BF.7.247;
9.BF.15.157; 9.BF.15.158; 9.BF.15.196; 9.BF.15.223; 9.BF.15.240;
9.BF.15.244; 9.BF.15.243; 9.BF.15.247; 9.BF.16.157; 9.BF.16.158;
9.BF.16.196; 9.BF.16.223; 9.BF.16.240; 9.BF.16.244; 9.BF.16.243;
9.BF.16.247; 9.BF.18.157; 9.BF.18.158; 9.BF.18.196; 9.BF.18.223;
9.BF.18.240; 9.BF.18.244; 9.BF.18.243; 9.BF.18.247; 9.BF.26.157;
9.BF.26.158; 9.BF.26.196; 9.BF.26.223; 9.BF.26.240; 9.BF.26.244;
9.BF.26.243; 9.BF.26.247; 9.BF.27.157; 9.BF.27.158; 9.BF.27.196;
9.BF.27.223; 9.BF.27.240; 9.BF.27.244; 9.BF.27.243; 9.BF.27.247;
9.BF.29.157; 9.BF.29.158; 9.BF.29.196; 9.BF.29.223; 9.BF.29.240;
9.BF.29.244; 9.BF.29.243; 9.BF.29.247; 9.BF.54.157; 9.BF.54.158;
9.BF.54.196; 9.BF.54.223; 9.BF.54.240; 9.BF.54.244; 9.BF.54.243;
9.BF.54.247; 9.BF.55.157; 9.BF.55.158; 9.BF.55.196; 9.BF.55.223;
9.BF.55.240; 9.BF.55.244; 9.BF.55.243; 9.BF.55.247; 9.BF.56.157;
9.BF.56.158; 9.BF.56.196; 9.BF.56.223; 9.BF.56.240; 9.BF.56.244;
9.BF.56.243; 9.BF.56.247; 9.BF.157.157; 9.BF.157.158; 9.BF.157.196;
9.BF.157.223; 9.BF.157.240; 9.BF.157.244; 9.BF.157.243; 9.BF.157.247;
9.BF.196.157; 9.BF.196.158; 9.BF.196.196; 9.BF.196.223; 9.BF.196.240;
9.BF.196.244; 9.BF.196.243; 9.BF.196.247; 9.BF.223.157; 9.BF.223.158;
9.BF.223.196; 9.BF.223.223; 9.BF.223.240; 9.BF.223.244; 9.BF.223.243;
9.BF.223.247; 9.BF.240.157; 9.BF.240.158; 9.BF.240.196; 9.BF.240.223;
9.BF.240.240; 9.BF.240.244; 9.BF.240.243; 9.BF.240.247; 9.BF.244.157;
9.BF.244.158; 9.BF.244.196; 9.BF.244.223; 9.BF.244.240; 9.BF.244.244;
9.BF.244.243; 9.BF.244.247; 9.BF.247.157; 9.BF.247.158; 9.BF.247.196;
9.BF.247.223; 9.BF.247.240; 9.BF.247.244; 9.BF.247.243; 9.BF.247.247;
Prodrugs of 9.CI 9.CI.4.157; 9.CI.4.158; 9.CI.4.196; 9.CI.4.223; 9.CI.4.240; 9.CI.4.244;
9.CI.4.243; 9.CI.4.247; 9.CI.5.157; 9.CI.5.158; 9.CI.5.196; 9.CI.5.223;
9.CI.5.240; 9.CI.5.244; 9.CI.5.243; 9.CI.5.247; 9.CI.7.157; 9.CI.7.158;
9.CI.7.196; 9.CI.7.223; 9.CI.7.240; 9.CI.7.244; 9.CI.7.243; 9.CI.7.247;
9.CI.15.157; 9.CI.15.158; 9.CI.15.196; 9.CI.15.223; 9.CI.15.240; 9.CI.15.244;
9.CI.15.243; 9.CI.15.247; 9.CI.16.157; 9.CI.16.158; 9.CI.16.196; 9.CI.16.223;
9.CI.16.240; 9.CI.16.244; 9.CI.16.243; 9.CI.16.247; 9.CI.18.157; 9.CI.18.158;
9.CI.18.196; 9.CI.18.223; 9.CI.18.240; 9.CI.18.244; 9.CI.18.243; 9.CI.18.247;
9.CI.26.157; 9.CI.26.158; 9.CI.26.196; 9.CI.26.223; 9.CI.26.240; 9.CI.26.244;
9.CI.26.243; 9.CI.26.247; 9.CI.27.157; 9.CI.27.158; 9.CI.27.196; 9.CI.27.223;
9.CI.27.240; 9.CI.27.244; 9.CI.27.243; 9.CI.27.247; 9.CI.29.157; 9.CI.29.158;
9.CI.29.196; 9.CI.29.223; 9.CI.29.240; 9.CI.29.244; 9.CI.29.243; 9.CI.29.247;
9.CI.54.157; 9.CI.54.158; 9.CI.54.196; 9.CI.54.223; 9.CI.54.240; 9.CI.54.244;
9.CI.54.243; 9.CI.54.247; 9.CI.55.157; 9.CI.55.158; 9.CI.55.196; 9.CI.55.223;
9.CI.55.240; 9.CI.55.244; 9.CI.55.243; 9.CI.55.247; 9.CI.56.157; 9.CI.56.158;
9.CI.56.196; 9.CI.56.223; 9.CI.56.240; 9.CI.56.244; 9.CI.56.243; 9.CI.56.247;
9.CI.157.157; 9.CI.157.158; 9.CI.157.196; 9.CI.157.223; 9.CI.157.240;
9.CI.157.244; 9.CI.157.243; 9.CI.157.247; 9.CI.196.157; 9.CI.196.158;
9.CI.196.196; 9.CI.196.223; 9.CI.196.240; 9.CI.196.244; 9.CI.196.243;
9.CI.196.247; 9.CI.223.157; 9.CI.223.158; 9.CI.223.196; 9.CI.223.223;
9.CI.223.240; 9.CI.223.244; 9.CI.223.243; 9.CI.223.247; 9.CI.240.157;
9.CI.240.158; 9.CI.240.196; 9.CI.240.223; 9.CI.240.240; 9.CI.240.244;
9.CI.240.243; 9.CI.240.247; 9.CI.244.157; 9.CI.244.158; 9.CI.244.196;
9.CI.244.223; 9.CI.244.240; 9.CI.244.244; 9.CI.244.243; 9.CI.244.247;
9.CI.247.157; 9.CI.247.158; 9.CI.247.196; 9.CI.247.223; 9.CI.247.240;
9.CI.247.244; 9.CI.247.243; 9.CI.247.247;

TABLE 100-continued

Prodrugs of 9.CO

9.CO.4.157; 9.CO.4.158; 9.CO.4.196; 9.CO.4.223; 9.CO.4.240; 9.CO.4.244;
9.CO.4.243; 9.CO.4.247; 9.CO.5.157; 9.CO.5.158; 9.CO.5.196; 9.CO.5.223;
9.CO.5.240; 9.CO.5.244; 9.CO.5.243; 9.CO.5.247; 9.CO.7.157; 9.CO.7.158;
9.CO.7.196; 9.CO.7.223; 9.CO.7.240; 9.CO.7.244; 9.CO.7.243; 9.CO.7.247;
9.CO.15.157; 9.CO.15.158; 9.CO.15.196; 9.CO.15.223; 9.CO.15.240;
9.CO.15.244; 9.CO.15.243; 9.CO.15.247; 9.CO.16.157; 9.CO.16.158;
9.CO.16.196; 9.CO.16.223; 9.CO.16.240; 9.CO.16.244; 9.CO.16.243;
9.CO.16.247; 9.CO.18.157; 9.CO.18.158; 9.CO.18.196; 9.CO.18.223;
9.CO.18.240; 9.CO.18.244; 9.CO.18.243; 9.CO.18.247; 9.CO.26.157;
9.CO.26.158; 9.CO.26.196; 9.CO.26.223; 9.CO.26.240; 9.CO.26.244;
9.CO.26.243; 9.CO.26.247; 9.CO.27.157; 9.CO.27.158; 9.CO.27.196;
9.CO.27.223; 9.CO.27.240; 9.CO.27.244; 9.CO.27.243; 9.CO.27.247;
9.CO.29.157; 9.CO.29.158; 9.CO.29.196; 9.CO.29.223; 9.CO.29.240;
9.CO.29.244; 9.CO.29.243; 9.CO.29.247; 9.CO.54.157; 9.CO.54.158;
9.CO.54.196; 9.CO.54.223; 9.CO.54.240; 9.CO.54.244; 9.CO.54.243;
9.CO.54.247; 9.CO.55.157; 9.CO.55.158; 9.CO.55.196; 9.CO.55.223;
9.CO.55.240; 9.CO.55.244; 9.CO.55.243; 9.CO.55.247; 9.CO.56.157;
9.CO.56.158; 9.CO.56.196; 9.CO.56.223; 9.CO.56.240; 9.CO.56.244;
9.CO.56.243; 9.CO.56.247; 9.CO.157.157; 9.CO.157.158; 9.CO.157.196;
9.CO.157.223; 9.CO.157.240; 9.CO.157.244; 9.CO.157.243; 9.CO.157.247;
9.CO.196.157; 9.CO.196.158; 9.CO.196.196; 9.CO.196.223; 9.CO.196.240;
9.CO.196.244; 9.CO.196.243; 9.CO.196.247; 9.CO.223.157; 9.CO.223.158;
9.CO.223.196; 9.CO.223.223; 9.CO.223.240; 9.CO.223.244; 9.CO.223.243;
9.CO.223.247; 9.CO.240.157; 9.CO.240.158; 9.CO.240.196; 9.CO.240.223;
9.CO.240.240; 9.CO.240.244; 9.CO.240.243; 9.CO.240.247; 9.CO.244.157;
9.CO.244.158; 9.CO.244.196; 9.CO.244.223; 9.CO.244.240; 9.CO.244.244;
9.CO.244.243; 9.CO.244.247; 9.CO.247.157; 9.CO.247.158; 9.CO.247.196;
9.CO.247.223; 9.CO.247.240; 9.CO.247.244; 9.CO.247.243; 9.CO.247.247;

Prodrugs of 10.AH

10.AH.4.157; 10.AH.4.158; 10.AH.4.196; 10.AH.4.223; 10.AH.4.240;
10.AH.4.244; 10.AH.4.243; 10.AH.4.247; 10.AH.5.157; 10.AH.5.158;
10.AH.5.196; 10.AH.5.223; 10.AH.5.240; 10.AH.5.244; 10.AH.5.243;
10.AH.5.247; 10.AH.7.157; 10.AH.7.158; 10.AH.7.196; 10.AH.7.223;
10.AH.7.240; 10.AH.7.244; 10.AH.7.243; 10.AH.7.247; 10.AH.15.157;
10.AH.15.158; 10.AH.15.196; 10.AH.15.223; 10.AH.15.240; 10.AH.15.244;
10.AH.15.243; 10.AH.15.247; 10.AH.16.157; 10.AH.16.158; 10.AH.16.196;
10.AH.16.223; 10.AH.16.240; 10.AH.16.244; 10.AH.16.243; 10.AH.16.247;
10.AH.18.157; 10.AH.18.158; 10.AH.18.196; 10.AH.18.223; 10.AH.18.240;
10.AH.18.244; 10.AH.18.243; 10.AH.18.247; 10.AH.26.157; 10.AH.26.158;
10.AH.26.196; 10.AH.26.223; 10.AH.26.240; 10.AH.26.244; 10.AH.26.243;
10.AH.26.247; 10.AH.27.157; 10.AH.27.158; 10.AH.27.196; 10.AH.27.223;
10.AH.27.240; 10.AH.27.244; 10.AH.27.243; 10.AH.27.247; 10.AH.29.157;
10.AH.29.158; 10.AH.29.196; 10.AH.29.223; 10.AH.29.240; 10.AH.29.244;
10.AH.29.243; 10.AH.29.247; 10.AH.54.157; 10.AH.54.158; 10.AH.54.196;
10.AH.54.223; 10.AH.54.240; 10.AH.54.244; 10.AH.54.243; 10.AH.54.247;
10.AH.55.157; 10.AH.55.158; 10.AH.55.196; 10.AH.55.223; 10.AH.55.240;
10.AH.55.244; 10.AH.55.243; 10.AH.55.247; 10.AH.56.157; 10.AH.56.158;
10.AH.56.196; 10.AH.56.223; 10.AH.56.240; 10.AH.56.244; 10.AH.56.243;
10.AH.56.247; 10.AH.157.157; 10.AH.157.158; 10.AH.157.196;
10.AH.157.223; 10.AH.157.240; 10.AH.157.244; 10.AH.157.243;
10.AH.157.247; 10.AH.196.157; 10.AH.196.158; 10.AH.196.196;
10.AH.196.223; 10.AH.196.240; 10.AH.196.244; 10.AH.196.243;
10.AH.196.247; 10.AH.223.157; 10.AH.223.158; 10.AH.223.196;
10.AH.223.223; 10.AH.223.240; 10.AH.223.244; 10.AH.223.243;
10.AH.223.247; 10.AH.240.157; 10.AH.240.158; 10.AH.240.196;
10.AH.240.223; 10.AH.240.240; 10.AH.240.244; 10.AH.240.243;
10.AH.240.247; 10.AH.244.157; 10.AH.244.158; 10.AH.244.196;
10.AH.244.223; 10.AH.244.240; 10.AH.244.244; 10.AH.244.243;
10.AH.244.247; 10.AH.247.157; 10.AH.247.158; 10.AH.247.196;
10.AH.247.223; 10.AH.247.240; 10.AH.247.244; 10.AH.247.243;
10.AH.247.247;

Prodrugs of 10.AJ

10.AJ.4.157; 10.AJ.4.158; 10.AJ.4.196; 10.AJ.4.223; 10.AJ.4.240;
10.AJ.4.244; 10.AJ.4.243; 10.AJ.4.247; 10.AJ.5.157; 10.AJ.5.158; 10.AJ.5.196;
10.AJ.5.223; 10.AJ.5.240; 10.AJ.5.244; 10.AJ.5.243; 10.AJ.5.247; 10.AJ.7.157;
10.AJ.7.158; 10.AJ.7.196; 10.AJ.7.223; 10.AJ.7.240; 10.AJ.7.244; 10.AJ.7.243;
10.AJ.7.247; 10.AJ.15.157; 10.AJ.15.158; 10.AJ.15.196; 10.AJ.15.223;
10.AJ.15.240; 10.AJ.15.244; 10.AJ.15.243; 10.AJ.15.247; 10.AJ.16.157;
10.AJ.16.158; 10.AJ.16.196; 10.AJ.16.223; 10.AJ.16.240; 10.AJ.16.244;
10.AJ.16.243; 10.AJ.16.247; 10.AJ.18.157; 10.AJ.18.158; 10.AJ.18.196;
10.AJ.18.223; 10.AJ.18.240; 10.AJ.18.244; 10.AJ.18.243; 10.AJ.18.247;
10.AJ.26.157; 10.AJ.26.158; 10.AJ.26.196; 10.AJ.26.223; 10.AJ.26.240;
10.AJ.26.244; 10.AJ.26.243; 10.AJ.26.247; 10.AJ.27.157; 10.AJ.27.158;
10.AJ.27.196; 10.AJ.27.223; 10.AJ.27.240; 10.AJ.27.244; 10.AJ.27.243;
10.AJ.27.247; 10.AJ.29.157; 10.AJ.29.158; 10.AJ.29.196; 10.AJ.29.223;

TABLE 100-continued

10.AJ.29.240; 10.AJ.29.244; 10.AJ.29.243; 10.AJ.29.247; 10.AJ.54.157;
10.AJ.54.158; 10.AJ.54.196; 10.AJ.54.223; 10.AJ.54.240; 10.AJ.54.244;
10.AJ.54.243; 10.AJ.54.247; 10.AJ.55.157; 10.AJ.55.158; 10.AJ.55.196;
10.AJ.55.223; 10.AJ.55.240; 10.AJ.55.244; 10.AJ.55.243; 10.AJ.55.247;
10.AJ.56.157; 10.AJ.56.158; 10.AJ.56.196; 10.AJ.56.223; 10.AJ.56.240;
10.AJ.56.244; 10.AJ.56.243; 10.AJ.56.247; 10.AJ.157.157; 10.AJ.157.158;
10.AJ.157.196; 10.AJ.157.223; 10.AJ.157.240; 10.AJ.157.244; 10.AJ.157.243;
10.AJ.157.247; 10.AJ.196.157; 10.AJ.196.158; 10.AJ.196.196; 10.AJ.196.223;
10.AJ.196.240; 10.AJ.196.244; 10.AJ.196.243; 10.AJ.196.247; 10.AJ.223.157;
10.AJ.223.158; 10.AJ.223.196; 10.AJ.223.223; 10.AJ.223.240; 10.AJ.223.244;
10.AJ.223.243; 10.AJ.223.247; 10.AJ.240.157; 10.AJ.240.158; 10.AJ.240.196;
10.AJ.240.223; 10.AJ.240.240; 10.AJ.240.244; 10.AJ.240.243; 10.AJ.240.247;
10.AJ.244.157; 10.AJ.244.158; 10.AJ.244.196; 10.AJ.244.223; 10.AJ.244.240;
10.AJ.244.244; 10.AJ.244.243; 10.AJ.244.247; 10.AJ.247.157; 10.AJ.247.158;
10.AJ.247.196; 10.AJ.247.223; 10.AJ.247.240; 10.AJ.247.244; 10.AJ.247.243;
10.AJ.247.247;

Prodrugs of 10.AN

10.AN.4.157; 10.AN.4.158; 10.AN.4.196; 10.AN.4.223; 10.AN.4.240;
10.AN.4.244; 10.AN.4.243; 10.AN.4.247; 10.AN.5.157; 10.AN.5.158;
10.AN.5.196; 10.AN.5.223; 10.AN.5.240; 10.AN.5.244; 10.AN.5.243;
10.AN.5.247; 10.AN.7.157; 10.AN.7.158; 10.AN.7.196; 10.AN.7.223;
10.AN.7.240; 10.AN.7.244; 10.AN.7.243; 10.AN.7.247; 10.AN.15.157;
10.AN.15.158; 10.AN.15.196; 10.AN.15.223; 10.AN.15.240; 10.AN.15.244;
10.AN.15.243; 10.AN.15.247; 10.AN.16.157; 10.AN.16.158; 10.AN.16.196;
10.AN.16.223; 10.AN.16.240; 10.AN.16.244; 10.AN.16.243; 10.AN.16.247;
10.AN.18.157; 10.AN.18.158; 10.AN.18.196; 10.AN.18.223; 10.AN.18.240;
10.AN.18.244; 10.AN.18.243; 10.AN.18.247; 10.AN.26.157; 10.AN.26.158;
10.AN.26.196; 10.AN.26.223; 10.AN.26.240; 10.AN.26.244; 10.AN.26.243;
10.AN.26.247; 10.AN.27.157; 10.AN.27.158; 10.AN.27.196; 10.AN.27.223;
10.AN.27.240; 10.AN.27.244; 10.AN.27.243; 10.AN.27.247; 10.AN.29.157;
10.AN.29.158; 10.AN.29.196; 10.AN.29.223; 10.AN.29.240; 10.AN.29.244;
10.AN.29.243; 10.AN.29.247; 10.AN.54.157; 10.AN.54.158; 10.AN.54.196;
10.AN.54.223; 10.AN.54.240; 10.AN.54.244; 10.AN.54.243; 10.AN.54.247;
10.AN.55.157; 10.AN.55.158; 10.AN.55.196; 10.AN.55.223; 10.AN.55.240;
10.AN.55.244; 10.AN.55.243; 10.AN.55.247; 10.AN.56.157; 10.AN.56.158;
10.AN.56.196; 10.AN.56.223; 10.AN.56.240; 10.AN.56.244; 10.AN.56.243;
10.AN.56.247; 10.AN.157.157; 10.AN.157.158; 10.AN.157.196;
10.AN.157.223; 10.AN.157.240; 10.AN.157.244; 10.AN.157.243;
10.AN.157.247; 10.AN.196.157; 10.AN.196.158; 10.AN.196.196;
10.AN.196.223; 10.AN.196.240; 10.AN.196.244; 10.AN.196.243;
10.AN.196.247; 10.AN.223.157; 10.AN.223.158; 10.AN.223.196;
10.AN.223.223; 10.AN.223.240; 10.AN.223.244; 10.AN.223.243;
10.AN.223.247; 10.AN.240.157; 10.AN.240.158; 10.AN.240.196;
10.AN.240.223; 10.AN.240.240; 10.AN.240.244; 10.AN.240.243;
10.AN.240.247; 10.AN.244.157; 10.AN.244.158; 10.AN.244.196;
10.AN.244.223; 10.AN.244.240; 10.AN.244.244; 10.AN.244.243;
10.AN.244.247; 10.AN.247.157; 10.AN.247.158; 10.AN.247.196;
10.AN.247.223; 10.AN.247.240; 10.AN.247.244; 10.AN.247.243; 10.AN.247.247;

Prodrugs of 10.AP

10.AP.4.157; 10.AP.4.158; 10.AP.4.196; 10.AP.4.223; 10.AP.4.240;
10.AP.4.244; 10.AP.4.243; 10.AP.4.247; 10.AP.5.157; 10.AP.5.158;
10.AP.5.196; 10.AP.5.223; 10.AP.5.240; 10.AP.5.244; 10.AP.5.243;
10.AP.5.247; 10.AP.7.157; 10.AP.7.158; 10.AP.7.196; 10.AP.7.223;
10.AP.7.240; 10.AP.7.244; 10.AP.7.243; 10.AP.7.247; 10.AP.15.157;
10.AP.15.158; 10.AP.15.196; 10.AP.15.223; 10.AP.15.240; 10.AP.15.244;
10.AP.15.243; 10.AP.15.247; 10.AP.16.157; 10.AP.16.158; 10.AP.16.196;
10.AP.16.223; 10.AP.16.240; 10.AP.16.244; 10.AP.16.243; 10.AP.16.247;
10.AP.18.157; 10.AP.18.158; 10.AP.18.196; 10.AP.18.223; 10.AP.18.240;
10.AP.18.244; 10.AP.18.243; 10.AP.18.247; 10.AP.26.157; 10.AP.26.158;
10.AP.26.196; 10.AP.26.223; 10.AP.26.240; 10.AP.26.244; 10.AP.26.243;
10.AP.26.247; 10.AP.27.157; 10.AP.27.158; 10.AP.27.196; 10.AP.27.223;
10.AP.27.240; 10.AP.27.244; 10.AP.27.243; 10.AP.27.247; 10.AP.29.157;
10.AP.29.158; 10.AP.29.196; 10.AP.29.223; 10.AP.29.240; 10.AP.29.244;
10.AP.29.243; 10.AP.29.247; 10.AP.54.157; 10.AP.54.158; 10.AP.54.196;
10.AP.54.223; 10.AP.54.240; 10.AP.54.244; 10.AP.54.243; 10.AP.54.247;
10.AP.55.157; 10.AP.55.158; 10.AP.55.196; 10.AP.55.223; 10.AP.55.240;
10.AP.55.244; 10.AP.55.243; 10.AP.55.247; 10.AP.56.157; 10.AP.56.158;
10.AP.56.196; 10.AP.56.223; 10.AP.56.240; 10.AP.56.244; 10.AP.56.243;
10.AP.56.247; 10.AP.157.157; 10.AP.157.158; 10.AP.157.196; 10.AP.157.223;
10.AP.157.240; 10.AP.157.244; 10.AP.157.243; 10.AP.157.247;
10.AP.196.157; 10.AP.196.158; 10.AP.196.196; 10.AP.196.223;
10.AP.196.240; 10.AP.196.244; 10.AP.196.243; 10.AP.196.247;
10.AP.223.157; 10.AP.223.158; 10.AP.223.196; 10.AP.223.223;
10.AP.223.240; 10.AP.223.244; 10.AP.223.243; 10.AP.223.247;
10.AP.240.157; 10.AP.240.158; 10.AP.240.196; 10.AP.240.223;
10.AP.240.240; 10.AP.240.244; 10.AP.240.243; 10.AP.240.247;
10.AP.244.157; 10.AP.244.158; 10.AP.244.196; 10.AP.244.223;

TABLE 100-continued

10.AP.244.240; 10.AP.244.244; 10.AP.244.243; 10.AP.244.247;
10.AP.247.157; 10.AP.247.158; 10.AP.247.196; 10.AP.247.223;
10.AP.247.240; 10.AP.247.244; 10.AP.247.243; 10.AP.247.247;

Prodrugs of 10.AZ

10.AZ.4.157; 10.AZ.4.158; 10.AZ.4.196; 10.AZ.4.223; 10.AZ.4.240;
10.AZ.4.244; 10.AZ.4.243; 10.AZ.4.247; 10.AZ.5.157; 10.AZ.5.158;
10.AZ.5.196; 10.AZ.5.223; 10.AZ.5.240; 10.AZ.5.244; 10.AZ.5.243;
10.AZ.5.247; 10.AZ.7.157; 10.AZ.7.158; 10.AZ.7.196; 10.AZ.7.223;
10.AZ.7.240; 10.AZ.7.244; 10.AZ.7.243; 10.AZ.7.247; 10.AZ.15.157;
10.AZ.15.158; 10.AZ.15.196; 10.AZ.15.223; 10.AZ.15.240; 10.AZ.15.244;
10.AZ.15.243; 10.AZ.15.247; 10.AZ.16.157; 10.AZ.16.158; 10.AZ.16.196;
10.AZ.16.223; 10.AZ.16.240; 10.AZ.16.244; 10.AZ.16.243; 10.AZ.16.247;
10.AZ.18.157; 10.AZ.18.158; 10.AZ.18.196; 10.AZ.18.223; 10.AZ.18.240;
10.AZ.18.244; 10.AZ.18.243; 10.AZ.18.247; 10.AZ.26.157; 10.AZ.26.158;
10.AZ.26.196; 10.AZ.26.223; 10.AZ.26.240; 10.AZ.26.244; 10.AZ.26.243;
10.AZ.26.247; 10.AZ.27.157; 10.AZ.27.158; 10.AZ.27.196; 10.AZ.27.223;
10.AZ.27.240; 10.AZ.27.244; 10.AZ.27.243; 10.AZ.27.247; 10.AZ.29.157;
10.AZ.29.158; 10.AZ.29.196; 10.AZ.29.223; 10.AZ.29.240; 10.AZ.29.244;
10.AZ.29.243; 10.AZ.29.247; 10.AZ.54.157; 10.AZ.54.158; 10.AZ.54.196;
10.AZ.54.223; 10.AZ.54.240; 10.AZ.54.244; 10.AZ.54.243; 10.AZ.54.247;
10.AZ.55.157; 10.AZ.55.158; 10.AZ.55.196; 10.AZ.55.223; 10.AZ.55.240;
10.AZ.55.244; 10.AZ.55.243; 10.AZ.55.247; 10.AZ.56.157; 10.AZ.56.158;
10.AZ.56.196; 10.AZ.56.223; 10.AZ.56.240; 10.AZ.56.244; 10.AZ.56.243;
10.AZ.56.247; 10.AZ.157.157; 10.AZ.157.158; 10.AZ.157.196; 10.AZ.157.223;
10.AZ.157.240; 10.AZ.157.244; 10.AZ.157.243; 10.AZ.157.247;
10.AZ.196.157; 10.AZ.196.158; 10.AZ.196.196; 10.AZ.196.223;
10.AZ.196.240; 10.AZ.196.244; 10.AZ.196.243; 10.AZ.196.247;
10.AZ.223.157; 10.AZ.223.158; 10.AZ.223.196; 10.AZ.223.223;
10.AZ.223.240; 10.AZ.223.244; 10.AZ.223.243; 10.AZ.223.247;
10.AZ.240.157; 10.AZ.240.158; 10.AZ.240.196; 10.AZ.240.223;
10.AZ.240.240; 10.AZ.240.244; 10.AZ.240.243; 10.AZ.240.247;
10.AZ.244.157; 10.AZ.244.158; 10.AZ.244.196; 10.AZ.244.223;
10.AZ.244.240; 10.AZ.244.244; 10.AZ.244.243; 10.AZ.244.247;
10.AZ.247.157; 10.AZ.247.158; 10.AZ.247.196; 10.AZ.247.223;
10.AZ.247.240; 10.AZ.247.244; 10.AZ.247.243; 10.AZ.247.247;

Prodrugs of 10.BF

10.BF.4.157; 10.BF.4.158; 10.BF.4.196; 10.BF.4.223; 10.BF.4.240;
10.BF.4.244; 10.BF.4.243; 10.BF.4.247; 10.BF.5.157; 10.BF.5.158;
10.BF.5.196; 10.BF.5.223; 10.BF.5.240; 10.BF.5.244; 10.BF.5.243;
10.BF.5.247; 10.BF.7.157; 10.BF.7.158; 10.BF.7.196; 10.BF.7.223;
10.BF.7.240; 10.BF.7.244; 10.BF.7.243; 10.BF.7.247; 10.BF.15.157;
10.BF.15.158; 10.BF.15.196; 10.BF.15.223; 10.BF.15.240; 10.BF.15.244;
10.BF.15.243; 10.BF.15.247; 10.BF.16.157; 10.BF.16.158; 10.BF.16.196;
10.BF.16.223; 10.BF.16.240; 10.BF.16.244; 10.BF.16.243; 10.BF.16.247;
10.BF.18.157; 10.BF.18.158; 10.BF.18.196; 10.BF.18.223; 10.BF.18.240;
10.BF.18.244; 10.BF.18.243; 10.BF.18.247; 10.BF.26.157; 10.BF.26.158;
10.BF.26.196; 10.BF.26.223; 10.BF.26.240; 10.BF.26.244; 10.BF.26.243;
10.BF.26.247; 10.BF.27.157; 10.BF.27.158; 10.BF.27.196; 10.BF.27.223;
10.BF.27.240; 10.BF.27.244; 10.BF.27.243; 10.BF.27.247; 10.BF.29.157;
10.BF.29.158; 10.BF.29.196; 10.BF.29.223; 10.BF.29.240; 10.BF.29.244;
10.BF.29.243; 10.BF.29.247; 10.BF.54.157; 10.BF.54.158; 10.BF.54.196;
10.BF.54.223; 10.BF.54.240; 10.BF.54.244; 10.BF.54.243; 10.BF.54.247;
10.BF.55.157; 10.BF.55.158; 10.BF.55.196; 10.BF.55.223; 10.BF.55.240;
10.BF.55.244; 10.BF.55.243; 10.BF.55.247; 10.BF.56.157; 10.BF.56.158;
10.BF.56.196; 10.BF.56.223; 10.BF.56.240; 10.BF.56.244; 10.BF.56.243;
10.BF.56.247; 10.BF.157.157; 10.BF.157.158; 10.BF.157.196; 10.BF.157.223;
10.BF.157.240; 10.BF.157.244; 10.BF.157.243; 10.BF.157.247; 10.BF.196.157;
10.BF.196.158; 10.BF.196.196; 10.BF.196.223; 10.BF.196.240; 10.BF.196.244;
10.BF.196.243; 10.BF.196.247; 10.BF.223.157; 10.BF.223.158; 10.BF.223.196;
10.BF.223.223; 10.BF.223.240; 10.BF.223.244; 10.BF.223.243; 10.BF.223.247;
10.BF.240.157; 10.BF.240.158; 10.BF.240.196; 10.BF.240.223; 10.BF.240.240;
10.BF.240.244; 10.BF.240.243; 10.BF.240.247; 10.BF.244.157; 10.BF.244.158;
10.BF.244.196; 10.BF.244.223; 10.BF.244.240; 10.BF.244.244; 10.BF.244.243;
10.BF.244.247; 10.BF.247.157; 10.BF.247.158; 10.BF.247.196; 10.BF.247.223;
10.BF.247.240; 10.BF.247.244; 10.BF.247.243; 10.BF.247.247;

Prodrugs of 10.CI

10.CI.4.157; 10.CI.4.158; 10.CI.4.196; 10.CI.4.223; 10.CI.4.240;
10.CI.4.244; 10.CI.4.243; 10.CI.4.247; 10.CI.5.157; 10.CI.5.158; 10.CI.5.196;
10.CI.5.223; 10.CI.5.240; 10.CI.5.244; 10.CI.5.243; 10.CI.5.247; 10.CI.7.157;
10.CI.7.158; 10.CI.7.196; 10.CI.7.223; 10.CI.7.240; 10.CI.7.244; 10.CI.7.243;
10.CI.7.247; 10.CI.15.157; 10.CI.15.158; 10.CI.15.196; 10.CI.15.223;
10.CI.15.240; 10.CI.15.244; 10.CI.15.243; 10.CI.15.247; 10.CI.16.157;
10.CI.16.158; 10.CI.16.196; 10.CI.16.223; 10.CI.16.240; 10.CI.16.244;
10.CI.16.243; 10.CI.16.247; 10.CI.18.157; 10.CI.18.158; 10.CI.18.196;
10.CI.18.223; 10.CI.18.240; 10.CI.18.244; 10.CI.18.243; 10.CI.18.247;
10.CI.26.157; 10.CI.26.158; 10.CI.26.196; 10.CI.26.223; 10.CI.26.240;

TABLE 100-continued

10.CI.26.244; 10.CI.26.243; 10.CI.26.247; 10.CI.27.157; 10.CI.27.158;
10.CI.27.196; 10.CI.27.223; 10.CI.27.240; 10.CI.27.244; 10.CI.27.243;
10.CI.27.247; 10.CI.29.157; 10.CI.29.158; 10.CI.29.196; 10.CI.29.223;
10.CI.29.240; 10.CI.29.244; 10.CI.29.243; 10.CI.29.247; 10.CI.54.157;
10.CI.54.158; 10.CI.54.196; 10.CI.54.223; 10.CI.54.240; 10.CI.54.244;
10.CI.54.243; 10.CI.54.247; 10.CI.55.157; 10.CI.55.158; 10.CI.55.196;
10.CI.55.223; 10.CI.55.240; 10.CI.55.244; 10.CI.55.243; 10.CI.55.247;
10.CI.56.157; 10.CI.56.158; 10.CI.56.196; 10.CI.56.223; 10.CI.56.240;
10.CI.56.244; 10.CI.56.243; 10.CI.56.247; 10.CI.157.157; 10.CI.157.158;
10.CI.157.196; 10.CI.157.223; 10.CI.157.240; 10.CI.157.244; 10.CI.157.243;
10.CI.157.247; 10.CI.196.157; 10.CI.196.158; 10.CI.196.196; 10.CI.196.223;
10.CI.196.240; 10.CI.196.244; 10.CI.196.243; 10.CI.196.247; 10.CI.223.157;
10.CI.223.158; 10.CI.223.196; 10.CI.223.223; 10.CI.223.240; 10.CI.223.244;
10.CI.223.243; 10.CI.223.247; 10.CI.240.157; 10.CI.240.158; 10.CI.240.196;
10.CI.240.223; 10.CI.240.240; 10.CI.240.244; 10.CI.240.243; 10.CI.240.247;
10.CI.244.157; 10.CI.244.158; 10.CI.244.196; 10.CI.244.223; 10.CI.244.240;
10.CI.244.244; 10.CI.244.243; 10.CI.244.247; 10.CI.247.157; 10.CI.247.158;
10.CI.247.196; 10.CI.247.223; 10.CI.247.240; 10.CI.247.244; 10.CI.247.243;
10.CI.247.247;
Prodrugs of 10.CO 10.CO.4.157; 10.CO.4.158; 10.CO.4.196; 10.CO.4.223; 10.CO.4.240;
10.CO.4.244; 10.CO.4.243; 10.CO.4.247; 10.CO.5.157; 10.CO.5.158;
10.CO.5.196; 10.CO.5.223; 10.CO.5.240; 10.CO.5.244; 10.CO.5.243;
10.CO.5.247; 10.CO.7.157; 10.CO.7.158; 10.CO.7.196; 10.CO.7.223;
10.CO.7.240; 10.CO.7.244; 10.CO.7.243; 10.CO.7.247; 10.CO.15.157;
10.CO.15.158; 10.CO.15.196; 10.CO.15.223; 10.CO.15.240; 10.CO.15.244;
10.CO.15.243; 10.CO.15.247; 10.CO.16.157; 10.CO.16.158; 10.CO.16.196;
10.CO.16.223; 10.CO.16.240; 10.CO.16.244; 10.CO.16.243; 10.CO.16.247;
10.CO.18.157; 10.CO.18.158; 10.CO.18.196; 10.CO.18.223; 10.CO.18.240;
10.CO.18.244; 10.CO.18.243; 10.CO.18.247; 10.CO.26.157; 10.CO.26.158;
10.CO.26.196; 10.CO.26.223; 10.CO.26.240; 10.CO.26.244; 10.CO.26.243;
10.CO.26.247; 10.CO.27.157; 10.CO.27.158; 10.CO.27.196; 10.CO.27.223;
10.CO.27.240; 10.CO.27.244; 10.CO.27.243; 10.CO.27.247; 10.CO.29.157;
10.CO.29.158; 10.CO.29.196; 10.CO.29.223; 10.CO.29.240; 10.CO.29.244;
10.CO.29.243; 10.CO.29.247; 10.CO.54.157; 10.CO.54.158; 10.CO.54.196;
10.CO.54.223; 10.CO.54.240; 10.CO.54.244; 10.CO.54.243; 10.CO.54.247;
10.CO.55.157; 10.CO.55.158; 10.CO.55.196; 10.CO.55.223; 10.CO.55.240;
10.CO.55.244; 10.CO.55.243; 10.CO.55.247; 10.CO.56.157; 10.CO.56.158;
10.CO.56.196; 10.CO.56.223; 10.CO.56.240; 10.CO.56.244; 10.CO.56.243;
10.CO.56.247; 10.CO.157.157; 10.CO.157.158; 10.CO.157.196;
10.CO.157.223; 10.CO.157.240; 10.CO.157.244; 10.CO.157.243;
10.CO.157.247; 10.CO.196.157; 10.CO.196.158; 10.CO.196.196;
10.CO.196.223; 10.CO.196.240; 10.CO.196.244; 10.CO.196.243;
10.CO.196.247; 10.CO.223.157; 10.CO.223.158; 10.CO.223.196;
10.CO.223.223; 10.CO.223.240; 10.CO.223.244; 10.CO.223.243;
10.CO.223.247; 10.CO.240.157; 10.CO.240.158; 10.CO.240.196;
10.CO.240.223; 10.CO.240.240; 10.CO.240.244; 10.CO.240.243;
10.CO.240.247; 10.CO.244.157; 10.CO.244.158; 10.CO.244.196;
10.CO.244.223; 10.CO.244.240; 10.CO.244.244; 10.CO.244.243;
10.CO.244.247; 10.CO.247.157; 10.CO.247.158; 10.CO.247.196;
10.CO.247.223; 10.CO.247.240; 10.CO.247.244; 10.CO.247.243; 10.CO.247.247;
Prodrugs of 11.AH 11.AH.4.157; 11.AH.4.158; 11.AH.4.196; 11.AH.4.223; 11.AH.4.240;
11.AH.4.244; 11.AH.4.243; 11.AH.4.247; 11.AH.5.157; 11.AH.5.158;
11.AH.5.196; 11.AH.5.223; 11.AH.5.240; 11.AH.5.244; 11.AH.5.243;
11.AH.5.247; 11.AH.7.157; 11.AH.7.158; 11.AH.7.196; 11.AH.7.223;
11.AH.7.240; 11.AH.7.244; 11.AH.7.243; 11.AH.7.247; 11.AH.15.157;
11.AH.15.158; 11.AH.15.196; 11.AH.15.223; 11.AH.15.240; 11.AH.15.244;
11.AH.15.243; 11.AH.15.247; 11.AH.16.157; 11.AH.16.158; 11.AH.16.196;
11.AH.16.223; 11.AH.16.240; 11.AH.16.244; 11.AH.16.243; 11.AH.16.247;
11.AH.18.157; 11.AH.18.158; 11.AH.18.196; 11.AH.18.223; 11.AH.18.240;
11.AH.18.244; 11.AH.18.243; 11.AH.18.247; 11.AH.26.157; 11.AH.26.158;
11.AH.26.196; 11.AH.26.223; 11.AH.26.240; 11.AH.26.244; 11.AH.26.243;
11.AH.26.247; 11.AH.27.157; 11.AH.27.158; 11.AH.27.196; 11.AH.27.223;
11.AH.27.240; 11.AH.27.244; 11.AH.27.243; 11.AH.27.247; 11.AH.29.157;
11.AH.29.158; 11.AH.29.196; 11.AH.29.223; 11.AH.29.240; 11.AH.29.244;
11.AH.29.243; 11.AH.29.247; 11.AH.54.157; 11.AH.54.158; 11.AH.54.196;
11.AH.54.223; 11.AH.54.240; 11.AH.54.244; 11.AH.54.243; 11.AH.54.247;
11.AH.55.157; 11.AH.55.158; 11.AH.55.196; 11.AH.55.223; 11.AH.55.240;
11.AH.55.244; 11.AH.55.243; 11.AH.55.247; 11.AH.56.157; 11.AH.56.158;
11.AH.56.196; 11.AH.56.223; 11.AH.56.240; 11.AH.56.244; 11.AH.56.243;
11.AH.56.247; 11.AH.157.157; 11.AH.157.158; 11.AH.157.196;
11.AH.157.223; 11.AH.157.240; 11.AH.157.244; 11.AH.157.243;
11.AH.157.247; 11.AH.196.157; 11.AH.196.158; 11.AH.196.196;
11.AH.196.223; 11.AH.196.240; 11.AH.196.244; 11.AH.196.243;
11.AH.196.247; 11.AH.223.157; 11.AH.223.158; 11.AH.223.196;
11.AH.223.223; 11.AH.223.240; 11.AH.223.244; 11.AH.223.243;

TABLE 100-continued

11.AH.223.247; 11.AH.240.157; 11.AH.240.158; 11.AH.240.196;
11.AH.240.223; 11.AH.240.240; 11.AH.240.244; 11.AH.240.243;
11.AH.240.247; 11.AH.244.157; 11.AH.244.158; 11.AH.244.196;
11.AH.244.223; 11.AH.244.240; 11.AH.244.244; 11.AH.244.243;
11.AH.244.247; 11.AH.247.157; 11.AH.247.158; 11.AH.247.196;
11.AH.247.223; 11.AH.247.240; 11.AH.247.244; 11.AH.247.243;
11.AH.247.247;

Prodrugs of 11.AJ

11.AJ.4.157; 11.AJ.4.158; 11.AJ.4.196; 11.AJ.4.223; 11.AJ.4.240;
11.AJ.4.244; 11.AJ.4.243; 11.AJ.4.247; 11.AJ.5.157; 11.AJ.5.158; 11.AJ.5.196;
11.AJ.5.223; 11.AJ.5.240; 11.AJ.5.244; 11.AJ.5.243; 11.AJ.5.247; 11.AJ.7.157;
11.AJ.7.158; 11.AJ.7.196; 11.AJ.7.223; 11.AJ.7.240; 11.AJ.7.244; 11.AJ.7.243;
11.AJ.7.247; 11.AJ.15.157; 11.AJ.15.158; 11.AJ.15.196; 11.AJ.15.223;
11.AJ.15.240; 11.AJ.15.244; 11.AJ.15.243; 11.AJ.15.247; 11.AJ.16.157;
11.AJ.16.158; 11.AJ.16.196; 11.AJ.16.223; 11.AJ.16.240; 11.AJ.16.244;
11.AJ.16.243; 11.AJ.16.247; 11.AJ.18.157; 11.AJ.18.158; 11.AJ.18.196;
11.AJ.18.223; 11.AJ.18.240; 11.AJ.18.244; 11.AJ.18.243; 11.AJ.18.247;
11.AJ.26.157; 11.AJ.26.158; 11.AJ.26.196; 11.AJ.26.223; 11.AJ.26.240;
11.AJ.26.244; 11.AJ.26.243; 11.AJ.26.247; 11.AJ.27.157; 11.AJ.27.158;
11.AJ.27.196; 11.AJ.27.223; 11.AJ.27.240; 11.AJ.27.244; 11.AJ.27.243;
11.AJ.27.247; 11.AJ.29.157; 11.AJ.29.158; 11.AJ.29.196; 11.AJ.29.223;
11.AJ.29.240; 11.AJ.29.244; 11.AJ.29.243; 11.AJ.29.247; 11.AJ.54.157;
11.AJ.54.158; 11.AJ.54.196; 11.AJ.54.223; 11.AJ.54.240; 11.AJ.54.244;
11.AJ.54.243; 11.AJ.54.247; 11.AJ.55.157; 11.AJ.55.158; 11.AJ.55.196;
11.AJ.55.223; 11.AJ.55.240; 11.AJ.55.244; 11.AJ.55.243; 11.AJ.55.247;
11.AJ.56.157; 11.AJ.56.158; 11.AJ.56.196; 11.AJ.56.223; 11.AJ.56.240;
11.AJ.56.244; 11.AJ.56.243; 11.AJ.56.247; 11.AJ.157.157; 11.AJ.157.158;
11.AJ.157.196; 11.AJ.157.223; 11.AJ.157.240; 11.AJ.157.244; 11.AJ.157.243;
11.AJ.157.247; 11.AJ.196.157; 11.AJ.196.158; 11.AJ.196.196; 11.AJ.196.223;
11.AJ.196.240; 11.AJ.196.244; 11.AJ.196.243; 11.AJ.196.247; 11.AJ.223.157;
11.AJ.223.158; 11.AJ.223.196; 11.AJ.223.223; 11.AJ.223.240; 11.AJ.223.244;
11.AJ.223.243; 11.AJ.223.247; 11.AJ.240.157; 11.AJ.240.158; 11.AJ.240.196;
11.AJ.240.223; 11.AJ.240.240; 11.AJ.240.244; 11.AJ.240.243; 11.AJ.240.247;
11.AJ.244.157; 11.AJ.244.158; 11.AJ.244.196; 11.AJ.244.223; 11.AJ.244.240;
11.AJ.244.244; 11.AJ.244.243; 11.AJ.244.247; 11.AJ.247.157; 11.AJ.247.158;
11.AJ.247.196; 11.AJ.247.223; 11.AJ.247.240; 11.AJ.247.244; 11.AJ.247.243; 11.AJ.247.247;

Prodrugs of 11.AN

11.AN.4.157; 11.AN.4.158; 11.AN.4.196; 11.AN.4.223; 11.AN.4.240;
11.AN.4.244; 11.AN.4.243; 11.AN.4.247; 11.AN.5.157; 11.AN.5.158;
11.AN.5.196; 11.AN.5.223; 11.AN.5.240; 11.AN.5.244; 11.AN.5.243;
11.AN.5.247; 11.AN.7.157; 11.AN.7.158; 11.AN.7.196; 11.AN.7.223;
11.AN.7.240; 11.AN.7.244; 11.AN.7.243; 11.AN.7.247; 11.AN.15.157;
11.AN.15.158; 11.AN.15.196; 11.AN.15.223; 11.AN.15.240; 11.AN.15.244;
11.AN.15.243; 11.AN.15.247; 11.AN.16.157; 11.AN.16.158; 11.AN.16.196;
11.AN.16.223; 11.AN.16.240; 11.AN.16.244; 11.AN.16.243; 11.AN.16.247;
11.AN.18.157; 11.AN.18.158; 11.AN.18.196; 11.AN.18.223; 11.AN.18.240;
11.AN.18.244; 11.AN.18.243; 11.AN.18.247; 11.AN.26.157; 11.AN.26.158;
11.AN.26.196; 11.AN.26.223; 11.AN.26.240; 11.AN.26.244; 11.AN.26.243;
11.AN.26.247; 11.AN.27.157; 11.AN.27.158; 11.AN.27.196; 11.AN.27.223;
11.AN.27.240; 11.AN.27.244; 11.AN.27.243; 11.AN.27.247; 11.AN.29.157;
11.AN.29.158; 11.AN.29.196; 11.AN.29.223; 11.AN.29.240; 11.AN.29.244;
11.AN.29.243; 11.AN.29.247; 11.AN.54.157; 11.AN.54.158; 11.AN.54.196;
11.AN.54.223; 11.AN.54.240; 11.AN.54.244; 11.AN.54.243; 11.AN.54.247;
11.AN.55.157; 11.AN.55.158; 11.AN.55.196; 11.AN.55.223; 11.AN.55.240;
11.AN.55.244; 11.AN.55.243; 11.AN.55.247; 11.AN.56.157; 11.AN.56.158;
11.AN.56.196; 11.AN.56.223; 11.AN.56.240; 11.AN.56.244; 11.AN.56.243;
11.AN.56.247; 11.AN.157.157; 11.AN.157.158; 11.AN.157.196;
11.AN.157.223; 11.AN.157.240; 11.AN.157.244; 11.AN.157.243;
11.AN.157.247; 11.AN.196.157; 11.AN.196.158; 11.AN.196.196;
11.AN.196.223; 11.AN.196.240; 11.AN.196.244; 11.AN.196.243;
11.AN.196.247; 11.AN.223.157; 11.AN.223.158; 11.AN.223.196;
11.AN.223.223; 11.AN.223.240; 11.AN.223.244; 11.AN.223.243;
11.AN.223.247; 11.AN.240.157; 11.AN.240.158; 11.AN.240.196;
11.AN.240.223; 11.AN.240.240; 11.AN.240.244; 11.AN.240.243;
11.AN.240.247; 11.AN.244.157; 11.AN.244.158; 11.AN.244.196;
11.AN.244.223; 11.AN.244.240; 11.AN.244.244; 11.AN.244.243;
11.AN.244.247; 11.AN.247.157; 11.AN.247.158; 11.AN.247.196;
11.AN.247.223; 11.AN.247.240; 11.AN.247.244; 11.AN.247.243;
11.AN.247.247;

Prodrugs of 11.AP

11.AP.4.157; 11.AP.4.158; 11.AP.4.196; 11.AP.4.223; 11.AP.4.240;
11.AP.4.244; 11.AP.4.243; 11.AP.4.247; 11.AP.5.157; 11.AP.5.158;
11.AP.5.196; 11.AP.5.223; 11.AP.5.240; 11.AP.5.244; 11.AP.5.243;
11.AP.5.247; 11.AP.7.157; 11.AP.7.158; 11.AP.7.196; 11.AP.7.223;
11.AP.7.240; 11.AP.7.244; 11.AP.7.243; 11.AP.7.247; 11.AP.15.157;
11.AP.15.158; 11.AP.15.196; 11.AP.15.223; 11.AP.15.240; 11.AP.15.244;

TABLE 100-continued

11.AP.15.243; 11.AP.15.247; 11.AP.16.157; 11.AP.16.158; 11.AP.16.196;
11.AP.16.223; 11.AP.16.240; 11.AP.16.244; 11.AP.16.243; 11.AP.16.247;
11.AP.18.157; 11.AP.18.158; 11.AP.18.196; 11.AP.18.223; 11.AP.18.240;
11.AP.18.244; 11.AP.18.243; 11.AP.18.247; 11.AP.26.157; 11.AP.26.158;
11.AP.26.196; 11.AP.26.223; 11.AP.26.240; 11.AP.26.244; 11.AP.26.243;
11.AP.26.247; 11.AP.27.157; 11.AP.27.158; 11.AP.27.196; 11.AP.27.223;
11.AP.27.240; 11.AP.27.244; 11.AP.27.243; 11.AP.27.247; 11.AP.29.157;
11.AP.29.158; 11.AP.29.196; 11.AP.29.223; 11.AP.29.240; 11.AP.29.244;
11.AP.29.243; 11.AP.29.247; 11.AP.54.157; 11.AP.54.158; 11.AP.54.196;
11.AP.54.223; 11.AP.54.240; 11.AP.54.244; 11.AP.54.243; 11.AP.54.247;
11.AP.55.157; 11.AP.55.158; 11.AP.55.196; 11.AP.55.223; 11.AP.55.240;
11.AP.55.244; 11.AP.55.243; 11.AP.55.247; 11.AP.56.157; 11.AP.56.158;
11.AP.56.196; 11.AP.56.223; 11.AP.56.240; 11.AP.56.244; 11.AP.56.243;
11.AP.56.247; 11.AP.157.157; 11.AP.157.158; 11.AP.157.196; 11.AP.157.223;
11.AP.157.240; 11.AP.157.244; 11.AP.157.243; 11.AP.157.247;
11.AP.196.157; 11.AP.196.158; 11.AP.196.196; 11.AP.196.223;
11.AP.196.240; 11.AP.196.244; 11.AP.196.243; 11.AP.196.247;
11.AP.223.157; 11.AP.223.158; 11.AP.223.196; 11.AP.223.223;
11.AP.223.240; 11.AP.223.244; 11.AP.223.243; 11.AP.223.247;
11.AP.240.157; 11.AP.240.158; 11.AP.240.196; 11.AP.240.223;
11.AP.240.240; 11.AP.240.244; 11.AP.240.243; 11.AP.240.247;
11.AP.244.157; 11.AP.244.158; 11.AP.244.196; 11.AP.244.223;
11.AP.244.240; 11.AP.244.244; 11.AP.244.243; 11.AP.244.247;
11.AP.247.157; 11.AP.247.158; 11.AP.247.196; 11.AP.247.223;
11.AP.247.240; 11.AP.247.244; 11.AP.247.243; 11.AP.247.247;
Prodrugs of 11.AZ 11.AZ.4.157; 11.AZ.4.158; 11.AZ.4.196; 11.AZ.4.223; 11.AZ.4.240;
11.AZ.4.244; 11.AZ.4.243; 11.AZ.4.247; 11.AZ.5.157; 11.AZ.5.158;
11.AZ.5.196; 11.AZ.5.223; 11.AZ.5.240; 11.AZ.5.244; 11.AZ.5.243;
11.AZ.5.247; 11.AZ.7.157; 11.AZ.7.158; 11.AZ.7.196; 11.AZ.7.223;
11.AZ.7.240; 11.AZ.7.244; 11.AZ.7.243; 11.AZ.7.247; 11.AZ.15.157;
11.AZ.15.158; 11.AZ.15.196; 11.AZ.15.223; 11.AZ.15.240; 11.AZ.15.244;
11.AZ.15.243; 11.AZ.15.247; 11.AZ.16.157; 11.AZ.16.158; 11.AZ.16.196;
11.AZ.16.223; 11.AZ.16.240; 11.AZ.16.244; 11.AZ.16.243; 11.AZ.16.247;
11.AZ.18.157; 11.AZ.18.158; 11.AZ.18.196; 11.AZ.18.223; 11.AZ.18.240;
11.AZ.18.244; 11.AZ.18.243; 11.AZ.18.247; 11.AZ.26.157; 11.AZ.26.158;
11.AZ.26.196; 11.AZ.26.223; 11.AZ.26.240; 11.AZ.26.244; 11.AZ.26.243;
11.AZ.26.247; 11.AZ.27.157; 11.AZ.27.158; 11.AZ.27.196; 11.AZ.27.223;
11.AZ.27.240; 11.AZ.27.244; 11.AZ.27.243; 11.AZ.27.247; 11.AZ.29.157;
11.AZ.29.158; 11.AZ.29.196; 11.AZ.29.223; 11.AZ.29.240; 11.AZ.29.244;
11.AZ.29.243; 11.AZ.29.247; 11.AZ.54.157; 11.AZ.54.158; 11.AZ.54.196;
11.AZ.54.223; 11.AZ.54.240; 11.AZ.54.244; 11.AZ.54.243; 11.AZ.54.247;
11.AZ.55.157; 11.AZ.55.158; 11.AZ.55.196; 11.AZ.55.223; 11.AZ.55.240;
11.AZ.55.244; 11.AZ.55.243; 11.AZ.55.247; 11.AZ.56.157; 11.AZ.56.158;
11.AZ.56.196; 11.AZ.56.223; 11.AZ.56.240; 11.AZ.56.244; 11.AZ.56.243;
11.AZ.56.247; 11.AZ.157.157; 11.AZ.157.158; 11.AZ.157.196; 11.AZ.157.223;
11.AZ.157.240; 11.AZ.157.244; 11.AZ.157.243; 11.AZ.157.247;
11.AZ.196.157; 11.AZ.196.158; 11.AZ.196.196; 11.AZ.196.223;
11.AZ.196.240; 11.AZ.196.244; 11.AZ.196.243; 11.AZ.196.247;
11.AZ.223.157; 11.AZ.223.158; 11.AZ.223.196; 11.AZ.223.223;
11.AZ.223.240; 11.AZ.223.244; 11.AZ.223.243; 11.AZ.223.247;
11.AZ.240.157; 11.AZ.240.158; 11.AZ.240.196; 11.AZ.240.223;
11.AZ.240.240; 11.AZ.240.244; 11.AZ.240.243; 11.AZ.240.247;
11.AZ.244.157; 11.AZ.244.158; 11.AZ.244.196; 11.AZ.244.223;
11.AZ.244.240; 11.AZ.244.244; 11.AZ.244.243; 11.AZ.244.247;
11.AZ.247.157; 11.AZ.247.158; 11.AZ.247.196; 11.AZ.247.223;
11.AZ.247.240; 11.AZ.247.244; 11.AZ.247.243; 11.AZ.247.247;
Prodrugs of 11.BF 11.BF.4.157; 11.BF.4.158; 11.BF.4.196; 11.BF.4.223; 11.BF.4.240;
11.BF.4.244; 11.BF.4.243; 11.BF.4.247; 11.BF.5.157; 11.BF.5.158;
11.BF.5.196; 11.BF.5.223; 11.BF.5.240; 11.BF.5.244; 11.BF.5.243;
11.BF.5.247; 11.BF.7.157; 11.BF.7.158; 11.BF.7.196; 11.BF.7.223;
11.BF.7.240; 11.BF.7.244; 11.BF.7.243; 11.BF.7.247; 11.BF.15.157;
11.BF.15.158; 11.BF.15.196; 11.BF.15.223; 11.BF.15.240; 11.BF.15.244;
11.BF.15.243; 11.BF.15.247; 11.BF.16.157; 11.BF.16.158; 11.BF.16.196;
11.BF.16.223; 11.BF.16.240; 11.BF.16.244; 11.BF.16.243; 11.BF.16.247;
11.BF.18.157; 11.BF.18.158; 11.BF.18.196; 11.BF.18.223; 11.BF.18.240;
11.BF.18.244; 11.BF.18.243; 11.BF.18.247; 11.BF.26.157; 11.BF.26.158;
11.BF.26.196; 11.BF.26.223; 11.BF.26.240; 11.BF.26.244; 11.BF.26.243;
11.BF.26.247; 11.BF.27.157; 11.BF.27.158; 11.BF.27.196; 11.BF.27.223;
11.BF.27.240; 11.BF.27.244; 11.BF.27.243; 11.BF.27.247; 11.BF.29.157;
11.BF.29.158; 11.BF.29.196; 11.BF.29.223; 11.BF.29.240; 11.BF.29.244;
11.BF.29.243; 11.BF.29.247; 11.BF.54.157; 11.BF.54.158; 11.BF.54.196;
11.BF.54.223; 11.BF.54.240; 11.BF.54.244; 11.BF.54.243; 11.BF.54.247;
11.BF.55.157; 11.BF.55.158; 11.BF.55.196; 11.BF.55.223; 11.BF.55.240;
11.BF.55.244; 11.BF.55.243; 11.BF.55.247; 11.BF.56.157; 11.BF.56.158;
11.BF.56.196; 11.BF.56.223; 11.BF.56.240; 11.BF.56.244; 11.BF.56.243;

TABLE 100-continued

11.BF.56.247; 11.BF.157.157; 11.BF.157.158; 11.BF.157.196; 11.BF.157.223;
11.BF.157.240; 11.BF.157.244; 11.BF.157.243; 11.BF.157.247; 11.BF.196.157;
11.BF.196.158; 11.BF.196.196; 11.BF.196.223; 11.BF.196.240; 11.BF.196.244;
11.BF.196.243; 11.BF.196.247; 11.BF.223.157; 11.BF.223.158; 11.BF.223.196;
11.BF.223.223; 11.BF.223.240; 11.BF.223.244; 11.BF.223.243; 11.BF.223.247;
11.BF.240.157; 11.BF.240.158; 11.BF.240.196; 11.BF.240.223; 11.BF.240.240;
11.BF.240.244; 11.BF.240.243; 11.BF.240.247; 11.BF.244.157; 11.BF.244.158;
11.BF.244.196; 11.BF.244.223; 11.BF.244.240; 11.BF.244.244; 11.BF.244.243;
11.BF.244.247; 11.BF.247.157; 11.BF.247.158; 11.BF.247.196; 11.BF.247.223;
11.BF.247.240; 11.BF.247.244; 11.BF.247.243; 11.BF.247.247;
Prodrugs of 11.CI 11.CI.4.157; 11.CI.4.158; 11.CI.4.196; 11.CI.4.223; 11.CI.4.240;
11.CI.4.244; 11.CI.4.243; 11.CI.4.247; 11.CI.5.157; 11.CI.5.158; 11.CI.5.196;
11.CI.5.223; 11.CI.5.240; 11.CI.5.244; 11.CI.5.243; 11.CI.5.247; 11.CI.7.157;
11.CI.7.158; 11.CI.7.196; 11.CI.7.223; 11.CI.7.240; 11.CI.7.244; 11.CI.7.243;
11.CI.7.247; 11.CI.15.157; 11.CI.15.158; 11.CI.15.196; 11.CI.15.223;
11.CI.15.240; 11.CI.15.244; 11.CI.15.243; 11.CI.15.247; 11.CI.16.157;
11.CI.16.158; 11.CI.16.196; 11.CI.16.223; 11.CI.16.240; 11.CI.16.244;
11.CI.16.243; 11.CI.16.247; 11.CI.18.157; 11.CI.18.158; 11.CI.18.196;
11.CI.18.223; 11.CI.18.240; 11.CI.18.244; 11.CI.18.243; 11.CI.18.247;
11.CI.26.157; 11.CI.26.158; 11.CI.26.196; 11.CI.26.223; 11.CI.26.240;
11.CI.26.244; 11.CI.26.243; 11.CI.26.247; 11.CI.27.157; 11.CI.27.158;
11.CI.27.196; 11.CI.27.223; 11.CI.27.240; 11.CI.27.244; 11.CI.27.243;
11.CI.27.247; 11.CI.29.157; 11.CI.29.158; 11.CI.29.196; 11.CI.29.223;
11.CI.29.240; 11.CI.29.244; 11.CI.29.243; 11.CI.29.247; 11.CI.54.157;
11.CI.54.158; 11.CI.54.196; 11.CI.54.223; 11.CI.54.240; 11.CI.54.244;
11.CI.54.243; 11.CI.54.247; 11.CI.55.157; 11.CI.55.158; 11.CI.55.196;
11.CI.55.223; 11.CI.55.240; 11.CI.55.244; 11.CI.55.243; 11.CI.55.247;
11.CI.56.157; 11.CI.56.158; 11.CI.56.196; 11.CI.56.223; 11.CI.56.240;
11.CI.56.244; 11.CI.56.243; 11.CI.56.247; 11.CI.157.157; 11.CI.157.158;
11.CI.157.196; 11.CI.157.223; 11.CI.157.240; 11.CI.157.244; 11.CI.157.243;
11.CI.157.247; 11.CI.196.157; 11.CI.196.158; 11.CI.196.196; 11.CI.196.223;
11.CI.196.240; 11.CI.196.244; 11.CI.196.243; 11.CI.196.247; 11.CI.223.157;
11.CI.223.158; 11.CI.223.196; 11.CI.223.223; 11.CI.223.240; 11.CI.223.244;
11.CI.223.243; 11.CI.223.247; 11.CI.240.157; 11.CI.240.158; 11.CI.240.196;
11.CI.240.223; 11.CI.240.240; 11.CI.240.244; 11.CI.240.243; 11.CI.240.247;
11.CI.244.157; 11.CI.244.158; 11.CI.244.196; 11.CI.244.223; 11.CI.244.240;
11.CI.244.244; 11.CI.244.243; 11.CI.244.247; 11.CI.247.157; 11.CI.247.158;
11.CI.247.196; 11.CI.247.223; 11.CI.247.240; 11.CI.247.244; 11.CI.247.243;
11.CI.247.247;
Prodrugs of 11.CO 11.CO.4.157; 11.CO.4.158; 11.CO.4.196; 11.CO.4.223; 11.CO.4.240;
11.CO.4.244; 11.CO.4.243; 11.CO.4.247; 11.CO.5.157; 11.CO.5.158;
11.CO.5.196; 11.CO.5.223; 11.CO.5.240; 11.CO.5.244; 11.CO.5.243;
11.CO.5.247; 11.CO.7.157; 11.CO.7.158; 11.CO.7.196; 11.CO.7.223;
11.CO.7.240; 11.CO.7.244; 11.CO.7.243; 11.CO.7.247; 11.CO.15.157;
11.CO.15.158; 11.CO.15.196; 11.CO.15.223; 11.CO.15.240; 11.CO.15.244;
11.CO.15.243; 11.CO.15.247; 11.CO.16.157; 11.CO.16.158; 11.CO.16.196;
11.CO.16.223; 11.CO.16.240; 11.CO.16.244; 11.CO.16.243; 11.CO.16.247;
11.CO.18.157; 11.CO.18.158; 11.CO.18.196; 11.CO.18.223; 11.CO.18.240;
11.CO.18.244; 11.CO.18.243; 11.CO.18.247; 11.CO.26.157; 11.CO.26.158;
11.CO.26.196; 11.CO.26.223; 11.CO.26.240; 11.CO.26.244; 11.CO.26.243;
11.CO.26.247; 11.CO.27.157; 11.CO.27.158; 11.CO.27.196; 11.CO.27.223;
11.CO.27.240; 11.CO.27.244; 11.CO.27.243; 11.CO.27.247; 11.CO.29.157;
11.CO.29.158; 11.CO.29.196; 11.CO.29.223; 11.CO.29.240; 11.CO.29.244;
11.CO.29.243; 11.CO.29.247; 11.CO.54.157; 11.CO.54.158; 11.CO.54.196;
11.CO.54.223; 11.CO.54.240; 11.CO.54.244; 11.CO.54.243; 11.CO.54.247;
11.CO.55.157; 11.CO.55.158; 11.CO.55.196; 11.CO.55.223; 11.CO.55.240;
11.CO.55.244; 11.CO.55.243; 11.CO.55.247; 11.CO.56.157; 11.CO.56.158;
11.CO.56.196; 11.CO.56.223; 11.CO.56.240; 11.CO.56.244; 11.CO.56.243;
11.CO.56.247; 11.CO.157.157; 11.CO.157.158; 11.CO.157.196;
11.CO.157.223; 11.CO.157.240; 11.CO.157.244; 11.CO.157.243;
11.CO.157.247; 11.CO.196.157; 11.CO.196.158; 11.CO.196.196;
11.CO.196.223; 11.CO.196.240; 11.CO.196.244; 11.CO.196.243;
11.CO.196.247; 11.CO.223.157; 11.CO.223.158; 11.CO.223.196;
11.CO.223.223; 11.CO.223.240; 11.CO.223.244; 11.CO.223.243;
11.CO.223.247; 11.CO.240.157; 11.CO.240.158; 11.CO.240.196;
11.CO.240.223; 11.CO.240.240; 11.CO.240.244; 11.CO.240.243;
11.CO.240.247; 11.CO.244.157; 11.CO.244.158; 11.CO.244.196;
11.CO.244.223; 11.CO.244.240; 11.CO.244.244; 11.CO.244.243;
11.CO.244.247; 11.CO.247.157; 11.CO.247.158; 11.CO.247.196;
11.CO.247.223; 11.CO.247.240; 11.CO.247.244; 11.CO.247.243;
11.CO.247.247;
Prodrugs of 12.AH 12.AH.4.157; 12.AH.4.158; 12.AH.4.196; 12.AH.4.223; 12.AH.4.240;
12.AH.4.244; 12.AH.4.243; 12.AH.4.247; 12.AH.5.157; 12.AH.5.158;

TABLE 100-continued

12.AH.5.196; 12.AH.5.223; 12.AH.5.240; 12.AH.5.244; 12.AH.5.243;
12.AH.5.247; 12.AH.7.157; 12.AH.7.158; 12.AH.7.196; 12.AH.7.223;
12.AH.7.240; 12.AH.7.244; 12.AH.7.243; 12.AH.7.247; 12.AH.15.157;
12.AH.15.158; 12.AH.15.196; 12.AH.15.223; 12.AH.15.240; 12.AH.15.244;
12.AH.15.243; 12.AH.15.247; 12.AH.16.157; 12.AH.16.158; 12.AH.16.196;
12.AH.16.223; 12.AH.16.240; 12.AH.16.244; 12.AH.16.243; 12.AH.16.247;
12.AH.18.157; 12.AH.18.158; 12.AH.18.196; 12.AH.18.223; 12.AH.18.240;
12.AH.18.244; 12.AH.18.243; 12.AH.18.247; 12.AH.26.157; 12.AH.26.158;
12.AH.26.196; 12.AH.26.223; 12.AH.26.240; 12.AH.26.244; 12.AH.26.243;
12.AH.26.247; 12.AH.27.157; 12.AH.27.158; 12.AH.27.196; 12.AH.27.223;
12.AH.27.240; 12.AH.27.244; 12.AH.27.243; 12.AH.27.247; 12.AH.29.157;
12.AH.29.158; 12.AH.29.196; 12.AH.29.223; 12.AH.29.240; 12.AH.29.244;
12.AH.29.243; 12.AH.29.247; 12.AH.54.157; 12.AH.54.158; 12.AH.54.196;
12.AH.54.223; 12.AH.54.240; 12.AH.54.244; 12.AH.54.243; 12.AH.54.247;
12.AH.55.157; 12.AH.55.158; 12.AH.55.196; 12.AH.55.223; 12.AH.55.240;
12.AH.55.244; 12.AH.55.243; 12.AH.55.247; 12.AH.56.157; 12.AH.56.158;
12.AH.56.196; 12.AH.56.223; 12.AH.56.240; 12.AH.56.244; 12.AH.56.243;
12.AH.56.247; 12.AH.157.157; 12.AH.157.158; 12.AH.157.196;
12.AH.157.223; 12.AH.157.240; 12.AH.157.244; 12.AH.157.243;
12.AH.157.247; 12.AH.196.157; 12.AH.196.158; 12.AH.196.196;
12.AH.196.223; 12.AH.196.240; 12.AH.196.244; 12.AH.196.243;
12.AH.196.247; 12.AH.223.157; 12.AH.223.158; 12.AH.223.196;
12.AH.223.223; 12.AH.223.240; 12.AH.223.244; 12.AH.223.243;
12.AH.223.247; 12.AH.240.157; 12.AH.240.158; 12.AH.240.196;
12.AH.240.223; 12.AH.240.240; 12.AH.240.244; 12.AH.240.243;
12.AH.240.247; 12.AH.244.157; 12.AH.244.158; 12.AH.244.196;
12.AH.244.223; 12.AH.244.240; 12.AH.244.244; 12.AH.244.243;
12.AH.244.247; 12.AH.247.157; 12.AH.247.158; 12.AH.247.196;
12.AH.247.223; 12.AH.247.240; 12.AH.247.244; 12.AH.247.243; 12.AH.247.247;
Prodrugs of 12.AJ 12.AJ.4.157; 12.AJ.4.158; 12.AJ.4.196; 12.AJ.4.223; 12.AJ.4.240;
12.AJ.4.244; 12.AJ.4.243; 12.AJ.4.247; 12.AJ.5.157; 12.AJ.5.158; 12.AJ.5.196;
12.AJ.5.223; 12.AJ.5.240; 12.AJ.5.244; 12.AJ.5.243; 12.AJ.5.247; 12.AJ.7.157;
12.AJ.7.158; 12.AJ.7.196; 12.AJ.7.223; 12.AJ.7.240; 12.AJ.7.244; 12.AJ.7.243;
12.AJ.7.247; 12.AJ.15.157; 12.AJ.15.158; 12.AJ.15.196; 12.AJ.15.223;
12.AJ.15.240; 12.AJ.15.244; 12.AJ.15.243; 12.AJ.15.247; 12.AJ.16.157;
12.AJ.16.158; 12.AJ.16.196; 12.AJ.16.223; 12.AJ.16.240; 12.AJ.16.244;
12.AJ.16.243; 12.AJ.16.247; 12.AJ.18.157; 12.AJ.18.158; 12.AJ.18.196;
12.AJ.18.223; 12.AJ.18.240; 12.AJ.18.244; 12.AJ.18.243; 12.AJ.18.247;
12.AJ.26.157; 12.AJ.26.158; 12.AJ.26.196; 12.AJ.26.223; 12.AJ.26.240;
12.AJ.26.244; 12.AJ.26.243; 12.AJ.26.247; 12.AJ.27.157; 12.AJ.27.158;
12.AJ.27.196; 12.AJ.27.223; 12.AJ.27.240; 12.AJ.27.244; 12.AJ.27.243;
12.AJ.27.247; 12.AJ.29.157; 12.AJ.29.158; 12.AJ.29.196; 12.AJ.29.223;
12.AJ.29.240; 12.AJ.29.244; 12.AJ.29.243; 12.AJ.29.247; 12.AJ.54.157;
12.AJ.54.158; 12.AJ.54.196; 12.AJ.54.223; 12.AJ.54.240; 12.AJ.54.244;
12.AJ.54.243; 12.AJ.54.247; 12.AJ.55.157; 12.AJ.55.158; 12.AJ.55.196;
12.AJ.55.223; 12.AJ.55.240; 12.AJ.55.244; 12.AJ.55.243; 12.AJ.55.247;
12.AJ.56.157; 12.AJ.56.158; 12.AJ.56.196; 12.AJ.56.223; 12.AJ.56.240;
12.AJ.56.244; 12.AJ.56.243; 12.AJ.56.247; 12.AJ.157.157; 12.AJ.157.158;
12.AJ.157.196; 12.AJ.157.223; 12.AJ.157.240; 12.AJ.157.244; 12.AJ.157.243;
12.AJ.157.247; 12.AJ.196.157; 12.AJ.196.158; 12.AJ.196.196; 12.AJ.196.223;
12.AJ.196.240; 12.AJ.196.244; 12.AJ.196.243; 12.AJ.196.247; 12.AJ.223.157;
12.AJ.223.158; 12.AJ.223.196; 12.AJ.223.223; 12.AJ.223.240; 12.AJ.223.244;
12.AJ.223.243; 12.AJ.223.247; 12.AJ.240.157; 12.AJ.240.158; 12.AJ.240.196;
12.AJ.240.223; 12.AJ.240.240; 12.AJ.240.244; 12.AJ.240.243; 12.AJ.240.247;
12.AJ.244.157; 12.AJ.244.158; 12.AJ.244.196; 12.AJ.244.223; 12.AJ.244.240;
12.AJ.244.244; 12.AJ.244.243; 12.AJ.244.247; 12.AJ.247.157; 12.AJ.247.158;
12.AJ.247.196; 12.AJ.247.223; 12.AJ.247.240; 12.AJ.247.244; 12.AJ.247.243; 12.AJ.247.247;
Prodrugs of 12.AN 12.AN.4.157; 12.AN.4.158; 12.AN.4.196; 12.AN.4.223; 12.AN.4.240;
12.AN.4.244; 12.AN.4.243; 12.AN.4.247; 12.AN.5.157; 12.AN.5.158;
12.AN.5.196; 12.AN.5.223; 12.AN.5.240; 12.AN.5.244; 12.AN.5.243;
12.AN.5.247; 12.AN.7.157; 12.AN.7.158; 12.AN.7.196; 12.AN.7.223;
12.AN.7.240; 12.AN.7.244; 12.AN.7.243; 12.AN.7.247; 12.AN.15.157;
12.AN.15.158; 12.AN.15.196; 12.AN.15.223; 12.AN.15.240; 12.AN.15.244;
12.AN.15.243; 12.AN.15.247; 12.AN.16.157; 12.AN.16.158; 12.AN.16.196;
12.AN.16.223; 12.AN.16.240; 12.AN.16.244; 12.AN.16.243; 12.AN.16.247;
12.AN.18.157; 12.AN.18.158; 12.AN.18.196; 12.AN.18.223; 12.AN.18.240;
12.AN.18.244; 12.AN.18.243; 12.AN.18.247; 12.AN.26.157; 12.AN.26.158;
12.AN.26.196; 12.AN.26.223; 12.AN.26.240; 12.AN.26.244; 12.AN.26.243;
12.AN.26.247; 12.AN.27.157; 12.AN.27.158; 12.AN.27.196; 12.AN.27.223;
12.AN.27.240; 12.AN.27.244; 12.AN.27.243; 12.AN.27.247; 12.AN.29.157;
12.AN.29.158; 12.AN.29.196; 12.AN.29.223; 12.AN.29.240; 12.AN.29.244;
12.AN.29.243; 12.AN.29.247; 12.AN.54.157; 12.AN.54.158; 12.AN.54.196;
12.AN.54.223; 12.AN.54.240; 12.AN.54.244; 12.AN.54.243; 12.AN.54.247;
12.AN.55.157; 12.AN.55.158; 12.AN.55.196; 12.AN.55.223; 12.AN.55.240;
12.AN.55.244; 12.AN.55.243; 12.AN.55.247; 12.AN.56.157; 12.AN.56.158;

TABLE 100-continued

12.AN.56.196; 12.AN.56.223; 12.AN.56.240; 12.AN.56.244; 12.AN.56.243;
12.AN.56.247; 12.AN.157.157; 12.AN.157.158; 12.AN.157.196;
12.AN.157.223; 12.AN.157.240; 12.AN.157.244; 12.AN.157.243;
12.AN.157.247; 12.AN.196.157; 12.AN.196.158; 12.AN.196.196;
12.AN.196.223; 12.AN.196.240; 12.AN.196.244; 12.AN.196.243;
12.AN.196.247; 12.AN.223.157; 12.AN.223.158; 12.AN.223.196;
12.AN.223.223; 12.AN.223.240; 12.AN.223.244; 12.AN.223.243;
12.AN.223.247; 12.AN.240.157; 12.AN.240.158; 12.AN.240.196;
12.AN.240.223; 12.AN.240.240; 12.AN.240.244; 12.AN.240.243;
12.AN.240.247; 12.AN.244.157; 12.AN.244.158; 12.AN.244.196;
12.AN.244.223; 12.AN.244.240; 12.AN.244.244; 12.AN.244.243;
12.AN.244.247; 12.AN.247.157; 12.AN.247.158; 12.AN.247.196;
12.AN.247.223; 12.AN.247.240; 12.AN.247.244; 12.AN.247.243;
12.AN.247.247;
Prodrugs of 12.AP 12.AP.4.157; 12.AP.4.158; 12.AP.4.196; 12.AP.4.223; 12.AP.4.240;
12.AP.4.244; 12.AP.4.243; 12.AP.4.247; 12.AP.5.157; 12.AP.5.158;
12.AP.5.196; 12.AP.5.223; 12.AP.5.240; 12.AP.5.244; 12.AP.5.243;
12.AP.5.247; 12.AP.7.157; 12.AP.7.158; 12.AP.7.196; 12.AP.7.223;
12.AP.7.240; 12.AP.7.244; 12.AP.7.243; 12.AP.7.247; 12.AP.15.157;
12.AP.15.158; 12.AP.15.196; 12.AP.15.223; 12.AP.15.240; 12.AP.15.244;
12.AP.15.243; 12.AP.15.247; 12.AP.16.157; 12.AP.16.158; 12.AP.16.196;
12.AP.16.223; 12.AP.16.240; 12.AP.16.244; 12.AP.16.243; 12.AP.16.247;
12.AP.18.157; 12.AP.18.158; 12.AP.18.196; 12.AP.18.223; 12.AP.18.240;
12.AP.18.244; 12.AP.18.243; 12.AP.18.247; 12.AP.26.157; 12.AP.26.158;
12.AP.26.196; 12.AP.26.223; 12.AP.26.240; 12.AP.26.244; 12.AP.26.243;
12.AP.26.247; 12.AP.27.157; 12.AP.27.158; 12.AP.27.196; 12.AP.27.223;
12.AP.27.240; 12.AP.27.244; 12.AP.27.243; 12.AP.27.247; 12.AP.29.157;
12.AP.29.158; 12.AP.29.196; 12.AP.29.223; 12.AP.29.240; 12.AP.29.244;
12.AP.29.243; 12.AP.29.247; 12.AP.54.157; 12.AP.54.158; 12.AP.54.196;
12.AP.54.223; 12.AP.54.240; 12.AP.54.244; 12.AP.54.243; 12.AP.54.247;
12.AP.55.157; 12.AP.55.158; 12.AP.55.196; 12.AP.55.223; 12.AP.55.240;
12.AP.55.244; 12.AP.55.243; 12.AP.55.247; 12.AP.56.157; 12.AP.56.158;
12.AP.56.196; 12.AP.56.223; 12.AP.56.240; 12.AP.56.244; 12.AP.56.243;
12.AP.56.247; 12.AP.157.157; 12.AP.157.158; 12.AP.157.196; 12.AP.157.223;
12.AP.157.240; 12.AP.157.244; 12.AP.157.243; 12.AP.157.247;
12.AP.196.157; 12.AP.196.158; 12.AP.196.196; 12.AP.196.223;
12.AP.196.240; 12.AP.196.244; 12.AP.196.243; 12.AP.196.247;
12.AP.223.157; 12.AP.223.158; 12.AP.223.196; 12.AP.223.223;
12.AP.223.240; 12.AP.223.244; 12.AP.223.243; 12.AP.223.247;
12.AP.240.157; 12.AP.240.158; 12.AP.240.196; 12.AP.240.223;
12.AP.240.240; 12.AP.240.244; 12.AP.240.243; 12.AP.240.247;
12.AP.244.157; 12.AP.244.158; 12.AP.244.196; 12.AP.244.223;
12.AP.244.240; 12.AP.244.244; 12.AP.244.243; 12.AP.244.247;
12.AP.247.157; 12.AP.247.158; 12.AP.247.196; 12.AP.247.223;
12.AP.247.240; 12.AP.247.244; 12.AP.247.243; 12.AP.247.247;
Prodrugs of 12.AZ 12.AZ.4.157; 12.AZ.4.158; 12.AZ.4.196; 12.AZ.4.223; 12.AZ.4.240;
12.AZ.4.244; 12.AZ.4.243; 12.AZ.4.247; 12.AZ.5.157; 12.AZ.5.158;
12.AZ.5.196; 12.AZ.5.223; 12.AZ.5.240; 12.AZ.5.244; 12.AZ.5.243;
12.AZ.5.247; 12.AZ.7.157; 12.AZ.7.158; 12.AZ.7.196; 12.AZ.7.223;
12.AZ.7.240; 12.AZ.7.244; 12.AZ.7.243; 12.AZ.7.247; 12.AZ.15.157;
12.AZ.15.158; 12.AZ.15.196; 12.AZ.15.223; 12.AZ.15.240; 12.AZ.15.244;
12.AZ.15.243; 12.AZ.15.247; 12.AZ.16.157; 12.AZ.16.158; 12.AZ.16.196;
12.AZ.16.223; 12.AZ.16.240; 12.AZ.16.244; 12.AZ.16.243; 12.AZ.16.247;
12.AZ.18.157; 12.AZ.18.158; 12.AZ.18.196; 12.AZ.18.223; 12.AZ.18.240;
12.AZ.18.244; 12.AZ.18.243; 12.AZ.18.247; 12.AZ.26.157; 12.AZ.26.158;
12.AZ.26.196; 12.AZ.26.223; 12.AZ.26.240; 12.AZ.26.244; 12.AZ.26.243;
12.AZ.26.247; 12.AZ.27.157; 12.AZ.27.158; 12.AZ.27.196; 12.AZ.27.223;
12.AZ.27.240; 12.AZ.27.244; 12.AZ.27.243; 12.AZ.27.247; 12.AZ.29.157;
12.AZ.29.158; 12.AZ.29.196; 12.AZ.29.223; 12.AZ.29.240; 12.AZ.29.244;
12.AZ.29.243; 12.AZ.29.247; 12.AZ.54.157; 12.AZ.54.158; 12.AZ.54.196;
12.AZ.54.223; 12.AZ.54.240; 12.AZ.54.244; 12.AZ.54.243; 12.AZ.54.247;
12.AZ.55.157; 12.AZ.55.158; 12.AZ.55.196; 12.AZ.55.223; 12.AZ.55.240;
12.AZ.55.244; 12.AZ.55.243; 12.AZ.55.247; 12.AZ.56.157; 12.AZ.56.158;
12.AZ.56.196; 12.AZ.56.223; 12.AZ.56.240; 12.AZ.56.244; 12.AZ.56.243;
12.AZ.56.247; 12.AZ.157.157; 12.AZ.157.158; 12.AZ.157.196; 12.AZ.157.223;
12.AZ.157.240; 12.AZ.157.244; 12.AZ.157.243; 12.AZ.157.247;
12.AZ.196.157; 12.AZ.196.158; 12.AZ.196.196; 12.AZ.196.223;
12.AZ.196.240; 12.AZ.196.244; 12.AZ.196.243; 12.AZ.196.247;
12.AZ.223.157; 12.AZ.223.158; 12.AZ.223.196; 12.AZ.223.223;
12.AZ.223.240; 12.AZ.223.244; 12.AZ.223.243; 12.AZ.223.247;
12.AZ.240.157; 12.AZ.240.158; 12.AZ.240.196; 12.AZ.240.223;
12.AZ.240.240; 12.AZ.240.244; 12.AZ.240.243; 12.AZ.240.247;
12.AZ.244.157; 12.AZ.244.158; 12.AZ.244.196; 12.AZ.244.223;
12.AZ.244.240; 12.AZ.244.244; 12.AZ.244.243; 12.AZ.244.247;

TABLE 100-continued

12.AZ.247.157; 12.AZ.247.158; 12.AZ.247.196; 12.AZ.247.223;
12.AZ.247.240; 12.AZ.247.244; 12.AZ.247.243; 12.AZ.247.247;
Prodrugs of 12.BF 12.BF.4.157; 12.BF.4.158; 12.BF.4.196; 12.BF.4.223; 12.BF.4.240;
12.BF.4.244; 12.BF.4.243; 12.BF.4.247; 12.BF.5.157; 12.BF.5.158;
12.BF.5.196; 12.BF.5.223; 12.BF.5.240; 12.BF.5.244; 12.BF.5.243;
12.BF.5.247; 12.BF.7.157; 12.BF.7.158; 12.BF.7.196; 12.BF.7.223;
12.BF.7.240; 12.BF.7.244; 12.BF.7.243; 12.BF.7.247; 12.BF.15.157;
12.BF.15.158; 12.BF.15.196; 12.BF.15.223; 12.BF.15.240; 12.BF.15.244;
12.BF.15.243; 12.BF.15.247; 12.BF.16.157; 12.BF.16.158; 12.BF.16.196;
12.BF.16.223; 12.BF.16.240; 12.BF.16.244; 12.BF.16.243; 12.BF.16.247;
12.BF.18.157; 12.BF.18.158; 12.BF.18.196; 12.BF.18.223; 12.BF.18.240;
12.BF.18.244; 12.BF.18.243; 12.BF.18.247; 12.BF.26.157; 12.BF.26.158;
12.BF.26.196; 12.BF.26.223; 12.BF.26.240; 12.BF.26.244; 12.BF.26.243;
12.BF.26.247; 12.BF.27.157; 12.BF.27.158; 12.BF.27.196; 12.BF.27.223;
12.BF.27.240; 12.BF.27.244; 12.BF.27.243; 12.BF.27.247; 12.BF.29.157;
12.BF.29.158; 12.BF.29.196; 12.BF.29.223; 12.BF.29.240; 12.BF.29.244;
12.BF.29.243; 12.BF.29.247; 12.BF.54.157; 12.BF.54.158; 12.BF.54.196;
12.BF.54.223; 12.BF.54.240; 12.BF.54.244; 12.BF.54.243; 12.BF.54.247;
12.BF.55.157; 12.BF.55.158; 12.BF.55.196; 12.BF.55.223; 12.BF.55.240;
12.BF.55.244; 12.BF.55.243; 12.BF.55.247; 12.BF.56.157; 12.BF.56.158;
12.BF.56.196; 12.BF.56.223; 12.BF.56.240; 12.BF.56.244; 12.BF.56.243;
12.BF.56.247; 12.BF.157.157; 12.BF.157.158; 12.BF.157.196; 12.BF.157.223;
12.BF.157.240; 12.BF.157.244; 12.BF.157.243; 12.BF.157.247; 12.BF.196.157;
12.BF.196.158; 12.BF.196.196; 12.BF.196.223; 12.BF.196.240; 12.BF.196.244;
12.BF.196.243; 12.BF.196.247; 12.BF.223.157; 12.BF.223.158; 12.BF.223.196;
12.BF.223.223; 12.BF.223.240; 12.BF.223.244; 12.BF.223.243; 12.BF.223.247;
12.BF.240.157; 12.BF.240.158; 12.BF.240.196; 12.BF.240.223; 12.BF.240.240;
12.BF.240.244; 12.BF.240.243; 12.BF.240.247; 12.BF.244.157; 12.BF.244.158;
12.BF.244.196; 12.BF.244.223; 12.BF.244.240; 12.BF.244.244; 12.BF.244.243;
12.BF.244.247; 12.BF.247.157; 12.BF.247.158; 12.BF.247.196; 12.BF.247.223;
12.BF.247.240; 12.BF.247.244; 12.BF.247.243; 12.BF.247.247;
Prodrugs of 12.CI 12.CI.4.157; 12.CI.4.158; 12.CI.4.196; 12.CI.4.223; 12.CI.4.240;
12.CI.4.244; 12.CI.4.243; 12.CI.4.247; 12.CI.5.157; 12.CI.5.158; 12.CI.5.196;
12.CI.5.223; 12.CI.5.240; 12.CI.5.244; 12.CI.5.243; 12.CI.5.247; 12.CI.7.157;
12.CI.7.158; 12.CI.7.196; 12.CI.7.223; 12.CI.7.240; 12.CI.7.244; 12.CI.7.243;
12.CI.7.247; 12.CI.15.157; 12.CI.15.158; 12.CI.15.196; 12.CI.15.223;
12.CI.15.240; 12.CI.15.244; 12.CI.15.243; 12.CI.15.247; 12.CI.16.157;
12.CI.16.158; 12.CI.16.196; 12.CI.16.223; 12.CI.16.240; 12.CI.16.244;
12.CI.16.243; 12.CI.16.247; 12.CI.18.157; 12.CI.18.158; 12.CI.18.196;
12.CI.18.223; 12.CI.18.240; 12.CI.18.244; 12.CI.18.243; 12.CI.18.247;
12.CI.26.157; 12.CI.26.158; 12.CI.26.196; 12.CI.26.223; 12.CI.26.240;
12.CI.26.244; 12.CI.26.243; 12.CI.26.247; 12.CI.27.157; 12.CI.27.158;
12.CI.27.196; 12.CI.27.223; 12.CI.27.240; 12.CI.27.244; 12.CI.27.243;
12.CI.27.247; 12.CI.29.157; 12.CI.29.158; 12.CI.29.196; 12.CI.29.223;
12.CI.29.240; 12.CI.29.244; 12.CI.29.243; 12.CI.29.247; 12.CI.54.157;
12.CI.54.158; 12.CI.54.196; 12.CI.54.223; 12.CI.54.240; 12.CI.54.244;
12.CI.54.243; 12.CI.54.247; 12.CI.55.157; 12.CI.55.158; 12.CI.55.196;
12.CI.55.223; 12.CI.55.240; 12.CI.55.244; 12.CI.55.243; 12.CI.55.247;
12.CI.56.157; 12.CI.56.158; 12.CI.56.196; 12.CI.56.223; 12.CI.56.240;
12.CI.56.244; 12.CI.56.243; 12.CI.56.247; 12.CI.157.157; 12.CI.157.158;
12.CI.157.196; 12.CI.157.223; 12.CI.157.240; 12.CI.157.244; 12.CI.157.243;
12.CI.157.247; 12.CI.196.157; 12.CI.196.158; 12.CI.196.196; 12.CI.196.223;
12.CI.196.240; 12.CI.196.244; 12.CI.196.243; 12.CI.196.247; 12.CI.223.157;
12.CI.223.158; 12.CI.223.196; 12.CI.223.223; 12.CI.223.240; 12.CI.223.244;
12.CI.223.243; 12.CI.223.247; 12.CI.240.157; 12.CI.240.158; 12.CI.240.196;
12.CI.240.223; 12.CI.240.240; 12.CI.240.244; 12.CI.240.243; 12.CI.240.247;
12.CI.244.157; 12.CI.244.158; 12.CI.244.196; 12.CI.244.223; 12.CI.244.240;
12.CI.244.244; 12.CI.244.243; 12.CI.244.247; 12.CI.247.157; 12.CI.247.158;
12.CI.247.196; 12.CI.247.223; 12.CI.247.240; 12.CI.247.244; 12.CI.247.243;
12.CI.247.247;
Prodrugs of 12.CO 12.CO.4.157; 12.CO.4.158; 12.CO.4.196; 12.CO.4.223; 12.CO.4.240;
12.CO.4.244; 12.CO.4.243; 12.CO.4.247; 12.CO.5.157; 12.CO.5.158;
12.CO.5.196; 12.CO.5.223; 12.CO.5.240; 12.CO.5.244; 12.CO.5.243;
12.CO.5.247; 12.CO.7.157; 12.CO.7.158; 12.CO.7.196; 12.CO.7.223;
12.CO.7.240; 12.CO.7.244; 12.CO.7.243; 12.CO.7.247; 12.CO.15.157;
12.CO.15.158; 12.CO.15.196; 12.CO.15.223; 12.CO.15.240; 12.CO.15.244;
12.CO.15.243; 12.CO.15.247; 12.CO.16.157; 12.CO.16.158; 12.CO.16.196;
12.CO.16.223; 12.CO.16.240; 12.CO.16.244; 12.CO.16.243; 12.CO.16.247;
12.CO.18.157; 12.CO.18.158; 12.CO.18.196; 12.CO.18.223; 12.CO.18.240;
12.CO.18.244; 12.CO.18.243; 12.CO.18.247; 12.CO.26.157; 12.CO.26.158;
12.CO.26.196; 12.CO.26.223; 12.CO.26.240; 12.CO.26.244; 12.CO.26.243;
12.CO.26.247; 12.CO.27.157; 12.CO.27.158; 12.CO.27.196; 12.CO.27.223;
12.CO.27.240; 12.CO.27.244; 12.CO.27.243; 12.CO.27.247; 12.CO.29.157;

TABLE 100-continued

12.CO.29.158; 12.CO.29.196; 12.CO.29.223; 12.CO.29.240; 12.CO.29.244;
12.CO.29.243; 12.CO.29.247; 12.CO.54.157; 12.CO.54.158; 12.CO.54.196;
12.CO.54.223; 12.CO.54.240; 12.CO.54.244; 12.CO.54.243; 12.CO.54.247;
12.CO.55.157; 12.CO.55.158; 12.CO.55.196; 12.CO.55.223; 12.CO.55.240;
12.CO.55.244; 12.CO.55.243; 12.CO.55.247; 12.CO.56.157; 12.CO.56.158;
12.CO.56.196; 12.CO.56.223; 12.CO.56.240; 12.CO.56.244; 12.CO.56.243;
12.CO.56.247; 12.CO.157.157; 12.CO.157.158; 12.CO.157.196;
12.CO.157.223; 12.CO.157.240; 12.CO.157.244; 12.CO.157.243;
12.CO.157.247; 12.CO.196.157; 12.CO.196.158; 12.CO.196.196;
12.CO.196.223; 12.CO.196.240; 12.CO.196.244; 12.CO.196.243;
12.CO.196.247; 12.CO.223.157; 12.CO.223.158; 12.CO.223.196;
12.CO.223.223; 12.CO.223.240; 12.CO.223.244; 12.CO.223.243;
12.CO.223.247; 12.CO.240.157; 12.CO.240.158; 12.CO.240.196;
12.CO.240.223; 12.CO.240.240; 12.CO.240.244; 12.CO.240.243;
12.CO.240.247; 12.CO.244.157; 12.CO.244.158; 12.CO.244.196;
12.CO.244.223; 12.CO.244.240; 12.CO.244.244; 12.CO.244.243;
12.CO.244.247; 12.CO.247.157; 12.CO.247.158; 12.CO.247.196;
12.CO.247.223; 12.CO.247.240; 12.CO.247.244; 12.CO.247.243;
12.CO.247.247.

Prodrugs of 13.B

13.B.228.228; 13.B.228.229; 13.B.228.230; 13.B.228.231; 13.B.228.236;
13.B.228.237; 13.B.228.238; 13.B.228.239; 13.B.228.154; 13.B.228.157;
13.B.228.166; 13.B.228.169; 13.B.228.172; 13.B.228.175; 13.B.228.240;
13.B.228.244; 13.B.229.228; 13.B.229.229; 13.B.229.230; 13.B.229.231;
13.B.229.236; 13.B.229.237; 13.B.229.238; 13.B.229.239; 13.B.229.154;
13.B.229.157; 13.B.229.166; 13.B.229.169; 13.B.229.172; 13.B.229.175;
13.B.229.240; 13.B.229.244; 13.B.230.228; 13.B.230.229; 13.B.230.230;
13.B.230.231; 13.B.230.236; 13.B.230.237; 13.B.230.238; 13.B.230.239;
13.B.230.154; 13.B.230.157; 13.B.230.166; 13.B.230.169; 13.B.230.172;
13.B.230.175; 13.B.230.240; 13.B.230.244; 13.B.231.228; 13.B.231.229;
13.B.231.230; 13.B.231.231; 13.B.231.236; 13.B.231.237; 13.B.231.238;
13.B.231.239; 13.B.231.154; 13.B.231.157; 13.B.231.166; 13.B.231.169;
13.B.231.172; 13.B.231.175; 13.B.231.240; 13.B.231.244; 13.B.236.228;
13.B.236.229; 13.B.236.230; 13.B.236.231; 13.B.236.236; 13.B.236.237;
13.B.236.238; 13.B.236.239; 13.B.236.154; 13.B.236.157; 13.B.236.166;
13.B.236.169; 13.B.236.172; 13.B.236.175; 13.B.236.240; 13.B.236.244;
13.B.237.228; 13.B.237.229; 13.B.237.230; 13.B.237.231; 13.B.237.236;
13.B.237.237; 13.B.237.238; 13.B.237.239; 13.B.237.154; 13.B.237.157;
13.B.237.166; 13.B.237.169; 13.B.237.172; 13.B.237.175; 13.B.237.240;
13.B.237.244; 13.B.238.228; 13.B.238.229; 13.B.238.230; 13.B.238.231;
13.B.238.236; 13.B.238.237; 13.B.238.238; 13.B.238.239; 13.B.238.154;
13.B.238.157; 13.B.238.166; 13.B.238.169; 13.B.238.172; 13.B.238.175;
13.B.238.240; 13.B.238.244; 13.B.239.228; 13.B.239.229; 13.B.239.230;
13.B.239.231; 13.B.239.236; 13.B.239.237; 13.B.239.238; 13.B.239.239;
13.B.239.154; 13.B.239.157; 13.B.239.166; 13.B.239.169; 13.B.239.172;
13.B.239.175; 13.B.239.240; 13.B.239.244; 13.B.154.228; 13.B.154.229;
13.B.154.230; 13.B.154.231; 13.B.154.236; 13.B.154.237; 13.B.154.238;
13.B.154.239; 13.B.154.154; 13.B.154.157; 13.B.154.166; 13.B.154.169;
13.B.154.172; 13.B.154.175; 13.B.154.240; 13.B.154.244; 13.B.157.228;
13.B.157.229; 13.B.157.230; 13.B.157.231; 13.B.157.236; 13.B.157.237;
13.B.157.238; 13.B.157.239; 13.B.157.154; 13.B.157.157; 13.B.157.166;
13.B.157.169; 13.B.157.172; 13.B.157.175; 13.B.157.240; 13.B.157.244;
13.B.166.228; 13.B.166.229; 13.B.166.230; 13.B.166.231; 13.B.166.236;
13.B.166.237; 13.B.166.238; 13.B.166.239; 13.B.166.154; 13.B.166.157;
13.B.166.166; 13.B.166.169; 13.B.166.172; 13.B.166.175; 13.B.166.240;
13.B.166.244; 13.B.169.228; 13.B.169.229; 13.B.169.230; 13.B.169.231;
13.B.169.236; 13.B.169.237; 13.B.169.238; 13.B.169.239; 13.B.169.154;
13.B.169.157; 13.B.169.166; 13.B.169.169; 13.B.169.172; 13.B.169.175;
13.B.169.240; 13.B.169.244; 13.B.172.228; 13.B.172.229; 13.B.172.230;
13.B.172.231; 13.B.172.236; 13.B.172.237; 13.B.172.238; 13.B.172.239;
13.B.172.154; 13.B.172.157; 13.B.172.166; 13.B.172.169; 13.B.172.172;
13.B.172.175; 13.B.172.240; 13.B.172.244; 13.B.175.228; 13.B.175.229;
13.B.175.230; 13.B.175.231; 13.B.175.236; 13.B.175.237; 13.B.175.238;
13.B.175.239; 13.B.175.154; 13.B.175.157; 13.B.175.166; 13.B.175.169;
13.B.175.172; 13.B.175.175; 13.B.175.240; 13.B.175.244; 13.B.240.228;
13.B.240.229; 13.B.240.230; 13.B.240.231; 13.B.240.236; 13.B.240.237;
13.B.240.238; 13.B.240.239; 13.B.240.154; 13.B.240.157; 13.B.240.166;
13.B.240.169; 13.B.240.172; 13.B.240.175; 13.B.240.240; 13.B.240.244;
13.B.244.228; 13.B.244.229; 13.B.244.230; 13.B.244.231; 13.B.244.236;
13.B.244.237; 13.B.244.238; 13.B.244.239; 13.B.244.154; 13.B.244.157;
13.B.244.166; 13.B.244.169; 13.B.244.172; 13.B.244.175; 13.B.244.240;
13.B.244.244;

Prodrugs of 13.D

13.D.228.228; 13.D.228.229; 13.D.228.230; 13.D.228.231; 13.D.228.236;
13.D.228.237; 13.D.228.238; 13.D.228.239; 13.D.228.154; 13.D.228.157;
13.D.228.166; 13.D.228.169; 13.D.228.172; 13.D.228.175; 13.D.228.240;
13.D.228.244; 13.D.229.228; 13.D.229.229; 13.D.229.230; 13.D.229.231;

TABLE 100-continued

13.D.229.236; 13.D.229.237; 13.D.229.238; 13.D.229.239; 13.D.229.154;
13.D.229.157; 13.D.229.166; 13.D.229.169; 13.D.229.172; 13.D.229.175;
13.D.229.240; 13.D.229.244; 13.D.230.228; 13.D.230.229; 13.D.230.230;
13.D.230.231; 13.D.230.236; 13.D.230.237; 13.D.230.238; 13.D.230.239;
13.D.230.154; 13.D.230.157; 13.D.230.166; 13.D.230.169; 13.D.230.172;
13.D.230.175; 13.D.230.240; 13.D.230.244; 13.D.231.228; 13.D.231.229;
13.D.231.230; 13.D.231.231; 13.D.231.236; 13.D.231.237; 13.D.231.238;
13.D.231.239; 13.D.231.154; 13.D.231.157; 13.D.231.166; 13.D.231.169;
13.D.231.172; 13.D.231.175; 13.D.231.240; 13.D.231.244; 13.D.236.228;
13.D.236.229; 13.D.236.230; 13.D.236.231; 13.D.236.236; 13.D.236.237;
13.D.236.238; 13.D.236.239; 13.D.236.154; 13.D.236.157; 13.D.236.166;
13.D.236.169; 13.D.236.172; 13.D.236.175; 13.D.236.240; 13.D.236.244;
13.D.237.228; 13.D.237.229; 13.D.237.230; 13.D.237.231; 13.D.237.236;
13.D.237.237; 13.D.237.238; 13.D.237.239; 13.D.237.154; 13.D.237.157;
13.D.237.166; 13.D.237.169; 13.D.237.172; 13.D.237.175; 13.D.237.240;
13.D.237.244; 13.D.238.228; 13.D.238.229; 13.D.238.230; 13.D.238.231;
13.D.238.236; 13.D.238.237; 13.D.238.238; 13.D.238.239; 13.D.238.154;
13.D.238.157; 13.D.238.166; 13.D.238.169; 13.D.238.172; 13.D.238.175;
13.D.238.240; 13.D.238.244; 13.D.239.228; 13.D.239.229; 13.D.239.230;
13.D.239.231; 13.D.239.236; 13.D.239.237; 13.D.239.238; 13.D.239.239;
13.D.239.154; 13.D.239.157; 13.D.239.166; 13.D.239.169; 13.D.239.172;
13.D.239.175; 13.D.239.240; 13.D.239.244; 13.D.154.228; 13.D.154.229;
13.D.154.230; 13.D.154.231; 13.D.154.236; 13.D.154.237; 13.D.154.238;
13.D.154.239; 13.D.154.154; 13.D.154.157; 13.D.154.166; 13.D.154.169;
13.D.154.172; 13.D.154.175; 13.D.154.240; 13.D.154.244; 13.D.157.228;
13.D.157.229; 13.D.157.230; 13.D.157.231; 13.D.157.236; 13.D.157.237;
13.D.157.238; 13.D.157.239; 13.D.157.154; 13.D.157.157; 13.D.157.166;
13.D.157.169; 13.D.157.172; 13.D.157.175; 13.D.157.240; 13.D.157.244;
13.D.166.228; 13.D.166.229; 13.D.166.230; 13.D.166.231; 13.D.166.236;
13.D.166.237; 13.D.166.238; 13.D.166.239; 13.D.166.154; 13.D.166.157;
13.D.166.166; 13.D.166.169; 13.D.166.172; 13.D.166.175; 13.D.166.240;
13.D.166.244; 13.D.169.228; 13.D.169.229; 13.D.169.230; 13.D.169.231;
13.D.169.236; 13.D.169.237; 13.D.169.238; 13.D.169.239; 13.D.169.154;
13.D.169.157; 13.D.169.166; 13.D.169.169; 13.D.169.172; 13.D.169.175;
13.D.169.240; 13.D.169.244; 13.D.172.228; 13.D.172.229; 13.D.172.230;
13.D.172.231; 13.D.172.236; 13.D.172.237; 13.D.172.238; 13.D.172.239;
13.D.172.154; 13.D.172.157; 13.D.172.166; 13.D.172.169; 13.D.172.172;
13.D.172.175; 13.D.172.240; 13.D.172.244; 13.D.175.228; 13.D.175.229;
13.D.175.230; 13.D.175.231; 13.D.175.236; 13.D.175.237; 13.D.175.238;
13.D.175.239; 13.D.175.154; 13.D.175.157; 13.D.175.166; 13.D.175.169;
13.D.175.172; 13.D.175.175; 13.D.175.240; 13.D.175.244; 13.D.240.228;
13.D.240.229; 13.D.240.230; 13.D.240.231; 13.D.240.236; 13.D.240.237;
13.D.240.238; 13.D.240.239; 13.D.240.154; 13.D.240.157; 13.D.240.166;
13.D.240.169; 13.D.240.172; 13.D.240.175; 13.D.240.240; 13.D.240.244;
13.D.244.228; 13.D.244.229; 13.D.244.230; 13.D.244.231; 13.D.244.236;
13.D.244.237; 13.D.244.238; 13.D.244.239; 13.D.244.154; 13.D.244.157;
13.D.244.166; 13.D.244.169; 13.D.244.172; 13.D.244.175; 13.D.244.240; 13.D.244.244;
Prodrugs of 13.E 13.E.228.228; 13.E.228.229; 13.E.228.230; 13.E.228.231; 13.E.228.236;
13.E.228.237; 13.E.228.238; 13.E.228.239; 13.E.228.154; 13.E.228.157;
13.E.228.166; 13.E.228.169; 13.E.228.172; 13.E.228.175; 13.E.228.240;
13.E.228.244; 13.E.229.228; 13.E.229.229; 13.E.229.230; 13.E.229.231;
13.E.229.236; 13.E.229.237; 13.E.229.238; 13.E.229.239; 13.E.229.154;
13.E.229.157; 13.E.229.166; 13.E.229.169; 13.E.229.172; 13.E.229.175;
13.E.229.240; 13.E.229.244; 13.E.230.228; 13.E.230.229; 13.E.230.230;
13.E.230.231; 13.E.230.236; 13.E.230.237; 13.E.230.238; 13.E.230.239;
13.E.230.154; 13.E.230.157; 13.E.230.166; 13.E.230.169; 13.E.230.172;
13.E.230.175; 13.E.230.240; 13.E.230.244; 13.E.231.228; 13.E.231.229;
13.E.231.230; 13.E.231.231; 13.E.231.236; 13.E.231.237; 13.E.231.238;
13.E.231.239; 13.E.231.154; 13.E.231.157; 13.E.231.166; 13.E.231.169;
13.E.231.172; 13.E.231.175; 13.E.231.240; 13.E.231.244; 13.E.236.228;
13.E.236.229; 13.E.236.230; 13.E.236.231; 13.E.236.236; 13.E.236.237;
13.E.236.238; 13.E.236.239; 13.E.236.154; 13.E.236.157; 13.E.236.166;
13.E.236.169; 13.E.236.172; 13.E.236.175; 13.E.236.240; 13.E.236.244;
13.E.237.228; 13.E.237.229; 13.E.237.230; 13.E.237.231; 13.E.237.236;
13.E.237.237; 13.E.237.238; 13.E.237.239; 13.E.237.154; 13.E.237.157;
13.E.237.166; 13.E.237.169; 13.E.237.172; 13.E.237.175; 13.E.237.240;
13.E.237.244; 13.E.238.228; 13.E.238.229; 13.E.238.230; 13.E.238.231;
13.E.238.236; 13.E.238.237; 13.E.238.238; 13.E.238.239; 13.E.238.154;
13.E.238.157; 13.E.238.166; 13.E.238.169; 13.E.238.172; 13.E.238.175;
13.E.238.240; 13.E.238.244; 13.E.239.228; 13.E.239.229; 13.E.239.230;
13.E.239.231; 13.E.239.236; 13.E.239.237; 13.E.239.238; 13.E.239.239;
13.E.239.154; 13.E.239.157; 13.E.239.166; 13.E.239.169; 13.E.239.172;
13.E.239.175; 13.E.239.240; 13.E.239.244; 13.E.154.228; 13.E.154.229;
13.E.154.230; 13.E.154.231; 13.E.154.236; 13.E.154.237; 13.E.154.238;
13.E.154.239; 13.E.154.154; 13.E.154.157; 13.E.154.166; 13.E.154.169;
13.E.154.172; 13.E.154.175; 13.E.154.240; 13.E.154.244; 13.E.157.228;
13.E.157.229; 13.E.157.230; 13.E.157.231; 13.E.157.236; 13.E.157.237;

TABLE 100-continued

13.E.157.238; 13.E.157.239; 13.E.157.154; 13.E.157.157; 13.E.157.166;
13.E.157.169; 13.E.157.172; 13.E.157.175; 13.E.157.240; 13.E.157.244;
13.E.166.228; 13.E.166.229; 13.E.166.230; 13.E.166.231; 13.E.166.236;
13.E.166.237; 13.E.166.238; 13.E.166.239; 13.E.166.154; 13.E.166.157;
13.E.166.166; 13.E.166.169; 13.E.166.172; 13.E.166.175; 13.E.166.240;
13.E.166.244; 13.E.169.228; 13.E.169.229; 13.E.169.230; 13.E.169.231;
13.E.169.236; 13.E.169.237; 13.E.169.238; 13.E.169.239; 13.E.169.154;
13.E.169.157; 13.E.169.166; 13.E.169.169; 13.E.169.172; 13.E.169.175;
13.E.169.240; 13.E.169.244; 13.E.172.228; 13.E.172.229; 13.E.172.230;
13.E.172.231; 13.E.172.236; 13.E.172.237; 13.E.172.238; 13.E.172.239;
13.E.172.154; 13.E.172.157; 13.E.172.166; 13.E.172.169; 13.E.172.172;
13.E.172.175; 13.E.172.240; 13.E.172.244; 13.E.175.228; 13.E.175.229;
13.E.175.230; 13.E.175.231; 13.E.175.236; 13.E.175.237; 13.E.175.238;
13.E.175.239; 13.E.175.154; 13.E.175.157; 13.E.175.166; 13.E.175.169;
13.E.175.172; 13.E.175.175; 13.E.175.240; 13.E.175.244; 13.E.240.228;
13.E.240.229; 13.E.240.230; 13.E.240.231; 13.E.240.236; 13.E.240.237;
13.E.240.238; 13.E.240.239; 13.E.240.154; 13.E.240.157; 13.E.240.166;
13.E.240.169; 13.E.240.172; 13.E.240.175; 13.E.240.240; 13.E.240.244;
13.E.244.228; 13.E.244.229; 13.E.244.230; 13.E.244.231; 13.E.244.236;
13.E.244.237; 13.E.244.238; 13.E.244.239; 13.E.244.154; 13.E.244.157;
13.E.244.166; 13.E.244.169; 13.E.244.172; 13.E.244.175; 13.E.244.240;
13.E.244.244;

Prodrugs of 13.G

13.G.228.228; 13.G.228.229; 13.G.228.230; 13.G.228.231; 13.G.228.236;
13.G.228.237; 13.G.228.238; 13.G.228.239; 13.G.228.154; 13.G.228.157;
13.G.228.166; 13.G.228.169; 13.G.228.172; 13.G.228.175; 13.G.228.240;
13.G.228.244; 13.G.229.228; 13.G.229.229; 13.G.229.230; 13.G.229.231;
13.G.229.236; 13.G.229.237; 13.G.229.238; 13.G.229.239; 13.G.229.154;
13.G.229.157; 13.G.229.166; 13.G.229.169; 13.G.229.172; 13.G.229.175;
13.G.229.240; 13.G.229.244; 13.G.230.228; 13.G.230.229; 13.G.230.230;
13.G.230.231; 13.G.230.236; 13.G.230.237; 13.G.230.238; 13.G.230.239;
13.G.230.154; 13.G.230.157; 13.G.230.166; 13.G.230.169; 13.G.230.172;
13.G.230.175; 13.G.230.240; 13.G.230.244; 13.G.231.228; 13.G.231.229;
13.G.231.230; 13.G.231.231; 13.G.231.236; 13.G.231.237; 13.G.231.238;
13.G.231.239; 13.G.231.154; 13.G.231.157; 13.G.231.166; 13.G.231.169;
13.G.231.172; 13.G.231.175; 13.G.231.240; 13.G.231.244; 13.G.236.228;
13.G.236.229; 13.G.236.230; 13.G.236.231; 13.G.236.236; 13.G.236.237;
13.G.236.238; 13.G.236.239; 13.G.236.154; 13.G.236.157; 13.G.236.166;
13.G.236.169; 13.G.236.172; 13.G.236.175; 13.G.236.240; 13.G.236.244;
13.G.237.228; 13.G.237.229; 13.G.237.230; 13.G.237.231; 13.G.237.236;
13.G.237.237; 13.G.237.238; 13.G.237.239; 13.G.237.154; 13.G.237.157;
13.G.237.166; 13.G.237.169; 13.G.237.172; 13.G.237.175; 13.G.237.240;
13.G.237.244; 13.G.238.228; 13.G.238.229; 13.G.238.230; 13.G.238.231;
13.G.238.236; 13.G.238.237; 13.G.238.238; 13.G.238.239; 13.G.238.154;
13.G.238.157; 13.G.238.166; 13.G.238.169; 13.G.238.172; 13.G.238.175;
13.G.238.240; 13.G.238.244; 13.G.239.228; 13.G.239.229; 13.G.239.230;
13.G.239.231; 13.G.239.236; 13.G.239.237; 13.G.239.238; 13.G.239.239;
13.G.239.154; 13.G.239.157; 13.G.239.166; 13.G.239.169; 13.G.239.172;
13.G.239.175; 13.G.239.240; 13.G.239.244; 13.G.154.228; 13.G.154.229;
13.G.154.230; 13.G.154.231; 13.G.154.236; 13.G.154.237; 13.G.154.238;
13.G.154.239; 13.G.154.154; 13.G.154.157; 13.G.154.166; 13.G.154.169;
13.G.154.172; 13.G.154.175; 13.G.154.240; 13.G.154.244; 13.G.157.228;
13.G.157.229; 13.G.157.230; 13.G.157.231; 13.G.157.236; 13.G.157.237;
13.G.157.238; 13.G.157.239; 13.G.157.154; 13.G.157.157; 13.G.157.166;
13.G.157.169; 13.G.157.172; 13.G.157.175; 13.G.157.240; 13.G.157.244;
13.G.166.228; 13.G.166.229; 13.G.166.230; 13.G.166.231; 13.G.166.236;
13.G.166.237; 13.G.166.238; 13.G.166.239; 13.G.166.154; 13.G.166.157;
13.G.166.166; 13.G.166.169; 13.G.166.172; 13.G.166.175; 13.G.166.240;
13.G.166.244; 13.G.169.228; 13.G.169.229; 13.G.169.230; 13.G.169.231;
13.G.169.236; 13.G.169.237; 13.G.169.238; 13.G.169.239; 13.G.169.154;
13.G.169.157; 13.G.169.166; 13.G.169.169; 13.G.169.172; 13.G.169.175;
13.G.169.240; 13.G.169.244; 13.G.172.228; 13.G.172.229; 13.G.172.230;
13.G.172.231; 13.G.172.236; 13.G.172.237; 13.G.172.238; 13.G.172.239;
13.G.172.154; 13.G.172.157; 13.G.172.166; 13.G.172.169; 13.G.172.172;
13.G.172.175; 13.G.172.240; 13.G.172.244; 13.G.175.228; 13.G.175.229;
13.G.175.230; 13.G.175.231; 13.G.175.236; 13.G.175.237; 13.G.175.238;
13.G.175.239; 13.G.175.154; 13.G.175.157; 13.G.175.166; 13.G.175.169;
13.G.175.172; 13.G.175.175; 13.G.175.240; 13.G.175.244; 13.G.240.228;
13.G.240.229; 13.G.240.230; 13.G.240.231; 13.G.240.236; 13.G.240.237;
13.G.240.238; 13.G.240.239; 13.G.240.154; 13.G.240.157; 13.G.240.166;
13.G.240.169; 13.G.240.172; 13.G.240.175; 13.G.240.240; 13.G.240.244;
13.G.244.228; 13.G.244.229; 13.G.244.230; 13.G.244.231; 13.G.244.236;
13.G.244.237; 13.G.244.238; 13.G.244.239; 13.G.244.154; 13.G.244.157;
13.G.244.166; 13.G.244.169; 13.G.244.172; 13.G.244.175; 13.G.244.240;
13.G.244.244;

TABLE 100-continued

Prodrugs of 13.I

13.I.228.228; 13.I.228.229; 13.I.228.230; 13.I.228.231; 13.I.228.236;
13.I.228.237; 13.I.228.238; 13.I.228.239; 13.I.228.154; 13.I.228.157;
13.I.228.166; 13.I.228.169; 13.I.228.172; 13.I.228.175; 13.I.228.240;
13.I.228.244; 13.I.229.228; 13.I.229.229; 13.I.229.230; 13.I.229.231;
13.I.229.236; 13.I.229.237; 13.I.229.238; 13.I.229.239; 13.I.229.154;
13.I.229.157; 13.I.229.166; 13.I.229.169; 13.I.229.172; 13.I.229.175;
13.I.229.240; 13.I.229.244; 13.I.230.228; 13.I.230.229; 13.I.230.230;
13.I.230.231; 13.I.230.236; 13.I.230.237; 13.I.230.238; 13.I.230.239;
13.I.230.154; 13.I.230.157; 13.I.230.166; 13.I.230.169; 13.I.230.172;
13.I.230.175; 13.I.230.240; 13.I.230.244; 13.I.231.228; 13.I.231.229;
13.I.231.230; 13.I.231.231; 13.I.231.236; 13.I.231.237; 13.I.231.238;
13.I.231.239; 13.I.231.154; 13.I.231.157; 13.I.231.166; 13.I.231.169;
13.I.231.172; 13.I.231.175; 13.I.231.240; 13.I.231.244; 13.I.236.228;
13.I.236.229; 13.I.236.230; 13.I.236.231; 13.I.236.236; 13.I.236.237;
13.I.236.238; 13.I.236.239; 13.I.236.154; 13.I.236.157; 13.I.236.166;
13.I.236.169; 13.I.236.172; 13.I.236.175; 13.I.236.240; 13.I.236.244;
13.I.237.228; 13.I.237.229; 13.I.237.230; 13.I.237.231; 13.I.237.236;
13.I.237.237; 13.I.237.238; 13.I.237.239; 13.I.237.154; 13.I.237.157;
13.I.237.166; 13.I.237.169; 13.I.237.172; 13.I.237.175; 13.I.237.240;
13.I.237.244; 13.I.238.228; 13.I.238.229; 13.I.238.230; 13.I.238.231;
13.I.238.236; 13.I.238.237; 13.I.238.238; 13.I.238.239; 13.I.238.154;
13.I.238.157; 13.I.238.166; 13.I.238.169; 13.I.238.172; 13.I.238.175;
13.I.238.240; 13.I.238.244; 13.I.239.228; 13.I.239.229; 13.I.239.230;
13.I.239.231; 13.I.239.236; 13.I.239.237; 13.I.239.238; 13.I.239.239;
13.I.239.154; 13.I.239.157; 13.I.239.166; 13.I.239.169; 13.I.239.172;
13.I.239.175; 13.I.239.240; 13.I.239.244; 13.I.154.228; 13.I.154.229;
13.I.154.230; 13.I.154.231; 13.I.154.236; 13.I.154.237; 13.I.154.238;
13.I.154.239; 13.I.154.154; 13.I.154.157; 13.I.154.166; 13.I.154.169;
13.I.154.172; 13.I.154.175; 13.I.154.240; 13.I.154.244; 13.I.157.228;
13.I.157.229; 13.I.157.230; 13.I.157.231; 13.I.157.236; 13.I.157.237;
13.I.157.238; 13.I.157.239; 13.I.157.154; 13.I.157.157; 13.I.157.166;
13.I.157.169; 13.I.157.172; 13.I.157.175; 13.I.157.240; 13.I.157.244;
13.I.166.228; 13.I.166.229; 13.I.166.230; 13.I.166.231; 13.I.166.236;
13.I.166.237; 13.I.166.238; 13.I.166.239; 13.I.166.154; 13.I.166.157;
13.I.166.166; 13.I.166.169; 13.I.166.172; 13.I.166.175; 13.I.166.240;
13.I.166.244; 13.I.169.228; 13.I.169.229; 13.I.169.230; 13.I.169.231;
13.I.169.236; 13.I.169.237; 13.I.169.238; 13.I.169.239; 13.I.169.154;
13.I.169.157; 13.I.169.166; 13.I.169.169; 13.I.169.172; 13.I.169.175;
13.I.169.240; 13.I.169.244; 13.I.172.228; 13.I.172.229; 13.I.172.230;
13.I.172.231; 13.I.172.236; 13.I.172.237; 13.I.172.238; 13.I.172.239;
13.I.172.154; 13.I.172.157; 13.I.172.166; 13.I.172.169; 13.I.172.172;
13.I.172.175; 13.I.172.240; 13.I.172.244; 13.I.175.228; 13.I.175.229;
13.I.175.230; 13.I.175.231; 13.I.175.236; 13.I.175.237; 13.I.175.238;
13.I.175.239; 13.I.175.154; 13.I.175.157; 13.I.175.166; 13.I.175.169;
13.I.175.172; 13.I.175.175; 13.I.175.240; 13.I.175.244; 13.I.240.228;
13.I.240.229; 13.I.240.230; 13.I.240.231; 13.I.240.236; 13.I.240.237;
13.I.240.238; 13.I.240.239; 13.I.240.154; 13.I.240.157; 13.I.240.166;
13.I.240.169; 13.I.240.172; 13.I.240.175; 13.I.240.240; 13.I.240.244;
13.I.244.228; 13.I.244.229; 13.I.244.230; 13.I.244.231; 13.I.244.236;
13.I.244.237; 13.I.244.238; 13.I.244.239; 13.I.244.154; 13.I.244.157;
13.I.244.166; 13.I.244.169; 13.I.244.172; 13.I.244.175; 13.I.244.240;
13.I.244.244;

Prodrugs of 13.J

13.J.228.228; 13.J.228.229; 13.J.228.230; 13.J.228.231; 13.J.228.236;
13.J.228.237; 13.J.228.238; 13.J.228.239; 13.J.228.154; 13.J.228.157;
13.J.228.166; 13.J.228.169; 13.J.228.172; 13.J.228.175; 13.J.228.240;
13.J.228.244; 13.J.229.228; 13.J.229.229; 13.J.229.230; 13.J.229.231;
13.J.229.236; 13.J.229.237; 13.J.229.238; 13.J.229.239; 13.J.229.154;
13.J.229.157; 13.J.229.166; 13.J.229.169; 13.J.229.172; 13.J.229.175;
13.J.229.240; 13.J.229.244; 13.J.230.228; 13.J.230.229; 13.J.230.230;
13.J.230.231; 13.J.230.236; 13.J.230.237; 13.J.230.238; 13.J.230.239;
13.J.230.154; 13.J.230.157; 13.J.230.166; 13.J.230.169; 13.J.230.172;
13.J.230.175; 13.J.230.240; 13.J.230.244; 13.J.231.228; 13.J.231.229;
13.J.231.230; 13.J.231.231; 13.J.231.236; 13.J.231.237; 13.J.231.238;
13.J.231.239; 13.J.231.154; 13.J.231.157; 13.J.231.166; 13.J.231.169;
13.J.231.172; 13.J.231.175; 13.J.231.240; 13.J.231.244; 13.J.236.228;
13.J.236.229; 13.J.236.230; 13.J.236.231; 13.J.236.236; 13.J.236.237;
13.J.236.238; 13.J.236.239; 13.J.236.154; 13.J.236.157; 13.J.236.166;
13.J.236.169; 13.J.236.172; 13.J.236.175; 13.J.236.240; 13.J.236.244;
13.J.237.228; 13.J.237.229; 13.J.237.230; 13.J.237.231; 13.J.237.236;
13.J.237.237; 13.J.237.238; 13.J.237.239; 13.J.237.154; 13.J.237.157;
13.J.237.166; 13.J.237.169; 13.J.237.172; 13.J.237.175; 13.J.237.240;
13.J.237.244; 13.J.238.228; 13.J.238.229; 13.J.238.230; 13.J.238.231;
13.J.238.236; 13.J.238.237; 13.J.238.238; 13.J.238.239; 13.J.238.154;
13.J.238.157; 13.J.238.166; 13.J.238.169; 13.J.238.172; 13.J.238.175;
13.J.238.240; 13.J.238.244; 13.J.239.228; 13.J.239.229; 13.J.239.230;

TABLE 100-continued

13.J.239.231; 13.J.239.236; 13.J.239.237; 13.J.239.238; 13.J.239.239;
13.J.239.154; 13.J.239.157; 13.J.239.166; 13.J.239.169; 13.J.239.172;
13.J.239.175; 13.J.239.240; 13.J.239.244; 13.J.154.228; 13.J.154.229;
13.J.154.230; 13.J.154.231; 13.J.154.236; 13.J.154.237; 13.J.154.238;
13.J.154.239; 13.J.154.154; 13.J.154.157; 13.J.154.166; 13.J.154.169;
13.J.154.172; 13.J.154.175; 13.J.154.240; 13.J.154.244; 13.J.157.228;
13.J.157.229; 13.J.157.230; 13.J.157.231; 13.J.157.236; 13.J.157.237;
13.J.157.238; 13.J.157.239; 13.J.157.154; 13.J.157.157; 13.J.157.166;
13.J.157.169; 13.J.157.172; 13.J.157.175; 13.J.157.240; 13.J.157.244;
13.J.166.228; 13.J.166.229; 13.J.166.230; 13.J.166.231; 13.J.166.236;
13.J.166.237; 13.J.166.238; 13.J.166.239; 13.J.166.154; 13.J.166.157;
13.J.166.166; 13.J.166.169; 13.J.166.172; 13.J.166.175; 13.J.166.240;
13.J.166.244; 13.J.169.228; 13.J.169.229; 13.J.169.230; 13.J.169.231;
13.J.169.236; 13.J.169.237; 13.J.169.238; 13.J.169.239; 13.J.169.154;
13.J.169.157; 13.J.169.166; 13.J.169.169; 13.J.169.172; 13.J.169.175;
13.J.169.240; 13.J.169.244; 13.J.172.228; 13.J.172.229; 13.J.172.230;
13.J.172.231; 13.J.172.236; 13.J.172.237; 13.J.172.238; 13.J.172.239;
13.J.172.154; 13.J.172.157; 13.J.172.166; 13.J.172.169; 13.J.172.172;
13.J.172.175; 13.J.172.240; 13.J.172.244; 13.J.175.228; 13.J.175.229;
13.J.175.230; 13.J.175.231; 13.J.175.236; 13.J.175.237; 13.J.175.238;
13.J.175.239; 13.J.175.154; 13.J.175.157; 13.J.175.166; 13.J.175.169;
13.J.175.172; 13.J.175.175; 13.J.175.240; 13.J.175.244; 13.J.240.228;
13.J.240.229; 13.J.240.230; 13.J.240.231; 13.J.240.236; 13.J.240.237;
13.J.240.238; 13.J.240.239; 13.J.240.154; 13.J.240.157; 13.J.240.166;
13.J.240.169; 13.J.240.172; 13.J.240.175; 13.J.240.240; 13.J.240.244;
13.J.244.228; 13.J.244.229; 13.J.244.230; 13.J.244.231; 13.J.244.236;
13.J.244.237; 13.J.244.238; 13.J.244.239; 13.J.244.154; 13.J.244.157;
13.J.244.166; 13.J.244.169; 13.J.244.172; 13.J.244.175; 13.J.244.240;
13.J.244.244;
Prodrugs of 13.L 13.L.228.228; 13.L.228.229; 13.L.228.230; 13.L.228.231; 13.L.228.236;
13.L.228.237; 13.L.228.238; 13.L.228.239; 13.L.228.154; 13.L.228.157;
13.L.228.166; 13.L.228.169; 13.L.228.172; 13.L.228.175; 13.L.228.240;
13.L.228.244; 13.L.229.228; 13.L.229.229; 13.L.229.230; 13.L.229.231;
13.L.229.236; 13.L.229.237; 13.L.229.238; 13.L.229.239; 13.L.229.154;
13.L.229.157; 13.L.229.166; 13.L.229.169; 13.L.229.172; 13.L.229.175;
13.L.229.240; 13.L.229.244; 13.L.230.228; 13.L.230.229; 13.L.230.230;
13.L.230.231; 13.L.230.236; 13.L.230.237; 13.L.230.238; 13.L.230.239;
13.L.230.154; 13.L.230.157; 13.L.230.166; 13.L.230.169; 13.L.230.172;
13.L.230.175; 13.L.230.240; 13.L.230.244; 13.L.231.228; 13.L.231.229;
13.L.231.230; 13.L.231.231; 13.L.231.236; 13.L.231.237; 13.L.231.238;
13.L.231.239; 13.L.231.154; 13.L.231.157; 13.L.231.166; 13.L.231.169;
13.L.231.172; 13.L.231.175; 13.L.231.240; 13.L.231.244; 13.L.236.228;
13.L.236.229; 13.L.236.230; 13.L.236.231; 13.L.236.236; 13.L.236.237;
13.L.236.238; 13.L.236.239; 13.L.236.154; 13.L.236.157; 13.L.236.166;
13.L.236.169; 13.L.236.172; 13.L.236.175; 13.L.236.240; 13.L.236.244;
13.L.237.228; 13.L.237.229; 13.L.237.230; 13.L.237.231; 13.L.237.236;
13.L.237.237; 13.L.237.238; 13.L.237.239; 13.L.237.154; 13.L.237.157;
13.L.237.166; 13.L.237.169; 13.L.237.172; 13.L.237.175; 13.L.237.240;
13.L.237.244; 13.L.238.228; 13.L.238.229; 13.L.238.230; 13.L.238.231;
13.L.238.236; 13.L.238.237; 13.L.238.238; 13.L.238.239; 13.L.238.154;
13.L.238.157; 13.L.238.166; 13.L.238.169; 13.L.238.172; 13.L.238.175;
13.L.238.240; 13.L.238.244; 13.L.239.228; 13.L.239.229; 13.L.239.230;
13.L.239.231; 13.L.239.236; 13.L.239.237; 13.L.239.238; 13.L.239.239;
13.L.239.154; 13.L.239.157; 13.L.239.166; 13.L.239.169; 13.L.239.172;
13.L.239.175; 13.L.239.240; 13.L.239.244; 13.L.154.228; 13.L.154.229;
13.L.154.230; 13.L.154.231; 13.L.154.236; 13.L.154.237; 13.L.154.238;
13.L.154.239; 13.L.154.154; 13.L.154.157; 13.L.154.166; 13.L.154.169;
13.L.154.172; 13.L.154.175; 13.L.154.240; 13.L.154.244; 13.L.157.228;
13.L.157.229; 13.L.157.230; 13.L.157.231; 13.L.157.236; 13.L.157.237;
13.L.157.238; 13.L.157.239; 13.L.157.154; 13.L.157.157; 13.L.157.166;
13.L.157.169; 13.L.157.172; 13.L.157.175; 13.L.157.240; 13.L.157.244;
13.L.166.228; 13.L.166.229; 13.L.166.230; 13.L.166.231; 13.L.166.236;
13.L.166.237; 13.L.166.238; 13.L.166.239; 13.L.166.154; 13.L.166.157;
13.L.166.166; 13.L.166.169; 13.L.166.172; 13.L.166.175; 13.L.166.240;
13.L.166.244; 13.L.169.228; 13.L.169.229; 13.L.169.230; 13.L.169.231;
13.L.169.236; 13.L.169.237; 13.L.169.238; 13.L.169.239; 13.L.169.154;
13.L.169.157; 13.L.169.166; 13.L.169.169; 13.L.169.172; 13.L.169.175;
13.L.169.240; 13.L.169.244; 13.L.172.228; 13.L.172.229; 13.L.172.230;
13.L.172.231; 13.L.172.236; 13.L.172.237; 13.L.172.238; 13.L.172.239;
13.L.172.154; 13.L.172.157; 13.L.172.166; 13.L.172.169; 13.L.172.172;
13.L.172.175; 13.L.172.240; 13.L.172.244; 13.L.175.228; 13.L.175.229;
13.L.175.230; 13.L.175.231; 13.L.175.236; 13.L.175.237; 13.L.175.238;
13.L.175.239; 13.L.175.154; 13.L.175.157; 13.L.175.166; 13.L.175.169;
13.L.175.172; 13.L.175.175; 13.L.175.240; 13.L.175.244; 13.L.240.228;
13.L.240.229; 13.L.240.230; 13.L.240.231; 13.L.240.236; 13.L.240.237;
13.L.240.238; 13.L.240.239; 13.L.240.154; 13.L.240.157; 13.L.240.166;
13.L.240.169; 13.L.240.172; 13.L.240.175; 13.L.240.240; 13.L.240.244;

TABLE 100-continued

13.L.244.228; 13.L.244.229; 13.L.244.230; 13.L.244.231; 13.L.244.236;
13.L.244.237; 13.L.244.238; 13.L.244.239; 13.L.244.154; 13.L.244.157;
13.L.244.166; 13.L.244.169; 13.L.244.172; 13.L.244.175; 13.L.244.240;
13.L.244.244;
Prodrugs of 13.O 13.O.228.228; 13.O.228.229; 13.O.228.230; 13.O.228.231; 13.O.228.236;
13.O.228.237; 13.O.228.238; 13.O.228.239; 13.O.228.154; 13.O.228.157;
13.O.228.166; 13.O.228.169; 13.O.228.172; 13.O.228.175; 13.O.228.240;
13.O.228.244; 13.O.229.228; 13.O.229.229; 13.O.229.230; 13.O.229.231;
13.O.229.236; 13.O.229.237; 13.O.229.238; 13.O.229.239; 13.O.229.154;
13.O.229.157; 13.O.229.166; 13.O.229.169; 13.O.229.172; 13.O.229.175;
13.O.229.240; 13.O.229.244; 13.O.230.228; 13.O.230.229; 13.O.230.230;
13.O.230.231; 13.O.230.236; 13.O.230.237; 13.O.230.238; 13.O.230.239;
13.O.230.154; 13.O.230.157; 13.O.230.166; 13.O.230.169; 13.O.230.172;
13.O.230.175; 13.O.230.240; 13.O.230.244; 13.O.231.228; 13.O.231.229;
13.O.231.230; 13.O.231.231; 13.O.231.236; 13.O.231.237; 13.O.231.238;
13.O.231.239; 13.O.231.154; 13.O.231.157; 13.O.231.166; 13.O.231.169;
13.O.231.172; 13.O.231.175; 13.O.231.240; 13.O.231.244; 13.O.236.228;
13.O.236.229; 13.O.236.230; 13.O.236.231; 13.O.236.236; 13.O.236.237;
13.O.236.238; 13.O.236.239; 13.O.236.154; 13.O.236.157; 13.O.236.166;
13.O.236.169; 13.O.236.172; 13.O.236.175; 13.O.236.240; 13.O.236.244;
13.O.237.228; 13.O.237.229; 13.O.237.230; 13.O.237.231; 13.O.237.236;
13.O.237.237; 13.O.237.238; 13.O.237.239; 13.O.237.154; 13.O.237.157;
13.O.237.166; 13.O.237.169; 13.O.237.172; 13.O.237.175; 13.O.237.240;
13.O.237.244; 13.O.238.228; 13.O.238.229; 13.O.238.230; 13.O.238.231;
13.O.238.236; 13.O.238.237; 13.O.238.238; 13.O.238.239; 13.O.238.154;
13.O.238.157; 13.O.238.166; 13.O.238.169; 13.O.238.172; 13.O.238.175;
13.O.238.240; 13.O.238.244; 13.O.239.228; 13.O.239.229; 13.O.239.230;
13.O.239.231; 13.O.239.236; 13.O.239.237; 13.O.239.238; 13.O.239.239;
13.O.239.154; 13.O.239.157; 13.O.239.166; 13.O.239.169; 13.O.239.172;
13.O.239.175; 13.O.239.240; 13.O.239.244; 13.O.154.228; 13.O.154.229;
13.O.154.230; 13.O.154.231; 13.O.154.236; 13.O.154.237; 13.O.154.238;
13.O.154.239; 13.O.154.154; 13.O.154.157; 13.O.154.166; 13.O.154.169;
13.O.154.172; 13.O.154.175; 13.O.154.240; 13.O.154.244; 13.O.157.228;
13.O.157.229; 13.O.157.230; 13.O.157.231; 13.O.157.236; 13.O.157.237;
13.O.157.238; 13.O.157.239; 13.O.157.154; 13.O.157.157; 13.O.157.166;
13.O.157.169; 13.O.157.172; 13.O.157.175; 13.O.157.240; 13.O.157.244;
13.O.166.228; 13.O.166.229; 13.O.166.230; 13.O.166.231; 13.O.166.236;
13.O.166.237; 13.O.166.238; 13.O.166.239; 13.O.166.154; 13.O.166.157;
13.O.166.166; 13.O.166.169; 13.O.166.172; 13.O.166.175; 13.O.166.240;
13.O.166.244; 13.O.169.228; 13.O.169.229; 13.O.169.230; 13.O.169.231;
13.O.169.236; 13.O.169.237; 13.O.169.238; 13.O.169.239; 13.O.169.154;
13.O.169.157; 13.O.169.166; 13.O.169.169; 13.O.169.172; 13.O.169.175;
13.O.169.240; 13.O.169.244; 13.O.172.228; 13.O.172.229; 13.O.172.230;
13.O.172.231; 13.O.172.236; 13.O.172.237; 13.O.172.238; 13.O.172.239;
13.O.172.154; 13.O.172.157; 13.O.172.166; 13.O.172.169; 13.O.172.172;
13.O.172.175; 13.O.172.240; 13.O.172.244; 13.O.175.228; 13.O.175.229;
13.O.175.230; 13.O.175.231; 13.O.175.236; 13.O.175.237; 13.O.175.238;
13.O.175.239; 13.O.175.154; 13.O.175.157; 13.O.175.166; 13.O.175.169;
13.O.175.172; 13.O.175.175; 13.O.175.240; 13.O.175.244; 13.O.240.228;
13.O.240.229; 13.O.240.230; 13.O.240.231; 13.O.240.236; 13.O.240.237;
13.O.240.238; 13.O.240.239; 13.O.240.154; 13.O.240.157; 13.O.240.166;
13.O.240.169; 13.O.240.172; 13.O.240.175; 13.O.240.240; 13.O.240.244;
13.O.244.228; 13.O.244.229; 13.O.244.230; 13.O.244.231; 13.O.244.236;
13.O.244.237; 13.O.244.238; 13.O.244.239; 13.O.244.154; 13.O.244.157;
13.O.244.166; 13.O.244.169; 13.O.244.172; 13.O.244.175; 13.O.244.240;
13.O.244.244;
Prodrugs of 13.P 13.P.228.228; 13.P.228.229; 13.P.228.230; 13.P.228.231; 13.P.228.236;
13.P.228.237; 13.P.228.238; 13.P.228.239; 13.P.228.154; 13.P.228.157;
13.P.228.166; 13.P.228.169; 13.P.228.172; 13.P.228.175; 13.P.228.240;
13.P.228.244; 13.P.229.228; 13.P.229.229; 13.P.229.230; 13.P.229.231;
13.P.229.236; 13.P.229.237; 13.P.229.238; 13.P.229.239; 13.P.229.154;
13.P.229.157; 13.P.229.166; 13.P.229.169; 13.P.229.172; 13.P.229.175;
13.P.229.240; 13.P.229.244; 13.P.230.228; 13.P.230.229; 13.P.230.230;
13.P.230.231; 13.P.230.236; 13.P.230.237; 13.P.230.238; 13.P.230.239;
13.P.230.154; 13.P.230.157; 13.P.230.166; 13.P.230.169; 13.P.230.172;
13.P.230.175; 13.P.230.240; 13.P.230.244; 13.P.231.228; 13.P.231.229;
13.P.231.230; 13.P.231.231; 13.P.231.236; 13.P.231.237; 13.P.231.238;
13.P.231.239; 13.P.231.154; 13.P.231.157; 13.P.231.166; 13.P.231.169;
13.P.231.172; 13.P.231.175; 13.P.231.240; 13.P.231.244; 13.P.236.228;
13.P.236.229; 13.P.236.230; 13.P.236.231; 13.P.236.236; 13.P.236.237;
13.P.236.238; 13.P.236.239; 13.P.236.154; 13.P.236.157; 13.P.236.166;
13.P.236.169; 13.P.236.172; 13.P.236.175; 13.P.236.240; 13.P.236.244;
13.P.237.228; 13.P.237.229; 13.P.237.230; 13.P.237.231; 13.P.237.236;
13.P.237.237; 13.P.237.238; 13.P.237.239; 13.P.237.154; 13.P.237.157;
13.P.237.166; 13.P.237.169; 13.P.237.172; 13.P.237.175; 13.P.237.240;

TABLE 100-continued

13.P.237.244; 13.P.238.228; 13.P.238.229; 13.P.238.230; 13.P.238.231;
13.P.238.236; 13.P.238.237; 13.P.238.238; 13.P.238.239; 13.P.238.154;
13.P.238.157; 13.P.238.166; 13.P.238.169; 13.P.238.172; 13.P.238.175;
13.P.238.240; 13.P.238.244; 13.P.239.228; 13.P.239.229; 13.P.239.230;
13.P.239.231; 13.P.239.236; 13.P.239.237; 13.P.239.238; 13.P.239.239;
13.P.239.154; 13.P.239.157; 13.P.239.166; 13.P.239.169; 13.P.239.172;
13.P.239.175; 13.P.239.240; 13.P.239.244; 13.P.154.228; 13.P.154.229;
13.P.154.230; 13.P.154.231; 13.P.154.236; 13.P.154.237; 13.P.154.238;
13.P.154.239; 13.P.154.154; 13.P.154.157; 13.P.154.166; 13.P.154.169;
13.P.154.172; 13.P.154.175; 13.P.154.240; 13.P.154.244; 13.P.157.228;
13.P.157.229; 13.P.157.230; 13.P.157.231; 13.P.157.236; 13.P.157.237;
13.P.157.238; 13.P.157.239; 13.P.157.154; 13.P.157.157; 13.P.157.166;
13.P.157.169; 13.P.157.172; 13.P.157.175; 13.P.157.240; 13.P.157.244;
13.P.166.228; 13.P.166.229; 13.P.166.230; 13.P.166.231; 13.P.166.236;
13.P.166.237; 13.P.166.238; 13.P.166.239; 13.P.166.154; 13.P.166.157;
13.P.166.166; 13.P.166.169; 13.P.166.172; 13.P.166.175; 13.P.166.240;
13.P.166.244; 13.P.169.228; 13.P.169.229; 13.P.169.230; 13.P.169.231;
13.P.169.236; 13.P.169.237; 13.P.169.238; 13.P.169.239; 13.P.169.154;
13.P.169.157; 13.P.169.166; 13.P.169.169; 13.P.169.172; 13.P.169.175;
13.P.169.240; 13.P.169.244; 13.P.172.228; 13.P.172.229; 13.P.172.230;
13.P.172.231; 13.P.172.236; 13.P.172.237; 13.P.172.238; 13.P.172.239;
13.P.172.154; 13.P.172.157; 13.P.172.166; 13.P.172.169; 13.P.172.172;
13.P.172.175; 13.P.172.240; 13.P.172.244; 13.P.175.228; 13.P.175.229;
13.P.175.230; 13.P.175.231; 13.P.175.236; 13.P.175.237; 13.P.175.238;
13.P.175.239; 13.P.175.154; 13.P.175.157; 13.P.175.166; 13.P.175.169;
13.P.175.172; 13.P.175.175; 13.P.175.240; 13.P.175.244; 13.P.240.228;
13.P.240.229; 13.P.240.230; 13.P.240.231; 13.P.240.236; 13.P.240.237;
13.P.240.238; 13.P.240.239; 13.P.240.154; 13.P.240.157; 13.P.240.166;
13.P.240.169; 13.P.240.172; 13.P.240.175; 13.P.240.240; 13.P.240.244;
13.P.244.228; 13.P.244.229; 13.P.244.230; 13.P.244.231; 13.P.244.236;
13.P.244.237; 13.P.244.238; 13.P.244.239; 13.P.244.154; 13.P.244.157;
13.P.244.166; 13.P.244.169; 13.P.244.172; 13.P.244.175; 13.P.244.240;
13.P.244.244;

Prodrugs of 13.U

13.U.228.228; 13.U.228.229; 13.U.228.230; 13.U.228.231; 13.U.228.236;
13.U.228.237; 13.U.228.238; 13.U.228.239; 13.U.228.154; 13.U.228.157;
13.U.228.166; 13.U.228.169; 13.U.228.172; 13.U.228.175; 13.U.228.240;
13.U.228.244; 13.U.229.228; 13.U.229.229; 13.U.229.230; 13.U.229.231;
13.U.229.236; 13.U.229.237; 13.U.229.238; 13.U.229.239; 13.U.229.154;
13.U.229.157; 13.U.229.166; 13.U.229.169; 13.U.229.172; 13.U.229.175;
13.U.229.240; 13.U.229.244; 13.U.230.228; 13.U.230.229; 13.U.230.230;
13.U.230.231; 13.U.230.236; 13.U.230.237; 13.U.230.238; 13.U.230.239;
13.U.230.154; 13.U.230.157; 13.U.230.166; 13.U.230.169; 13.U.230.172;
13.U.230.175; 13.U.230.240; 13.U.230.244; 13.U.231.228; 13.U.231.229;
13.U.231.230; 13.U.231.231; 13.U.231.236; 13.U.231.237; 13.U.231.238;
13.U.231.239; 13.U.231.154; 13.U.231.157; 13.U.231.166; 13.U.231.169;
13.U.231.172; 13.U.231.175; 13.U.231.240; 13.U.231.244; 13.U.236.228;
13.U.236.229; 13.U.236.230; 13.U.236.231; 13.U.236.236; 13.U.236.237;
13.U.236.238; 13.U.236.239; 13.U.236.154; 13.U.236.157; 13.U.236.166;
13.U.236.169; 13.U.236.172; 13.U.236.175; 13.U.236.240; 13.U.236.244;
13.U.237.228; 13.U.237.229; 13.U.237.230; 13.U.237.231; 13.U.237.236;
13.U.237.237; 13.U.237.238; 13.U.237.239; 13.U.237.154; 13.U.237.157;
13.U.237.166; 13.U.237.169; 13.U.237.172; 13.U.237.175; 13.U.237.240;
13.U.237.244; 13.U.238.228; 13.U.238.229; 13.U.238.230; 13.U.238.231;
13.U.238.236; 13.U.238.237; 13.U.238.238; 13.U.238.239; 13.U.238.154;
13.U.238.157; 13.U.238.166; 13.U.238.169; 13.U.238.172; 13.U.238.175;
13.U.238.240; 13.U.238.244; 13.U.239.228; 13.U.239.229; 13.U.239.230;
13.U.239.231; 13.U.239.236; 13.U.239.237; 13.U.239.238; 13.U.239.239;
13.U.239.154; 13.U.239.157; 13.U.239.166; 13.U.239.169; 13.U.239.172;
13.U.239.175; 13.U.239.240; 13.U.239.244; 13.U.154.228; 13.U.154.229;
13.U.154.230; 13.U.154.231; 13.U.154.236; 13.U.154.237; 13.U.154.238;
13.U.154.239; 13.U.154.154; 13.U.154.157; 13.U.154.166; 13.U.154.169;
13.U.154.172; 13.U.154.175; 13.U.154.240; 13.U.154.244; 13.U.157.228;
13.U.157.229; 13.U.157.230; 13.U.157.231; 13.U.157.236; 13.U.157.237;
13.U.157.238; 13.U.157.239; 13.U.157.154; 13.U.157.157; 13.U.157.166;
13.U.157.169; 13.U.157.172; 13.U.157.175; 13.U.157.240; 13.U.157.244;
13.U.166.228; 13.U.166.229; 13.U.166.230; 13.U.166.231; 13.U.166.236;
13.U.166.237; 13.U.166.238; 13.U.166.239; 13.U.166.154; 13.U.166.157;
13.U.166.166; 13.U.166.169; 13.U.166.172; 13.U.166.175; 13.U.166.240;
13.U.166.244; 13.U.169.228; 13.U.169.229; 13.U.169.230; 13.U.169.231;
13.U.169.236; 13.U.169.237; 13.U.169.238; 13.U.169.239; 13.U.169.154;
13.U.169.157; 13.U.169.166; 13.U.169.169; 13.U.169.172; 13.U.169.175;
13.U.169.240; 13.U.169.244; 13.U.172.228; 13.U.172.229; 13.U.172.230;
13.U.172.231; 13.U.172.236; 13.U.172.237; 13.U.172.238; 13.U.172.239;
13.U.172.154; 13.U.172.157; 13.U.172.166; 13.U.172.169; 13.U.172.172;
13.U.172.175; 13.U.172.240; 13.U.172.244; 13.U.175.228; 13.U.175.229;
13.U.175.230; 13.U.175.231; 13.U.175.236; 13.U.175.237; 13.U.175.238;
13.U.175.239; 13.U.175.154; 13.U.175.157; 13.U.175.166; 13.U.175.169;

TABLE 100-continued

13.U.175.172; 13.U.175.175; 13.U.175.240; 13.U.175.244; 13.U.240.228;
13.U.240.229; 13.U.240.230; 13.U.240.231; 13.U.240.236; 13.U.240.237;
13.U.240.238; 13.U.240.239; 13.U.240.154; 13.U.240.157; 13.U.240.166;
13.U.240.169; 13.U.240.172; 13.U.240.175; 13.U.240.240; 13.U.240.244;
13.U.244.228; 13.U.244.229; 13.U.244.230; 13.U.244.231; 13.U.244.236;
13.U.244.237; 13.U.244.238; 13.U.244.239; 13.U.244.154; 13.U.244.157;
13.U.244.166; 13.U.244.169; 13.U.244.172; 13.U.244.175; 13.U.244.240; 13.U.244.244;

Prodrugs of 13.W

13.W.228.228; 13.W.228.229; 13.W.228.230; 13.W.228.231; 13.W.228.236;
13.W.228.237; 13.W.228.238; 13.W.228.239; 13.W.228.154; 13.W.228.157;
13.W.228.166; 13.W.228.169; 13.W.228.172; 13.W.228.175; 13.W.228.240;
13.W.228.244; 13.W.229.228; 13.W.229.229; 13.W.229.230; 13.W.229.231;
13.W.229.236; 13.W.229.237; 13.W.229.238; 13.W.229.239; 13.W.229.154;
13.W.229.157; 13.W.229.166; 13.W.229.169; 13.W.229.172; 13.W.229.175;
13.W.229.240; 13.W.229.244; 13.W.230.228; 13.W.230.229; 13.W.230.230;
13.W.230.231; 13.W.230.236; 13.W.230.237; 13.W.230.238; 13.W.230.239;
13.W.230.154; 13.W.230.157; 13.W.230.166; 13.W.230.169; 13.W.230.172;
13.W.230.175; 13.W.230.240; 13.W.230.244; 13.W.231.228; 13.W.231.229;
13.W.231.230; 13.W.231.231; 13.W.231.236; 13.W.231.237; 13.W.231.238;
13.W.231.239; 13.W.231.154; 13.W.231.157; 13.W.231.166; 13.W.231.169;
13.W.231.172; 13.W.231.175; 13.W.231.240; 13.W.231.244; 13.W.236.228;
13.W.236.229; 13.W.236.230; 13.W.236.231; 13.W.236.236; 13.W.236.237;
13.W.236.238; 13.W.236.239; 13.W.236.154; 13.W.236.157; 13.W.236.166;
13.W.236.169; 13.W.236.172; 13.W.236.175; 13.W.236.240; 13.W.236.244;
13.W.237.228; 13.W.237.229; 13.W.237.230; 13.W.237.231; 13.W.237.236;
13.W.237.237; 13.W.237.238; 13.W.237.239; 13.W.237.154; 13.W.237.157;
13.W.237.166; 13.W.237.169; 13.W.237.172; 13.W.237.175; 13.W.237.240;
13.W.237.244; 13.W.238.228; 13.W.238.229; 13.W.238.230; 13.W.238.231;
13.W.238.236; 13.W.238.237; 13.W.238.238; 13.W.238.239; 13.W.238.154;
13.W.238.157; 13.W.238.166; 13.W.238.169; 13.W.238.172; 13.W.238.175;
13.W.238.240; 13.W.238.244; 13.W.239.228; 13.W.239.229; 13.W.239.230;
13.W.239.231; 13.W.239.236; 13.W.239.237; 13.W.239.238; 13.W.239.239;
13.W.239.154; 13.W.239.157; 13.W.239.166; 13.W.239.169; 13.W.239.172;
13.W.239.175; 13.W.239.240; 13.W.239.244; 13.W.154.228; 13.W.154.229;
13.W.154.230; 13.W.154.231; 13.W.154.236; 13.W.154.237; 13.W.154.238;
13.W.154.239; 13.W.154.154; 13.W.154.157; 13.W.154.166; 13.W.154.169;
13.W.154.172; 13.W.154.175; 13.W.154.240; 13.W.154.244; 13.W.157.228;
13.W.157.229; 13.W.157.230; 13.W.157.231; 13.W.157.236; 13.W.157.237;
13.W.157.238; 13.W.157.239; 13.W.157.154; 13.W.157.157; 13.W.157.166;
13.W.157.169; 13.W.157.172; 13.W.157.175; 13.W.157.240; 13.W.157.244;
13.W.166.228; 13.W.166.229; 13.W.166.230; 13.W.166.231; 13.W.166.236;
13.W.166.237; 13.W.166.238; 13.W.166.239; 13.W.166.154; 13.W.166.157;
13.W.166.166; 13.W.166.169; 13.W.166.172; 13.W.166.175; 13.W.166.240;
13.W.166.244; 13.W.169.228; 13.W.169.229; 13.W.169.230; 13.W.169.231;
13.W.169.236; 13.W.169.237; 13.W.169.238; 13.W.169.239; 13.W.169.154;
13.W.169.157; 13.W.169.166; 13.W.169.169; 13.W.169.172; 13.W.169.175;
13.W.169.240; 13.W.169.244; 13.W.172.228; 13.W.172.229; 13.W.172.230;
13.W.172.231; 13.W.172.236; 13.W.172.237; 13.W.172.238; 13.W.172.239;
13.W.172.154; 13.W.172.157; 13.W.172.166; 13.W.172.169; 13.W.172.172;
13.W.172.175; 13.W.172.240; 13.W.172.244; 13.W.175.228; 13.W.175.229;
13.W.175.230; 13.W.175.231; 13.W.175.236; 13.W.175.237; 13.W.175.238;
13.W.175.239; 13.W.175.154; 13.W.175.157; 13.W.175.166; 13.W.175.169;
13.W.175.172; 13.W.175.175; 13.W.175.240; 13.W.175.244; 13.W.240.228;
13.W.240.229; 13.W.240.230; 13.W.240.231; 13.W.240.236; 13.W.240.237;
13.W.240.238; 13.W.240.239; 13.W.240.154; 13.W.240.157; 13.W.240.166;
13.W.240.169; 13.W.240.172; 13.W.240.175; 13.W.240.240; 13.W.240.244;
13.W.244.228; 13.W.244.229; 13.W.244.230; 13.W.244.231; 13.W.244.236;
13.W.244.237; 13.W.244.238; 13.W.244.239; 13.W.244.154; 13.W.244.157;
13.W.244.166; 13.W.244.169; 13.W.244.172; 13.W.244.175; 13.W.244.240;
13.W.244.244;

Prodrugs of 13.Y

13.Y.228.228; 13.Y.228.229; 13.Y.228.230; 13.Y.228.231; 13.Y.228.236;
13.Y.228.237; 13.Y.228.238; 13.Y.228.239; 13.Y.228.154; 13.Y.228.157;
13.Y.228.166; 13.Y.228.169; 13.Y.228.172; 13.Y.228.175; 13.Y.228.240;
13.Y.228.244; 13.Y.229.228; 13.Y.229.229; 13.Y.229.230; 13.Y.229.231;
13.Y.229.236; 13.Y.229.237; 13.Y.229.238; 13.Y.229.239; 13.Y.229.154;
13.Y.229.157; 13.Y.229.166; 13.Y.229.169; 13.Y.229.172; 13.Y.229.175;
13.Y.229.240; 13.Y.229.244; 13.Y.230.228; 13.Y.230.229; 13.Y.230.230;
13.Y.230.231; 13.Y.230.236; 13.Y.230.237; 13.Y.230.238; 13.Y.230.239;
13.Y.230.154; 13.Y.230.157; 13.Y.230.166; 13.Y.230.169; 13.Y.230.172;
13.Y.230.175; 13.Y.230.240; 13.Y.230.244; 13.Y.231.228; 13.Y.231.229;
13.Y.231.230; 13.Y.231.231; 13.Y.231.236; 13.Y.231.237; 13.Y.231.238;
13.Y.231.239; 13.Y.231.154; 13.Y.231.157; 13.Y.231.166; 13.Y.231.169;
13.Y.231.172; 13.Y.231.175; 13.Y.231.240; 13.Y.231.244; 13.Y.236.228;
13.Y.236.229; 13.Y.236.230; 13.Y.236.231; 13.Y.236.236; 13.Y.236.237;
13.Y.236.238; 13.Y.236.239; 13.Y.236.154; 13.Y.236.157; 13.Y.236.166;
13.Y.236.169; 13.Y.236.172; 13.Y.236.175; 13.Y.236.240; 13.Y.236.244;

TABLE 100-continued

13.Y.237.228; 13.Y.237.229; 13.Y.237.230; 13.Y.237.231; 13.Y.237.236;
13.Y.237.237; 13.Y.237.238; 13.Y.237.239; 13.Y.237.154; 13.Y.237.157;
13.Y.237.166; 13.Y.237.169; 13.Y.237.172; 13.Y.237.175; 13.Y.237.240;
13.Y.237.244; 13.Y.238.228; 13.Y.238.229; 13.Y.238.230; 13.Y.238.231;
13.Y.238.236; 13.Y.238.237; 13.Y.238.238; 13.Y.238.239; 13.Y.238.154;
13.Y.238.157; 13.Y.238.166; 13.Y.238.169; 13.Y.238.172; 13.Y.238.175;
13.Y.238.240; 13.Y.238.244; 13.Y.239.228; 13.Y.239.229; 13.Y.239.230;
13.Y.239.231; 13.Y.239.236; 13.Y.239.237; 13.Y.239.238; 13.Y.239.239;
13.Y.239.154; 13.Y.239.157; 13.Y.239.166; 13.Y.239.169; 13.Y.239.172;
13.Y.239.175; 13.Y.239.240; 13.Y.239.244; 13.Y.154.228; 13.Y.154.229;
13.Y.154.230; 13.Y.154.231; 13.Y.154.236; 13.Y.154.237; 13.Y.154.238;
13.Y.154.239; 13.Y.154.154; 13.Y.154.157; 13.Y.154.166; 13.Y.154.169;
13.Y.154.172; 13.Y.154.175; 13.Y.154.240; 13.Y.154.244; 13.Y.157.228;
13.Y.157.229; 13.Y.157.230; 13.Y.157.231; 13.Y.157.236; 13.Y.157.237;
13.Y.157.238; 13.Y.157.239; 13.Y.157.154; 13.Y.157.157; 13.Y.157.166;
13.Y.157.169; 13.Y.157.172; 13.Y.157.175; 13.Y.157.240; 13.Y.157.244;
13.Y.166.228; 13.Y.166.229; 13.Y.166.230; 13.Y.166.231; 13.Y.166.236;
13.Y.166.237; 13.Y.166.238; 13.Y.166.239; 13.Y.166.154; 13.Y.166.157;
13.Y.166.166; 13.Y.166.169; 13.Y.166.172; 13.Y.166.175; 13.Y.166.240;
13.Y.166.244; 13.Y.169.228; 13.Y.169.229; 13.Y.169.230; 13.Y.169.231;
13.Y.169.236; 13.Y.169.237; 13.Y.169.238; 13.Y.169.239; 13.Y.169.154;
13.Y.169.157; 13.Y.169.166; 13.Y.169.169; 13.Y.169.172; 13.Y.169.175;
13.Y.169.240; 13.Y.169.244; 13.Y.172.228; 13.Y.172.229; 13.Y.172.230;
13.Y.172.231; 13.Y.172.236; 13.Y.172.237; 13.Y.172.238; 13.Y.172.239;
13.Y.172.154; 13.Y.172.157; 13.Y.172.166; 13.Y.172.169; 13.Y.172.172;
13.Y.172.175; 13.Y.172.240; 13.Y.172.244; 13.Y.175.228; 13.Y.175.229;
13.Y.175.230; 13.Y.175.231; 13.Y.175.236; 13.Y.175.237; 13.Y.175.238;
13.Y.175.239; 13.Y.175.154; 13.Y.175.157; 13.Y.175.166; 13.Y.175.169;
13.Y.175.172; 13.Y.175.175; 13.Y.175.240; 13.Y.175.244; 13.Y.240.228;
13.Y.240.229; 13.Y.240.230; 13.Y.240.231; 13.Y.240.236; 13.Y.240.237;
13.Y.240.238; 13.Y.240.239; 13.Y.240.154; 13.Y.240.157; 13.Y.240.166;
13.Y.240.169; 13.Y.240.172; 13.Y.240.175; 13.Y.240.240; 13.Y.240.244;
13.Y.244.228; 13.Y.244.229; 13.Y.244.230; 13.Y.244.231; 13.Y.244.236;
13.Y.244.237; 13.Y.244.238; 13.Y.244.239; 13.Y.244.154; 13.Y.244.157;
13.Y.244.166; 13.Y.244.169; 13.Y.244.172; 13.Y.244.175; 13.Y.244.240;
13.Y.244.244;

Prodrugs of 14.AH

14.AH.4.157; 14.AH.4.158; 14.AH.4.196; 14.AH.4.223; 14.AH.4.240;
14.AH.4.244; 14.AH.4.243; 14.AH.4.247; 14.AH.5.157; 14.AH.5.158;
14.AH.5.196; 14.AH.5.223; 14.AH.5.240; 14.AH.5.244; 14.AH.5.243;
14.AH.5.247; 14.AH.7.157; 14.AH.7.158; 14.AH.7.196; 14.AH.7.223;
14.AH.7.240; 14.AH.7.244; 14.AH.7.243; 14.AH.7.247; 14.AH.15.157;
14.AH.15.158; 14.AH.15.196; 14.AH.15.223; 14.AH.15.240; 14.AH.15.244;
14.AH.15.243; 14.AH.15.247; 14.AH.16.157; 14.AH.16.158; 14.AH.16.196;
14.AH.16.223; 14.AH.16.240; 14.AH.16.244; 14.AH.16.243; 14.AH.16.247;
14.AH.18.157; 14.AH.18.158; 14.AH.18.196; 14.AH.18.223; 14.AH.18.240;
14.AH.18.244; 14.AH.18.243; 14.AH.18.247; 14.AH.26.157; 14.AH.26.158;
14.AH.26.196; 14.AH.26.223; 14.AH.26.240; 14.AH.26.244; 14.AH.26.243;
14.AH.26.247; 14.AH.27.157; 14.AH.27.158; 14.AH.27.196; 14.AH.27.223;
14.AH.27.240; 14.AH.27.244; 14.AH.27.243; 14.AH.27.247; 14.AH.29.157;
14.AH.29.158; 14.AH.29.196; 14.AH.29.223; 14.AH.29.240; 14.AH.29.244;
14.AH.29.243; 14.AH.29.247; 14.AH.54.157; 14.AH.54.158; 14.AH.54.196;
14.AH.54.223; 14.AH.54.240; 14.AH.54.244; 14.AH.54.243; 14.AH.54.247;
14.AH.55.157; 14.AH.55.158; 14.AH.55.196; 14.AH.55.223; 14.AH.55.240;
14.AH.55.244; 14.AH.55.243; 14.AH.55.247; 14.AH.56.157; 14.AH.56.158;
14.AH.56.196; 14.AH.56.223; 14.AH.56.240; 14.AH.56.244; 14.AH.56.243;
14.AH.56.247; 14.AH.157.157; 14.AH.157.158; 14.AH.157.196;
14.AH.157.223; 14.AH.157.240; 14.AH.157.244; 14.AH.157.243;
14.AH.157.247; 14.AH.196.157; 14.AH.196.158; 14.AH.196.196;
14.AH.196.223; 14.AH.196.240; 14.AH.196.244; 14.AH.196.243;
14.AH.196.247; 14.AH.223.157; 14.AH.223.158; 14.AH.223.196;
14.AH.223.223; 14.AH.223.240; 14.AH.223.244; 14.AH.223.243;
14.AH.223.247; 14.AH.240.157; 14.AH.240.158; 14.AH.240.196;
14.AH.240.223; 14.AH.240.240; 14.AH.240.244; 14.AH.240.243;
14.AH.240.247; 14.AH.244.157; 14.AH.244.158; 14.AH.244.196;
14.AH.244.223; 14.AH.244.240; 14.AH.244.244; 14.AH.244.243;
14.AH.244.247; 14.AH.247.157; 14.AH.247.158; 14.AH.247.196;
14.AH.247.223; 14.AH.247.240; 14.AH.247.244; 14.AH.247.243; 14.AH.247.247;

Prodrugs of 14.AJ

14.AJ.4.157; 14.AJ.4.158; 14.AJ.4.196; 14.AJ.4.223; 14.AJ.4.240;
14.AJ.4.244; 14.AJ.4.243; 14.AJ.4.247; 14.AJ.5.157; 14.AJ.5.158; 14.AJ.5.196;
14.AJ.5.223; 14.AJ.5.240; 14.AJ.5.244; 14.AJ.5.243; 14.AJ.5.247; 14.AJ.7.157;
14.AJ.7.158; 14.AJ.7.196; 14.AJ.7.223; 14.AJ.7.240; 14.AJ.7.244; 14.AJ.7.243;
14.AJ.7.247; 14.AJ.15.157; 14.AJ.15.158; 14.AJ.15.196; 14.AJ.15.223;
14.AJ.15.240; 14.AJ.15.244; 14.AJ.15.243; 14.AJ.15.247; 14.AJ.16.157;
14.AJ.16.158; 14.AJ.16.196; 14.AJ.16.223; 14.AJ.16.240; 14.AJ.16.244;
14.AJ.16.243; 14.AJ.16.247; 14.AJ.18.157; 14.AJ.18.158; 14.AJ.18.196;

TABLE 100-continued

14.AJ.18.223; 14.AJ.18.240; 14.AJ.18.244; 14.AJ.18.243; 14.AJ.18.247;
14.AJ.26.157; 14.AJ.26.158; 14.AJ.26.196; 14.AJ.26.223; 14.AJ.26.240;
14.AJ.26.244; 14.AJ.26.243; 14.AJ.26.247; 14.AJ.27.157; 14.AJ.27.158;
14.AJ.27.196; 14.AJ.27.223; 14.AJ.27.240; 14.AJ.27.244; 14.AJ.27.243;
14.AJ.27.247; 14.AJ.29.157; 14.AJ.29.158; 14.AJ.29.196; 14.AJ.29.223;
14.AJ.29.240; 14.AJ.29.244; 14.AJ.29.243; 14.AJ.29.247; 14.AJ.54.157;
14.AJ.54.158; 14.AJ.54.196; 14.AJ.54.223; 14.AJ.54.240; 14.AJ.54.244;
14.AJ.54.243; 14.AJ.54.247; 14.AJ.55.157; 14.AJ.55.158; 14.AJ.55.196;
14.AJ.55.223; 14.AJ.55.240; 14.AJ.55.244; 14.AJ.55.243; 14.AJ.55.247;
14.AJ.56.157; 14.AJ.56.158; 14.AJ.56.196; 14.AJ.56.223; 14.AJ.56.240;
14.AJ.56.244; 14.AJ.56.243; 14.AJ.56.247; 14.AJ.157.157; 14.AJ.157.158;
14.AJ.157.196; 14.AJ.157.223; 14.AJ.157.240; 14.AJ.157.244; 14.AJ.157.243;
14.AJ.157.247; 14.AJ.196.157; 14.AJ.196.158; 14.AJ.196.196; 14.AJ.196.223;
14.AJ.196.240; 14.AJ.196.244; 14.AJ.196.243; 14.AJ.196.247; 14.AJ.223.157;
14.AJ.223.158; 14.AJ.223.196; 14.AJ.223.223; 14.AJ.223.240; 14.AJ.223.244;
14.AJ.223.243; 14.AJ.223.247; 14.AJ.240.157; 14.AJ.240.158; 14.AJ.240.196;
14.AJ.240.223; 14.AJ.240.240; 14.AJ.240.244; 14.AJ.240.243; 14.AJ.240.247;
14.AJ.244.157; 14.AJ.244.158; 14.AJ.244.196; 14.AJ.244.223; 14.AJ.244.240;
14.AJ.244.244; 14.AJ.244.243; 14.AJ.244.247; 14.AJ.247.157; 14.AJ.247.158;
14.AJ.247.196; 14.AJ.247.223; 14.AJ.247.240; 14.AJ.247.244; 14.AJ.247.243;
14.AJ.247.247;
Prodrugs of 14.AN 14.AN.4.157; 14.AN.4.158; 14.AN.4.196; 14.AN.4.223; 14.AN.4.240;
14.AN.4.244; 14.AN.4.243; 14.AN.4.247; 14.AN.5.157; 14.AN.5.158;
14.AN.5.196; 14.AN.5.223; 14.AN.5.240; 14.AN.5.244; 14.AN.5.243;
14.AN.5.247; 14.AN.7.157; 14.AN.7.158; 14.AN.7.196; 14.AN.7.223;
14.AN.7.240; 14.AN.7.244; 14.AN.7.243; 14.AN.7.247; 14.AN.15.157;
14.AN.15.158; 14.AN.15.196; 14.AN.15.223; 14.AN.15.240; 14.AN.15.244;
14.AN.15.243; 14.AN.15.247; 14.AN.16.157; 14.AN.16.158; 14.AN.16.196;
14.AN.16.223; 14.AN.16.240; 14.AN.16.244; 14.AN.16.243; 14.AN.16.247;
14.AN.18.157; 14.AN.18.158; 14.AN.18.196; 14.AN.18.223; 14.AN.18.240;
14.AN.18.244; 14.AN.18.243; 14.AN.18.247; 14.AN.26.157; 14.AN.26.158;
14.AN.26.196; 14.AN.26.223; 14.AN.26.240; 14.AN.26.244; 14.AN.26.243;
14.AN.26.247; 14.AN.27.157; 14.AN.27.158; 14.AN.27.196; 14.AN.27.223;
14.AN.27.240; 14.AN.27.244; 14.AN.27.243; 14.AN.27.247; 14.AN.29.157;
14.AN.29.158; 14.AN.29.196; 14.AN.29.223; 14.AN.29.240; 14.AN.29.244;
14.AN.29.243; 14.AN.29.247; 14.AN.54.157; 14.AN.54.158; 14.AN.54.196;
14.AN.54.223; 14.AN.54.240; 14.AN.54.244; 14.AN.54.243; 14.AN.54.247;
14.AN.55.157; 14.AN.55.158; 14.AN.55.196; 14.AN.55.223; 14.AN.55.240;
14.AN.55.244; 14.AN.55.243; 14.AN.55.247; 14.AN.56.157; 14.AN.56.158;
14.AN.56.196; 14.AN.56.223; 14.AN.56.240; 14.AN.56.244; 14.AN.56.243;
14.AN.56.247; 14.AN.157.157; 14.AN.157.158; 14.AN.157.196;
14.AN.157.223; 14.AN.157.240; 14.AN.157.244; 14.AN.157.243;
14.AN.157.247; 14.AN.196.157; 14.AN.196.158; 14.AN.196.196;
14.AN.196.223; 14.AN.196.240; 14.AN.196.244; 14.AN.196.243;
14.AN.196.247; 14.AN.223.157; 14.AN.223.158; 14.AN.223.196;
14.AN.223.223; 14.AN.223.240; 14.AN.223.244; 14.AN.223.243;
14.AN.223.247; 14.AN.240.157; 14.AN.240.158; 14.AN.240.196;
14.AN.240.223; 14.AN.240.240; 14.AN.240.244; 14.AN.240.243;
14.AN.240.247; 14.AN.244.157; 14.AN.244.158; 14.AN.244.196;
14.AN.244.223; 14.AN.244.240; 14.AN.244.244; 14.AN.244.243;
14.AN.244.247; 14.AN.247.157; 14.AN.247.158; 14.AN.247.196;
14.AN.247.223; 14.AN.247.240; 14.AN.247.244; 14.AN.247.243; 14.AN.247.247;
Prodrugs of 14.AP 14.AP.4.157; 14.AP.4.158; 14.AP.4.196; 14.AP.4.223; 14.AP.4.240;
14.AP.4.244; 14.AP.4.243; 14.AP.4.247; 14.AP.5.157; 14.AP.5.158;
14.AP.5.196; 14.AP.5.223; 14.AP.5.240; 14.AP.5.244; 14.AP.5.243;
14.AP.5.247; 14.AP.7.157; 14.AP.7.158; 14.AP.7.196; 14.AP.7.223;
14.AP.7.240; 14.AP.7.244; 14.AP.7.243; 14.AP.7.247; 14.AP.15.157;
14.AP.15.158; 14.AP.15.196; 14.AP.15.223; 14.AP.15.240; 14.AP.15.244;
14.AP.15.243; 14.AP.15.247; 14.AP.16.157; 14.AP.16.158; 14.AP.16.196;
14.AP.16.223; 14.AP.16.240; 14.AP.16.244; 14.AP.16.243; 14.AP.16.247;
14.AP.18.157; 14.AP.18.158; 14.AP.18.196; 14.AP.18.223; 14.AP.18.240;
14.AP.18.244; 14.AP.18.243; 14.AP.18.247; 14.AP.26.157; 14.AP.26.158;
14.AP.26.196; 14.AP.26.223; 14.AP.26.240; 14.AP.26.244; 14.AP.26.243;
14.AP.26.247; 14.AP.27.157; 14.AP.27.158; 14.AP.27.196; 14.AP.27.223;
14.AP.27.240; 14.AP.27.244; 14.AP.27.243; 14.AP.27.247; 14.AP.29.157;
14.AP.29.158; 14.AP.29.196; 14.AP.29.223; 14.AP.29.240; 14.AP.29.244;
14.AP.29.243; 14.AP.29.247; 14.AP.54.157; 14.AP.54.158; 14.AP.54.196;

TABLE 100-continued

14.AP.54.223; 14.AP.54.240; 14.AP.54.244; 14.AP.54.243; 14.AP.54.247;
14.AP.55.157; 14.AP.55.158; 14.AP.55.196; 14.AP.55.223; 14.AP.55.240;
14.AP.55.244; 14.AP.55.243; 14.AP.55.247; 14.AP.56.157; 14.AP.56.158;
14.AP.56.196; 14.AP.56.223; 14.AP.56.240; 14.AP.56.244; 14.AP.56.243;
14.AP.56.247; 14.AP.157.157; 14.AP.157.158; 14.AP.157.196; 14.AP.157.223;
14.AP.157.240; 14.AP.157.244; 14.AP.157.243; 14.AP.157.247;
14.AP.196.157; 14.AP.196.158; 14.AP.196.196; 14.AP.196.223;
14.AP.196.240; 14.AP.196.244; 14.AP.196.243; 14.AP.196.247;
14.AP.223.157; 14.AP.223.158; 14.AP.223.196; 14.AP.223.223;
14.AP.223.240; 14.AP.223.244; 14.AP.223.243; 14.AP.223.247;
14.AP.240.157; 14.AP.240.158; 14.AP.240.196; 14.AP.240.223;
14.AP.240.240; 14.AP.240.244; 14.AP.240.243; 14.AP.240.247;
14.AP.244.157; 14.AP.244.158; 14.AP.244.196; 14.AP.244.223;
14.AP.244.240; 14.AP.244.244; 14.AP.244.243; 14.AP.244.247;
14.AP.247.157; 14.AP.247.158; 14.AP.247.196; 14.AP.247.223;
14.AP.247.240; 14.AP.247.244; 14.AP.247.243; 14.AP.247.247;
Prodrugs of 14.AZ 14.AZ.4.157; 14.AZ.4.158; 14.AZ.4.196; 14.AZ.4.223; 14.AZ.4.240;
14.AZ.4.244; 14.AZ.4.243; 14.AZ.4.247; 14.AZ.5.157; 14.AZ.5.158;
14.AZ.5.196; 14.AZ.5.223; 14.AZ.5.240; 14.AZ.5.244; 14.AZ.5.243;
14.AZ.5.247; 14.AZ.7.157; 14.AZ.7.158; 14.AZ.7.196; 14.AZ.7.223;
14.AZ.7.240; 14.AZ.7.244; 14.AZ.7.243; 14.AZ.7.247; 14.AZ.15.157;
14.AZ.15.158; 14.AZ.15.196; 14.AZ.15.223; 14.AZ.15.240; 14.AZ.15.244;
14.AZ.15.243; 14.AZ.15.247; 14.AZ.16.157; 14.AZ.16.158; 14.AZ.16.196;
14.AZ.16.223; 14.AZ.16.240; 14.AZ.16.244; 14.AZ.16.243; 14.AZ.16.247;
14.AZ.18.157; 14.AZ.18.158; 14.AZ.18.196; 14.AZ.18.223; 14.AZ.18.240;
14.AZ.18.244; 14.AZ.18.243; 14.AZ.18.247; 14.AZ.26.157; 14.AZ.26.158;
14.AZ.26.196; 14.AZ.26.223; 14.AZ.26.240; 14.AZ.26.244; 14.AZ.26.243;
14.AZ.26.247; 14.AZ.27.157; 14.AZ.27.158; 14.AZ.27.196; 14.AZ.27.223;
14.AZ.27.240; 14.AZ.27.244; 14.AZ.27.243; 14.AZ.27.247; 14.AZ.29.157;
14.AZ.29.158; 14.AZ.29.196; 14.AZ.29.223; 14.AZ.29.240; 14.AZ.29.244;
14.AZ.29.243; 14.AZ.29.247; 14.AZ.54.157; 14.AZ.54.158; 14.AZ.54.196;
14.AZ.54.223; 14.AZ.54.240; 14.AZ.54.244; 14.AZ.54.243; 14.AZ.54.247;
14.AZ.55.157; 14.AZ.55.158; 14.AZ.55.196; 14.AZ.55.223; 14.AZ.55.240;
14.AZ.55.244; 14.AZ.55.243; 14.AZ.55.247; 14.AZ.56.157; 14.AZ.56.158;
14.AZ.56.196; 14.AZ.56.223; 14.AZ.56.240; 14.AZ.56.244; 14.AZ.56.243;
14.AZ.56.247; 14.AZ.157.157; 14.AZ.157.158; 14.AZ.157.196; 14.AZ.157.223;
14.AZ.157.240; 14.AZ.157.244; 14.AZ.157.243; 14.AZ.157.247;
14.AZ.196.157; 14.AZ.196.158; 14.AZ.196.196; 14.AZ.196.223;
14.AZ.196.240; 14.AZ.196.244; 14.AZ.196.243; 14.AZ.196.247;
14.AZ.223.157; 14.AZ.223.158; 14.AZ.223.196; 14.AZ.223.223;
14.AZ.223.240; 14.AZ.223.244; 14.AZ.223.243; 14.AZ.223.247;
14.AZ.240.157; 14.AZ.240.158; 14.AZ.240.196; 14.AZ.240.223;
14.AZ.240.240; 14.AZ.240.244; 14.AZ.240.243; 14.AZ.240.247;
14.AZ.244.157; 14.AZ.244.158; 14.AZ.244.196; 14.AZ.244.223;
14.AZ.244.240; 14.AZ.244.244; 14.AZ.244.243; 14.AZ.244.247;
14.AZ.247.157; 14.AZ.247.158; 14.AZ.247.196; 14.AZ.247.223;
14.AZ.247.240; 14.AZ.247.244; 14.AZ.247.243; 14.AZ.247.247;
Prodrugs of 14.BF 14.BF.4.157; 14.BF.4.158; 14.BF.4.196; 14.BF.4.223; 14.BF.4.240;
14.BF.4.244; 14.BF.4.243; 14.BF.4.247; 14.BF.5.157; 14.BF.5.158;
14.BF.5.196; 14.BF.5.223; 14.BF.5.240; 14.BF.5.244; 14.BF.5.243;
14.BF.5.247; 14.BF.7.157; 14.BF.7.158; 14.BF.7.196; 14.BF.7.223;
14.BF.7.240; 14.BF.7.244; 14.BF.7.243; 14.BF.7.247; 14.BF.15.157;
14.BF.15.158; 14.BF.15.196; 14.BF.15.223; 14.BF.15.240; 14.BF.15.244;
14.BF.15.243; 14.BF.15.247; 14.BF.16.157; 14.BF.16.158; 14.BF.16.196;
14.BF.16.223; 14.BF.16.240; 14.BF.16.244; 14.BF.16.243; 14.BF.16.247;
14.BF.18.157; 14.BF.18.158; 14.BF.18.196; 14.BF.18.223; 14.BF.18.240;
14.BF.18.244; 14.BF.18.243; 14.BF.18.247; 14.BF.26.157; 14.BF.26.158;
14.BF.26.196; 14.BF.26.223; 14.BF.26.240; 14.BF.26.244; 14.BF.26.243;
14.BF.26.247; 14.BF.27.157; 14.BF.27.158; 14.BF.27.196; 14.BF.27.223;
14.BF.27.240; 14.BF.27.244; 14.BF.27.243; 14.BF.27.247; 14.BF.29.157;
14.BF.29.158; 14.BF.29.196; 14.BF.29.223; 14.BF.29.240; 14.BF.29.244;
14.BF.29.243; 14.BF.29.247; 14.BF.54.157; 14.BF.54.158; 14.BF.54.196;
14.BF.54.223; 14.BF.54.240; 14.BF.54.244; 14.BF.54.243; 14.BF.54.247;
14.BF.55.157; 14.BF.55.158; 14.BF.55.196; 14.BF.55.223; 14.BF.55.240;
14.BF.55.244; 14.BF.55.243; 14.BF.55.247; 14.BF.56.157; 14.BF.56.158;
14.BF.56.196; 14.BF.56.223; 14.BF.56.240; 14.BF.56.244; 14.BF.56.243;
14.BF.56.247; 14.BF.157.157; 14.BF.157.158; 14.BF.157.196; 14.BF.157.223;
14.BF.157.240; 14.BF.157.244; 14.BF.157.243; 14.BF.157.247; 14.BF.196.157;
14.BF.196.158; 14.BF.196.196; 14.BF.196.223; 14.BF.196.240; 14.BF.196.244;
14.BF.196.243; 14.BF.196.247; 14.BF.223.157; 14.BF.223.158; 14.BF.223.196;

TABLE 100-continued

14.BF.223.223; 14.BF.223.240; 14.BF.223.244; 14.BF.223.243; 14.BF.223.247;
14.BF.240.157; 14.BF.240.158; 14.BF.240.196; 14.BF.240.223; 14.BF.240.240;
14.BF.240.244; 14.BF.240.243; 14.BF.240.247; 14.BF.244.157; 14.BF.244.158;
14.BF.244.196; 14.BF.244.223; 14.BF.244.240; 14.BF.244.244; 14.BF.244.243;
14.BF.244.247; 14.BF.247.157; 14.BF.247.158; 14.BF.247.196; 14.BF.247.223;
14.BF.247.240; 14.BF.247.244; 14.BF.247.243; 14.BF.247.247;
Prodrugs of 14.CI 14.CI.4.157; 14.CI.4.158; 14.CI.4.196; 14.CI.4.223; 14.CI.4.240;
14.CI.4.244; 14.CI.4.243; 14.CI.4.247; 14.CI.5.157; 14.CI.5.158; 14.CI.5.196;
14.CI.5.223; 14.CI.5.240; 14.CI.5.244; 14.CI.5.243; 14.CI.5.247; 14.CI.7.157;
14.CI.7.158; 14.CI.7.196; 14.CI.7.223; 14.CI.7.240; 14.CI.7.244; 14.CI.7.243;
14.CI.7.247; 14.CI.15.157; 14.CI.15.158; 14.CI.15.196; 14.CI.15.223;
14.CI.15.240; 14.CI.15.244; 14.CI.15.243; 14.CI.15.247; 14.CI.16.157;
14.CI.16.158; 14.CI.16.196; 14.CI.16.223; 14.CI.16.240; 14.CI.16.244;
14.CI.16.243; 14.CI.16.247; 14.CI.18.157; 14.CI.18.158; 14.CI.18.196;
14.CI.18.223; 14.CI.18.240; 14.CI.18.244; 14.CI.18.243; 14.CI.18.247;
14.CI.26.157; 14.CI.26.158; 14.CI.26.196; 14.CI.26.223; 14.CI.26.240;
14.CI.26.244; 14.CI.26.243; 14.CI.26.247; 14.CI.27.157; 14.CI.27.158;
14.CI.27.196; 14.CI.27.223; 14.CI.27.240; 14.CI.27.244; 14.CI.27.243;
14.CI.27.247; 14.CI.29.157; 14.CI.29.158; 14.CI.29.196; 14.CI.29.223;
14.CI.29.240; 14.CI.29.244; 14.CI.29.243; 14.CI.29.247; 14.CI.54.157;
14.CI.54.158; 14.CI.54.196; 14.CI.54.223; 14.CI.54.240; 14.CI.54.244;
14.CI.54.243; 14.CI.54.247; 14.CI.55.157; 14.CI.55.158; 14.CI.55.196;
14.CI.55.223; 14.CI.55.240; 14.CI.55.244; 14.CI.55.243; 14.CI.55.247;
14.CI.56.157; 14.CI.56.158; 14.CI.56.196; 14.CI.56.223; 14.CI.56.240;
14.CI.56.244; 14.CI.56.243; 14.CI.56.247; 14.CI.157.157; 14.CI.157.158;
14.CI.157.196; 14.CI.157.223; 14.CI.157.240; 14.CI.157.244; 14.CI.157.243;
14.CI.157.247; 14.CI.196.157; 14.CI.196.158; 14.CI.196.196; 14.CI.196.223;
14.CI.196.240; 14.CI.196.244; 14.CI.196.243; 14.CI.196.247; 14.CI.223.157;
14.CI.223.158; 14.CI.223.196; 14.CI.223.223; 14.CI.223.240; 14.CI.223.244;
14.CI.223.243; 14.CI.223.247; 14.CI.240.157; 14.CI.240.158; 14.CI.240.196;
14.CI.240.223; 14.CI.240.240; 14.CI.240.244; 14.CI.240.243; 14.CI.240.247;
14.CI.244.157; 14.CI.244.158; 14.CI.244.196; 14.CI.244.223; 14.CI.244.240;
14.CI.244.244; 14.CI.244.243; 14.CI.244.247; 14.CI.247.157; 14.CI.247.158;
14.CI.247.196; 14.CI.247.223; 14.CI.247.240; 14.CI.247.244; 14.CI.247.243;
14.CI.247.247;
Prodrugs of 14.CO 14.CO.4.157; 14.CO.4.158; 14.CO.4.196; 14.CO.4.223; 14.CO.4.240;
14.CO.4.244; 14.CO.4.243; 14.CO.4.247; 14.CO.5.157; 14.CO.5.158;
14.CO.5.196; 14.CO.5.223; 14.CO.5.240; 14.CO.5.244; 14.CO.5.243;
14.CO.5.247; 14.CO.7.157; 14.CO.7.158; 14.CO.7.196; 14.CO.7.223;
14.CO.7.240; 14.CO.7.244; 14.CO.7.243; 14.CO.7.247; 14.CO.15.157;
14.CO.15.158; 14.CO.15.196; 14.CO.15.223; 14.CO.15.240; 14.CO.15.244;
14.CO.15.243; 14.CO.15.247; 14.CO.16.157; 14.CO.16.158; 14.CO.16.196;
14.CO.16.223; 14.CO.16.240; 14.CO.16.244; 14.CO.16.243; 14.CO.16.247;
14.CO.18.157; 14.CO.18.158; 14.CO.18.196; 14.CO.18.223; 14.CO.18.240;
14.CO.18.244; 14.CO.18.243; 14.CO.18.247; 14.CO.26.157; 14.CO.26.158;
14.CO.26.196; 14.CO.26.223; 14.CO.26.240; 14.CO.26.244; 14.CO.26.243;
14.CO.26.247; 14.CO.27.157; 14.CO.27.158; 14.CO.27.196; 14.CO.27.223;
14.CO.27.240; 14.CO.27.244; 14.CO.27.243; 14.CO.27.247; 14.CO.29.157;
14.CO.29.158; 14.CO.29.196; 14.CO.29.223; 14.CO.29.240; 14.CO.29.244;
14.CO.29.243; 14.CO.29.247; 14.CO.54.157; 14.CO.54.158; 14.CO.54.196;
14.CO.54.223; 14.CO.54.240; 14.CO.54.244; 14.CO.54.243; 14.CO.54.247;
14.CO.55.157; 14.CO.55.158; 14.CO.55.196; 14.CO.55.223; 14.CO.55.240;
14.CO.55.244; 14.CO.55.243; 14.CO.55.247; 14.CO.56.157; 14.CO.56.158;
14.CO.56.196; 14.CO.56.223; 14.CO.56.240; 14.CO.56.244; 14.CO.56.243;
14.CO.56.247; 14.CO.157.157; 14.CO.157.158; 14.CO.157.196;
14.CO.157.223; 14.CO.157.240; 14.CO.157.244; 14.CO.157.243;
14.CO.157.247; 14.CO.196.157; 14.CO.196.158; 14.CO.196.196;
14.CO.196.223; 14.CO.196.240; 14.CO.196.244; 14.CO.196.243;
14.CO.196.247; 14.CO.223.157; 14.CO.223.158; 14.CO.223.196;
14.CO.223.223; 14.CO.223.240; 14.CO.223.244; 14.CO.223.243;
14.CO.223.247; 14.CO.240.157; 14.CO.240.158; 14.CO.240.196;
14.CO.240.223; 14.CO.240.240; 14.CO.240.244; 14.CO.240.243;
14.CO.240.247; 14.CO.244.157; 14.CO.244.158; 14.CO.244.196;
14.CO.244.223; 14.CO.244.240; 14.CO.244.244; 14.CO.244.243;
14.CO.244.247; 14.CO.4.157; 14.CO.4.158; 14.CO.4.196; 14.CO.4.223;
14.CO.4.240; 14.CO.4.244; 14.CO.4.243; 14.CO.4.247;

All literature and patent citations herein are hereby expressly incorporated by reference at the locations of their citation. Specifically cited sections or pages of the above cited works are incorporated by reference with specificity. The invention has been described in detail sufficient to allow one of ordinary skill in the art to make and use the subject matter of the following claims. It is apparent that certain modifications of the methods and compositions of the following claims can be made within the scope and spirit of the invention.

In the claims hereinbelow, the subscript and superscripts of a given variable are distinct. For example, $R_1$ is distinct from $R^1$.

What is claimed is:

1. A conjugate or a pharmaceutically acceptable salt or solvate thereof, that is a compound of formula 509:

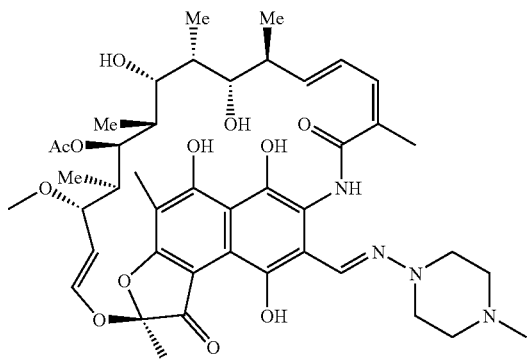

substituted with 1, 2, or 3 groups $A^0$, wherein:
$A^0$ is $A^1$, $A^2$ or $W^3$ with the proviso that the conjugate includes at least one $A^1$;

$A^1$ is:

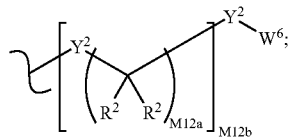

$A^2$ is:

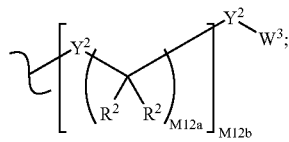

$A^3$ is:

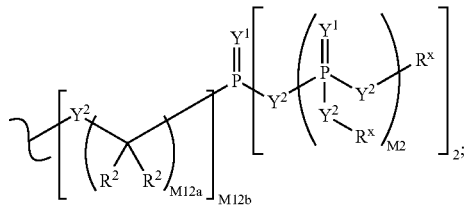

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$; and when $Y^2$ joins two phosphorous atoms $Y^2$ can also be $C(R^2)(R^2)$;

$R^x$ is independently H, $R^1$, $R^2$, $W^3$, a protecting group, or the formula:

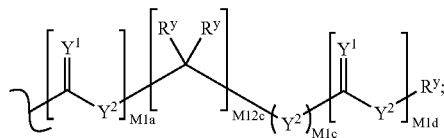

$R^y$ is independently H, $W^3$, $R^2$ or a protecting group;
$R^1$ is independently H or alkyl of 1 to 18 carbon atoms;
$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;
$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;
$R^{3a}$ is F, Cl, Br, I, $-CN$, $N_3$ or $-NO_2$;
$R^{3b}$ is $Y^1$;
$R^{3c}$ is $-R^x$, $-N(R^x)(R^x)$, $-SR^x$, $-S(O)R^x$, $-S(O)_2R^x$, $-S(O)(OR^x)$, $-S(O)_2(OR^x)$, $-OC(Y^1)R^x$, $-OC(Y^1)OR^x$, $-OC(Y^1)(N(R^x)(R^x))$, $-SC(Y^1)R^x$, $-SC(Y^1)OR^x$, $-SC(Y^1)(N(R^x)(R^x))$, $-N(R^x)C(Y^1)R^x$, $-N(R^x)C(Y^1)OR^x$, or $-N(R^x)C(Y^1)(N(R^x)(R^x))$;
$R^{3d}$ is $-C(Y^1)R^x$, $-C(Y^1)OR^x$ or $-C(Y^1)(N(R^x)(R^x))$;
$R^4$ is an alkyl of 1 to 18 carbon atoms, alkenyl of 2 to 18 carbon atoms, or alkynyl of 2 to 18 carbon atoms;
$R^5$ is $R^4$ wherein each $R^4$ is substituted with 0 to 3 $R^3$ groups;
$W^3$ is $W^4$ or $W^5$;
$W^4$ is $R^5$, $-C(Y^1)R^5$, $-C(Y^1)W^5$, $-SO_{M2}R^5$, or $-SO_{M2}W^5$;
$W^5$ is carbocycle wherein $W^5$ is independently substituted with 0 to 3 $R^2$ groups;
$W^6$ is $W^3$ independently substituted with 1, 2, or 3 $A^3$ groups;
M2 is 0, 1 or 2;
M12a is 1, 2, 3, 4, 5, 6, 7, 8, 9, 10, 11 or 12;
M12b is 0, 1, 2, 3, 4, 5, 6, 7, 8, 9, 10, 11 or 12;
M1a, M1c, and M1d are independently 0 or 1; and
M12c is 0, 1, 2, 3, 4, 5, 6, 7, 8, 9, 10, 11 or 12.

2. The conjugate of claim 1, or a pharmaceutically acceptable salt or solvate thereof, which has the formula:

$$[DRUG]-(A^0)_{nn}$$

wherein:

DRUG is a compound of formula 509;

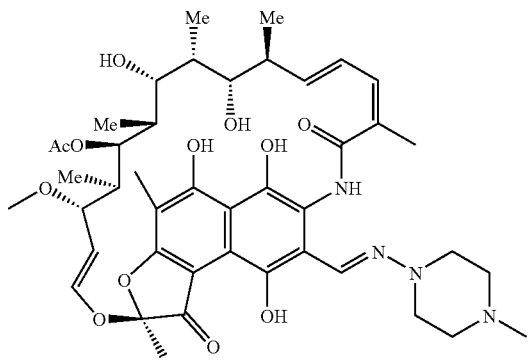

509 and nn is 1, 2, or 3.

3. The conjugate of claim 1 is formula 13 4:

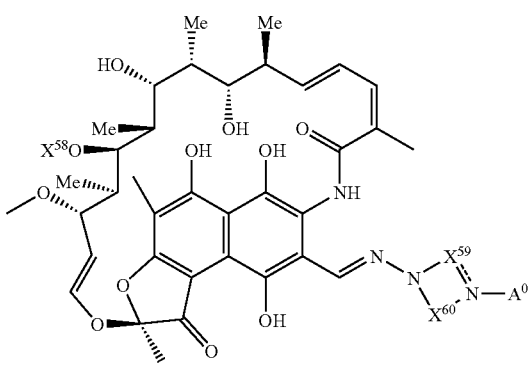

13 wherein:

one $A^0$ is $A^1$;

$X^{59}$ and $X^{60}$ are alkyl groups, taken together with the linked nitrogen atoms from a piperazine ring; $X^{58}$ is acetyl.

4. The conjugate of claim 3, wherein each $A^1$ is of the formula:

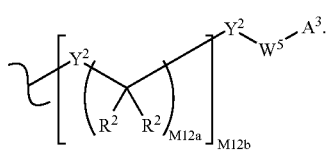

5. The conjugate of claim 3, wherein each $A^1$ is of the formula:

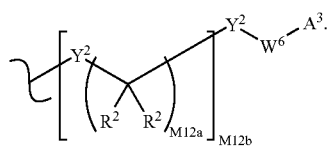

6. The conjugate of claim 3, wherein each $A^1$ is of the formula:

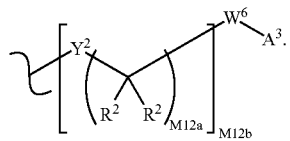

7. The conjugate of claim 3, wherein each $A^1$ is of the formula:

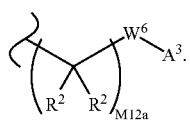

8. The conjugate of claim 3, wherein each $A^1$ is of the formula:

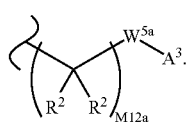

wherein: $W^{5a}$ is a carbocycle where $W^{5a}$ is independently substituted with 0 or 1 $R^2$ groups.

9. The conjugate of claim 3, wherein M12a is 1.

10. The conjugate of claim 3, wherein each $A^1$ is of the formula:

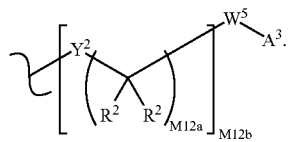

11. The conjugate of claim 3, wherein each $A^1$ is of the formula:

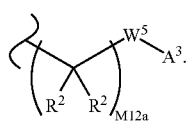

12. The conjugate of claim 3, wherein each $A^1$ is of the formula:

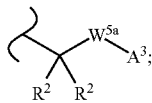

wherein: $W^{5a}$ is a carbocycle independently substituted with 0 or 1 $R^2$ groups.

13. The conjugate of claim 3, wherein each $A^1$ is of the formula:

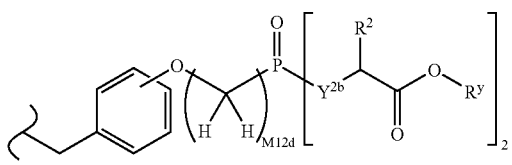

wherein:
$Y^{2b}$ is O or $N(R^2)$; and
M12d is 1, 2, 3, 4, 5, 6, 7 or 8.

14. The conjugate of claim 3, wherein each $A^1$ is of the formula:

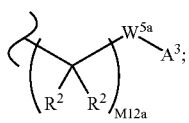

wherein: $W^{5a}$ is a carbocycle independently substituted with 0 or 1 $R^2$ groups.

15. The conjugate of claim 3, wherein each $A^1$ is of the formula:

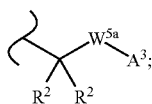

wherein: $W^{5a}$ is a carbocycle where $W^{5a}$ is independently substituted with 0 or 1 $R^2$ groups.

16. The conjugate of claim 3, wherein each $A^1$ is of the formula:

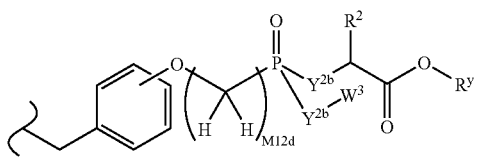

wherein:
$Y^{2b}$ is O or $N(R^2)$; and
M12d is 1, 2, 3, 4, 5, 6, 7 or 8.

17. The conjugate of claim 1 wherein each $A^2$ is of the formula:

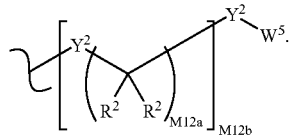

18. The conjugate of claim 1 wherein each $A^2$ is of the formula:

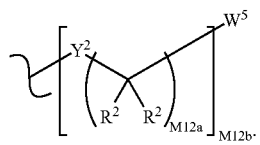

19. The conjugate of claim 1 wherein each M12b is 1.

20. The conjugate of claim 19 where M12b is 0, $Y^2$ is a bond and $W^5$ is a carbocycle where $W^5$ is optionally and independently substituted with 1, 2, or 3 $R^2$ groups.

21. The conjugate of claim 1 wherein each $A^2$ is of the formula:

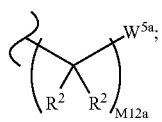

wherein: $W^{5a}$ is a carbocycle where $W^{5a}$ is optionally and independently substituted with 1, 2, or 3 $R^2$ groups.

22. The conjugate of claim 21 wherein M12a is 1.

23. The conjugate of claim 1 wherein each $A^2$ is selected from phenyl, substituted phenyl, benzyl, substituted benzyl, pyridyl and substituted pyridyl.

24. The conjugate of claim 1 wherein each $A^2$ is of the formula:

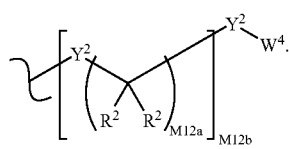

25. The conjugate of claim 2 wherein each $A^2$ is of the formula:

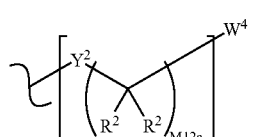

26. The conjugate of claim 25 wherein M12b is 1.

27. The conjugate of claim 1 wherein each $A^3$ is of the formula:

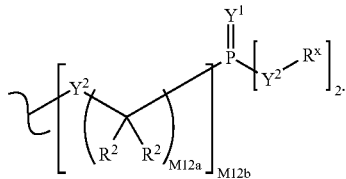

28. The conjugate of claim 1 wherein each $A^3$ is of the formula:

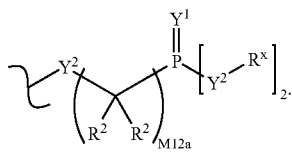

29. The conjugate of claim 1 wherein each $A^3$ is of the formula:

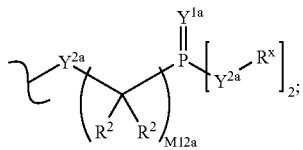

wherein:
$Y^{1a}$ is O or S; and
$Y^{2a}$ is O, N(R) or S.

30. The conjugate of claim 1 wherein each $A^3$ is of the formula:

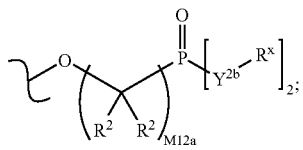

wherein $Y^{2b}$ is O or N($R^x$).

31. The conjugate of claim 1 wherein each $A^3$ is of the formula:

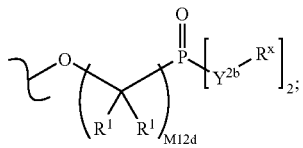

wherein:
$Y^{2b}$ is O or N($R^x$); and
M12d is 1, 2, 3, 4, 5, 6, 7 or 8.

32. The conjugate of claim 1 wherein each $A^3$ is of the formula:

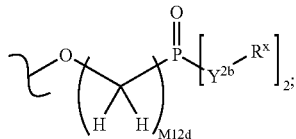

wherein:
$Y^{2b}$ is O or N($R^x$); and
M12d is 1, 2, 3, 4, 5, 6, 7 or 8.

33. The conjugate of claim 32 wherein M12d is 1.

34. The conjugate of claim 1 wherein each $A^3$ is of the formula:

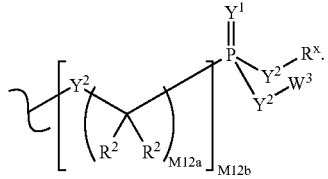

35. The conjugate of claim 1 wherein each $A^3$ is of the formula:

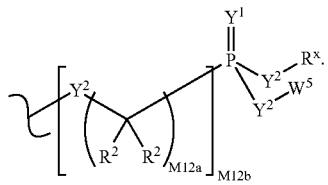

36. The conjugate of claim 35 wherein $W^5$ is a carbocycle.

37. The conjugate of claim 1 wherein each $A^3$ is of the formula:

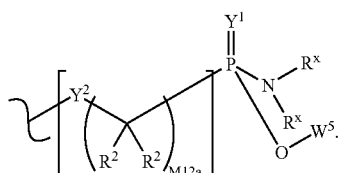

38. The conjugate of claim 37 wherein $W^5$ is phenyl.

39. The conjugate of claim 38 wherein M12b is 1.

40. The conjugate of claim 1 wherein each $A^3$ is of the formula:

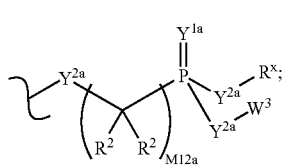

wherein:

$Y^{1a}$ is O or S; and $Y^{2a}$ is O, N(R$^x$) or S.

41. The conjugate of claim 1 wherein each A$^3$ is of the formula:

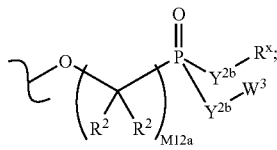

wherein Y$^{2b}$ is O or N(R$^x$).

42. The conjugate of claim 1 wherein each A$^3$ is of the formula:

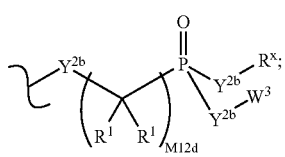

wherein:

$Y^{2b}$ is O or N(R$^x$); and

M12d is 1, 2, 3, 4, 5, 6, 7 or 8.

43. The conjugate of claim 42 wherein R$^1$ is H.

44. The conjugate of claim 43 wherein M12d is 1.

45. The conjugate of claim 1 wherein each A$^3$ is of the formula:

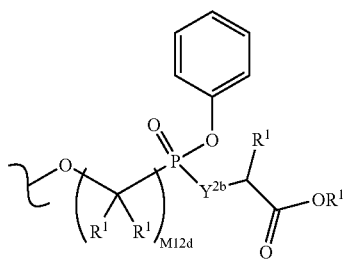

wherein the phenyl carbocycle is substituted with 0, 1, 2, or 3 R$^2$ groups.

46. The conjugate of claim 1 wherein each A$^3$ is of the formula:

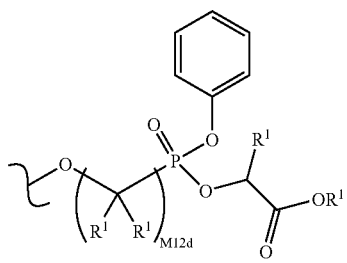

wherein the phenyl carbocycle is substituted with 0, 1, 2, or 3 R$^2$ groups.

47. The conjugate of claim 1 wherein each A$^3$ is of the formula:

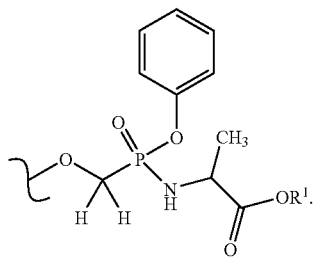

48. The conjugate of claim 1 wherein each A$^3$ is of the formula:

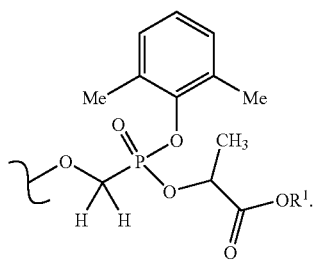

49. The conjugate of claim 1 wherein each A$^3$ is of the formula:

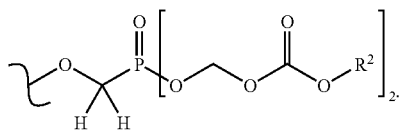

50. The conjugate of claim 1 wherein each A$^3$ is of the formula:

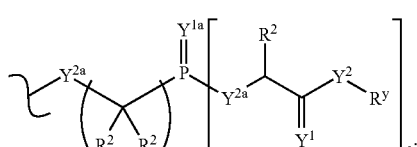

wherein:

$Y^{1a}$ is O or S; and $Y^{2a}$ is O, N(R$^2$) or S.

51. The conjugate of claim 1 wherein each A$^3$ is of the formula:

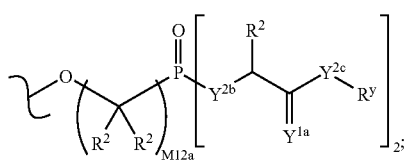

wherein:

$Y^{1a}$ is O or S;

$Y^{2b}$ is O or $N(R^2)$; and $Y^{2c}$ is O, $N(R^y)$ or S.

52. The conjugate of claim 1 wherein each $A^3$ is of the formula:

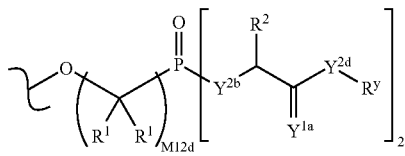

wherein:

$Y^{1a}$ is O or S;

$Y^{2b}$ is O or $N(R^2)$;

$Y^{2d}$ is O or $N(R^y)$; and

M12d is 1, 2, 3, 4, 5, 6, 7 or 8.

53. The conjugate of claim 1 wherein each $A^3$ is of the formula:

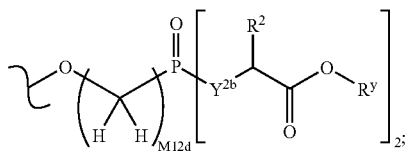

wherein:

$Y^{2b}$ is O or $N(R^2)$; and

M12d is 1, 2, 3, 4, 5, 6, 7 or 8.

54. The conjugate of claim 1 wherein each $A^3$ is of the formula:

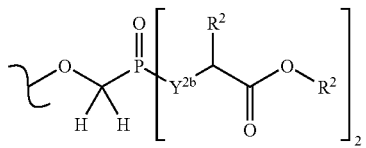

wherein $Y^{2b}$ is O or $N(R^2)$.

55. The conjugate of claim 1 wherein each $A^3$ is of the formula:

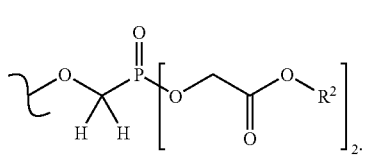

56. The conjugate of claim 1 wherein each $A^3$ is of the formula:

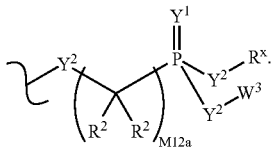

57. The conjugate of claim 1 wherein each $A^3$ is of the formula:

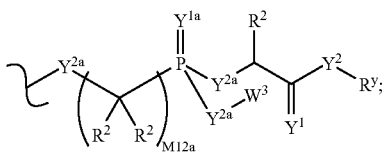

wherein:

$Y^{1a}$ is O or S; and $Y^{2a}$ is O, $N(R^2)$ or S.

58. The conjugate of claim 1 wherein each $A^3$ is of the formula:

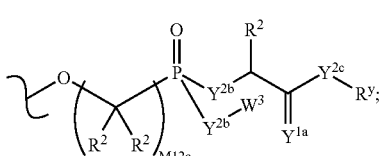

wherein:

$Y^{1a}$ is O or S;

$Y^{2b}$ is O or $N(R^2)$; and $Y^{2c}$ is O, $N(R^y)$ or S.

59. The conjugate of claim 1 wherein each $A^3$ is of the formula:

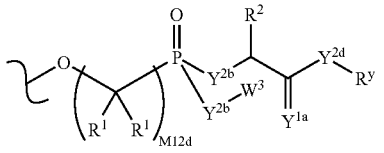

wherein:

$Y^{1a}$ is O or S;

$Y^{2b}$ is O or $N(R^2)$;

$Y^2d$ is O or $N(R^y)$; and

M12d is 1, 2, 3, 4, 5, 6, 7 or 8.

60. The conjugate of claim 1 wherein each $A^3$ is of the formula:

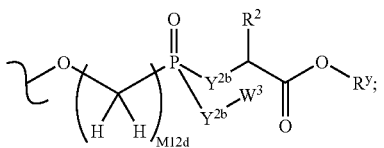

wherein:

Y$^{2b}$ is O or N(R$^2$); and

M12d is 1, 2, 3, 4, 5, 6, 7 or 8.

61. The conjugate of claim 1 wherein each A$^3$ is of the formula:

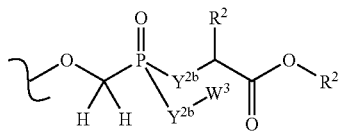

wherein Y$^{2b}$ is O or N(R$^2$).

62. The conjugate of claim 2 wherein A$^0$ is of the formula:

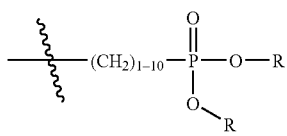

wherein each R is independently alkyl.

63. The conjugate of claim 2 which has the formula:

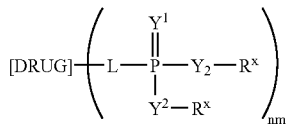

or a pharmaceutically acceptable salt or solvate thereof, wherein:

DRUG is a compound of formula 509;

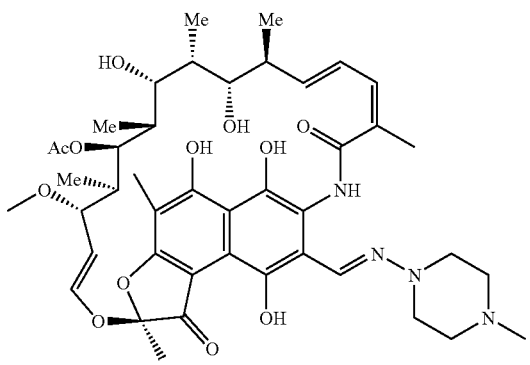

Y$^1$ is independently O, S, N(R$^x$), N(O)(R$^x$), N(OR$^x$), N(O)(OR$^x$), or N(N(R$^x$)(R$^x$));

Y$^2$ is independently a bond, O, N(R$^x$), N(O)(R$^x$), N(OR$^x$), N(O)(OR$^x$), N(N(R$^x$)(R$^x$)), —S(O)$_{M2}$—, or —S(O)$_{M2}$—S(O)$_{M2}$—;

R$^x$ is independently H, R$^2$, W$^3$, a protecting group, or the formula:

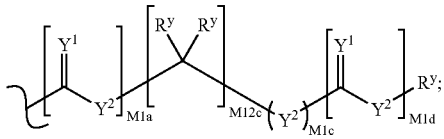

R$^y$ is independently H, W$^3$, R$^2$ or a protecting group;

R$^2$ is independently H, R$^3$ or R$^4$ wherein each R$^4$ is independently substituted with 0 to 3 R$^3$ groups;

R$^3$ is R$^{3a}$, R$^{3b}$, R$^{3c}$ or R$^{3d}$, provided that when R$^3$ is bound to a heteroatom, then R$^3$ is R$^{3c}$ or R$^{3d}$;

R$^{3a}$ is F, Cl, Br, I, —CN, N$_3$ or —NO$_2$;

R$^{3b}$ is Y$^1$;

R$^{3c}$ is R$^x$, —N(R$^x$)(R$^x$), —SR$^x$, —S(O)R$^x$, —S(O)$_2$R$^x$, —S(O)(OR$_x$), —S(O)$_2$(OR$^x$), —OC(Y$^1$)R$^x$, —OC(Y$^1$)OR$^x$, —OC(Y$^1$)(N(R$^x$)(R$^x$)), —SC(Y$^1$)R$^x$, —SC(Y$^1$)OR$^x$, —SC(Y$^1$)(N(R$^x$)(R$^x$)), —N(R$^x$)C(Y$^1$)R$^x$, —N(R$^x$)C(Y$^1$)OR$^x$, or —N(R$^x$)C(Y$^1$)(N(R$^x$)(R$^x$))

R$^{3d}$ is —C(Y$^1$)R$^x$, —C(Y$^1$)OR$^x$ or —C(Y$^1$)(N(R$^x$)(R$^x$));

R$^4$ is an alkyl of 1 to 18 carbon atoms, alkenyl of 2 to 18 carbon atoms, or alkynyl of 2 to 18 carbon atoms;

R$^5$ is R$^4$ wherein each R$^4$ is substituted with 0 to 3 R$^3$ groups;

W$^3$ is W$^4$ or W$^5$;

W$^4$ is R$^5$, —C(Y$^1$)R$^5$, —C(Y$^1$)W$^5$, —S$_2$R$^5$, or —SO$_2$W$^5$;

W$^5$ is carbocycle wherein W$^5$ is independently substituted with 0 to 3 R$^2$ groups;

M2 is 1, 2, or 3;

M1a, M1c, and M1d are independently 0 or 1;

M12c is 0, 1, 2, 3, 4, 5, 6, 7, 8, 9, 10, 11 or 12;

nn is 1, 2, or 3; and

L is a direct bond or a linking group.

64. The conjugate of claim 63 wherein each R$^x$ is of the formula:

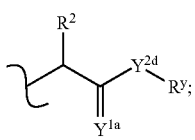

Y$^{1a}$ is O or S; and

Y$^{2c}$ is O, N(R$^y$) or S.

65. The conjugate of claim 63 wherein each R$^x$ is of the formula:

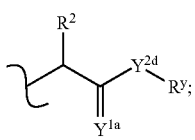

Y$^{1a}$ is O or S; and

Y$^{2d}$ is O or N(R$^y$).

66. The conjugate of claim 63 wherein each $R^x$ is of the formula:

$$\text{\{-CH(R}^2\text{)-C(=O)-O-R}^y\}$$

67. The conjugate of any one of claims 64-66 wherein each $R^y$ is independently H or alkyl of 1 to 10 carbons.

68. The conjugate of claim 63 wherein each $R^x$ is of the formula:

$$\text{\{-CH(R}^2\text{)-C(=O)-O-R}^2\}$$

69. The conjugate of claim 63 wherein each $R^x$ is of the formula:

$$\{-(C(R^2)(R^2))_{M12a}-Y^2-C(=Y^1)-R^y\}$$

70. The conjugate of claim 63 wherein each $R^x$ is of the formula:

$$\{-(C(R^2)(R^2))_{M12a}-C(=Y^1)-Y^2-R^y\}$$

71. The conjugate of claim 63 wherein each $Y^1$ is O or S.

72. The conjugate of claim 63 wherein each $Y^2$ is O, $N(R^y)$ or S.

73. The conjugate of claim 63 wherein nn is 1.

74. The conjugate of claim 63 wherein nn is 2.

75. The conjugate of claim 63 wherein nn is 3.

76. The conjugate of claim 63 wherein each L has a molecular weight of from about 20 daltons to about 400 daltons.

77. The conjugate of claim 63 wherein each L has a length of about 5 angstroms to about 300 angstroms.

78. The conjugate of claim 63 wherein each L separates the compound of formula 509 and the phosphorous of the phosphonate group by about 5 angstroms to about 200 angstroms, inclusive.

79. The conjugate of claim 63 wherein each L is a divalent, branched or unbranched, saturated or unsaturated, hydrocarbon chain, having from 2 to 25 carbon atoms, wherein one or more of the carbon atoms is optionally replaced by (—O—), and wherein the chain is optionally substituted on carbon with one or more substituents selected from $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo (=O), carboxy, aryl, aryloxy, heteroaryl, and heteroaryloxy.

80. The conjugate of claim 63 wherein each L is of the formula W-A wherein A is $(C_1-C_{24})$alkylene, $(C_2-C_{24})$alkenylene, $(C_2-C_{24})$alkynylene, $(C_3-C_8)$cycloalkylene, $(C_6-C_{10})$aryl or a combination thereof, wherein each W is —N(R)C(=O)—, —C(=O)N(R)—, —OC(=O)—, —C(=O)O—, —O—, —S—, —S(O)—, —S(O)$_2$—, —N(R)—, —C(=O)—, —N(R)C=N(R)—N(R)—, —C(R)=N(R)—, —S(O)$_{Mb}$$_2$—N(R)—, —N(R)—S(O)$_{M2}$—, or a direct bond; wherein each R is independently H or alkyl of 1 to 10 carbons.

81. The conjugate of claim 80 wherein each A is alkylene of 1 to 10 carbons.

82. The conjugate of claim 63 wherein each L is a divalent radical formed from a peptide.

83. The conjugate of claim 63 wherein each L is a divalent radical formed from an amino acid.

84. The conjugate of claim 63 wherein each L is a divalent radical formed from poly-L-glutamic acid, poly-L-aspartic acid, poly-L-histidine, poly-L-omithine, poly-L-serine, poly-L-threonine, poly-L-tyrosine, poly-L-leucine, poly-L-lysine-L-phenylalanine, poly-L-lysine or poly-L-lysine-L-tyrosine.

85. The conjugate of claim 63 wherein each L is of the formula W—(CH$_2$)$_n$ wherein, n is between about 1 and about 10; and W is —N(R)C(=O)—, —C(=O)N(R)—, —OC(=O)—, —C(=O)O—, —O—, —S—, —S(O)—, —S(O)$_2$—, —C(=O)—, —N(R)—, —N(R)C=N(R)—N(R)—, —C(R)=N(R)—, —S(O)$_{M2}$—N(R)—, —N(R)—S(O)$_{M2}$—, or a direct bond; wherein each R is independently H or $(C_1-C_6)$alkyl.

86. The conjugate of claim 63 wherein each L is methylene, ethylene, or propylene.

87. The conjugate of claim 63 wherein each L is linked to P at a carbon atom of L.

88. The conjugate as described in claim 1, which is isolated and purified.

89. A pharmaceutical composition comprising a pharmaceutical excipient and a conjugate as described in claim 1.

90. A unit dosage form comprising a conjugate as described in claim 1 and a pharmaceutically acceptable excipient.

91. The compound:

8.8

[Structure of rifamycin-derived compound with piperazinyl-methylphosphonate diethyl ester substituent]

or a pharmaceutically acceptable salt or solvate thereof.

* * * * *

UNITED STATES PATENT AND TRADEMARK OFFICE
CERTIFICATE OF CORRECTION

PATENT NO. : 7,300,924 B2
APPLICATION NO. : 10/833291
DATED : November 27, 2007
INVENTOR(S) : Constantine G. Boojamra, Aesop Cho and William J. Watkins It is certified that error appears in the above-identified patent and that said Letters Patent is hereby corrected as shown below:

In column 325, line 54, claim 3, delete "from" and insert --form--, therefore.

In column 328, line 56, claim 25, delete "2" and insert --1--, therefore.

In column 329, line 39, claim 29, delete "R" and insert --$R^x$--, therefore.

In column 334, line 55, claim 59, delete "$Y^2d$" and insert --$Y^{2d}$--, therefore.

In column 336, line 19, claim 63, delete "is $R^x$" and insert --is, -$R^x$--, therefore.

In column 336, line 23, claim 63, delete "))" and insert --));--, therefore.

In column 336, line 31, claim 63, delete "$S_2R^5$" and insert --$SO_2R^5$--, therefore.

In column 338, line 12, claim 80, delete "$S(O)_{Mb\ 2}$ -N(R)-," and insert --$S(O)_{M2}$-N(R)-,--, therefore.

In column 338, line 23, claim 84, delete "omithine" and insert --ornithine--, therefore.

UNITED STATES PATENT AND TRADEMARK OFFICE
CERTIFICATE OF CORRECTION

PATENT NO. : 7,300,924 B2
APPLICATION NO. : 10/833291
DATED : November 27, 2007
INVENTOR(S) : Constantine G. Boojamra, Aesop Cho and William J. Watkins It is certified that error appears in the above-identified patent and that said Letters Patent is hereby corrected as shown below:

In column 338, claim 91, lines 50-64, delete chemical structure and insert

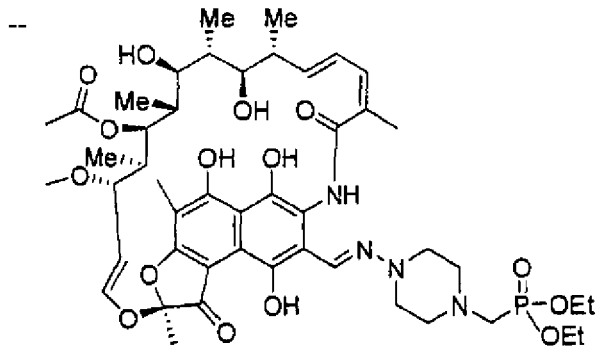

-- therefore.

Signed and Sealed this

Second Day of June, 2009

JOHN DOLL
*Acting Director of the United States Patent and Trademark Office*